United States Patent
Chae et al.

(10) Patent No.: US 11,450,808 B2
(45) Date of Patent: Sep. 20, 2022

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Mi Young Chae, Cheonan-si (KR); Hye Min Cho, Cheonan-si (KR); Min Ji Jo, Cheonan-si (KR); Soung Yun Mun, Cheonan-si (KR); Sun Hee Lee, Cheonan-si (KR); Nam Geol Lee, Cheonan-si (KR); Hyung Dong Lee, Cheonan-si (KR); Dae Hwan Oh, Cheonan-si (KR); Ga Eun Lee, Cheonan-si (KR); Sang Yong Park, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 360 days.

(21) Appl. No.: 16/652,383

(22) PCT Filed: Aug. 20, 2018

(86) PCT No.: PCT/KR2018/009503
§ 371 (c)(1),
(2) Date: Mar. 30, 2020

(87) PCT Pub. No.: WO2019/066250
PCT Pub. Date: Apr. 4, 2019

(65) Prior Publication Data
US 2020/0287140 A1    Sep. 10, 2020

(30) Foreign Application Priority Data

Sep. 29, 2017  (KR) .................. 10-2017-0127537
Apr. 4, 2018   (KR) .................. 10-2018-0039162
Jun. 25, 2018  (KR) .................. 10-2018-0072472

(51) Int. Cl.
H01L 51/00    (2006.01)
C07D 409/14   (2006.01)
H01L 51/50    (2006.01)

(52) U.S. Cl.
CPC ........ *H01L 51/0067* (2013.01); *C07D 409/14* (2013.01); *H01L 51/0073* (2013.01);
(Continued)

(58) Field of Classification Search
CPC ............. H01L 51/0067; H01L 51/0073; H01L 51/0074
See application file for complete search history.

(56) References Cited

FOREIGN PATENT DOCUMENTS

| CN | 1769269 A | 5/2006 |
|---|---|---|
| CN | 105218541 A | 1/2016 |

(Continued)

OTHER PUBLICATIONS

Prioritized Examination Report for corresponding Korean Patent Application No. 10-2021-0046353; dated Apr. 16, 2021, 6 pages.
(Continued)

*Primary Examiner* — Anthony Ho
(74) *Attorney, Agent, or Firm* — Vorys, Sater, Seymour and Pease LLP; Mih Suhn Koh

(57) ABSTRACT

Provided are a compound represented by Formula 1 or Formula A, an organic electric element comprising a first electrode, a second electrode, and an organic material layer formed between the first electrode and the second electrode and an electronic device thereof, wherein the compound represented by Formula 1 or Formula A is included in the organic material layer, and thereby the driving voltage of the
(Continued)

organic electronic device can be lowered, and the luminous efficiency and life time of the organic electronic device can be improved.

30 Claims, 1 Drawing Sheet

(52) U.S. Cl.
CPC ...... *H01L 51/0074* (2013.01); *H01L 51/5016* (2013.01); *H01L 51/5056* (2013.01); *H01L 51/5072* (2013.01); *H01L 51/5088* (2013.01); *H01L 51/5092* (2013.01)

(56) References Cited

FOREIGN PATENT DOCUMENTS

| | | |
|---|---|---|
| JP | 2007-059750 A | 3/2007 |
| KR | 10-2004-0086249 A | 10/2004 |
| KR | 10-2012-0129733 A | 11/2012 |
| KR | 10-2014-0142923 A | 12/2014 |
| KR | 10-2015-0031892 A | 3/2015 |
| KR | 10-2015-0079911 A | 7/2015 |
| KR | 10-2017-0083765 A | 7/2017 |
| KR | 10-2017-0084393 A | 7/2017 |
| KR | 10-1857632 B1 | 5/2018 |

OTHER PUBLICATIONS

The Notice of Preliminary Examination for corresponding KR Patent Application No. 10-2021-0046353, dated May 14, 2021, 8 pages.

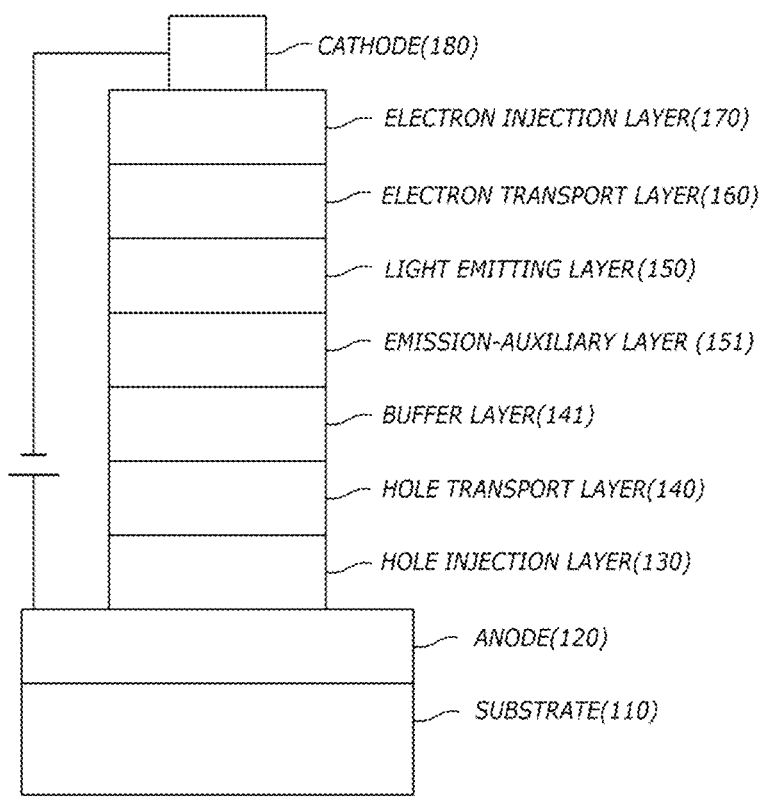

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2017-0127537, filed on Sep. 29, 2017, Korean Patent Application No. 10-2018-0039162, filed on Apr. 4, 2018, Korean Patent Application No. 10-2018-0072472, filed on Jun. 25, 2018, which are hereby incorporated by reference for all purposes as if fully set forth herein. Further, this application claims the benefit of priority in countries other than U.S., which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Further, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Further, the light emitting material may be divided into blue, green, and red light emitting material and yellow and orange light emitting material required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to a deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, the power consumption is a very important factor in the portable display with a limited power source of the battery, and efficiency and life span issue also is solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and $T_1$ values, inherent material properties (mobility, interfacial properties, etc.), and the like among the respective layers included in the organic material layer is given.

In addition, in the recent organic electroluminescent devices, an emission-auxiliary layer (multi-layered hole transport layer) must be present between the hole transport layer and the light emitting layer in order to solve the problems of luminescence in the hole transport layer and the driving voltage, and it is necessary to develop different emission-auxiliary layers according to respective light emitting layers.

In general, an electron is transferred from an electron transport layer to a light emitting layer and a hole is transferred from a hole transport layer to the light emitting layer, as a result, an exciton is formed by the recombination of the electron and hole within the light emitting layer.

However, material used in a hole transport layer has a low T1 value because the material should have a low HOMO value. As a result, the exciton generated in the light emitting layer is transferred to the hole transport layer and it causes charge unbalance in the light emitting layer, thereby emitting light at the interface of the hole transport layer.

When light is emitted from the interface of the hole transporting layer, the color purity and efficiency of the organic electronic element are lowered and the lifetime is shortened. Therefore, it is strongly desired to develop materials for the emission-auxiliary layer having a HOMO level between the HOMO energy level of the hole transporting layer and the HOMO energy level of the light emitting layer, a high T1 energy value and a hole mobility within a suitable driving voltage range (within a driving voltage range of blue element of a full device).

However, this cannot be achieved simply by the structural properties of the core of the emission-auxiliary layer material. An element having a high efficiency and a long life span can be realized when the characteristics of core and sub-substituents of the emission-auxiliary layer material, the proper combination of the emission-auxiliary layer and the hole transport layer, and the proper combination of the emission-auxiliary layer and the light emitting layer.

In order to fully exhibit the excellent characteristics of the organic electric element, materials forming the organic material layer in the element, such as a hole injection material, a hole transport material, a light emitting material, an electron transport material, an electron injection material, an emission-auxiliary layer material, etc. should be prerequisite to support by a stable and efficient material, and in particular, it is strongly required to develop material of host of a light emitting layer, a hole transport layer and an an emission-auxiliary layer.

Object, Technical Solution and Effects of the Invention

The present invention is to provide a compound lowering a driving voltage, improving luminous efficiency, color purity, stability and lifetime of the element, an organic electric element comprising the same, and an electronic device thereof.

In an aspect of the present invention, the present invention provides the compound represented by the following formula 1.

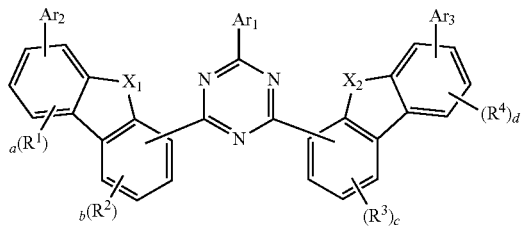

In another aspect of the present invention, the present invention provides the compound represented by the following Formula A.

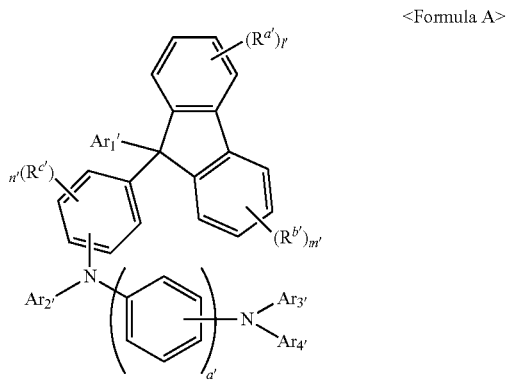

<Formula A>

In another aspect of the present invention, the present invention provides an organic electric element using the compound represented by formula 1 or A above and an electric device thereof.

By using the compound according to embodiments of the present invention, a driving voltage can be lowered and the luminous efficiency, color purity, stability and lifetime of the element can be largely improved.

BRIEF DESCRIPTION OF THE DRAWINGS

The FIGURE illustrates an example of an organic electroluminescent element according to the present invention: 100 is organic electric element, 110 is substrate, 120 is first electrode, 130 is hole injection layer, 140 is hole transport layer, 141 is buffer layer, 150 is light emitting layer, 151 is emission-auxiliary layer, 160 is electron transport layer, 170 is electron injection layer, and 180 is second electrode.

DETAILED DESCRIPTION

Unless otherwise stated, the term "aryl group" or "arylene group" as used herein has, but not limited to, 6 to 60 carbon atoms. The aryl group or arylene group in the present invention may comprise a monocyclic ring, ring assemblies, a fused polycyclic system, spiro compounds and the like.

The term "heterocyclic group" as used herein means a non-aromatic ring as well as an aromatic ring like "heteroaryl group" or "heteroarylene group", and unless otherwise stated, it means a ring comprising one or more heteroatoms and having 2 to 60 carbon atoms, but not limited thereto. Unless otherwise stated, the term "hetero atom" as used herein represents N, O, S, P or Si, and the heterocyclic group means a monocyclic form, ring assemblies, a fused polycyclic system or a spiro compound comprising heteroatom(s).

The term "heterocyclic group" as used herein means a ring comprising a heteroatom like N, O, S, P, Si or the like instead of carbon consisting of a ring, it comprises a non-aromatic ring as well as an aromatic ring like "heteroaryl group" or "heteroarylene group" and the compound comprising the heteroatom group like $SO_2$, $P=O$ or the like instead of carbon consisting of a ring such as the following compound.

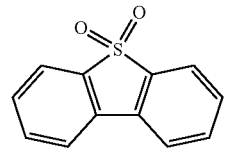 [SMILES: O=S1(=O)c2ccccc2-c2ccccc21]

Unless otherwise stated, the term "fluorenyl group" or "fluorenylene group" as used herein meansunivalent or bivalent functional group in which R, R' and R" are all hydrogen in the following structure, "substituted fluorenyl group" or "substituted fluorenylene group" means that at least any one of R, R' and R" is a substituent other than hydrogen, and it comprises spiro compound formed by linking R and R' together with the carbon bonded to them.

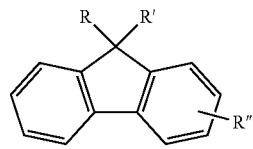

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as aparent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula:

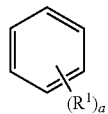

Wherein, the substituent $R^1$ is absent when a is an integer of zero, the sole $R^1$ is bonded to any one of the carbon atoms constituting the benzene ring when a is an integer of 1, when a is an integer of 2 or 3, the substituent $R^1$s may be bonded as follows and the substituents $R^1$s may be the same or different each other, and the substituent $R^1$s may be bonded to the carbon of the benzene ring in a similar manner when a is an integer of 4 to 6. Herein, the indication of the hydrogen bonded to the carbon which forms the benzene ring is omitted.

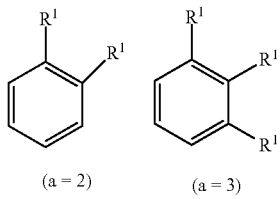

Hereinafter, referring to the FIGURE, a lamination structure of an organic electric element including the compound of the present invention will be described.

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or the organic material layer may further include a hole blocking layer, an electron blocking layer, an emission-auxiliary layer 151, an electron transport auxiliary layer, a buffer layer 141, etc., and the electron transport layer 160 or the like may serve as the hole blocking layer.

In addition, although not shown, the organic electric element according to an embodiment of the present invention may further include at least a protective layer or a layer for improving luminous efficiency. The layer for improving luminous efficiency may be formed on a surface that does not face the organic material layer of both surfaces of the first electrode or the second electrode.

The inventive compound employed in the organic material layer may be used as a material of a hole injection layer 130, a hole transport layer 140, an emission-auxiliary layer 151, an electron transport auxiliary layer, an electron transport layer 160, an electron injection layer 170 and the like, as a host or a dopant material of a light emitting layer 150, or as a material of a layer for improving luminous efficiency. For example, the compound according to Formula 1 of the present invention may be used as material of the light emitting layer 150, preferably, as host material of the light emitting layer 150, a mixture of the compound according to Formula 1 of the present invention and the compound according to Formula 12 of the present invention may be used as host material, and the compound according to Formula 20 of the present invention may be used as material of a hole transport layer or an emission-auxiliary layer. Preferably, the compound represented by Formula 21 or 22 of the present invention may be used as material of a hole transport layer, and the compound represented by Formula 23 or 24 of the present invention may be used as material of an emission-auxiliary layer. Also, the compound represented by Formula A of the present invention may be used as material of an emission-auxiliary layer, specially, a green emission-auxiliary layer.

Even if the core is the same core, the band gap, the electrical characteristics, the interface characteristics, and the like may be different depending on which substituent is bonded at which position. Therefore, it is necessary to study the selection of the core and the combination of the core and the sub-substituent bonded to the core. Specially, long life span and high efficiency can be simultaneously achieved when the optimal combination of energy levels and $T_1$ values, inherent material properties (mobility, interfacial properties, etc.), and the like among the respective layers of an organic material layer is achieved.

Therefore, according to the present invention, energy level and $T_1$ value between the respective layers of the organic material layer, inherent material properties (mobility, interfacial properties, etc.) and the like can be optimized by using as a host material of a light emitting layer a single compound represented by the Formula 1 or a mixture of the compound represented by the Formula 1 and the compound represented by the Formula 12, by using these compounds as a light-emitting layer material and simultaneously using the compound according to the formula 20 as a hole transport layer or an emission-auxiliary layer, and thus it is possible to simultaneously improve the life span and efficiency of the organic electric element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the compound according to an aspect of the present invention will be described.

The compound according to an aspect of the present invention is represented by formula 1 below.

<Formula 1>

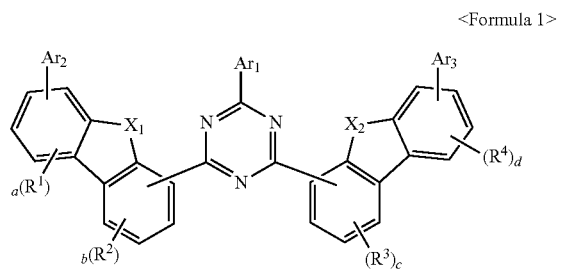

In the formula 1, each of symbols may be defined as follows.

$X_1$ and $X_2$ are each independently O or S, provided that $X_1$ and $X_2$ are different from each other. That is, one of $X_1$ and $X_2$ is O and the other is S.

$Ar_1$ to $Ar_3$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$).

When $Ar_1$ to $Ar_3$ are each an aryl group, $Ar_1$ to $Ar_3$ may be preferably a $C_6$-$C_{30}$ or a $C_6$-$C_{20}$ aryl group, more preferably a $C_6$-$C_{18}$ aryl group, for example, phenyl, biphenyl, naphthyl, phenanthryl, terphenyl or the like. When $Ar_1$ to $Ar_3$ are each a heterocyclic group, $Ar_1$ to $Ar_3$ may be preferably a $C_2$-$C_{30}$ or a $C_2$-$C_{20}$ heterocyclic group, more preferably a $C_2$-$C_{18}$ heterocyclic group, for example, pyrazine, thiophene, pyridine, pyrimidoindole, 5-phenyl-5H-pyrimidido[5,4-b]indole, quinazoline, benzoquinazoline, carbazole, dibenzoquinazole, dibenzofuran, benzothienopyrimidine, benzofuropyrimidine, phenothiazine, phenylphenothiazine and the like. When $Ar_1$ to $Ar_3$ are each a fluorenyl group, $Ar_1$ to $Ar_3$ may be 9,9-dimethyl-9H-fluorene, 9,9-diphenyl-9H-fluorene or the like.

When $Ar_2$ and $Ar_3$ are each an aryl group, $Ar_2$ and $Ar_3$ may be preferably a $C_6$-$C_{30}$ or a $C_6$-$C_{22}$ aryl group, more preferably a $C_6$-$C_{18}$ aryl group, for example, phenyl, biphenyl, naphthyl, phenanthryl, terphenyl or the like.

When $Ar_1$ to $Ar_3$ are each a heterocyclic group, $Ar_1$ to $Ar_3$ may be preferably a $C_2$-$C_{30}$ or a $C_2$-$C_{20}$ heterocyclic group, more preferably a $C_2$-$C_{18}$ heterocyclic group, for example, pyrazine, thiophene, pyridine, pyrimidoindole, 5-phenyl-5H-pyrimidido[5,4-b]indole, quinazoline, benzoquinazoline, carbazole, dibenzoquinazole, dibenzofuran, benzothienopyrimidine, benzofuropyrimidine, phenothiazine, phenylphenothiazine and the like. When $Ar_1$ to $Ar_3$ are each a fluorenyl group, $Ar_2$ and $Ar_3$ may be, for example, 9,9-dimethyl-9H-fluorene, 9,9-diphenyl-9H-fluorene or the like.

$R^1$ to $R^4$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent groups may be optionally linked to each other to form a $C_6$-$C_{60}$ aromatic ring, a $C_2$-$C_{60}$ heterocyclic group, a $C_3$-$C_{60}$ aliphatic ring, or a fused ring group formed by a $C_3$-$C_{60}$ aliphatic ring with a $C_6$-$C_{60}$ aromatic ring. Here, "adjacent groups are linked to each other" means that adjacent $R^1$s, adjacent $R^2$s, adjacent $R^3$s, or adjacent $R^4$s are respectively are linked to each other.

a to d are each an integer of 0 to 3, where each of these is an integer of 2 or more, each of $R^1$s, each of $R^2$s, each of $R^3$s or each of $R^4$s is the same or different from each other.

When $R^1$ to $R^4$ are each an aryl group, $R^1$ to $R^4$ may be preferably a $C_6$-$C_{30}$ or a $C_6$-$C_{20}$ aryl group, more preferably a $C_6$-$C_{18}$ aryl group, for example, phenyl, biphenyl, naphthyl, terphenyl or the like. When $R^1$ to $R^4$ are each a heterocyclic group, $R^1$ to $R^4$ may be preferably a $C_2$-$C_{30}$ or a $C_2$-$C_{20}$ heterocyclic group, more preferably a $C_2$-$C_8$ heterocyclic group, for example, triazine, pyrimidine, pyridine, quinazoline or the like.

The ring formed by linking between adjacent $R^1$s, between adjacent $R^2$s, between adjacent $R^3$, or between adjacent $R^4$ may be preferably a $C_6$-$C_{20}$ aromatic ring group, or a $C_2$-$C_{20}$ heterocyclic group containing at least one heteroatom selected from the group consisting of O, N, S, Si, and P, more preferably, a $C_6$-$C_{10}$ aromatic ring group, or a $C_2$-$C_{10}$ heterocyclic group containing at least one heteroatom selected from the group consisting of O, N, S, Si, and P, for example, benzene ring, naphthalene, phenanthrene, thiophene, benzothiophene, pyridine and the like. Therefore, when adjacent $R^1$s to adjacent $R^4$s are connected to each other to form a ring, an aromatic ring or a heterocycle comprising a benzene ring may be formed together with the benzene ring to which they are attached, preferably a $C_6$-$C_{14}$ aromatic ring or a $C_2$-$C_{14}$ heterocycle may be formed.

L' is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring.

When L' is an arylene group, L' may be preferably a $C_6$-$C_{30}$ or $C_6$-$C_{20}$ arylene group, more preferably a $C_6$-$C_{18}$ arylene group, for example, phenylene, biphenyl, naphthalene, terphenyl or the like.

$R_a$ and $R_b$ are each independently selected from the group consisting of hydrogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring.

When $R_a$ and $R_b$ are each an aryl group, $R_a$ and $R_b$ may be preferably a $C_6$-$C_{30}$ or $C_6$-$C_{20}$ aryl group, more preferably a $C_6$-$C_{18}$ aryl group, for example, phenyl, biphenyl, naphthyl, terphenyl or the like.

$Ar_1$ to $Ar_3$, $R^1$ to $R^4$, L', $R_a$, $R_b$, and the ring formed by bonding between neighboring $R^1$s to neighboring $R^4$s may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, and a $C_8$-$C_{20}$ arylalkenyl group.

That is, where $Ar_1$ to $Ar_3$, $R^1$ to $R^4$, L', $R_a$, $R_b$, and a ring formed by bonding between neighboring $R^1$s to neighboring $R^4$s are each an aryl group, an arylene group, an aromatic hydrocarbon, a fluorenyl group, a fluorenylene group, a heterocyclic group, an aliphatic ring (group), a fused ring (group), an alkyl group, an alkenyl group, an alkynyl group, an alkoxy group, an aryloxy group and the like, each of these may be further substituted with one or more substituents selected from the group consisting of substituents such as deuterium, halogen and the like.

For example, where $Ar_1$ to $Ar_3$, $R^1$ to $R^4$, L', $R_a$, $R_b$, and a ring formed by bonding between neighboring $R^1$s to neighboring $R^4$s are further substituted with an aryl group, the aryl group is preferably a $C_6$-$C_{20}$ aryl group, more preferably, a $C_6$-$C_{18}$ aryl group, for example, phenyl, naphthyl, biphenyl, terphenyl, and the like.

In addition, where $Ar_1$ to $Ar_3$, $R^1$ to $R^4$, L', $R_a$, $R_b$, and a ring formed by bonding between neighboring $R^1$s to neighboring $R^4$s are further substituted with a heterocyclic group, the heterocyclic group is preferably a $C_2$-$C_{20}$ heterocyclic group, more preferably, a $C_2$-$C_{12}$ heterocyclic group, for example, pyrazine, pyrimidine, pyridine, quinazoline, isoindole, carbazole, dibenzothiophene, and the like.

In addition, where $Ar_1$ to $Ar_3$, $R^1$ to $R^4$, L', $R_a$, $R_b$, and a ring formed by bonding between neighboring $R^1$s to $R^4$s are further substituted with an alkyl group, the alkyl group is preferably a $C_1$-$C_{10}$ alkyl group, more preferably, a $C_1$-$C_4$ alkyl group, for example, methyl, t-butyl and the like.

In addition, $Ar_1$ to $Ar_3$, $R^1$ to $R^4$, L', $R_a$, $R_b$, and a ring formed by bonding between neighboring $R^1$s to $R^4$s may be further substituted with the substituents such as F, CN, ethen and the like.

Formula 1 may be represented by one of the following Formula 2 to Formula 11.

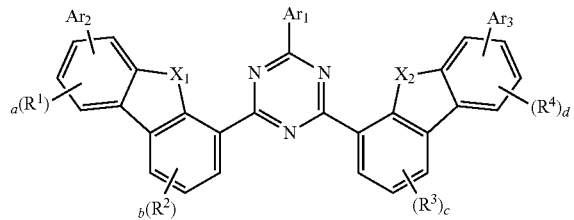

<Formula 2>

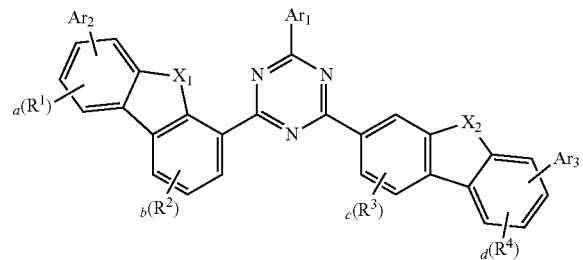

<Formula 3>

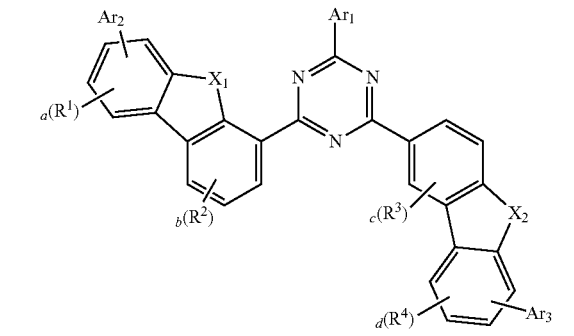

<Formula 4>

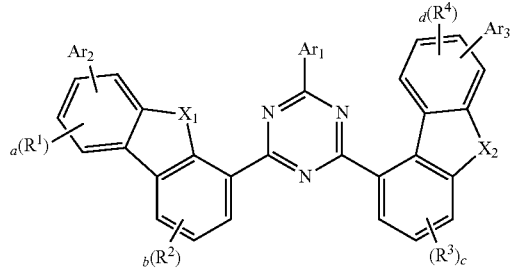

<Formula 5>

<Formula 6>

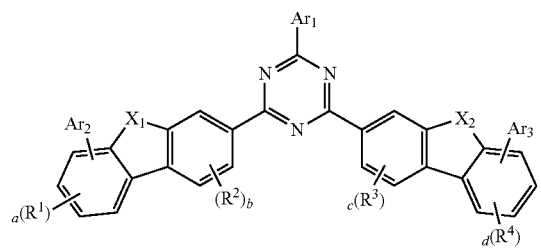

<Formula 7>

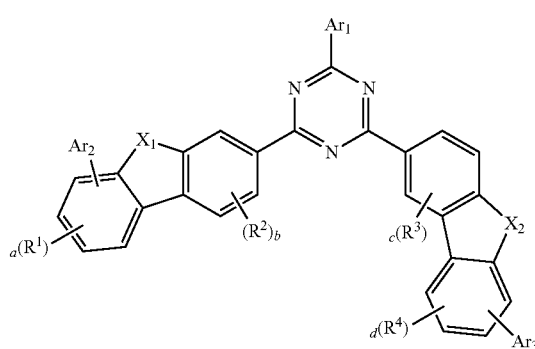

<Formula 8>

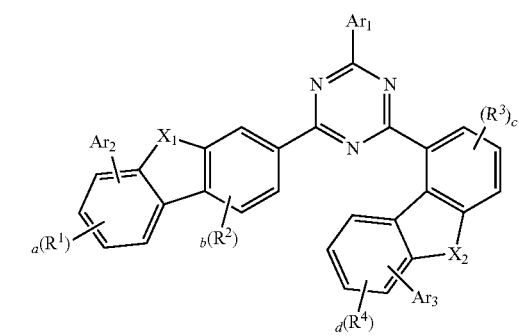

<Formula 9>

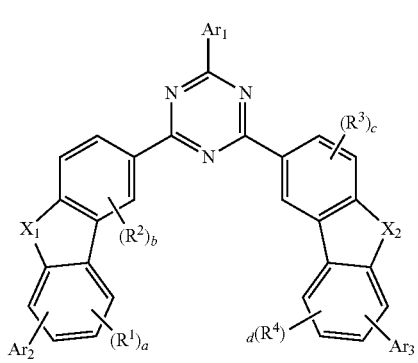

<Formula 10>

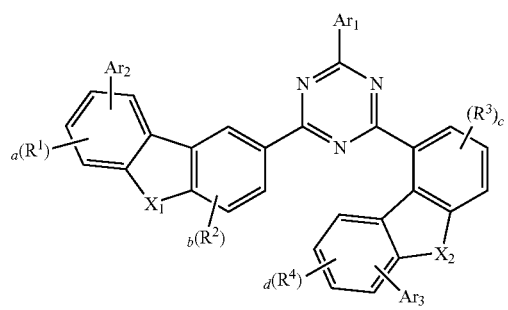

<Formula 11>

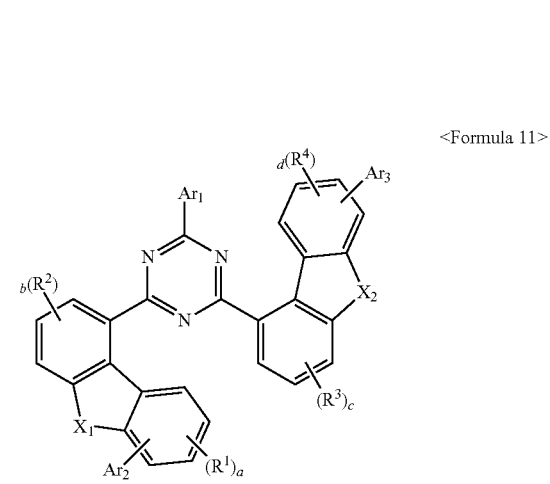

In Formulas 2 to 11, each symbol is as defined for Formula 1. For example, $X_1$, $X_2$, $Ar_1$ to $Ar_3$, $R^1$ to $R^4$, a, b, c and d are the same as defined for Formula 1.

Preferably, in Formulas 1 to 11, at least one of $Ar_1$ to $Ar_3$ may be a substituted or unsubstituted $C_6$-$C_{24}$ aryl group, more preferably, $Ar_1$ to $Ar_3$ may be all a substituted or unsubstituted $C_6$-$C_{12}$ aryl group, and $Ar_2$ and $Ar_3$ may be different from each other.

Specifically, the compound represented by formula 1 may be one of the following compounds, but it is not limited thereto.

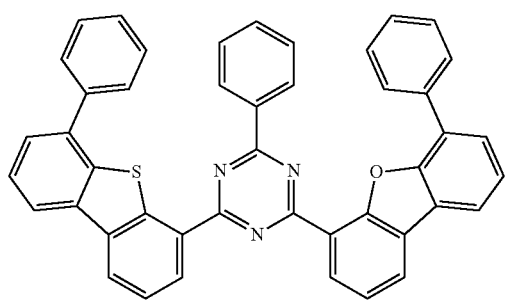

1-1

-continued
1-2
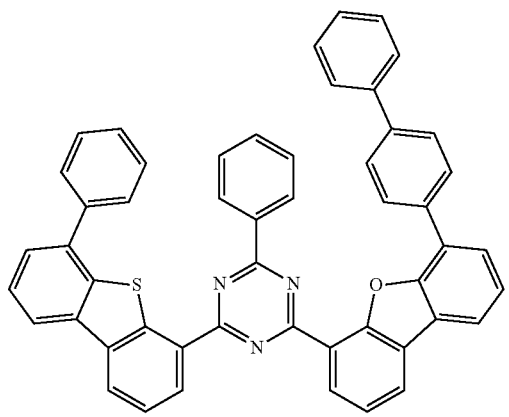
1-3
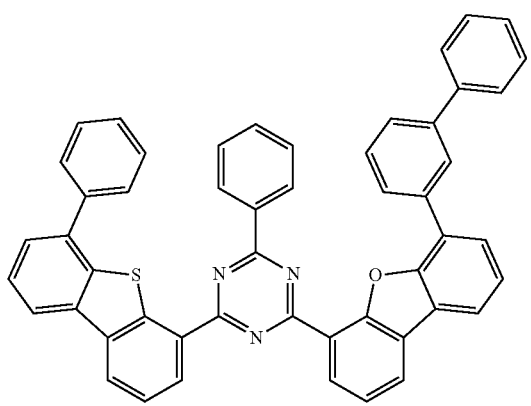
1-4
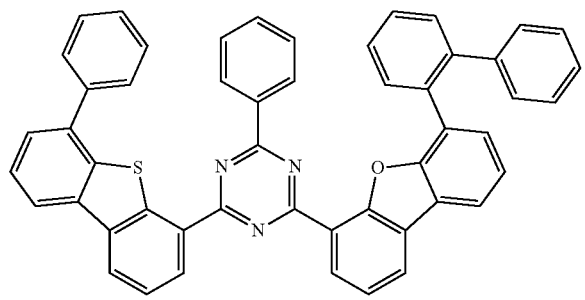
1-5
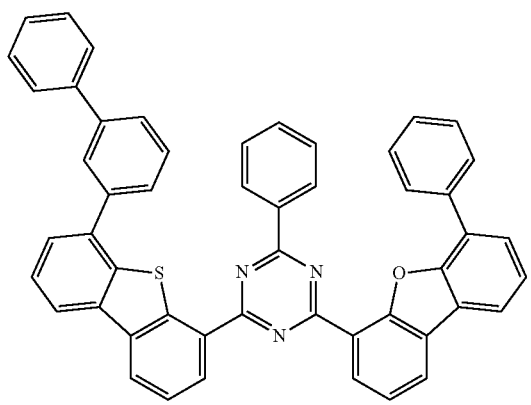
-continued
1-6
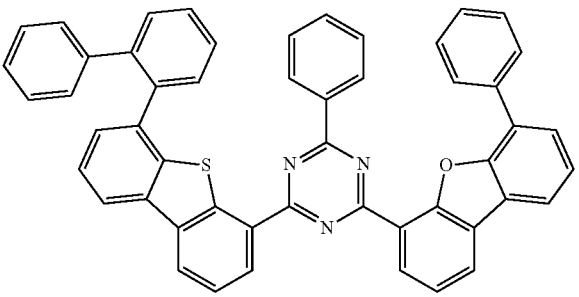
1-7
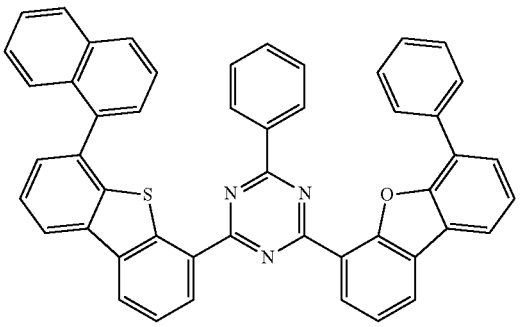
1-8
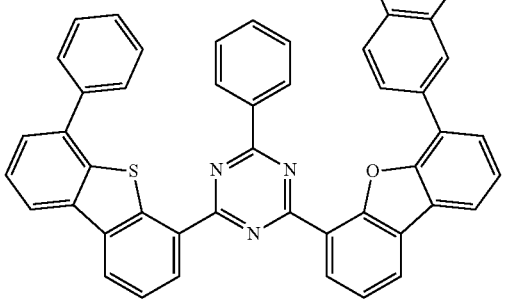
1-9
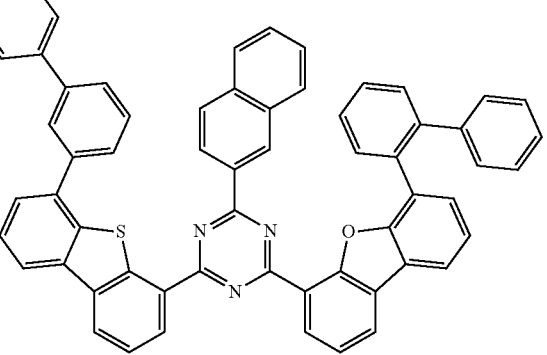

-continued
1-10
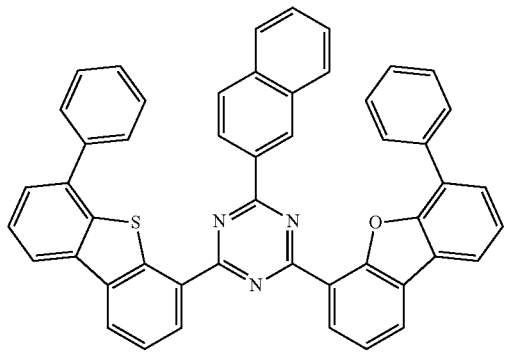
1-11
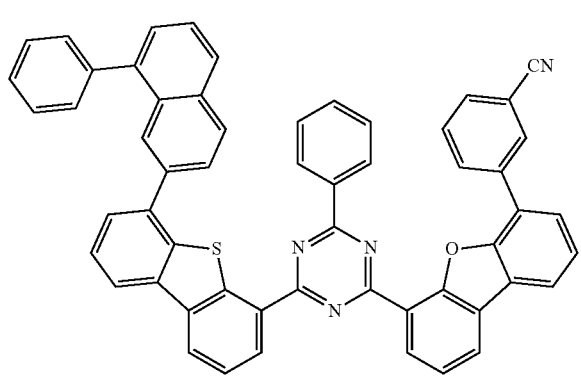
1-12
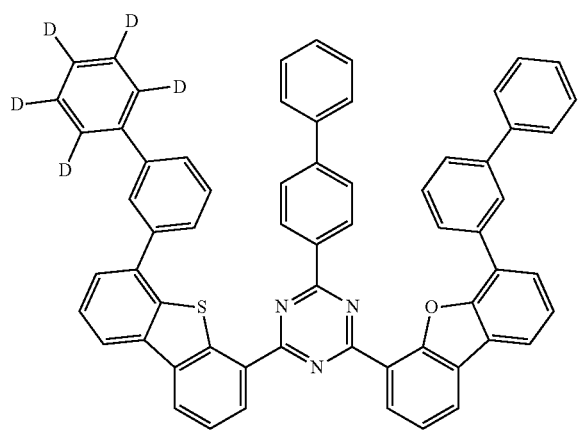
1-13
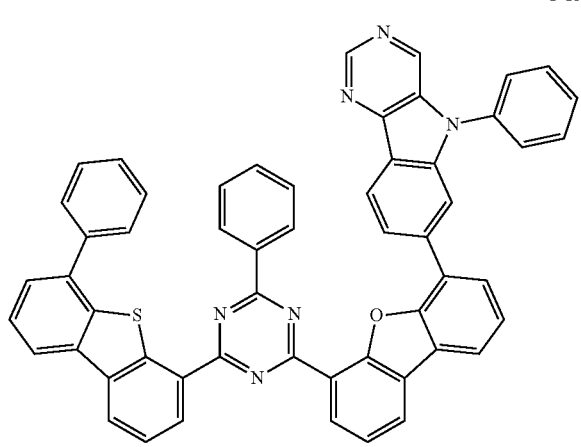
-continued
1-14
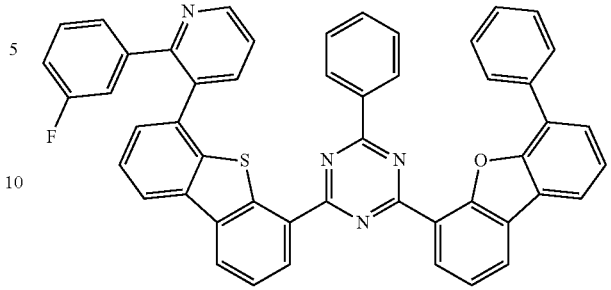
1-15
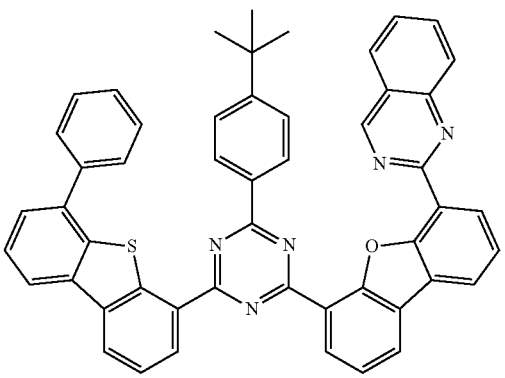
1-16
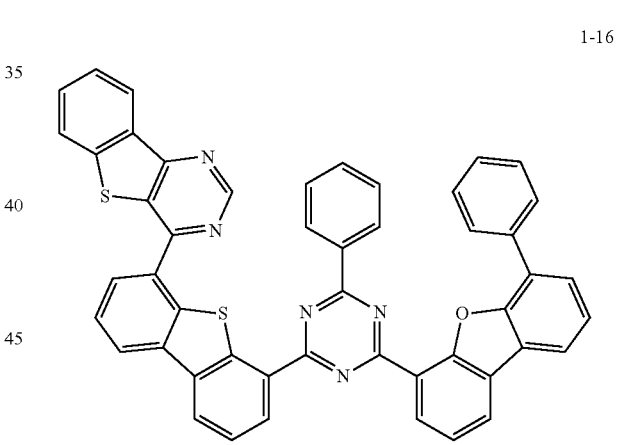
1-17
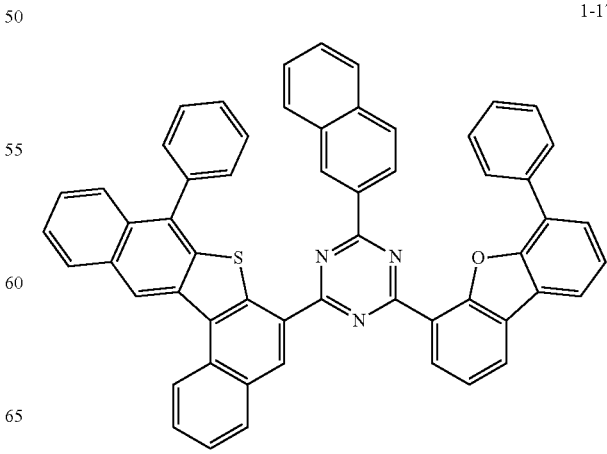

-continued
1-18
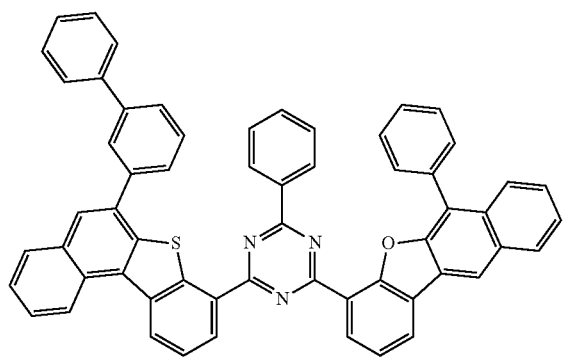
1-19
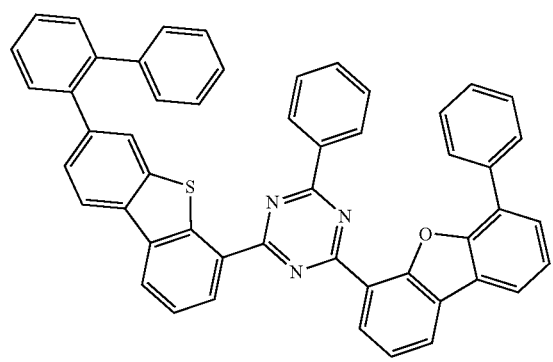
1-20
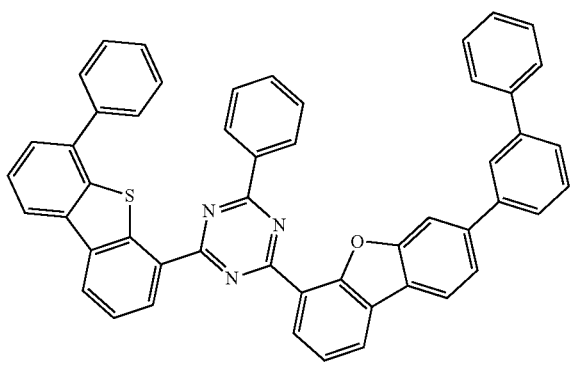
1-21
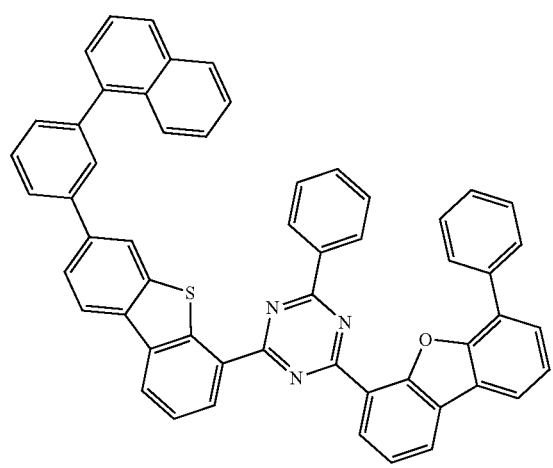
-continued
1-22
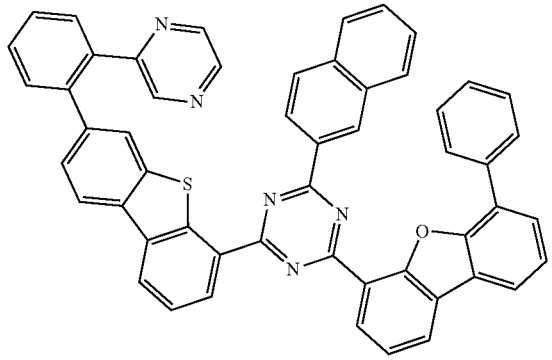
1-23
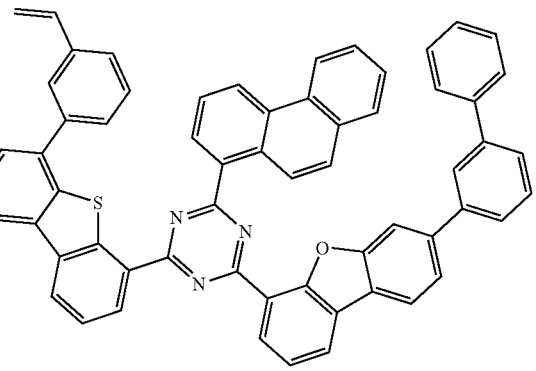
1-24
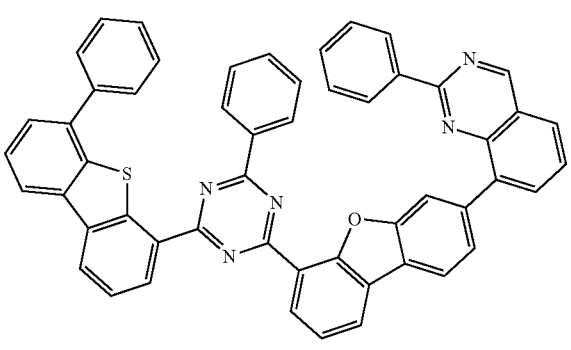
1-25
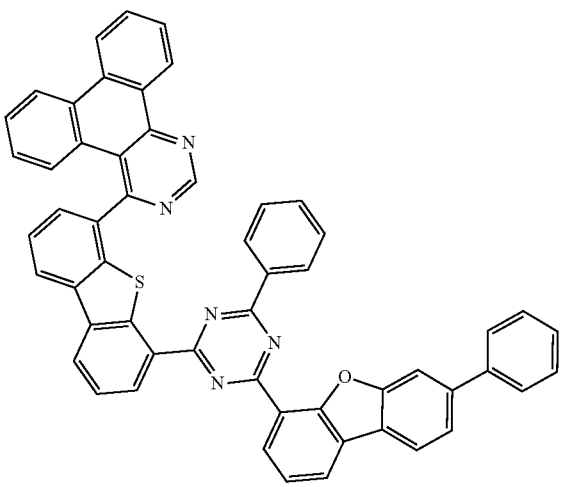

1-26
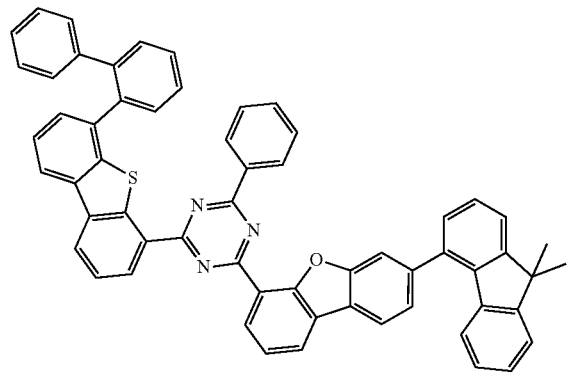
1-27
1-28
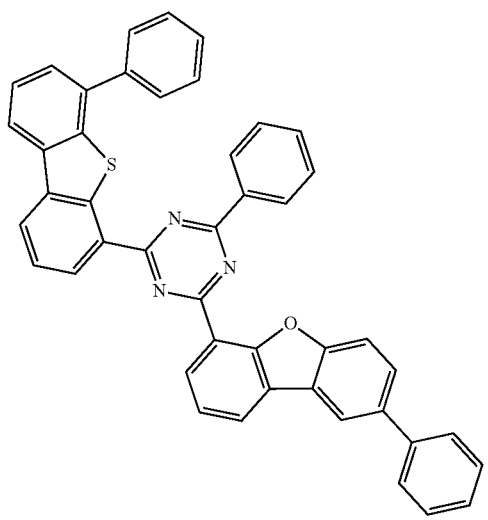
1-29
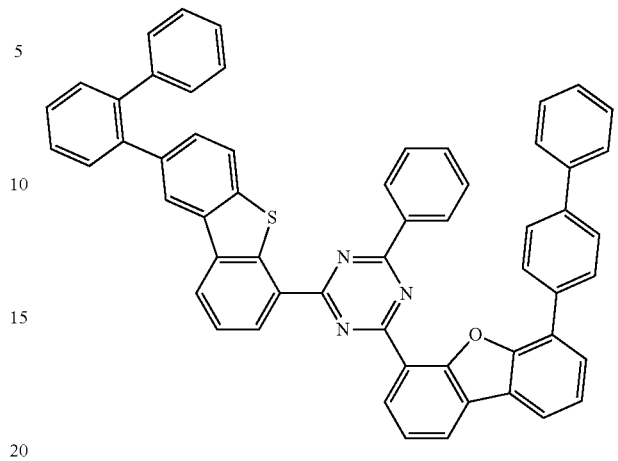
1-30
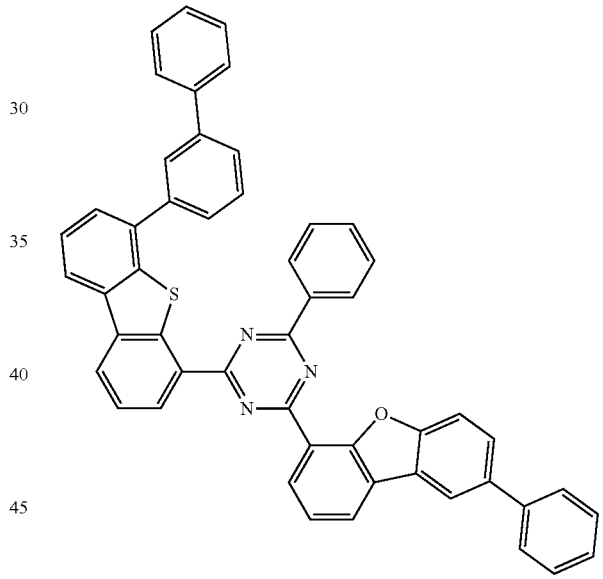
1-31
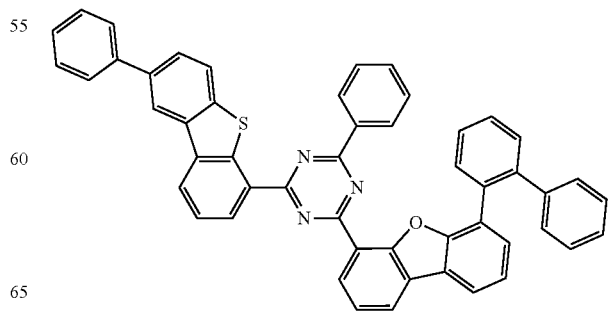

1-32
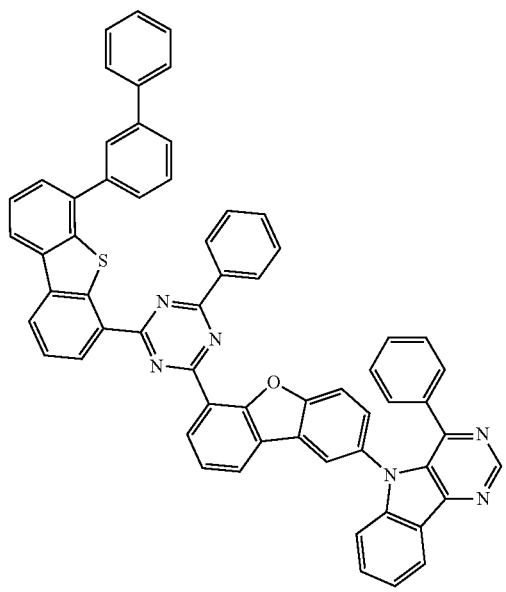
1-33
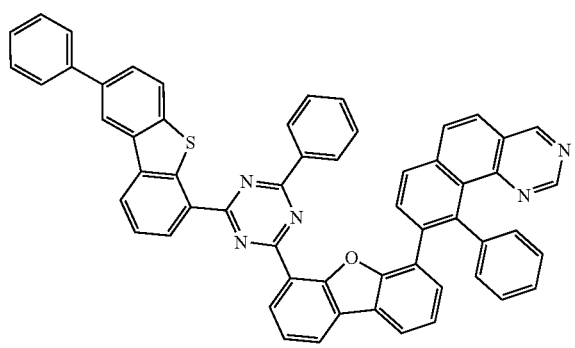
1-34
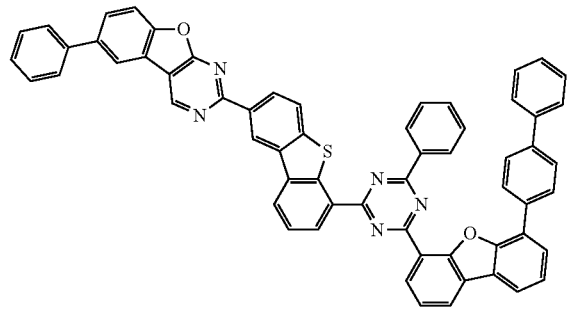
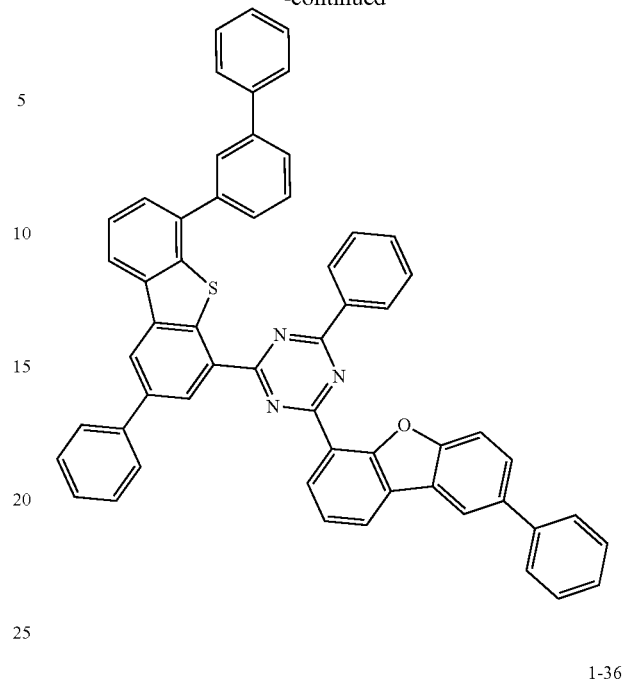
1-36
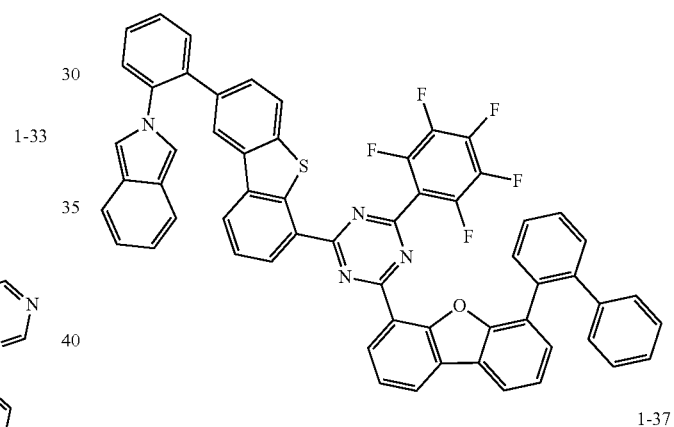
1-37
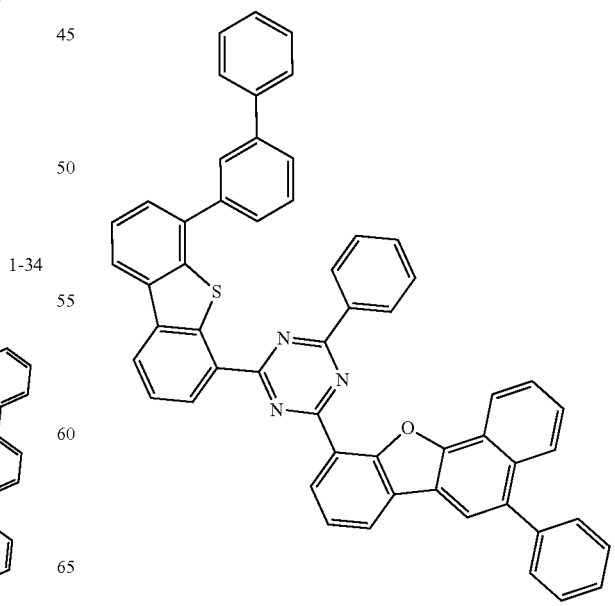

1-38
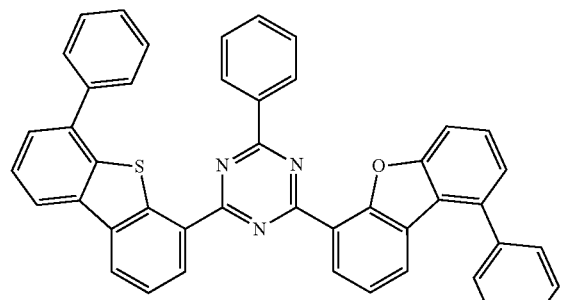
1-39
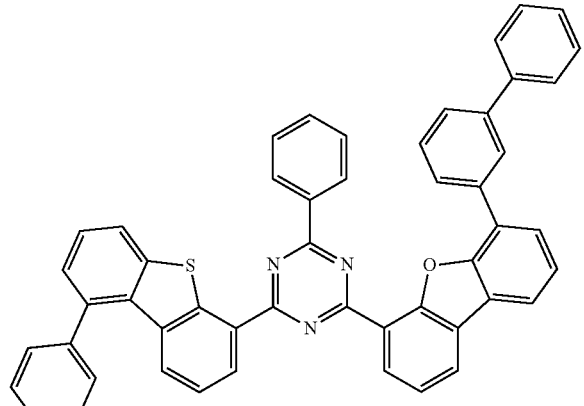
1-40
1-41
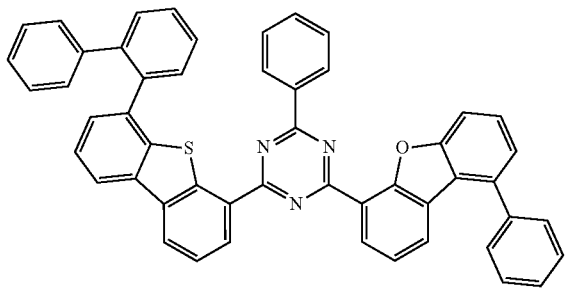
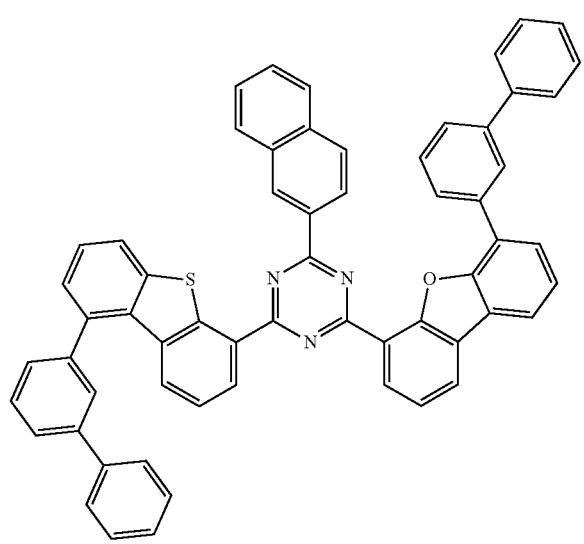
1-42
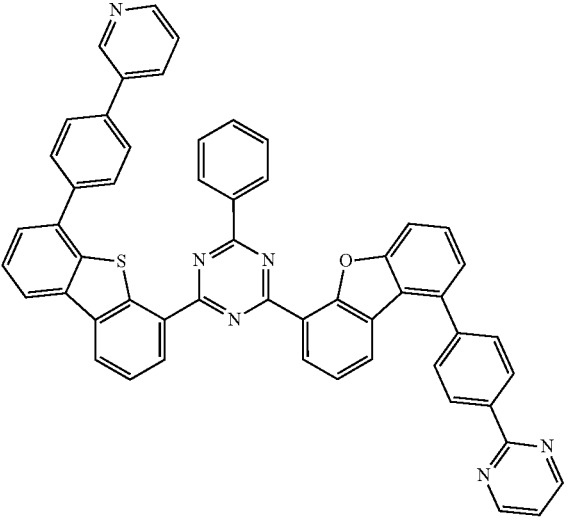
1-43
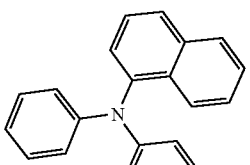
1-44

1-45
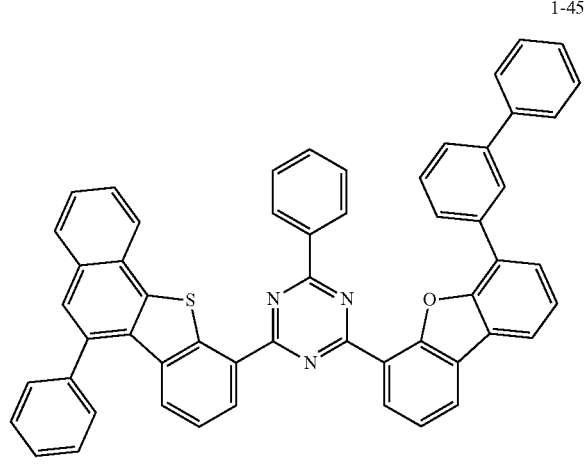
1-46
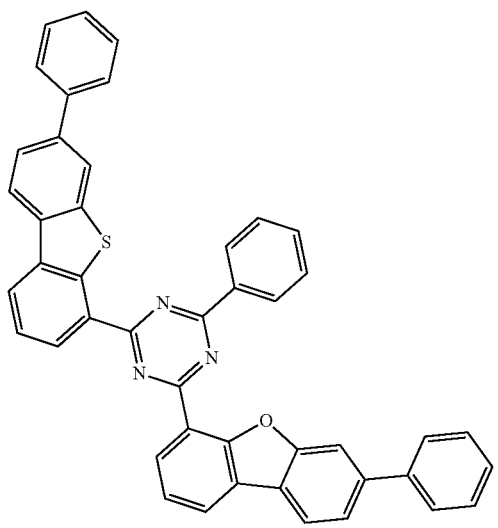
1-47
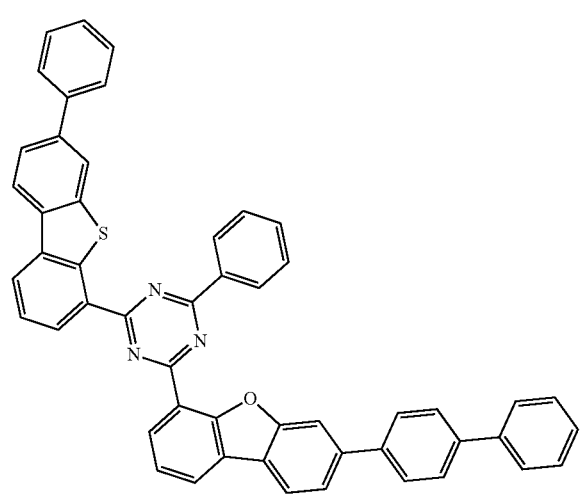
1-48
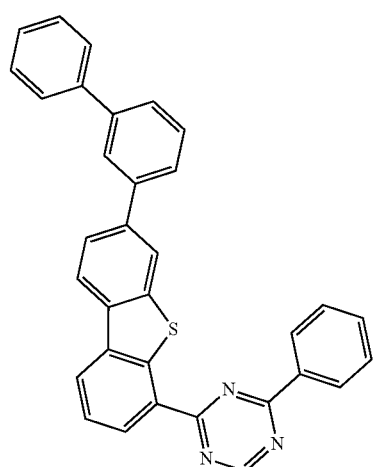
1-49
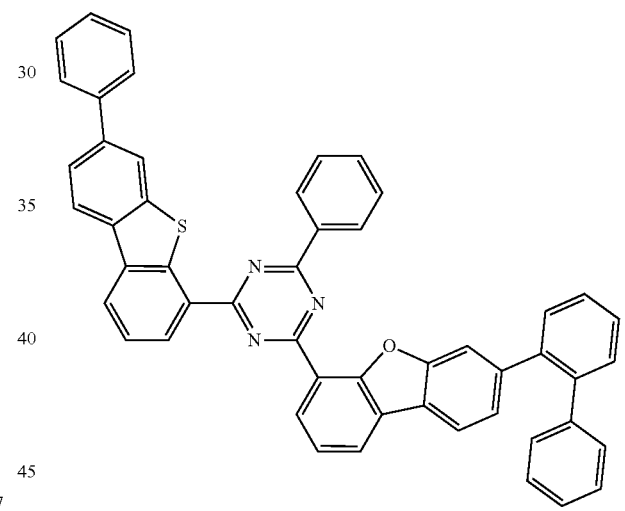
1-50
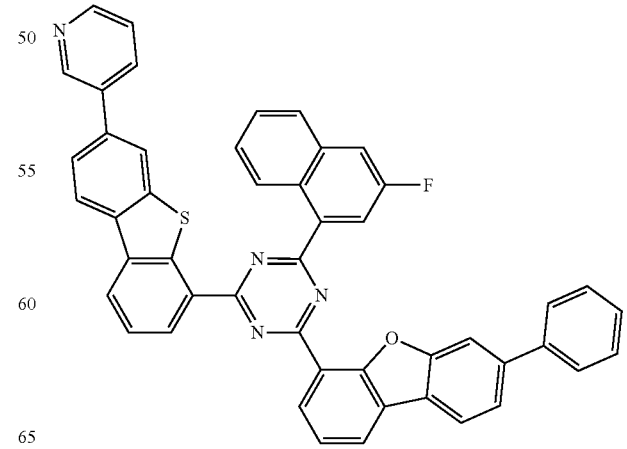

1-51
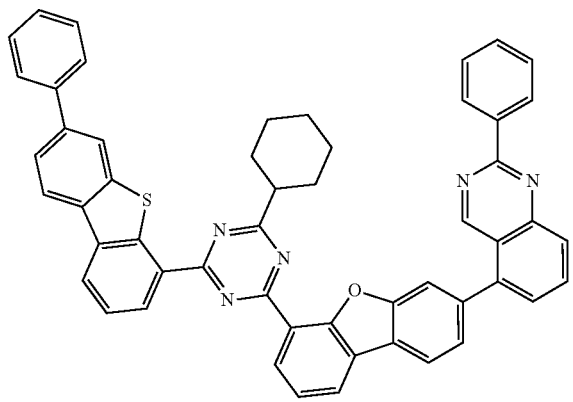
1-52
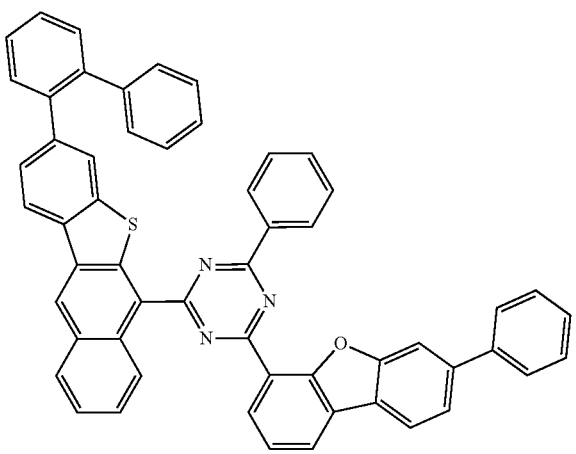
1-53
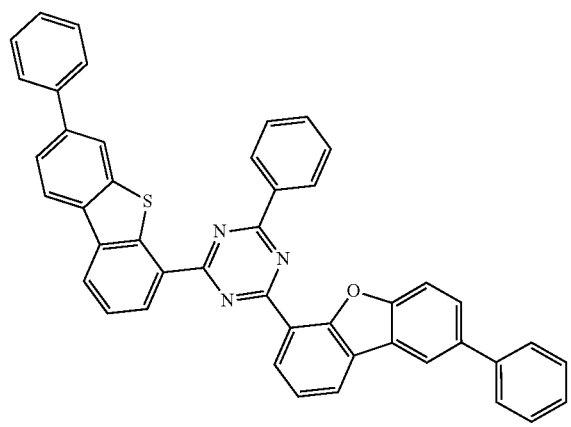
1-54
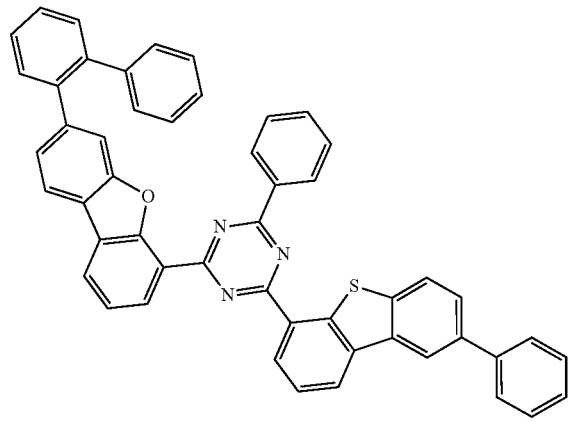
1-55
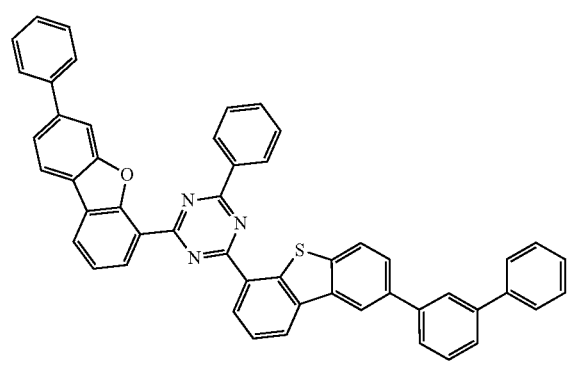
1-56
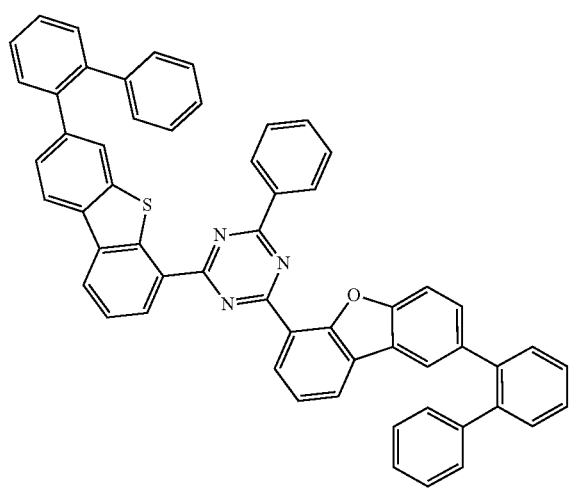

1-57
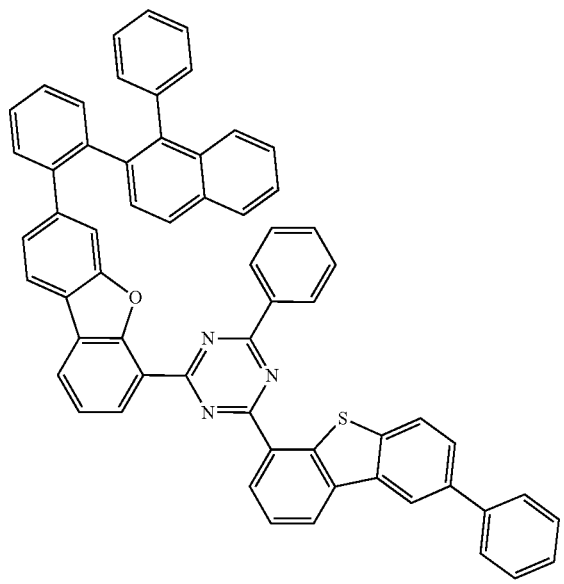
1-60
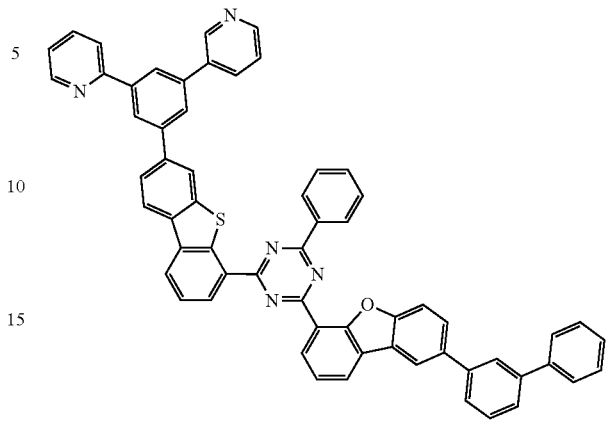
1-58
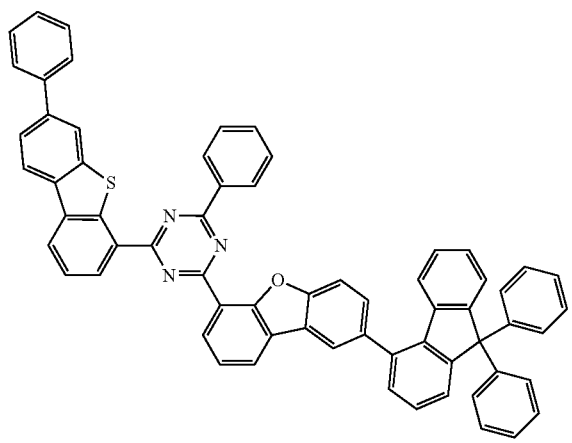
1-61
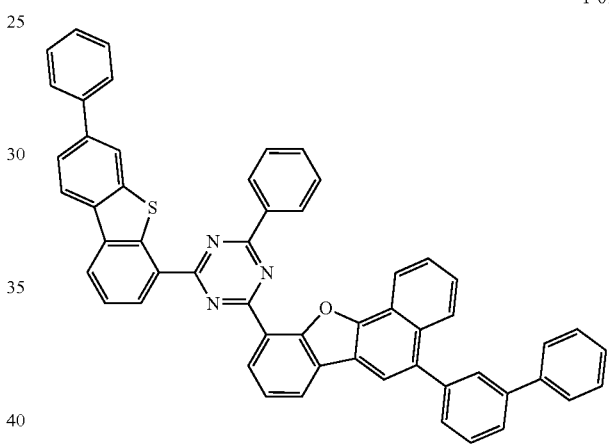
1-59
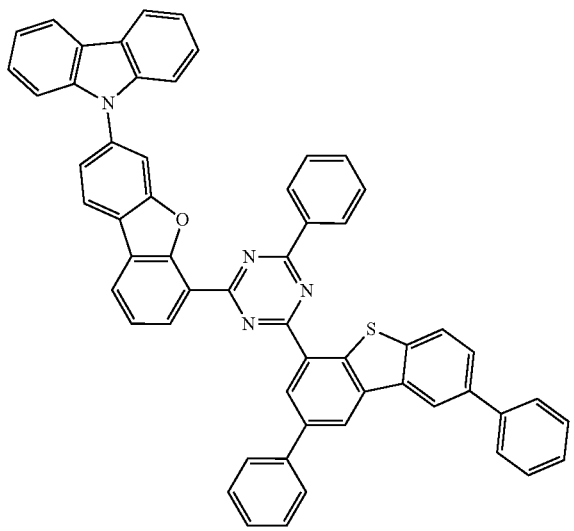
1-62
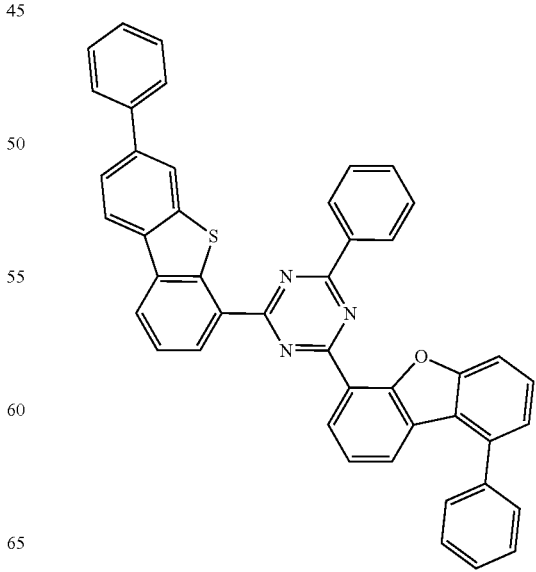

1-63
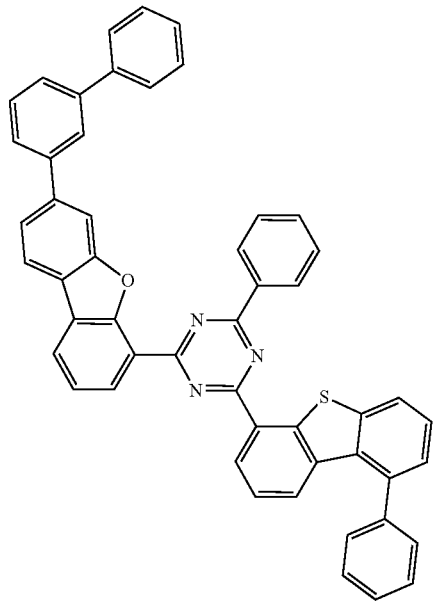
1-64
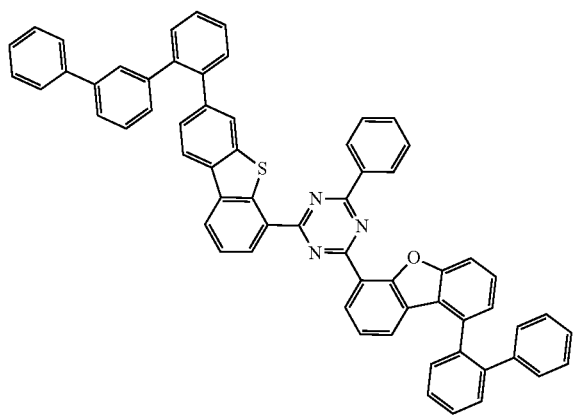
1-65
1-66
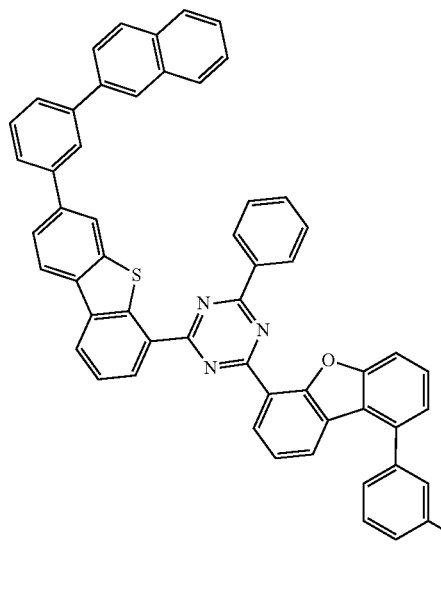
1-67
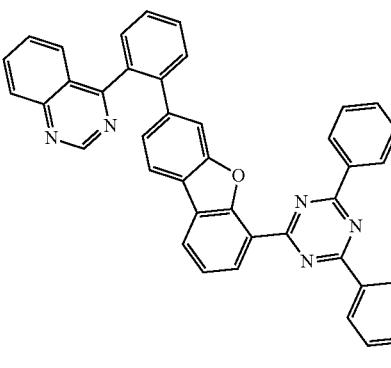
1-68
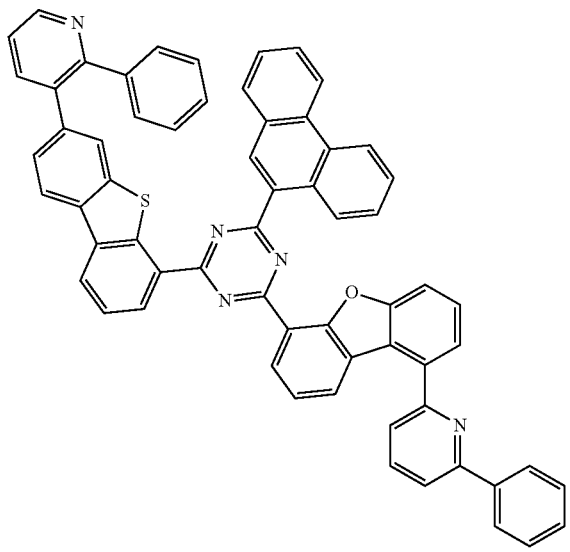

1-69
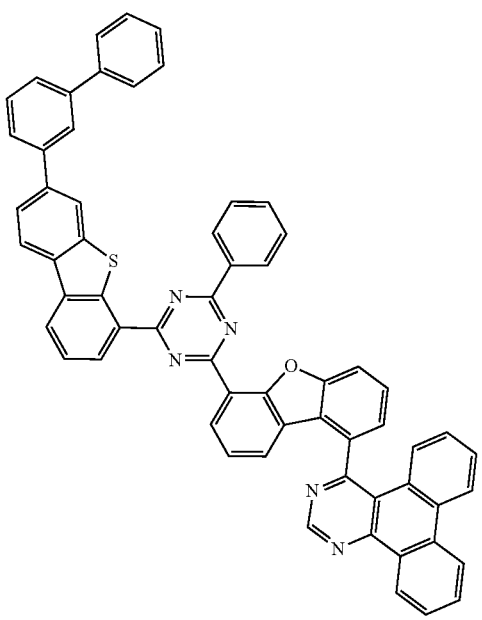
1-70
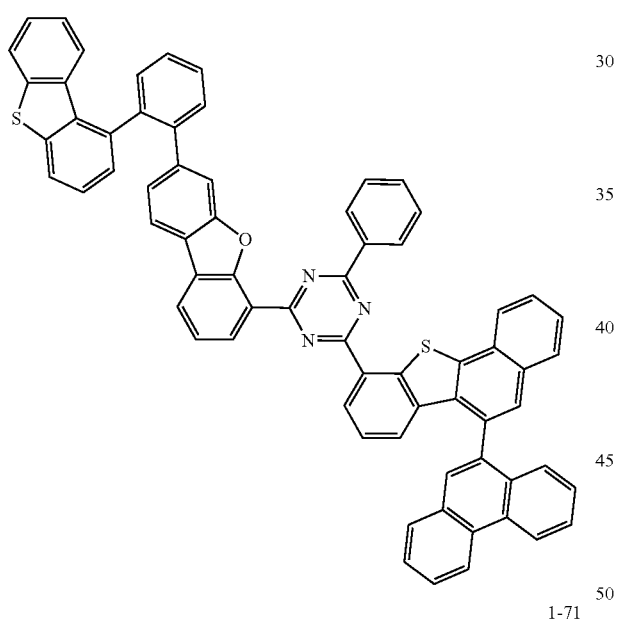
1-71
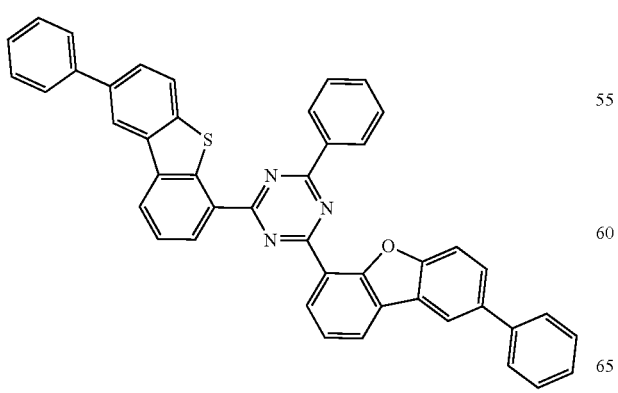
1-72
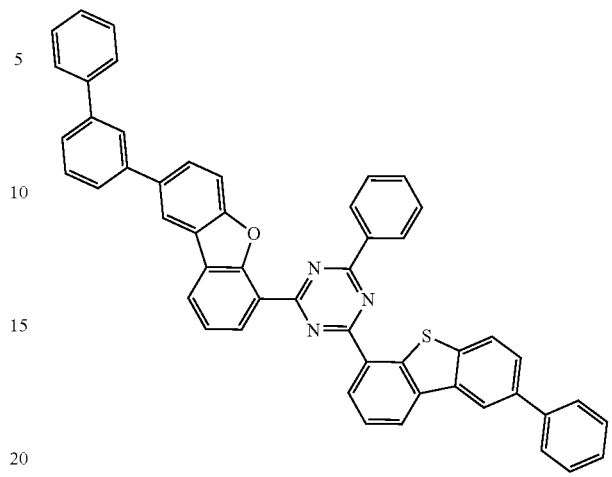
1-73

1-74
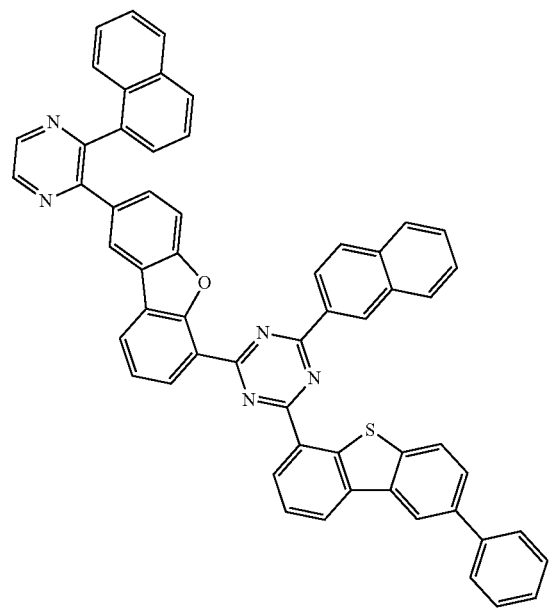
1-77
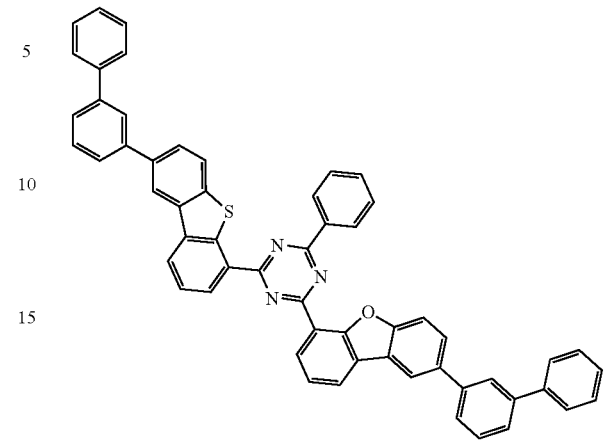
1-75
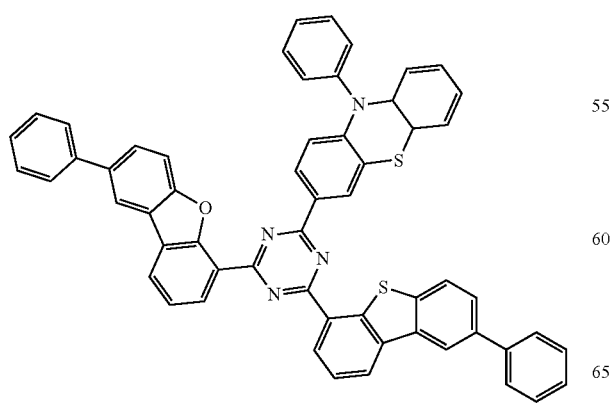
1-78
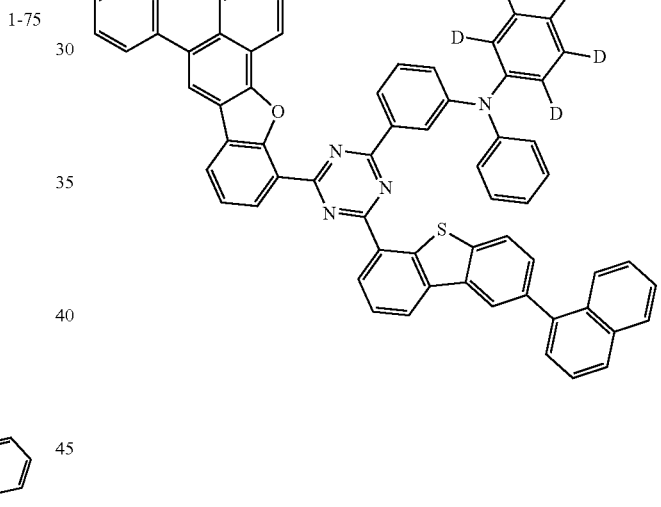
1-76
1-79

1-80
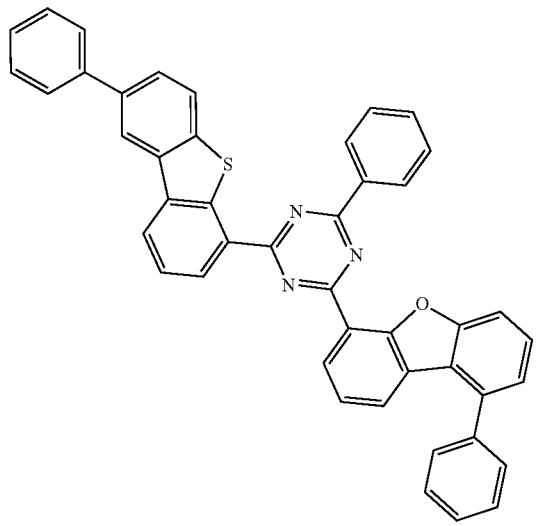
1-81
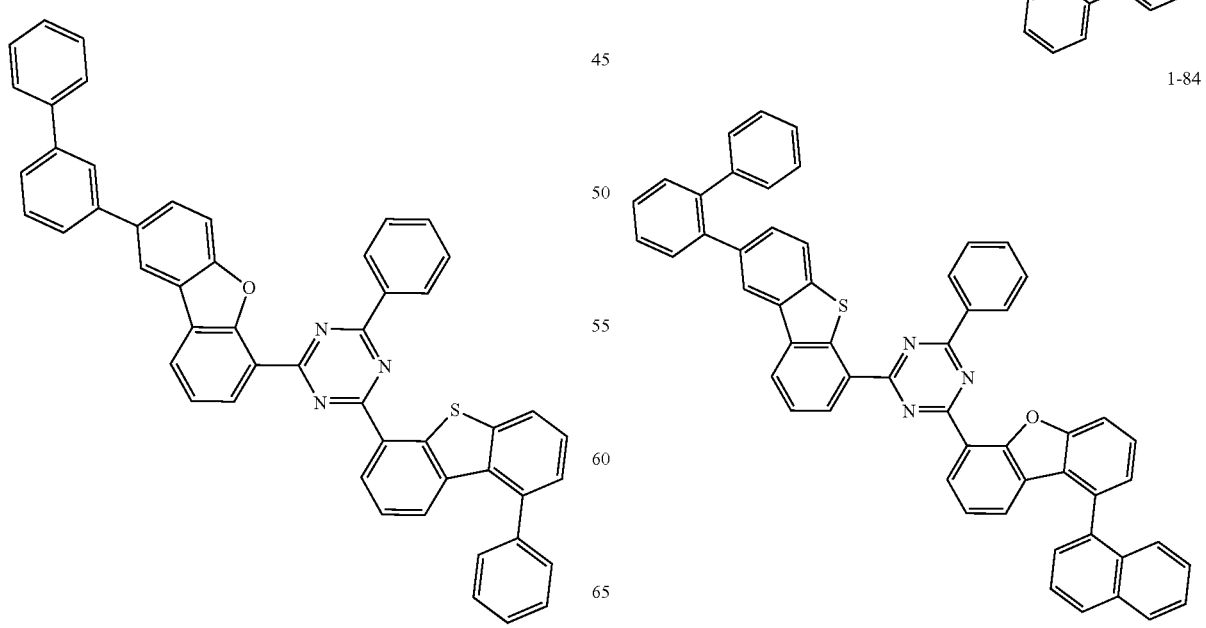
1-82
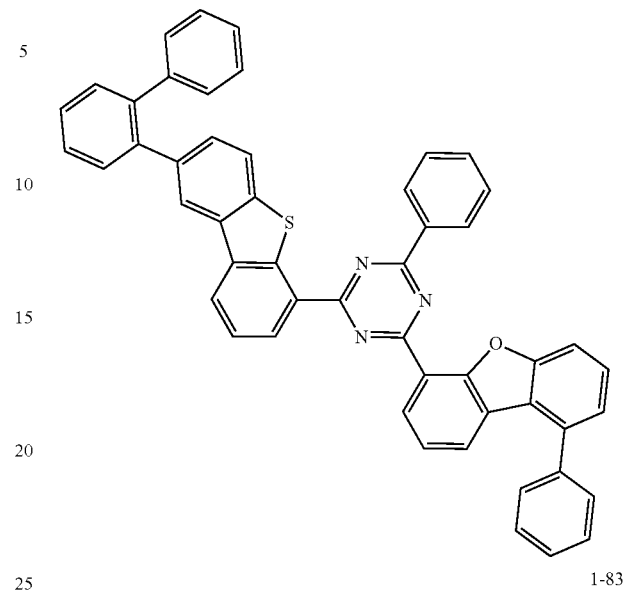
1-83
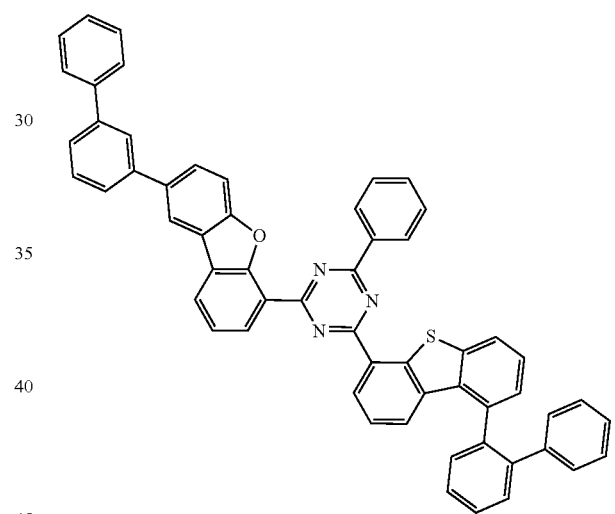
1-84

1-85
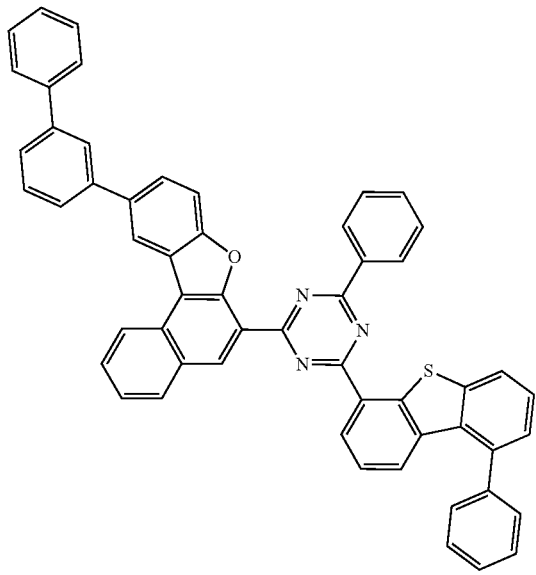
1-86
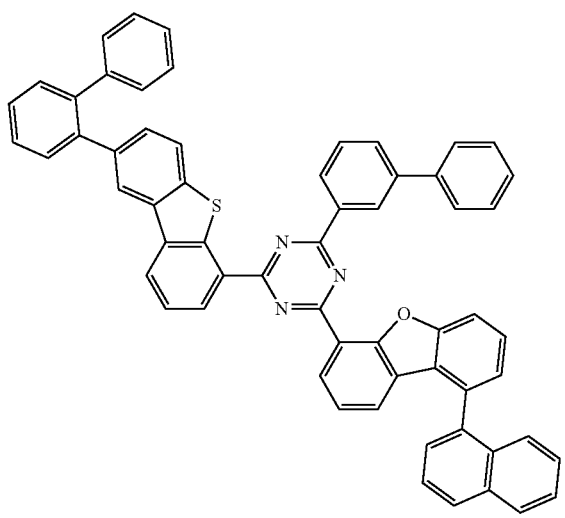
1-87
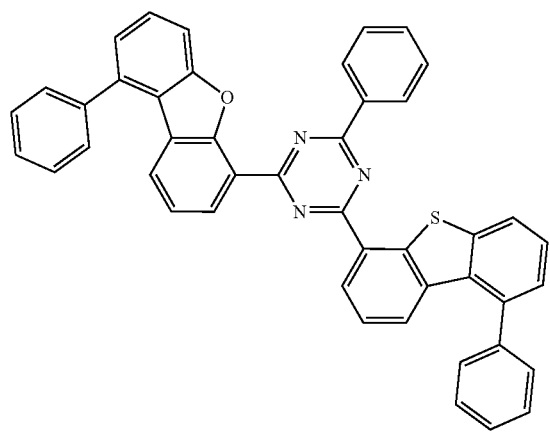
1-88
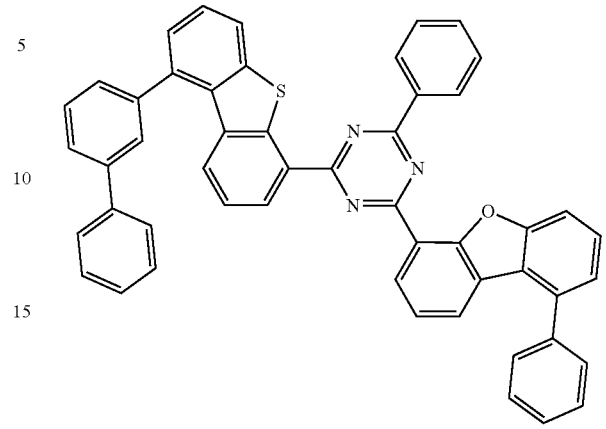
1-89
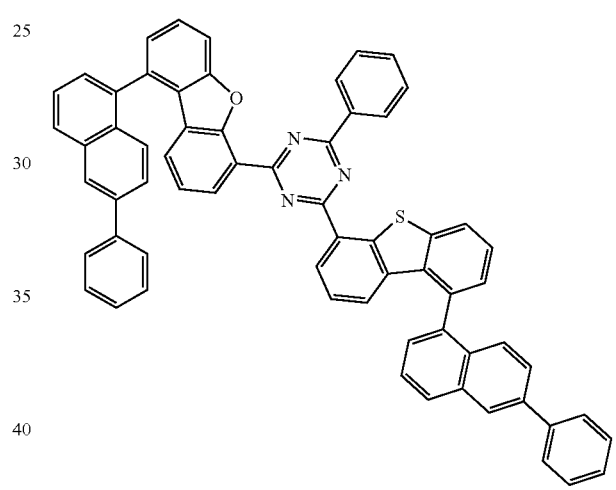
1-90
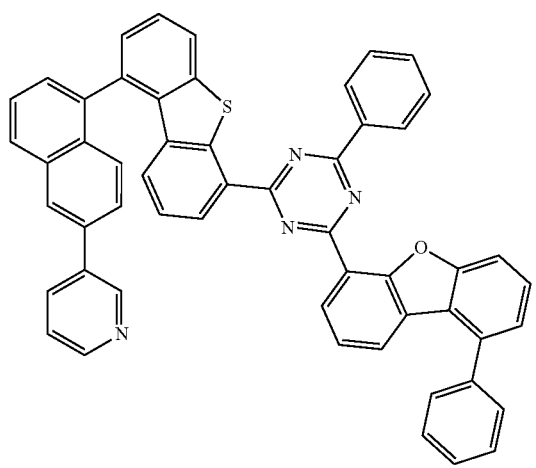

1-91
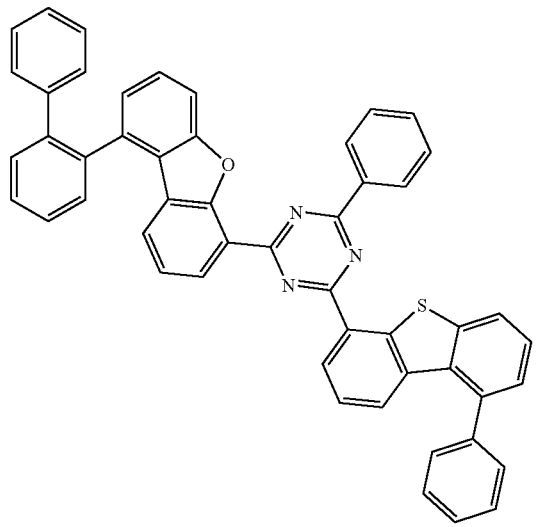
1-94
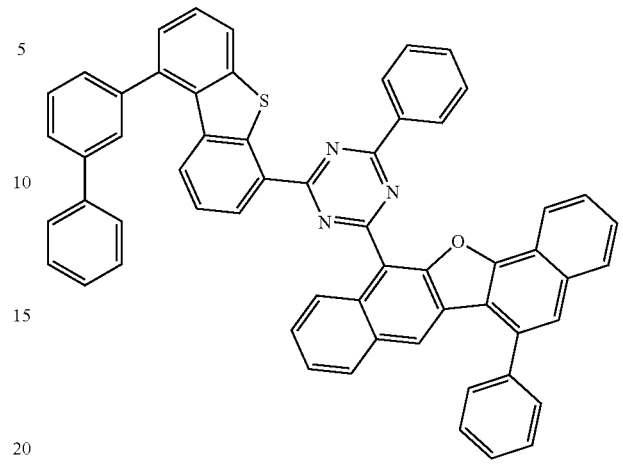
1-92
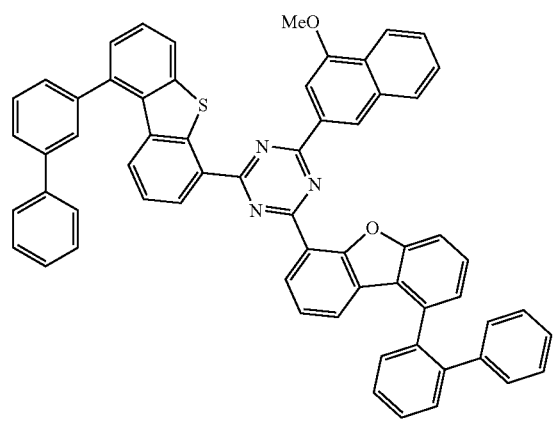
1-95
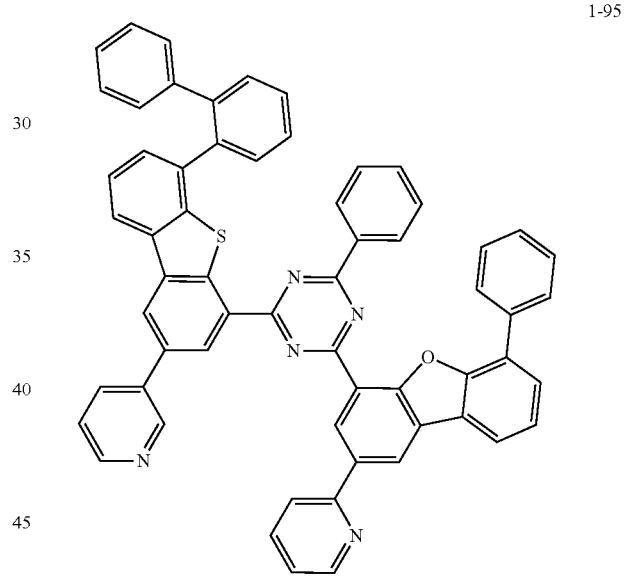
1-93
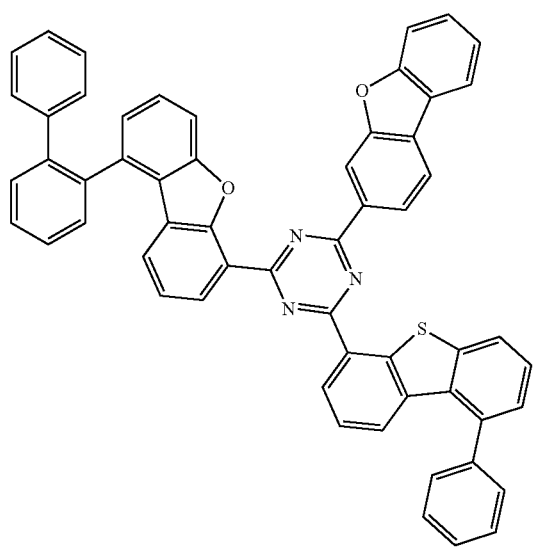
1-96
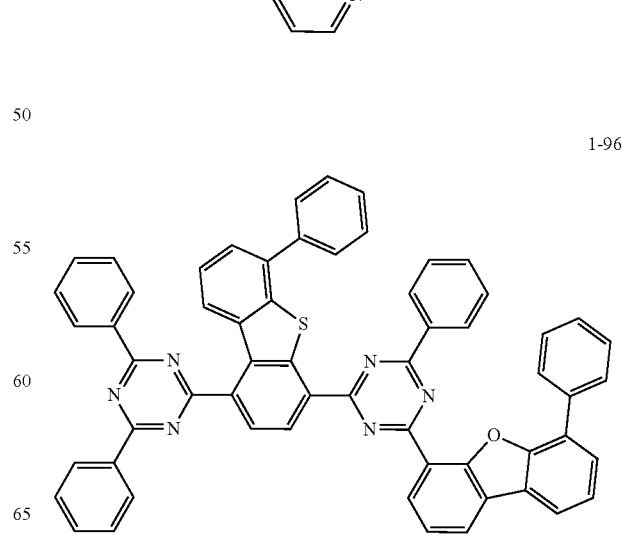

1-97
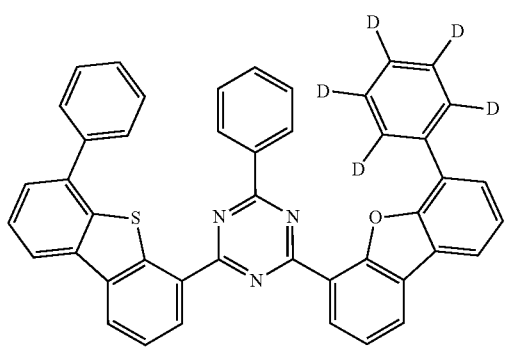
2-1
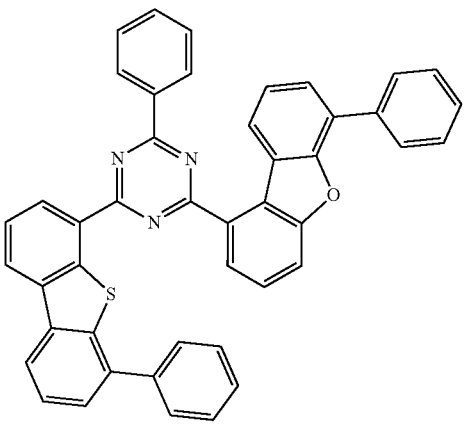
1-98
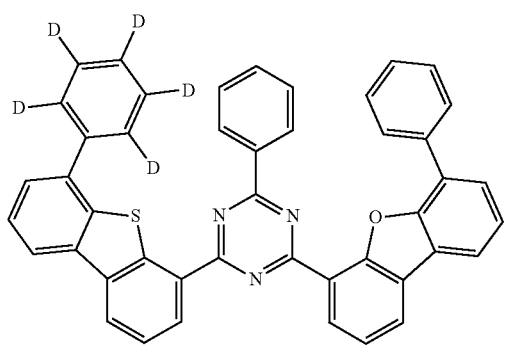
1-99
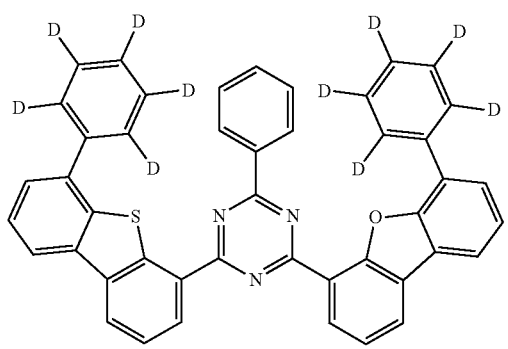
2-2
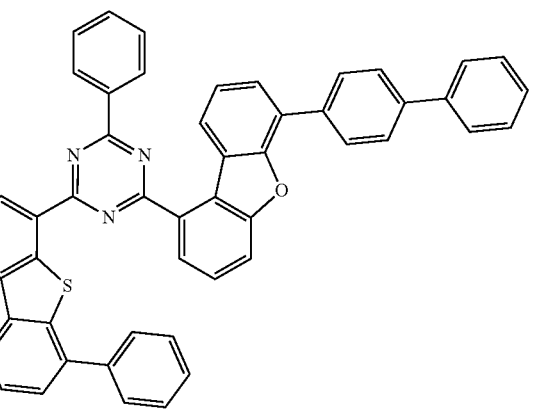
1-100
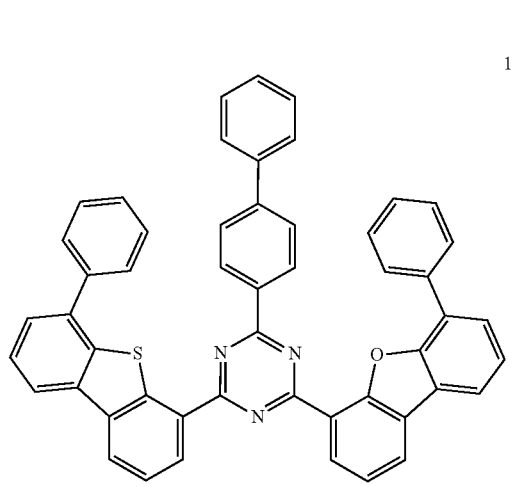
2-3
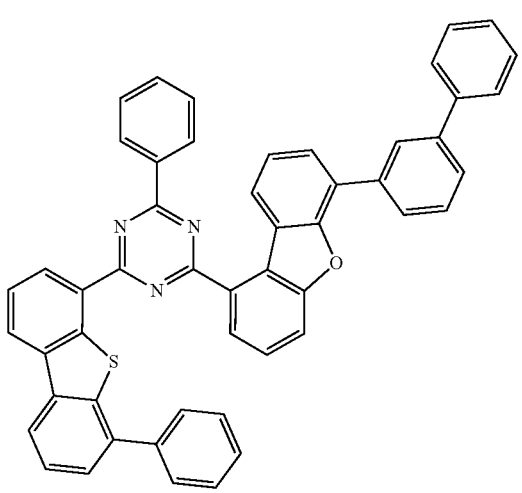

2-4
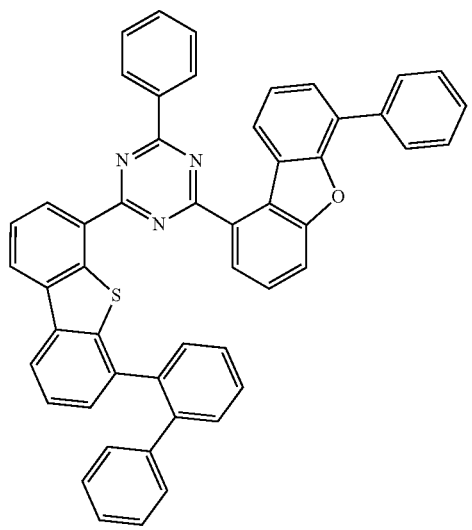
2-5
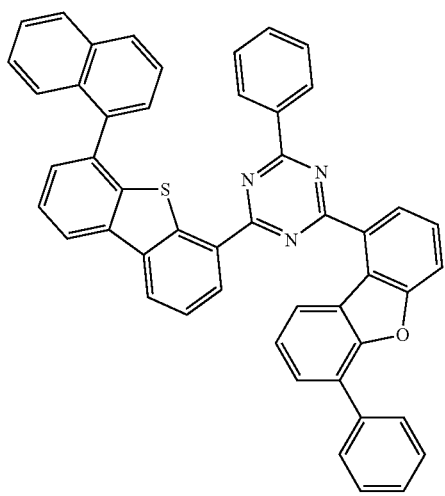
2-6
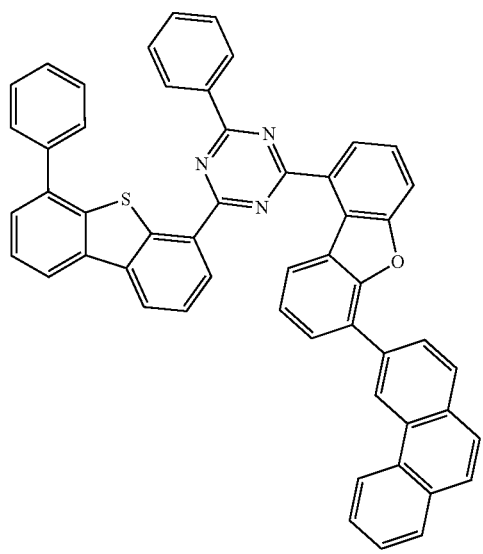
2-7
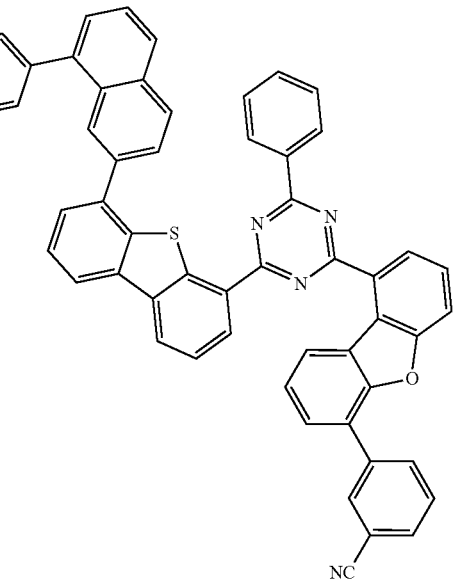
2-8
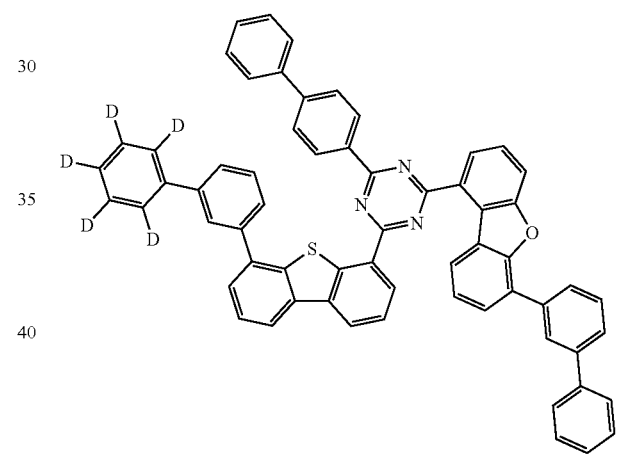
2-9
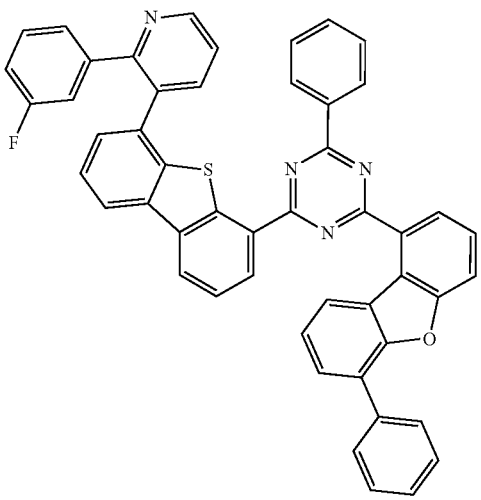

2-10
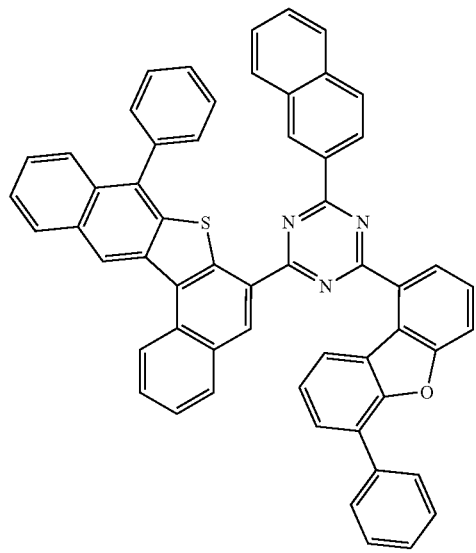
2-11
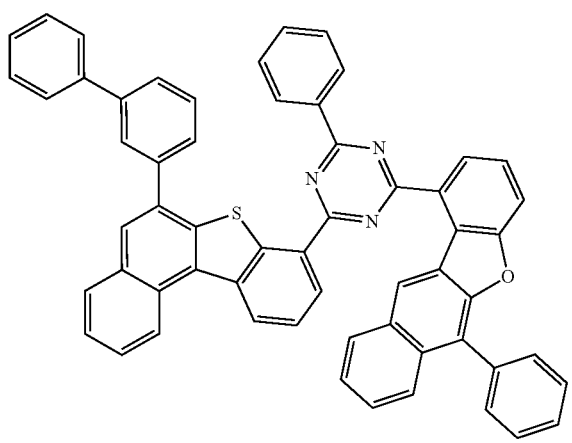
2-12
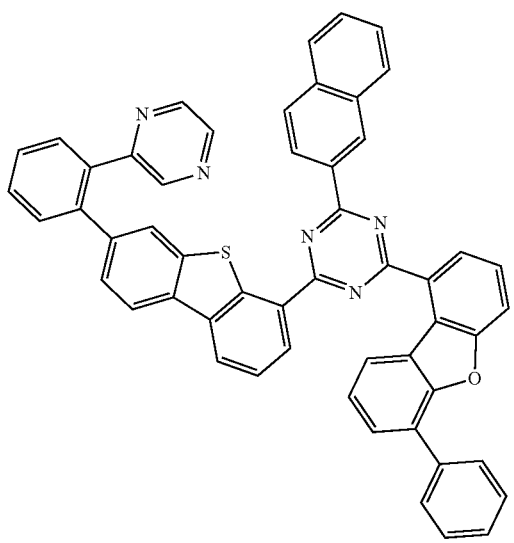
2-13
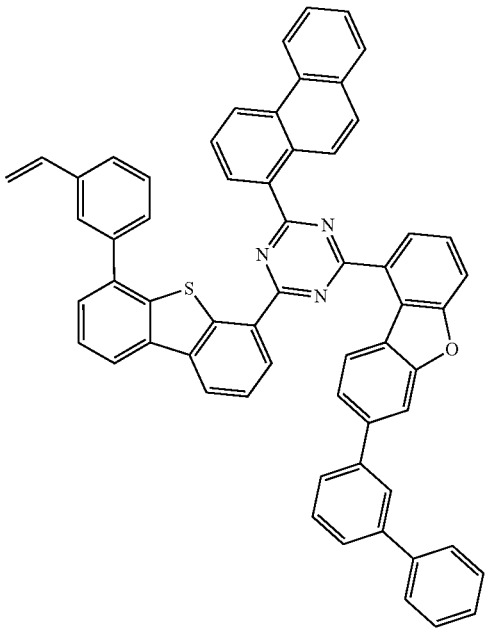
2-14
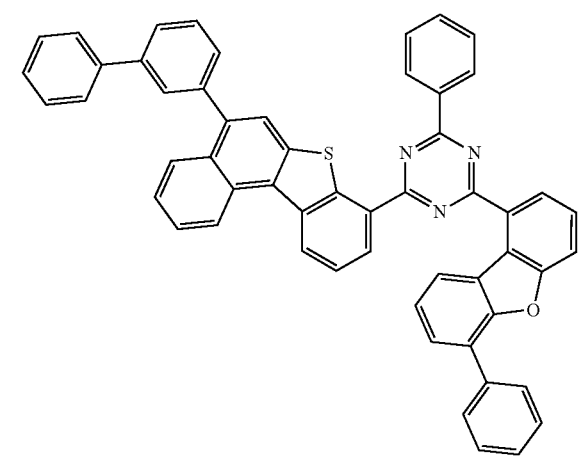
2-15
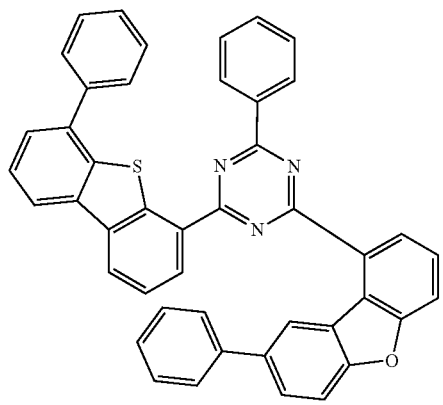

-continued
2-16
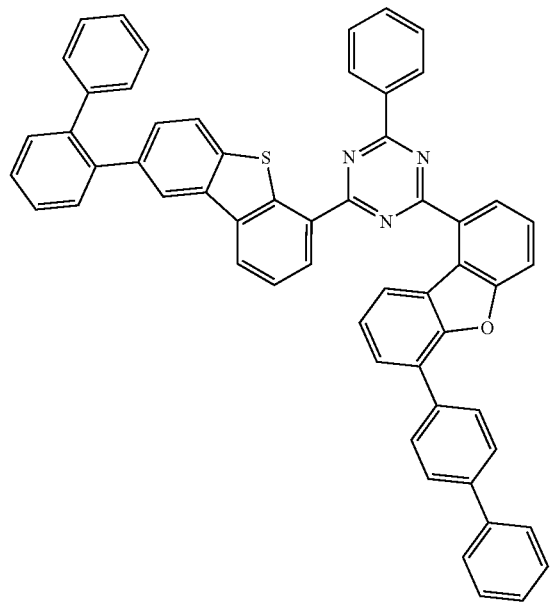
2-17
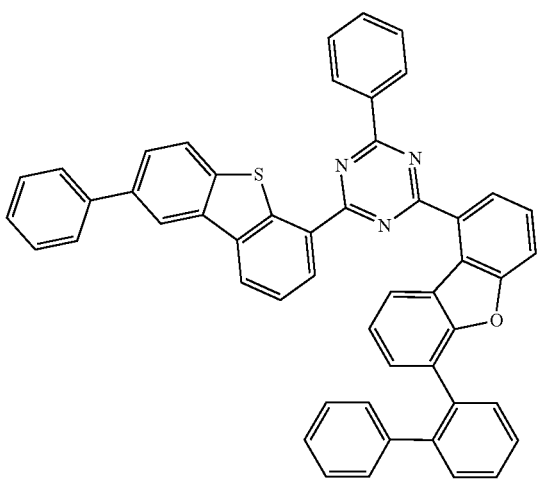
2-18
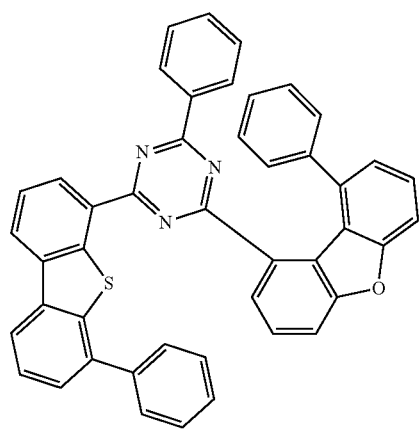
-continued
2-19
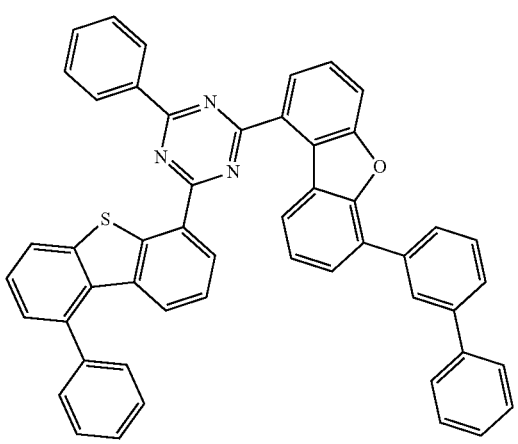
2-20
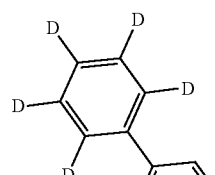
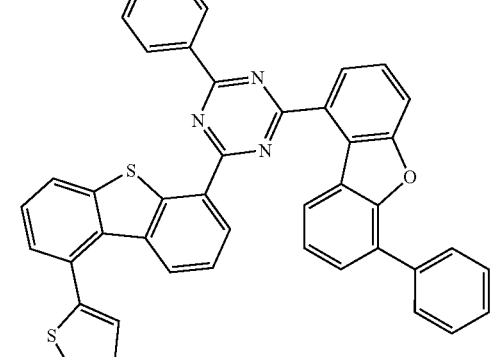
2-21
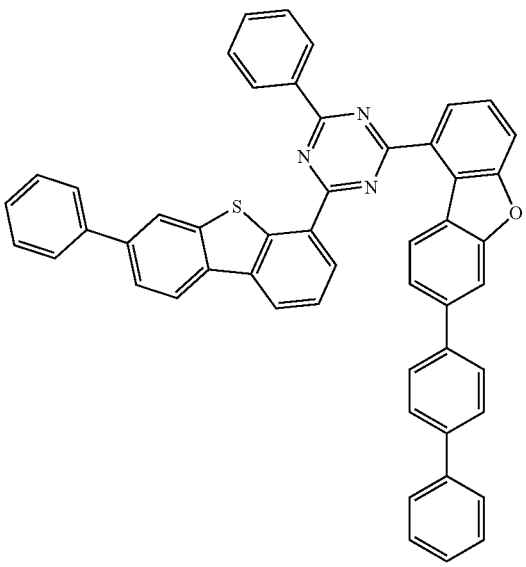

-continued
2-22
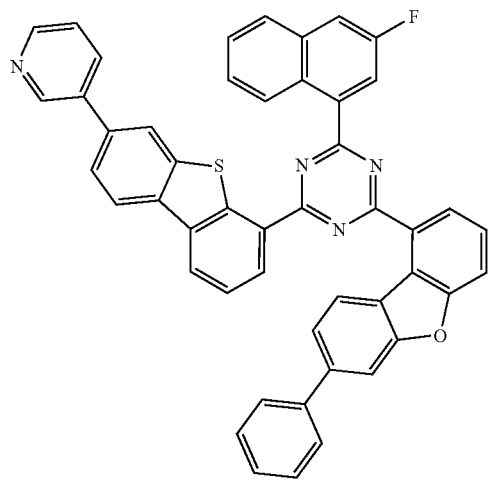
2-23
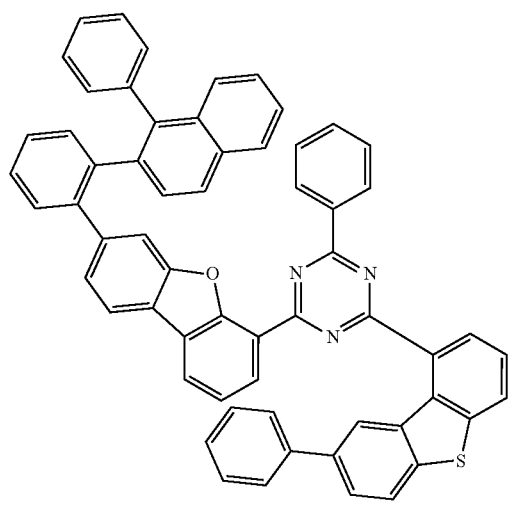
2-24
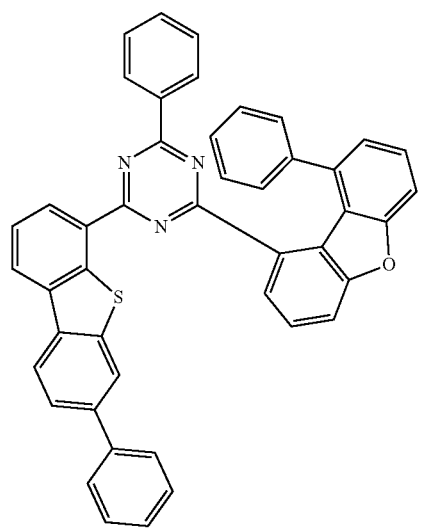
2-25
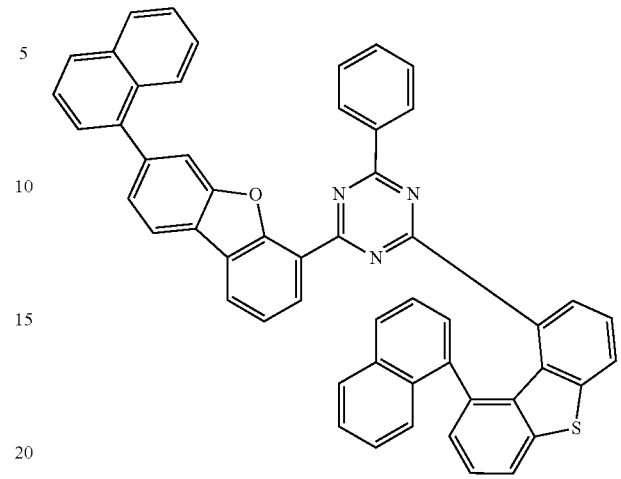
2-26
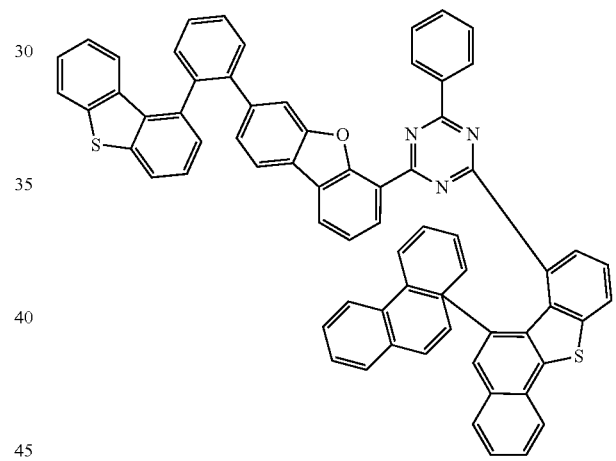
2-27
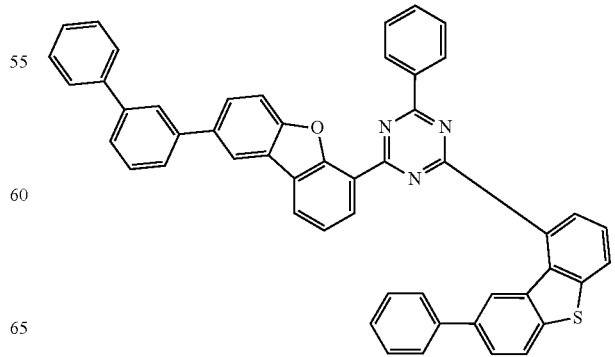

2-28
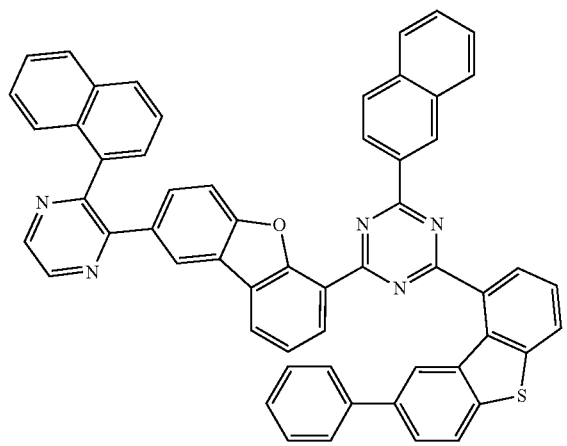
2-31
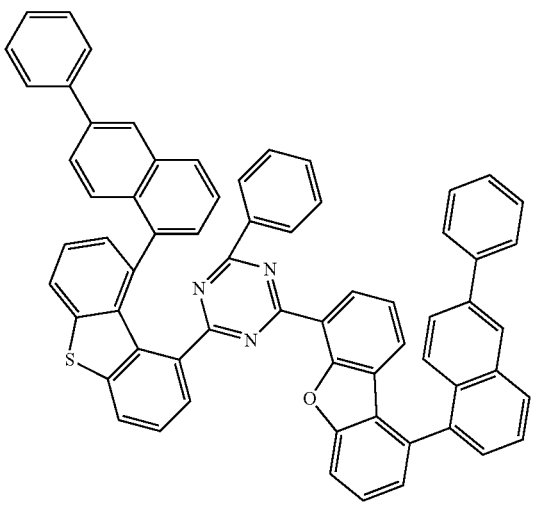
2-29
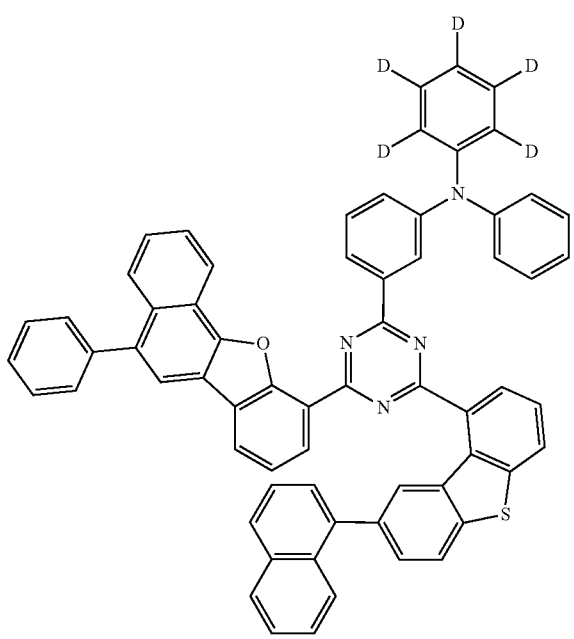
2-32
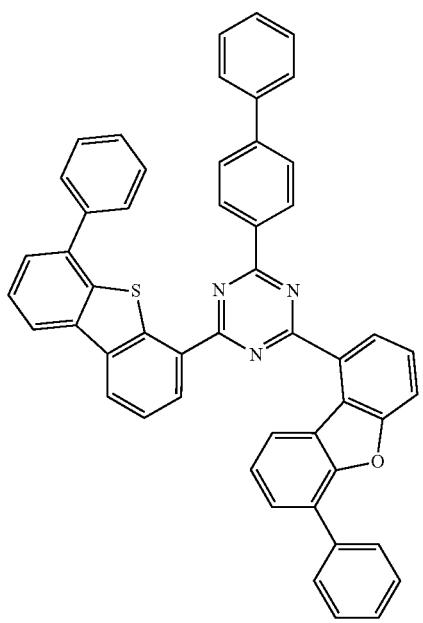
2-30
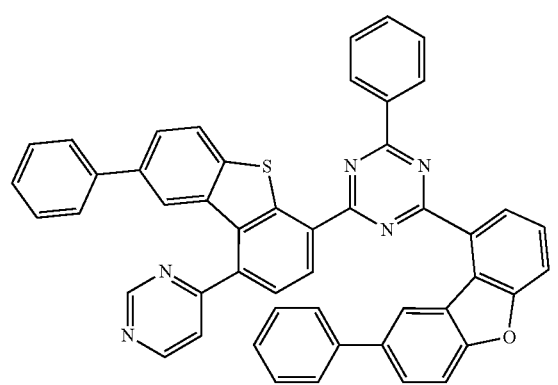
2-33
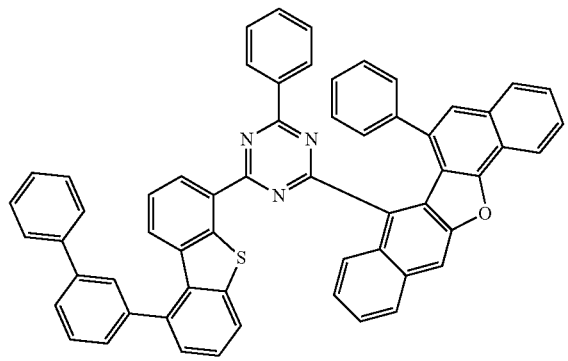

2-34
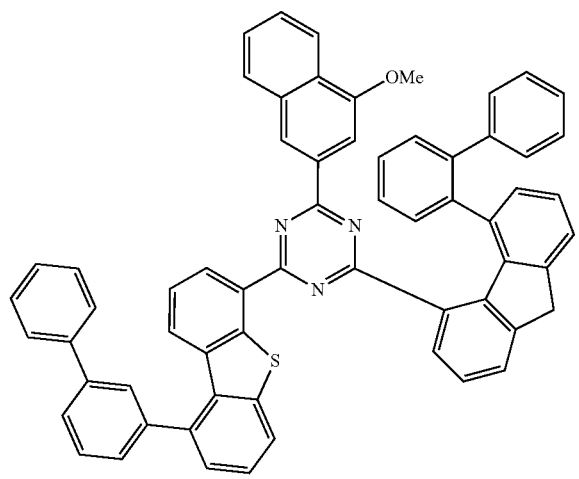
3-1
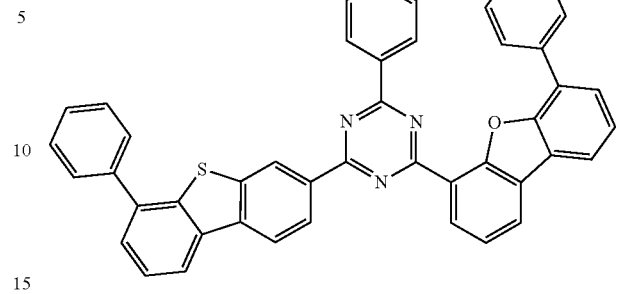
2-35
3-2
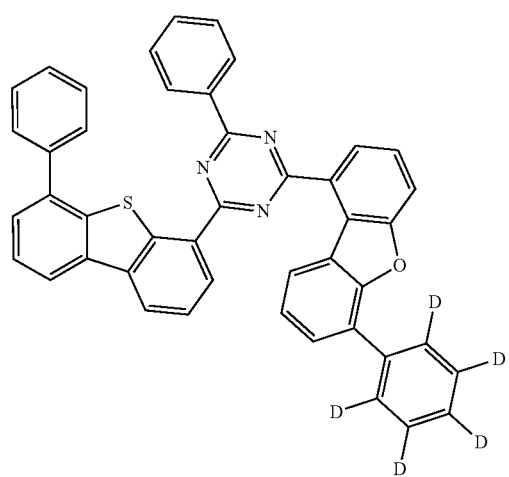
2-36
3-3
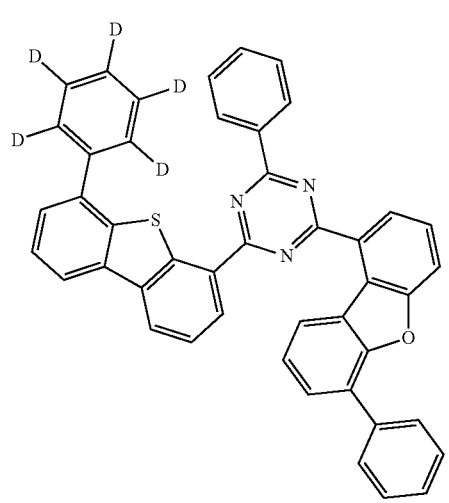
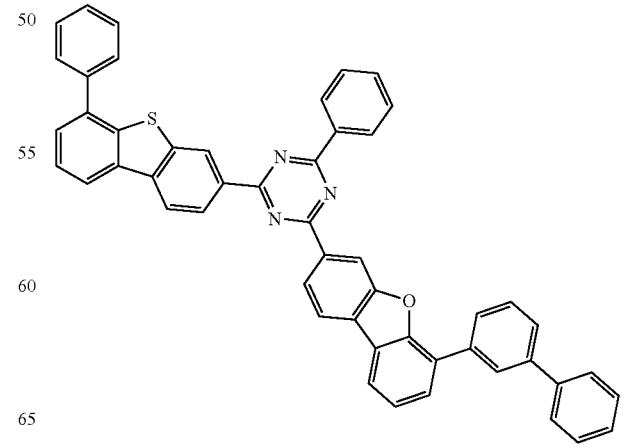

-continued
3-4
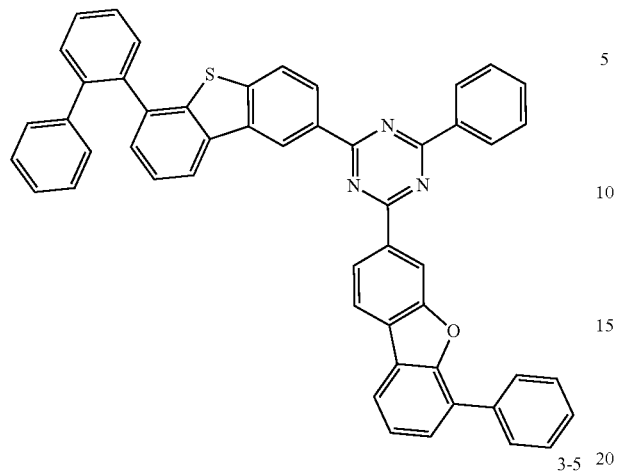
3-5
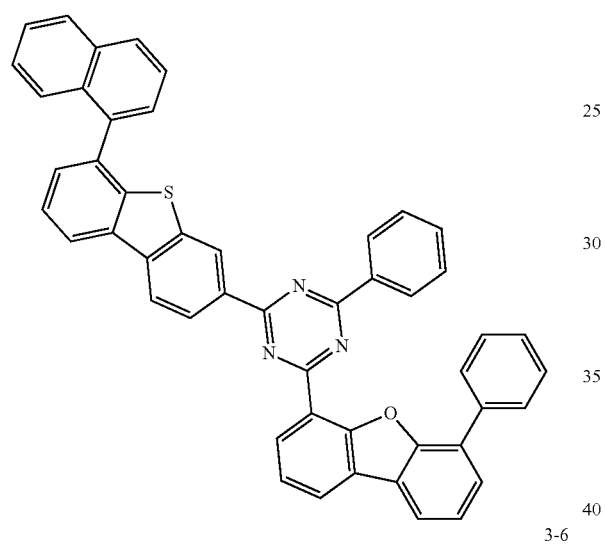
3-6
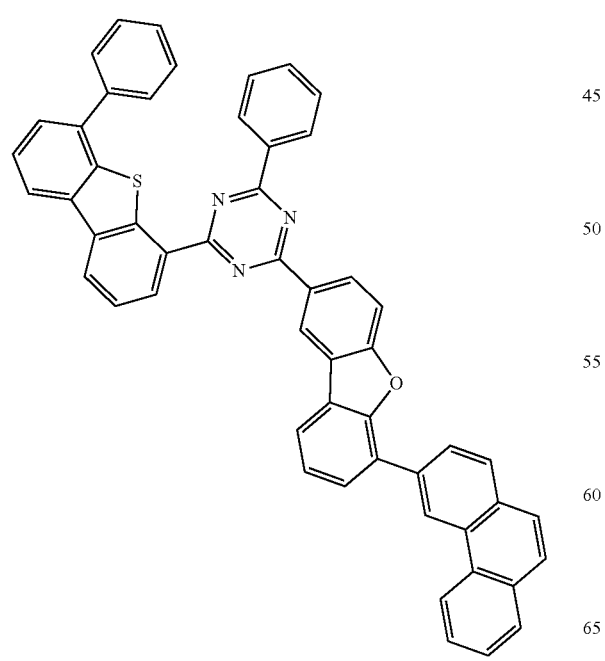
-continued
3-7
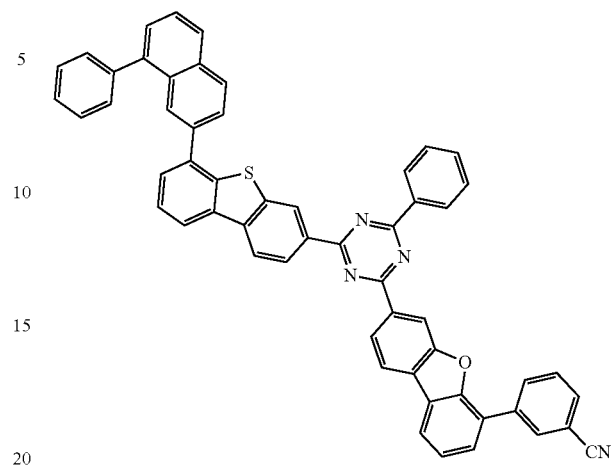
3-8
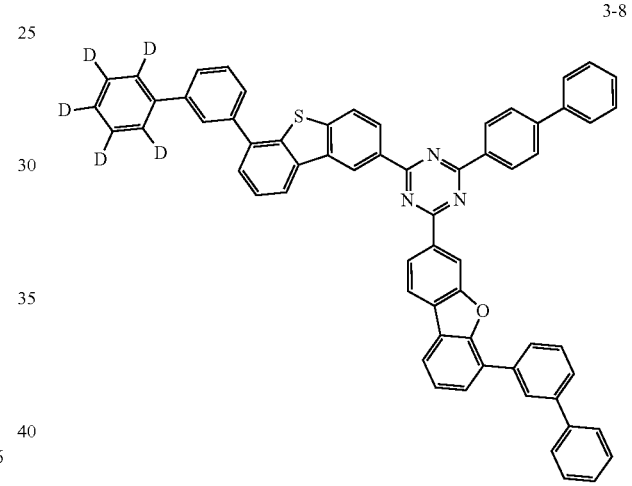
3-9
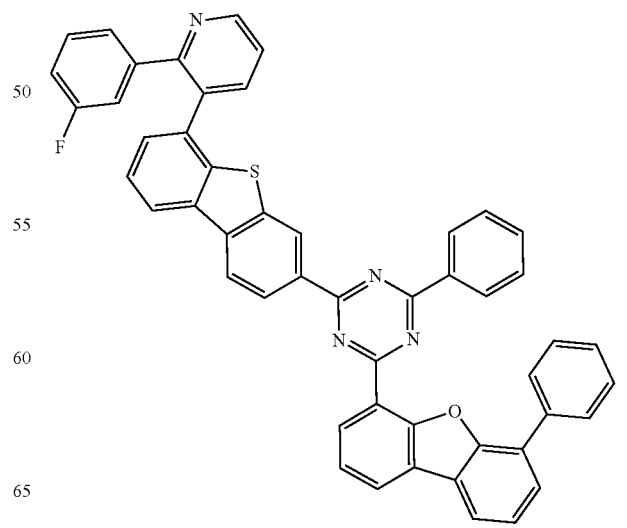

3-10
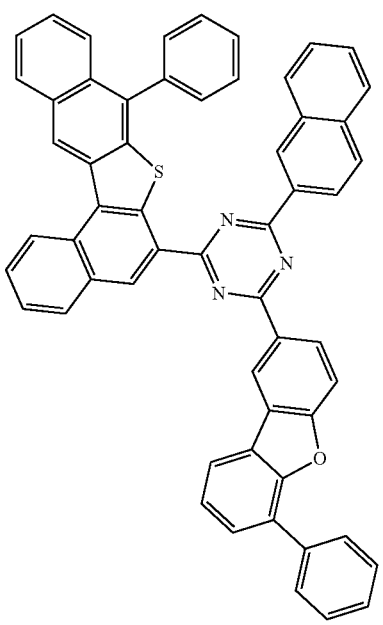
3-11
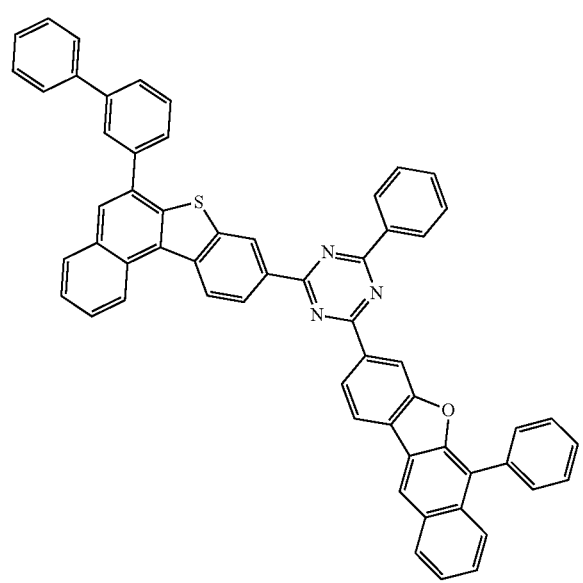
3-12
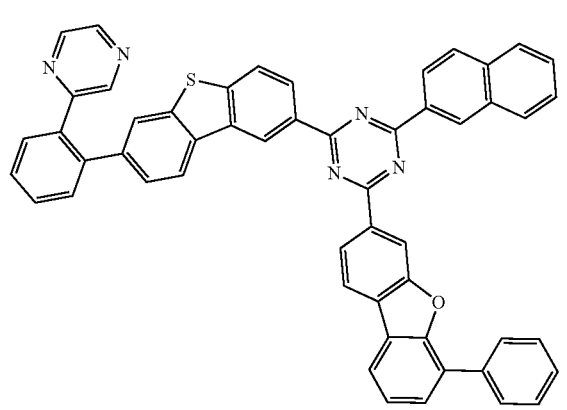
3-13
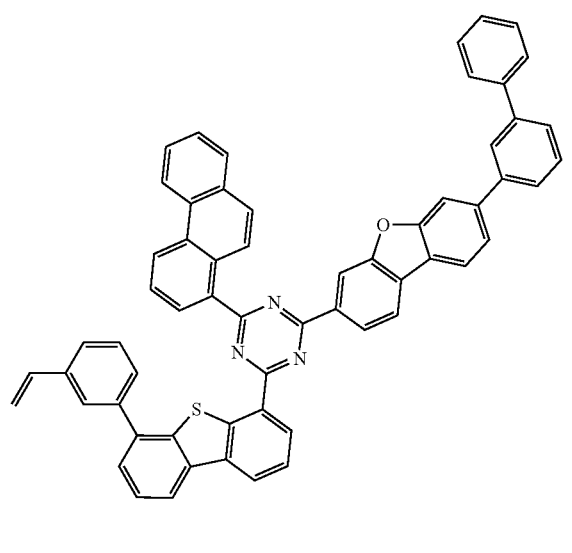
3-14
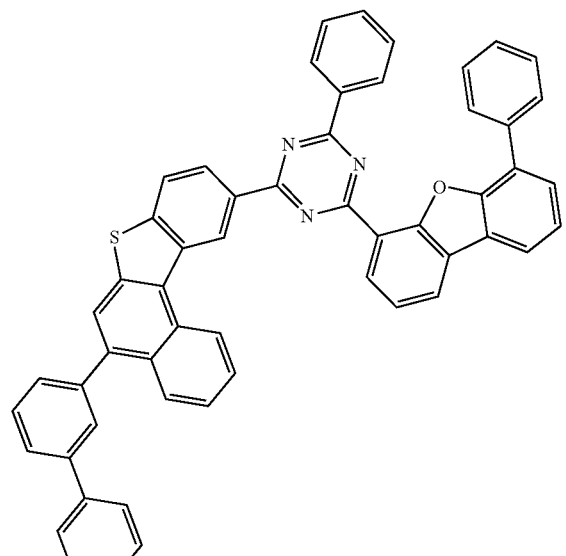
3-15

3-16
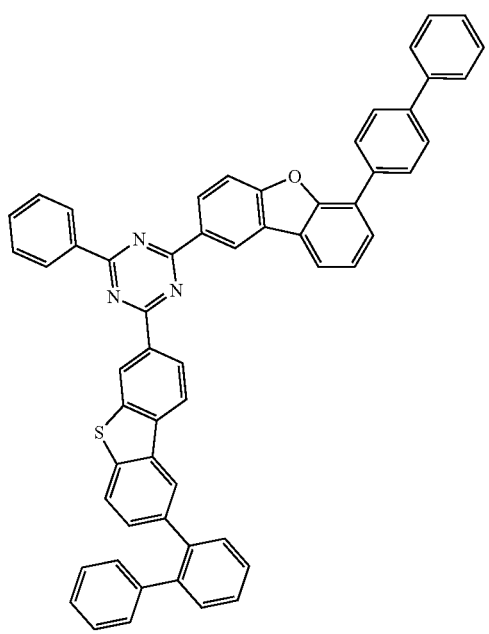
3-17
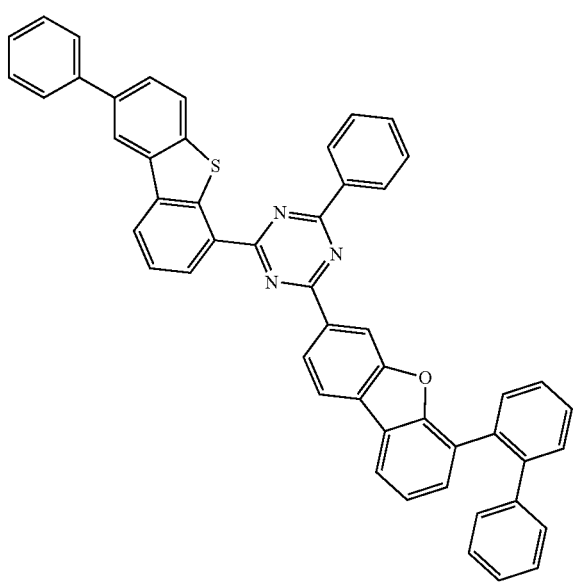
3-18
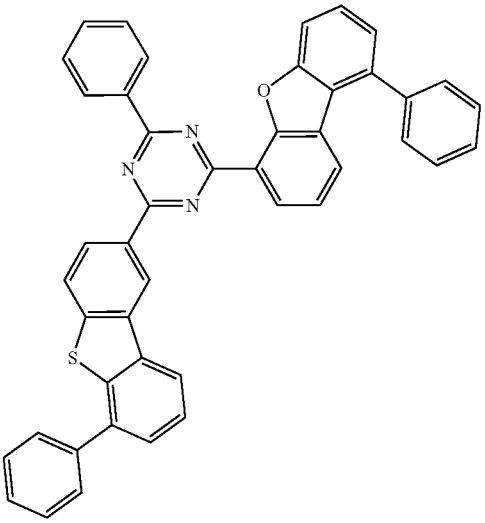
3-19
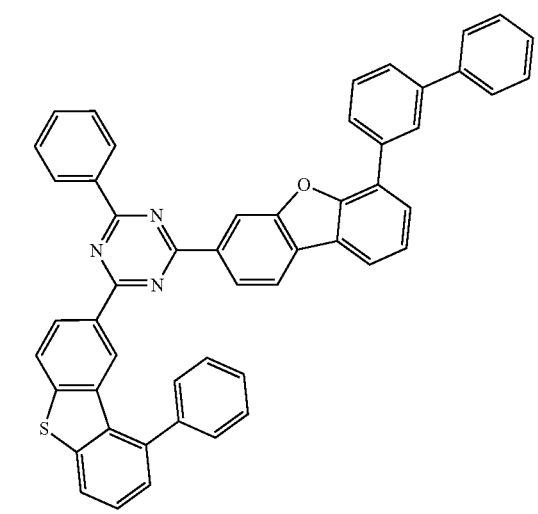
3-20
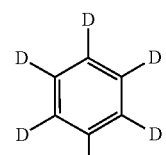
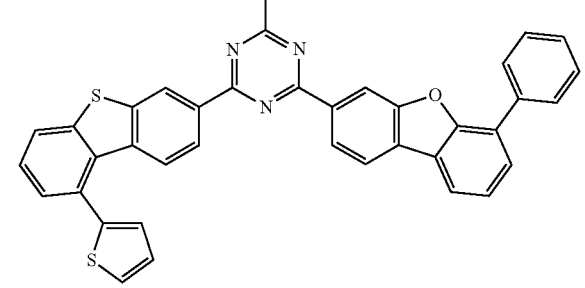

3-21
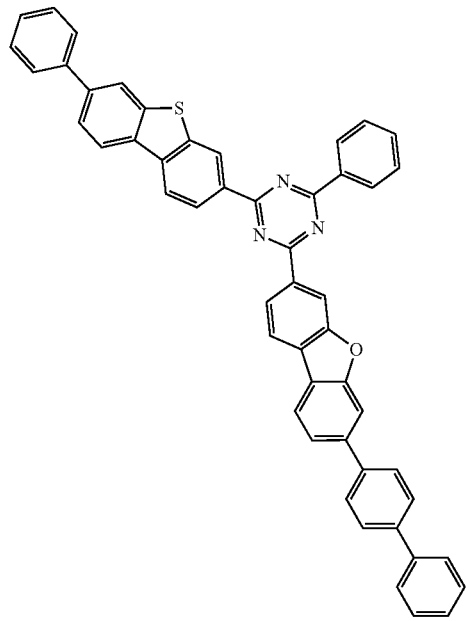
3-22
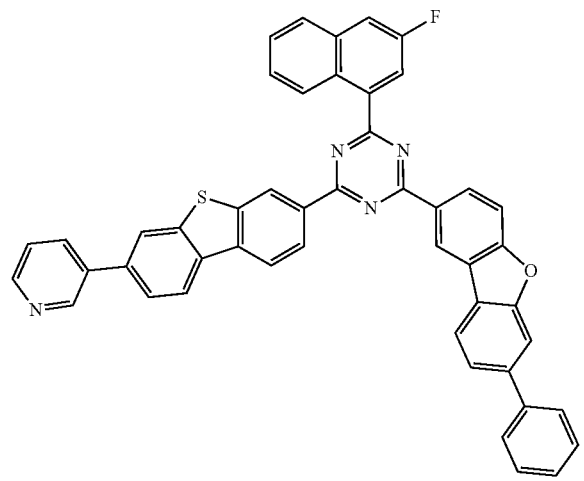
3-23
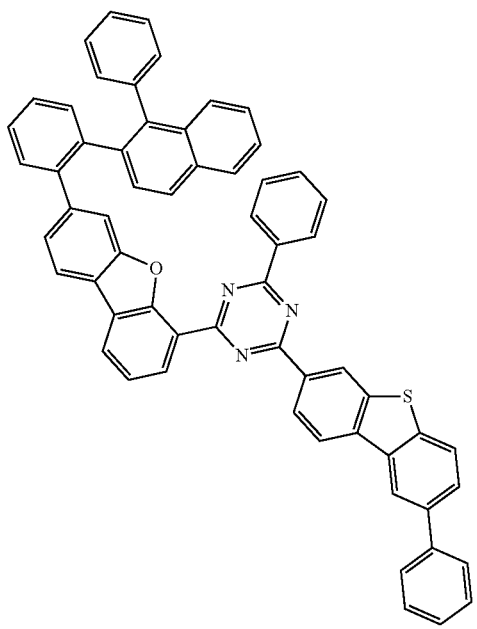
3-24
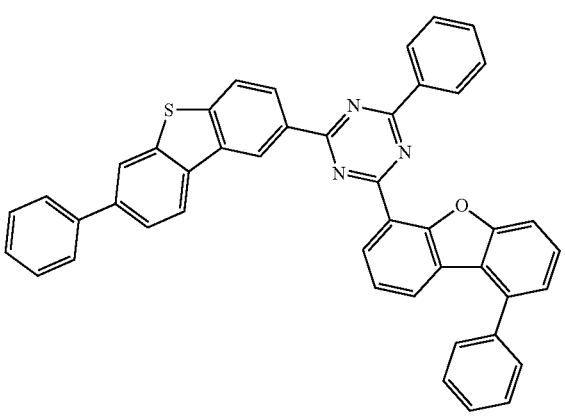
3-25
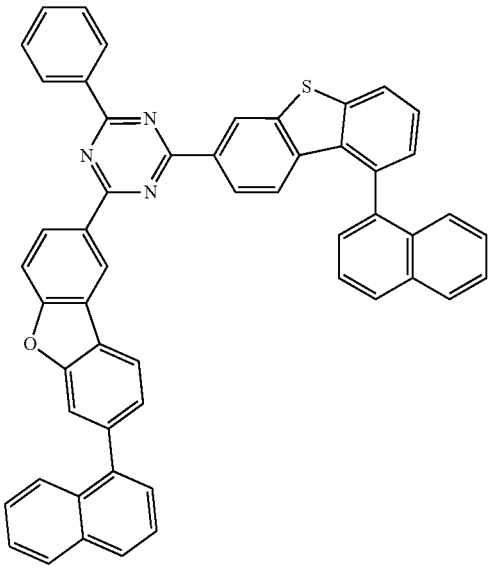

3-26
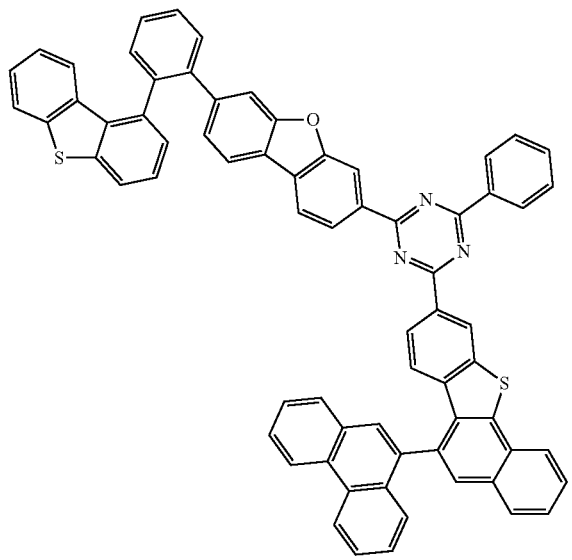
3-27
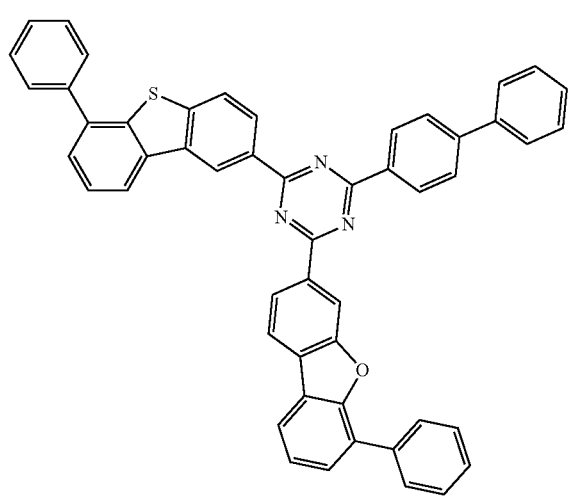
3-28
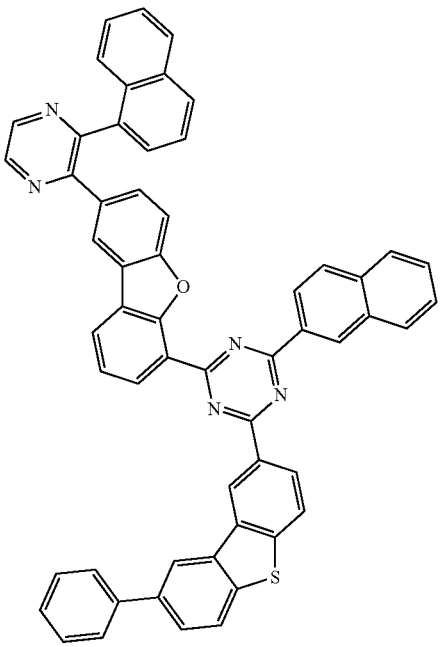
3-29
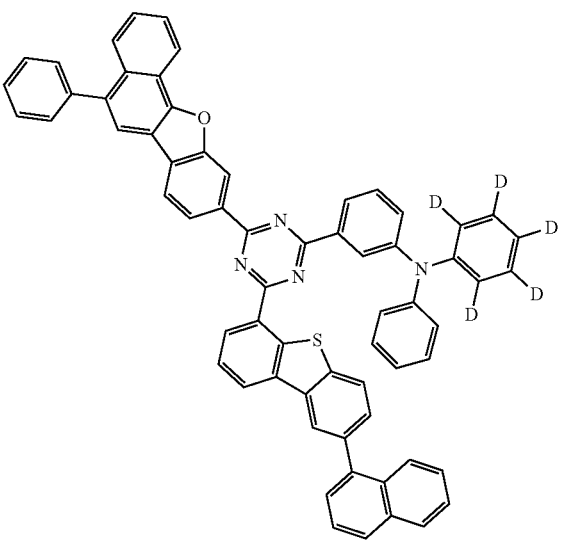

3-30
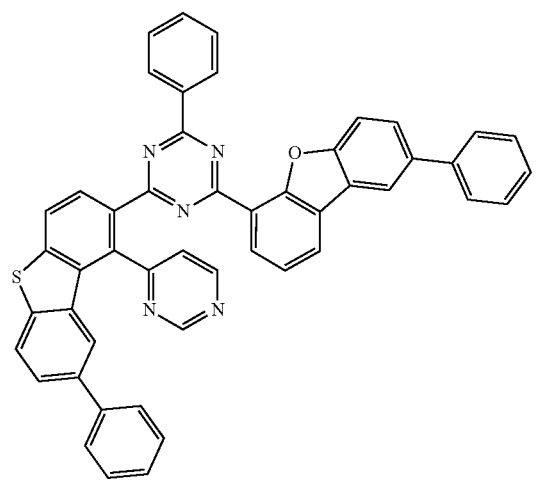
3-31
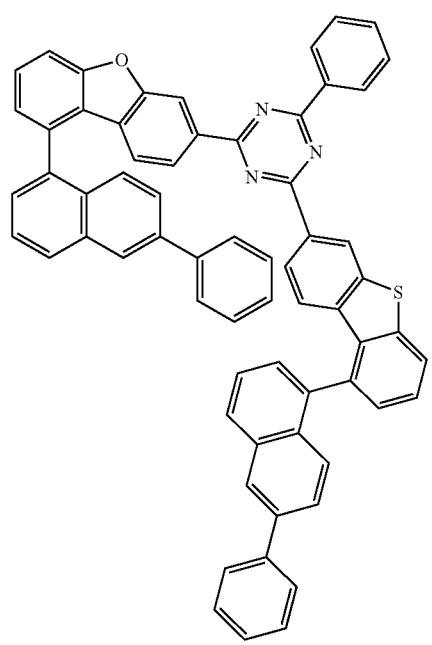
3-32
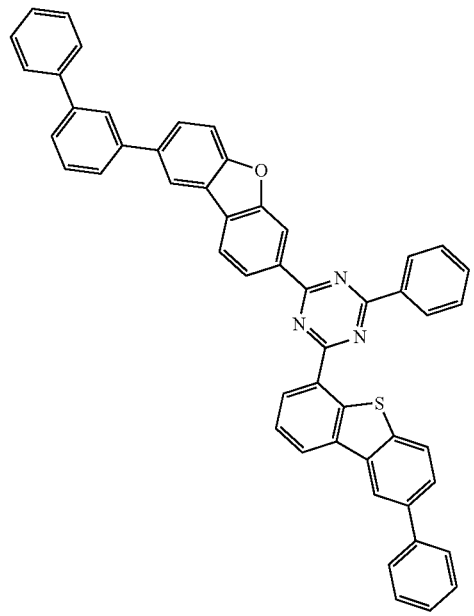
3-33
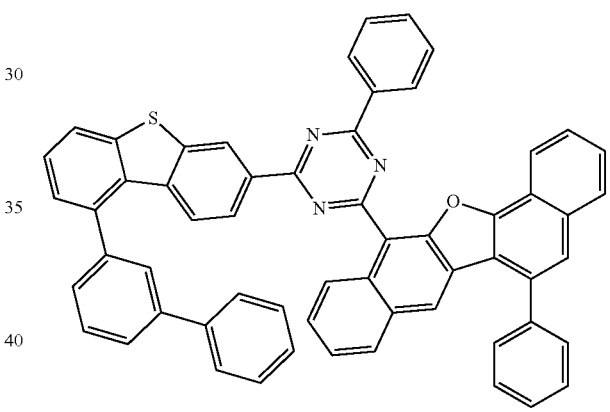
3-34
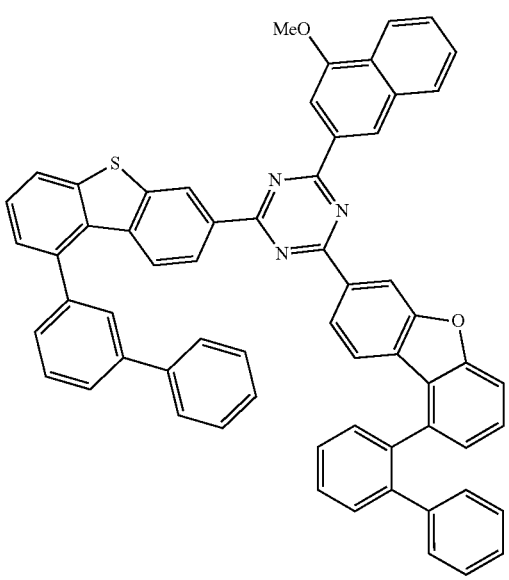

3-35
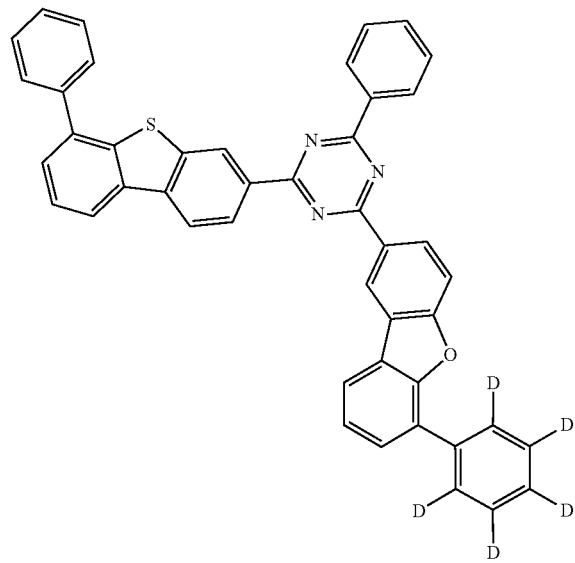
3-36
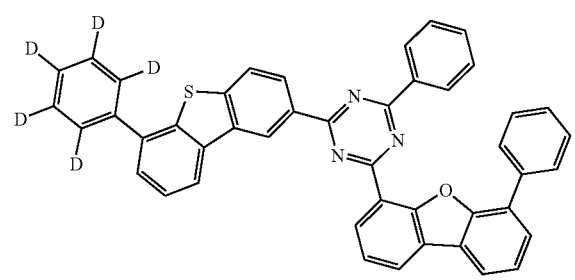
4-1
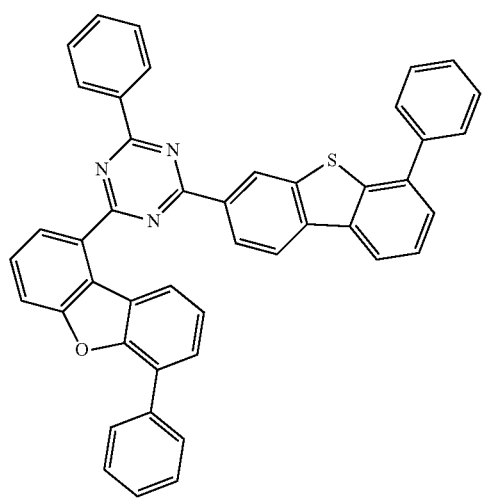
4-2
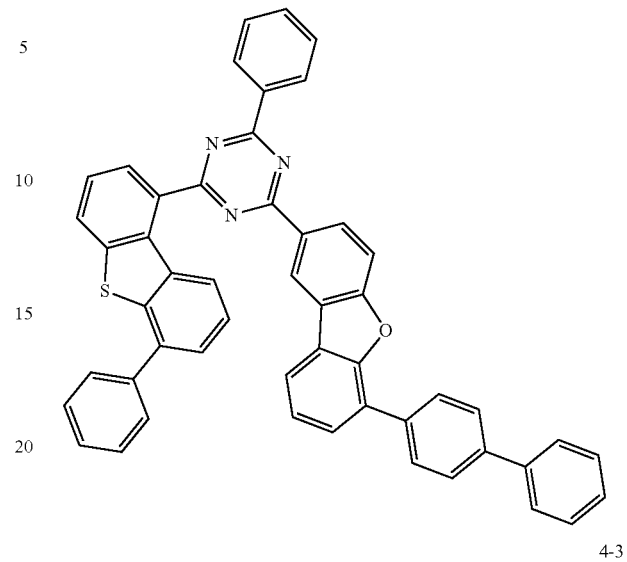
4-3
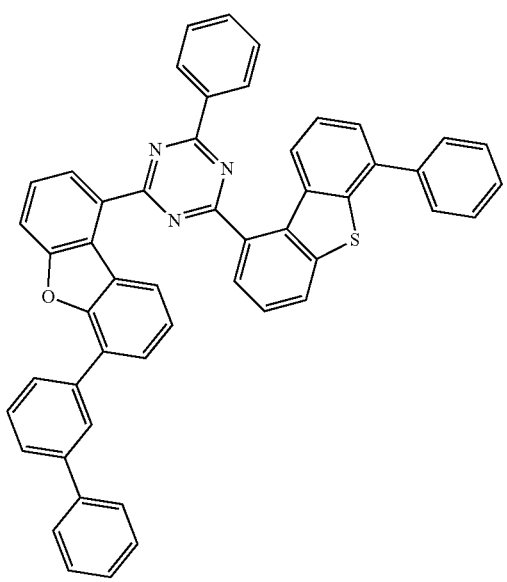
4-4
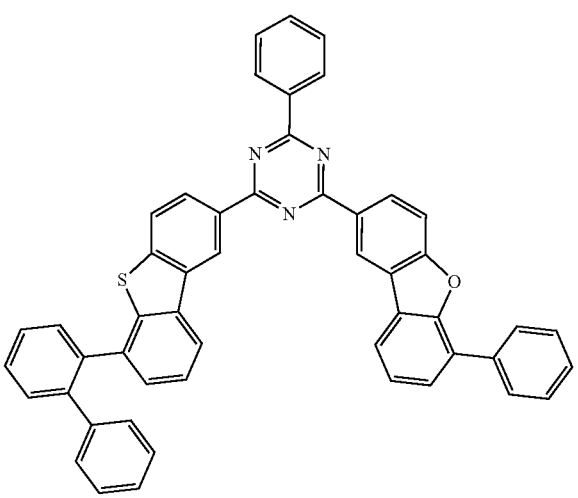

4-5
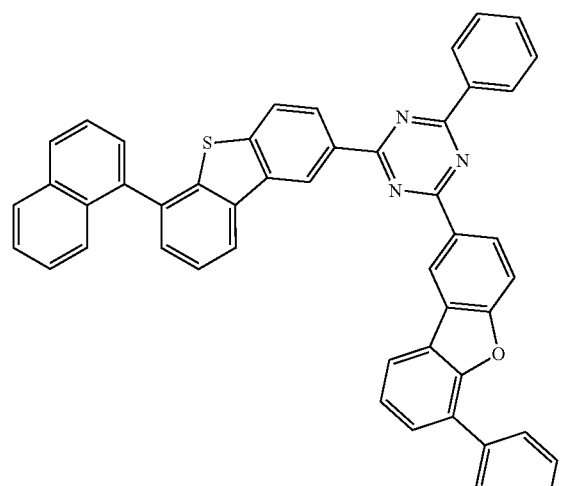
4-6
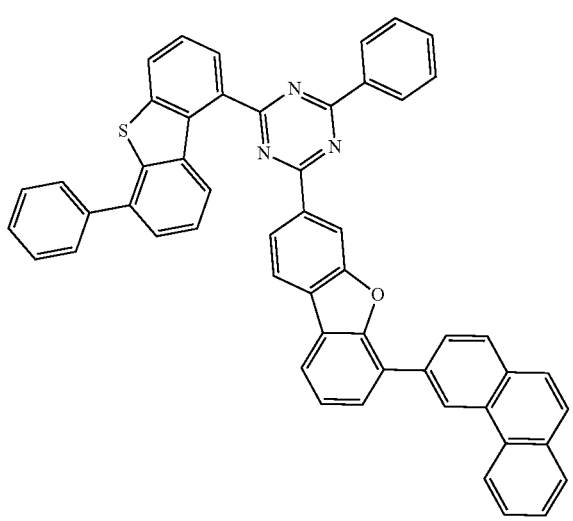
4-7
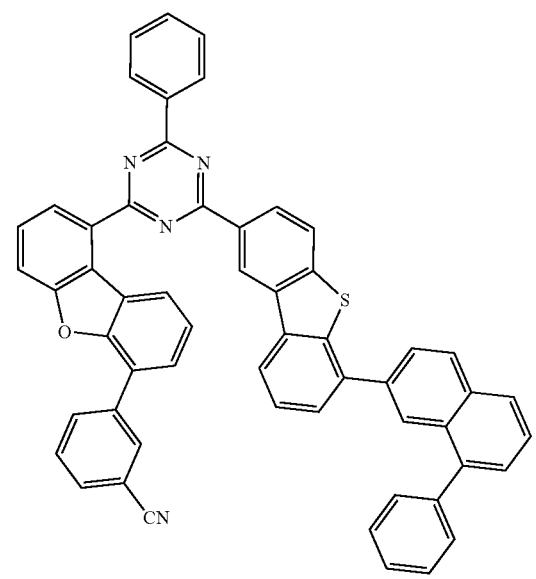
4-8
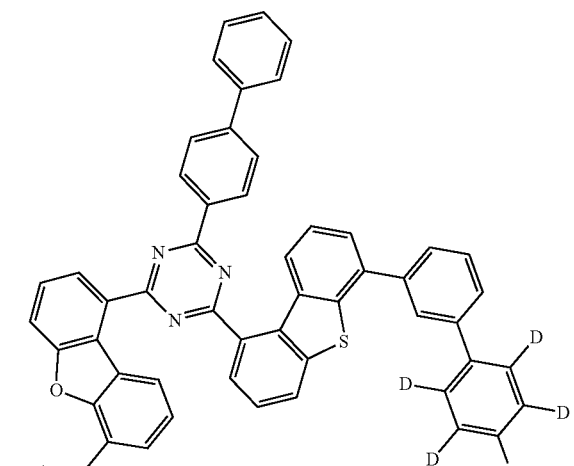
4-9
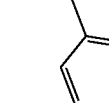
4-10
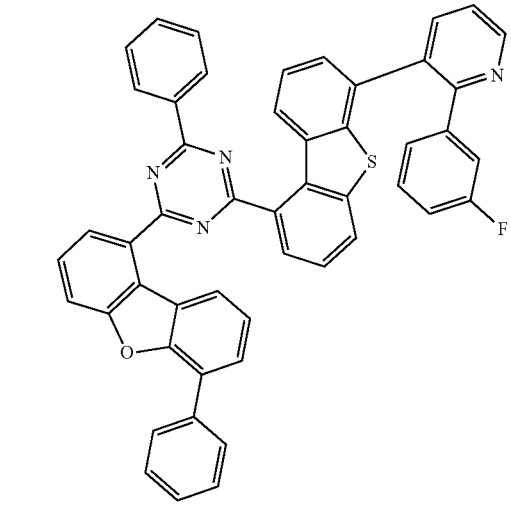

-continued
4-11
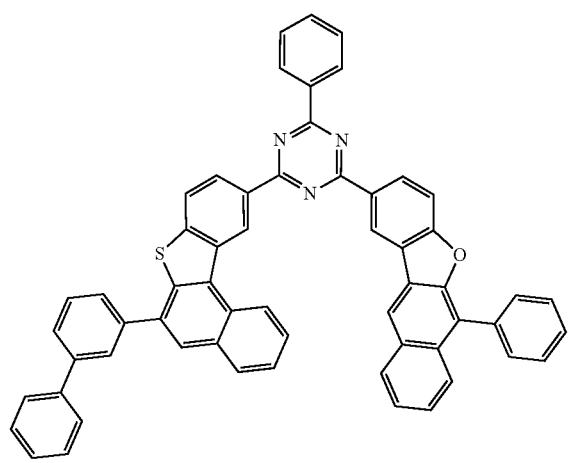
4-12
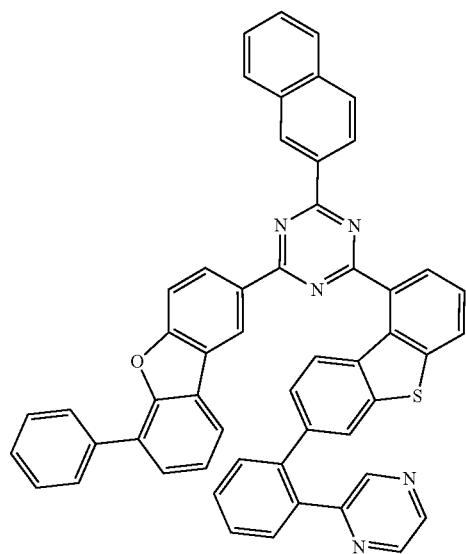
4-13
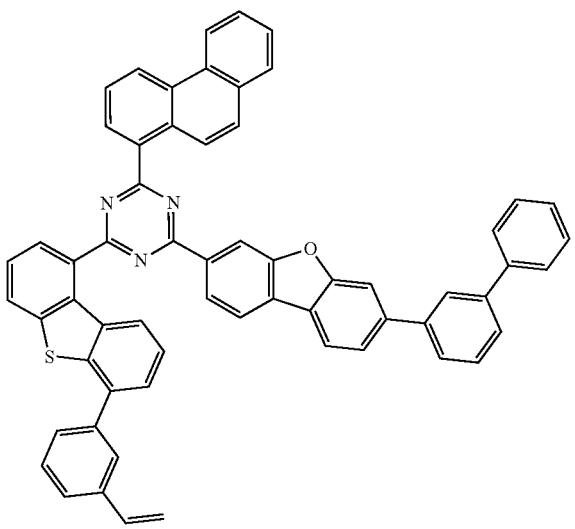
-continued
4-14
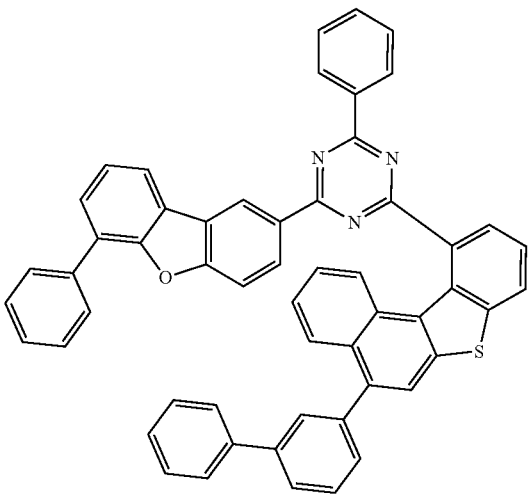
4-15
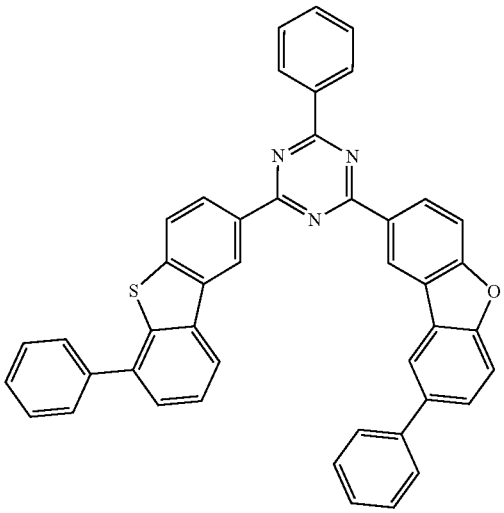
4-16
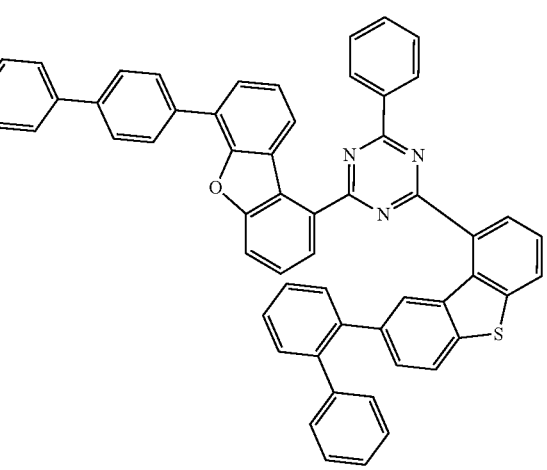

4-17
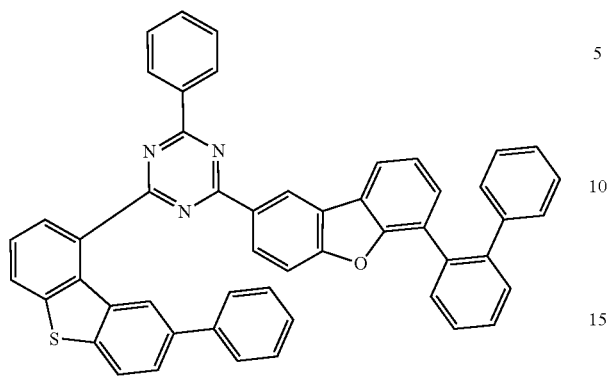
4-18
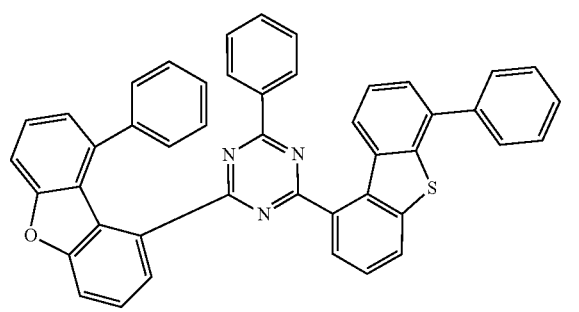
4-19
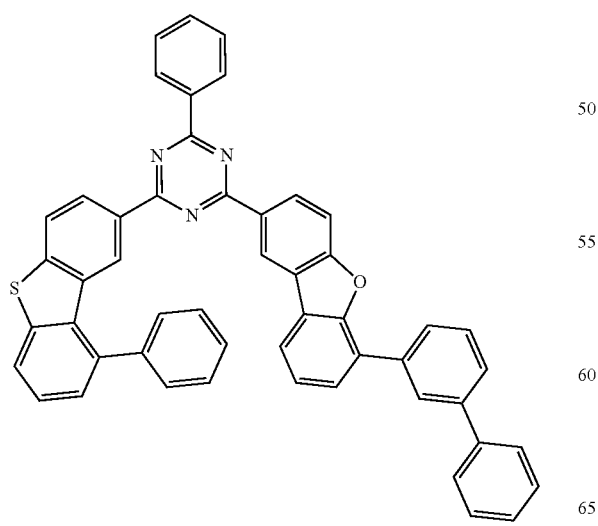
4-20
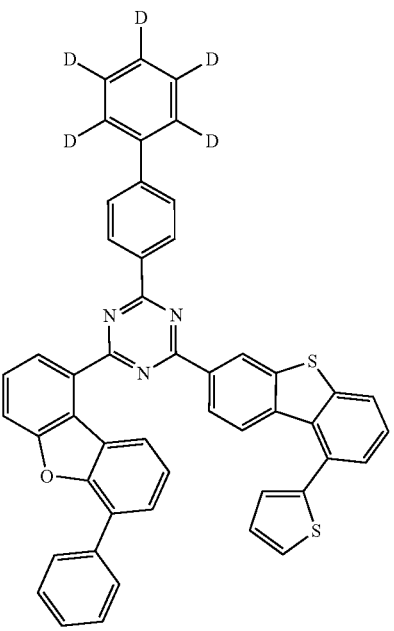
4-21
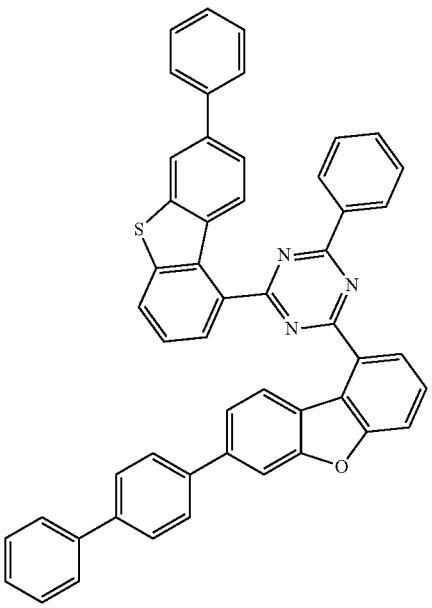

4-22
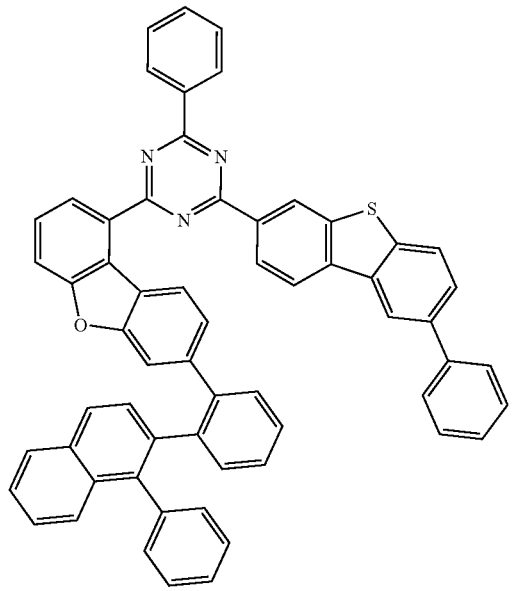
4-23
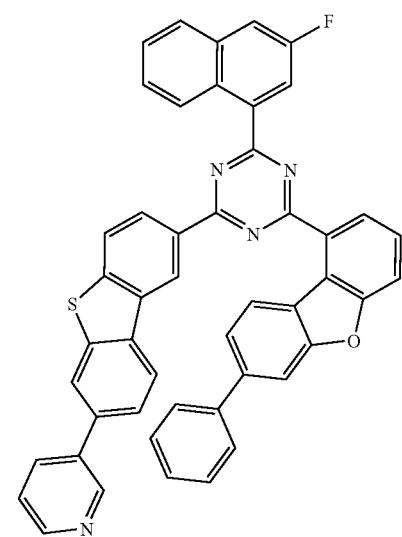
4-24
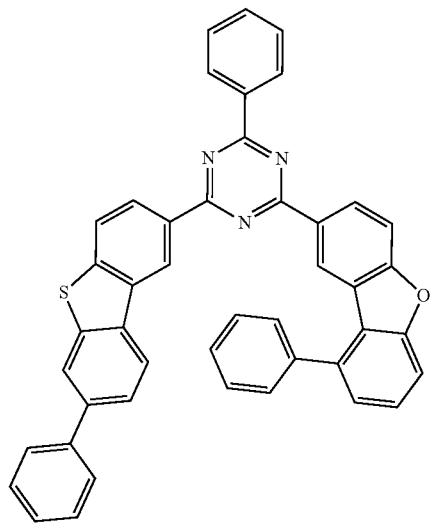
4-25
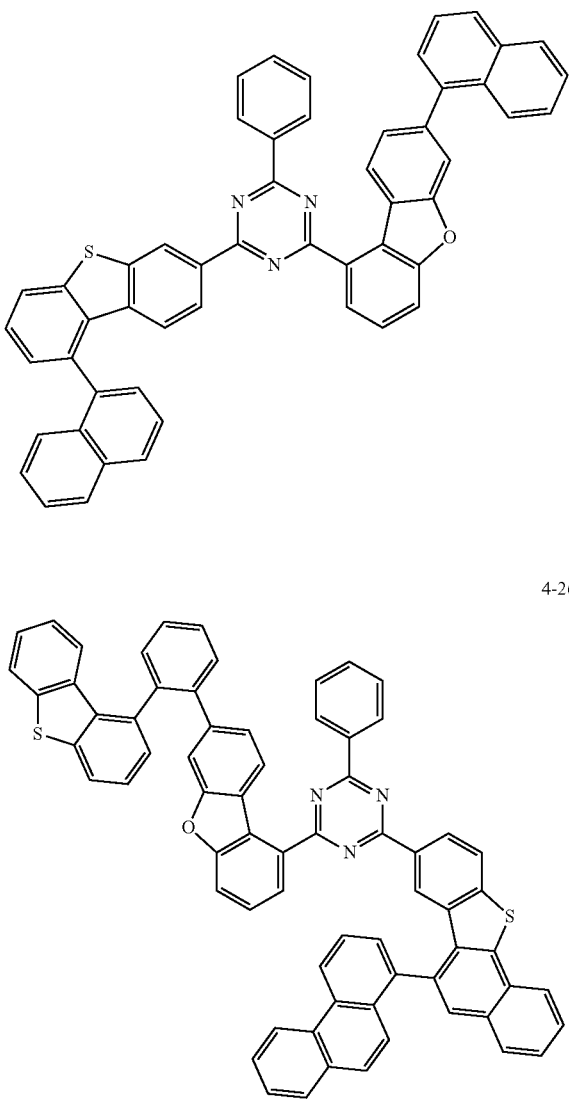
4-26
4-27
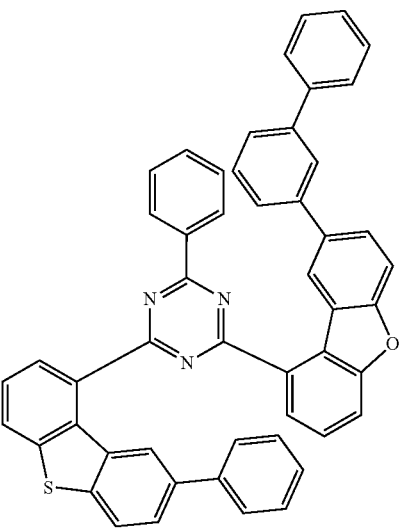

4-28
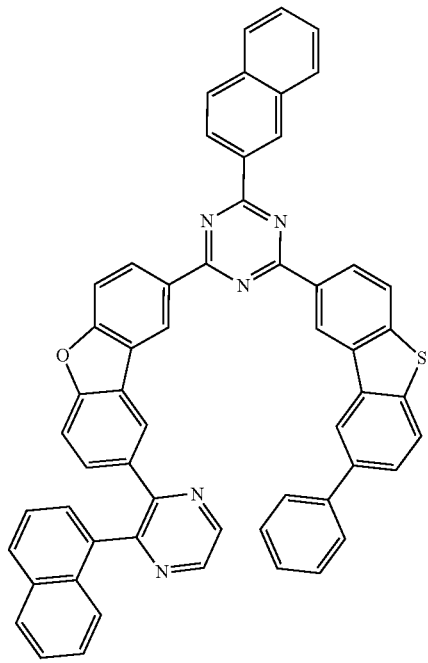
4-30
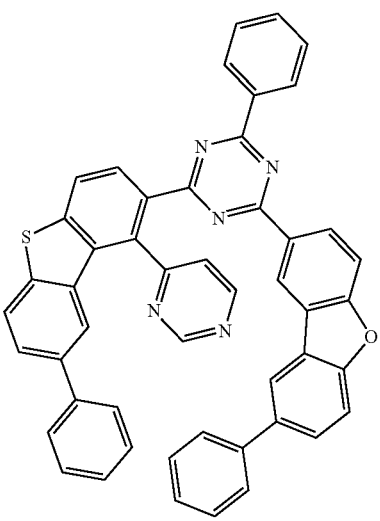
4-31
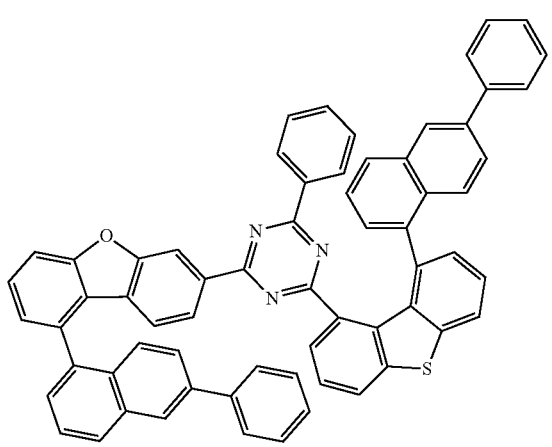
4-29
4-32
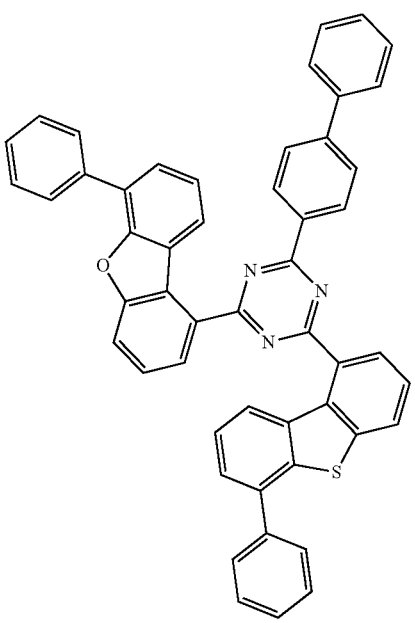

-continued
4-33
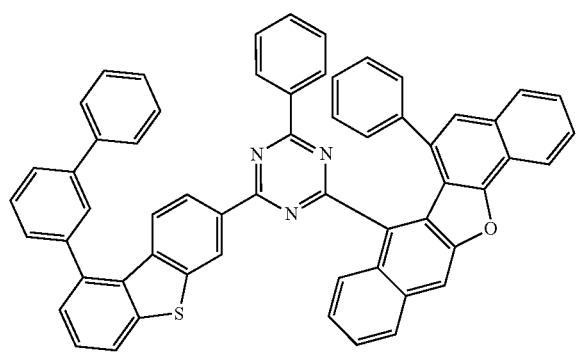
4-34
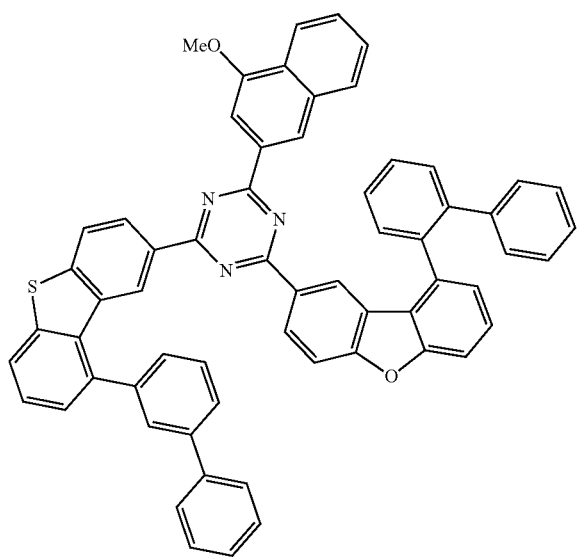
4-35
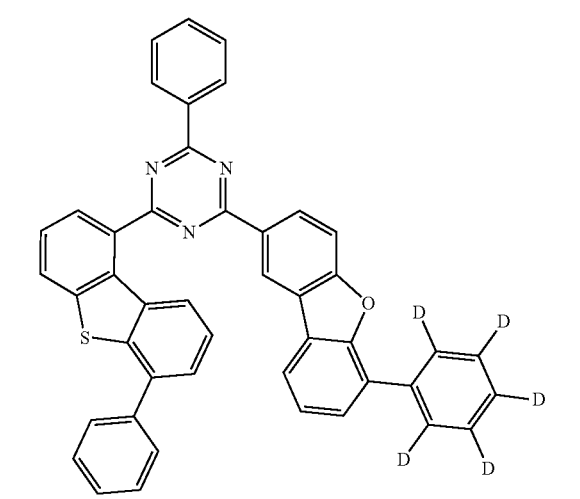
-continued
4-36
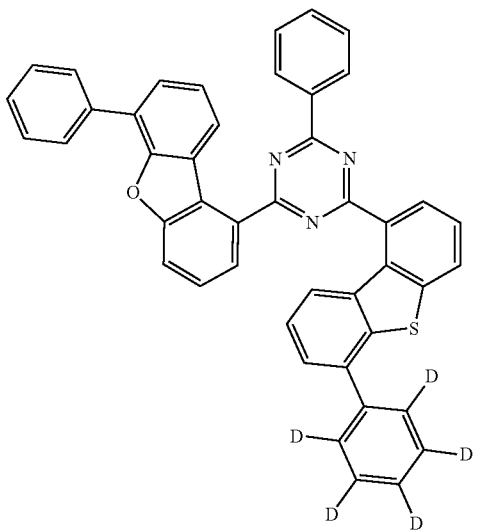
4-37
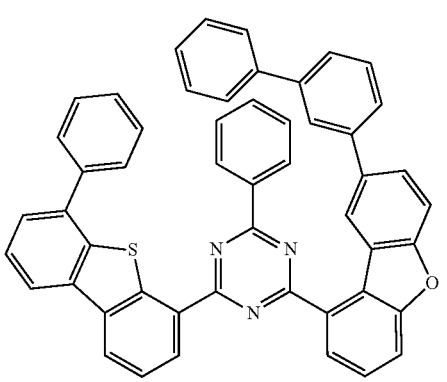
4-38
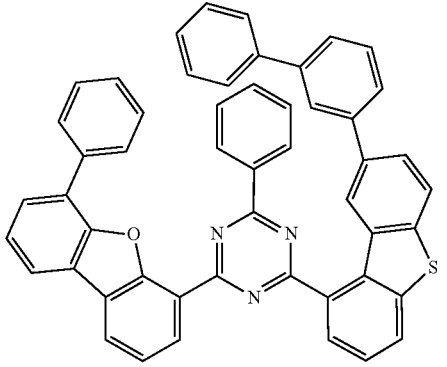
4-39
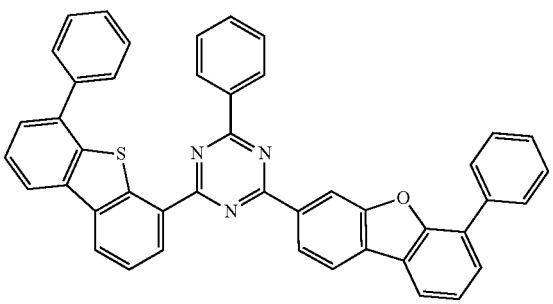

4-40
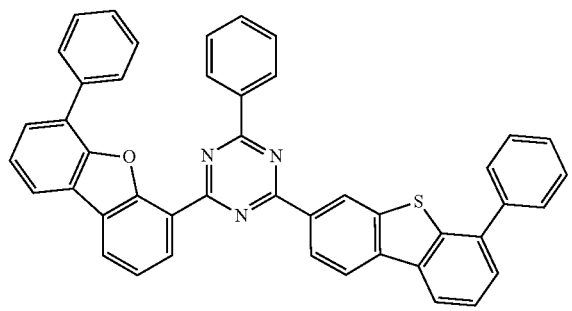
4-41
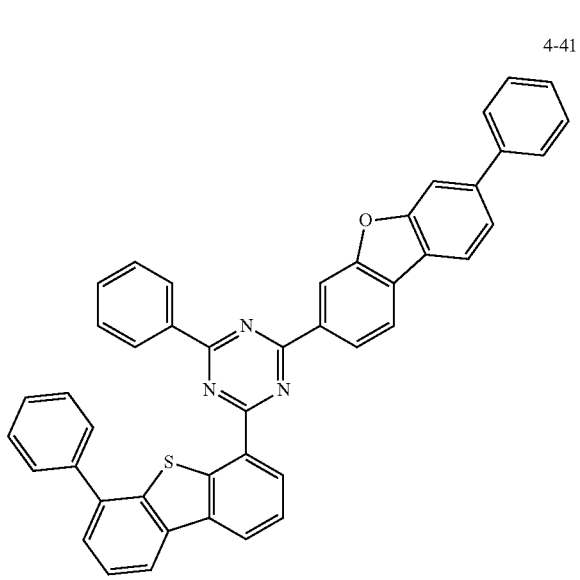
4-42
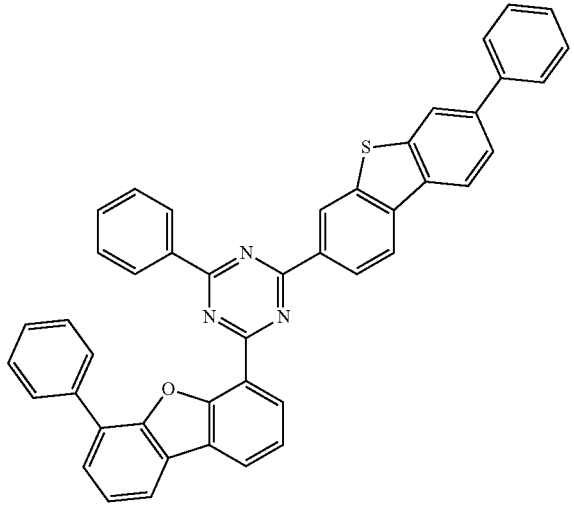
4-43
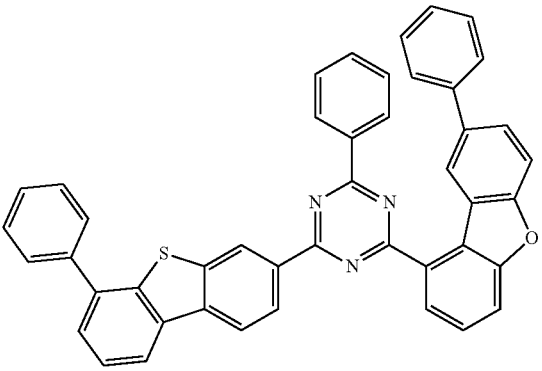
4-44
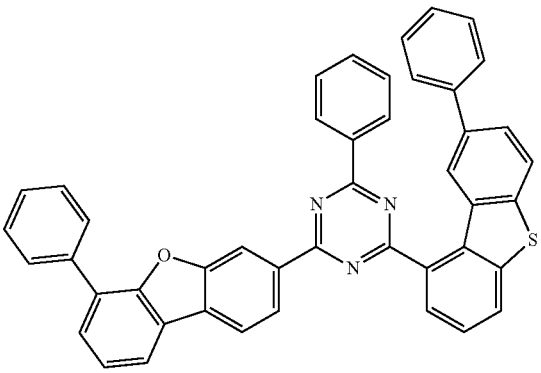
4-45
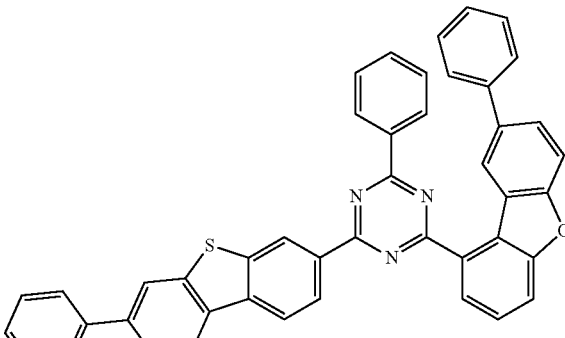
4-46
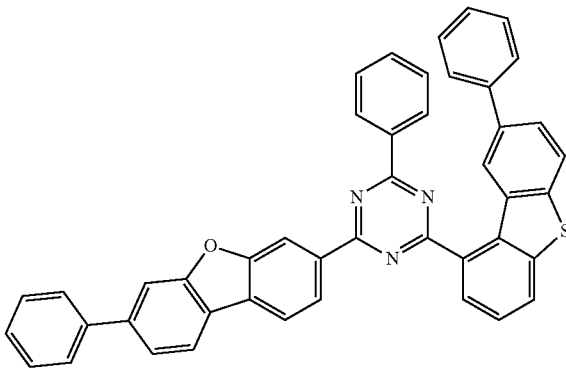
In another aspect of the present invention, the present invention provides an organic electric element comprising a first electrode, a second electrode, and an organic material layer formed between the first electrode and the second electrode, wherein the organic material layer comprises compound represented by Formula 1. The organic material layer comprises at least one layer of a hole injection layer, a hole transport layer, an emission-auxiliary layer, a light emitting layer, an electron transport auxiliary layer, an electron transport layer and an electron injection layer, preferably, the compound represented by Formula 1 is comprised in the light emitting layer, more preferably, a single compound or compounds of two or more kinds represented by Formula 1 may be used as host material of the light emitting layer.

In one embodiment according to the present invention, the light emitting layer may further comprise the compound represented by the following Formula 12.

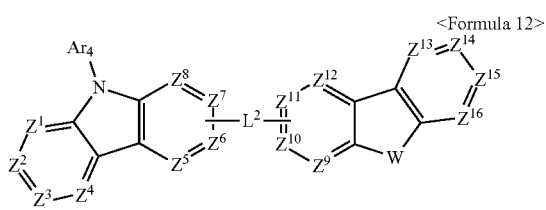

<Formula 12>

In Formula 12, each of symbols may be defined as follows.

$Z^1$ to $Z^4$, $Z^{13}$ to $Z^{16}$ are independently C(R) or N, $Z^5$ to $Z^{12}$ are independently C, C(R) or N.

$L^2$ is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring.

When $L^2$ is an arylene group, $L^2$ may be preferably a $C_6$-$C_{30}$ or $C_6$-$C_{20}$ arylene group, more preferably a $C_6$-$C_{18}$ arylene group, for example, phenylene, naphthalene, biphenyl, terphenyl or the like. When $L^2$ is a heterocyclic group, $L^2$ may be preferably a $C_2$-$C_{30}$ or $C_2$-$C_{20}$ heterocyclic group, more preferably a $C_2$-$C_{18}$ heterocyclic group, for example, carbazole, phenylcarbazole or the like.

W is N(Ar$_5$), N, O, S, C(R') or C(R')(R''), and W is N or C(R') when W is combined with $L^2$.

Ar$_4$ and Ar$_5$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group, -L'-N(R$_a$)(R$_b$) and a combination thereof. Here, the term "a combination thereof" means, for example, a combination of an aryl group and a heterocyclic group, a combination of an aryl group and an aliphatic ring, a combination of a heterocyclic group and an aliphatic ring group, and the like.

R, R' and R'' are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N(R$_a$)(R$_b$), adjacent R groups may be optionally linked to each other to form a ring, and R' and R'' may be optionally linked to each other to form a ring.

The ring formed by linking between adjacent R groups or between R' and R'' may be a $C_6$-$C_{60}$ aromatic ring group, a $C_2$-$C_{60}$ heterocyclic group containing at least one heteroatom selected from the group consisting of O, N, S, Si, and P, a $C_3$-$C_{60}$ aliphatic ring, or a fused ring group formed by a $C_3$-$C_{60}$ aliphatic ring with a $C_6$-$C_{60}$ aromatic ring, preferably, a $C_6$-$C_{20}$ aromatic ring group or a $C_2$-$C_{20}$ heterocyclic group, more preferably, a $C_6$-$C_{10}$ aromatic ring group or a $C_2$-$C_{10}$ heterocyclic group, for example, benzene, naphthalene, phenanthrene, thiophene, benzothiophene, pyridine and the like.

L', R$_a$ and R$_b$ are the same as defined for Formula 1.

$L^2$, Ar$_4$, Ar$_5$, R, R', R'', the ring formed by linking between adjacent R groups, and the ring formed by linking between R' and R'' may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, and a $C_8$-$C_{20}$ arylalkenyl group.

Preferably, Formula 12 is represented by one of Formulas 13 to 17.

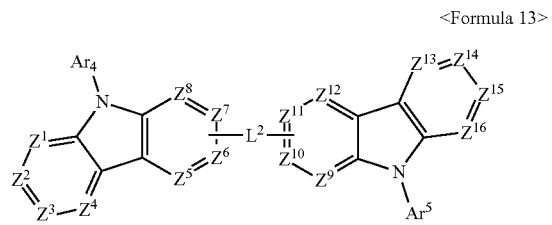

<Formula 13>

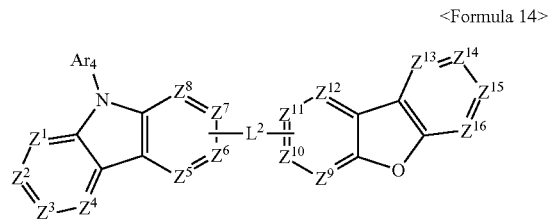

<Formula 14>

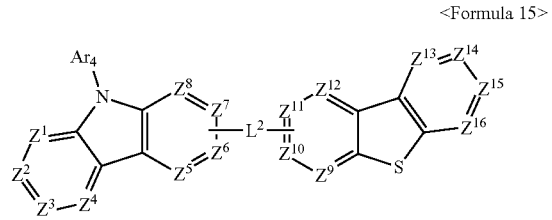

<Formula 15>

<Formula 16>

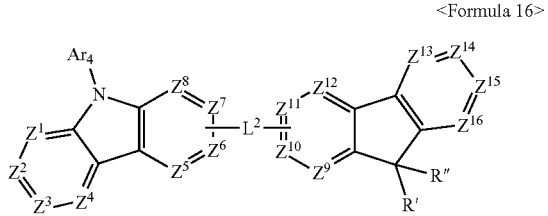

<Formula 17>

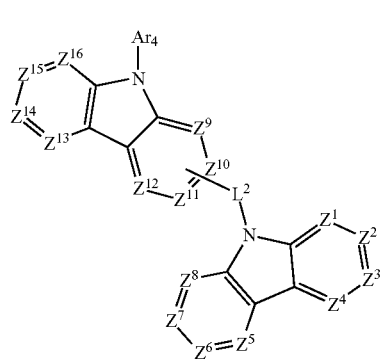

In Formulas 13 to 17, $Ar_4$, $Ar_5$, $Z^1$ to $Z^{16}$, $L^2$, R' and R" are the same as defined for Formula 12.

Preferably, in Formulas 13 to 17, at least one of $Ar_4$ and $Ar_5$ may be a substituted or unsubstituted $C_6$-$C_{30}$ aryl group, more preferably, both $Ar_4$ and $Ar_5$ are a $C_6$-$C_{30}$ aryl group.

Preferably, Formula 12 may be represented by Formula 18 or Formula 19.

<Formula 18>

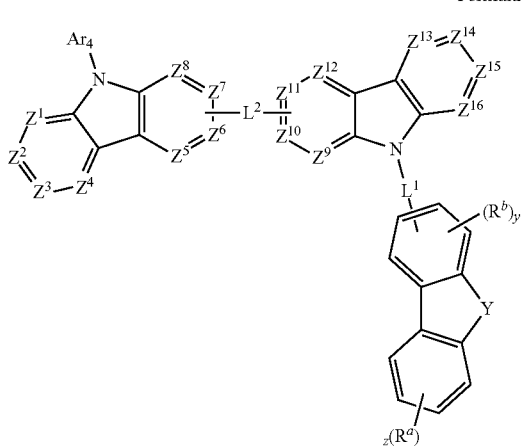

<Formula 19>

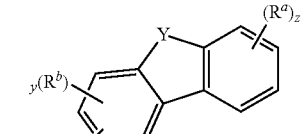

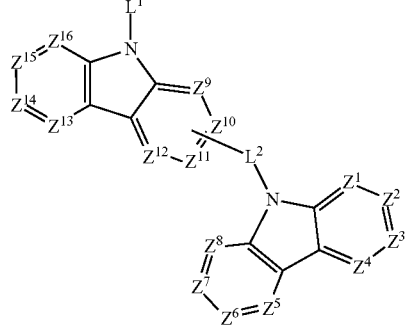

In Formulas 18 and 19, each of symbols may be defined as follows.

$Ar_4$, $Z^1$ to $Z^{16}$, and $L^2$ are the same as defined for Formula 12.

$L^1$ is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring.

When $L^1$ is an arylene group, $L^1$ may be preferably a $C_6$-$C_{30}$ or $C_6$-$C_{20}$ arylene group, more preferably a $C_6$-$C_{12}$ arylene group, for example, phenylene, naphthalene, biphenyl or the like;

Y is O, S or N—$Ar_6$.

$R^a$ and $R^b$ are each independently selected from the group consisting of deuterium, halogen, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group and a $C_8$-$C_{20}$ arylalkenyl group, and adjacent groups may be optionally linked to each other to form a $C_6$-$C_{60}$ aromatic ring, a $C_2$-$C_{60}$ heterocyclic group, a $C_3$-$C_{60}$ aliphatic ring, or a fused ring group formed by a $C_3$-$C_{60}$ aliphatic ring with a $C_6$-$C_{60}$ aromatic ring.

y is an integer of 0 to 3, and z is an integer of 0 to 4, where each of these is an integer of 2 or more, each of $R^a$s, each of $R^b$s is the same or different from each other.

$Ar_6$ is selected from the group consisting of a $C_6$-$C_{60}$ aryl group, a $C_6$-$C_{60}$ aryl group substituted with deuterium, a fluorenyl group, a $C_2$-$C_{60}$ heterocyclic group containing at least one heteroatom selected from the group consisting of O, N, S, Si, and P, a $C_3$-$C_{60}$ cycloalkyl group, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{60}$ alkoxyl group, a $C_6$-$C_{30}$ aryloxy group, a $C_7$-$C_{20}$ arylalkyl group and a $C_8$-$C_{20}$ arylalkenyl group. Preferably, $Ar_6$ is selected from the group consisting of a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group and a $C_8$-$C_{20}$ arylalkenyl group.
Specifically, the compound represented by formula 12 may be one of the following compounds, but it is not limited thereto.
5-1
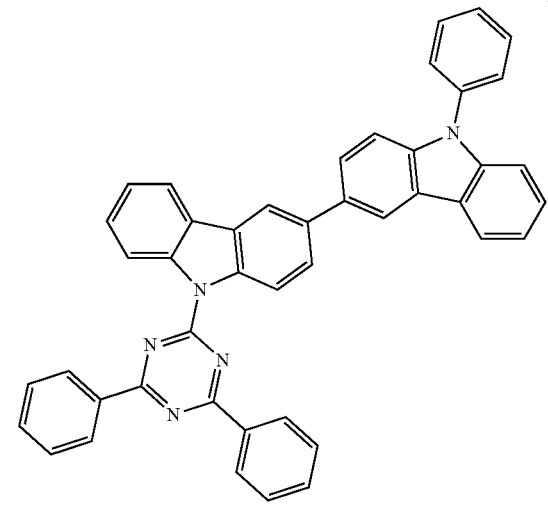
5-2
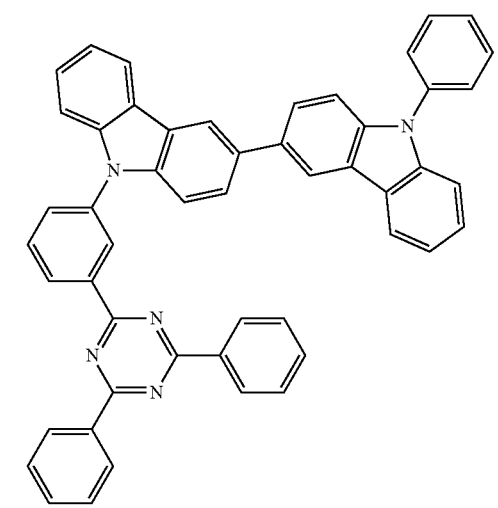
5-3
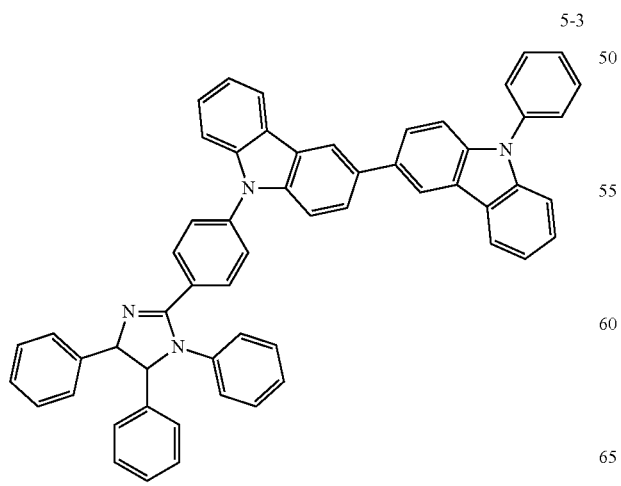
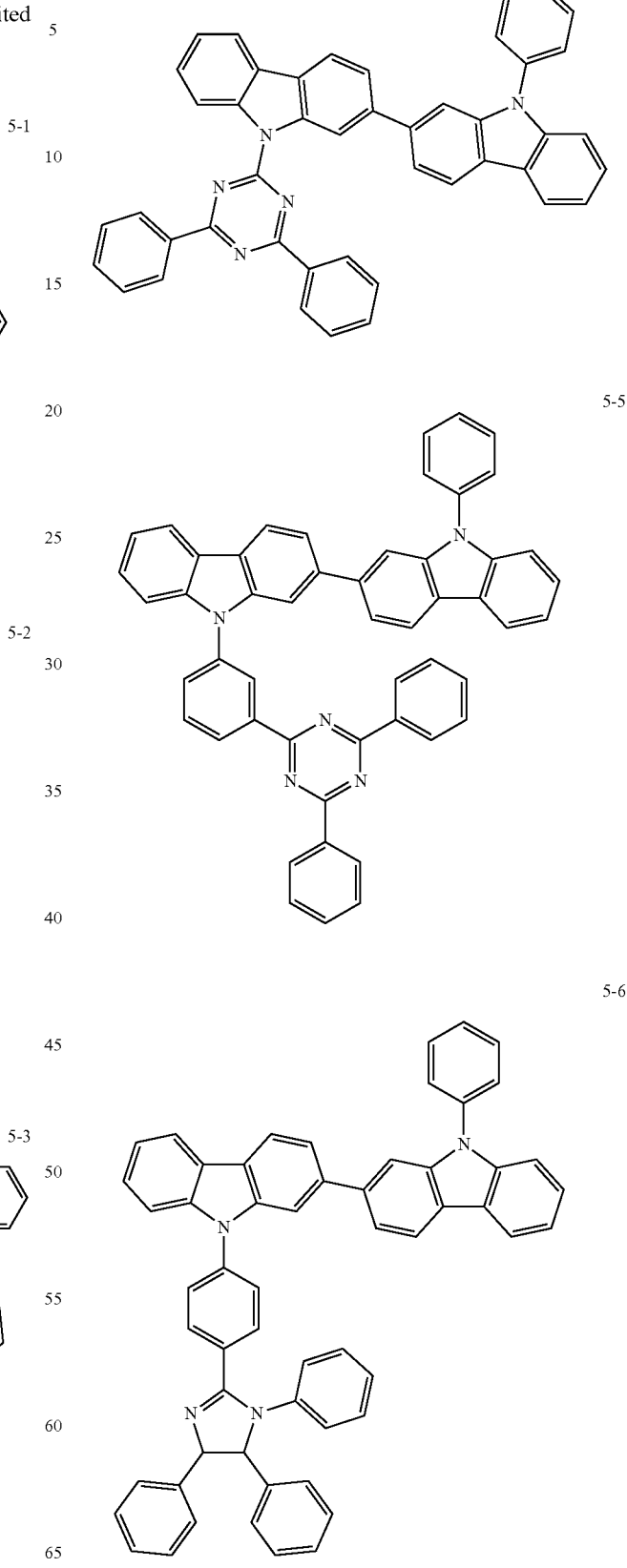

91
-continued
5-7
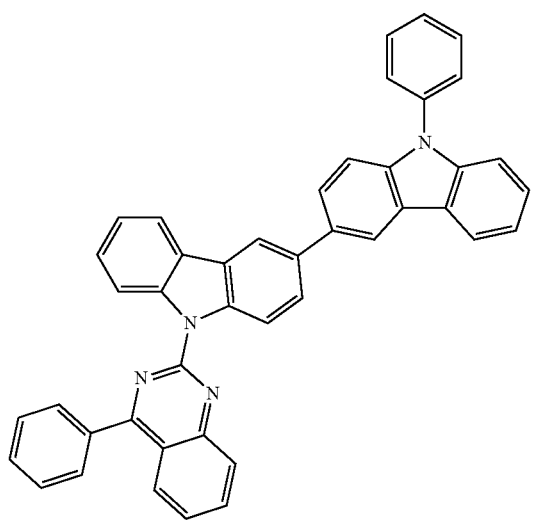
5-8
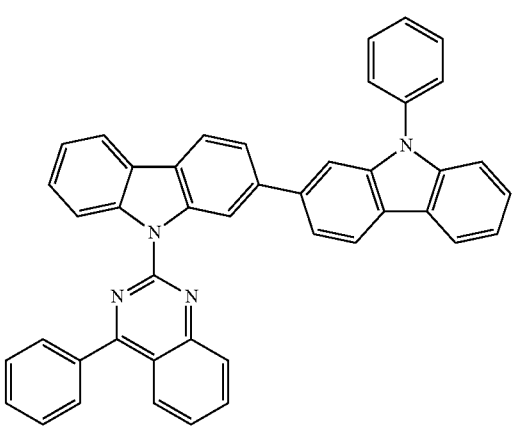
5-9
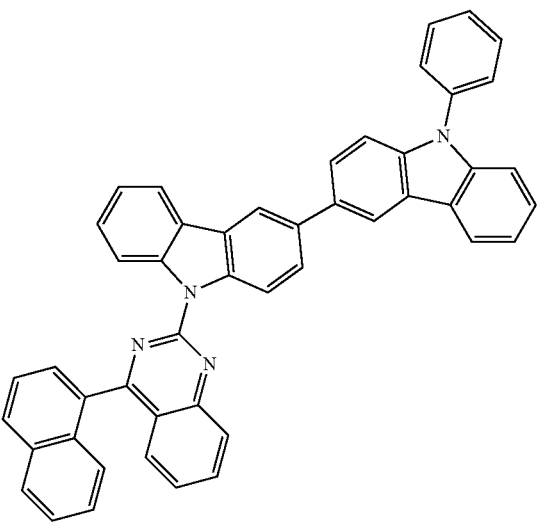
92
-continued
5-10
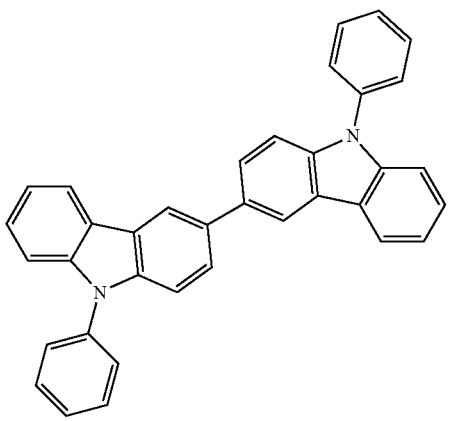
5-11
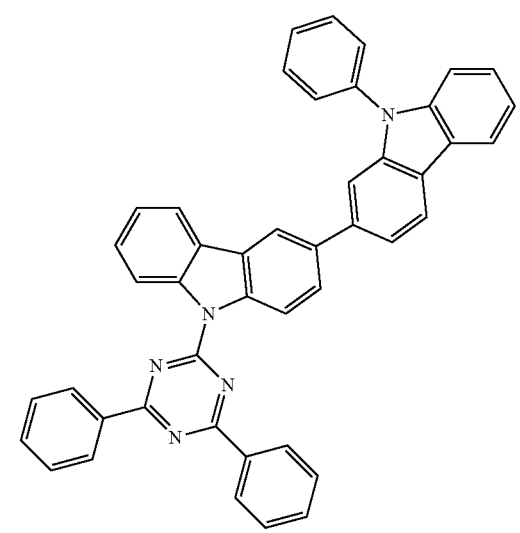
5-12

-continued
5-13
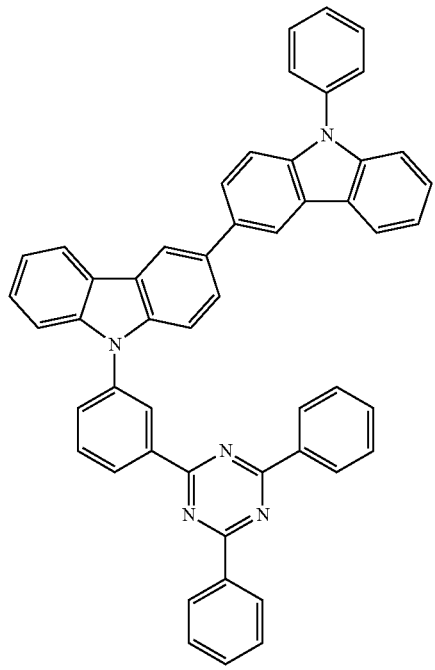
5-14
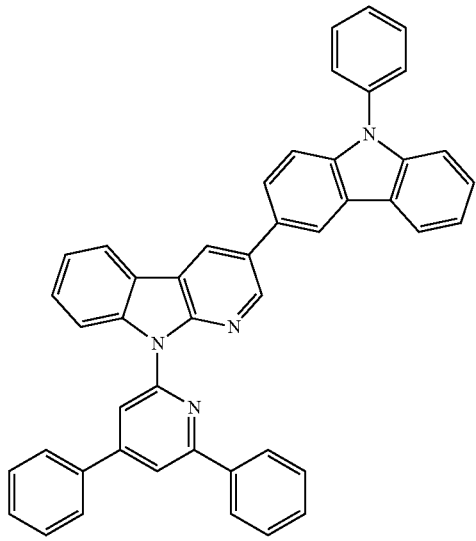
5-15
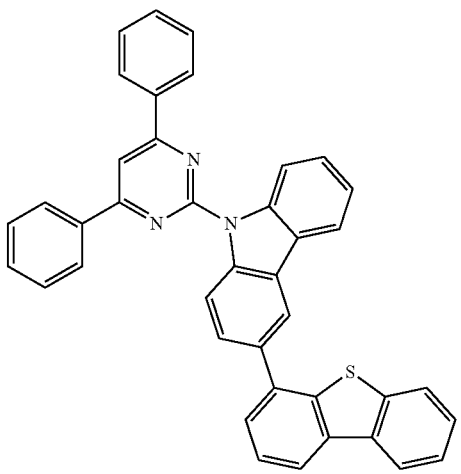
5-16
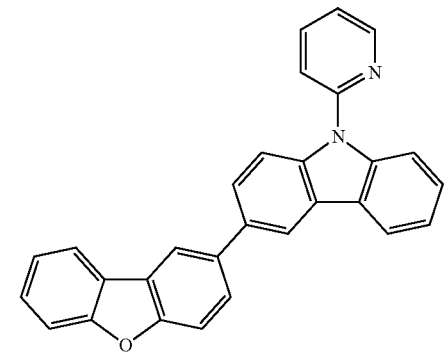
5-17
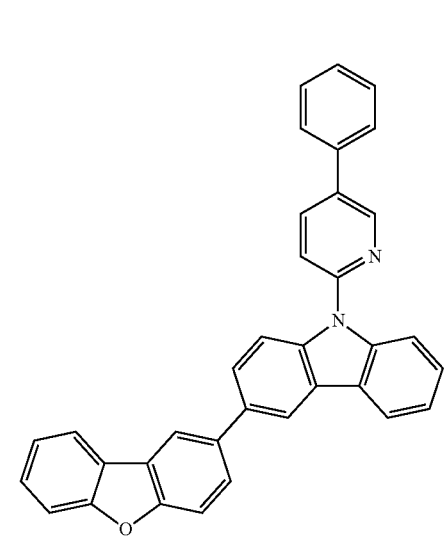

-continued
5-18
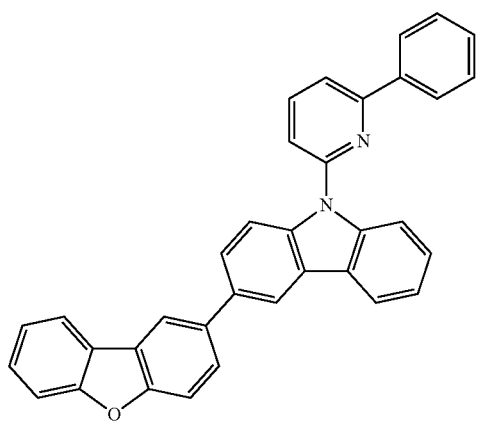
5-19
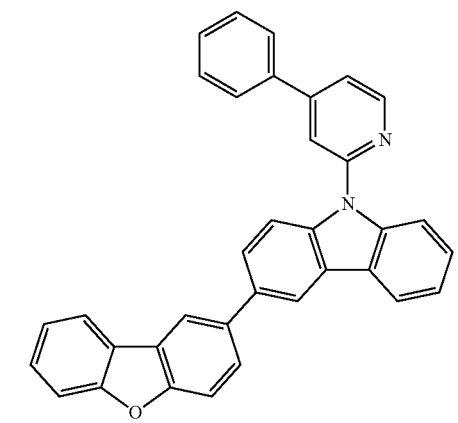
5-20
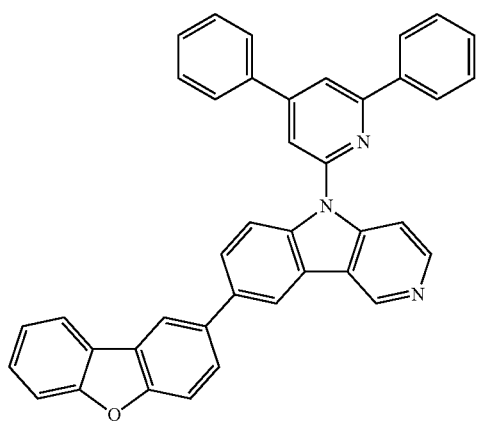
5-21
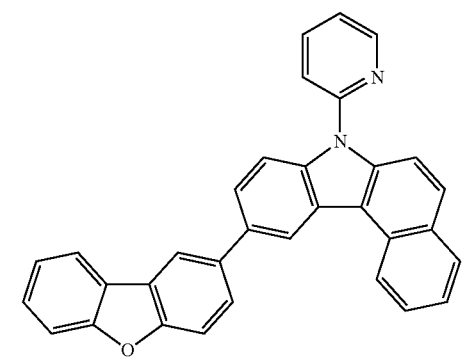
-continued
5-22
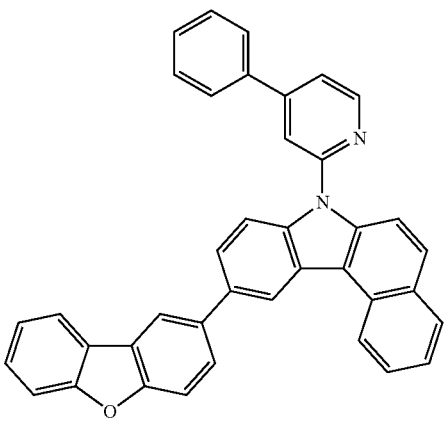
5-23
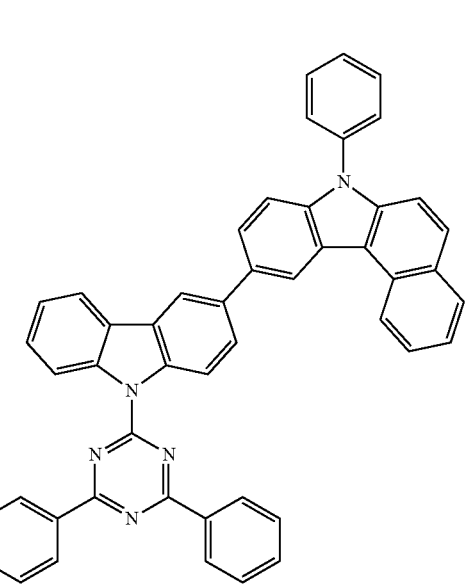
5-24
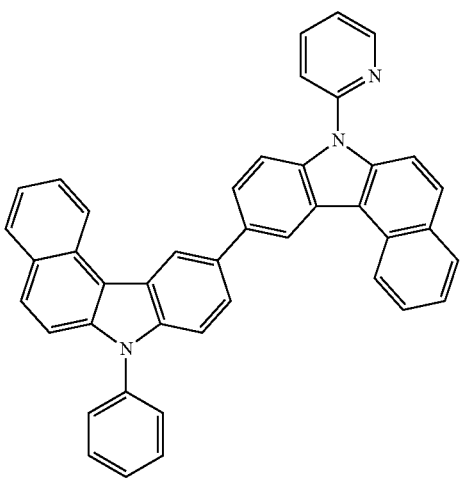

5-25
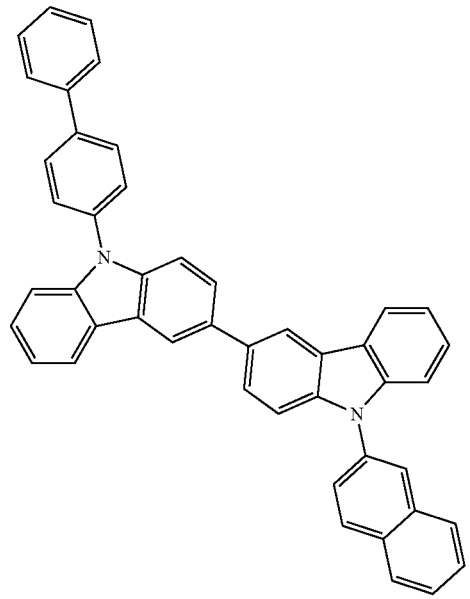
5-26
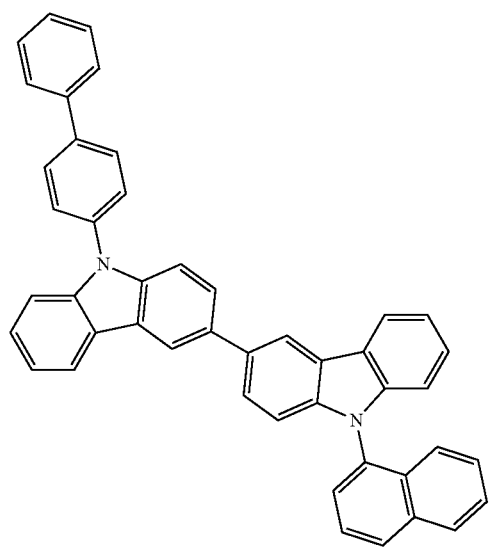
5-27
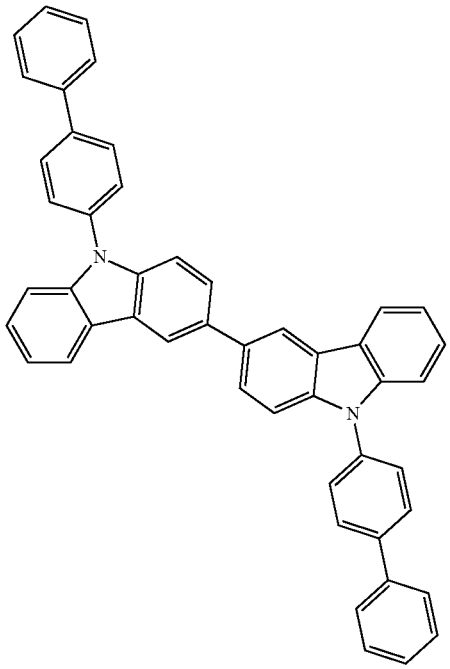
5-28
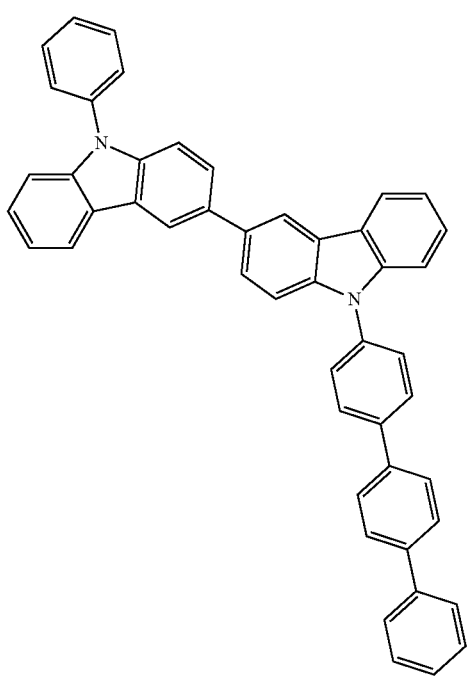

5-29
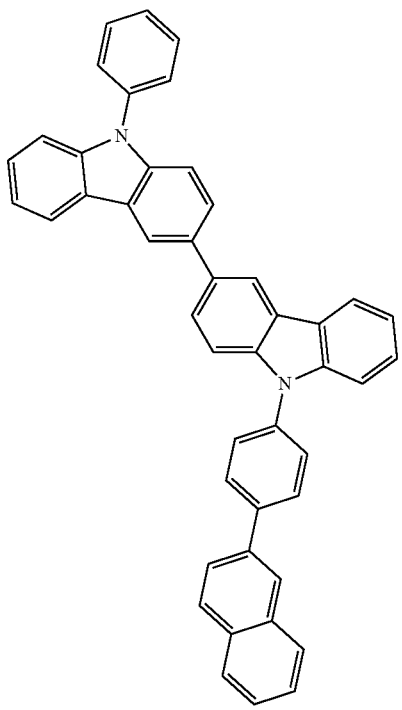
5-30
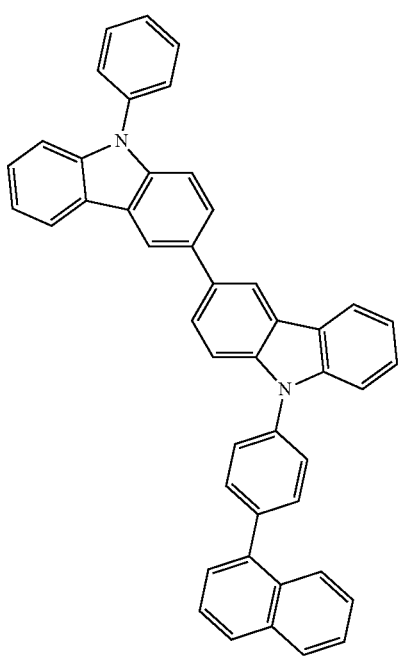
5-31
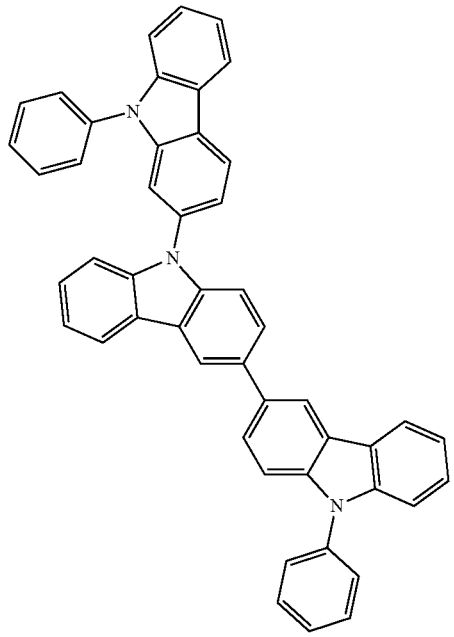
5-32
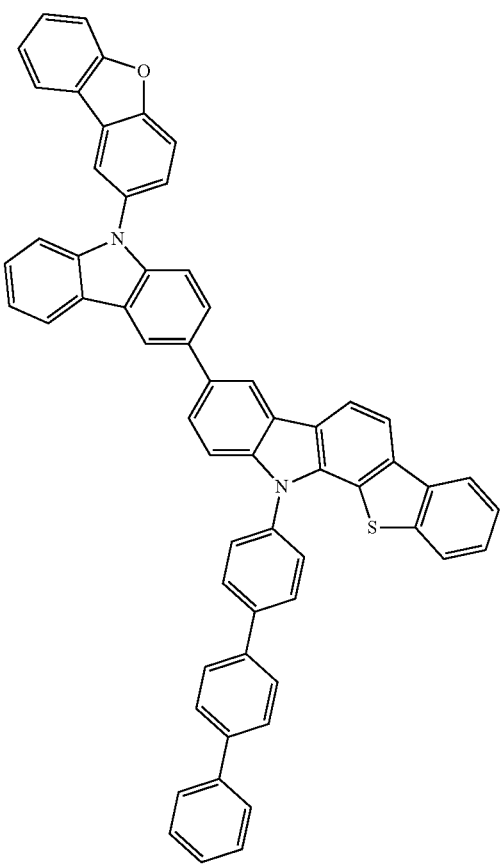

101
-continued
5-33
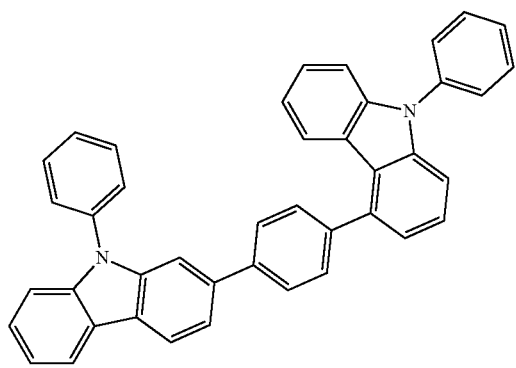
5-34
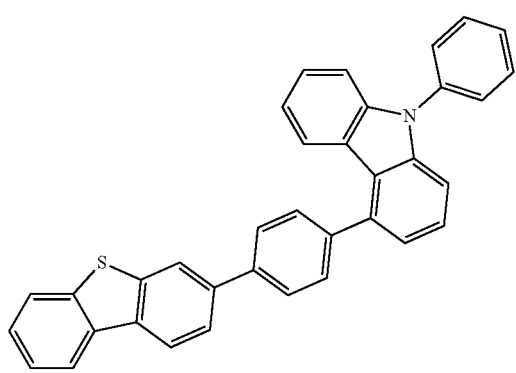
5-35
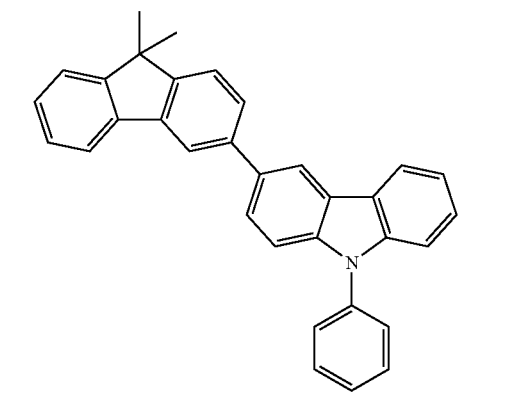
5-36
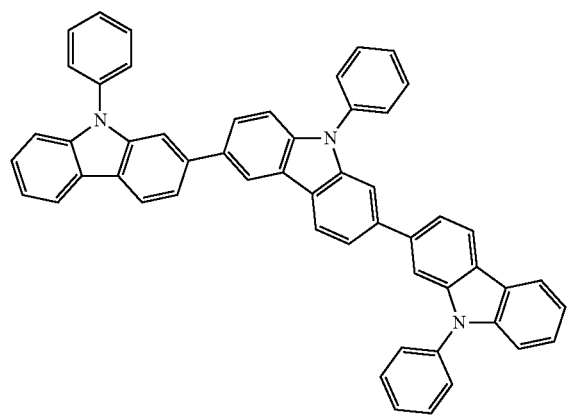
102
-continued
5-37
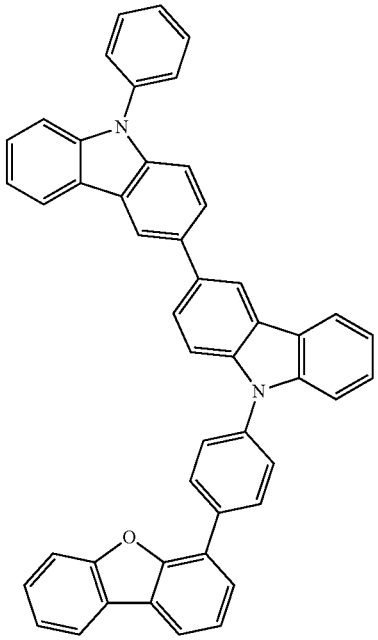
5-38
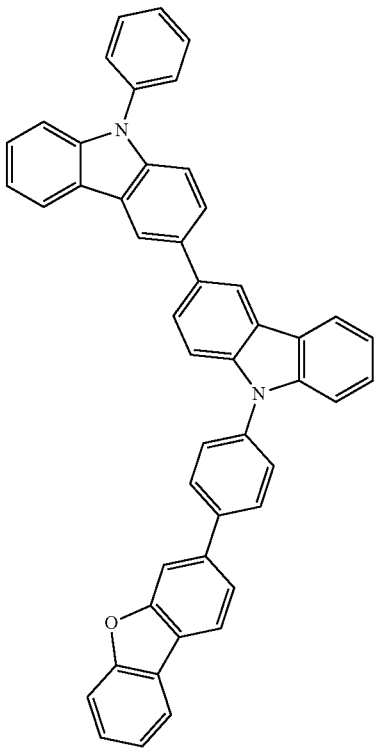

5-39
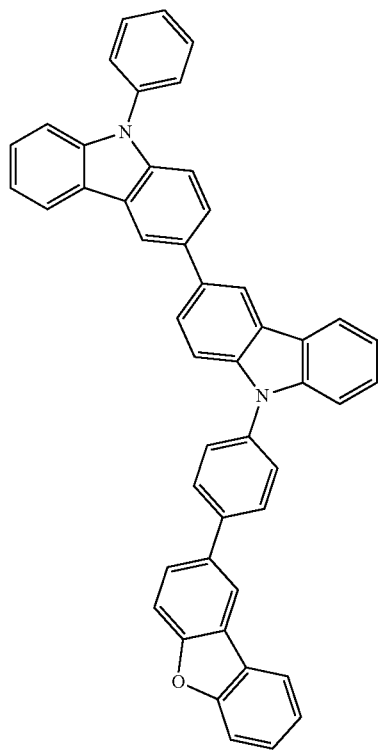
5-40
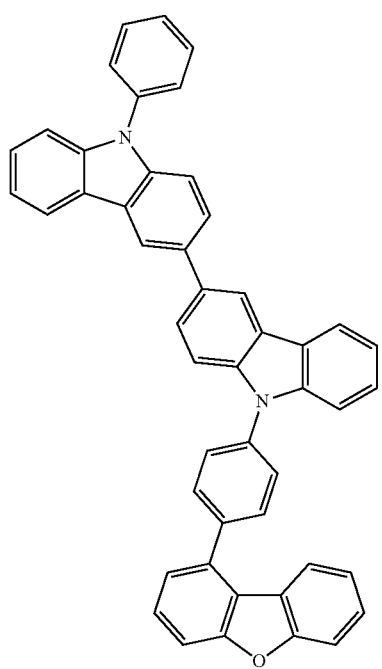
5-41
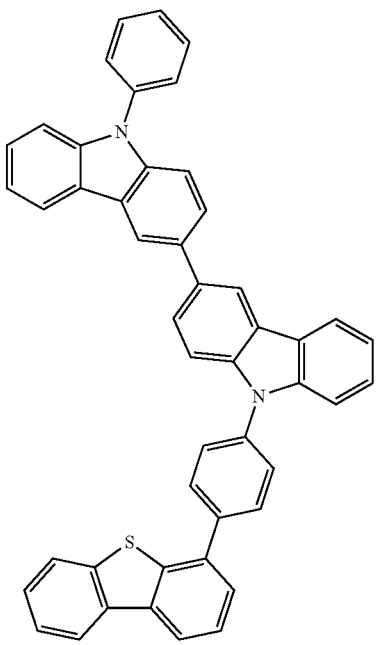
5-42
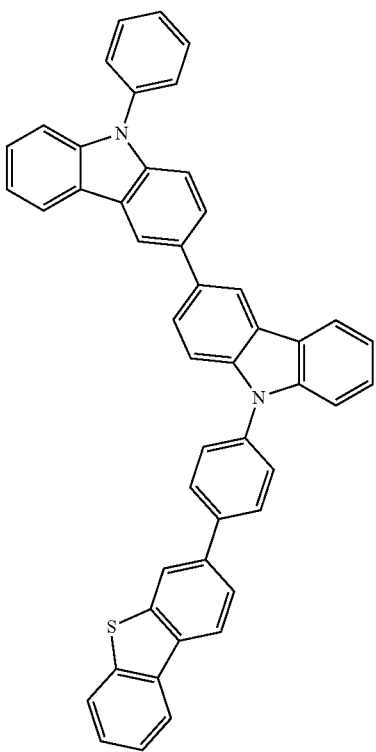

5-43
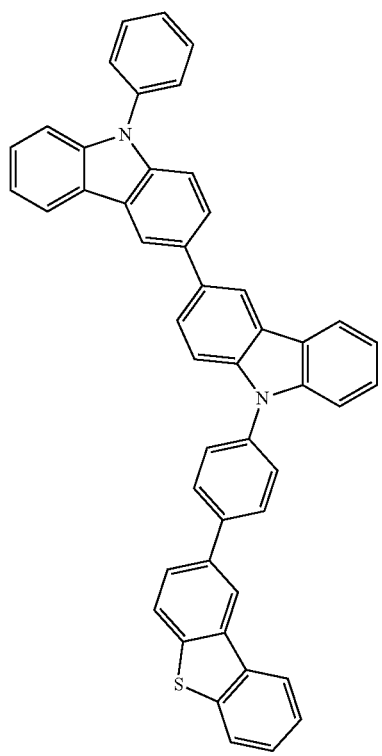
5-44
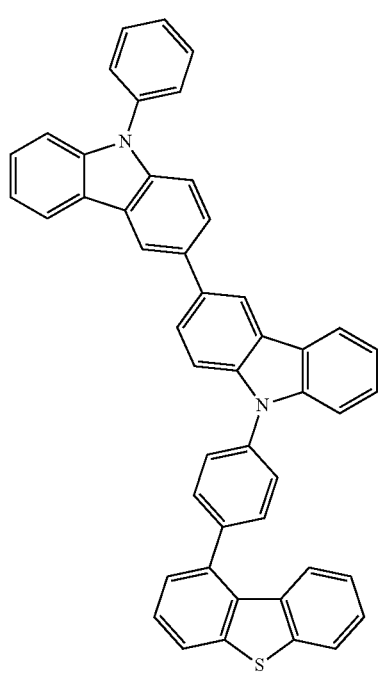
5-45
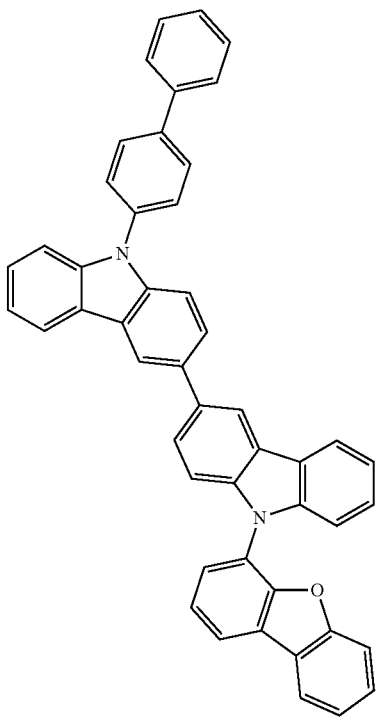
5-46
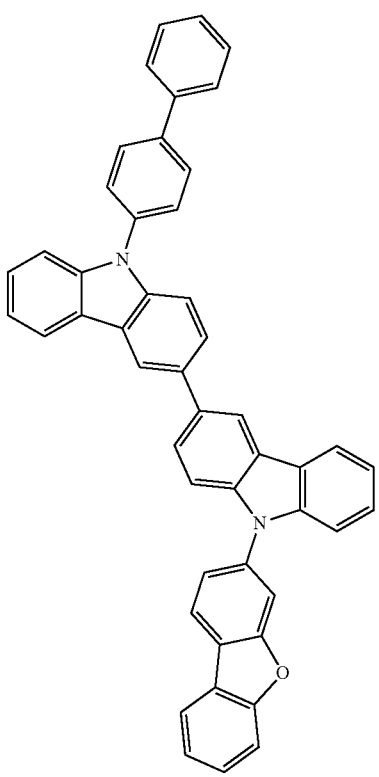

5-47
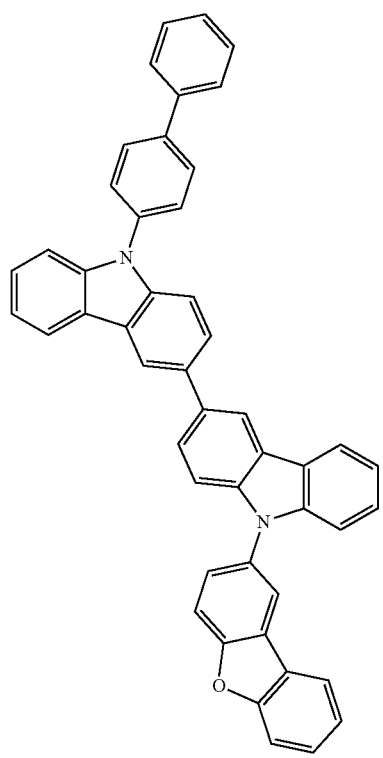
5-48
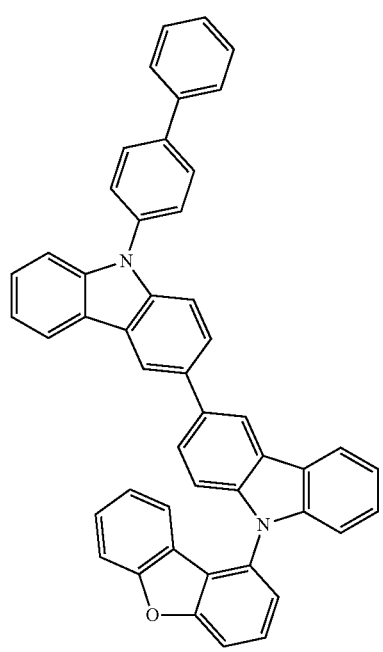
5-49
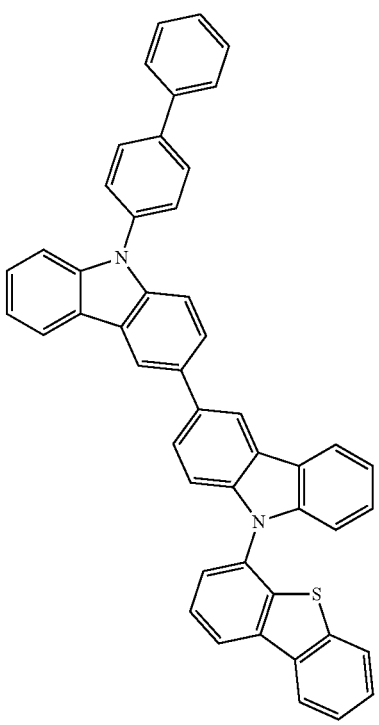
5-50
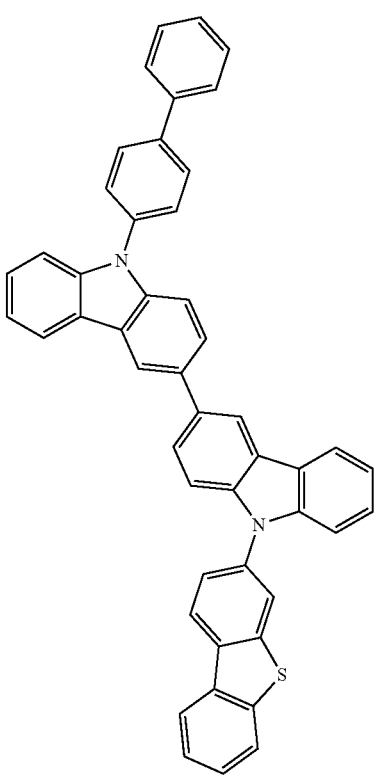

5-51
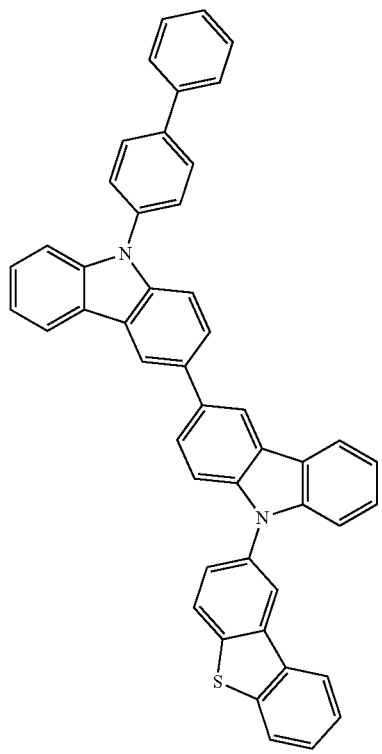
5-53
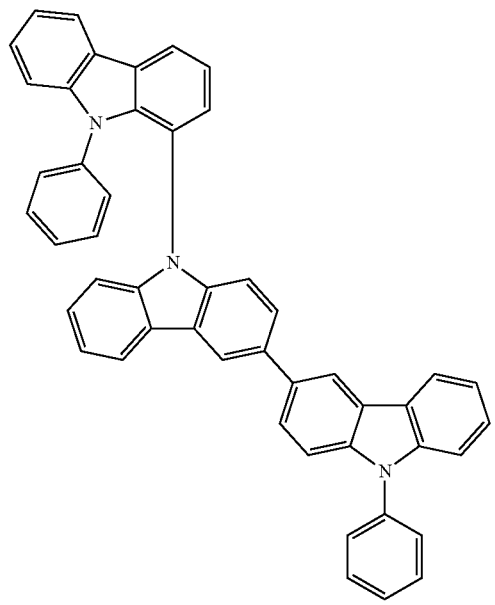
5-52
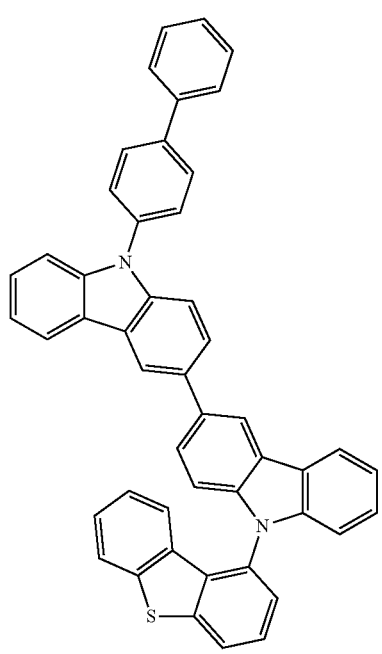
5-54
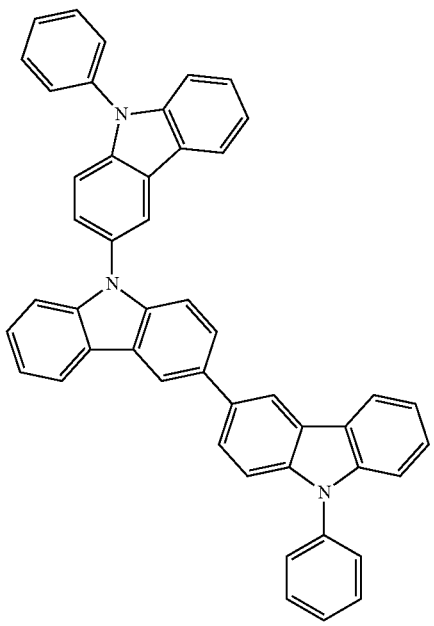

5-55
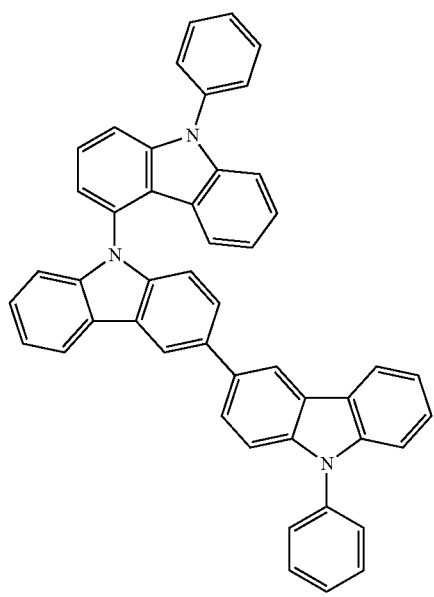
5-56
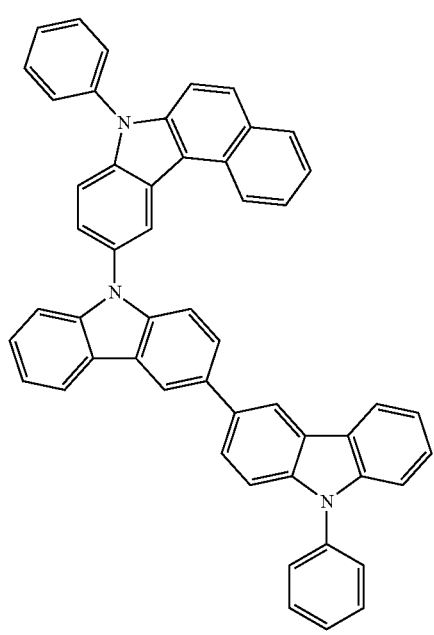
5-57
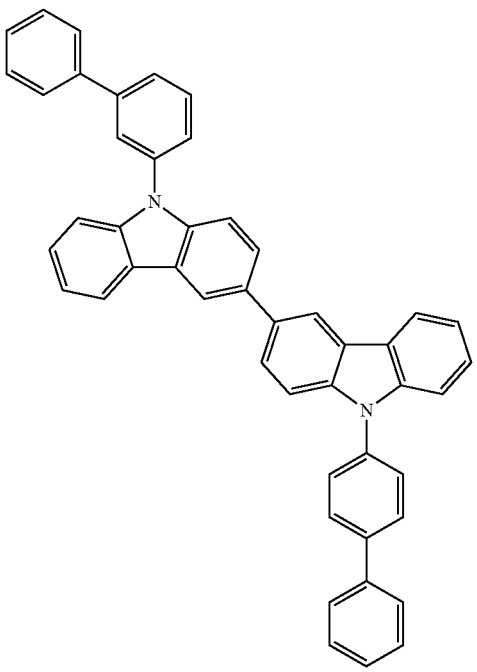
5-58
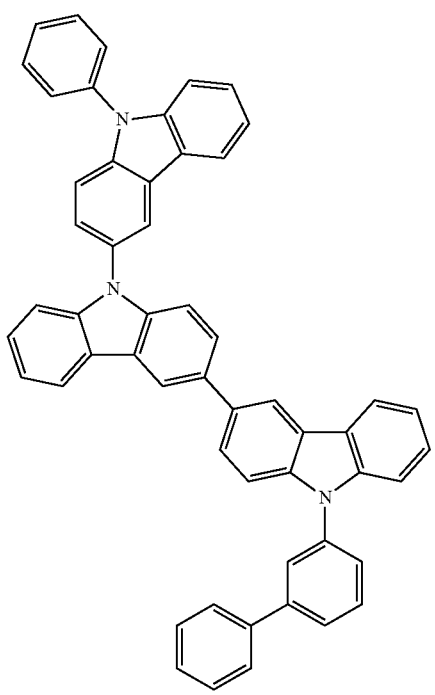

5-59

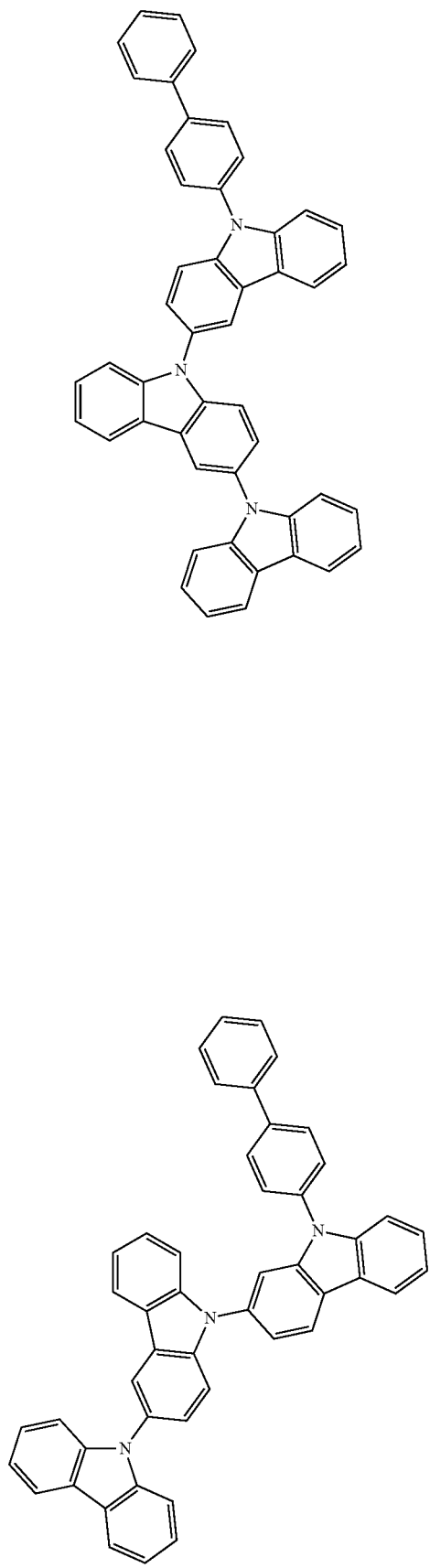

5-60

5-61

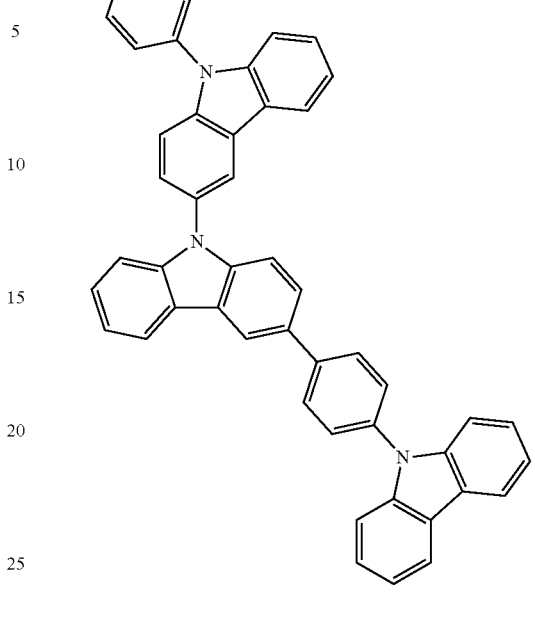

5-62

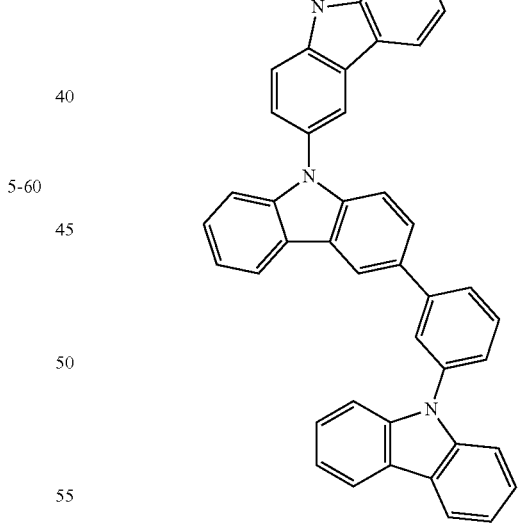

Preferably, the organic material layer of an organic element according to the present invention comprises a light emitting layer, a hole transport layer formed between the first electrode and the light emitting layer, and an emission-auxiliary layer formed between the light emitting layer and the hole transport layer, the light emitting layer comprises the compound represented by Formula 1, and the hole transport layer or the emission-auxiliary layer comprises the compound represented by Formula 20.

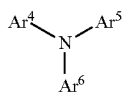
<Formula 20>

In Formula 20, each of symbols may be defined as follows.

$Ar^4$ and $Ar^5$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and $Ar^4$ and $Ar^5$ may be combined with each other to form a ring.

$Ar^6$ is selected from the group consisting of a $C_6$-$C_{60}$ aryl group, a fluorenyl group, and a $C_2$-$C_{60}$ heterocyclic group containing at least one heteroatom selected from the group consisting of O, N, S, Si, and P; or $Ar^6$ is selected from the group consisting of the following Formulas 1-a to 1-c.

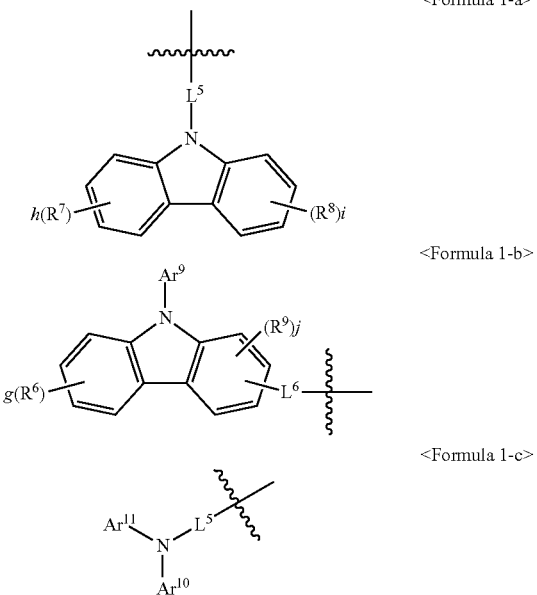

<Formula 1-a>

<Formula 1-b>

<Formula 1-c>

In Formula 1-a to 1-c, each of symbols may be defined as follows.

$Ar^9$ to $Ar^{11}$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$).

$L^5$ is selected from the group consisting of a $C_6$-$C_{60}$ arylene group, a fluorenylene group, and a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring.

$L^6$ is selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring.

$R^6$ to $R^9$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$).

h, i and g are each an integer of 0 to 4, j is an integer of 0 to 3, where each of these is an integer of 2 or more, a plurality of $R^6$s, a plurality of $R^7$s, a plurality of $R^8$s, a plurality of $R^9$s are the same as or different from each other. In addition, when h, i, j and g are each an integer of 2 or more, adjacent $R^6$ groups, adjacent $R^7$ groups, adjacent $R^8$ groups, or adjacent $R^9$ groups may be linked to each other to form a ring. Here, the ring formed by linking between adjacent groups may be a $C_6$-$C_{60}$ aromatic ring group, a $C_2$-$C_{60}$ heterocyclic group, a $C_3$-$C_{60}$ aliphatic ring, or a fused ring group formed by a $C_3$-$C_{60}$ aliphatic ring with a $C_6$-$C_{60}$ aromatic ring.

L', $R_a$ and $R_b$ are the same as defined for Formula 1.

$Ar^4$ to $Ar^6$, $Ar^9$ to $Ar^{11}$, $R^6$ to $R^9$, $L^5$, $L^6$, and the ring formed by bonding between neighboring groups may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, a $C_8$-$C_{20}$ arylalkenyl group and a combination thereof.

Preferably, the light emitting layer may further comprise the compound represented by Formula 12.

Preferably, the hole transport layer comprises the compound represented by the following Formula 21 or Formula 22 and the emission-auxiliary layer comprises the compound represented by the following Formula 23 or Formula 24.

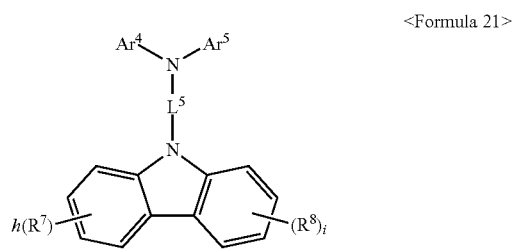

<Formula 21>

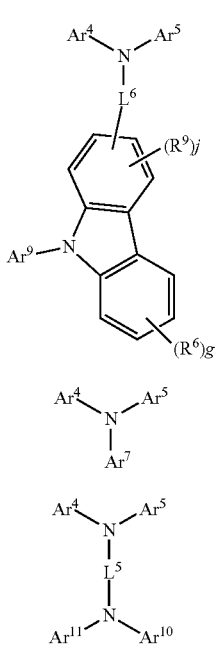

<Formula 22>

<Formula 23>

<Formula 24>

In Formulas 21 to 24, $Ar^4$, $Ar^5$, $Ar^9$ to $Ar^{11}$, h, i, g, j, $L^5$, $L^6$, $R^6$ to $R^9$ are the same as defined above, $Ar^7$ is selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, and a $C_3$-$C_{60}$ aliphatic ring.

Preferably, in Formula 24, at least one of $Ar^4$, $Ar^5$, $Ar^{10}$ and $Ar^{11}$ may be represented by Formula 24-1.

l', m' and n' are each an integer of 0 to 4, where each of these is an integer of 2 or more, a plural of $R^{a'}$'s, a plural of $R^{b'}$'s or a plural of $R^{c'}$'s are each the same or different from each other.

$Ar_{1'}$ is selected from the group consisting of a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom selected from the group consisting of O, N, S, Si, and P, $C_3$-$C_{20}$ cycloalkyl group, and a fused ring group formed by a $C_3$-$C_{60}$ aliphatic ring with a $C_6$-$C_{60}$ aromatic ring.

$R^{a'}$, $R^{b'}$, $R^{c'}$, $Ar_{1'}$ and the ring formed by bonding between neighboring may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, a $C_8$-$C_{20}$ arylalkenyl group and a combination thereof.

In addition, preferably, in Formula 24, $Ar_{1'}$ and $L^5$ are each independently a $C_6$-$C_{60}$ arylene group, for example, phenyl, biphenyl, o-terphenyl, m-terphenyl, p-terphenyl or naphthalene.

Preferably, Formula 24 may be represented by the following Formula A.

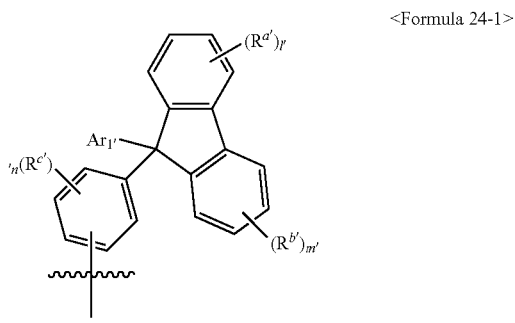

<Formula 24-1>

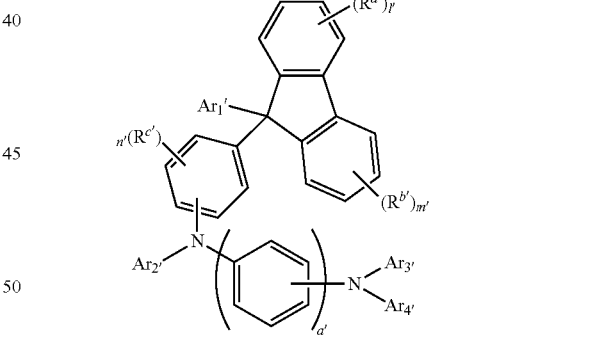

<Formula A>

In Formula 24-1, each of symbols may be defined as follows.

$R^{a'}$, $R^{b'}$ and $R^{c'}$ are each independently selected from the group consisting of hydrogen, deuterium, halogen, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom selected from the group consisting of O, N, S, Si, and P, $C_3$-$C_{20}$ cycloalkyl group, and a fused ring group formed by a $C_3$-$C_{60}$ aliphatic ring with a $C_6$-$C_{60}$ aromatic ring, and adjacent groups may be optionally linked to each other to form a ring. When adjacent $R^{a'}$ groups, adjacent $R^{b'}$ groups, or adjacent $R^{c'}$ groups are linked to each other to form a ring, the ring may be a $C_6$-$C_{60}$ aromatic ring group, a $C_2$-$C_{60}$ heterocyclic group, a $C_3$-$C_{60}$ aliphatic ring, or a fused ring group formed by a $C_3$-$C_{60}$ aliphatic ring with a $C_6$-$C_{60}$ aromatic ring.

In Formula A, $R^{a'}$, $R^{b'}$, $R^{c'}$, $Ar_{1'}$, l', m' and n' are the same as defined for Formula 24-1, $Ar_{2'}$ is the same as defined for $Ar^{11}$ in Formula 24, $Ar_{3'}$ is the same as defined for $Ar^4$ in Formula 24, $Ar_{4'}$ is the same as defined for $Ar^5$ in Formula 24, and a' is an integer of 1 to 3. That is, in Formula A, each of symbols may be defined as follows.

$R^{a'}$, $R^{b'}$ and $R^{c'}$ are each independently selected from the group consisting of hydrogen, deuterium, halogen, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom selected from the group consisting of O, N, S, Si, and P, $C_3$-$C_{20}$ cycloalkyl group, and a fused ring group formed by a $C_3$-$C_{60}$ aliphatic ring with a $C_6$-$C_{60}$ aromatic ring, and adjacent groups may be optionally linked to each other to form a ring. When adjacent $R^{a'}$ groups, adjacent $R^{b'}$ groups, or adjacent $R^{c'}$ groups are linked to each other to form a ring, the ring may be a $C_6$-$C_{60}$ aromatic ring group, a $C_2$-$C_{60}$ heterocyclic group, a $C_3$-$C_{60}$ aliphatic ring, or a fused ring group formed by a $C_3$-$C_{60}$ aliphatic ring with a $C_6$-$C_{60}$ aromatic ring.

l', m' and n' are each an integer of 0 to 4, where each of these is an integer of 2 or more, a plural of $R^{a'}$s, a plural of $R^{b'}$s or a plural of $R^{c'}$s are each the same or different from each other.

$Ar_{1'}$ is selected from the group consisting of a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom selected from the group consisting of O, N, S, Si, and P, $C_3$-$C_{20}$ cycloalkyl group, and a fused ring group formed by a $C_3$-$C_{60}$ aliphatic ring with a $C_6$-$C_{60}$ aromatic ring.

Where $Ar_{1'}$ is an aryl group, $Ar_{1'}$ may be preferably a $C_6$-$C_{18}$ aryl group, more preferably a $C_6$-$C_{12}$ aryl group, for example, phenyl, biphenyl, terphenyl, naphthyl or the like.

$Ar_{2'}$, $Ar_{3'}$ and $Ar_{4'}$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), $Ar^4$ and $Ar^5$ may be linked to each other to form a ring.

Where $Ar_{2'}$ is an aryl group, $Ar_{2'}$ may be preferably a $C_6$-$C_{30}$ aryl group, more preferably a $C_6$-$C_{18}$ aryl group, for example, phenyl, naphthyl, biphenyl, terphenyl or the like. Where $Ar_{2'}$ is a heterocyclic group, $Ar_{2'}$ may be preferably a $C_2$-$C_{30}$ heterocyclic group, more preferably a $C_2$-$C_{16}$ heterocyclic group, for example, dibenzofuran, dibenzothiophene and the like. Where $Ar_{2'}$ is a fluorenyl group, $Ar_{2'}$ may be 9,9-dimethylfluorene, 9,9-diphenylfluorene, 9,9'-spirobifluorene and the like.

Where $Ar_{3'}$ and $Ar_{4'}$ are each an aryl group, $Ar_{3'}$ and $Ar_{4'}$ may be preferably a $C_6$-$C_{30}$ aryl group, more preferably a $C_6$-$C_{18}$ aryl group, for example, phenyl, biphenyl, terphenyl, naphthyl, triphenylene, phenanthrene or the like. Where $Ar_{3'}$ and $Ar_{4'}$ are each a heterocyclic group, $Ar_{3'}$ and $Ar_{4'}$ may be preferably a $C_2$-$C_{30}$ heterocyclic group, more preferably a $C_2$-$C_{12}$ heterocyclic group, for example, dibenzofuran, dibenzothiophene and the like. Where $Ar_{3'}$ and $Ar_{4'}$ are each a fluorenyl group, $Ar_{3'}$ and $Ar_{4'}$ may be 9,9-dimethylfluorene, 9,9-diphenylfluorene, 9,9'-spirobifluorene and the like.

L' is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, $R_a$ and $R_b$ are each independently selected from the group consisting of hydrogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring.

$R^{a'}$, $R^{b'}$, $R^{c'}$, $R_a$, $R_b$, $Ar_{1'}$ to $Ar_{4'}$, L' and a ring formed by bonding between neighboring groups may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, a $C_8$-$C_{20}$ arylalkenyl group and a combination thereof.

Formula A may be represented by one of Formula B to Formula D.

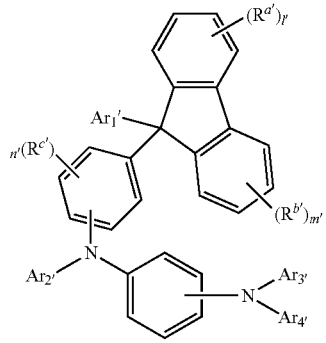

<Formula B>

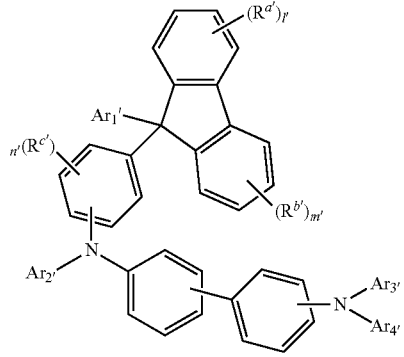

<Formula C>

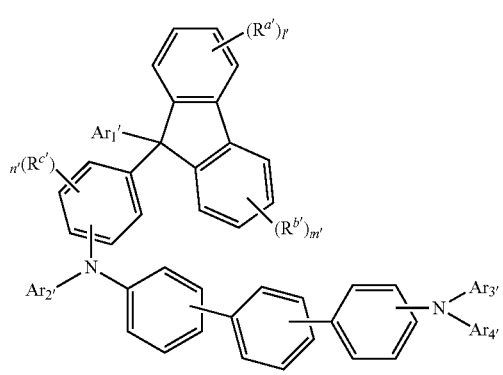

<Formula D>

In Formulas B to D, $R^{a'}$, $R^{b'}$, $R^{c'}$, l', m', n', $Ar_{1'}$ to $Ar_{4'}$ are the same as defined for Formula A.

In addition, Formula A may be represented by one of Formula E to Formula G.

<Formula E>
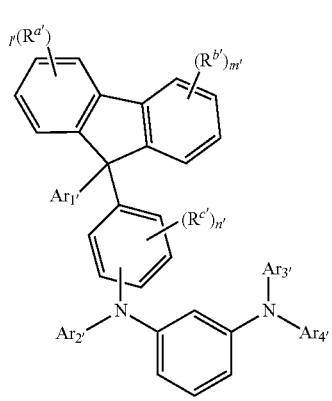
<Formula F>
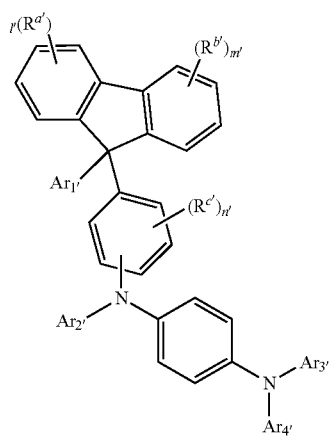
<Formula G>
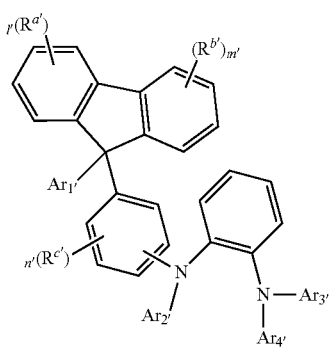
<Formula H>
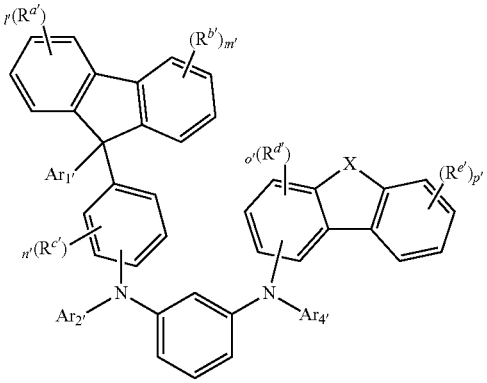
<Formula I>
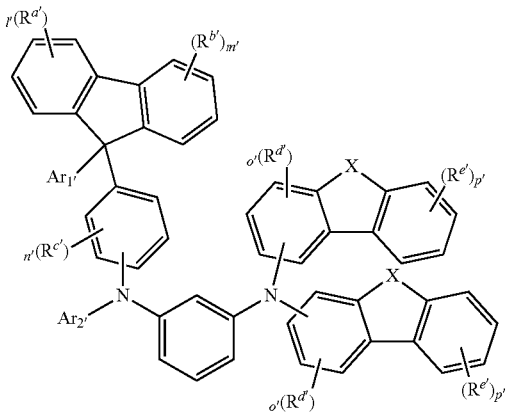
<Formula J>
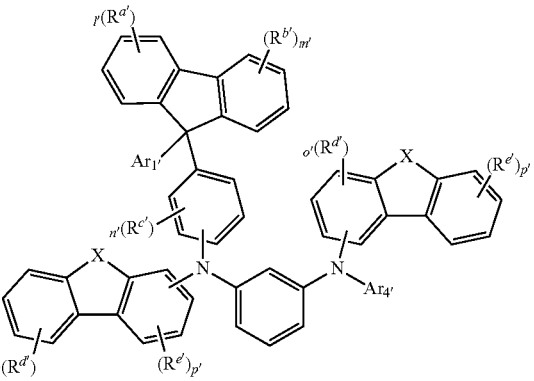
In Formulas E to G, $R^{a'}$, $R^{b'}$, $R^{c'}$, l', m', n', $Ar_{1'}$ to $Ar_{4'}$ are the same as defined for Formula A.
In addition, Formula A may be represented by one of Formula H to Formula K.

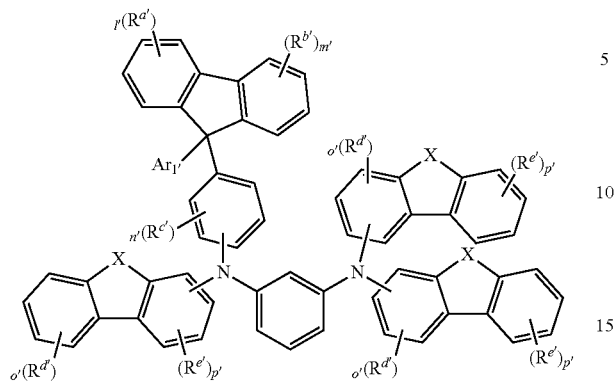

<Formula K>

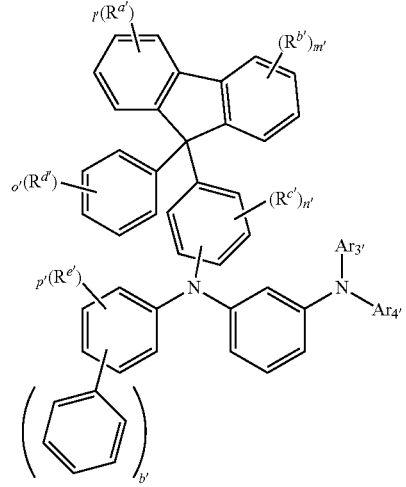

<Formula L>

In Formulas H to K, $R^{a'}$, $R^{b'}$, $R^{c'}$, l', m', n', $Ar_{1'}$ to $Ar_{3'}$ are the same as defined for Formula A.

X is independently O, S or C(R')(R"), $R^{d'}$, $R^{e'}$, R' and R" are each independently selected from the group consisting of hydrogen, deuterium, halogen, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom selected from the group consisting of O, N, S, Si, and P, $C_3$-$C_{20}$ cycloalkyl group, and a fused ring group formed by a $C_3$-$C_{60}$ aliphatic ring with a $C_6$-$C_{60}$ aromatic ring, and adjacent groups may be optionally linked to each other to form a ring. Where adjacent $R^{d'}$ groups or adjacent $R^{a'}$ groups are linked to each other to form a ring, the ring may be a $C_6$-$C_{60}$ aromatic ring group, a $C_2$-$C_{60}$ heterocyclic group, a $C_3$-$C_{60}$ aliphatic ring, or a fused ring group formed by a $C_3$-$C_{60}$ aliphatic ring with a $C_6$-$C_{60}$ aromatic ring, and when R' group and R" group are linked to each other to form a ring, a spiro compound may be formed together with C to which they are attached.

o' is independently an integer of 0 to 3, p' is independently an integer of 0 to 4, where o' is an integer of 2 or more, a plural of $R^{d'}$s are each the same or different from each other, where p' is an integer of 2 or more, a plural of $R^{e'}$s are each the same or different from each other.

$R^{d'}$, $R^{e'}$, R', R" and the ring formed by bonding between neighboring groups may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, a $C_8$-$C_{20}$ arylalkenyl group and a combination thereof.

Formula A may be represented by one of Formula L to Formula O.

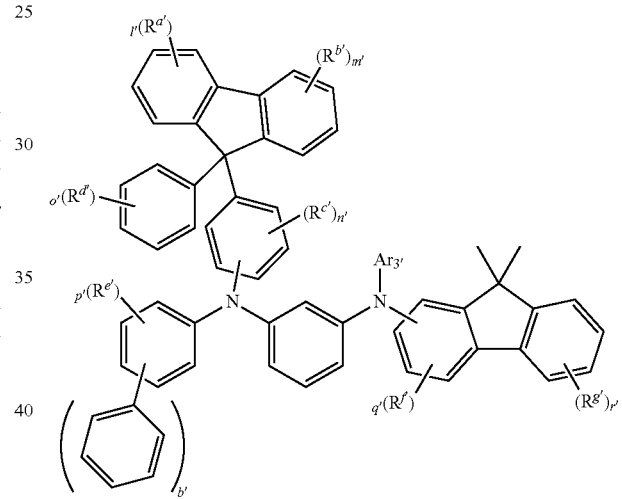

<Formula M>

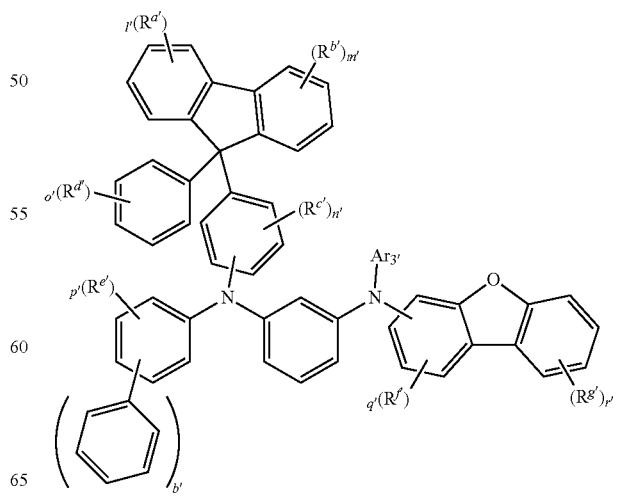

<Formula N>

<Formula O>

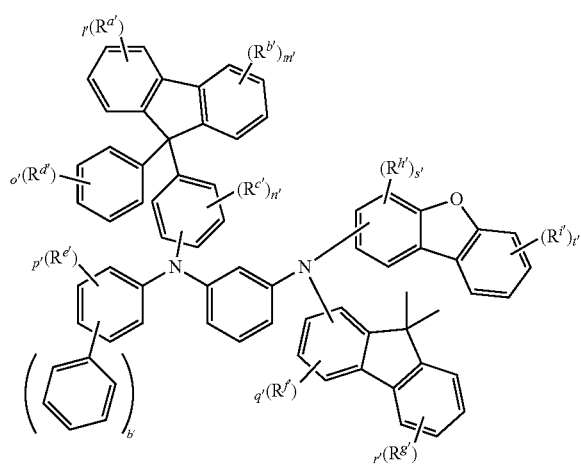

In Formulas H to K, $R^{a'}$, $R^{b'}$, $R^{c'}$, l', m', n', $Ar_{3'}$ and $Ar_{4'}$ are the same as defined for Formula A.

$R^{e'}$, $R^{f'}$, $R^{g'}$, $R^{h'}$ and $R^{i'}$ are each independently selected from the group consisting of hydrogen, deuterium, halogen, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom selected from the group consisting of O, N, S, Si, and P, $C_3$-$C_{20}$ cycloalkyl group, and a fused ring group formed by a $C_3$-$C_{60}$ aliphatic ring with a $C_6$-$C_{60}$ aromatic ring, and adjacent groups may be optionally linked to each other to form a ring. Where adjacent $R^{e'}$ groups, adjacent $R^{f'}$ groups, adjacent $R^{g'}$ groups, adjacent $R^{h'}$ groups, or adjacent $R^{i'}$ groups are linked to each other to form a ring, the ring may be a $C_6$-$C_{60}$ aromatic ring group, a $C_2$-$C_{60}$ heterocyclic group, a $C_3$-$C_{60}$ aliphatic ring, or a fused ring group formed by a $C_3$-$C_{60}$ aliphatic ring with a $C_6$-$C_{60}$ aromatic ring.

p', r' and t' are each independently an integer of 0 to 3, q' and s' are each independently an integer of 0 to 4, where each of these is an integer of 2 or more, each of $R^{e'}$'s, each of $R^{f'}$'s, each of $R^{g'}$'s, each of $R^{h'}$'s, and each of $R^{i'}$'s is each the same or different from each other.

b' is an integer of 0 to 3.

$R^{e'}$, $R^{f'}$, $R^{g'}$, $R^{h'}$, $R^{i'}$ and the ring formed by bonding between neighboring groups may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, a $C_8$-$C_{20}$ arylalkenyl group and a combination thereof.

Specifically, the compound represented by formula 20 may be one of the following compounds, but it is not limited thereto.

13-1

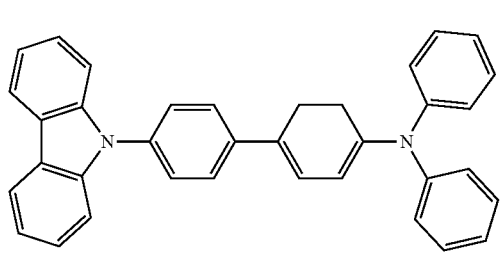

13-2

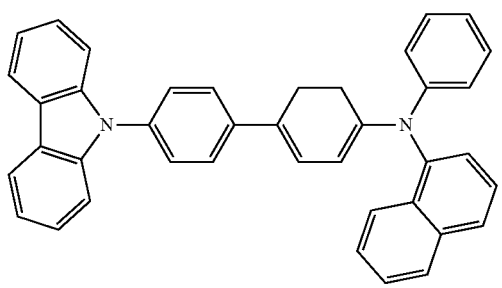

13-3

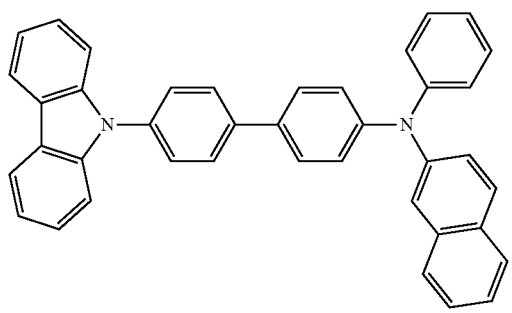

13-4

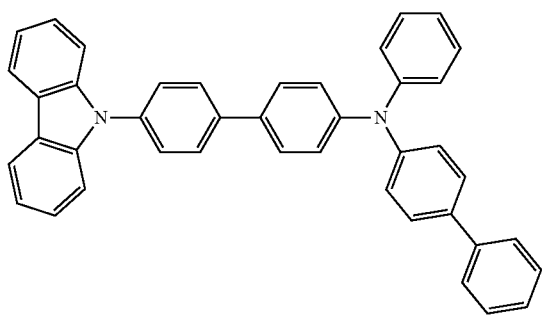

-continued
13-5
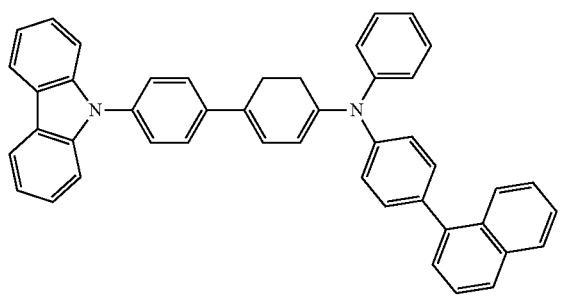
13-6
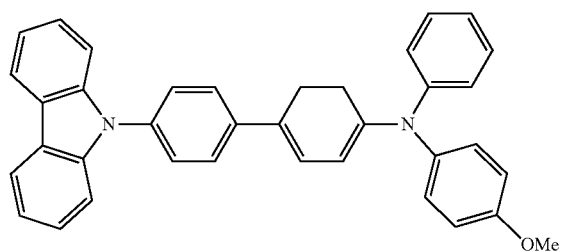
13-7
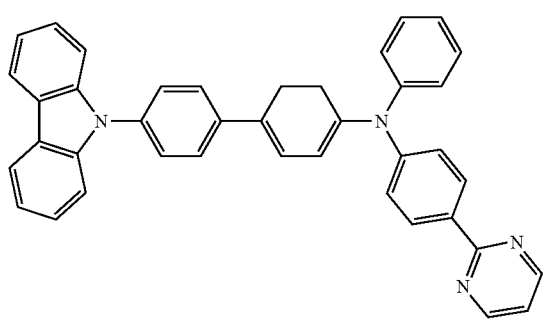
13-8
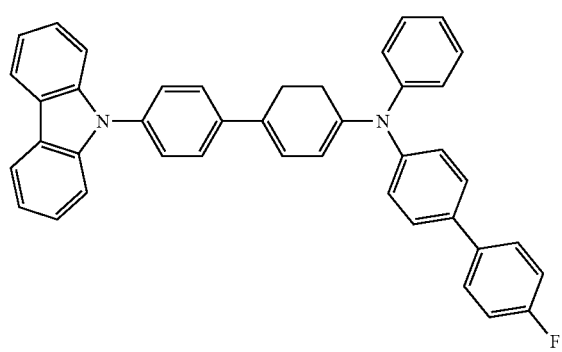
13-9
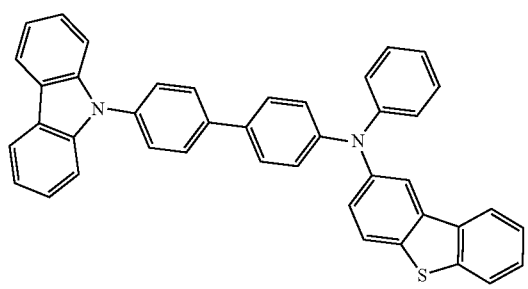
13-10
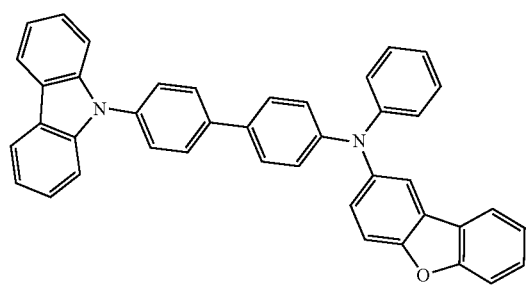
13-11
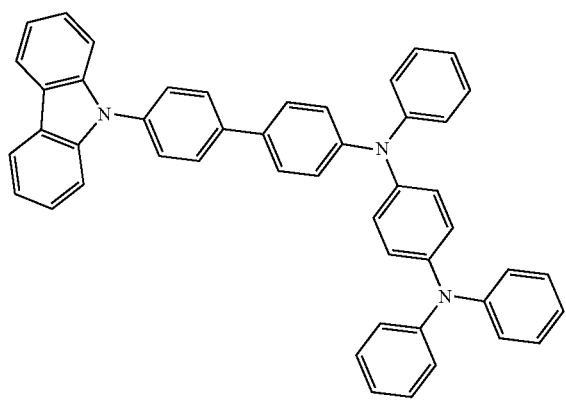
13-12
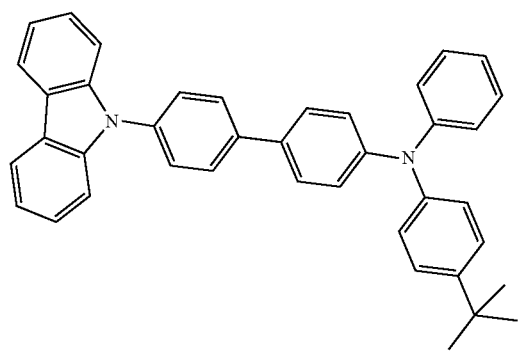

-continued
13-13
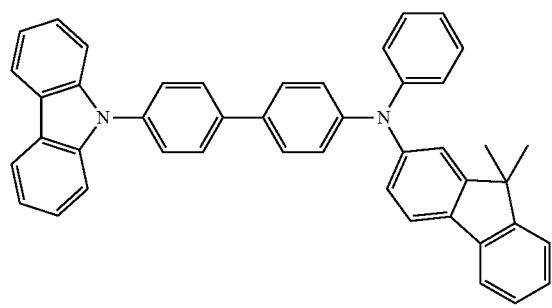
13-14
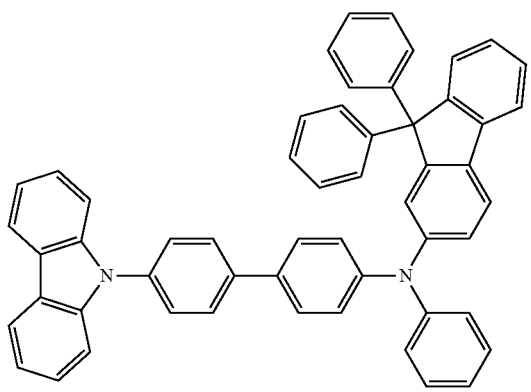
13-15
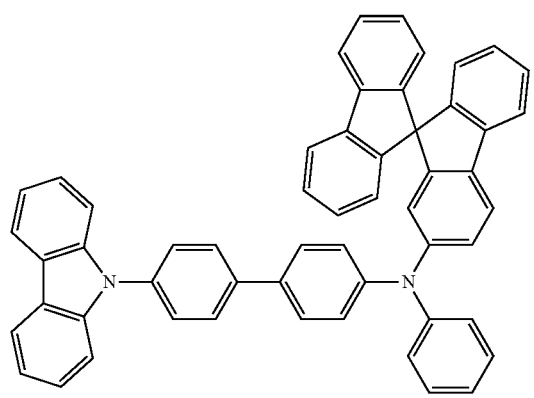
13-16
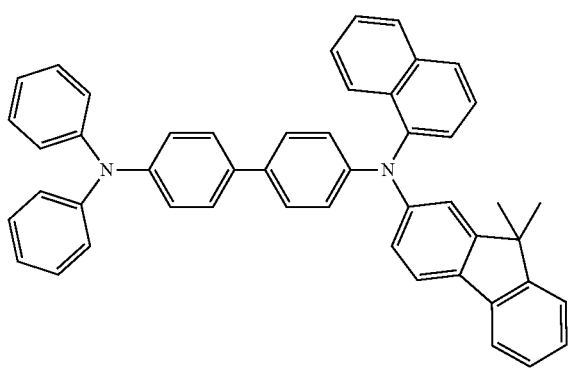
13-17
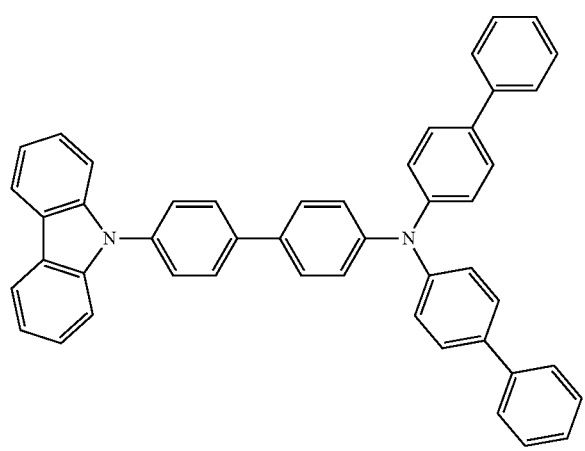
13-18
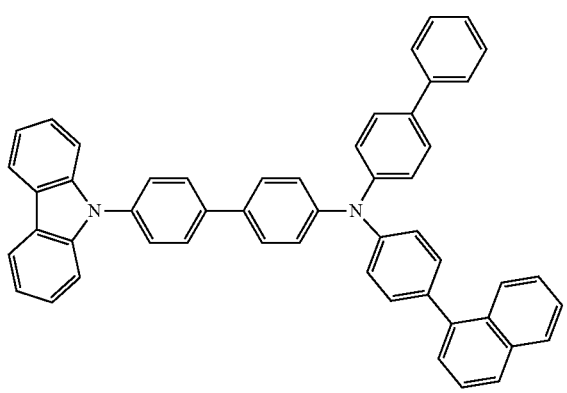

-continued
13-19
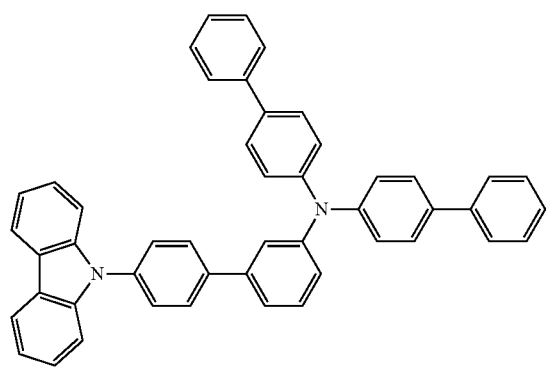
13-20
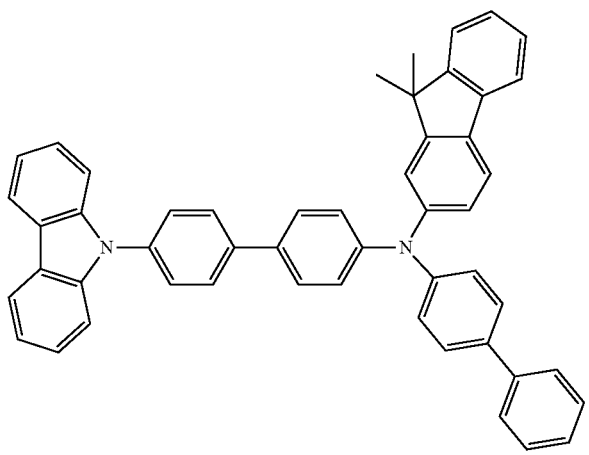
13-21
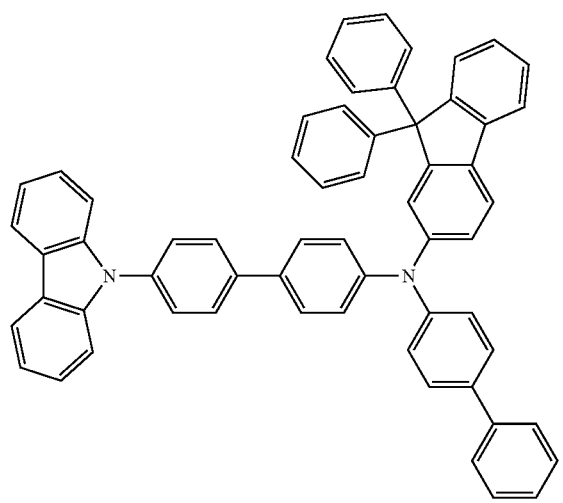
13-22
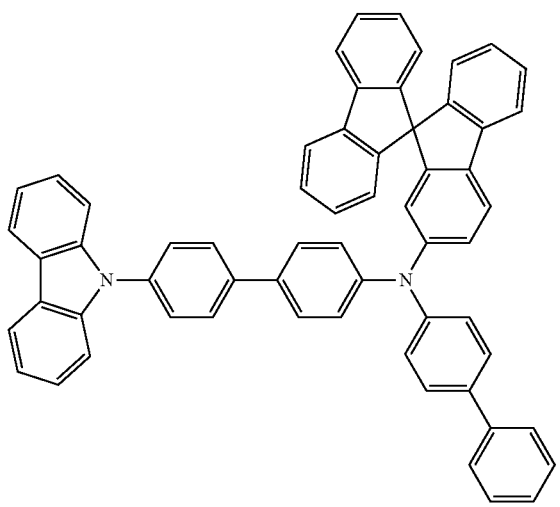
13-23
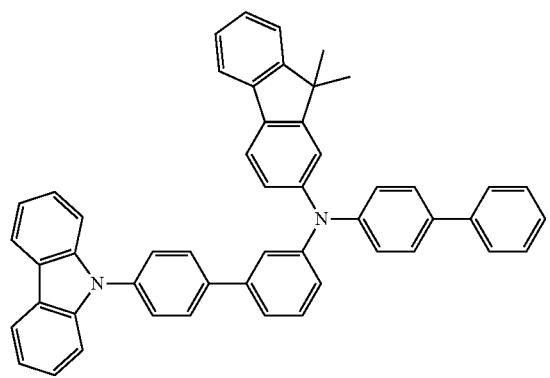
13-24
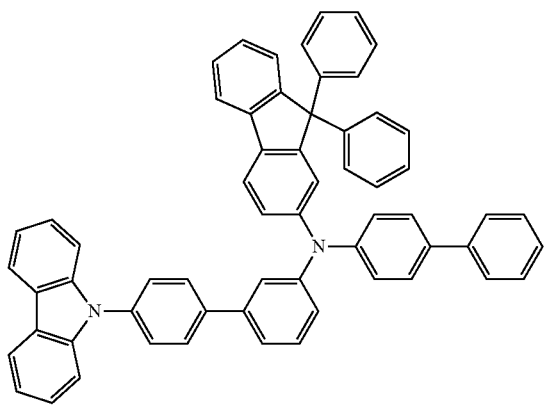

13-25
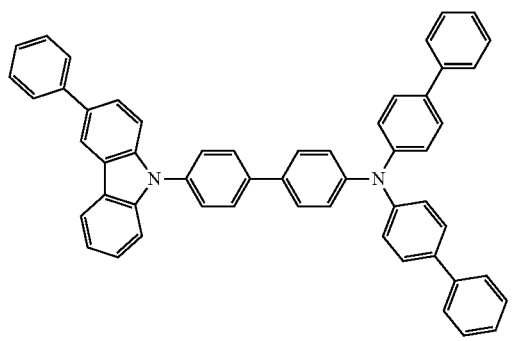
13-26
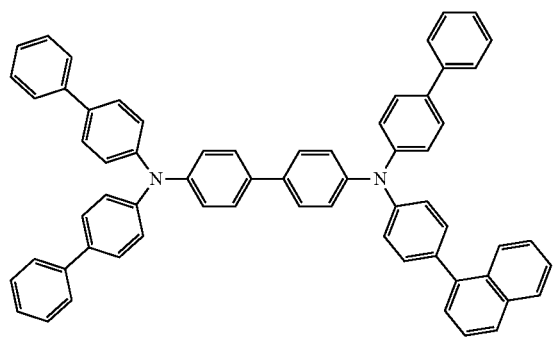
13-27
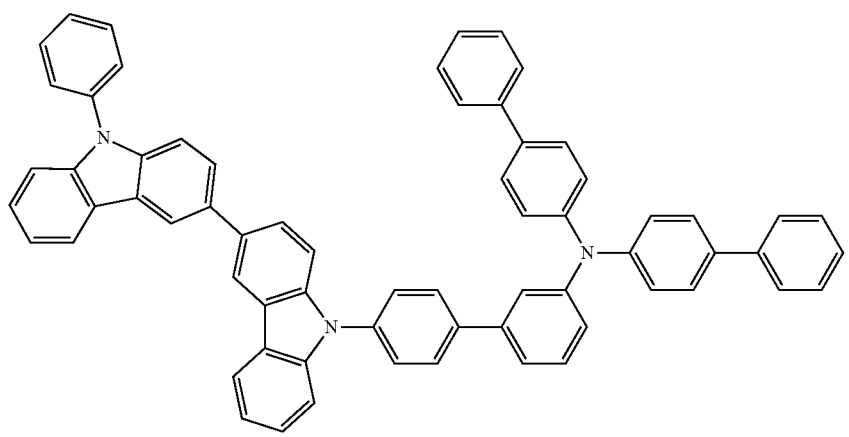
13-28
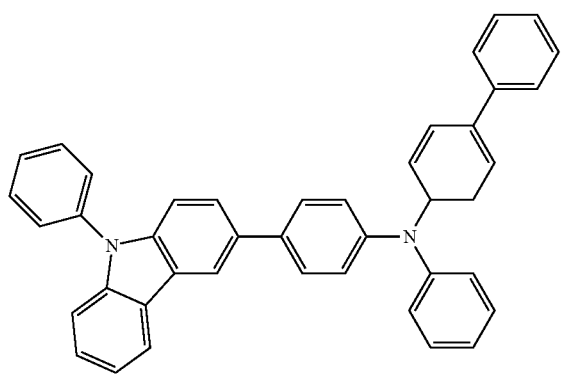
13-29
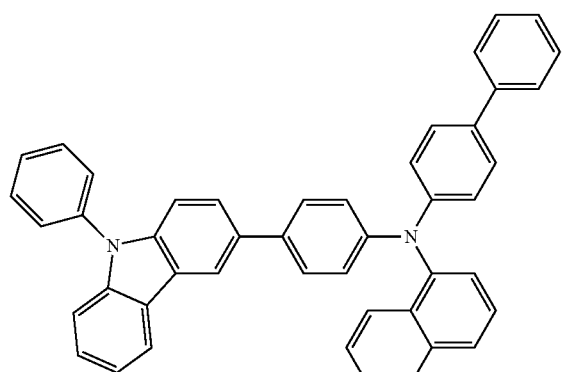

-continued
13-30
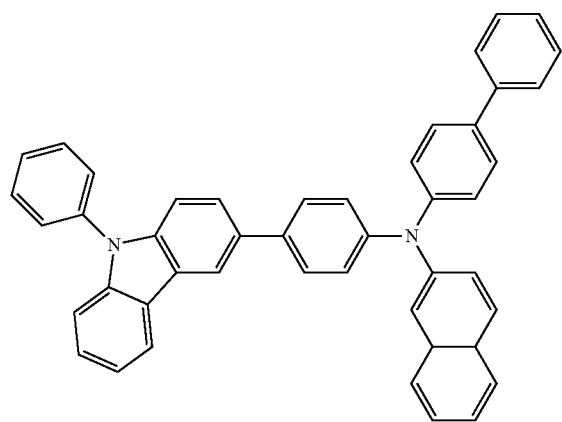
13-31
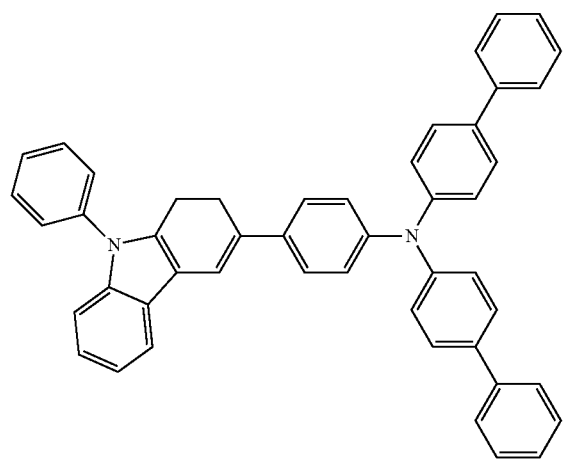
13-32
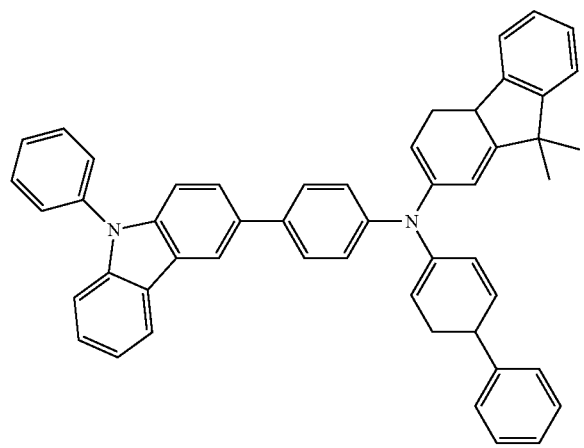
13-33
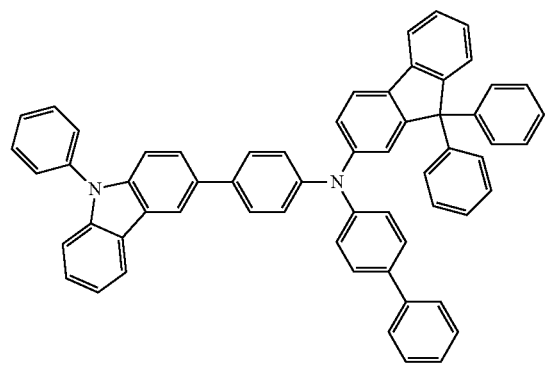
13-34
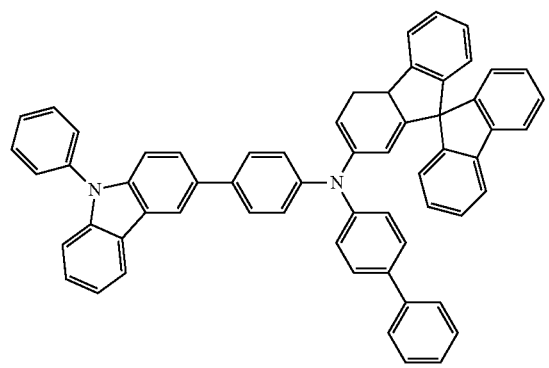
13-35
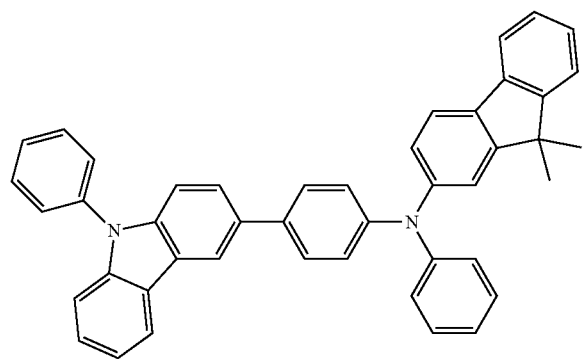

-continued
13-36
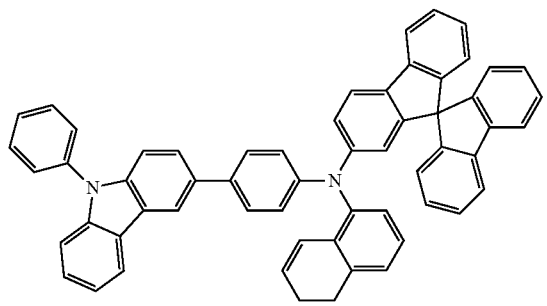
13-37
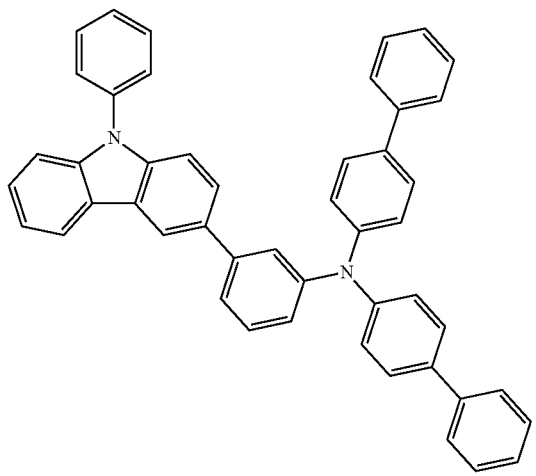
13-38
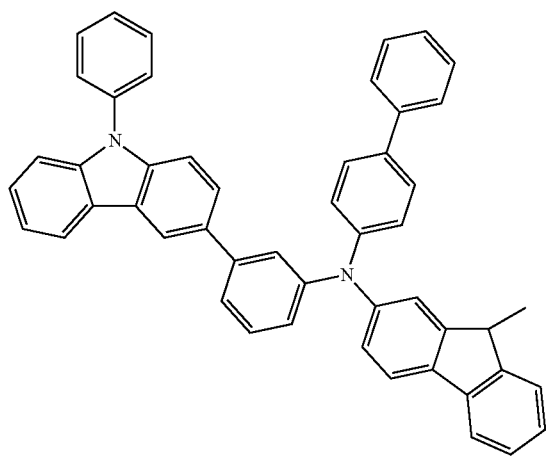
13-39
13-40
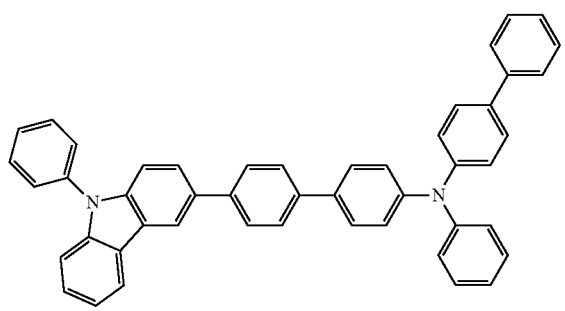
13-41
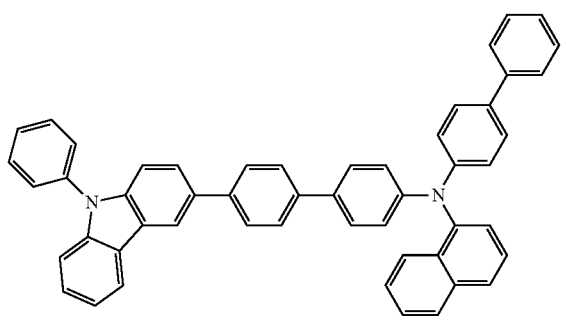

-continued
13-42
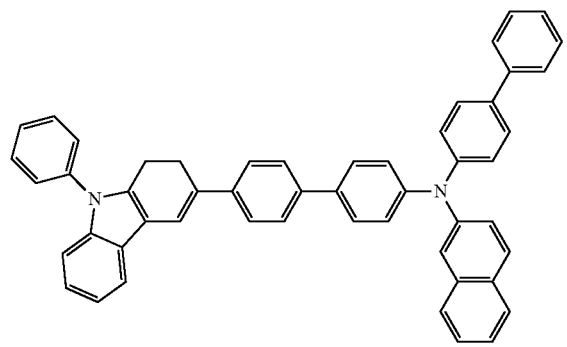
13-43
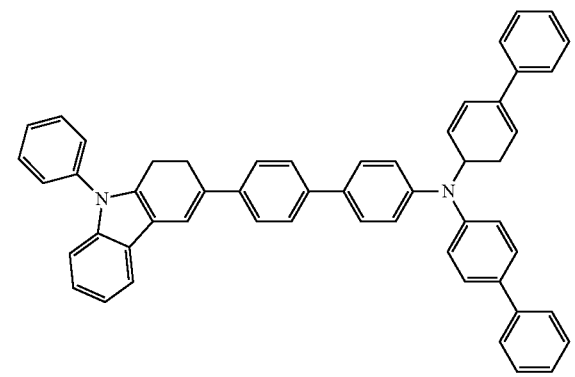
13-44
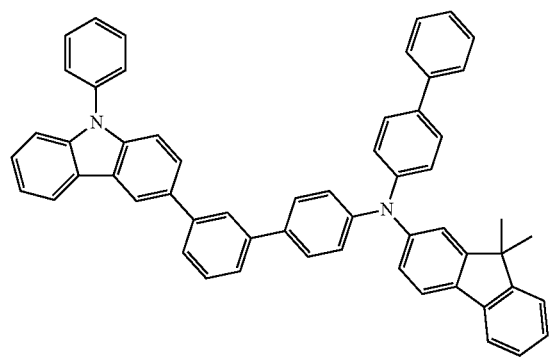
13-45
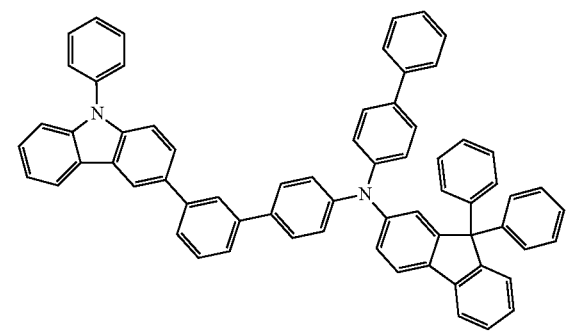
13-46
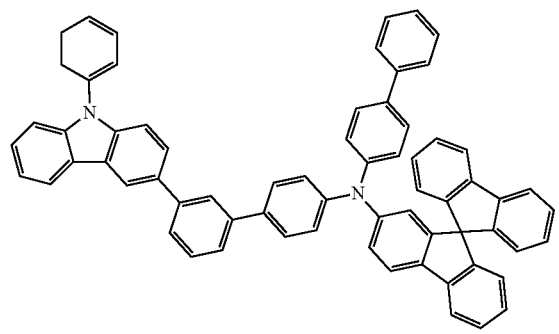
13-47
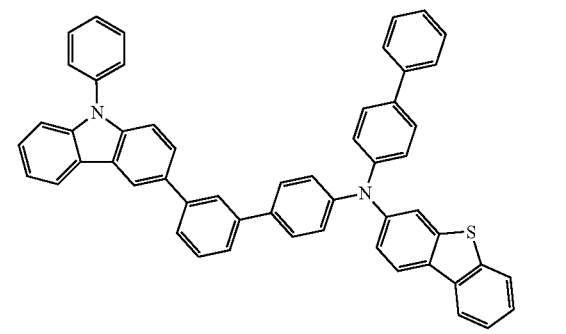
13-48
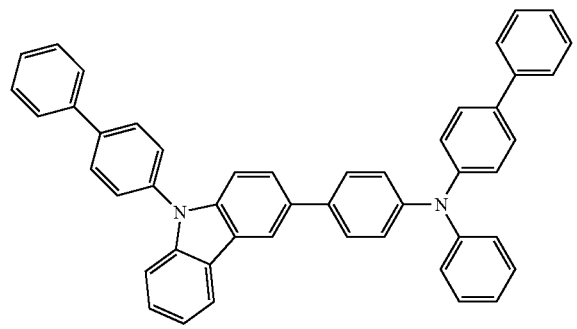
13-49
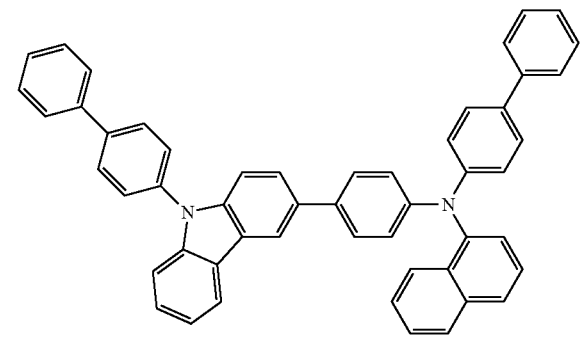

-continued
13-50
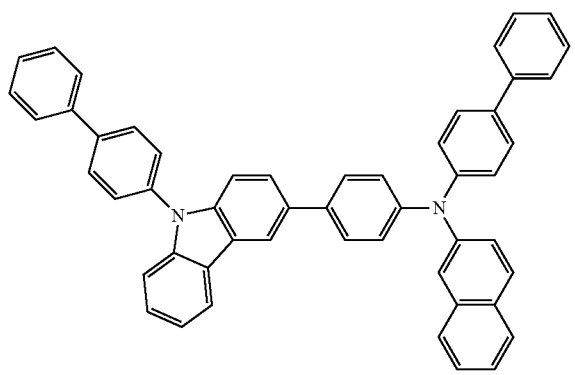
13-51
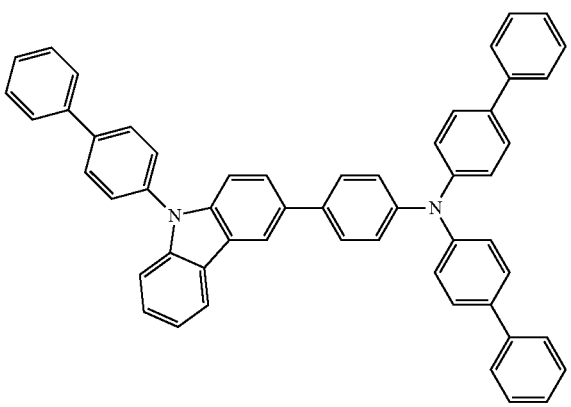
13-52
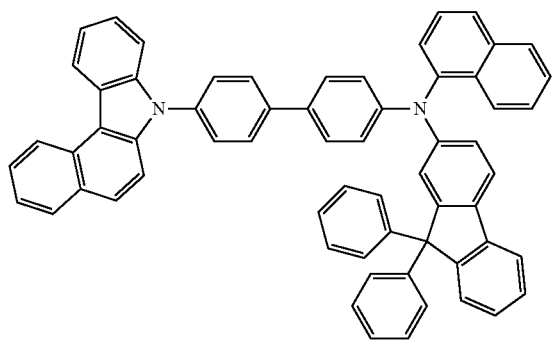
13-53
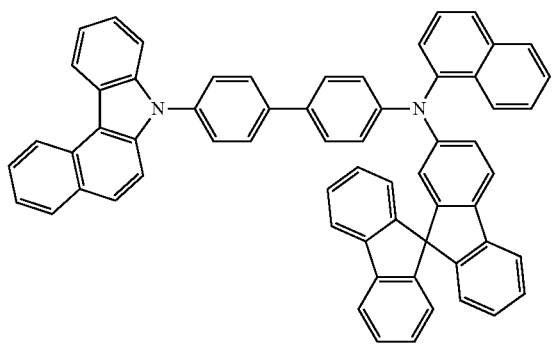
13-54
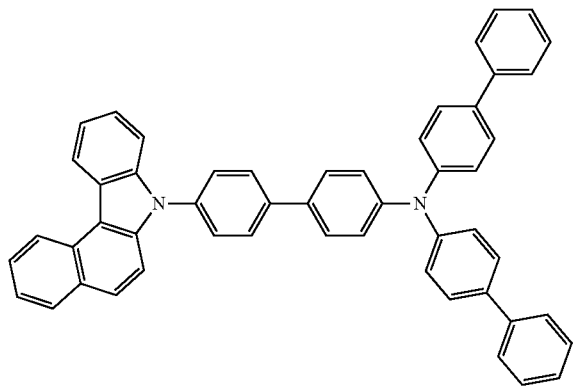
13-55
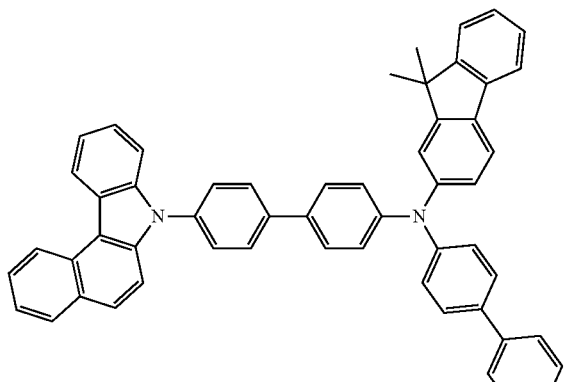
13-56
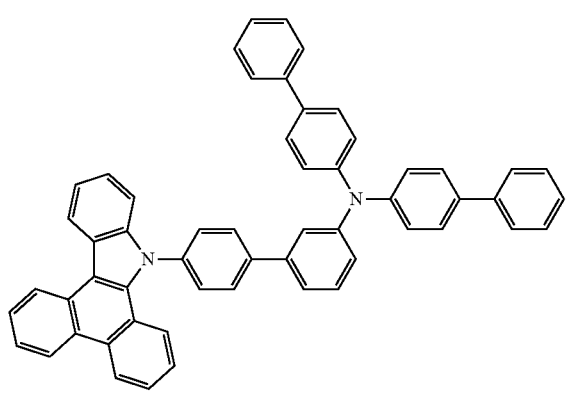
13-57
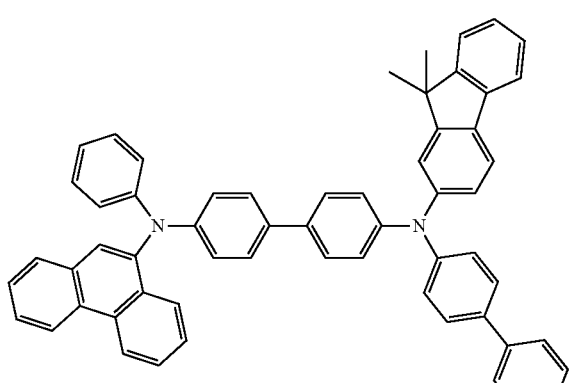

-continued
13-58
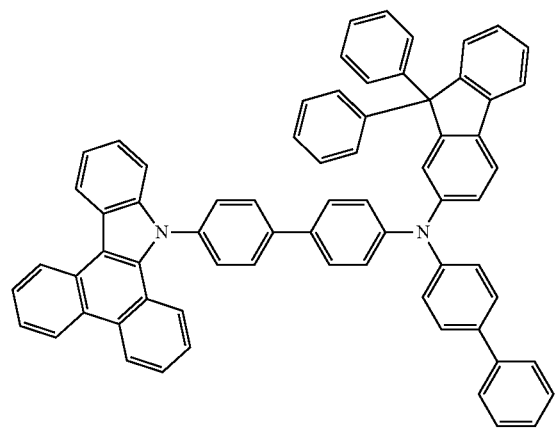
13-59
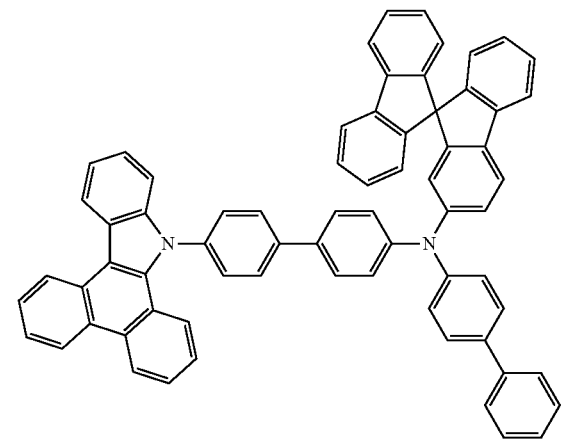
13-60
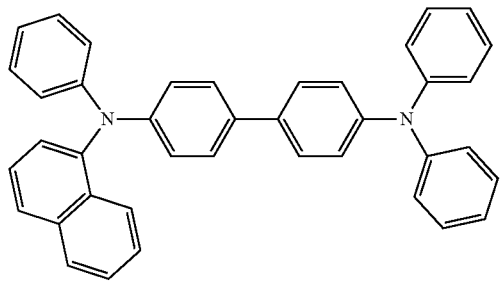
13-61
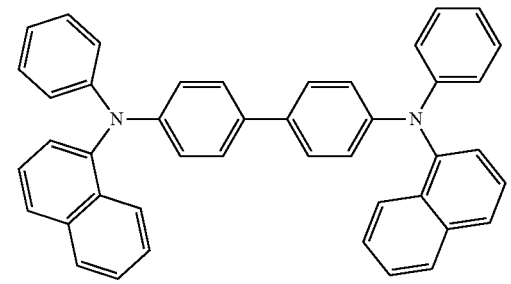
13-62
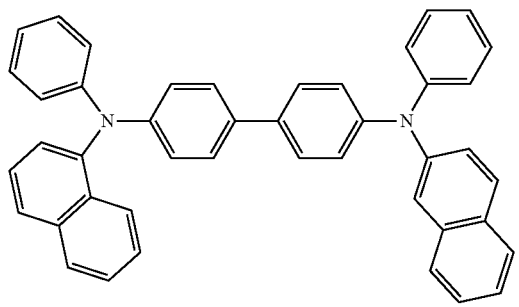
13-63
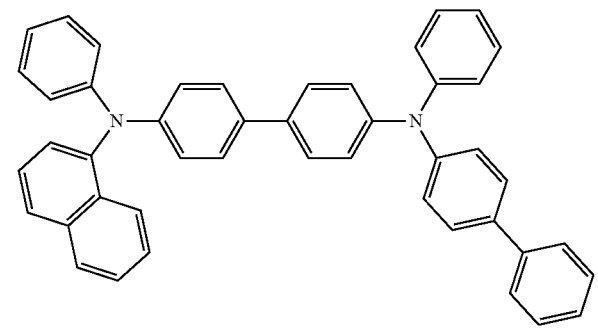
13-64
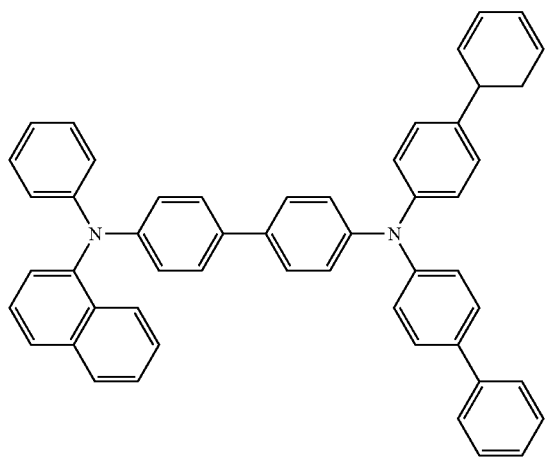
13-65
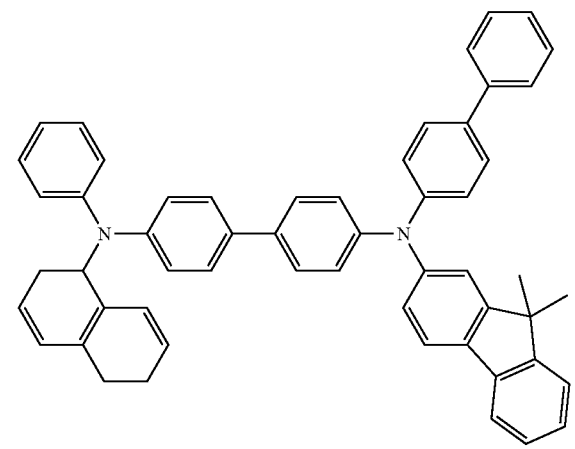

-continued
13-66
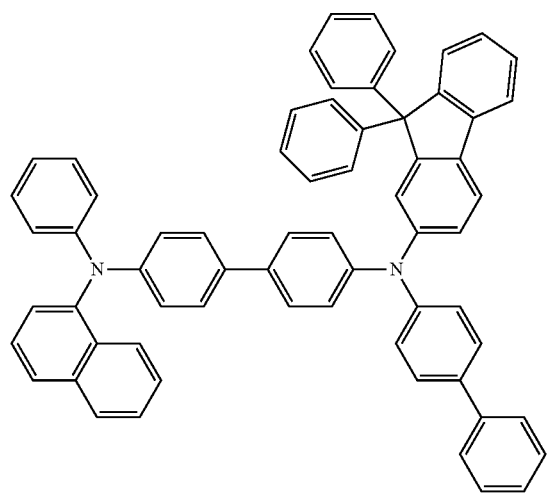
13-67
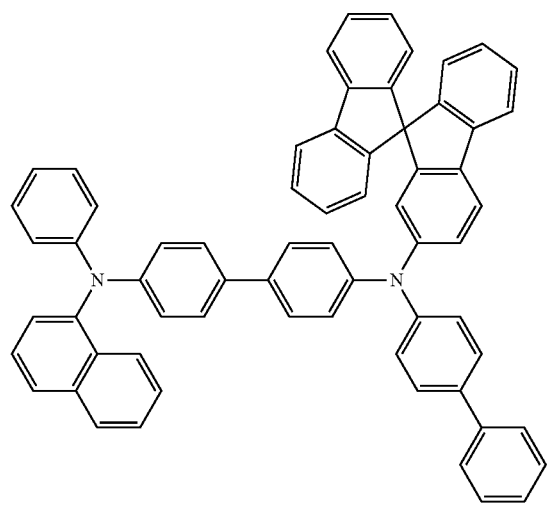
13-68
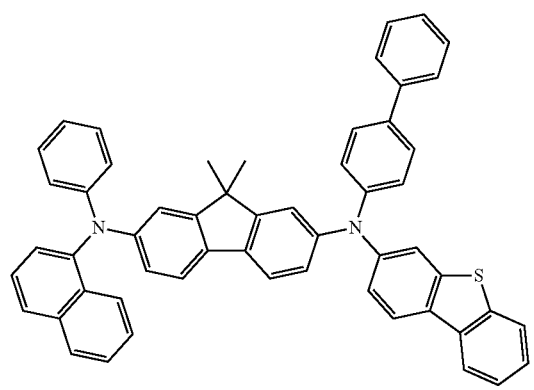
13-69
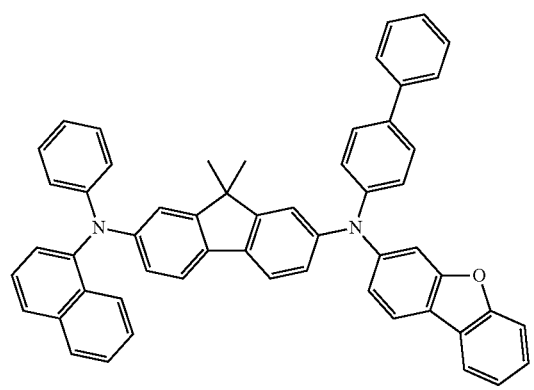
13-70
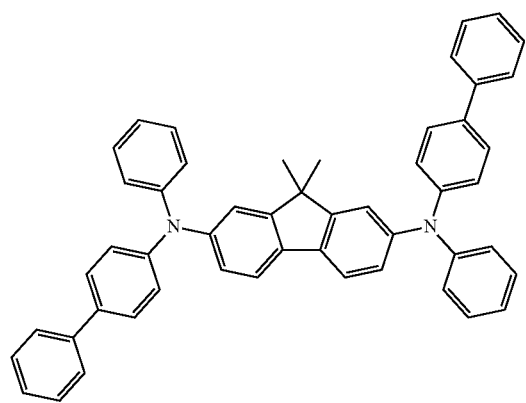
13-71
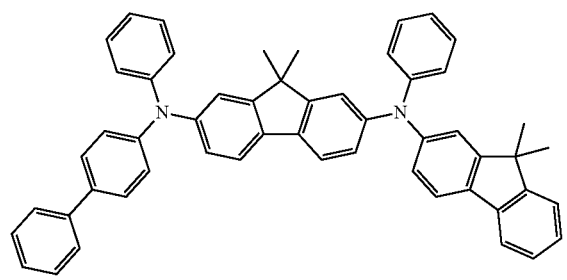

-continued
13-72
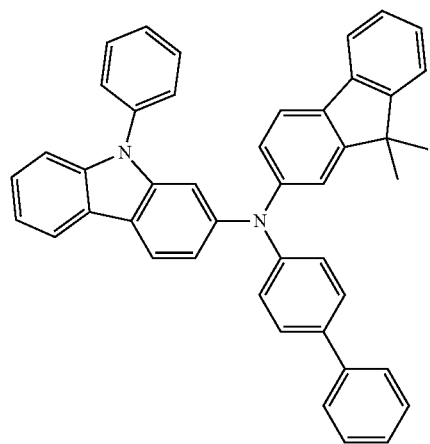
13-73
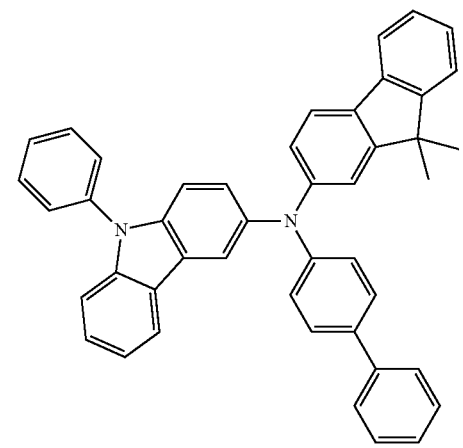
13-74
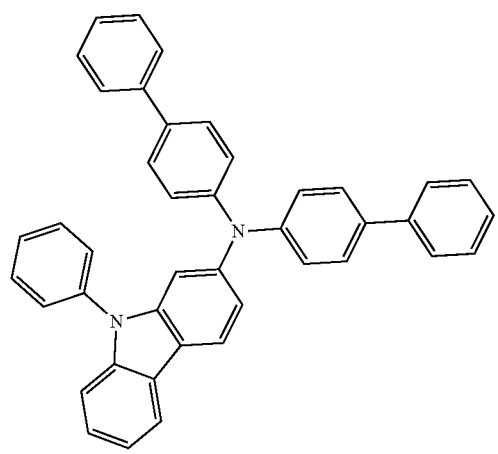
13-75
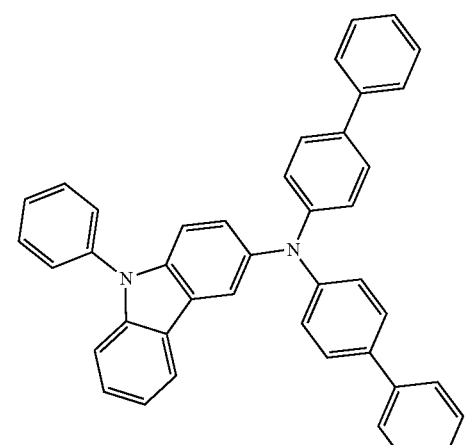
13-76
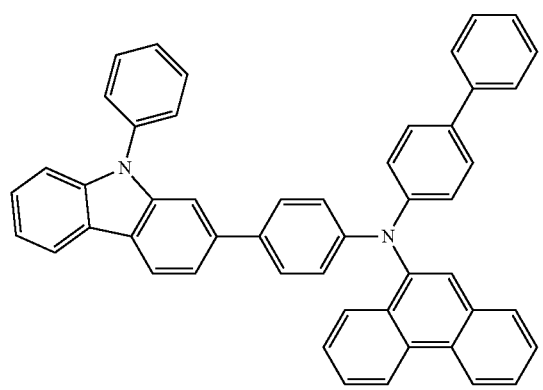
13-77
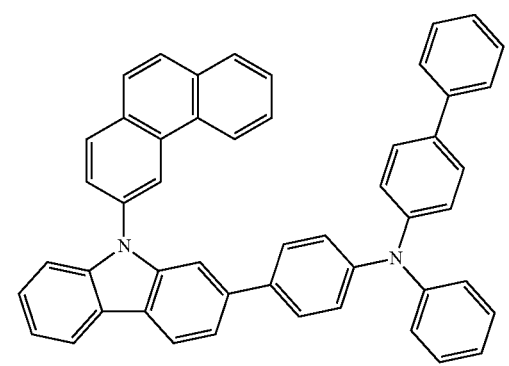

-continued
13-78
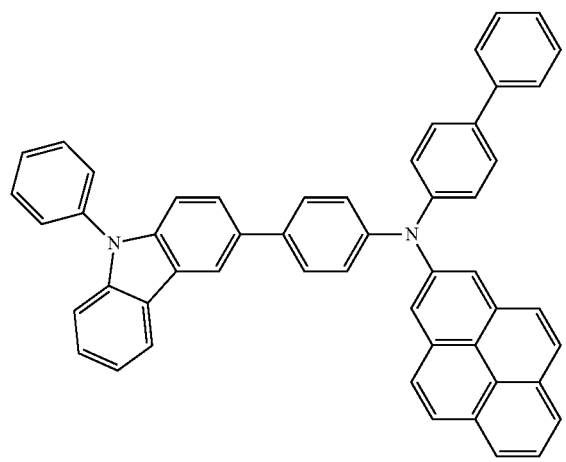
13-79
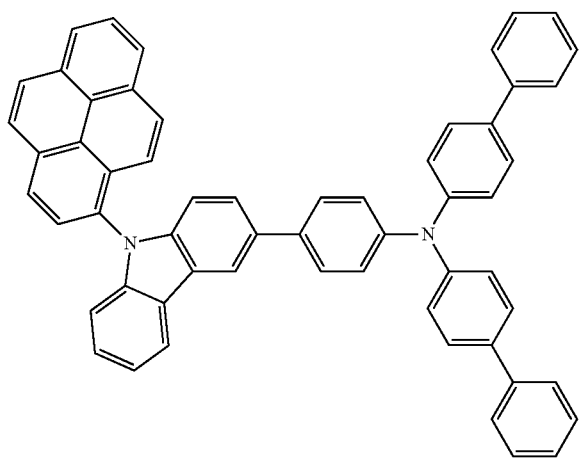
14-1
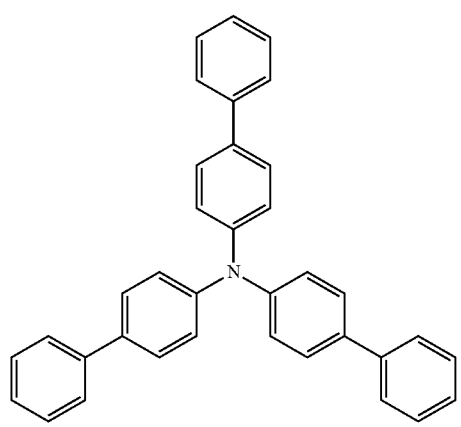
14-2
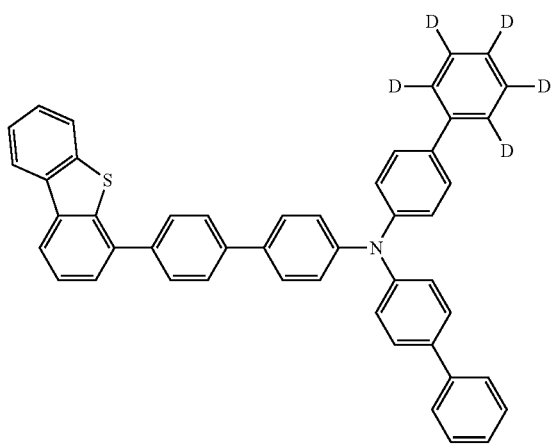
14-3
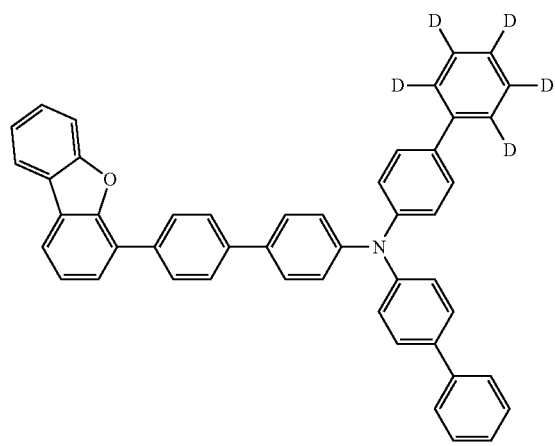
14-4
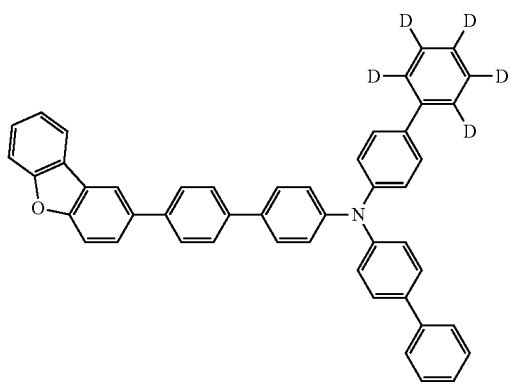

-continued
14-5
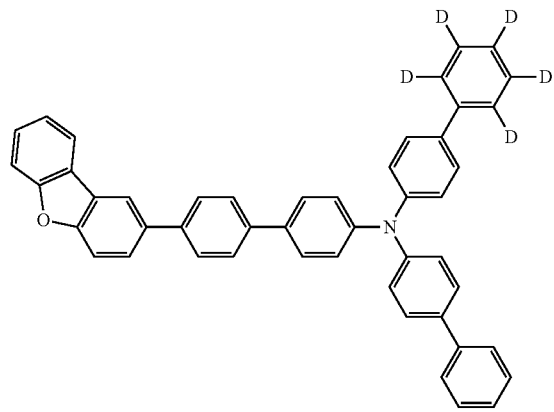
14-6
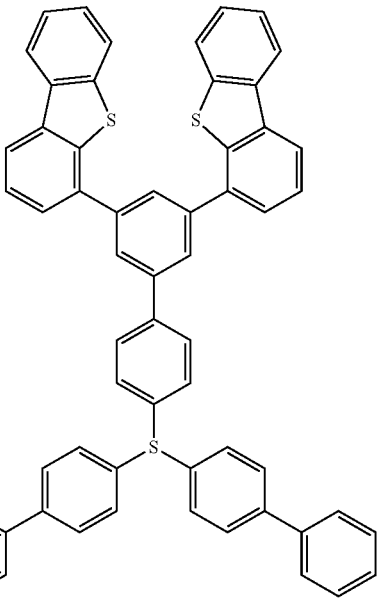
14-7
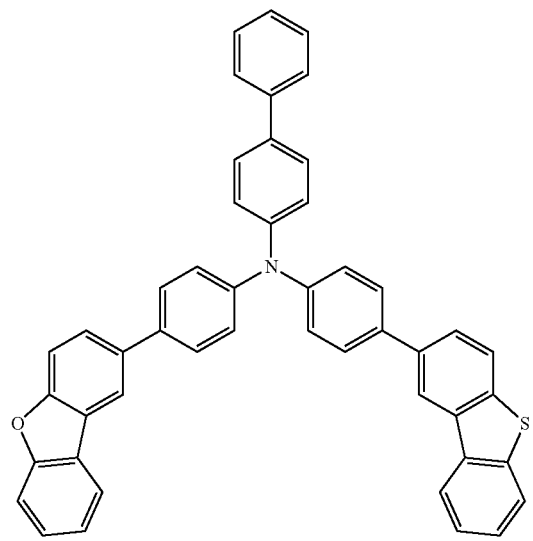
14-8
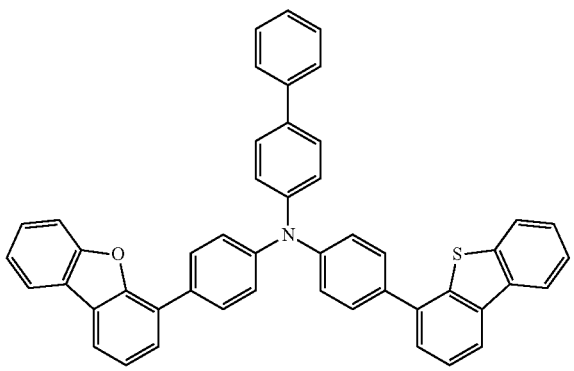
14-9
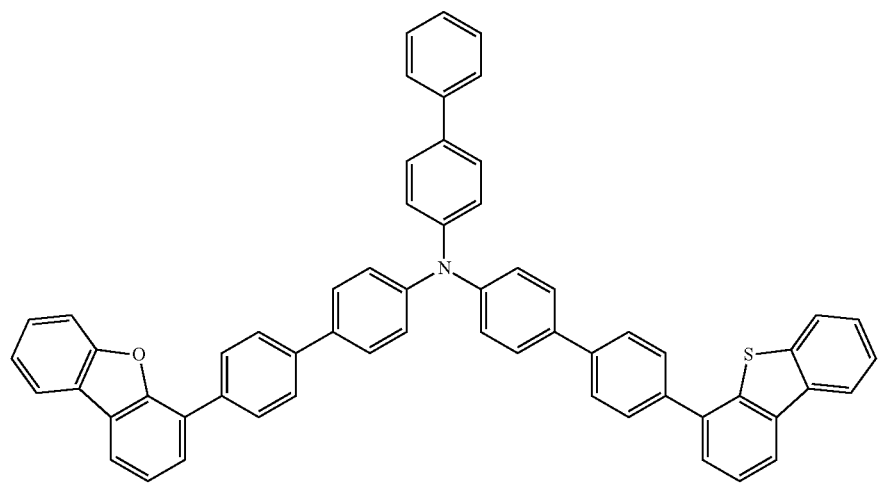

-continued
14-10
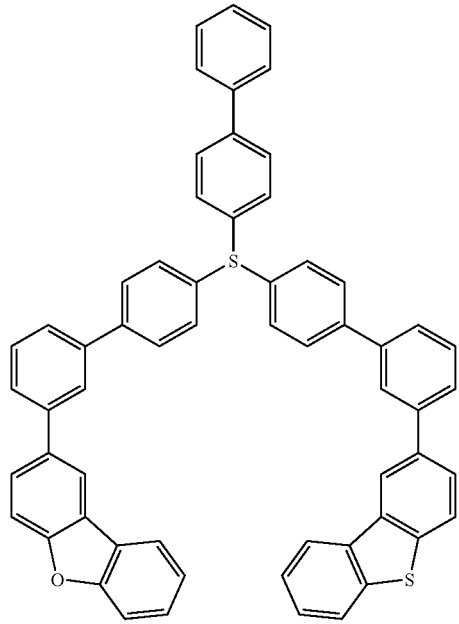
14-11
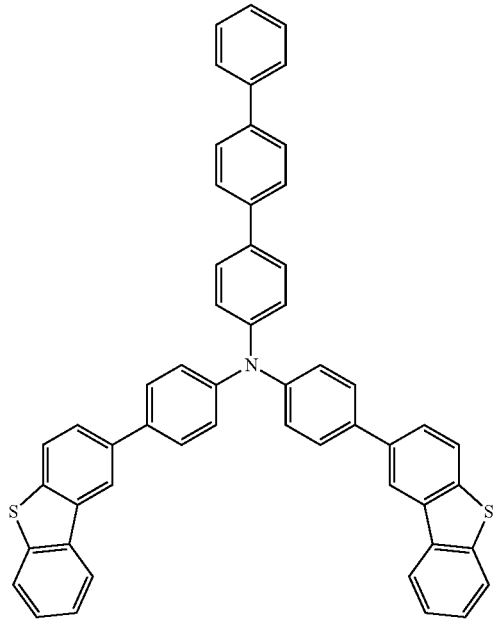
14-12
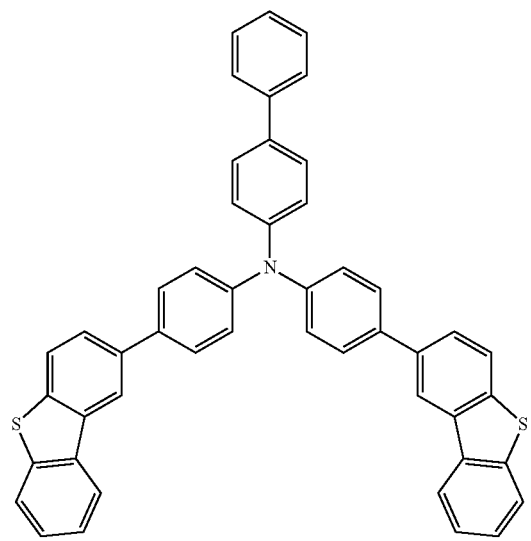
14-13
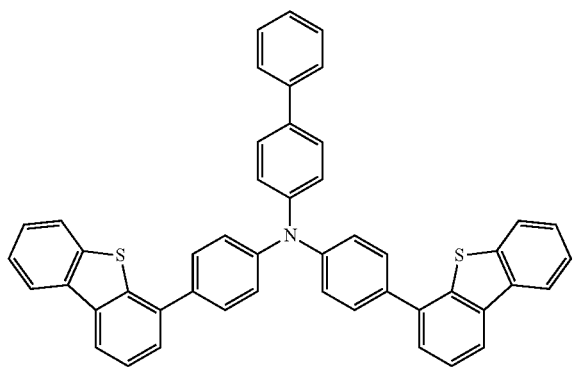
14-14
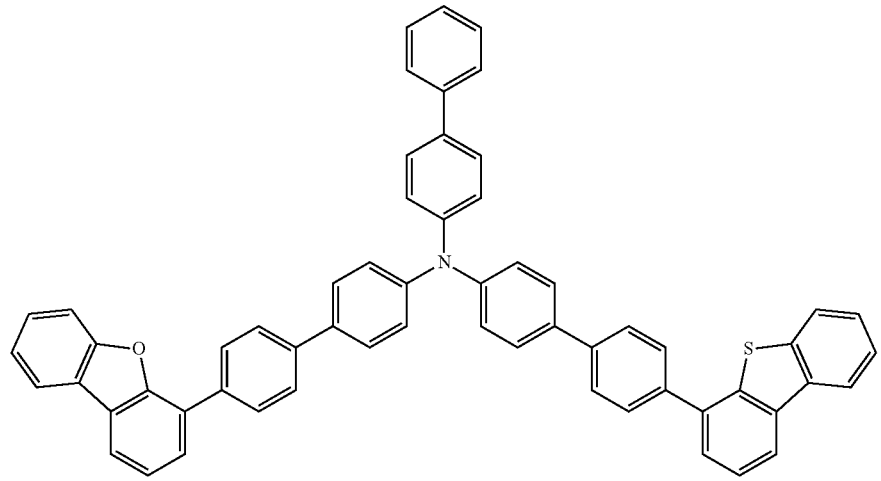

-continued
14-15
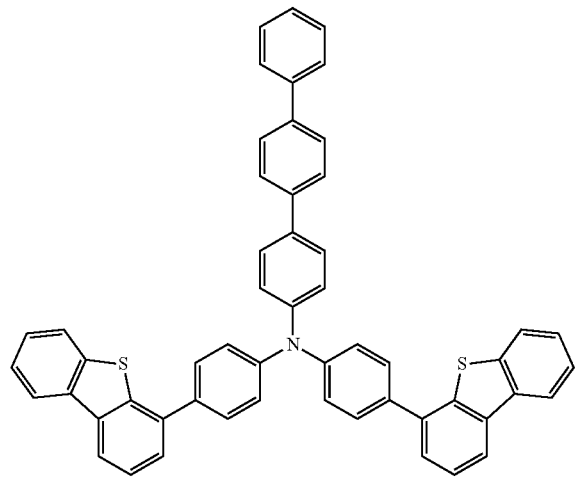
14-16
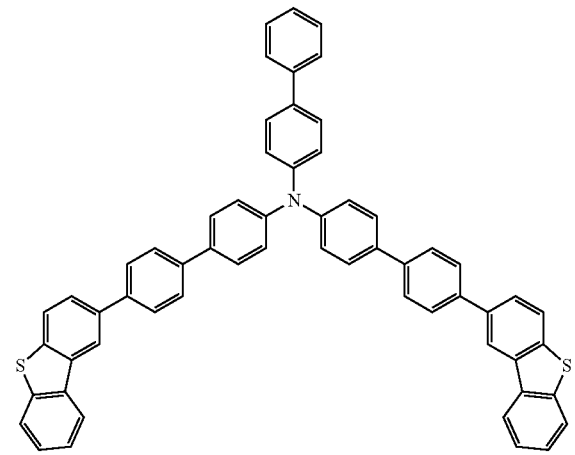
14-17
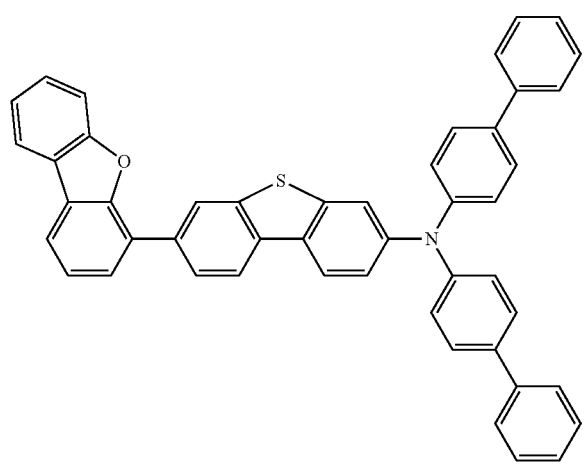
14-18
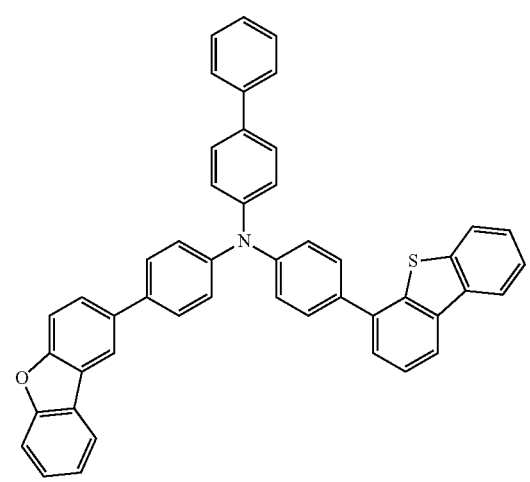
14-19
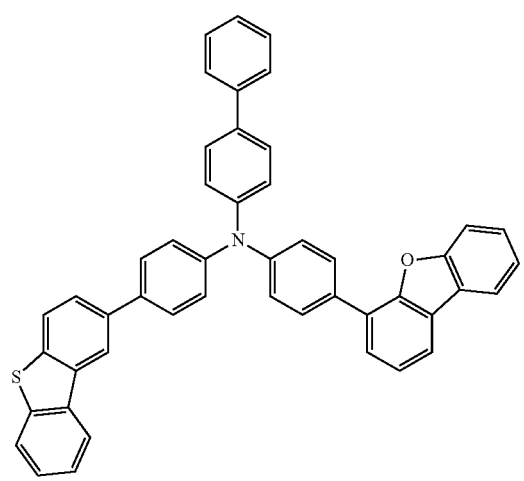
14-20
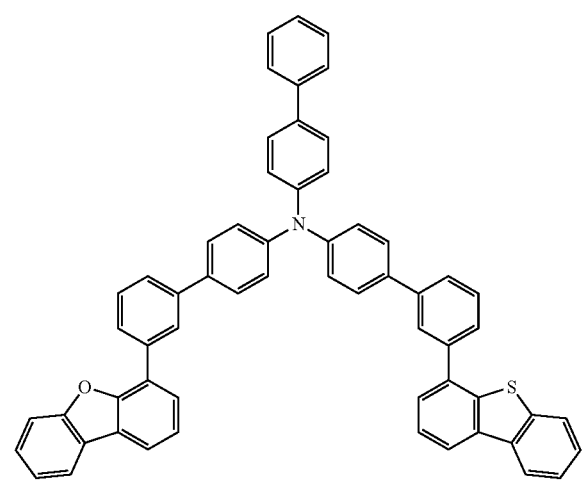

-continued
14-21
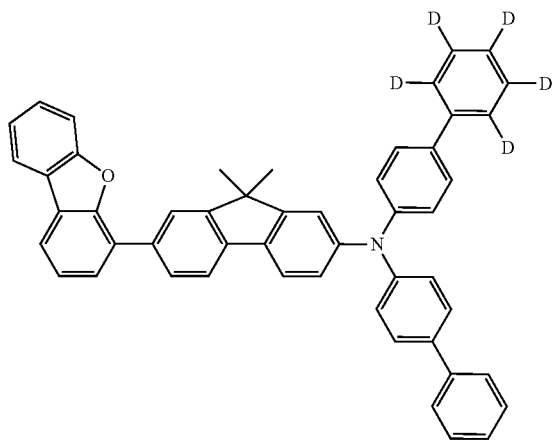
14-22
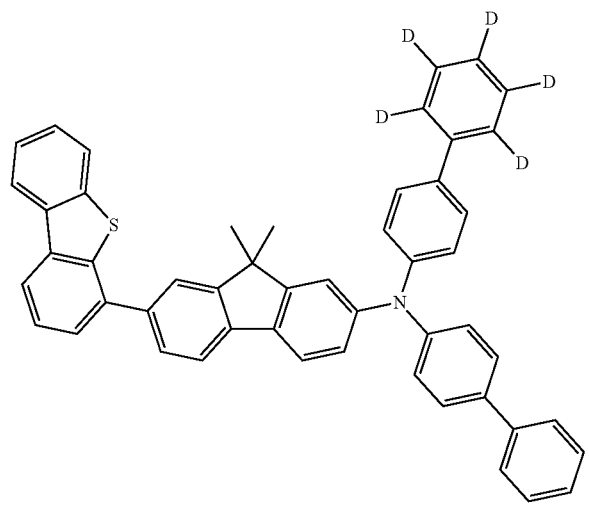
14-23
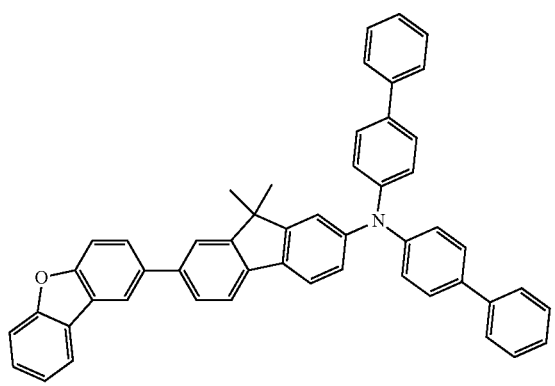
14-24
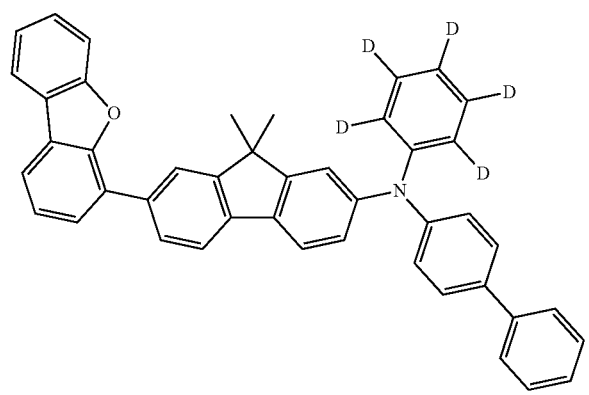
14-25
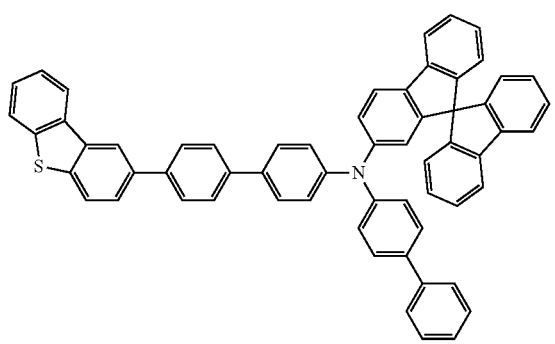
14-26
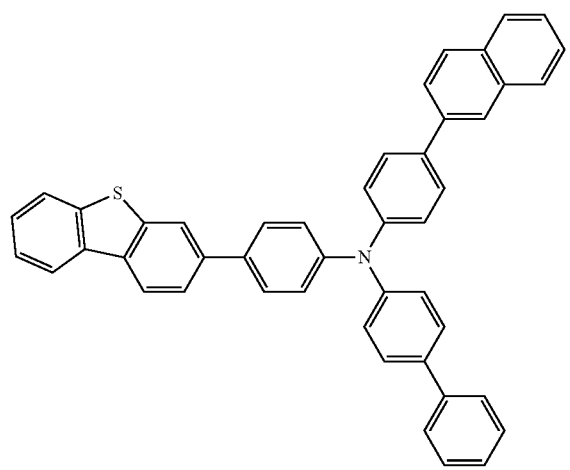

14-27
14-28
14-29
14-30
14-31
14-32

-continued
14-33
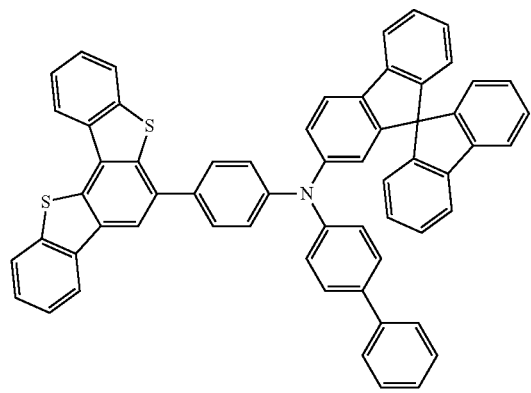
14-34
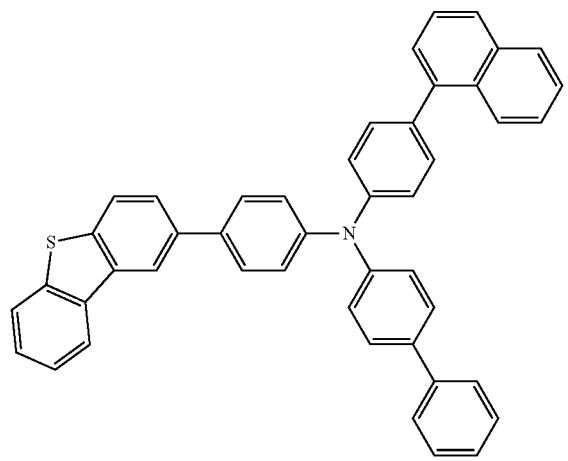
14-35
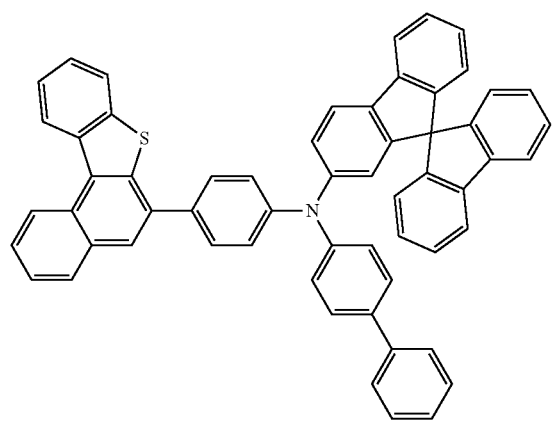
14-36
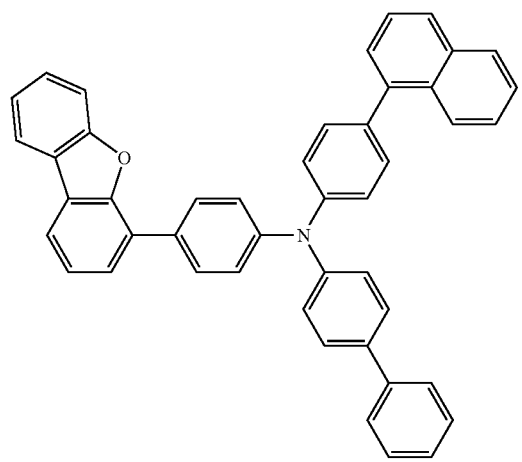
14-37
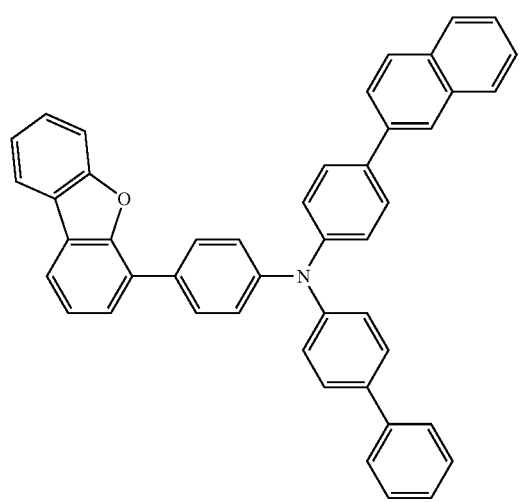
14-38
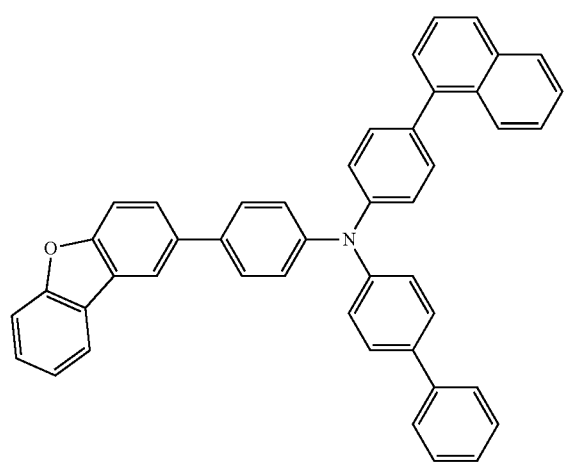

-continued
14-39
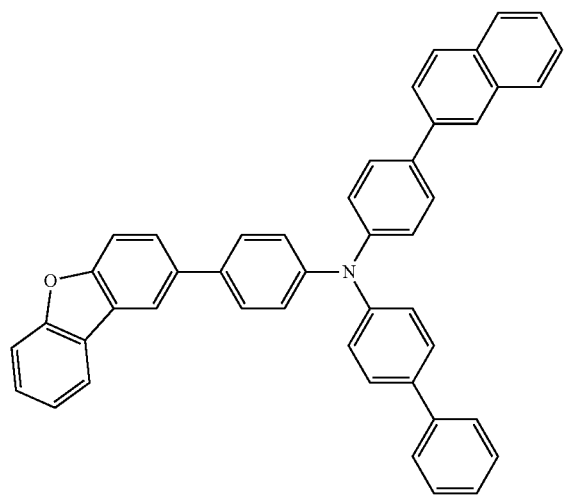
14-40
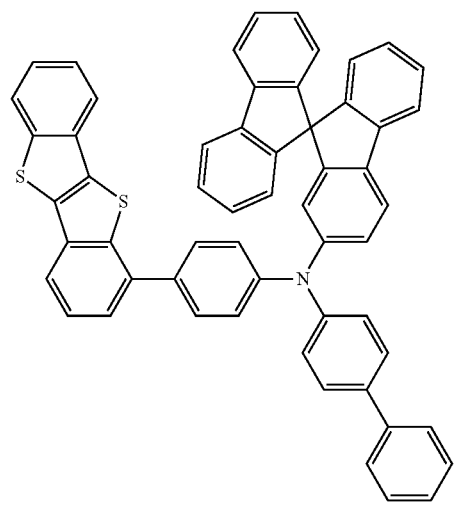
14-41
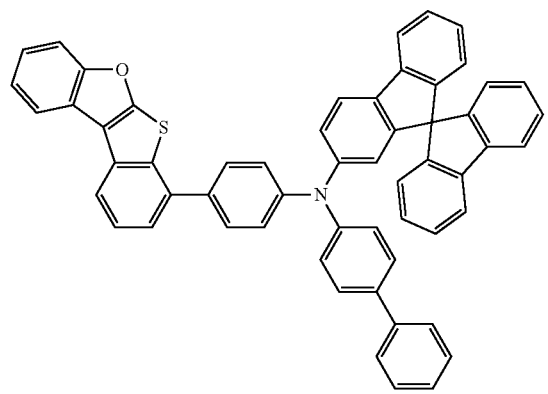
14-42
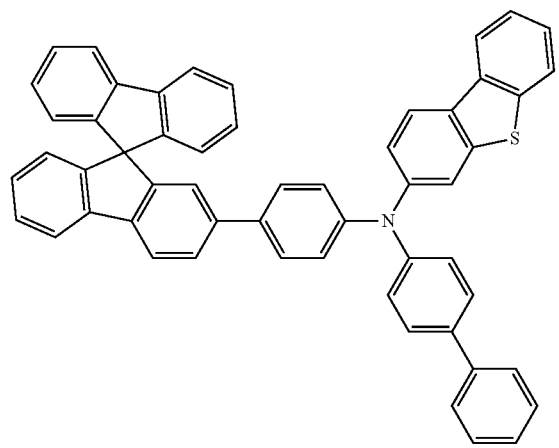
14-43
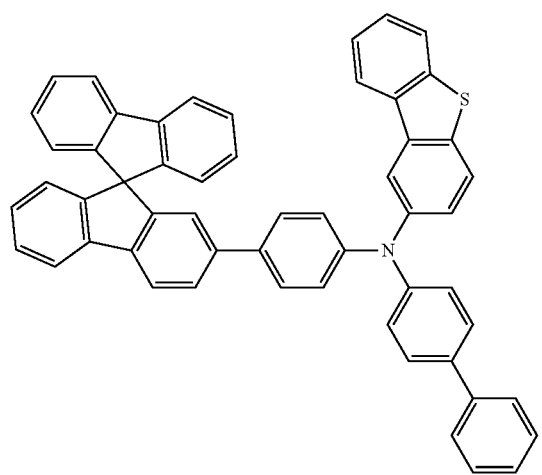
14-44
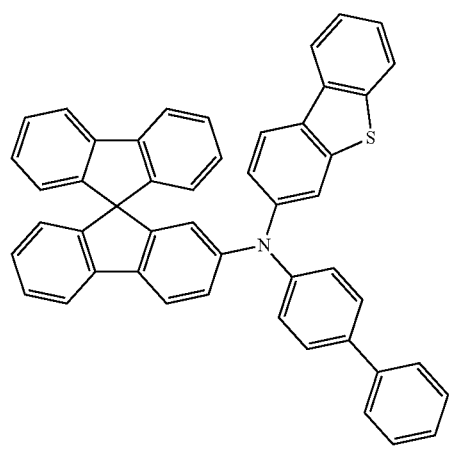

-continued
14-45
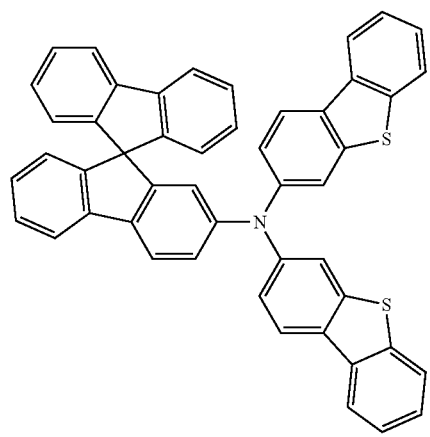
14-46
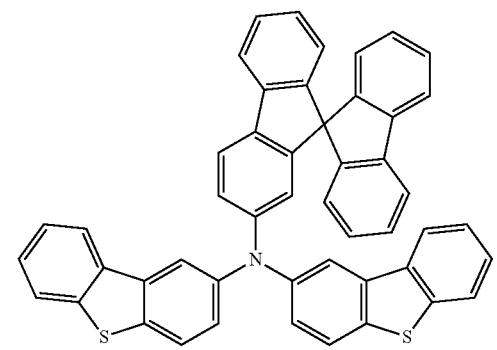
14-47
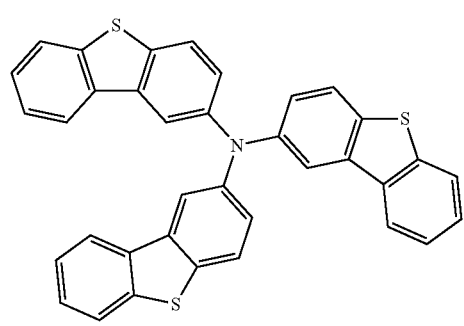
14-48
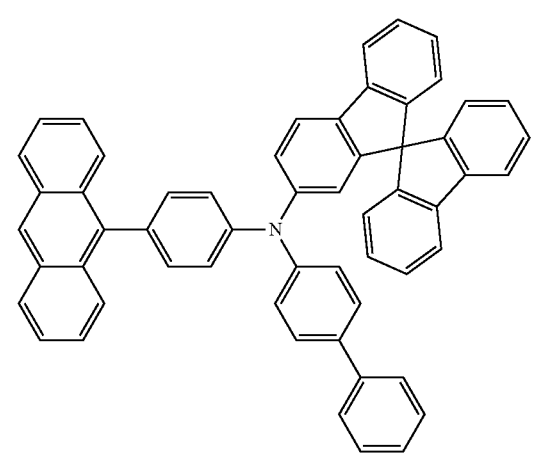
14-49
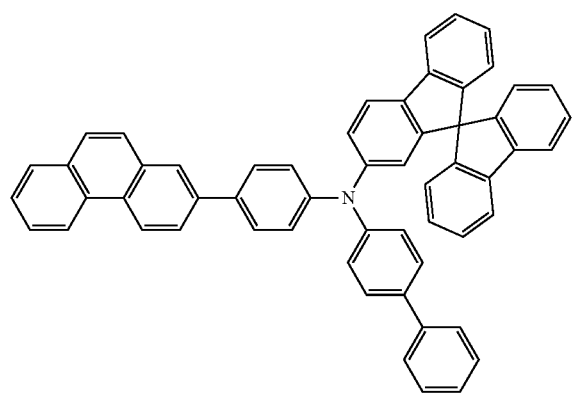
14-50
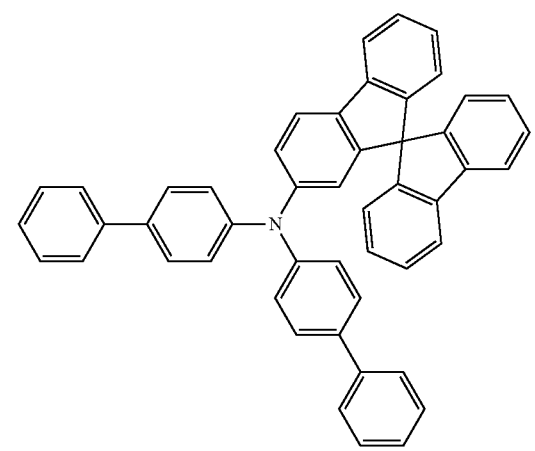

-continued
14-51
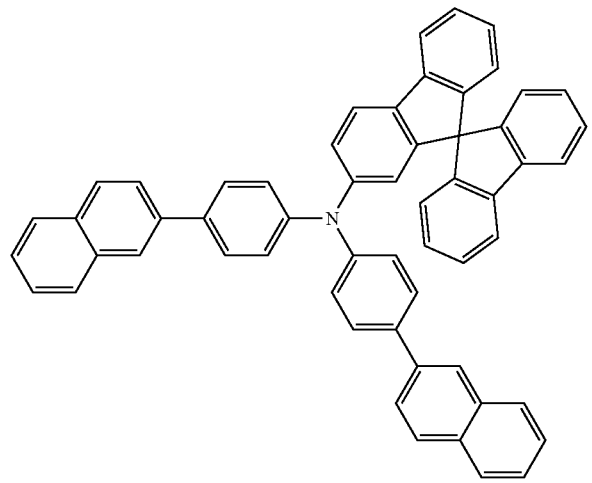
14-52
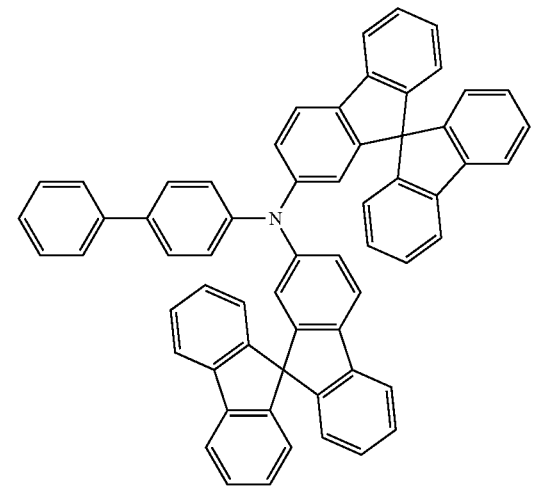
14-53
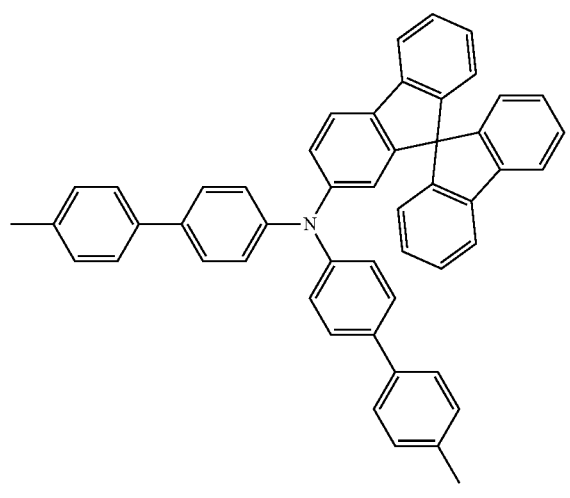
14-54
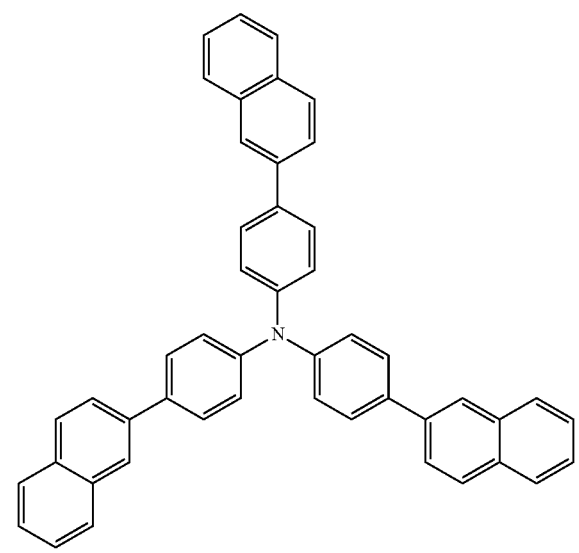
14-55
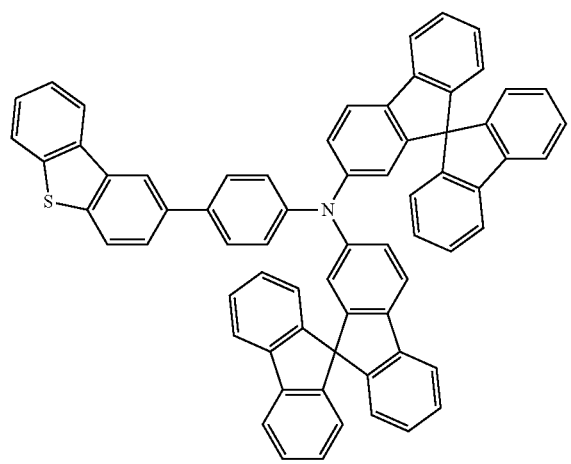
14-56
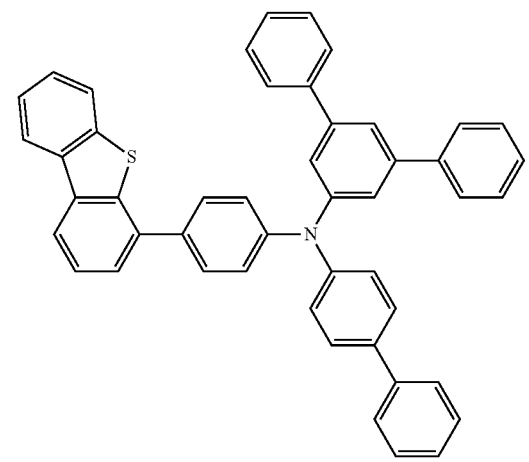

-continued
14-57
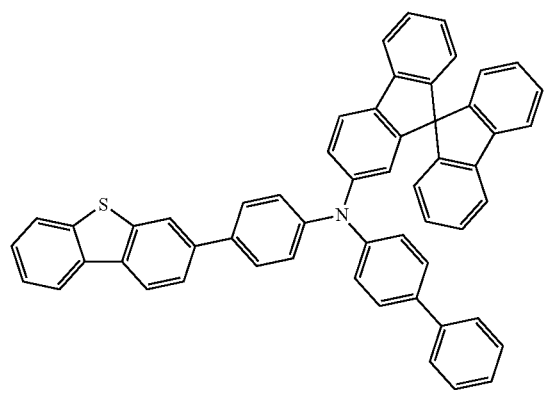
14-58
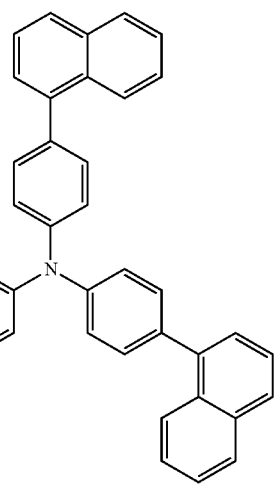
14-59
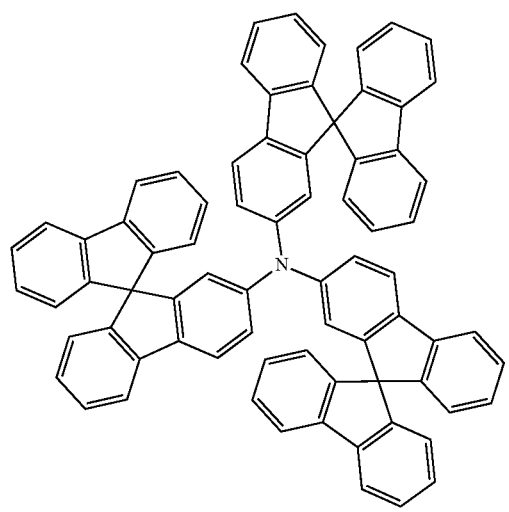
14-60
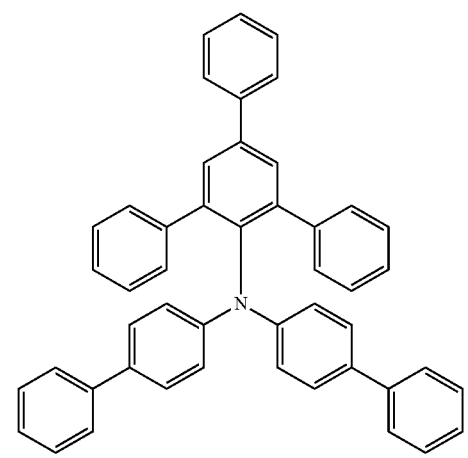
14-61
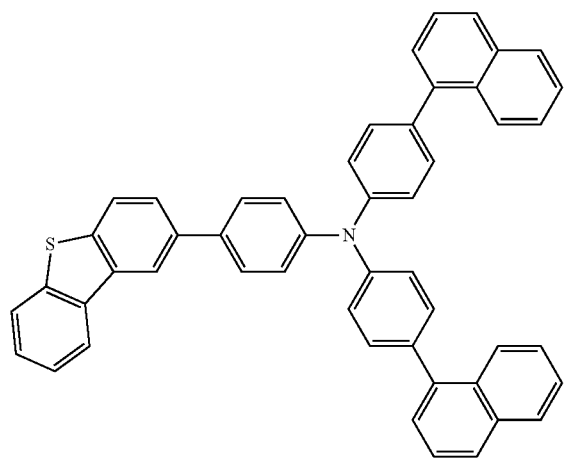
14-62
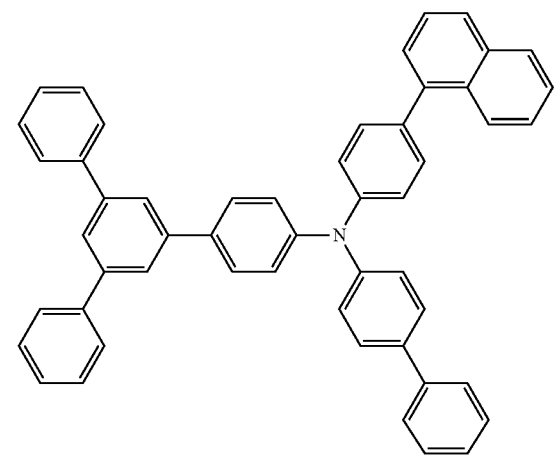

-continued
14-63
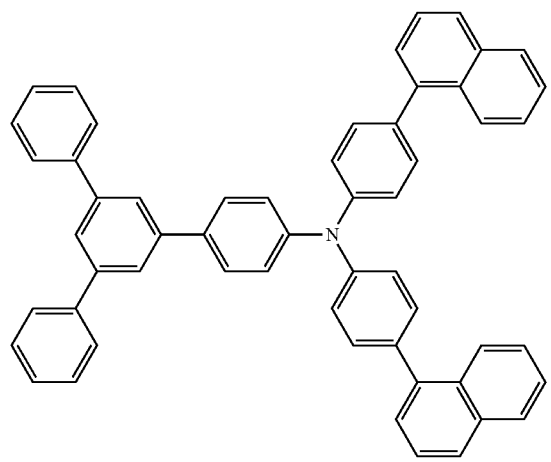
14-64
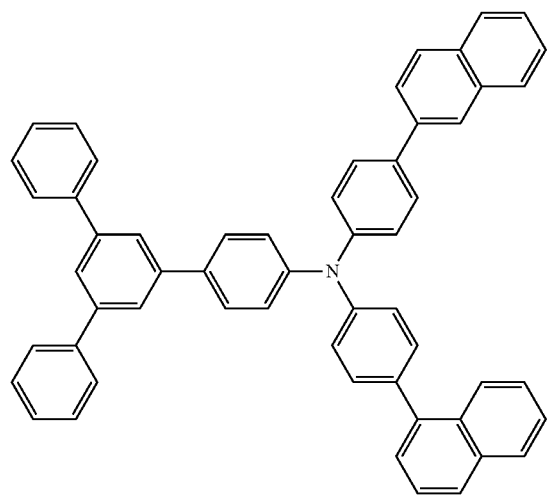
14-65
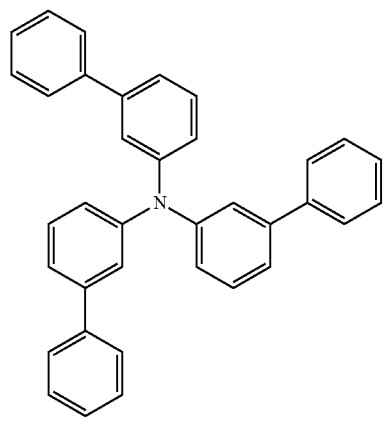
14-66
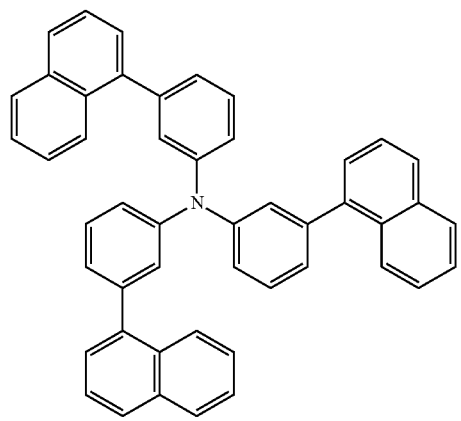
14-67
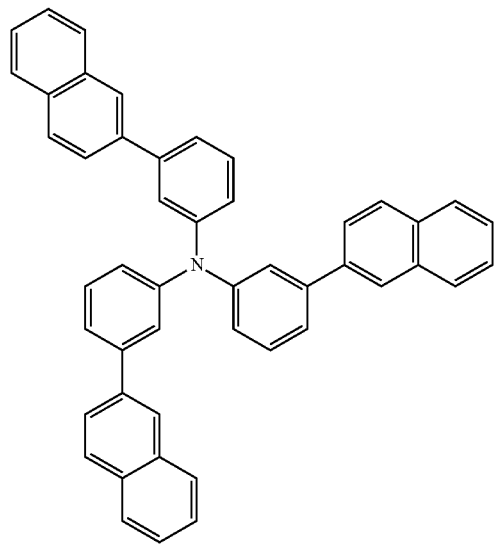
14-68
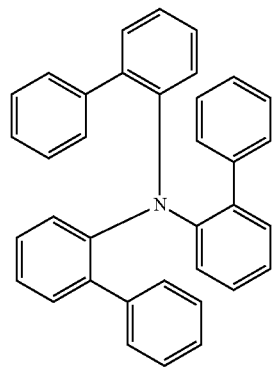

-continued
14-69
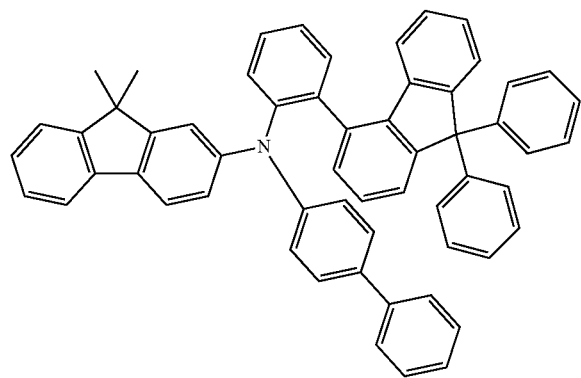
14-70
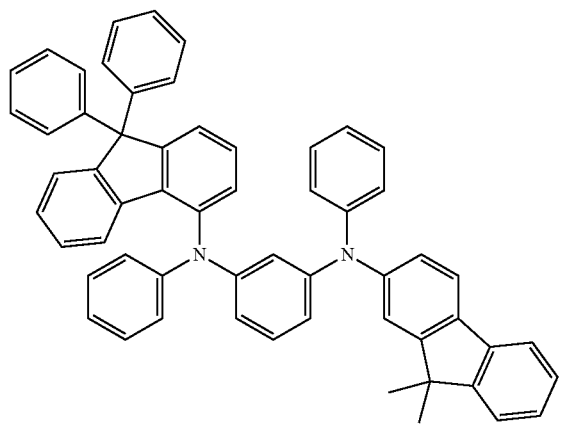
14-71
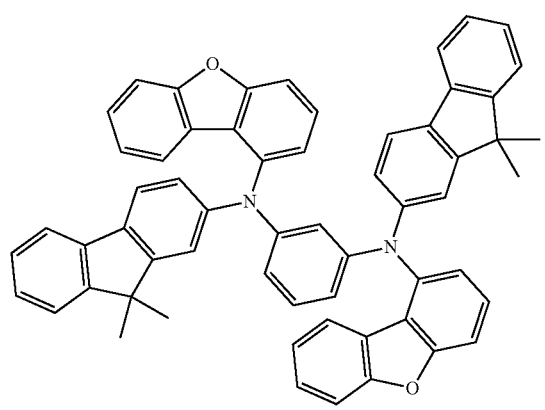
14-72
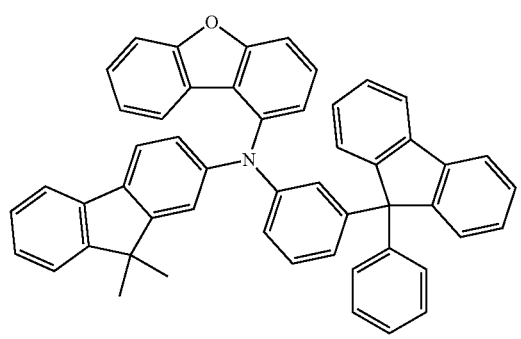
14-73
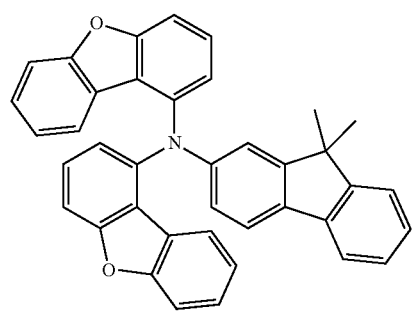
14-74
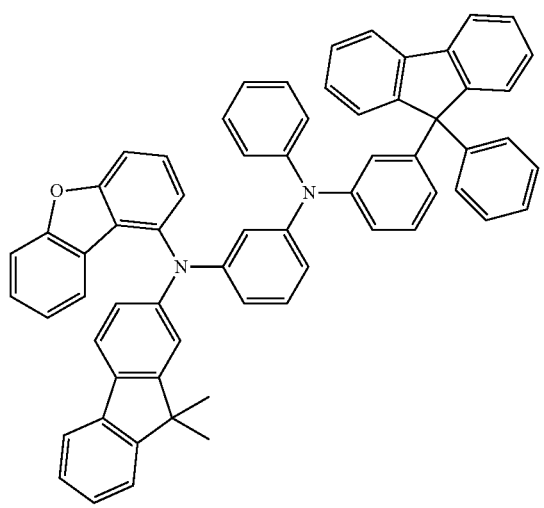

-continued
14-75
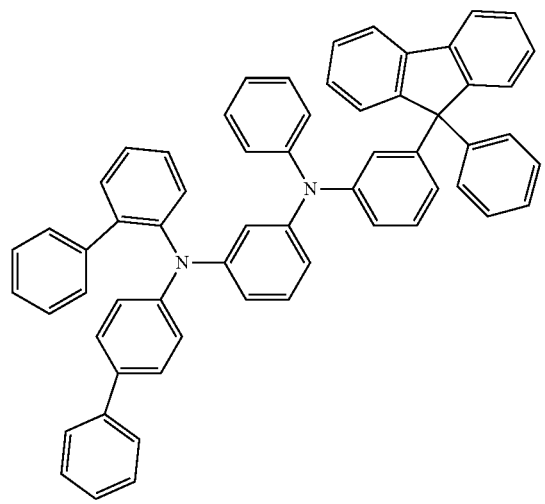
14-76
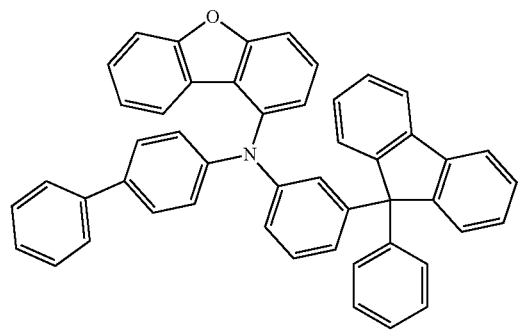
15-1
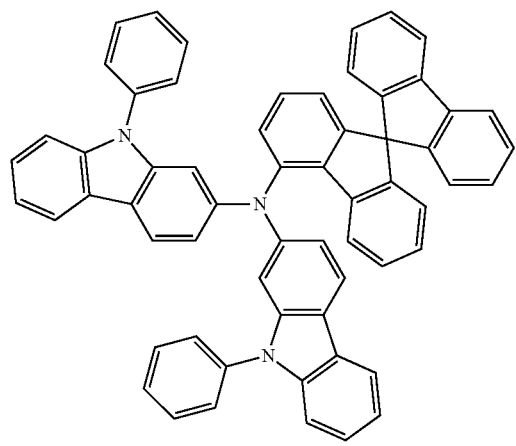
15-2
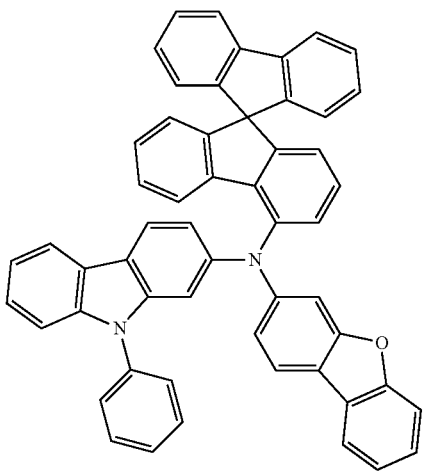
15-3
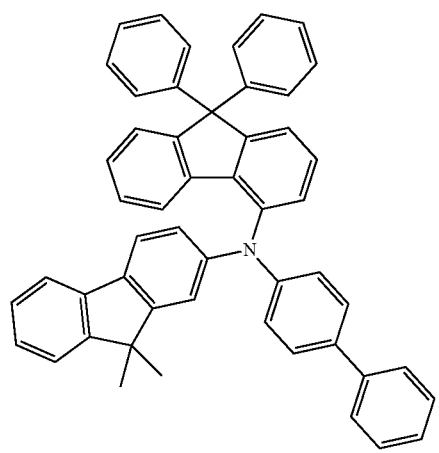
15-4
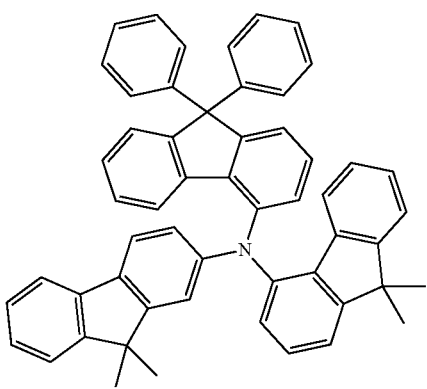

-continued
15-5
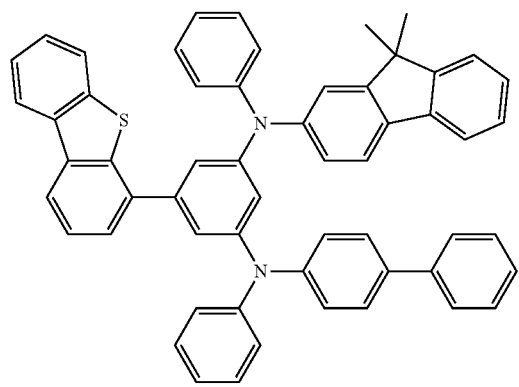
15-6
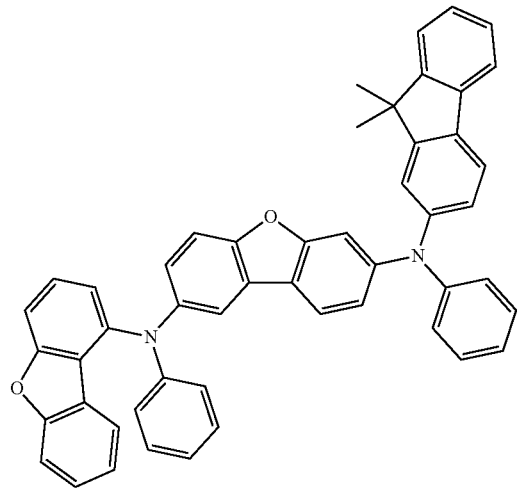
15-7
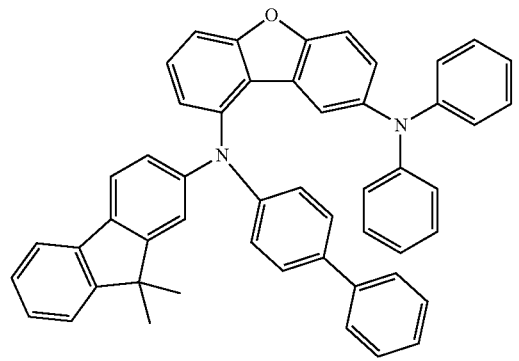
15-8
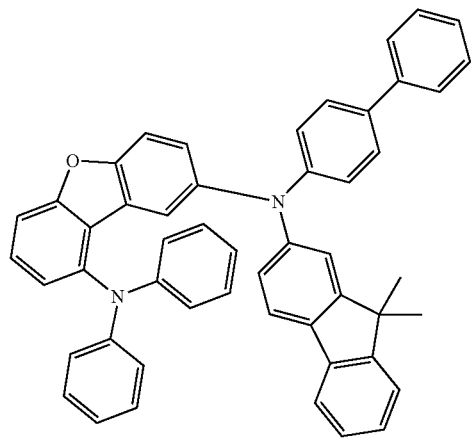
15-9
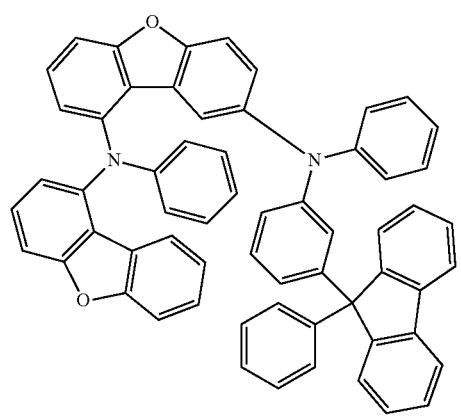
15-10
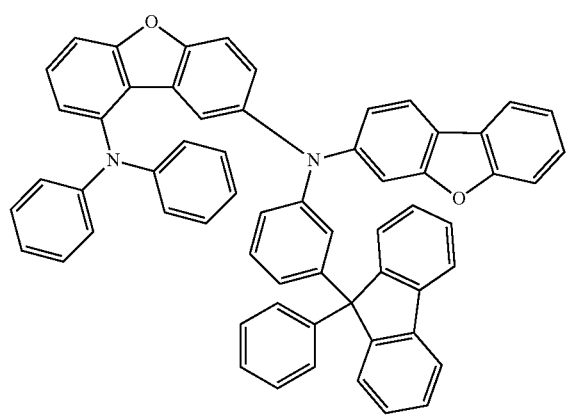

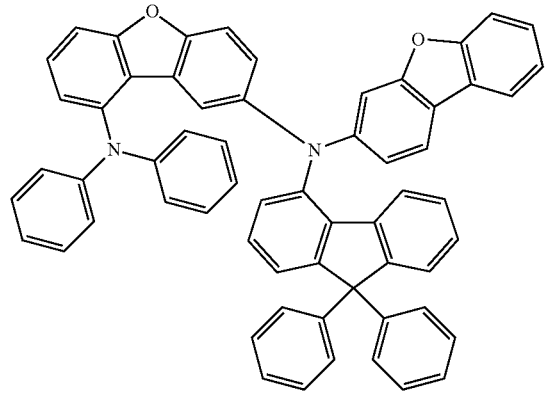
15-11
Specifically, the compound represented by formula A may be one of the following compounds, but it is not limited thereto.
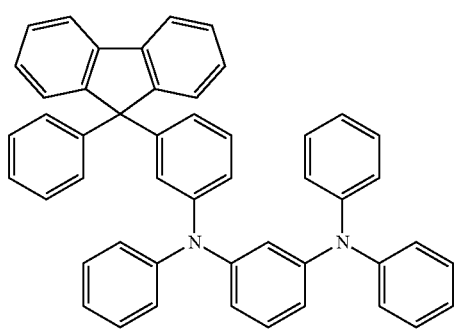
G-1
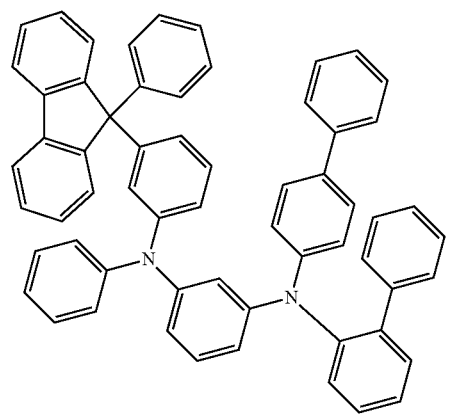
G-3
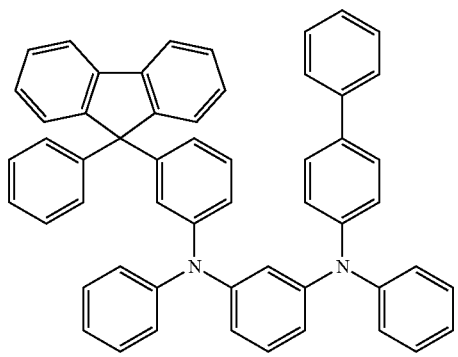
G-2
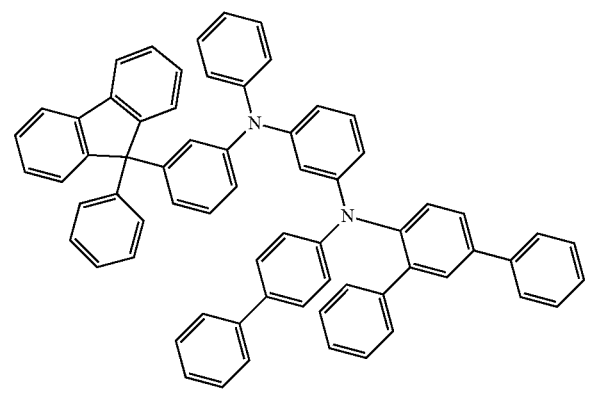
G-4

G-5
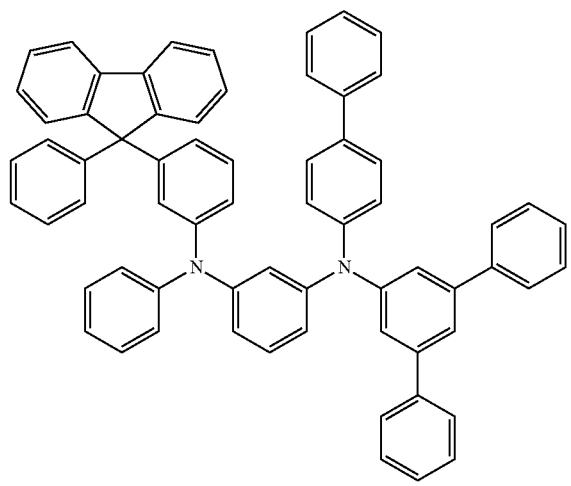
G-9
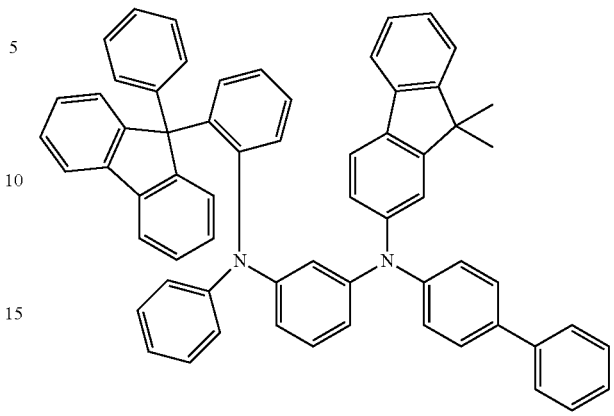
G-6
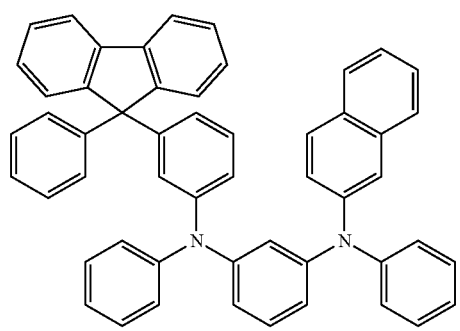
G-10
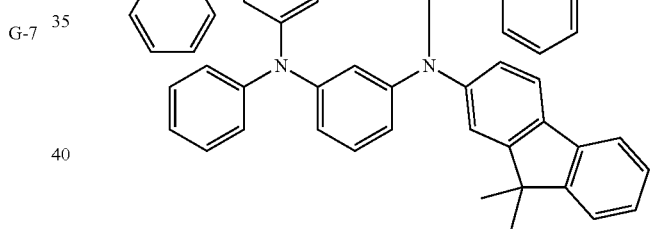
G-7
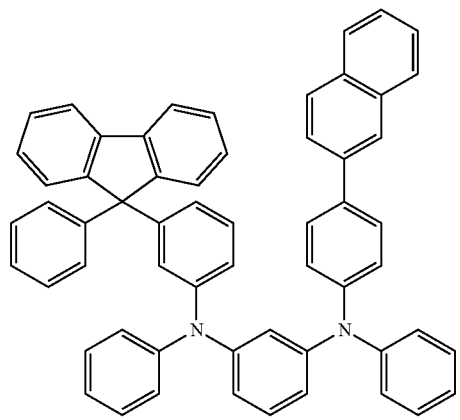
G-11
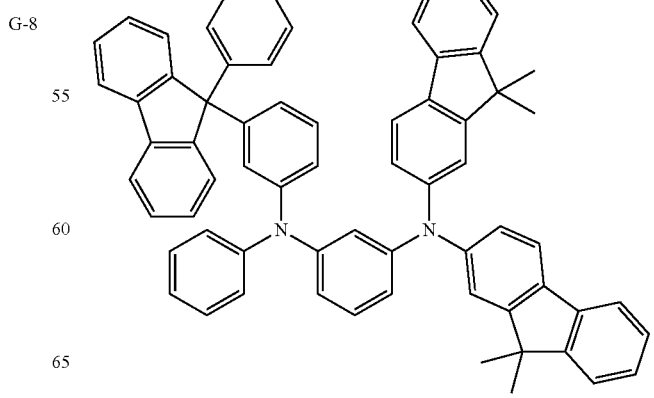
G-8

G-12
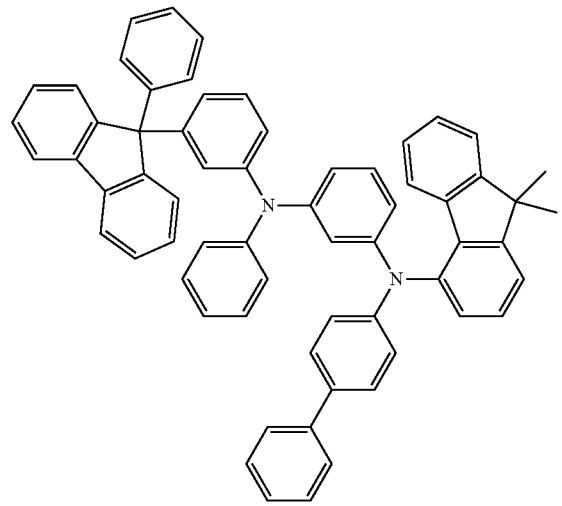
G-13
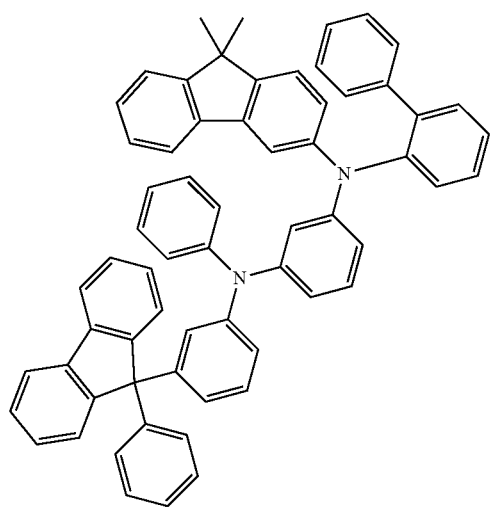
G-14
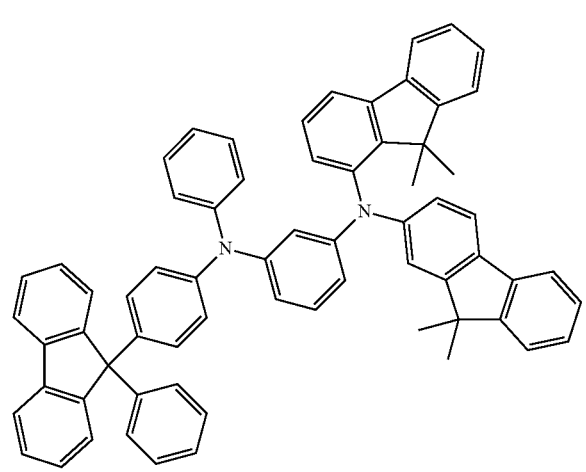
G-15
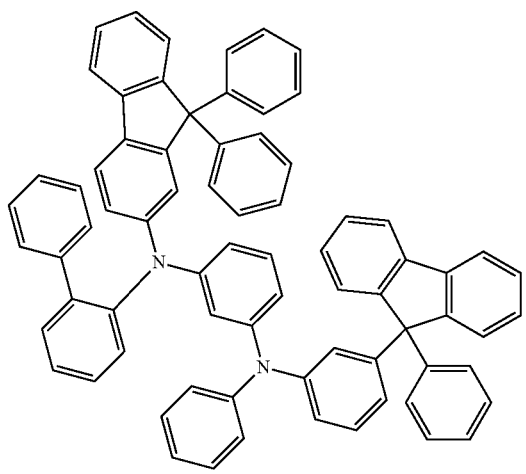
G-16
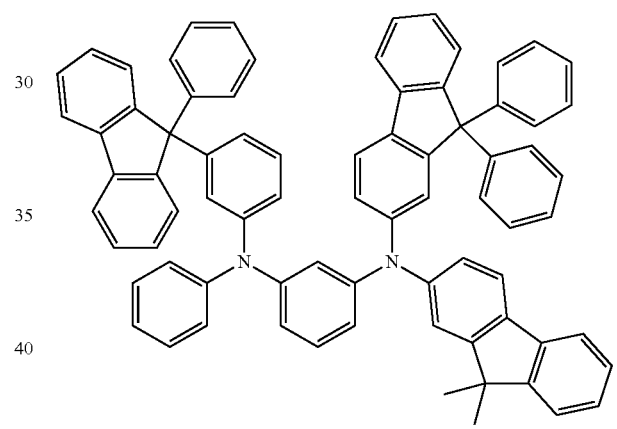
G-17
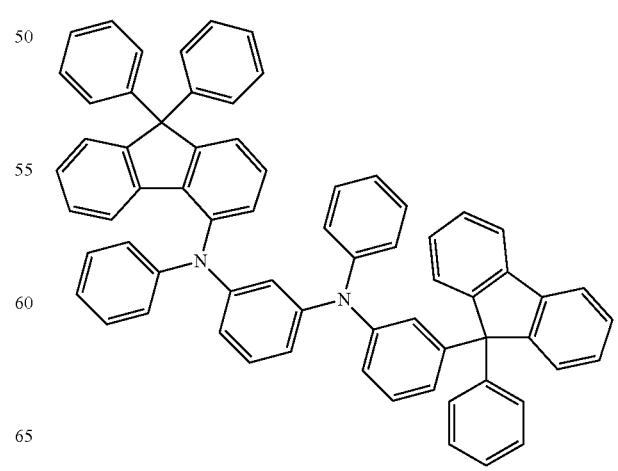

G-18
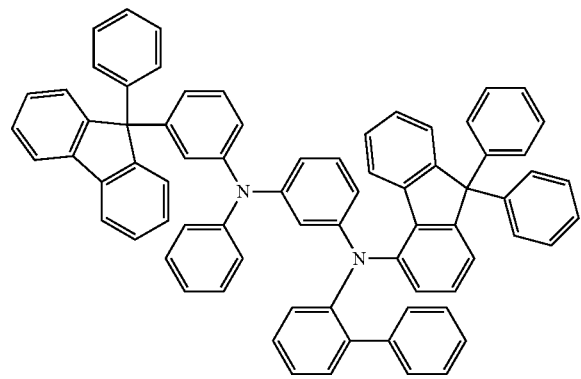
G-19
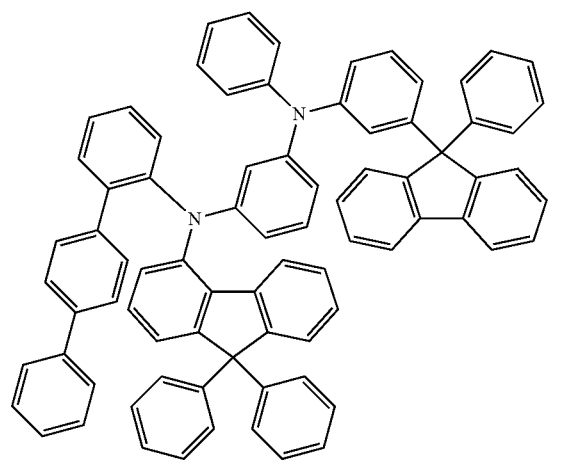
G-20
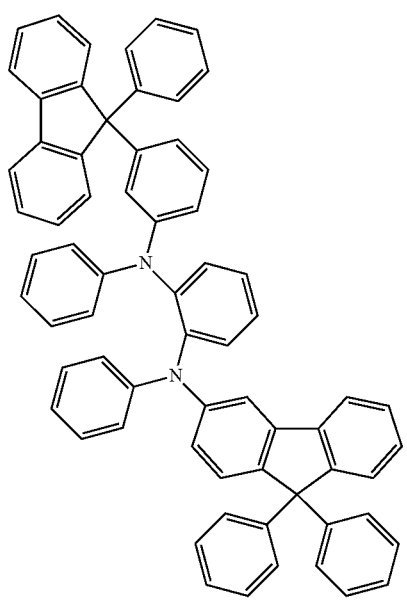
G-21
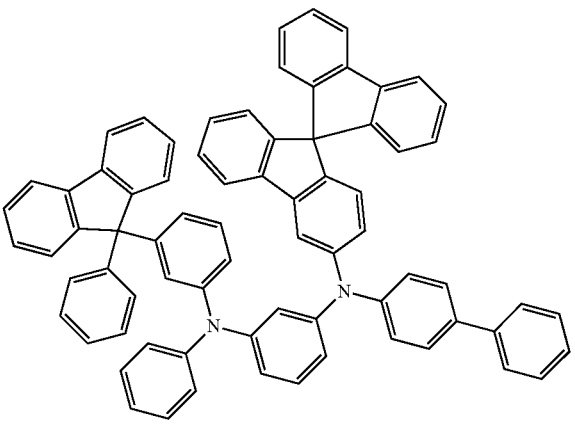
G-22
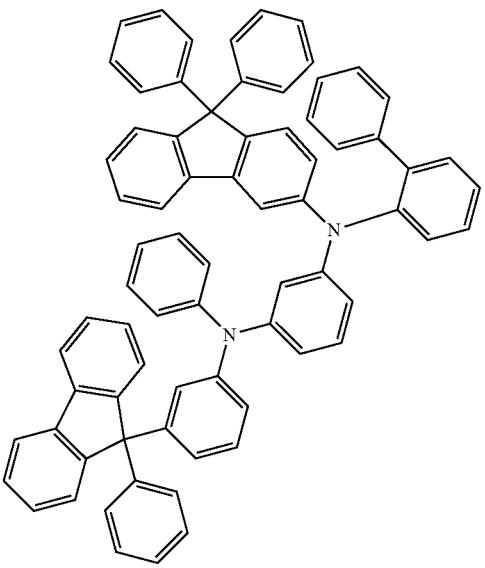
G-23
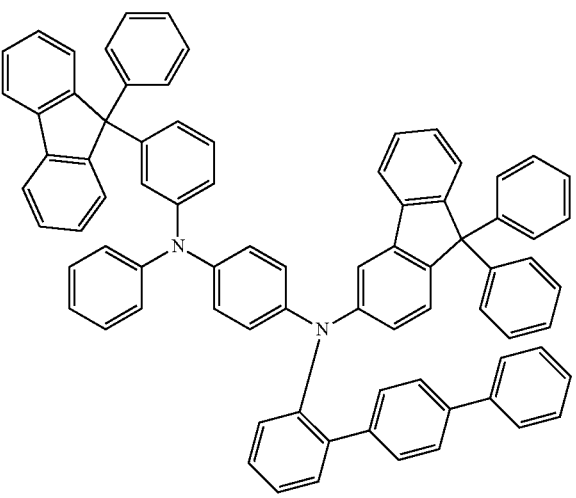

G-24
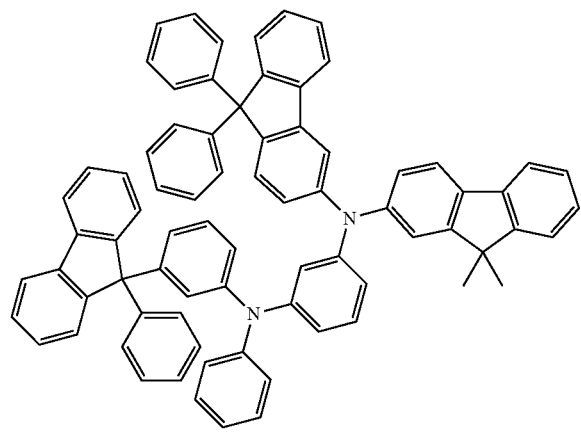
G-27
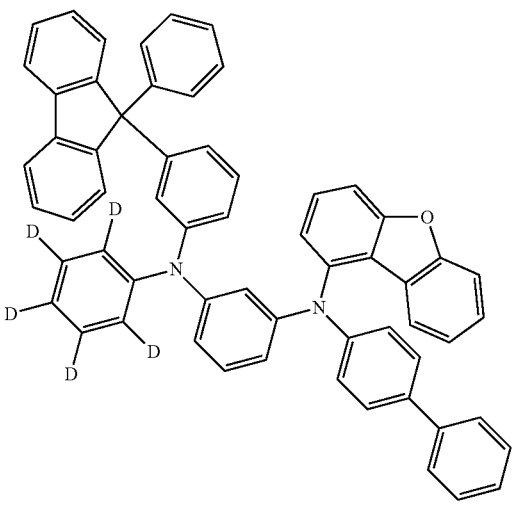
G-25
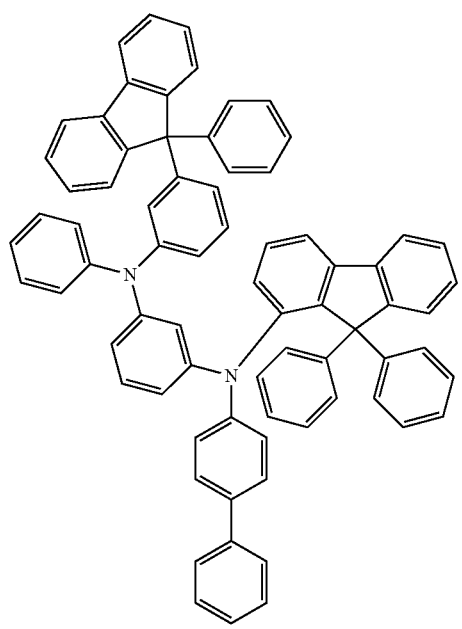
G-28
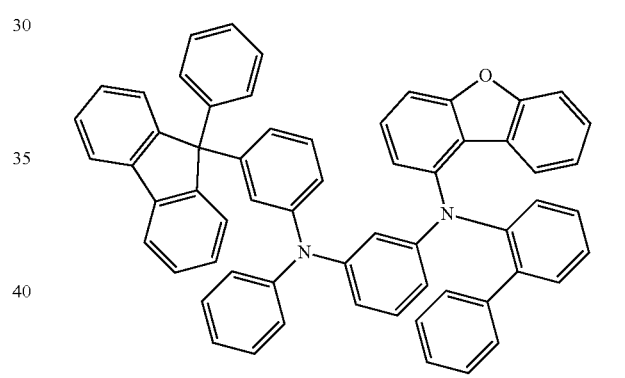
G-26
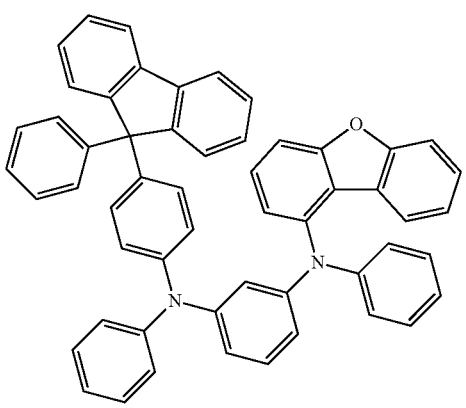
G-29
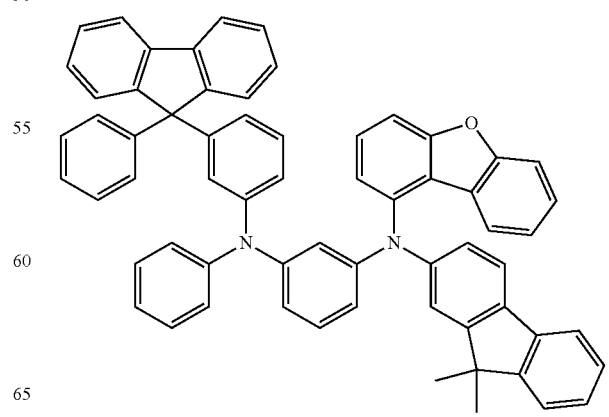

G-30
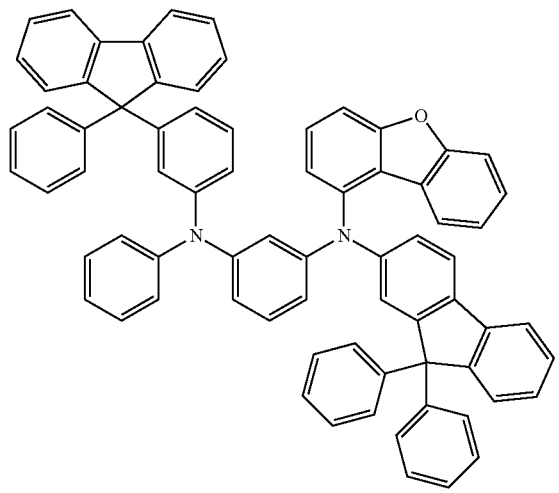
G-31
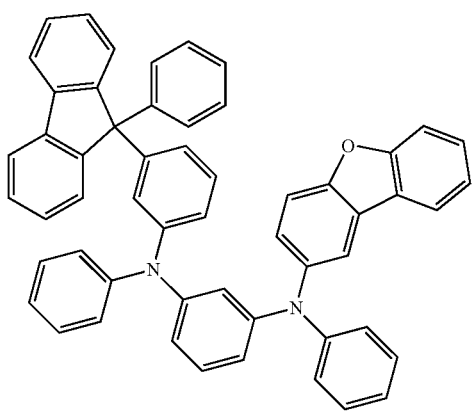
G-32
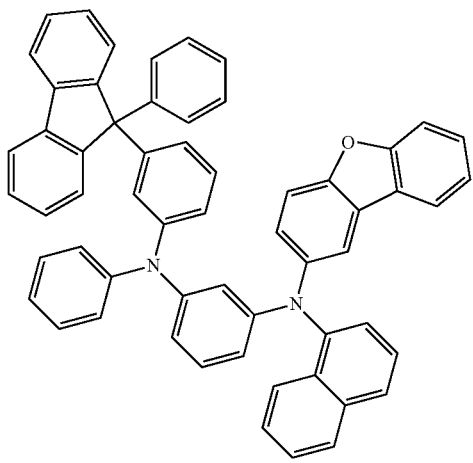
G-33
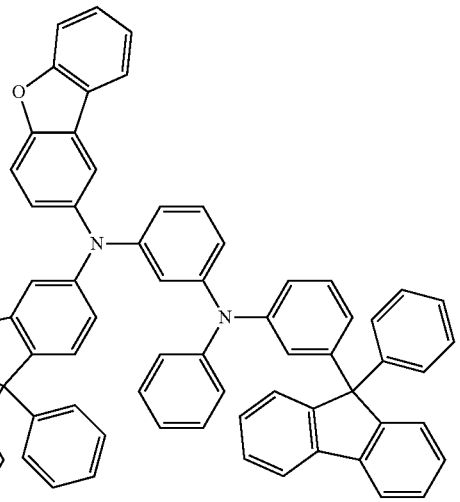
G-34
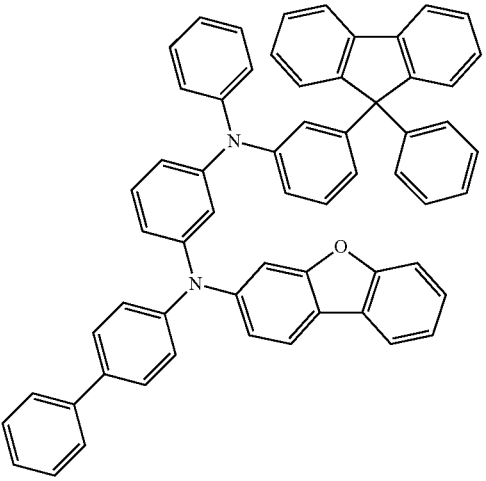
G-35
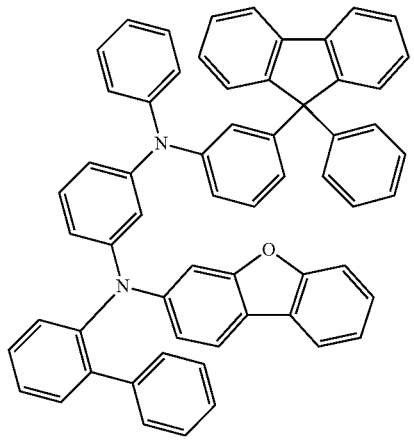

G-36
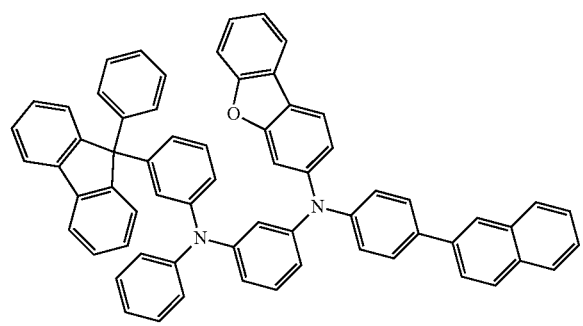
G-37
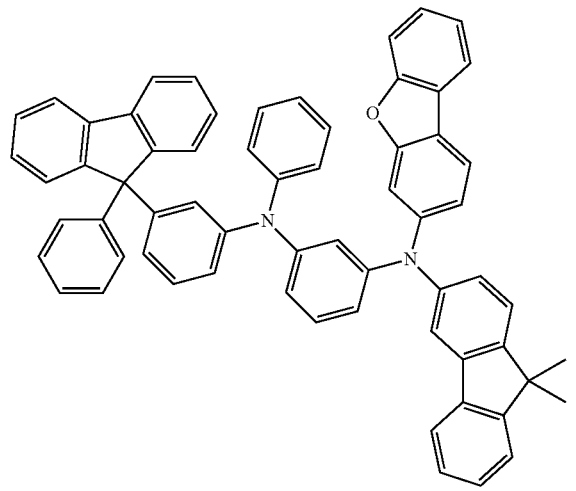
G-38
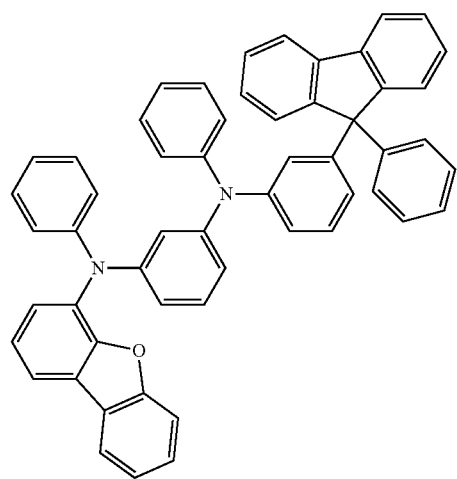
G-39
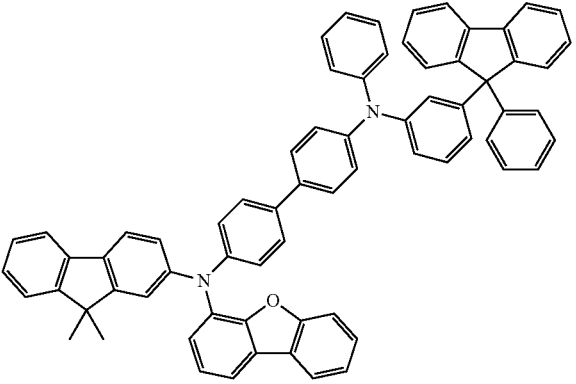
G-40
G-41
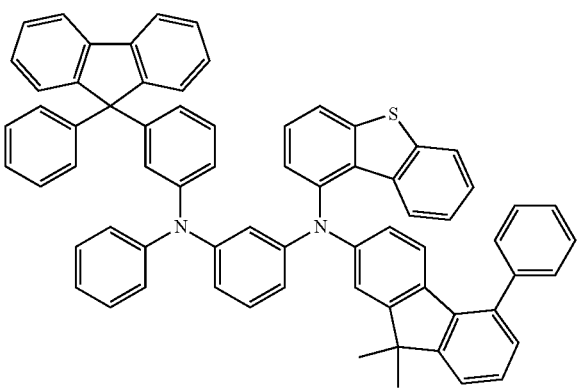
G-42
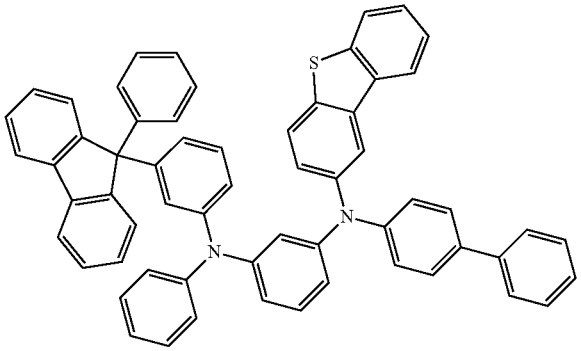

-continued
G-43
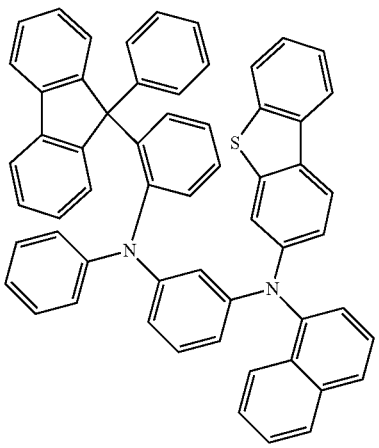
G-44
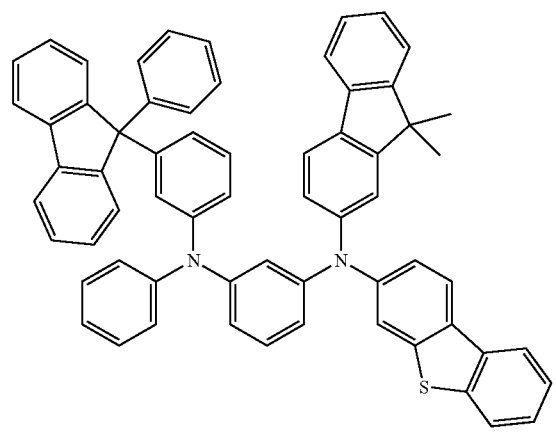
G-45
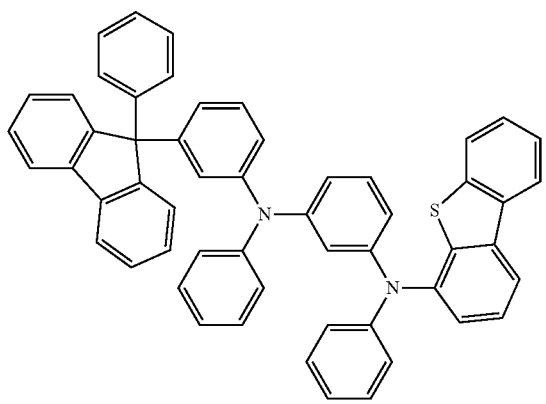
-continued
G-46
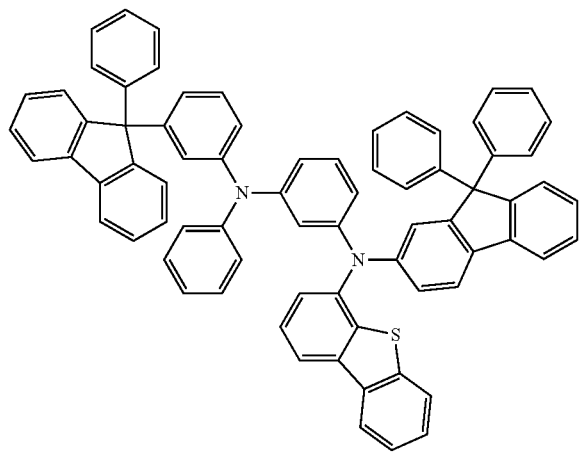
G-47
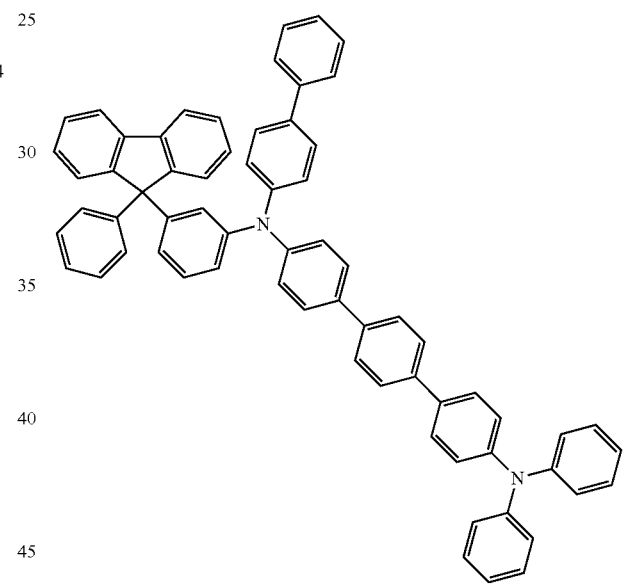
G-48
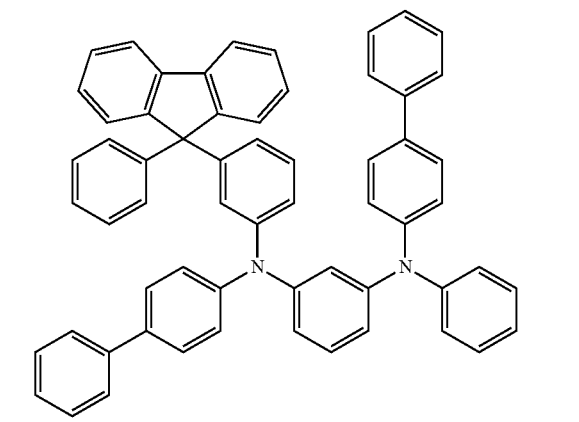

G-49
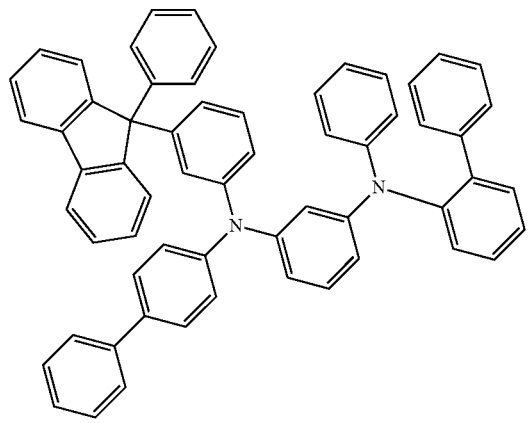
G-50
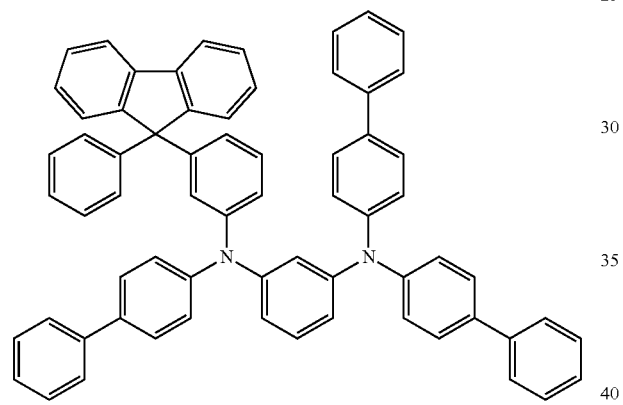
G-51
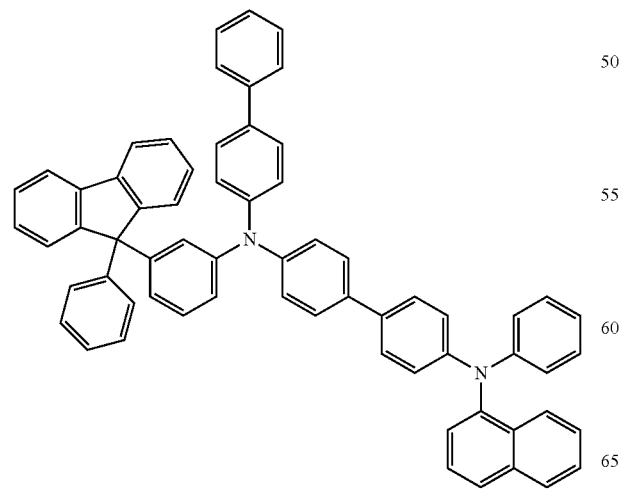
G-52
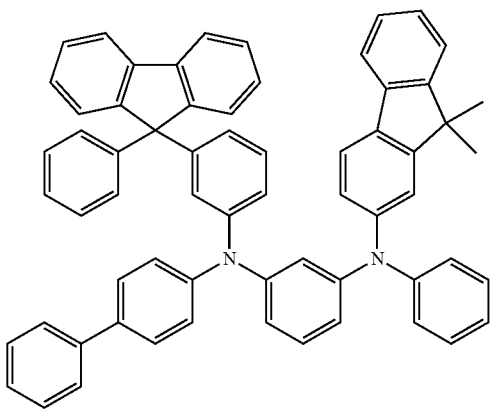
G-53
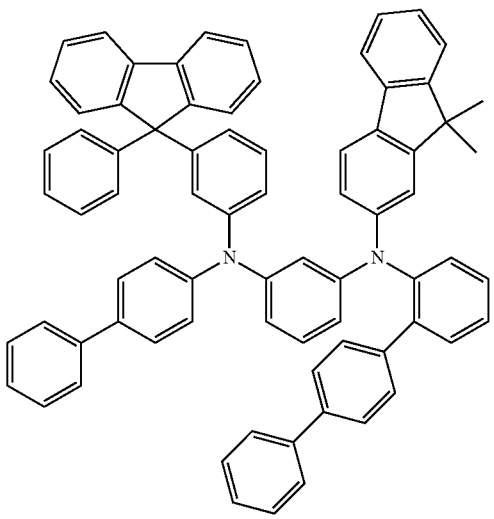
G-54
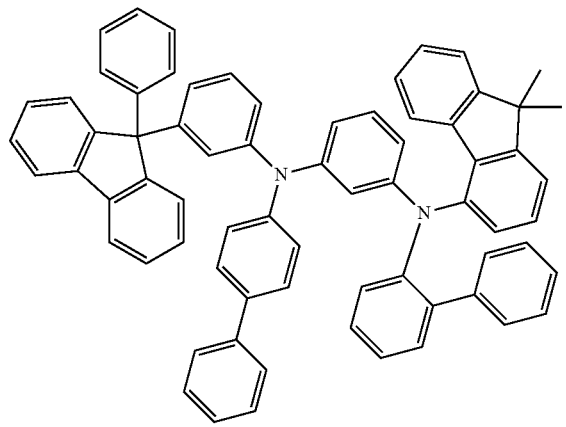

-continued
G-55
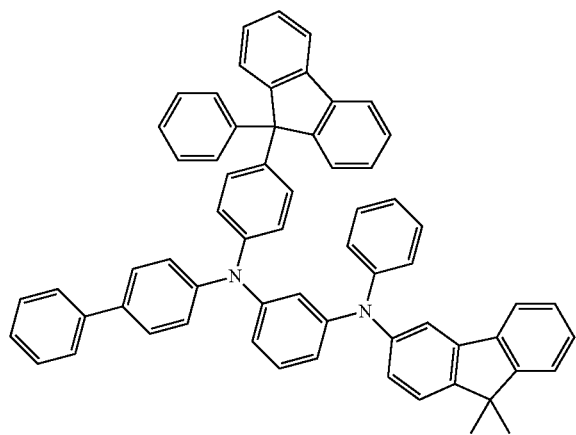
G-56
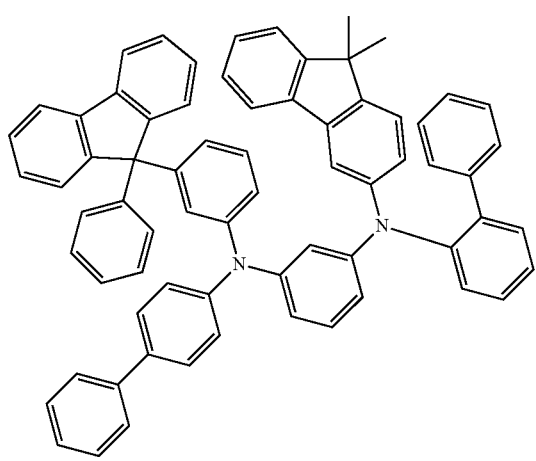
G-57
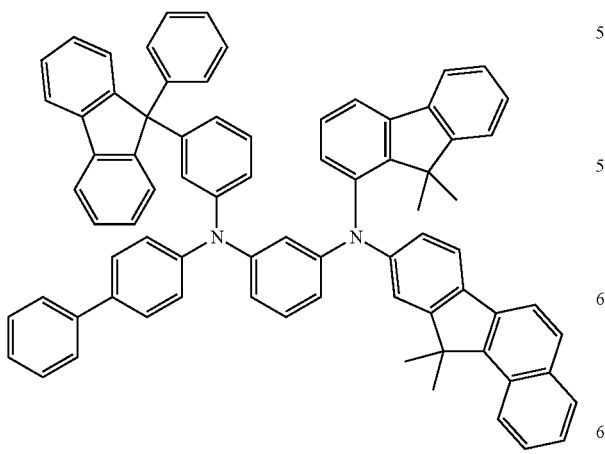
-continued
G-58
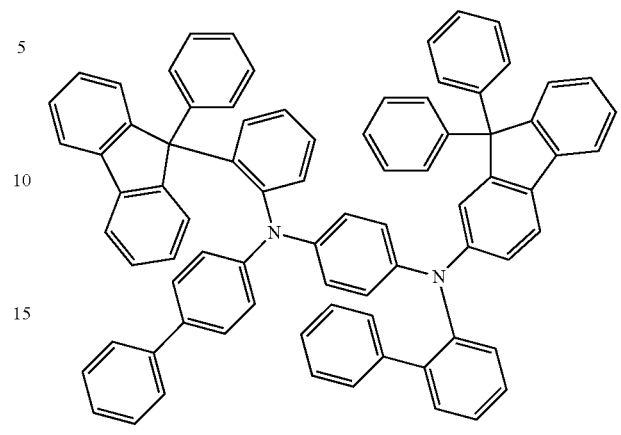
G-59
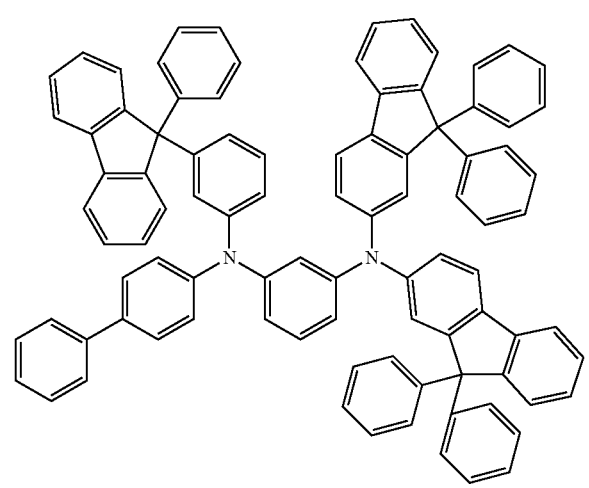
G-60
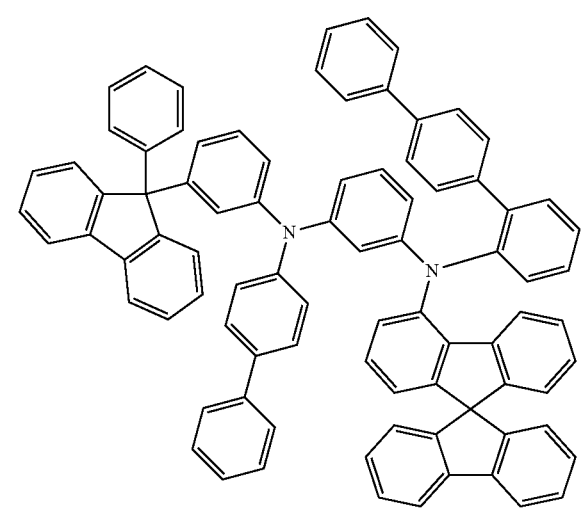

G-61
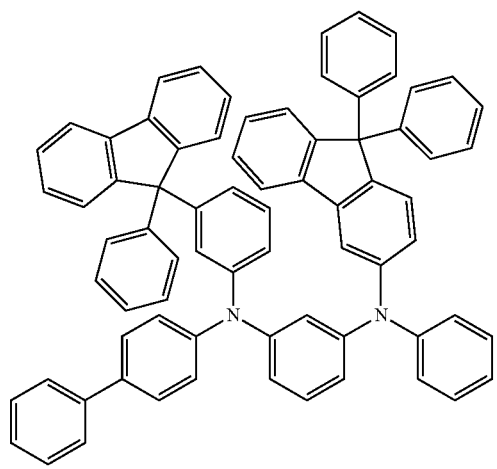
G-64
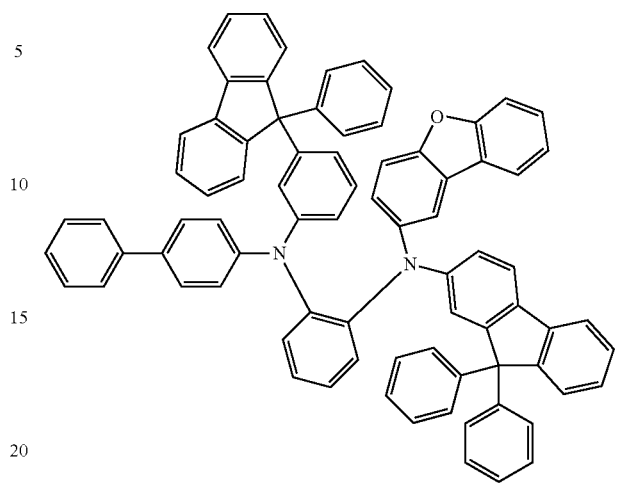
G-62
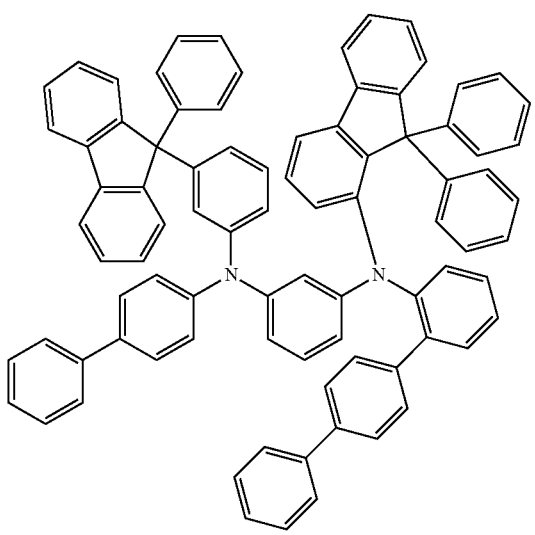
G-65
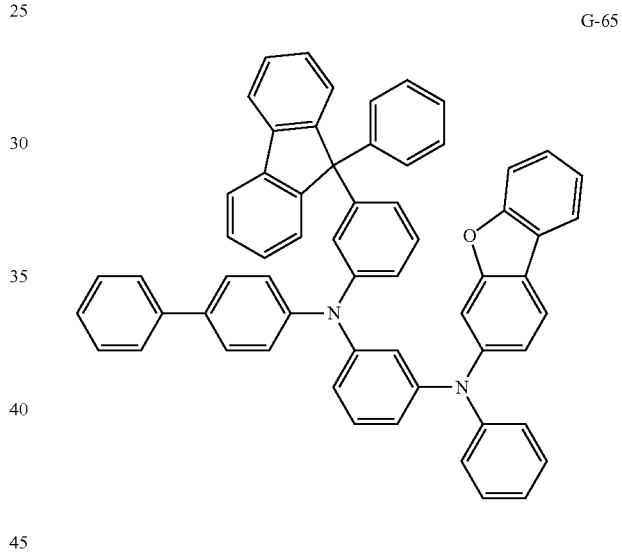
G-63
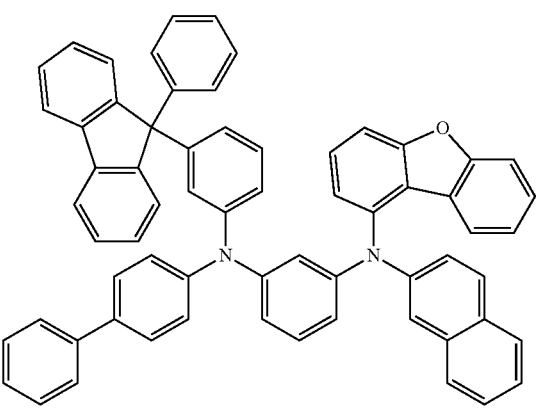
G-66
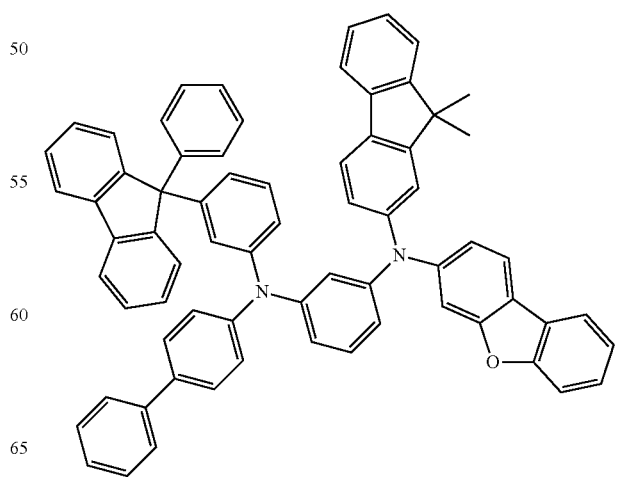

G-67
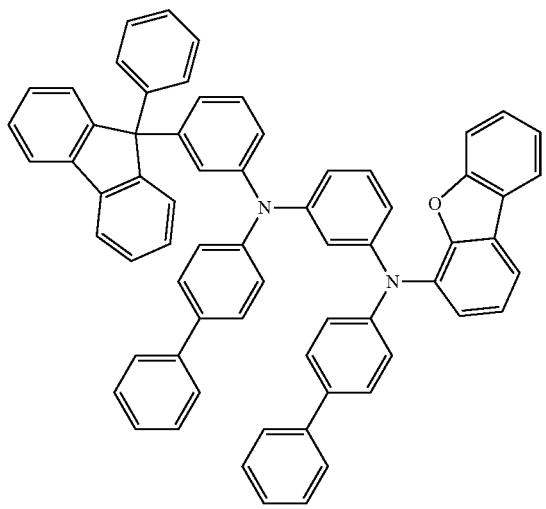
G-68
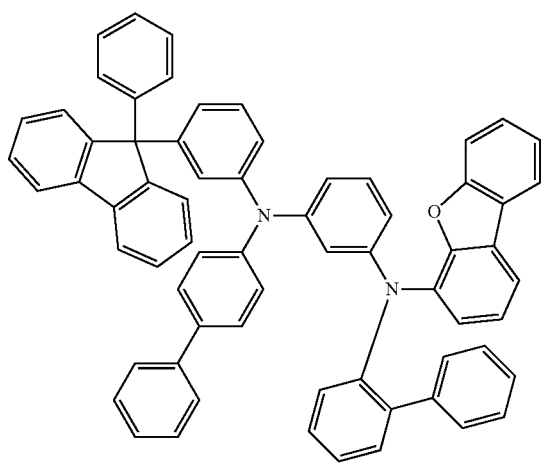
G-69
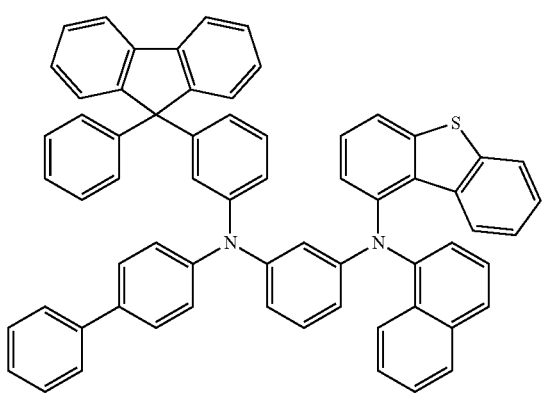
G-70
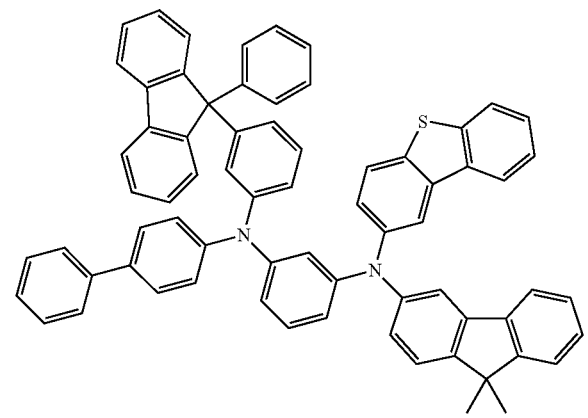
G-71
G-72
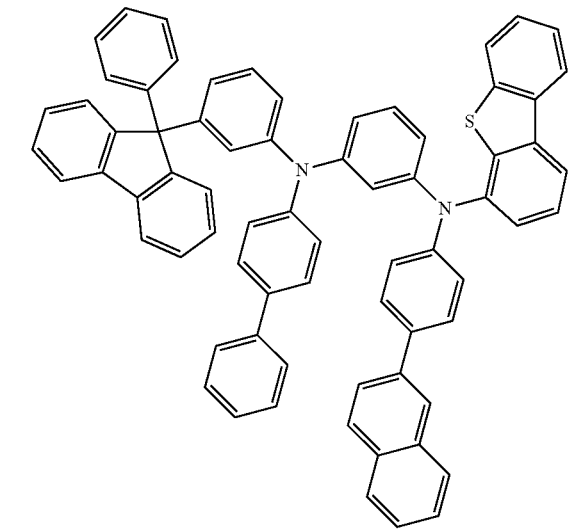

G-73
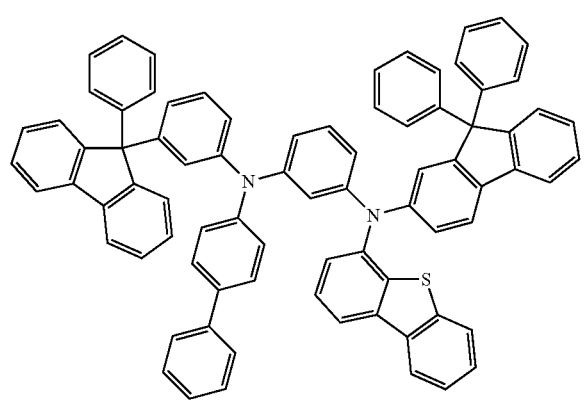
G-74
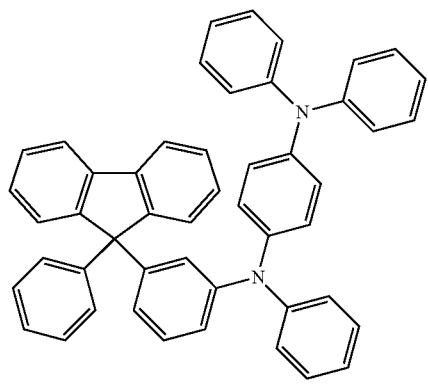
G-75
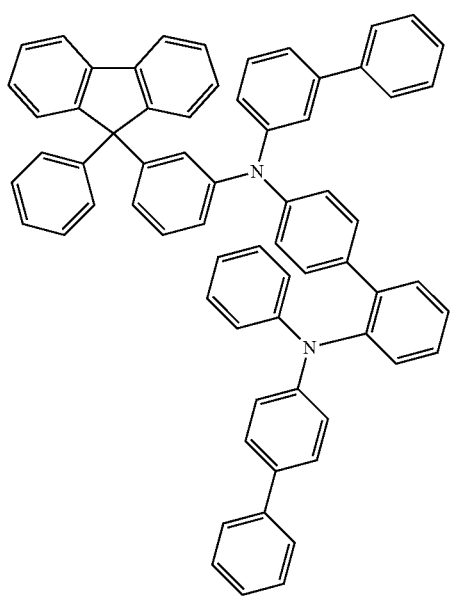
G-76
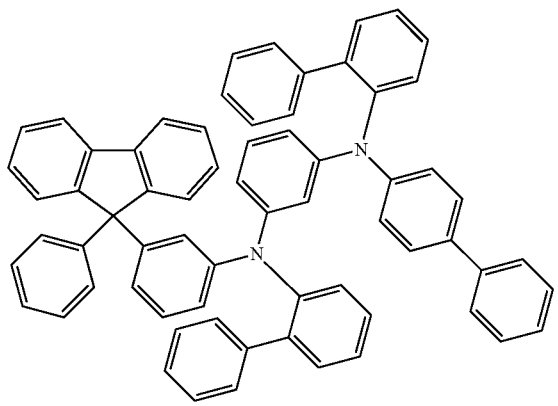
G-77
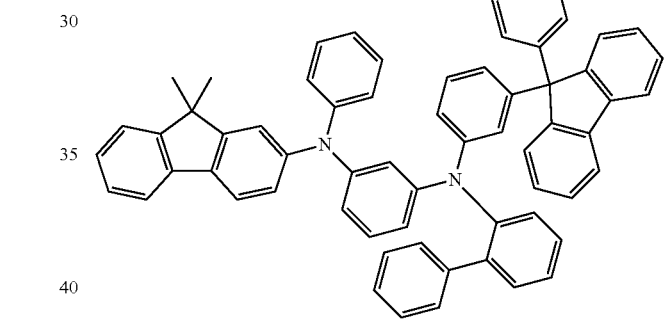
G-78
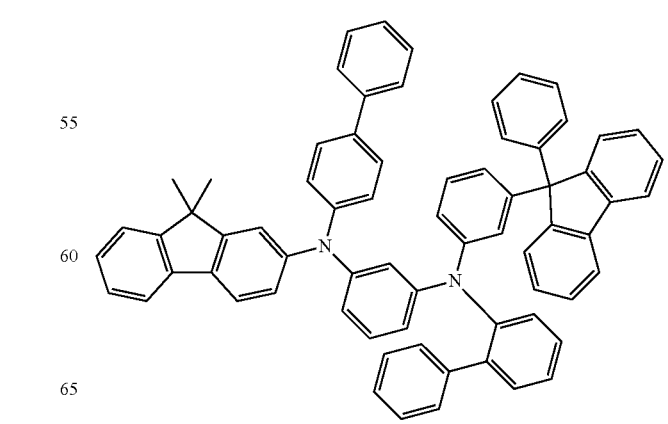

G-79
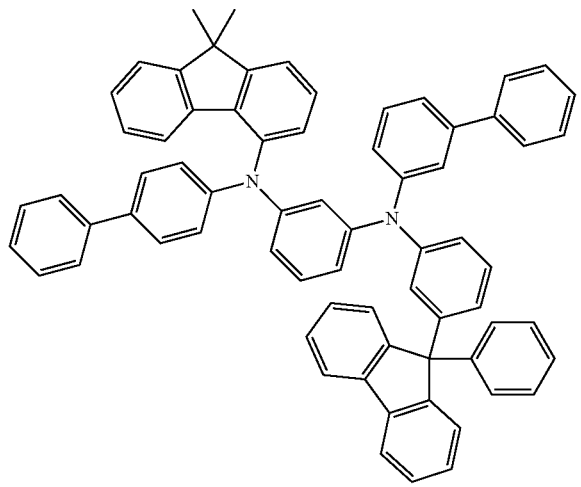
G-82
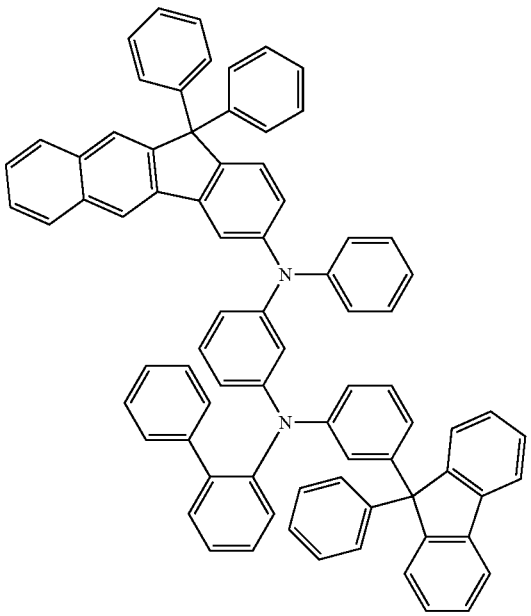
G-80
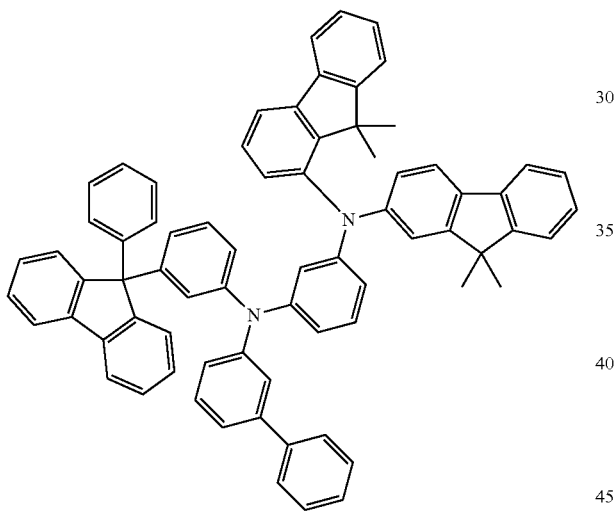
G-81
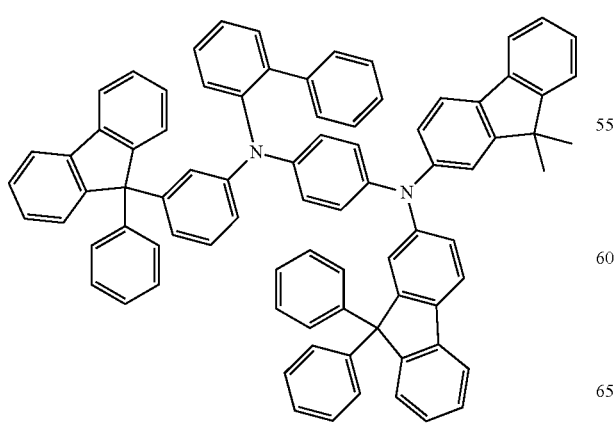
G-83
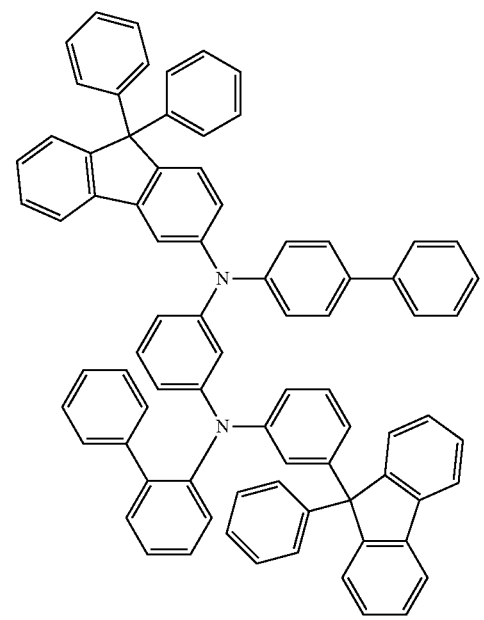

G-84
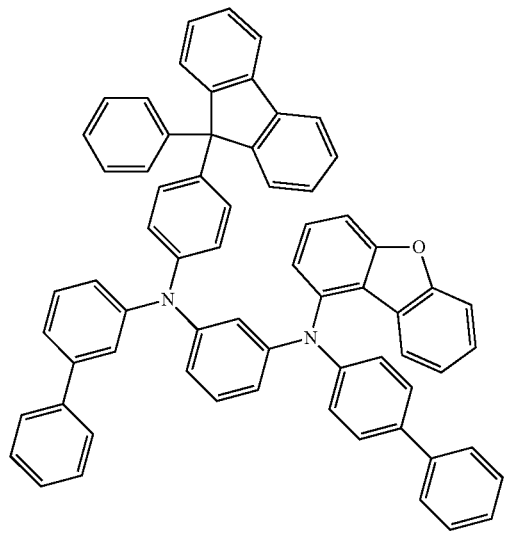
G-85
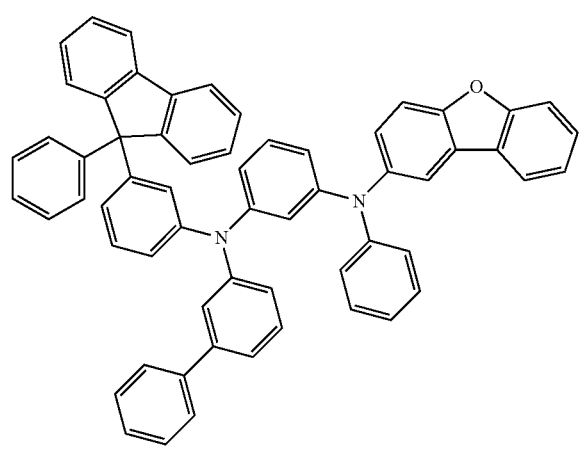
G-86
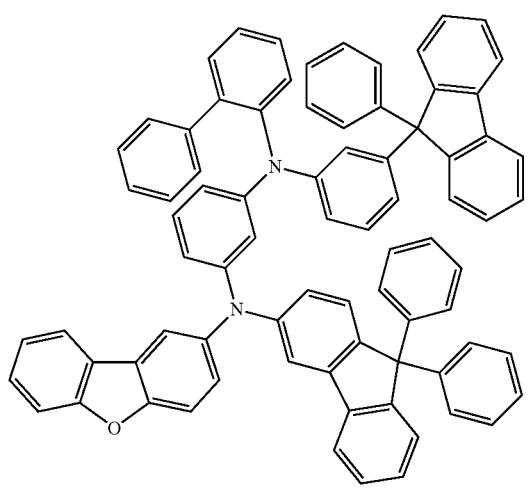
G-87
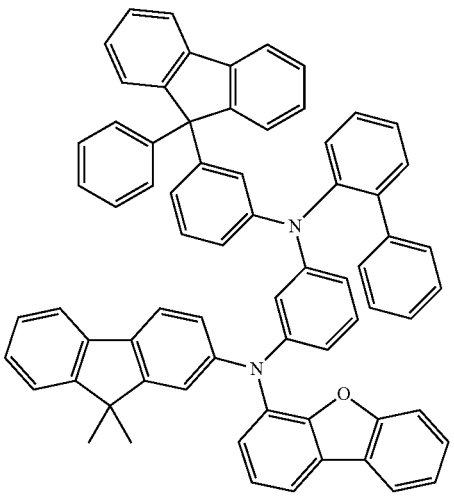
G-88
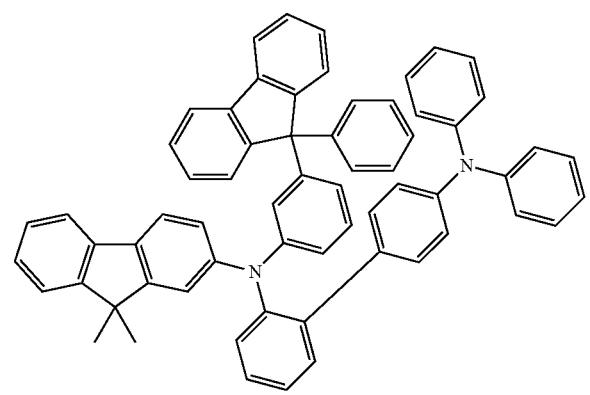
G-89
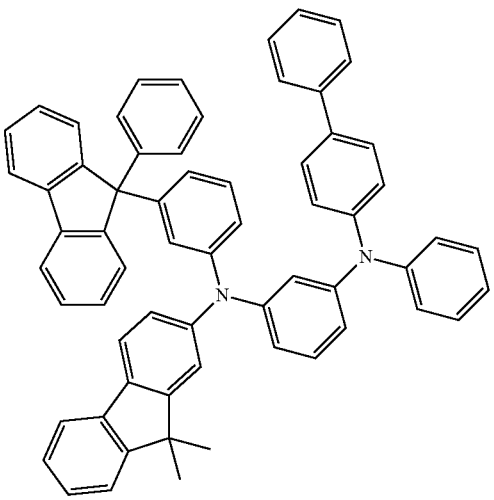

G-90
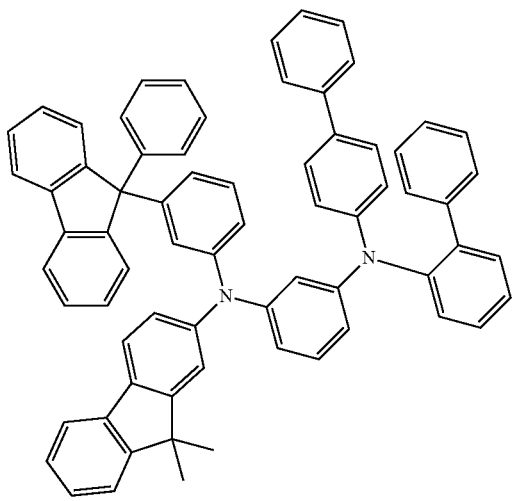
G-93
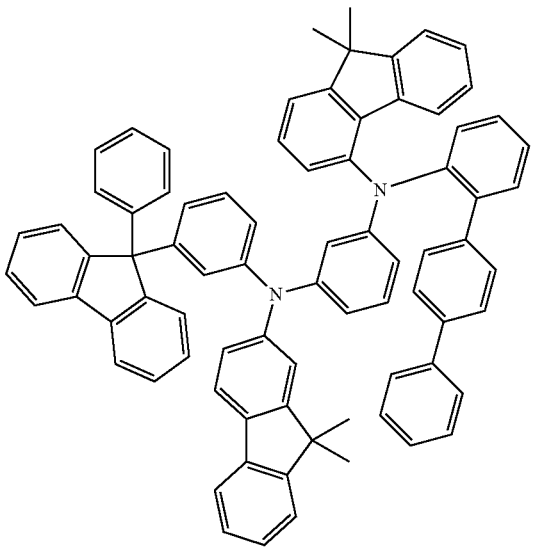
G-91
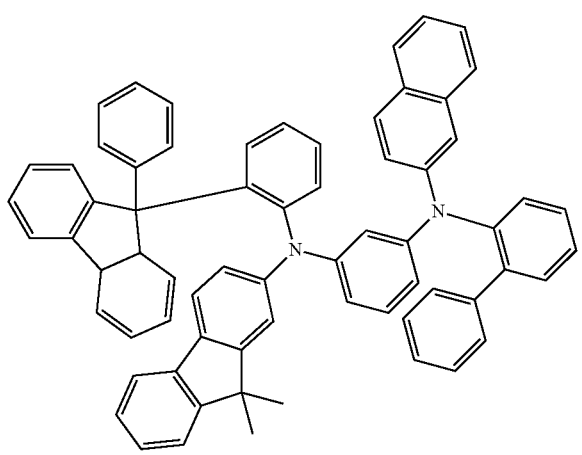
G-94
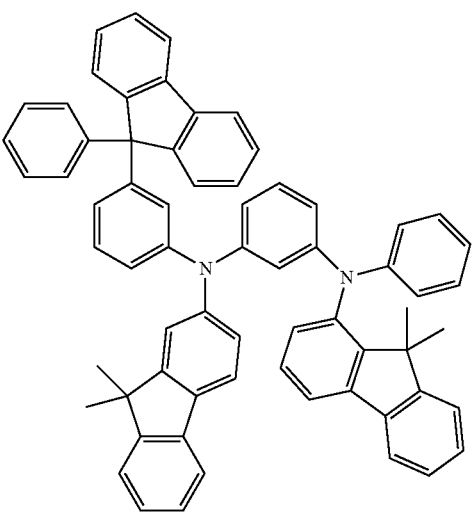
G-92
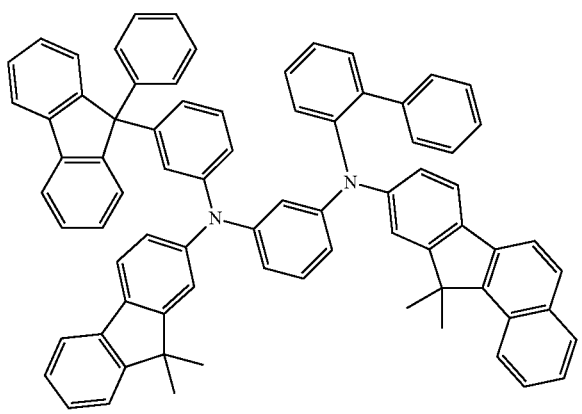
G-95
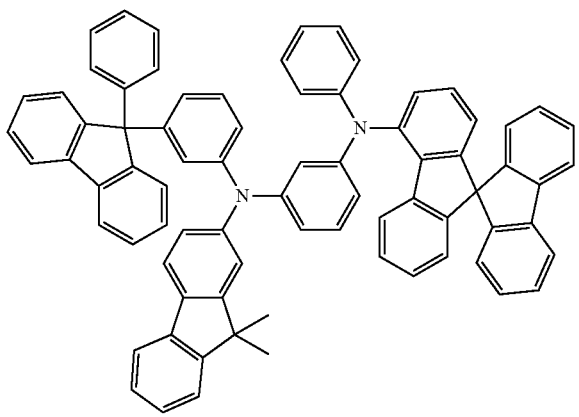

G-96
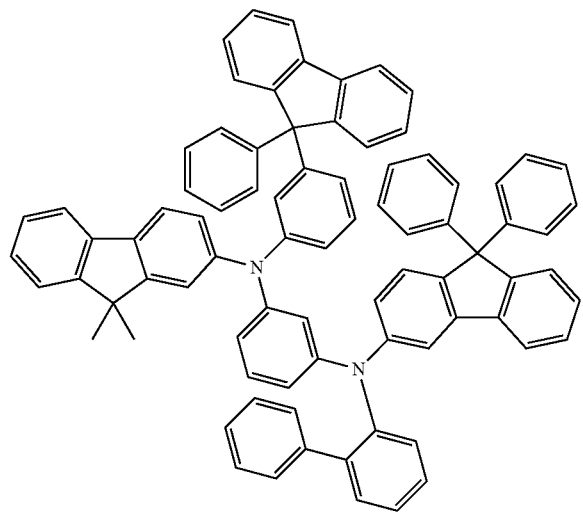
G-97
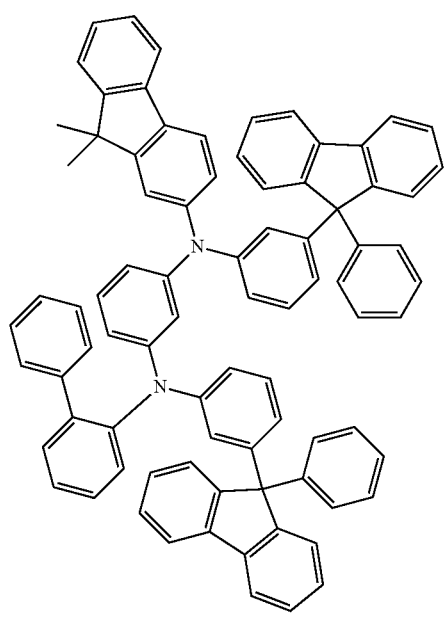
G-98
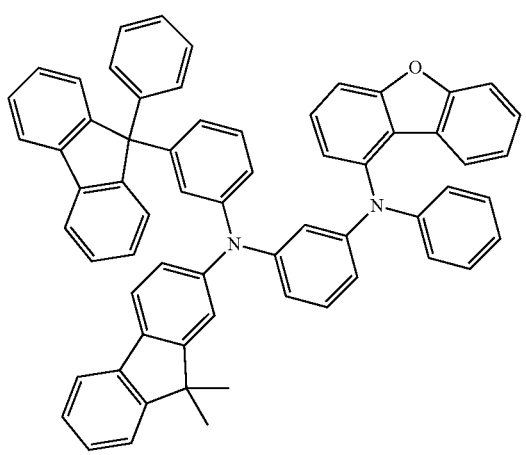
G-99
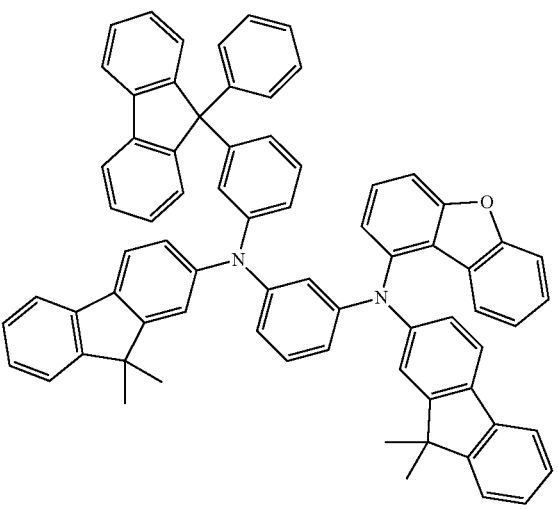
G-100
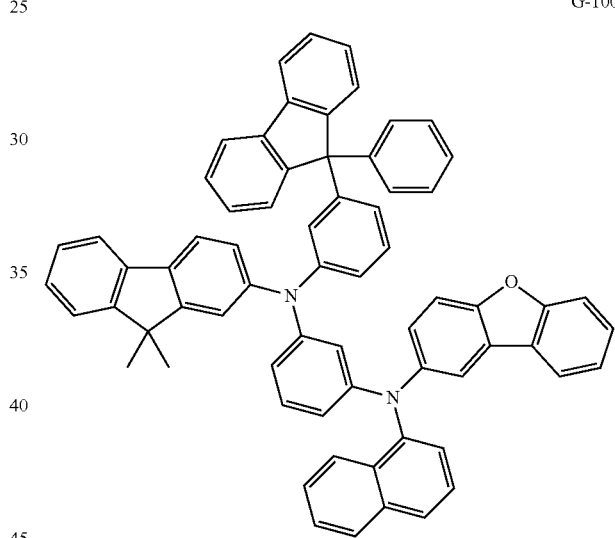
G-101
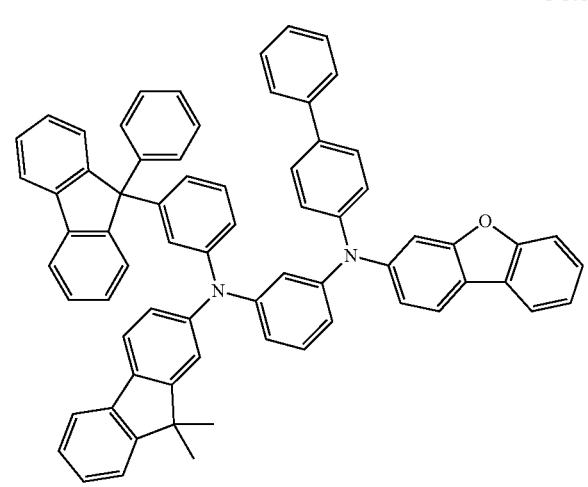

G-102
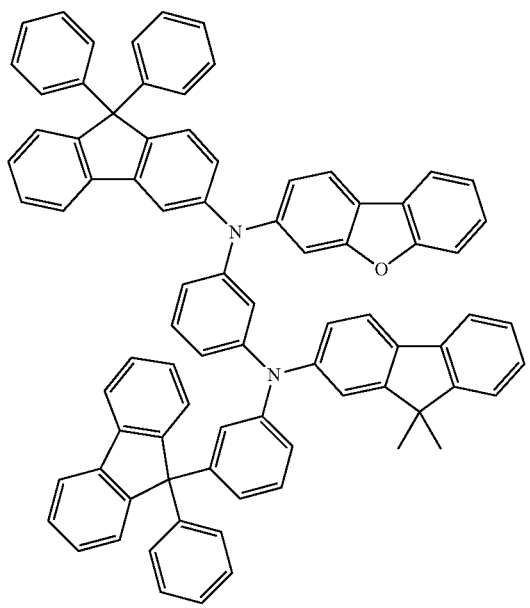
G-103
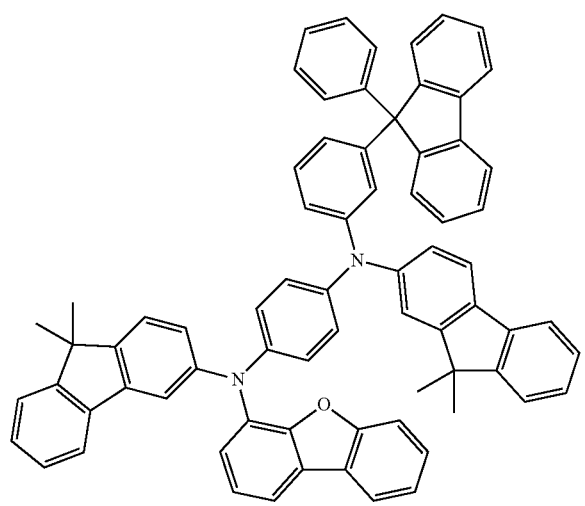
G-104
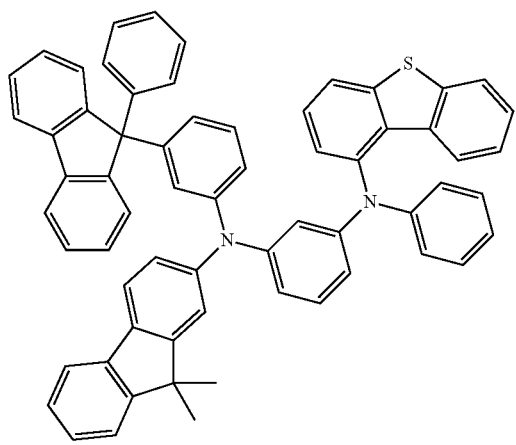
G-105
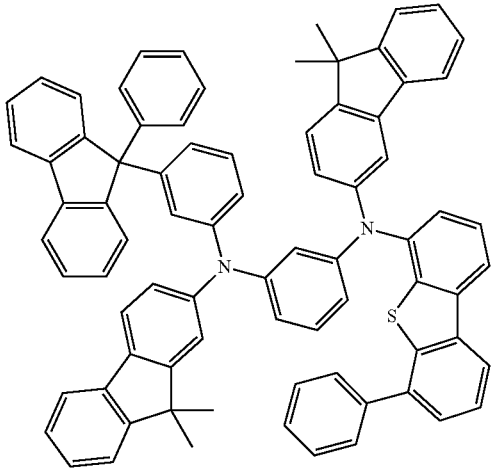
G-106
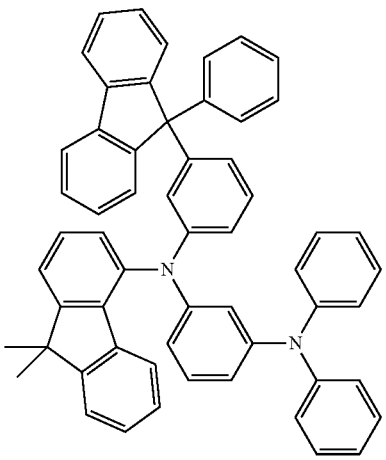
G-107
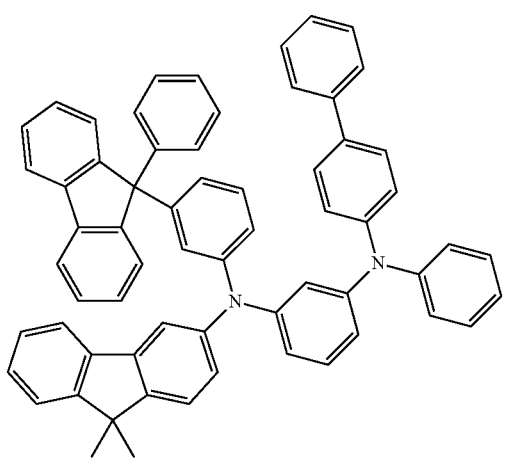

G-108
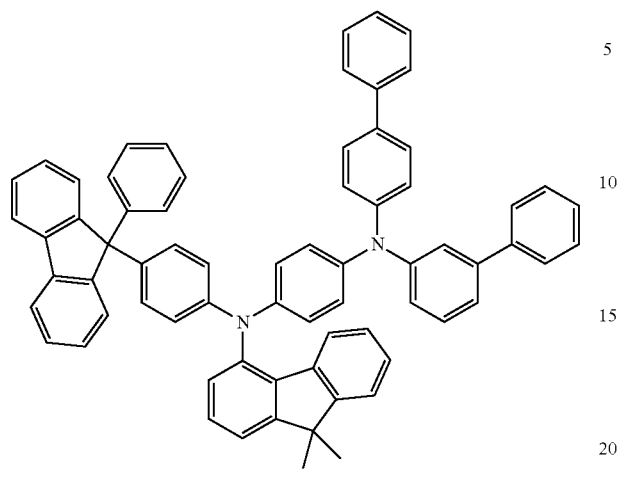
G-111
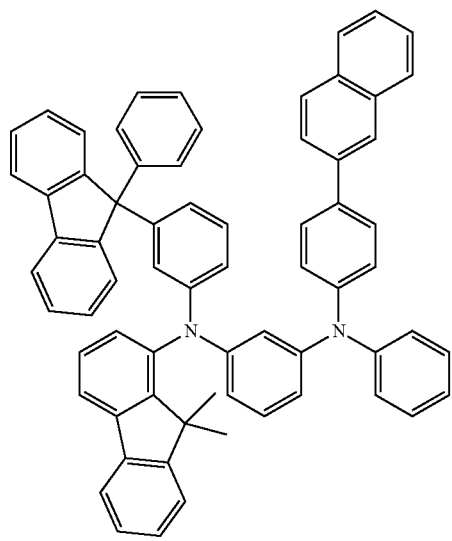
G-109
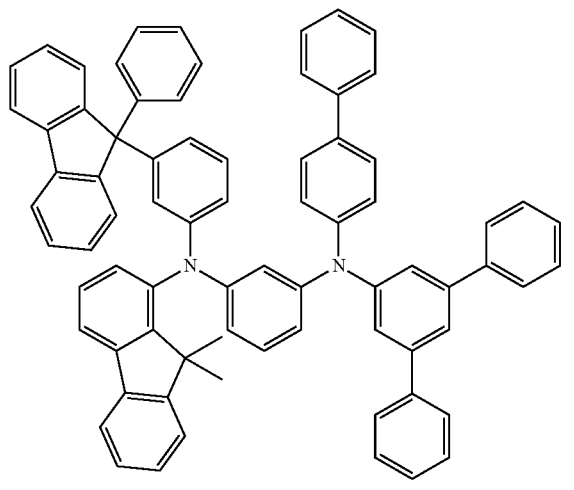
G-112
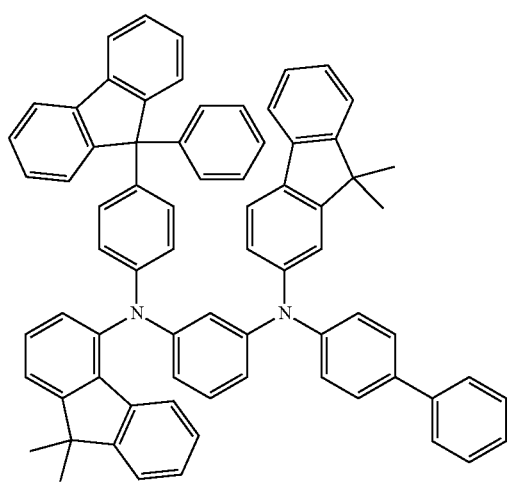
G-110
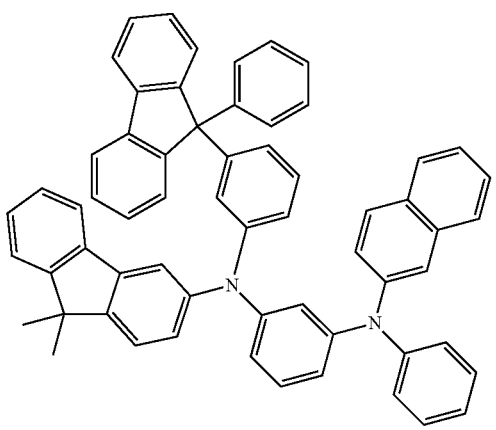
G-113
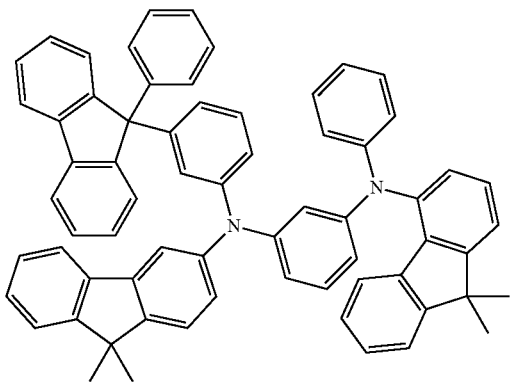

G-114
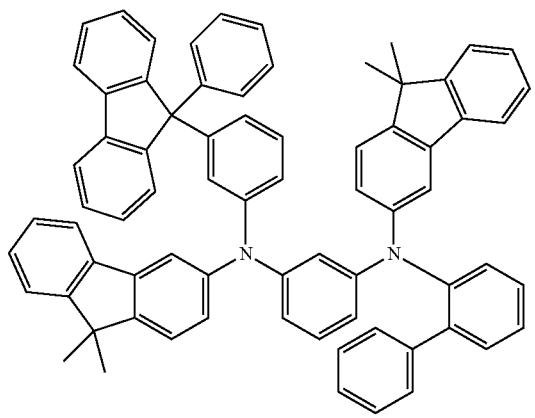
G-115
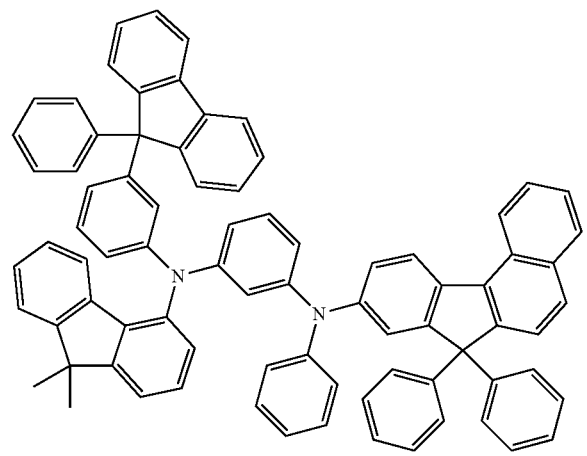
G-116
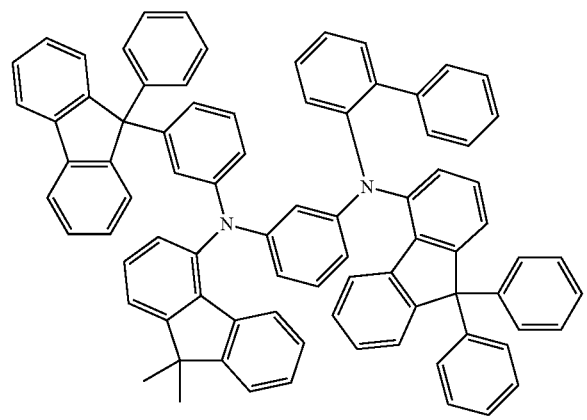
G-117
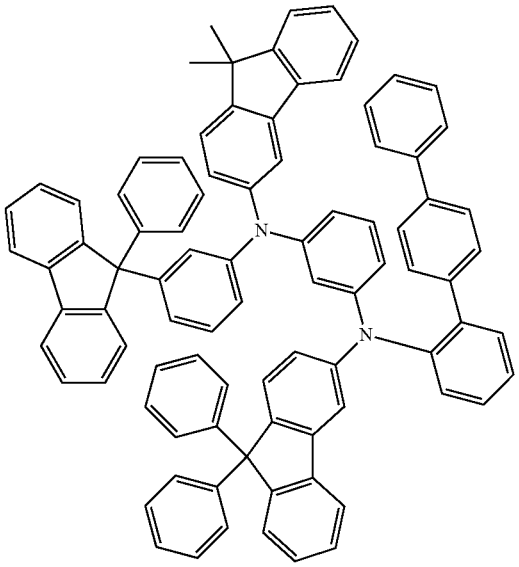
G-118
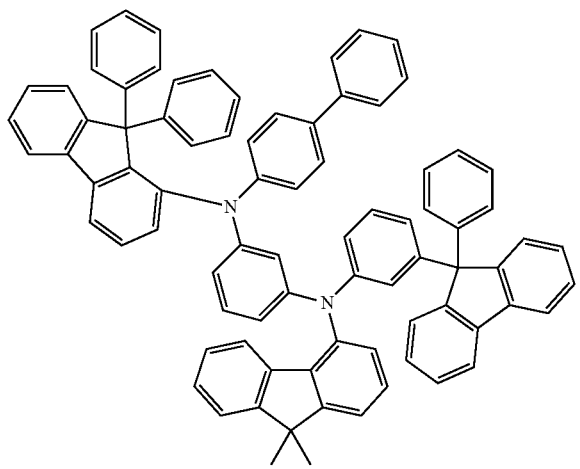
G-119
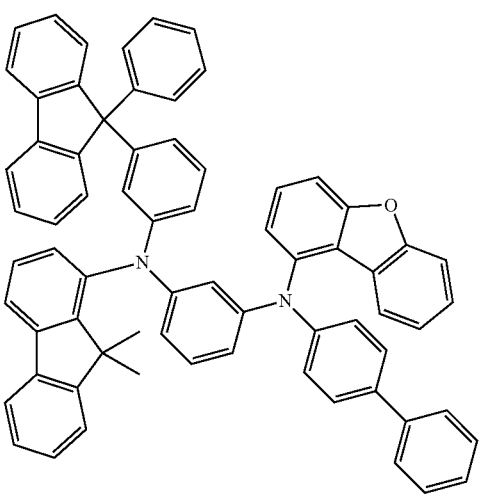

G-120
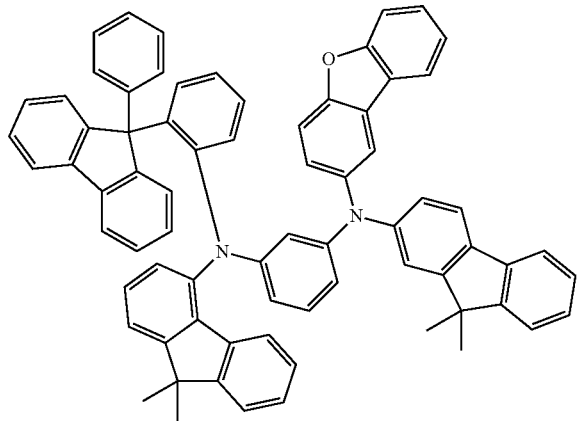
G-121
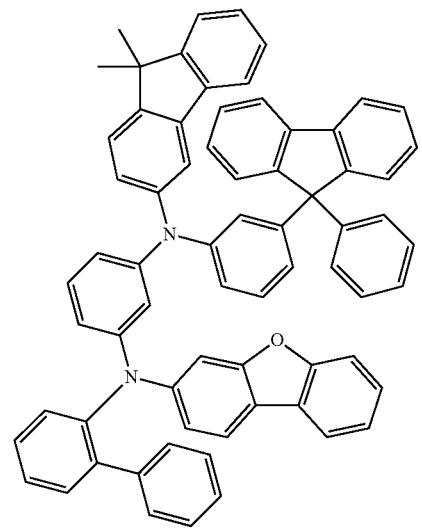
G-122
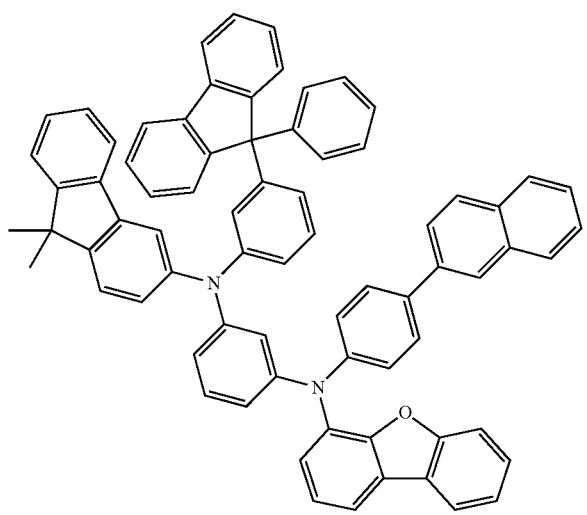
G-123
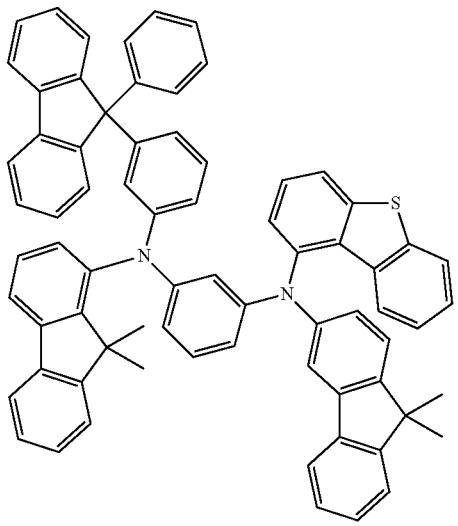
G-124
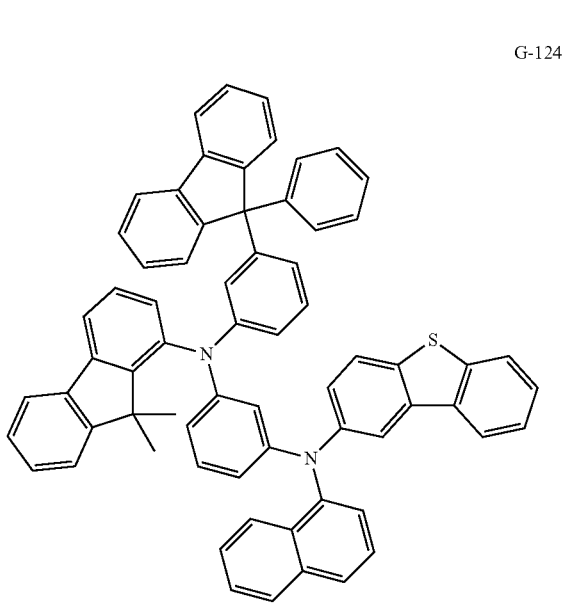
G-125
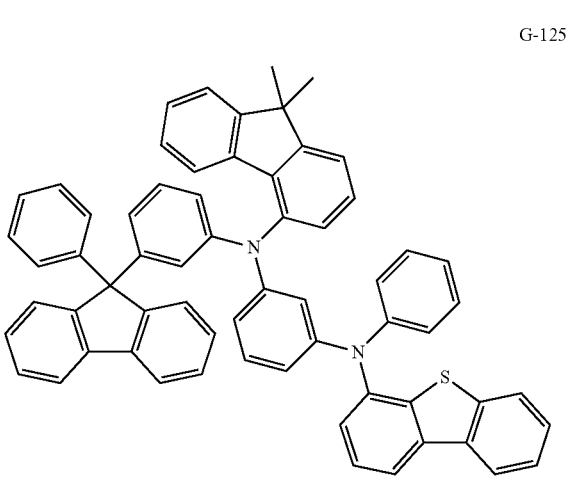

G-126
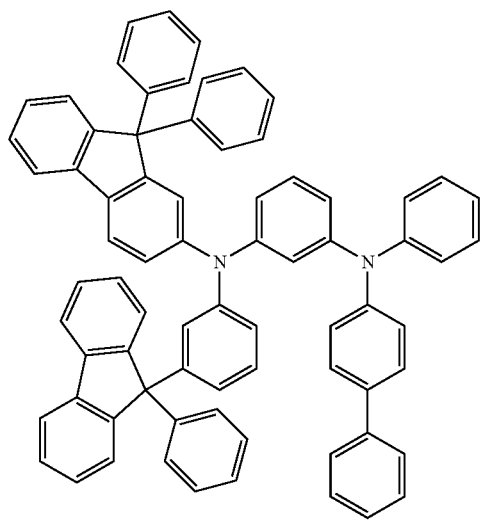
G-127
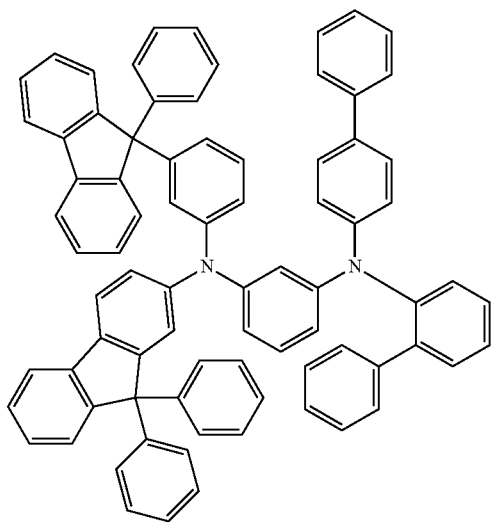
G-128
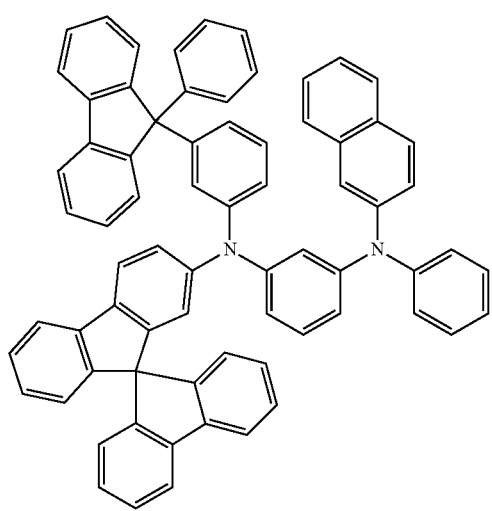
G-129
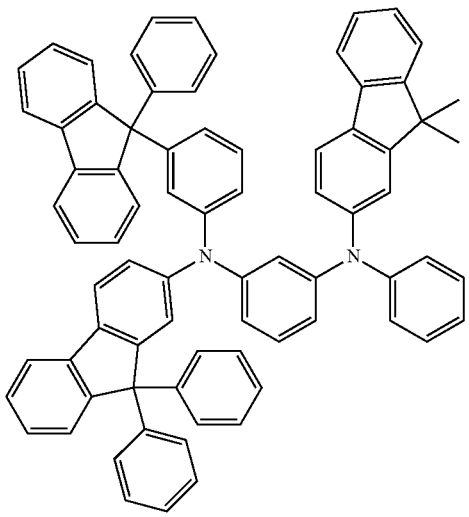
G-130
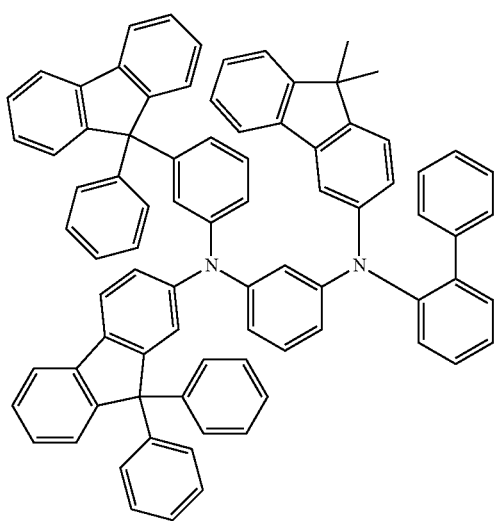
G-131
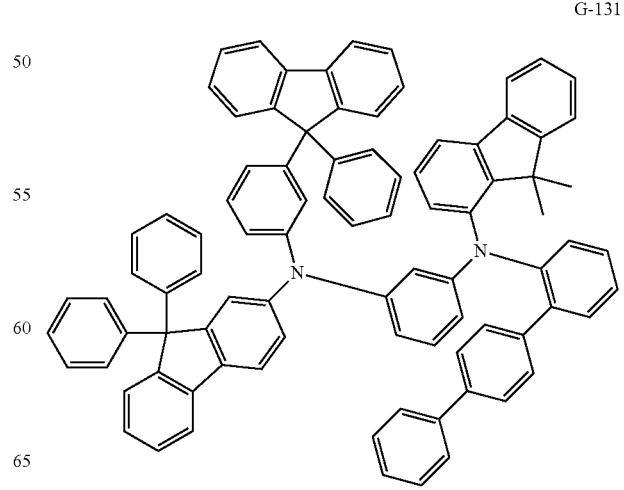

-continued
G-132
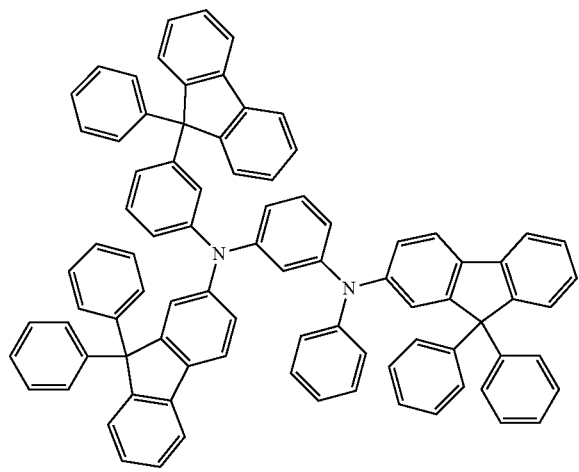
G-133
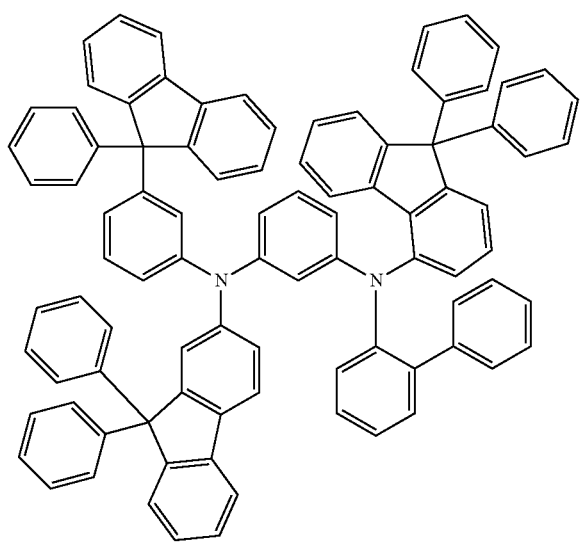
G-134
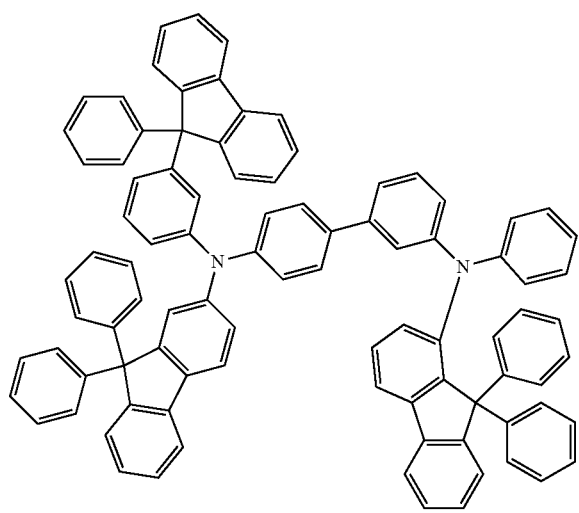
-continued
G-135
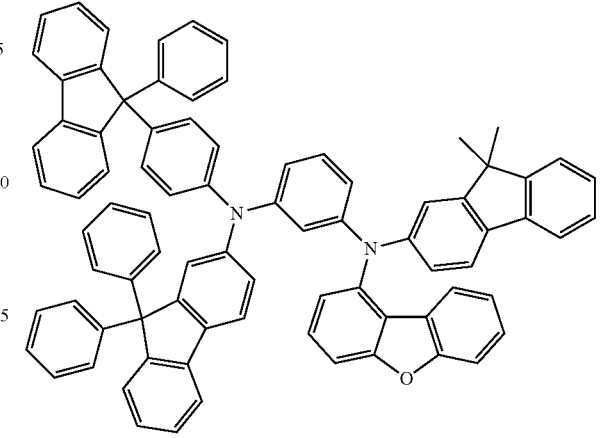
G-136
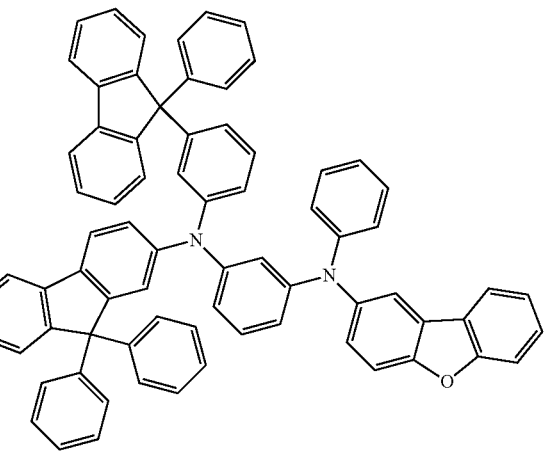
G-137
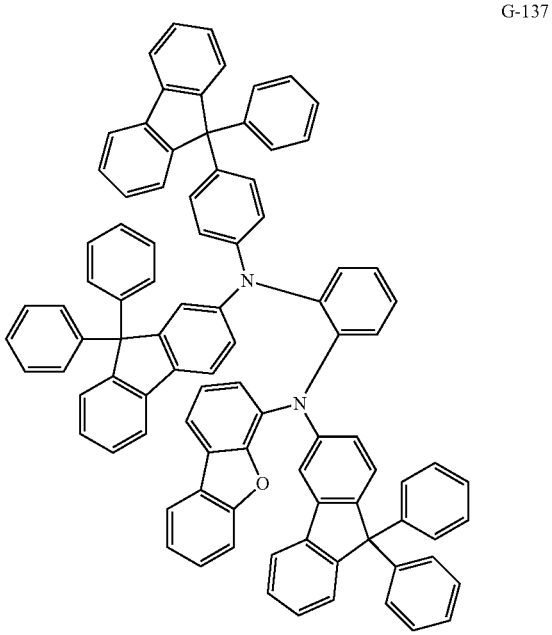

G-138
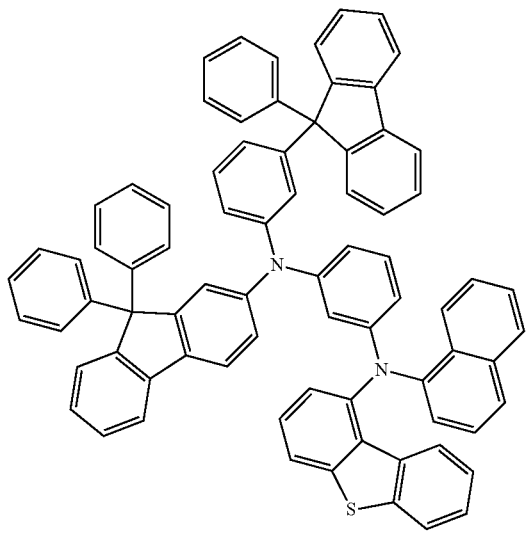
G-139
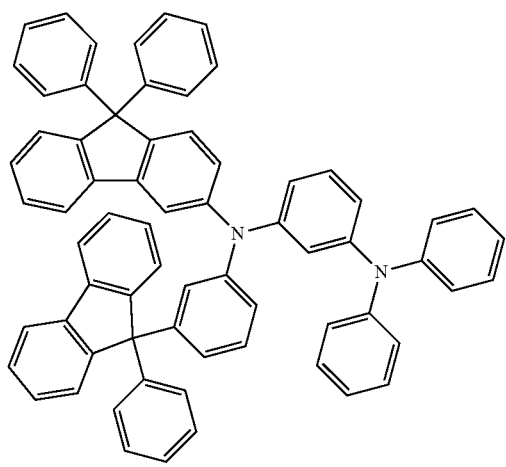
G-140
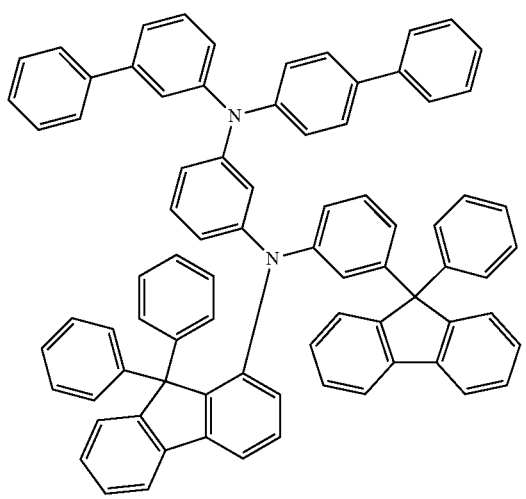
G-141
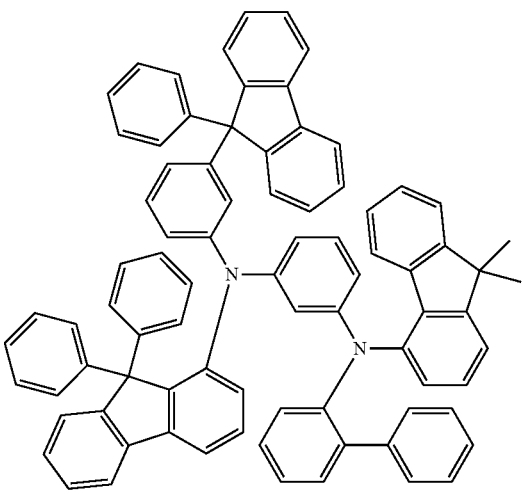
G-142
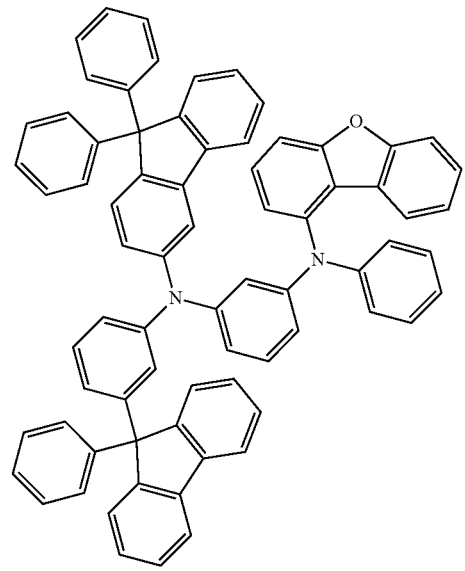

G-143
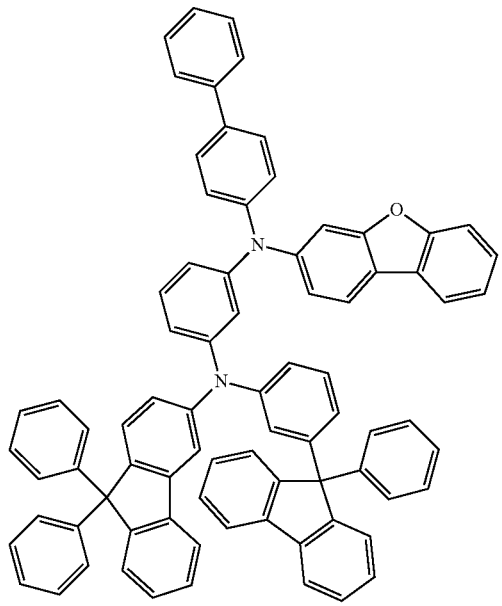
G-145
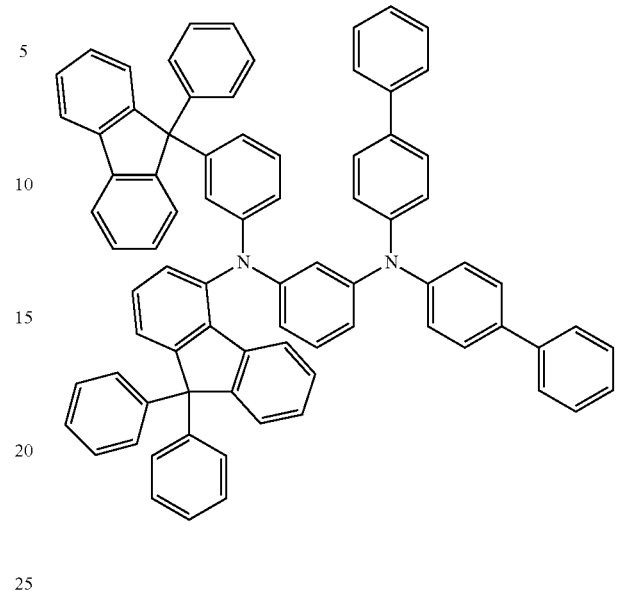
G-146
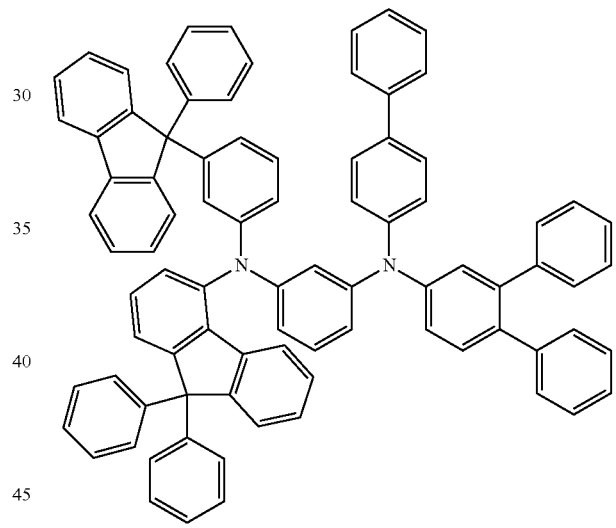
G-144
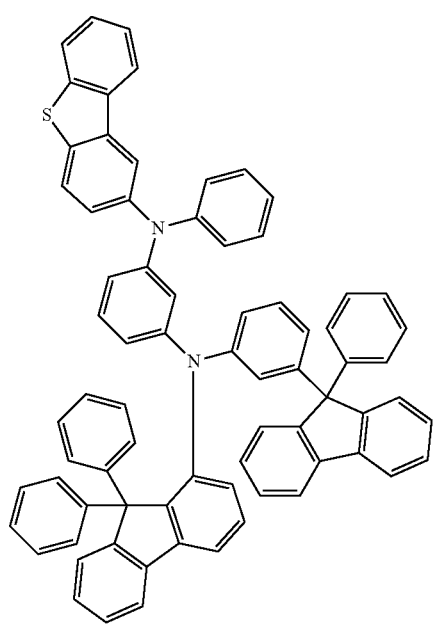
G-147
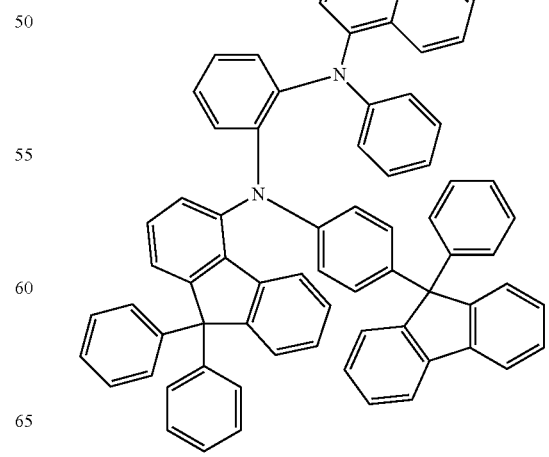

G-148
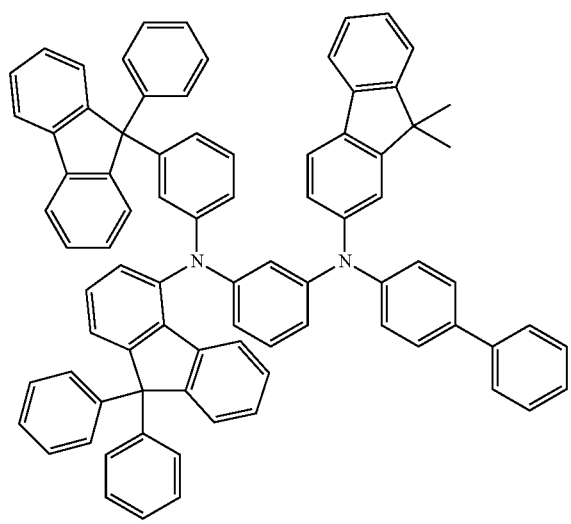
G-149
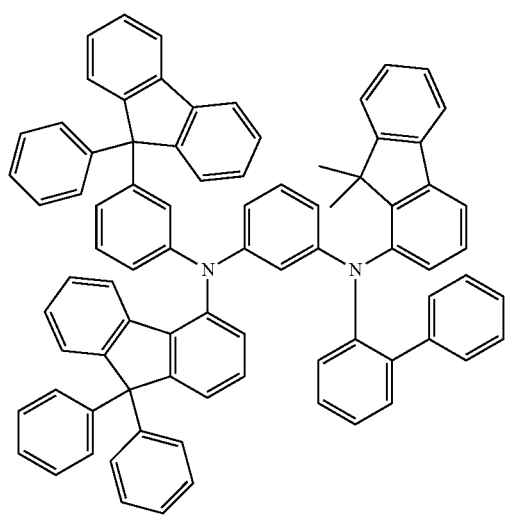
G-150
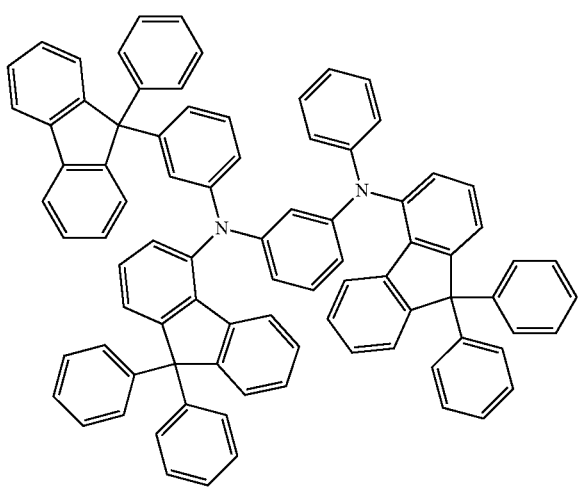
G-151
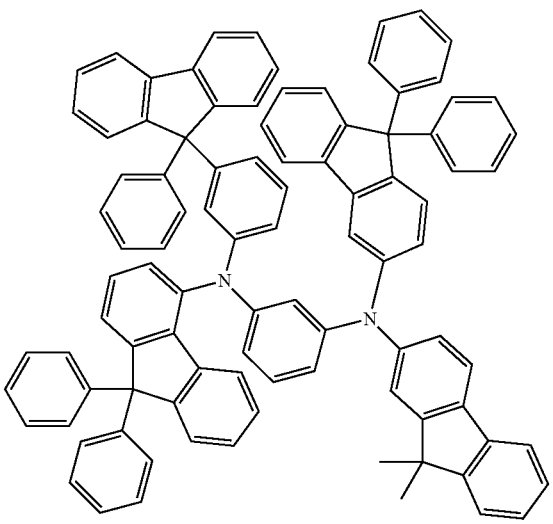
G-152
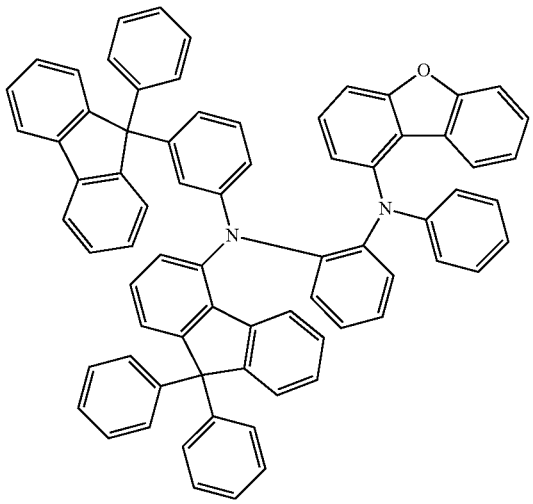
G-153
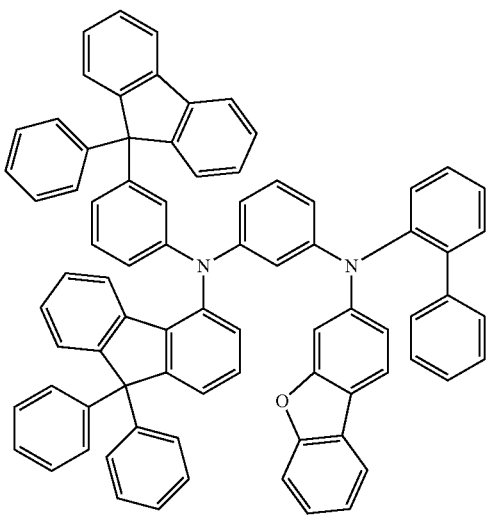

G-154
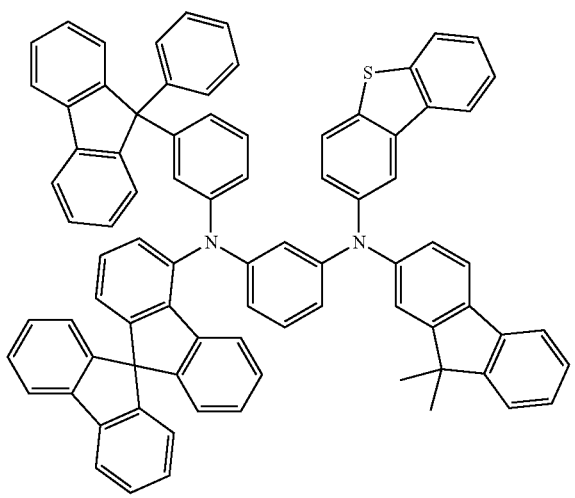
G-155
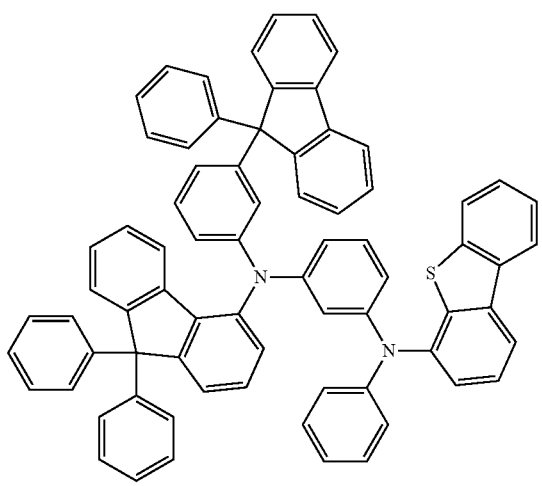
G-156
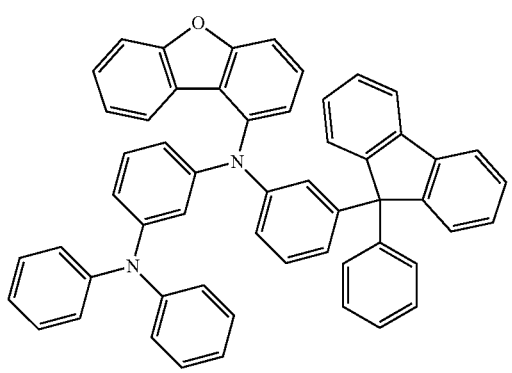
G-157
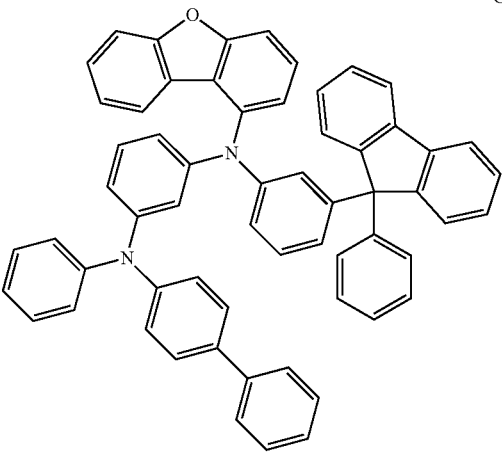
G-158
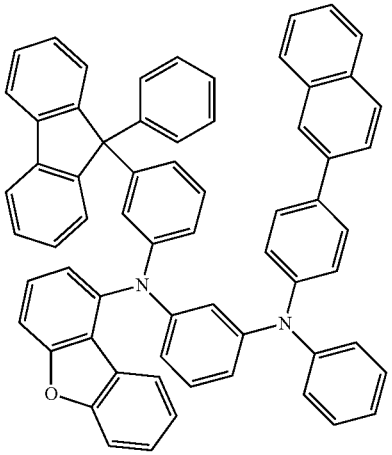
G-159
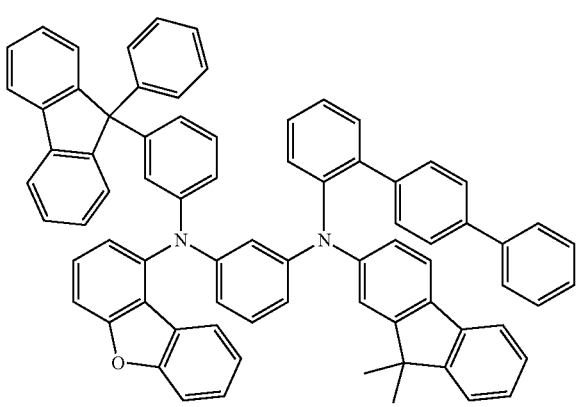

G-160
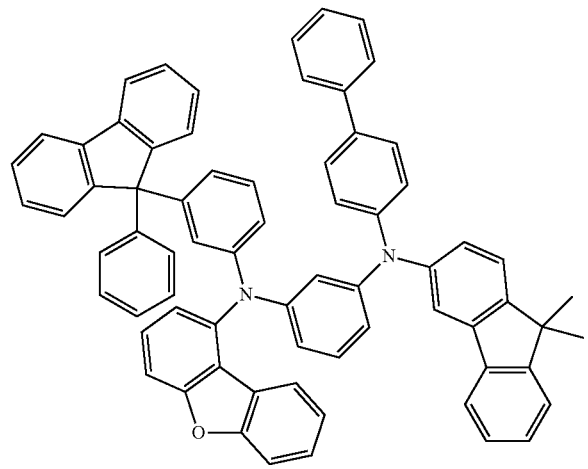
G-163
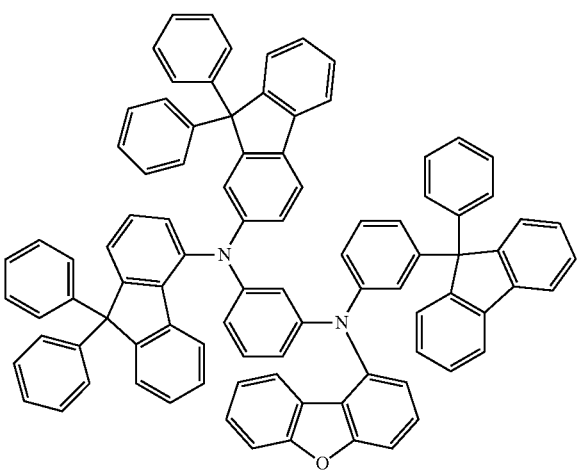
G-161
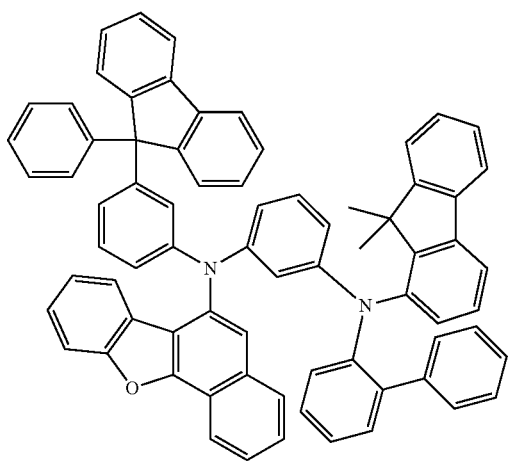
G-164
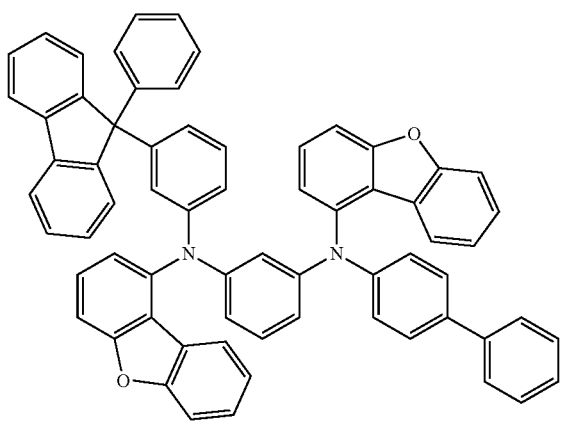
G-162
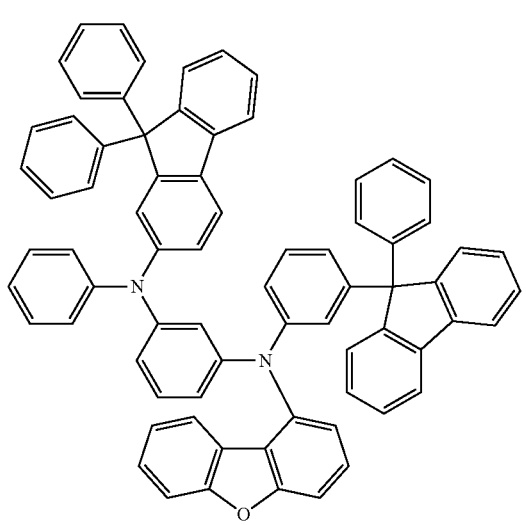
G-165
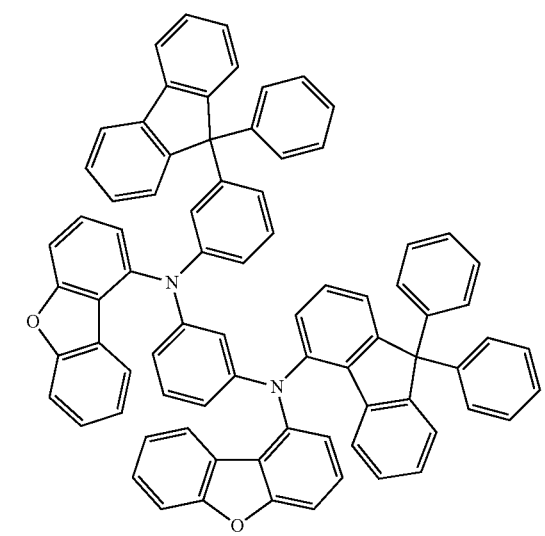

-continued
G-166
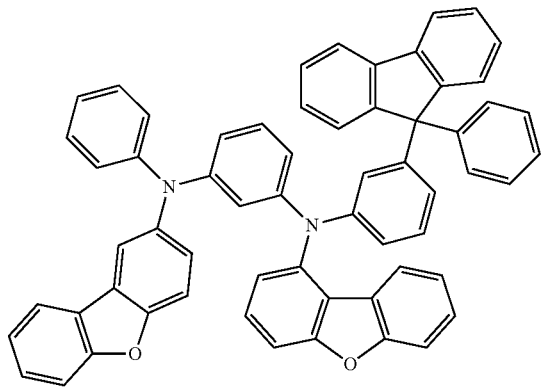
G-167
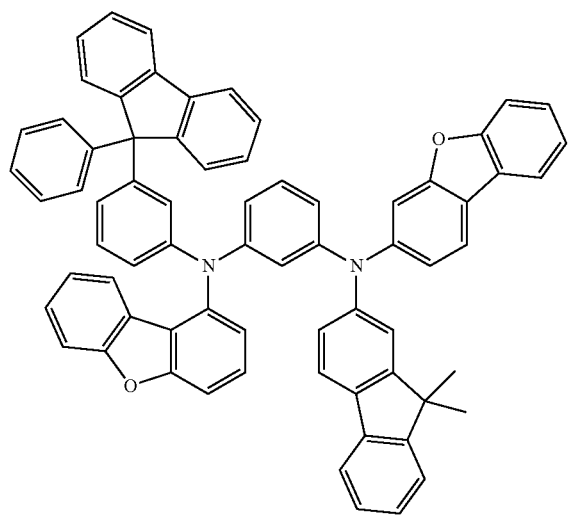
G-168
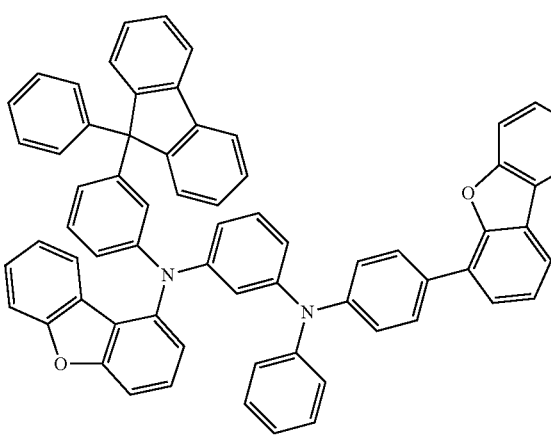
-continued
G-169
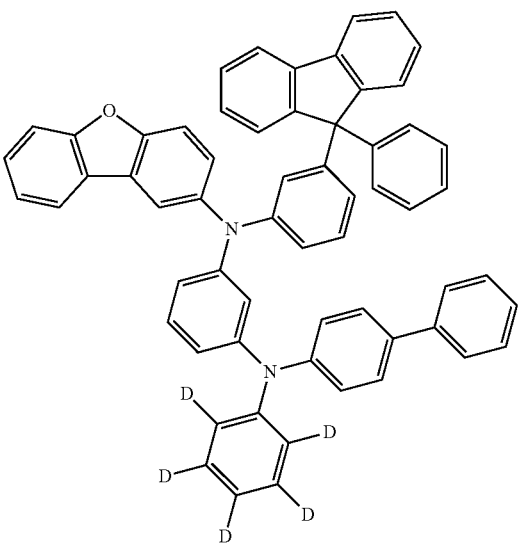
G-170
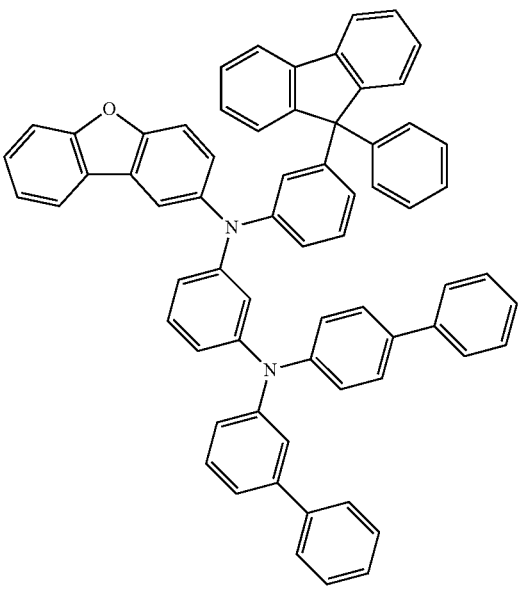

G-171
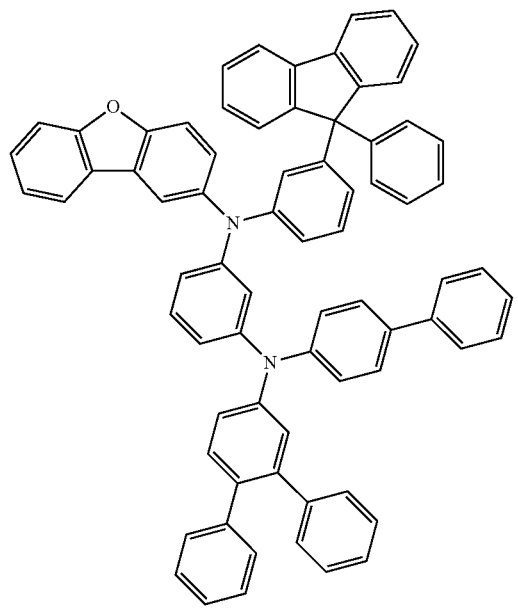
G-172
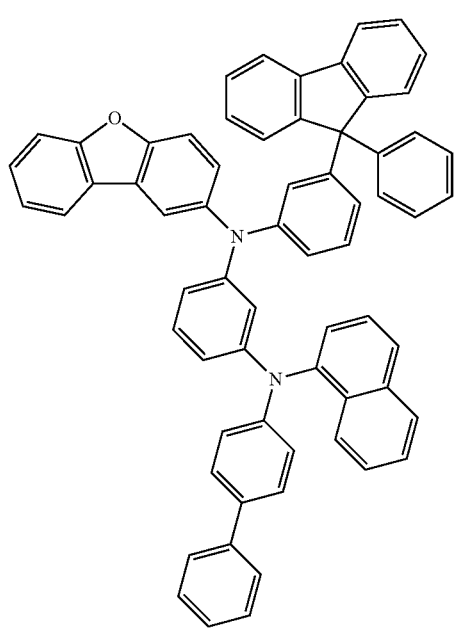
G-173
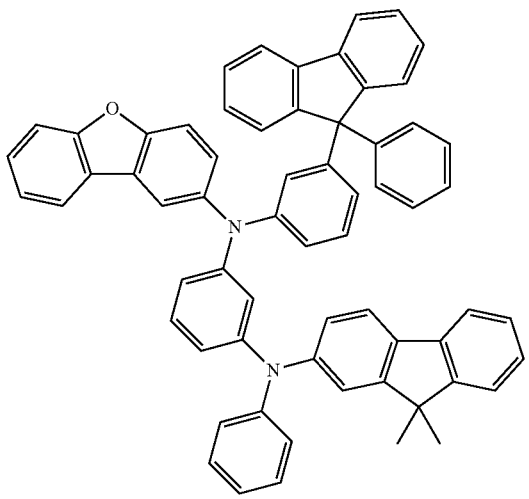
G-174
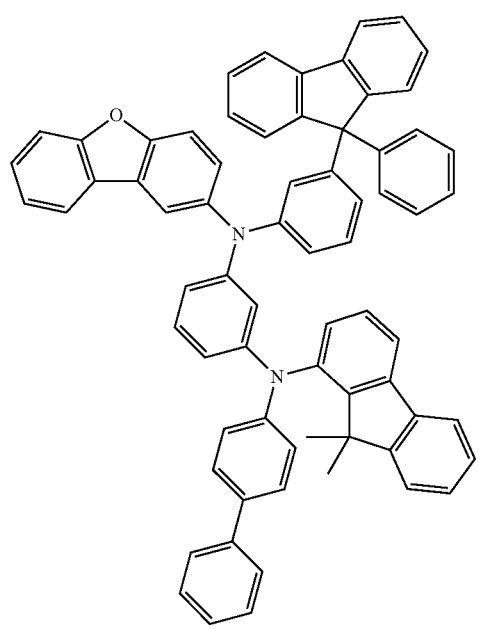
G-175

G-176
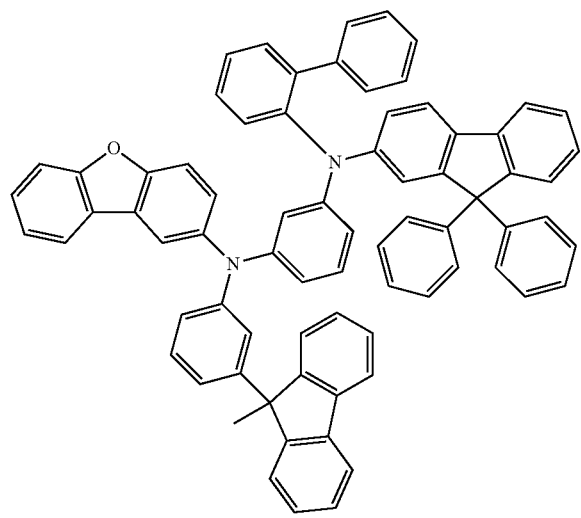
G-177
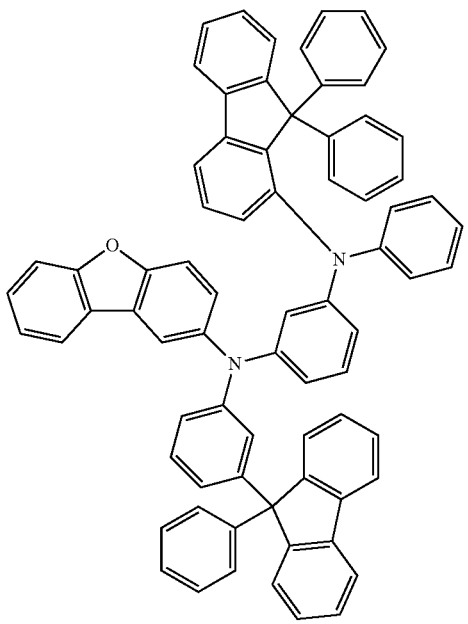
G-178
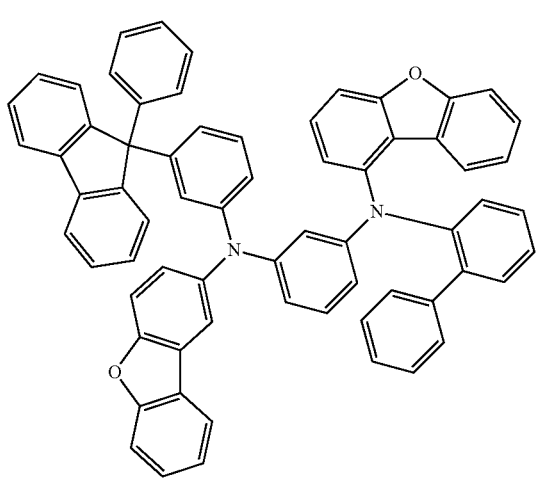
G-179
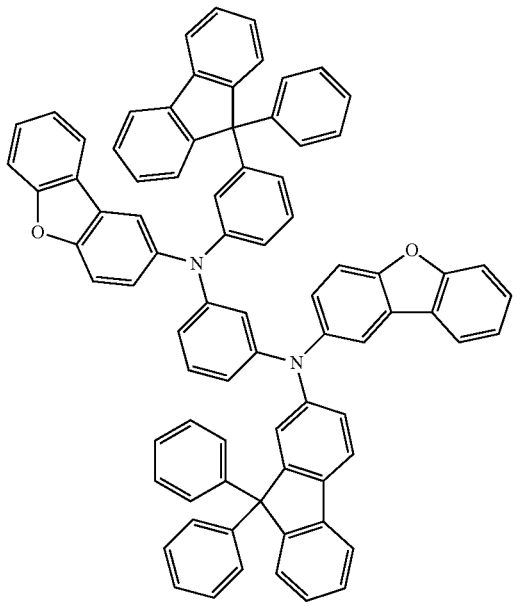
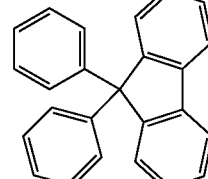
G-180
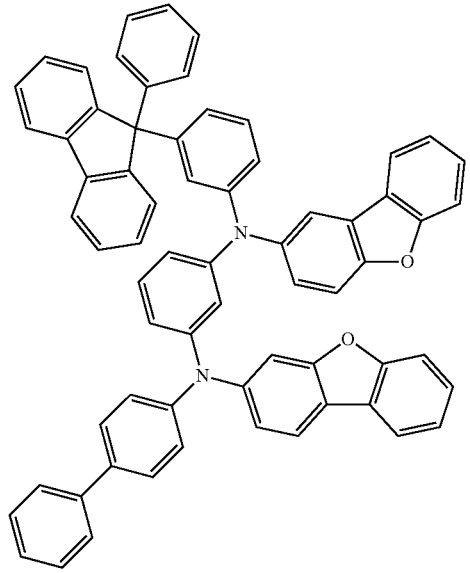
G-181
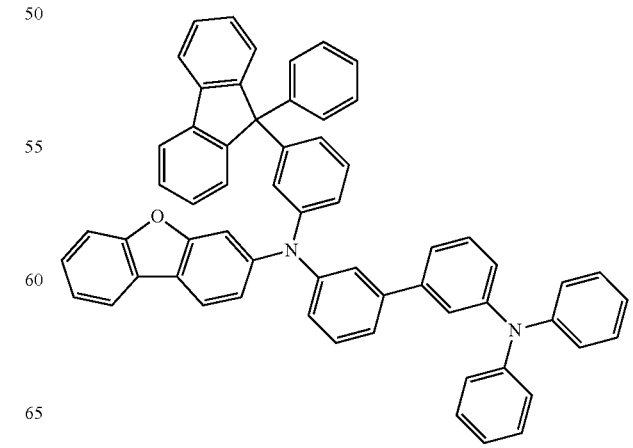

G-182
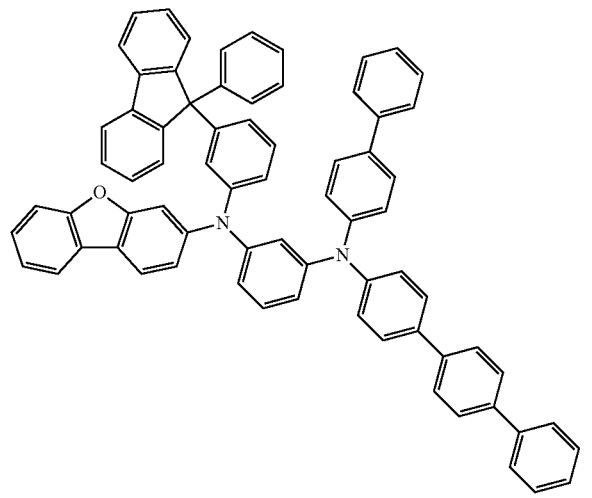
G-185
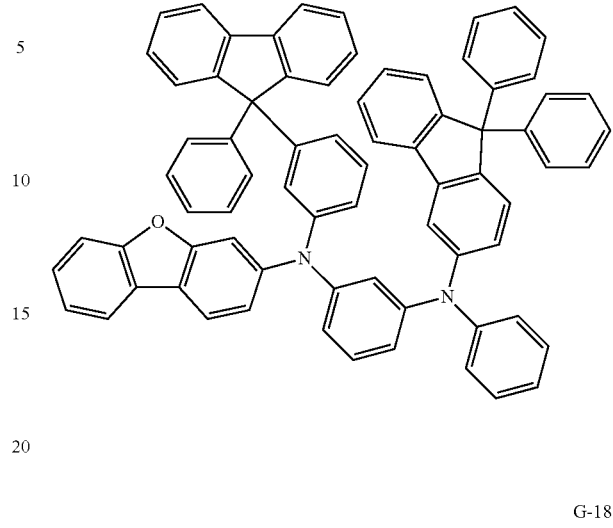
G-183
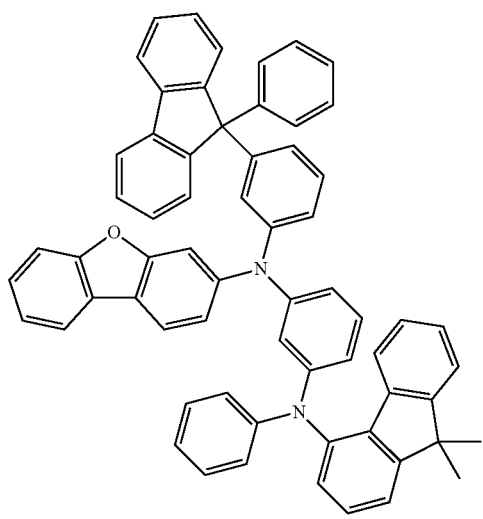
G-186
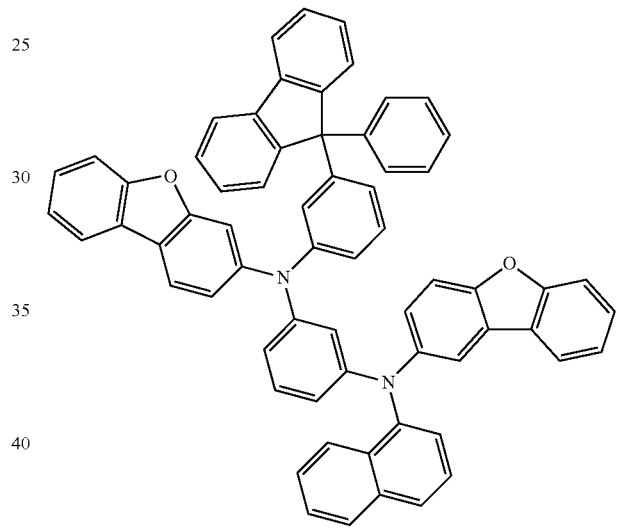
G-184
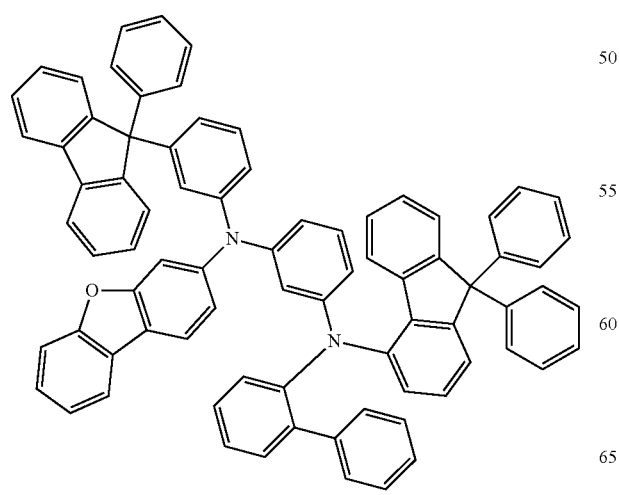
G-187
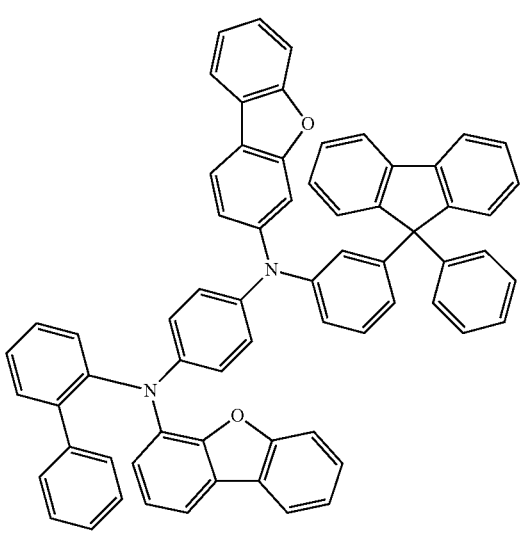

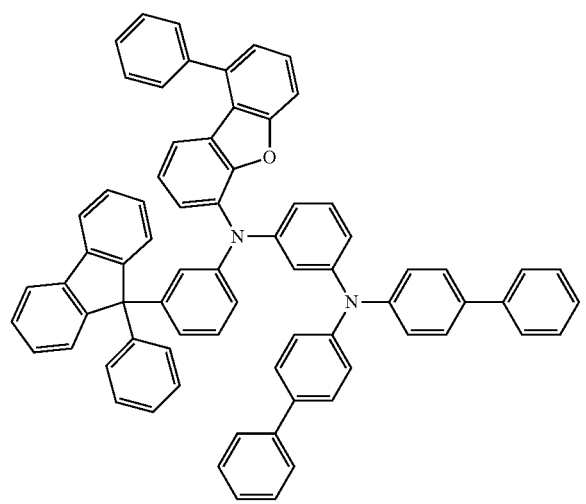
G-188
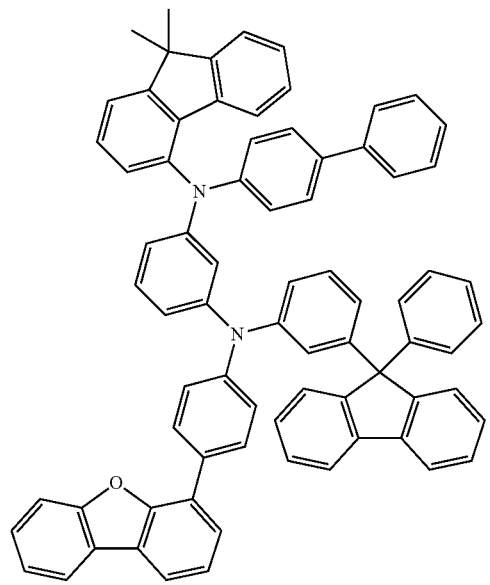
G-190
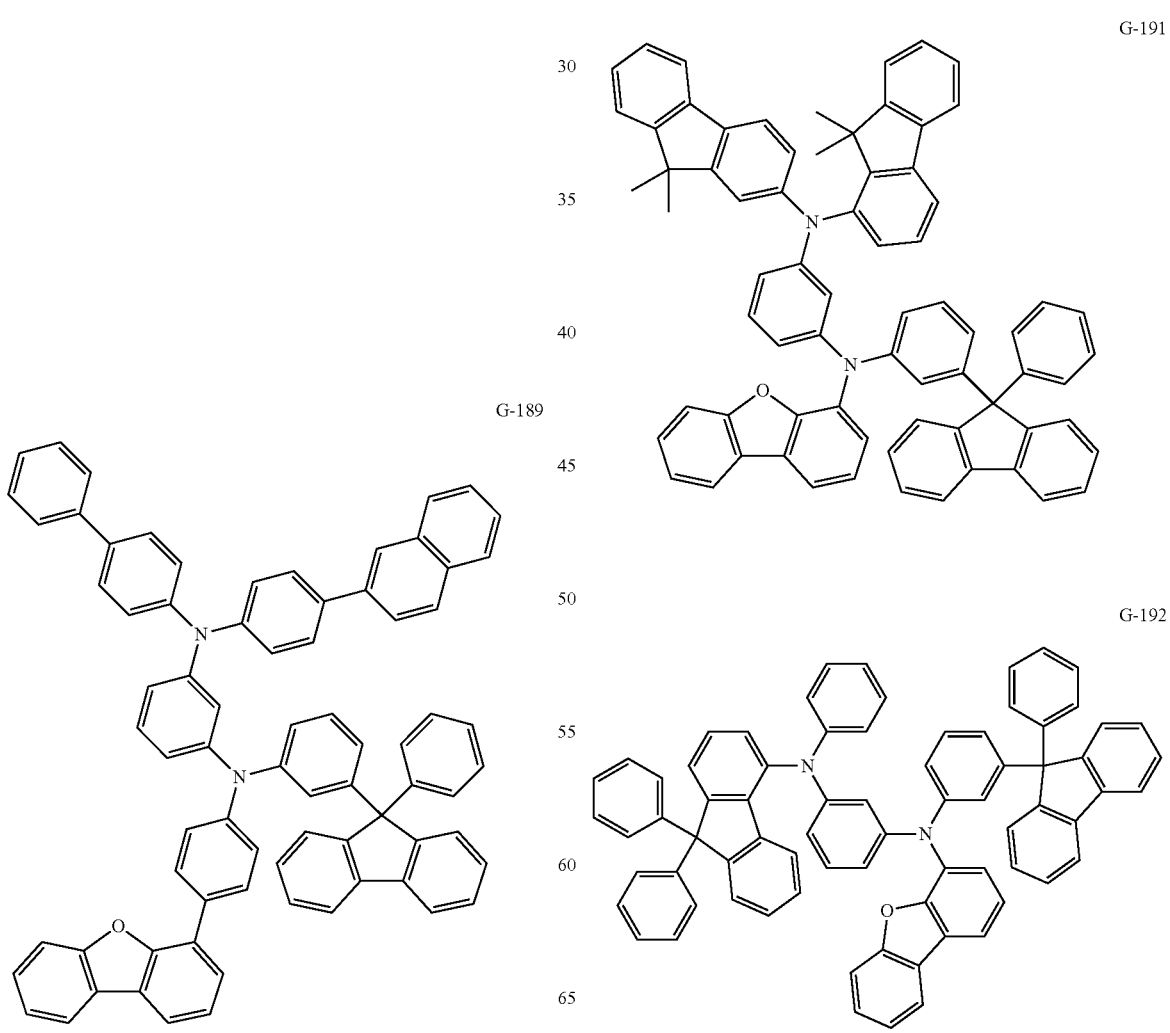
G-189
G-191
G-192

G-193
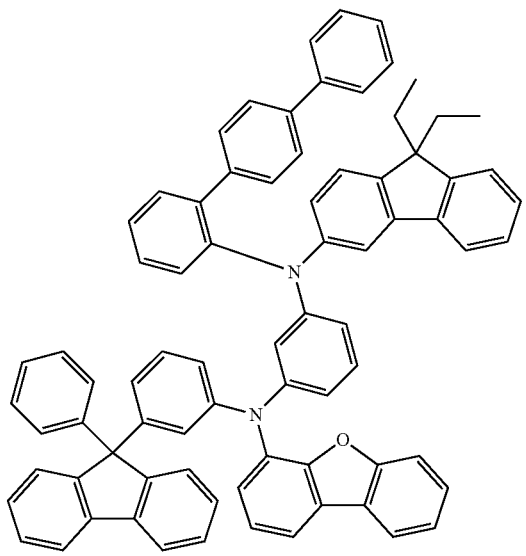
G-194
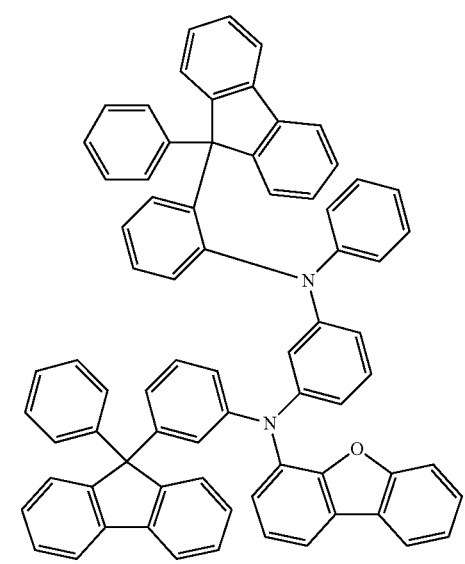
G-195
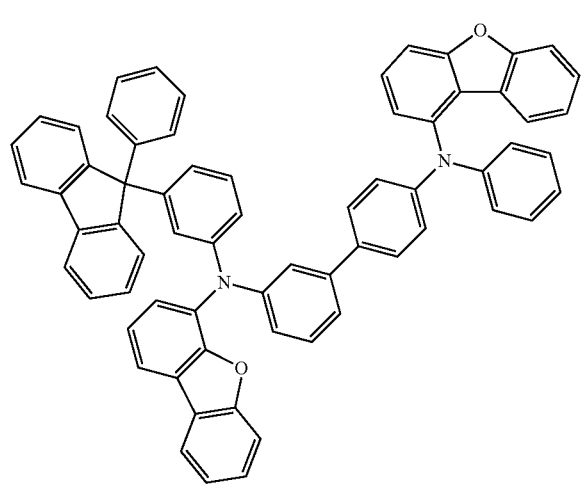
G-196
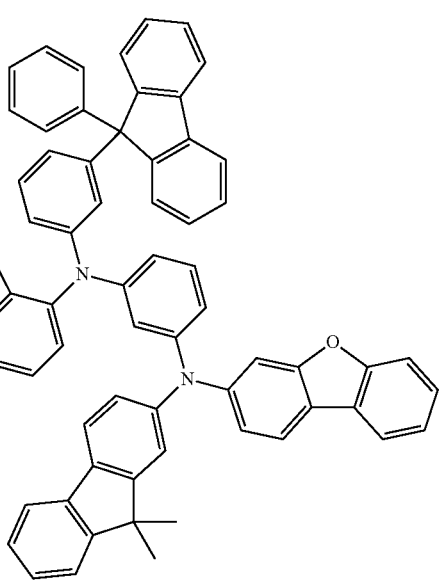
G-197
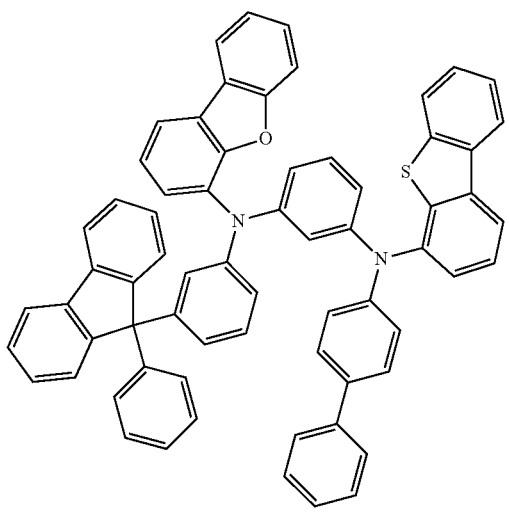
G-198
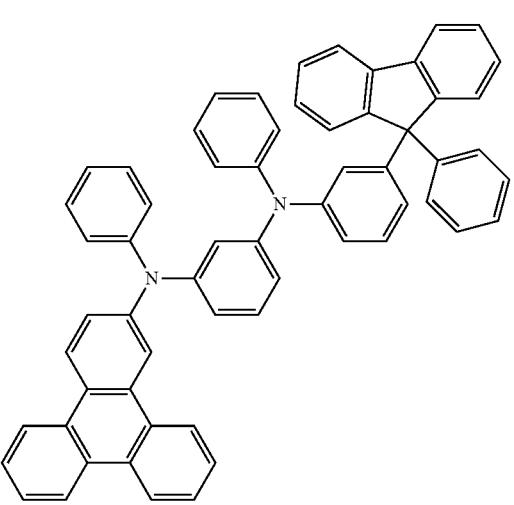

G-199
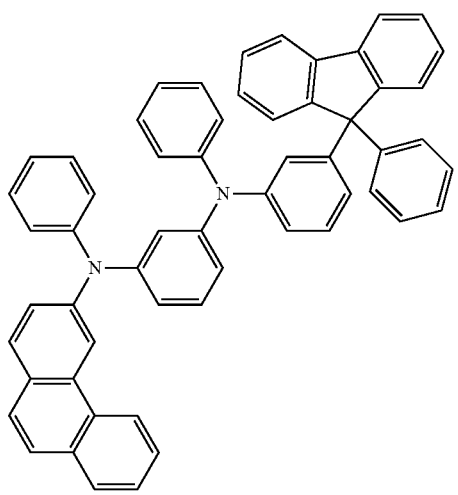

G-200
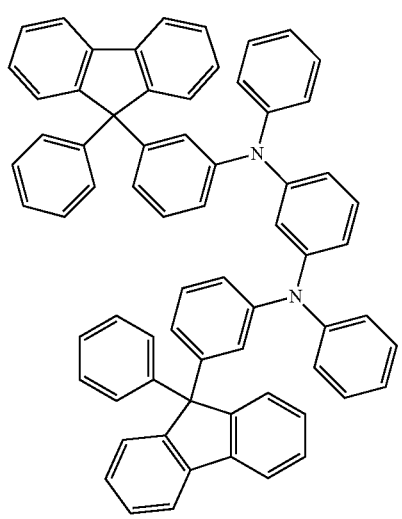

G-201
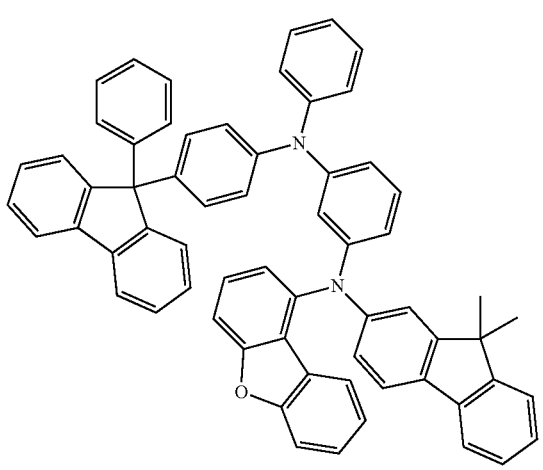

G-202
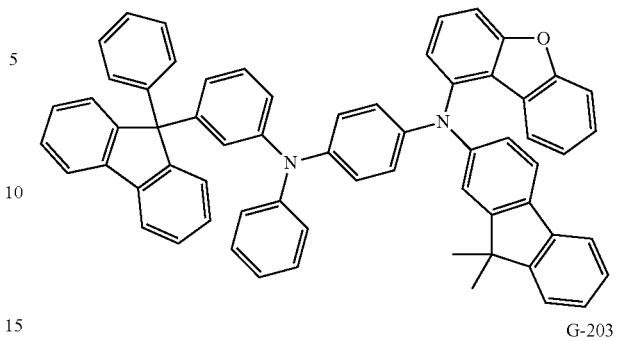

G-203

G-204

In another aspect of the present invention, the present invention provides an organic electric element comprising a first electrode, a second electrode, and an organic material layer formed between the first electrode and the second electrode, wherein the organic material layer comprises a single compound or compounds of two or more kinds represented by Formula 1.

In another aspect of the present invention, the present invention provides an organic electric element comprising a first electrode, a second electrode, and an organic material layer formed between the first electrode and the second electrode, wherein the organic material layer comprises a single compound or compounds of two or more kinds represented by Formula A.

The organic material layer comprises at least one layer of a hole injection layer, a hole transport layer, an emission-auxiliary layer, a light emitting layer, an electron transport auxiliary layer, an electron transport layer and an electron injection layer, and preferably, the compound represented by Formula 1 may be comprised in a light emitting layer and the compound represented by Formula A may be comprised in an emission-auxiliary layer, in particular, a green emission-auxiliary layer.

In another aspect of the present invention, the present invention provides an electronic device comprising a display device comprising the organic electric element, and a control unit for driving the display device, wherein the organic electric element comprises the compound represented by Formula 1 or A.

Hereinafter, synthesis examples of the compounds represented by Formulas 1, 12, 20 and A, respectively, and preparation methods of an organic electric element according to one embodiment of the present invention will be described in detail by way of examples. However, the present invention is not limited to the following examples.

SYNTHESIS EXAMPLE

Synthesis Example 1

As shown in Reaction Scheme 1 below, the compound represented by Formula 1 according to the present invention can be synthesized by reacting Sub 1 with Sub 2.

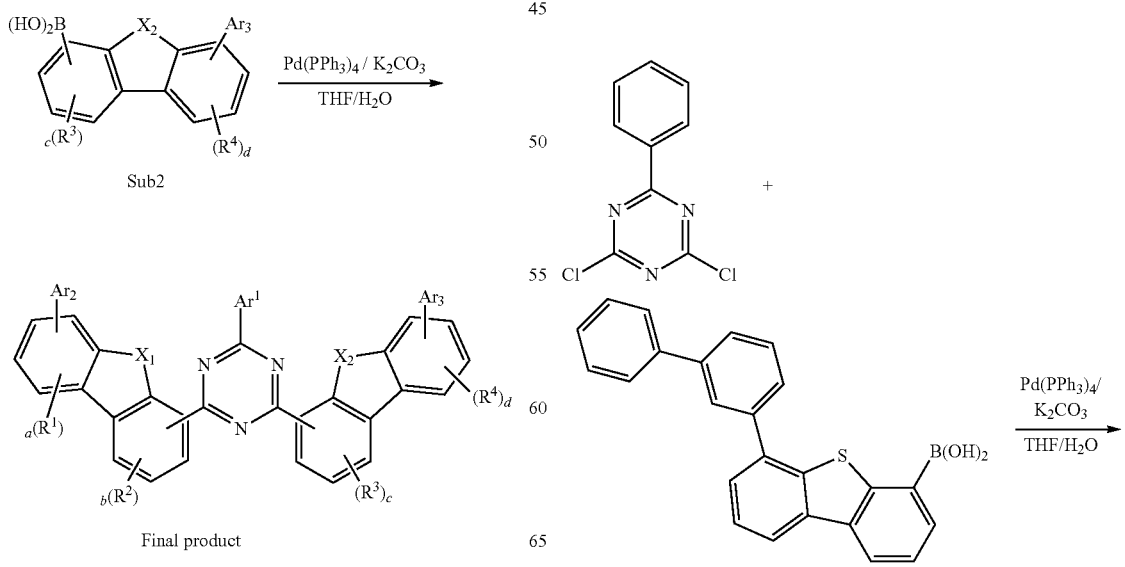

1. Synthesis Example of Sub 1

Sub 1 of the Reaction Scheme 1 can be synthesized according to the reaction route of the following Reaction Scheme 2, but there is no limitation thereto.

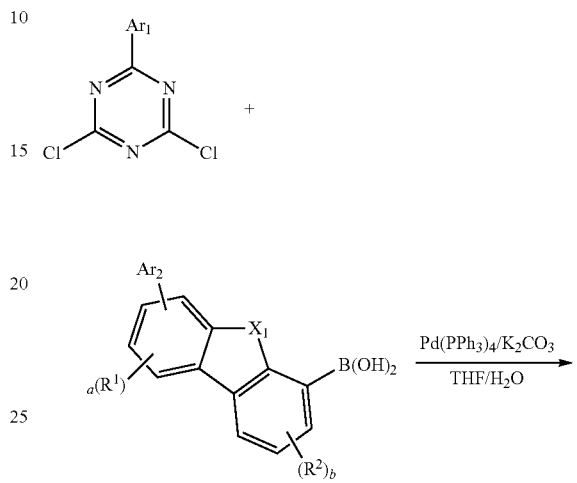

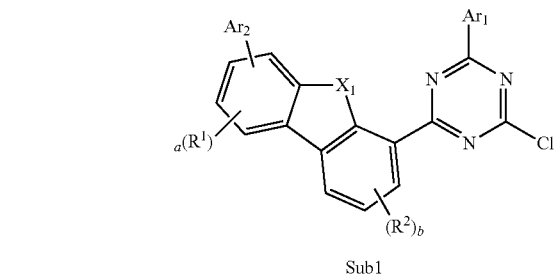

Synthesis of Sub 1-2

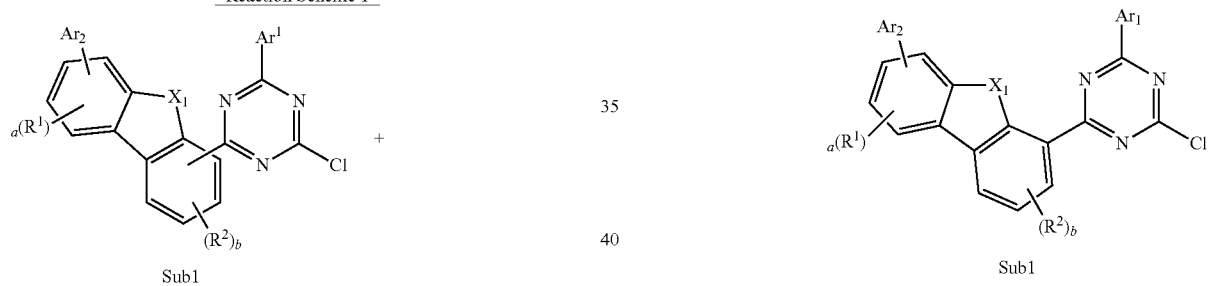

251
-continued

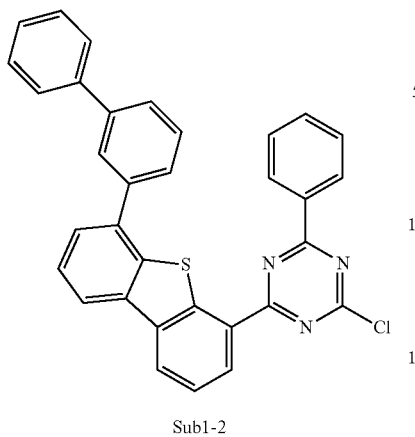

Sub1-2

After 2,4-dichloro-6-phenyl-1,3,5-triazine (25 g, 110.59 mmol) and (6-([1,1'-biphenyl]-3-yl)dibenzo[b,d]thiophen-4-yl)boronic acid (92.52 g, 243.30 mmol) were dissolved in THF (590 ml), Pd(PPh$_3$)$_4$ (5.11 g, 4.42 mmol), K$_2$CO$_3$ (45.85 g, 331.77 mmol) and water (295 ml) were added thereto and the mixture was stirred under reflux. When the reaction was completed, the reaction product was extracted with ether and water and the organic layer was concentrated. The concentrated organic layer was dried with MgSO$_4$ and concentrated. Thereafter, the concentrate was applied to a silica gel column to obtain 46.54 g (yield: 80%) of the product.

Synthesis of Sub 1-12

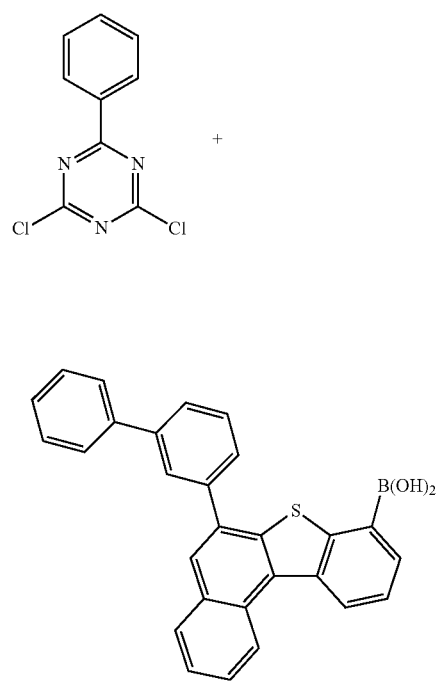

252
-continued

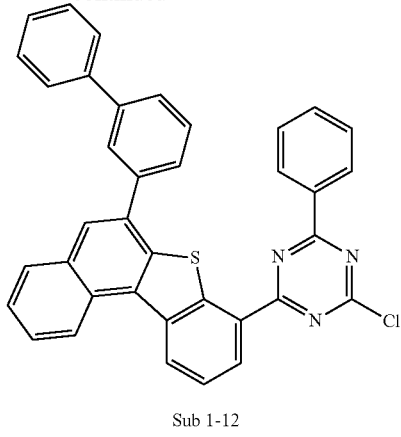

Sub 1-12

(6-([1,1'-biphenyl]-3-yl)benzo[b]naphtho[1,2-d]thiophen-8-yl)boronic acid (104.70 g, 243.30 mmol), Pd(PPh$_3$)$_4$ (0.04 eq.), K$_2$CO$_3$ (3 eq.), anhydrous THF and a small amount of water were added to 2,4-dichloro-6-phenyl-1,3,5-triazine (25 g, 110.59 mmol), and then 44.60 g (yield: 70%) of the product was obtained by the same method as in synthesis of Sub 1-2.

Synthesis of Sub 1-15

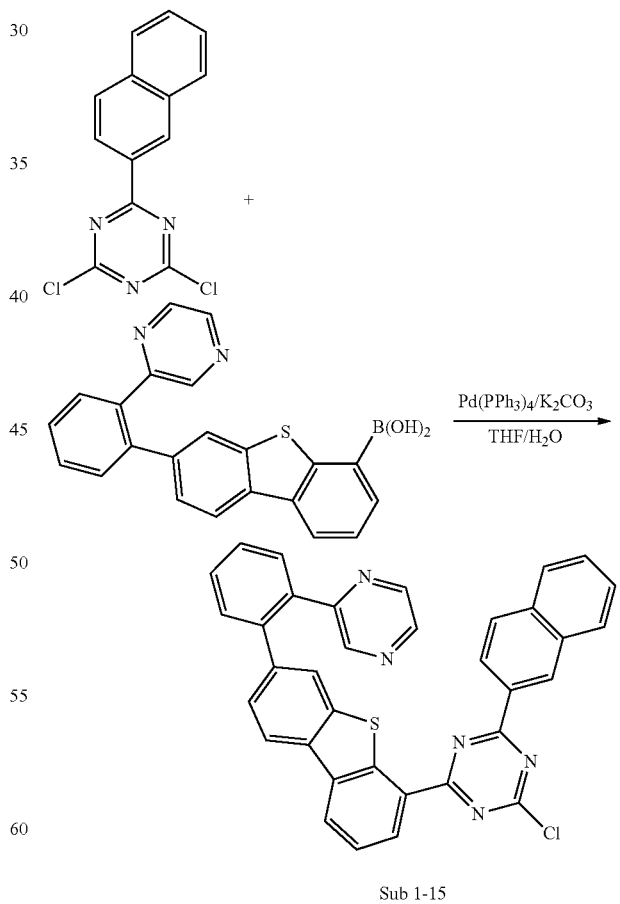

Sub 1-15

(7-(2-(pyrazin-2-yl)phenyl)dibenzo[b,d]thiophen-4-yl) boronic acid (76.14 g, 199.19 mmol), Pd(PPh$_3$)$_4$ (0.04 eq.), K$_2$CO$_3$ (3 eq.), anhydrous THF and a small amount of water were added to 2,4-dichloro-6-(naphthalen-2-yl)-1,3,5-triazine (25 g, 90.54 mmol), and then 35.59 g (yield: 68%) of the product was obtained by the same method as in synthesis of Sub 1-2.

Synthesis of Sub 1-22

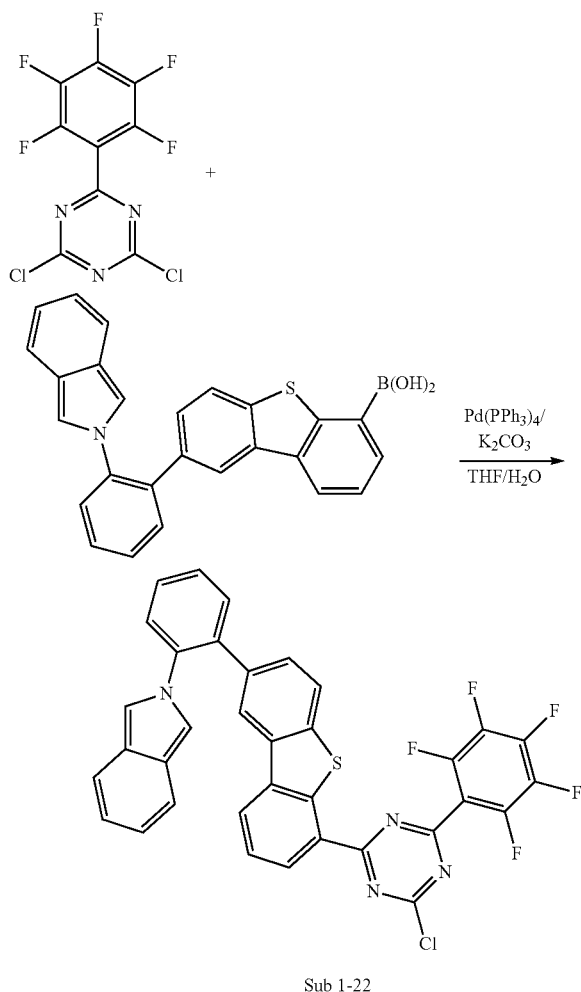

Sub 1-22

(8-(2-(2H-isoindol-2-yl)phenyl)dibenzo[b,d]thiophen-4-yl)boronic acid (116.77 g, 278.47 mmol), Pd(PPh₃)₄ (0.04 eq.), K₂CO₃ (3 eq.), anhydrous THF and a small amount of water were added to 2,4-dichloro-6-(perfluorophenyl)-1,3,5-triazine (40 g, 126.58 mmol), and then 49.75 g (yield: 60%) of the product was obtained by the same method as in synthesis of Sub 1-2.

Synthesis of Sub 1-37

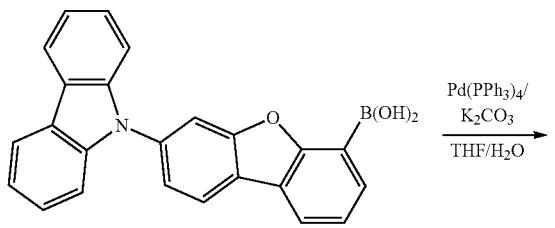

Sub 1-37

(7-(9H-carbazol-9-yl)dibenzo[b,d]furan-4-yl)boronic acid (157.85 g, 418.47 mmol), Pd(PPh₃)₄ (0.04 eq.), K₂CO₃ (3 eq.), anhydrous THF and a small amount of water were added to 2,4-dichloro-6-phenyl-1,3,5-triazine (43 g, 190.21 mmol), and then 64.66 g (yield: 65%) of the product was obtained by the same method as in synthesis of Sub 1-2.

Synthesis of Sub 1-67

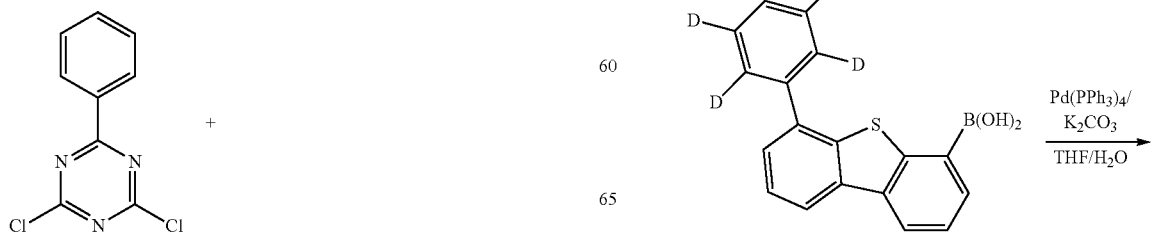

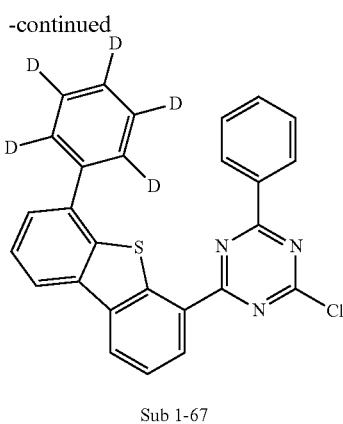

Sub 1-67

(6-(phenyl-d5)dibenzo[b,d]thiophen-4-yl)boronic acid (135.41 g, 437.94 mmol), Pd(PPh₃)₄ (0.04 eq.), K₂CO₃ (3 eq.), anhydrous THF and a small amount of water were added to 2,4-dichloro-6-phenyl-1,3,5-triazine (45 g, 199.06 mmol), and then 68.83 g (yield: 76%) of the product was obtained by the same method as in synthesis of Sub 1-2.

Synthesis of Sub 1-70

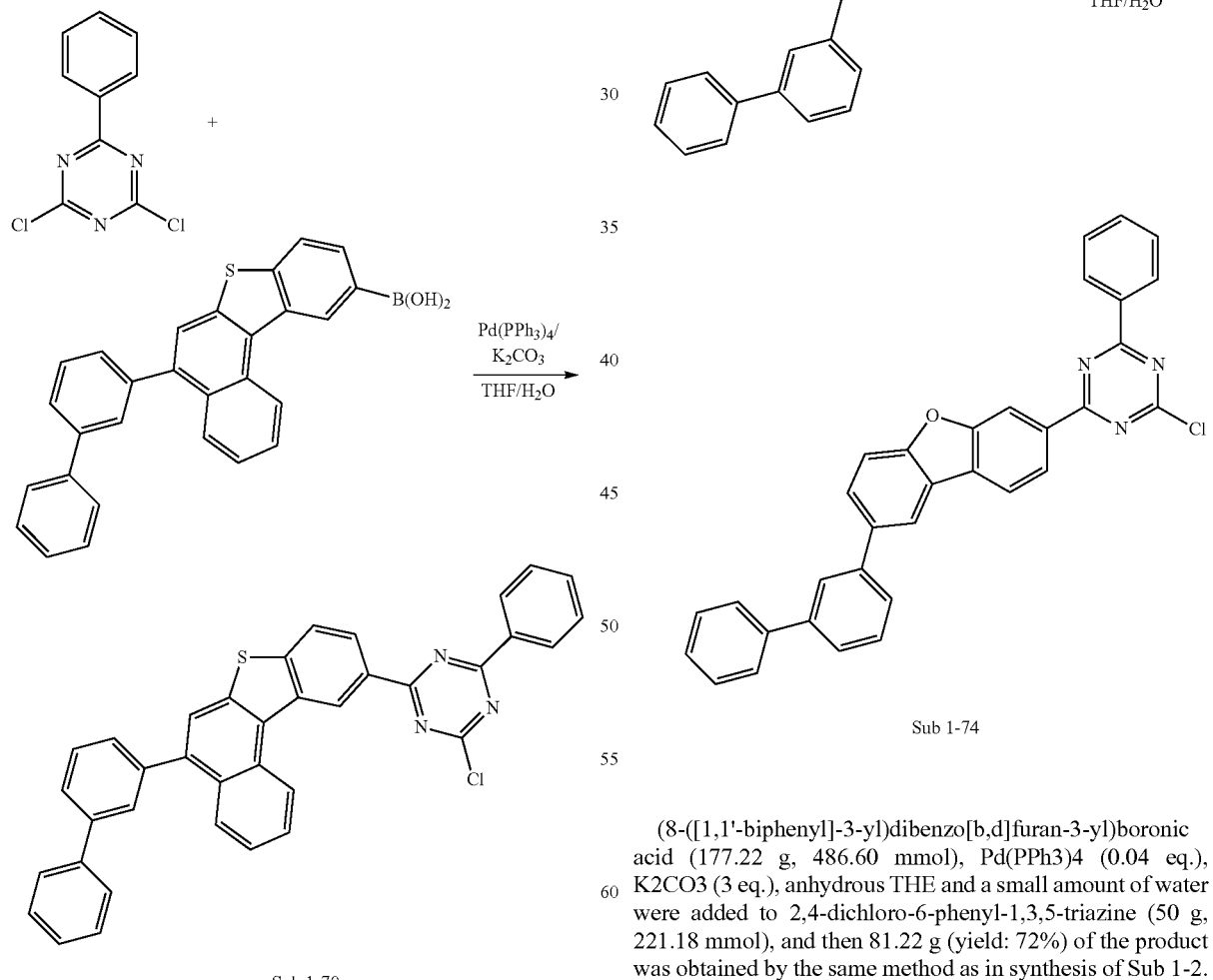

Sub 1-70

5-([1,1'-biphenyl]-3-yl)benzo[b]naphtho[1,2-d]thiophen-10-yl)boronic acid (188.46 g, 437.94 mmol), Pd(PPh₃)₄ (0.04 eq.), K₂CO₃ (3 eq.), anhydrous THF and a small amount of water were added to 2,4-dichloro-6-(dibenzo[b,d]furan-3-yl)-1,3,5-triazine (45 g, 199.06 mmol), and then 72.25 g (yield: 63%) of the product was obtained by the same method as in synthesis of Sub 1-2.

Synthesis of Sub 1-74

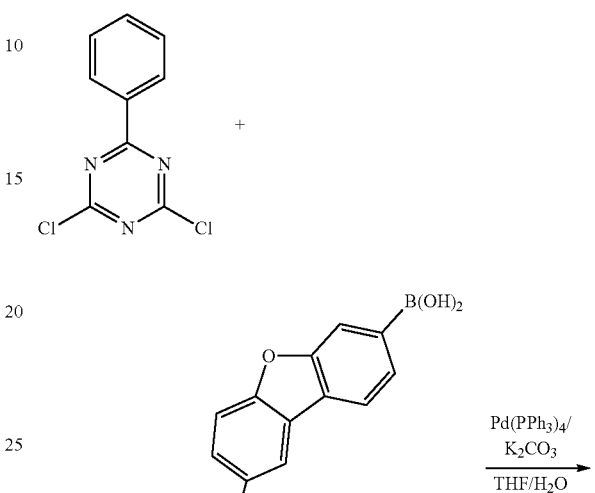

Sub 1-74

(8-([1,1'-biphenyl]-3-yl)dibenzo[b,d]furan-3-yl)boronic acid (177.22 g, 486.60 mmol), Pd(PPh3)4 (0.04 eq.), K2CO3 (3 eq.), anhydrous THF and a small amount of water were added to 2,4-dichloro-6-phenyl-1,3,5-triazine (50 g, 221.18 mmol), and then 81.22 g (yield: 72%) of the product was obtained by the same method as in synthesis of Sub 1-2.

The compound belonging to Sub 1 may be, but not limited to, the following compounds, and Table 1 shows FD-MS (Field Desorption-Mass Spectrometry) values of compounds belonging to Sub 1.

Sub 1-1
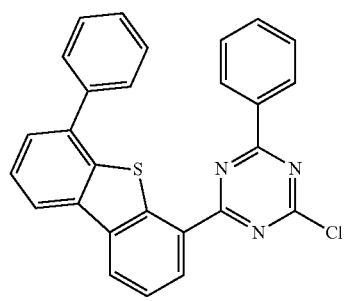
Sub 1-2
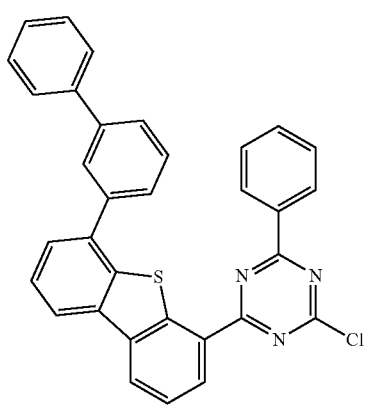
Sub 1-3
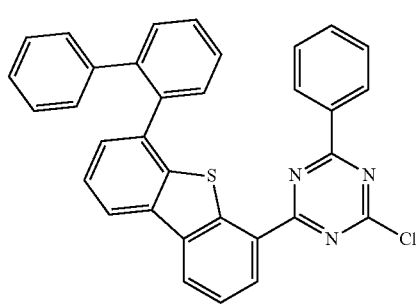
Sub 1-4
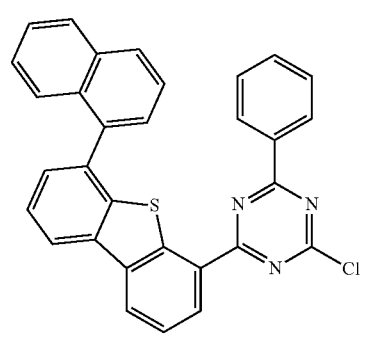
Sub 1-5
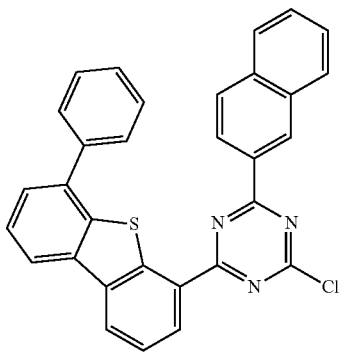
Sub 1-6
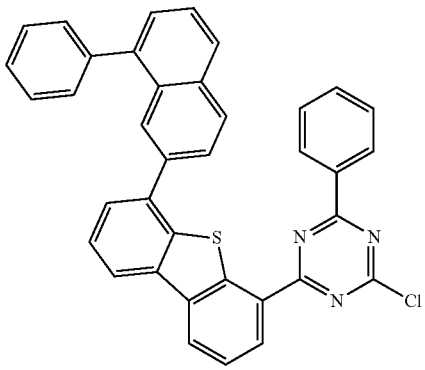
Sub 1-7
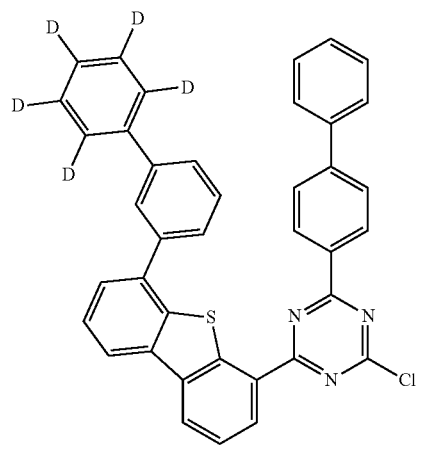
Sub 1-8
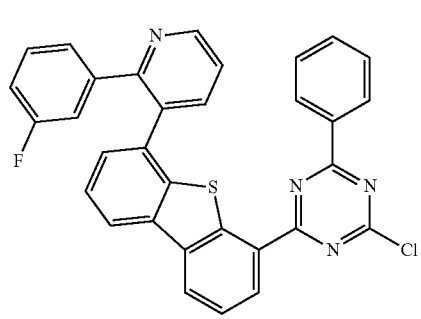

Sub 1-9
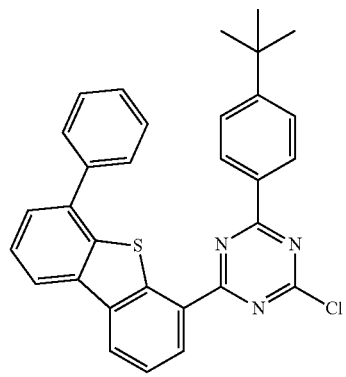
Sub 1-13
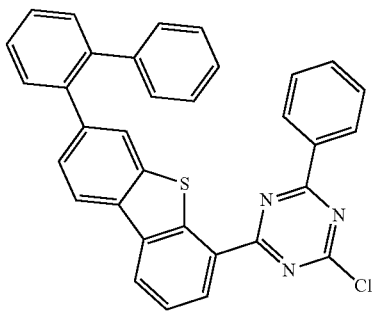
Sub 1-10
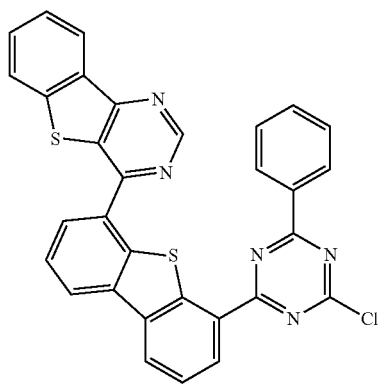
Sub 1-14
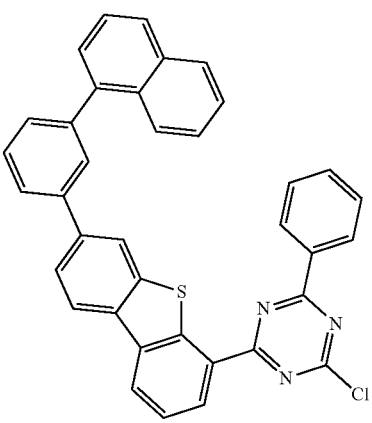
Sub 1-11
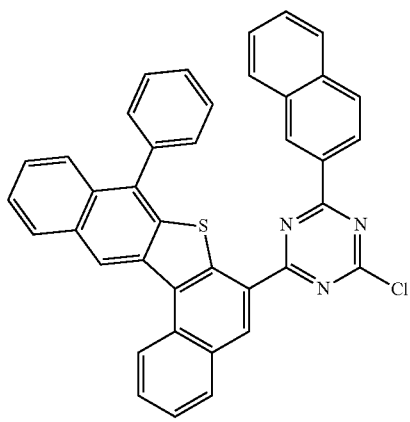
Sub 1-15
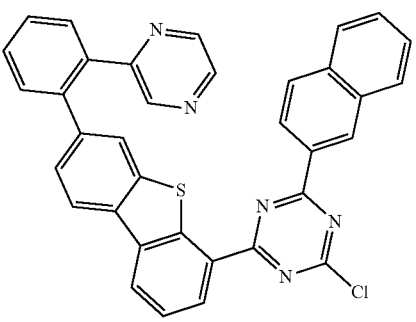
Sub 1-12
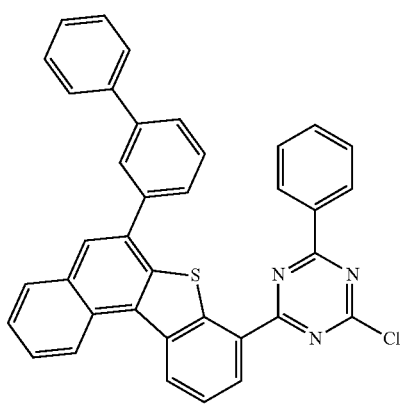
Sub 1-16
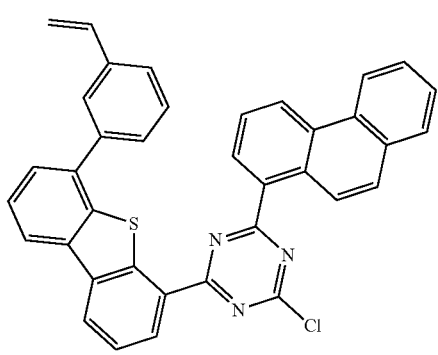

Sub 1-17
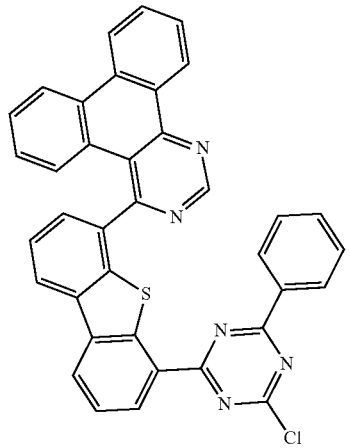
Sub 1-18
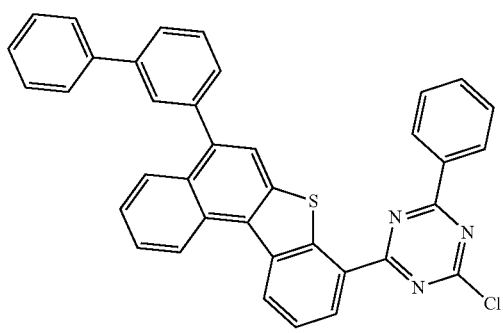
Sub 1-19
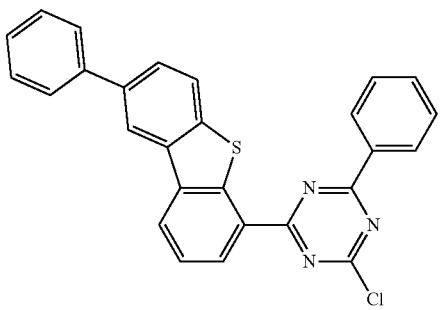
Sub 1-20
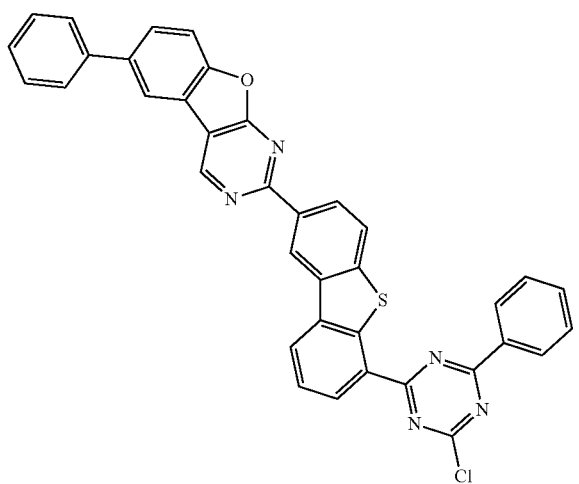
Sub 1-21
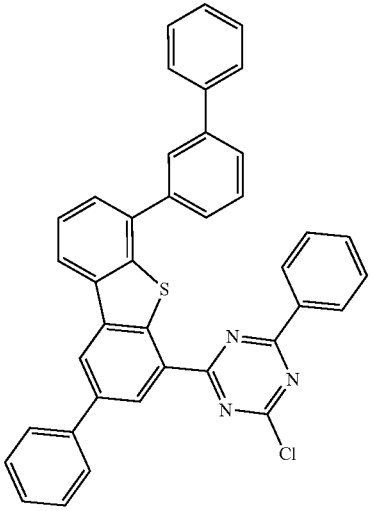
Sub 1-22
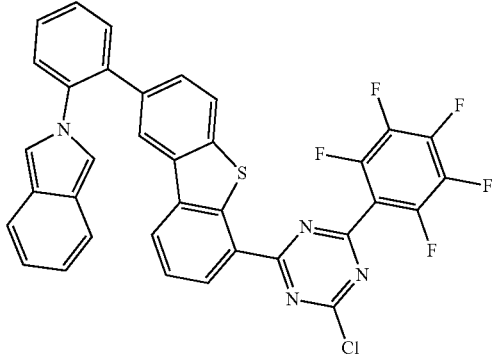
Sub 1-23
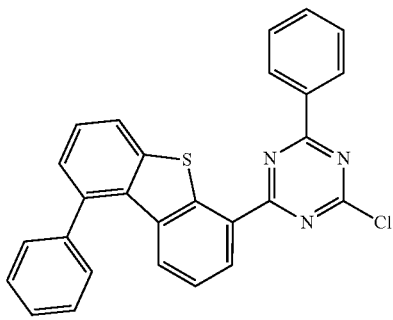

Sub 1-24
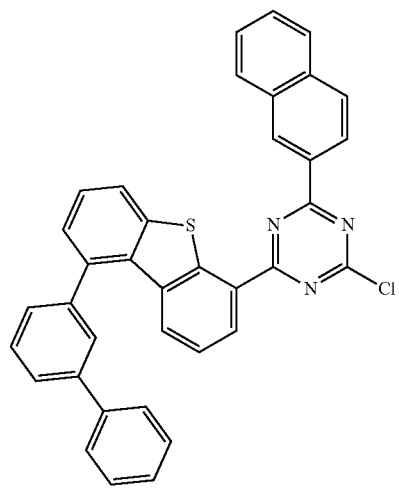
Sub 1-25
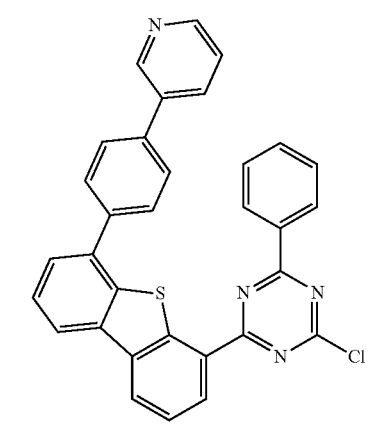
Sub 1-26
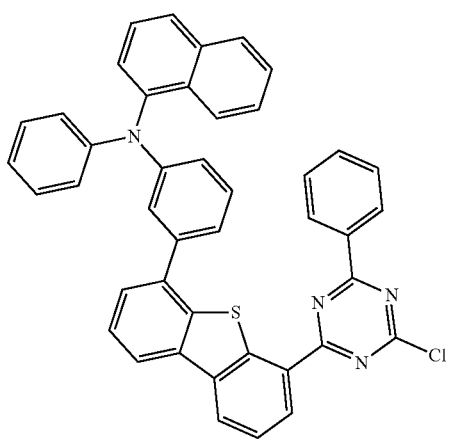
Sub 1-27
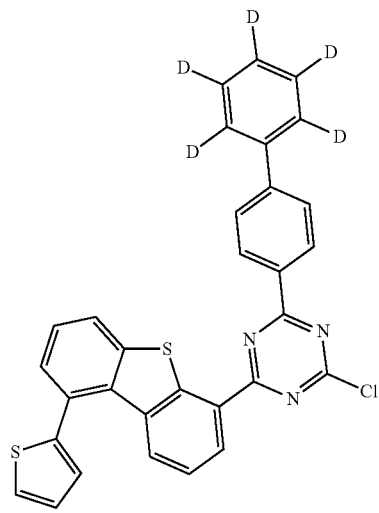
Sub 1-28
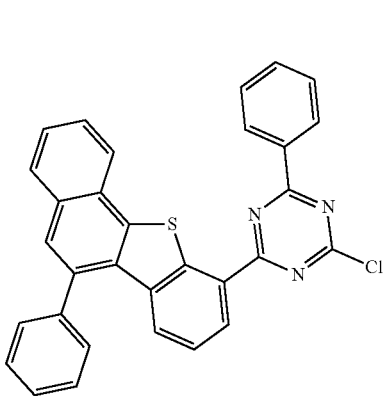
Sub 1-29
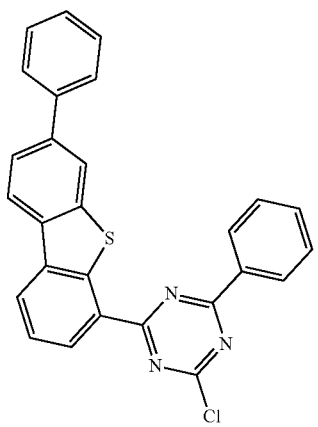

Sub 1-30
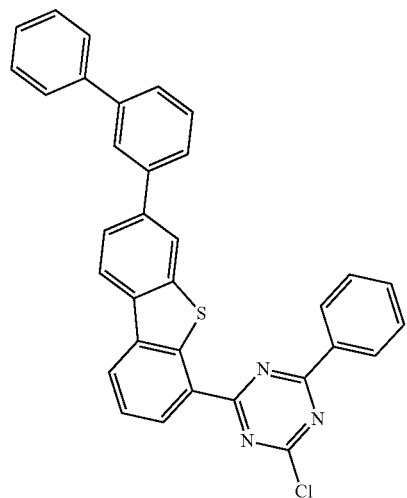
Sub 1-31
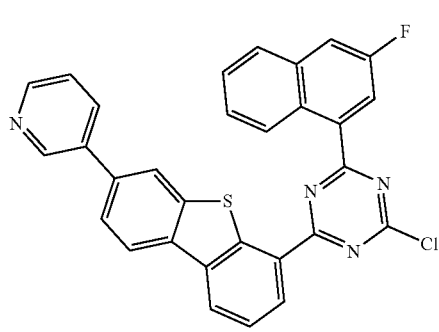
Sub 1-32
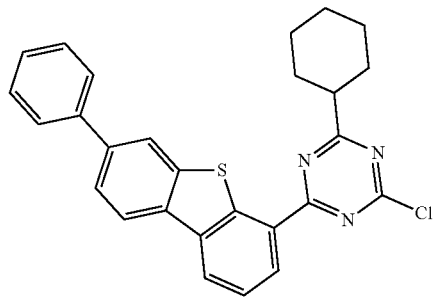
Sub 1-33
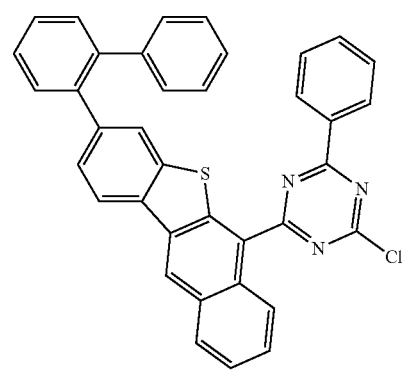
Sub 1-34
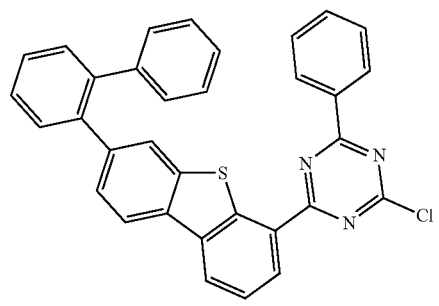
Sub 1-35
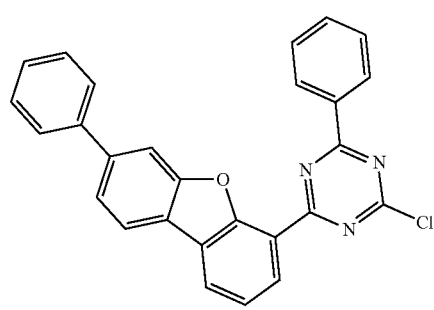
Sub 1-36
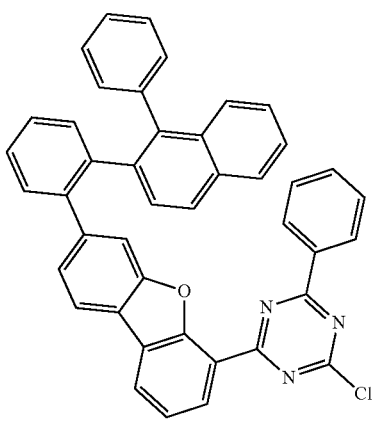
Sub 1-37
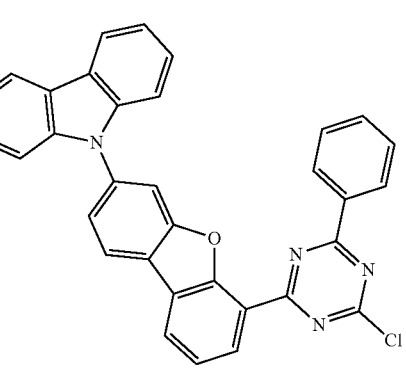

Sub 1-38
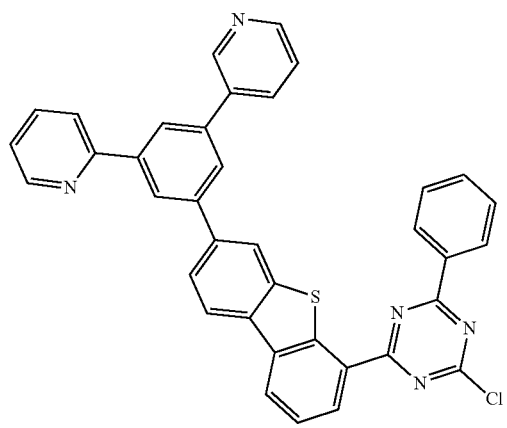
Sub 1-39
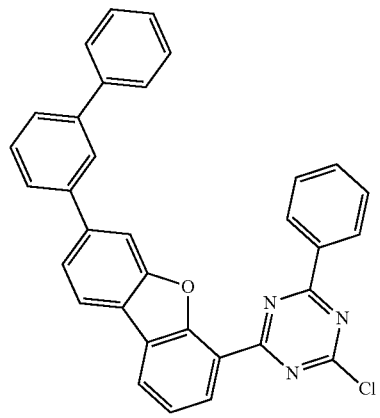
Sub 1-40
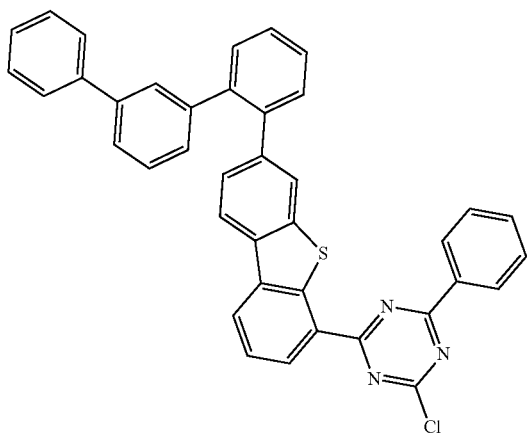
Sub 1-41
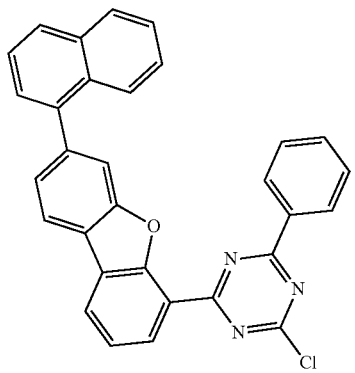
Sub 1-42
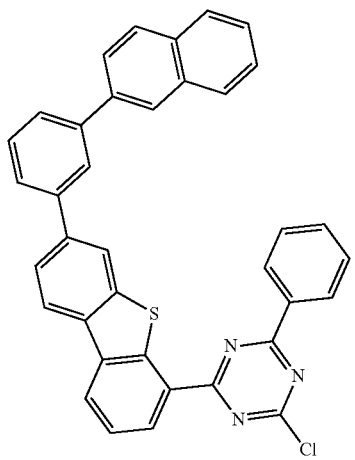
Sub 1-43
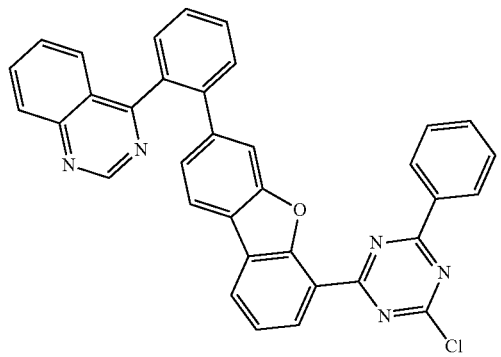
Sub 1-44
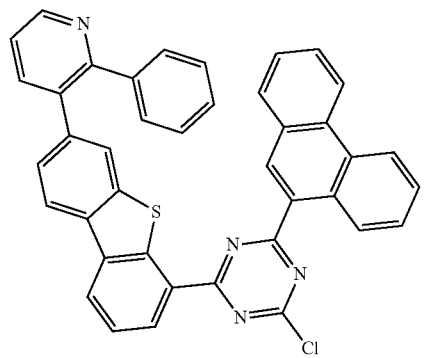

Sub 1-45
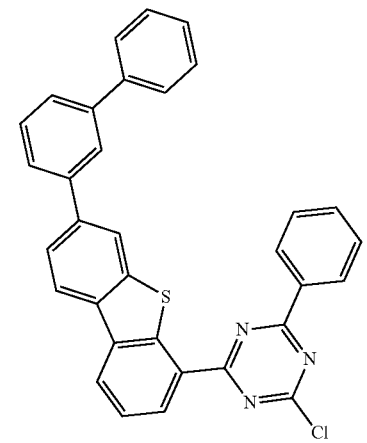
Sub 1-46
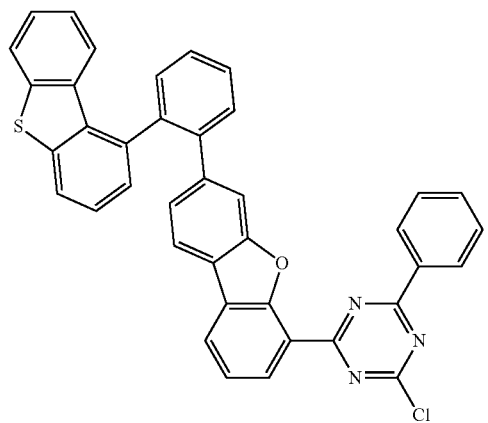
Sub 1-47
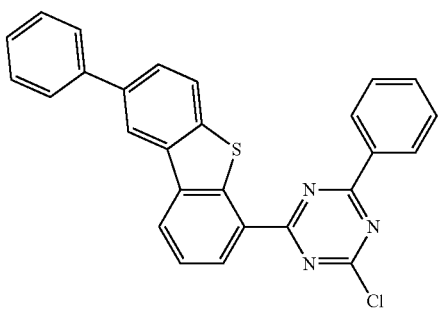
Sub 1-48
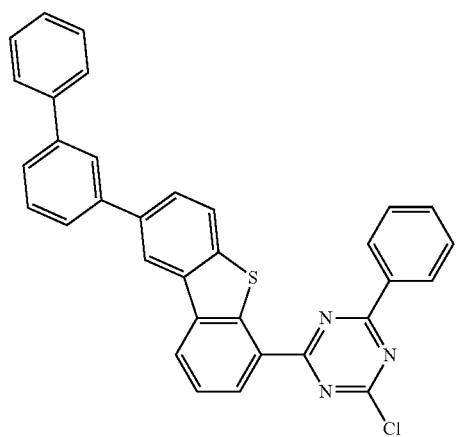
Sub 1-49
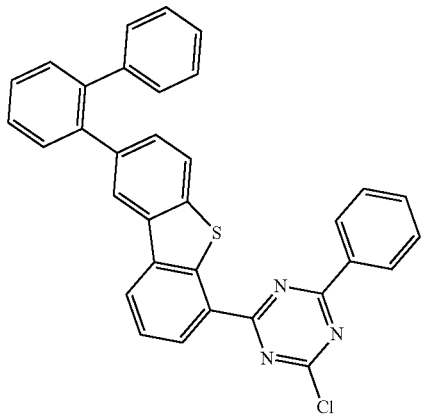
Sub 1-50
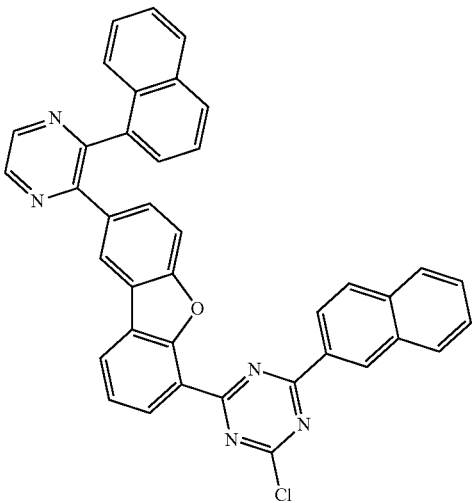
Sub 1-51
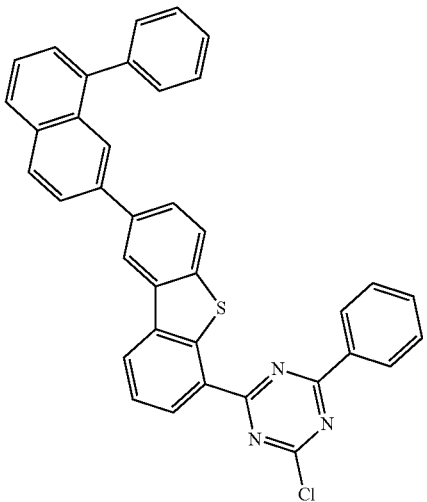

271
-continued
Sub 1-52
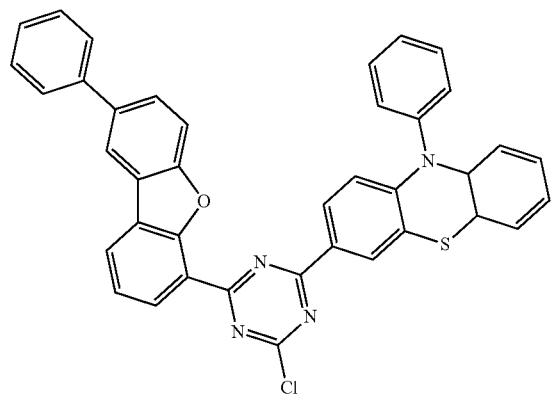
Sub 1-53
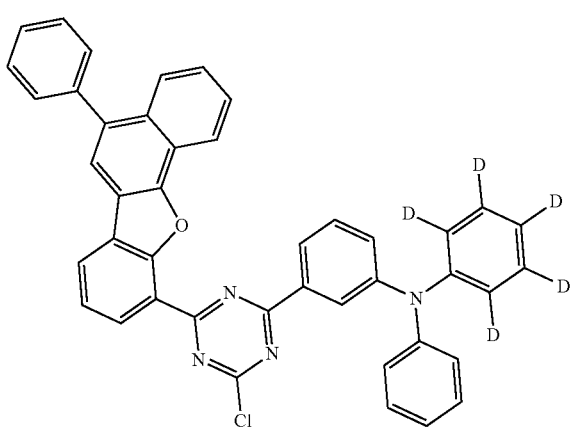
Sub 1-54
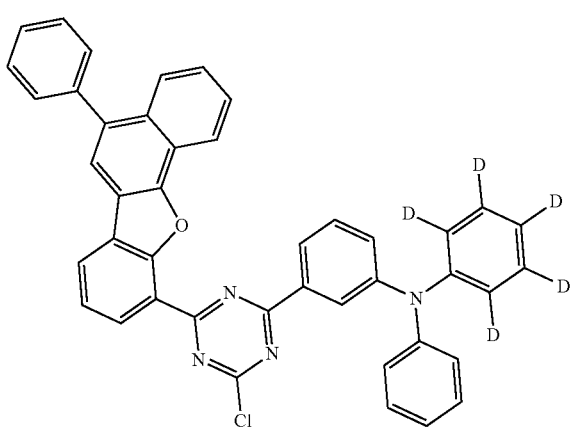
272
-continued
Sub 1-55
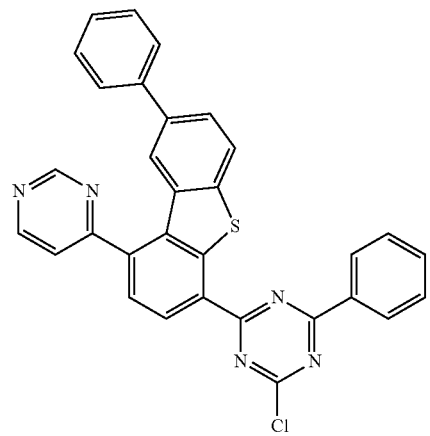
Sub 1-56
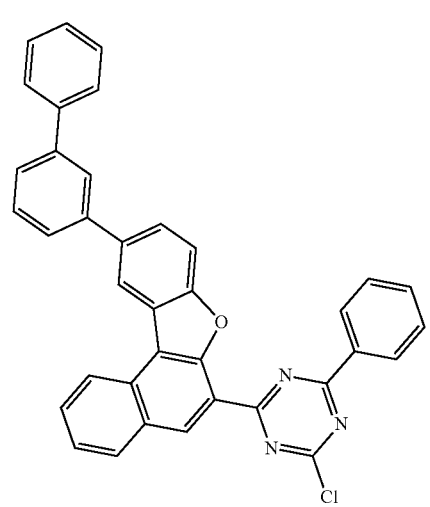
Sub 1-57
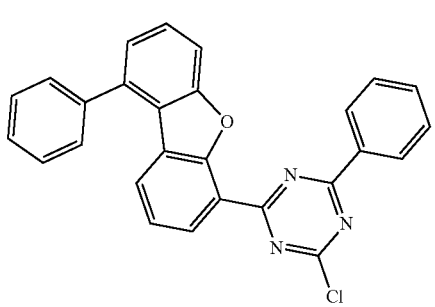
Sub 1-58
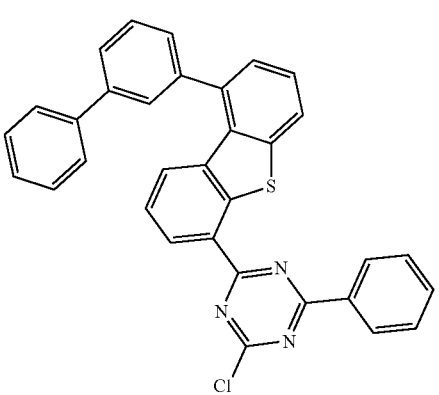

Sub 1-59
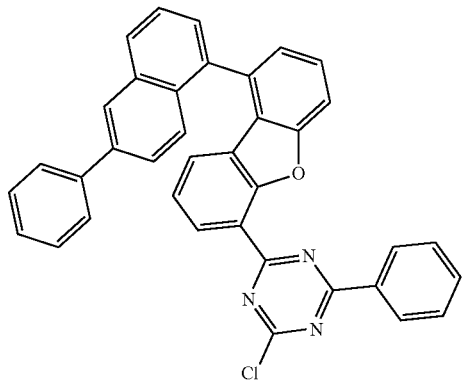
Sub 1-62
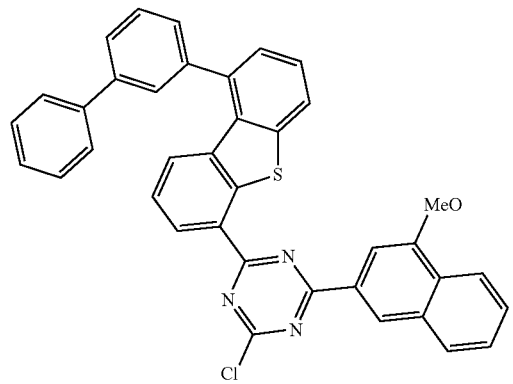
Sub 1-60
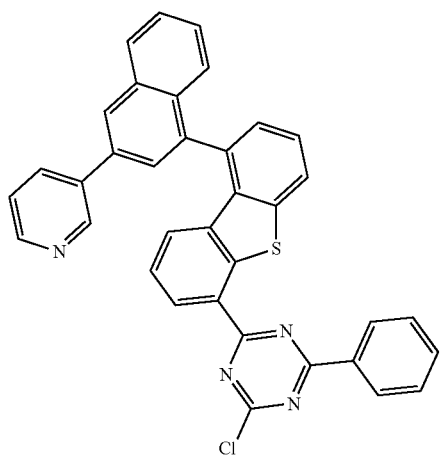
Sub 1-63
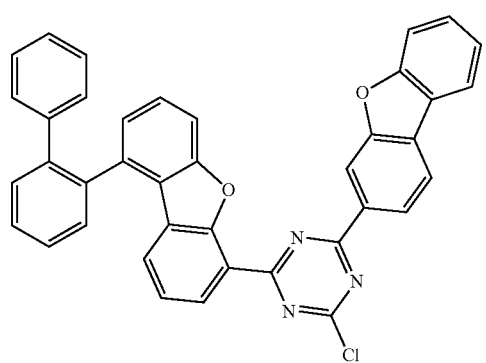
Sub 1-64
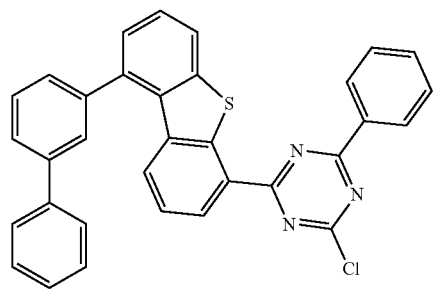
Sub 1-61
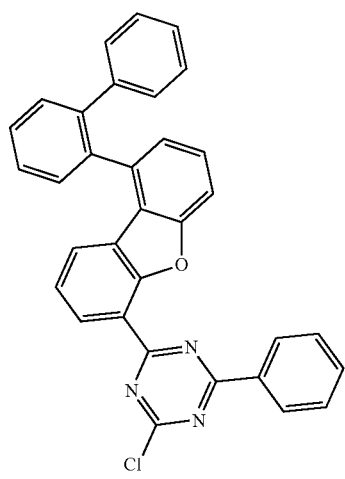
Sub 1-65
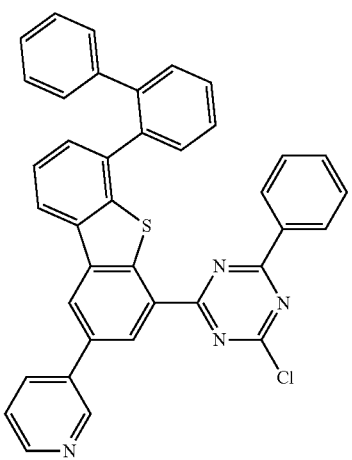

Sub 1-66
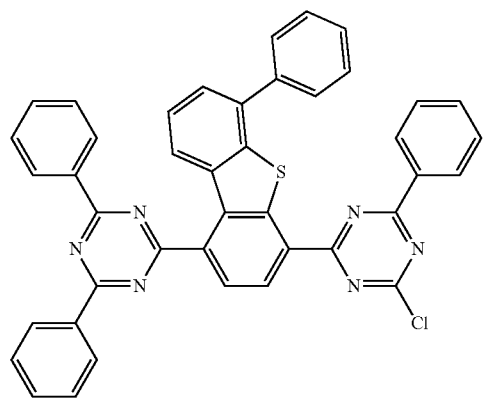
Sub 1-67
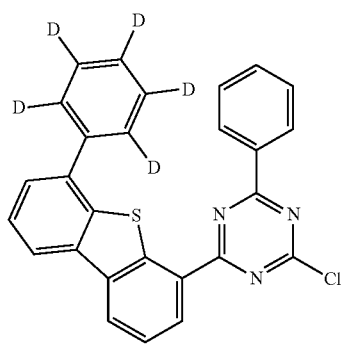
Sub 1-68
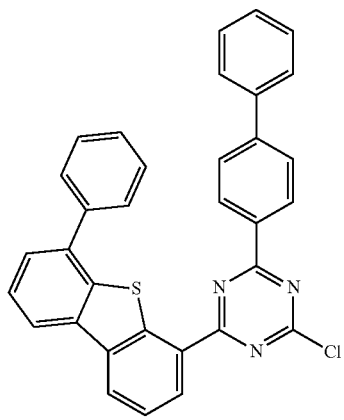
Sub 1-69
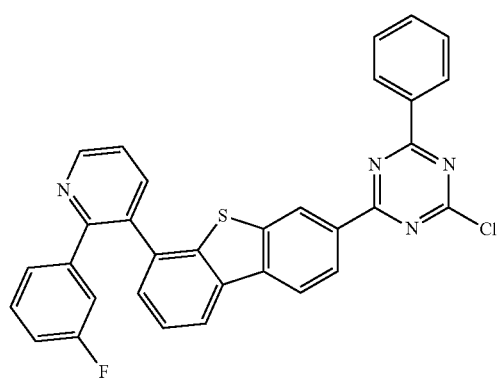
Sub 1-70
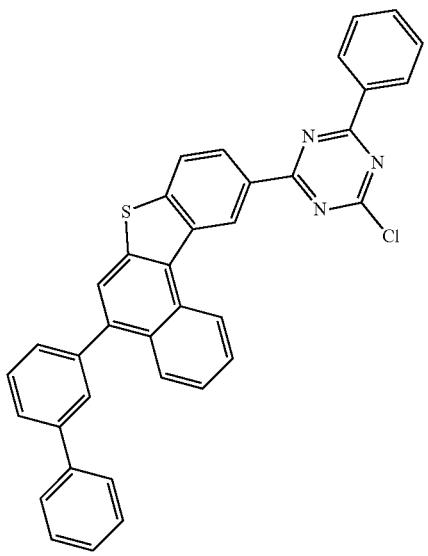
Sub 1-71
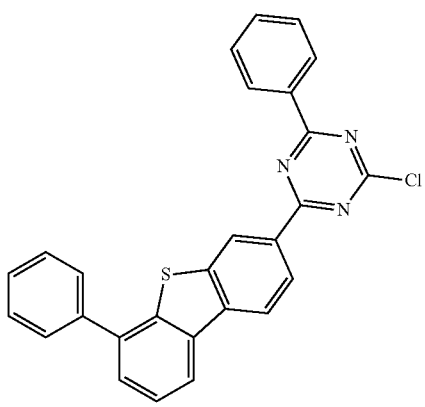
Sub 1-72
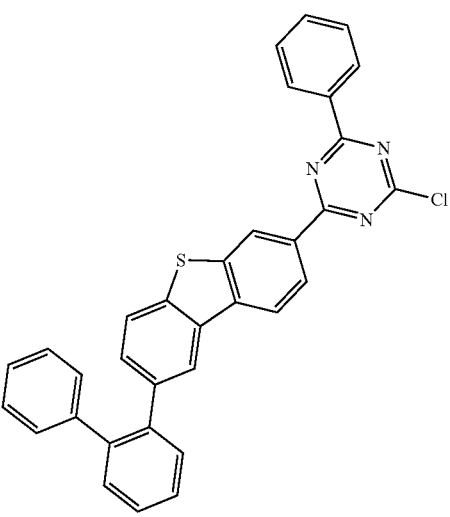

2. Synthesis Example of Sub 2

Sub 2 of the Reaction Scheme 1 can be synthesized according to the reaction route of the following Reaction Scheme 3, but there is no limitation thereto.

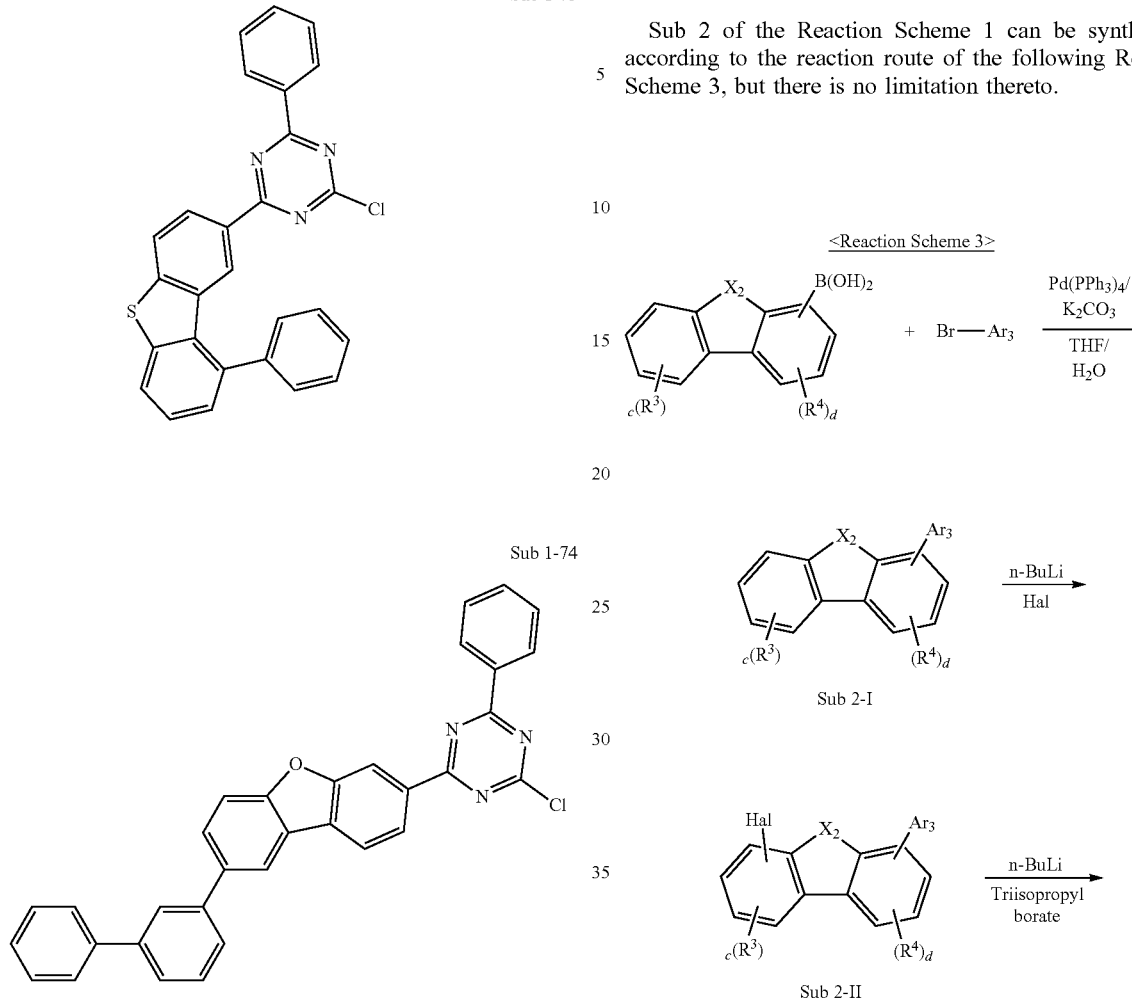

TABLE 1

| Compound | FD-MS | Compound | FD-MS |
|---|---|---|---|
| Sub 1-1 | m/z = 449.08 ($C_{27}H_{16}ClN_3S$ = 449.96) | Sub 1-2 | m/z = 525.11 ($C_{33}H_{20}ClN_3S$ = 526.05) |
| Sub 1-4 | m/z = 499.09 ($C_{31}H_{18}ClN_3S$ = 500.02) | Sub 1-6 | m/z = 575.12 ($C_{37}H_{22}ClN_3S$ = 576.11) |
| Sub 1-7 | m/z = 606.17 ($C_{39}H_{19}D_5ClN_3S$ = 607.18) | Sub 1-8 | m/z = 544.09 ($C_{32}H_{18}ClFN_4S$ = 545.03) |
| Sub 1-9 | m/z = 505.14 ($C_{31}H_{24}ClN_3S$ = 506.06) | Sub 1-10 | m/z = 557.05 ($C_{31}H_{16}ClN_5S_2$ = 558.07) |
| Sub 1-11 | m/z = 599.12 ($C_{39}H_{22}ClN_3S$ = 600.14) | Sub 1-12 | m/z = 575.12 ($C_{37}H_{22}ClN_3S$ = 576.11) |
| Sub 1-15 | m/z = 577.11 ($C_{35}H_{20}ClN_5S$ = 578.09) | Sub 1-16 | m/z = 575.12 ($C_{37}H_{22}ClN_3S$ = 576.11) |
| Sub 1-17 | m/z = 601.11 ($C_{37}H_{20}ClN_5S$ = 602.11) | Sub 1-20 | m/z = 617.11 ($C_{37}H_{20}ClN_5OS$ = 618.11) |
| Sub 1-21 | m/z = 601.14 ($C_{39}H_{24}ClN_3S$ = 602.15) | Sub 1-22 | m/z = 654.07 ($C_{35}H_{16}ClF_5N_4S$ = 655.04) |
| Sub 1-25 | m/z = 526.10 ($C_{32}H_{19}ClN_4S$ = 527.04) | Sub 1-26 | m/z = 666.16 ($C_{43}H_{27}ClN_4S$ = 667.23) |
| Sub 1-27 | m/z = 536.09 ($C_{31}H_{13}D_5ClN_3S_2$ = 537.11) | Sub 1-28 | m/z = 499.09 ($C_{31}H_{18}ClN_3S$ = 500.02) |
| Sub 1-31 | m/z = 518.08 ($C_{30}H_{16}ClFN_4S$ = 518.99) | Sub 1-32 | m/z = 455.12 ($C_{27}H_{22}ClN_3S$ = 456.00) |
| Sub 1-34 | m/z = 509.13 ($C_{33}H_{20}ClN_3O$ = 509.99) | Sub 1-35 | m/z = 433.10 ($C_{27}H_{16}ClN_3O$ = 433.90) |
| Sub 1-36 | m/z = 635.18 ($C_{43}H_{26}ClN_3O$ = 636.15) | Sub 1-37 | m/z = 522.12 ($C_{33}H_{19}ClN_4O$ = 522.99) |
| Sub 1-38 | m/z = 603.13 ($C_{37}H_{22}ClN_5S$ = 604.13) | Sub 1-41 | m/z = 483.11 ($C_{31}H_{18}ClN_3O$ = 483.96) |
| Sub 1-43 | m/z = 561.14 ($C_{35}H_{20}ClN_5O$ = 562.03) | Sub 1-44 | m/z = 626.14 ($C_{40}H_{23}ClN_4S$ = 627.16) |
| Sub 1-46 | m/z = 615.12 ($C_{37}H_{22}ClN_3OS$ = 616.14) | Sub 1-50 | m/z = 611.15 ($C_{39}H_{22}ClN_5O$ = 612.09) |
| Sub 1-52 | m/z = 632.14 ($C_{39}H_{25}ClN_4OS$ = 633.17) | Sub 1-54 | m/z = 655.22 ($C_{43}H_{22}D_5ClN_4O$ = 656.20) |
| Sub 1-55 | m/z = 527.10 ($C_{31}H_{18}ClN_5S$ = 528.03) | Sub 1-56 | m/z = 559.15 ($C_{37}H_{22}ClN_3O$ = 560.05) |
| Sub 1-60 | m/z = 576.12 ($C_{36}H_{21}ClN_4S$ = 577.10) | Sub 1-61 | m/z = 509.13 ($C_{33}H_{20}ClN_3O$ = 509.99) |
| Sub 1-62 | m/z = 605.13 ($C_{38}H_{24}ClN_3OS$ = 606.14) | Sub 1-63 | m/z = 599.14 ($C_{39}H_{22}ClN_3O_2$ = 600.07) |
| Sub 1-65 | m/z = 602.13 ($C_{38}H_{23}ClN_4S$ = 603.14) | Sub 1-66 | m/z = 680.15 ($C_{42}H_{25}ClN_6S$ = 681.21) |
| Sub 1-67 | m/z = 454.11 ($C_{27}H_{11}D_5ClN_3S$ = 454.99) | Sub 1-68 | m/z = 525.11 ($C_{33}H_{20}ClN_3S$ = 526.05) |
| Sub 1-69 | m/z = 544.09 ($C_{32}H_{18}ClFN_4S$ = 545.03) | Sub 1-70 | m/z = 575.12 ($C_{37}H_{22}ClN_3S$ = 576.11) |
| Sub 1-71 | m/z = 449.08 ($C_{27}H_{16}ClN_3S$ = 449.96) | Sub 1-71 | m/z = 525.11 ($C_{33}H_{20}ClN_3S$ = 526.05) |
| Sub 1-73 | m/z = 449.08 ($C_{27}H_{16}ClN_3S$ = 449.96) | Sub 1-74 | m/z = 509.13 ($C_{33}H_{20}ClN_3O$ = 509.99) |

Synthesis of Sub 2-3

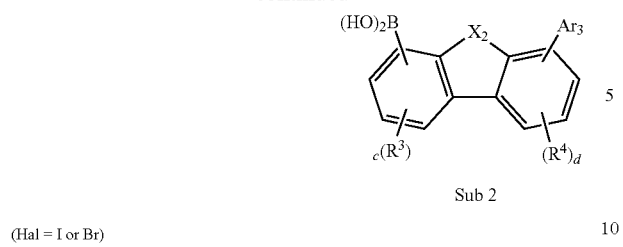

Sub 2

(Hal = I or Br)

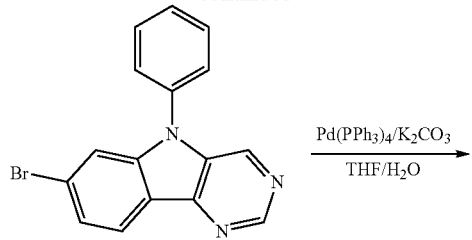

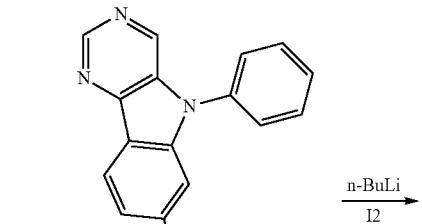

Sub 2-I-1

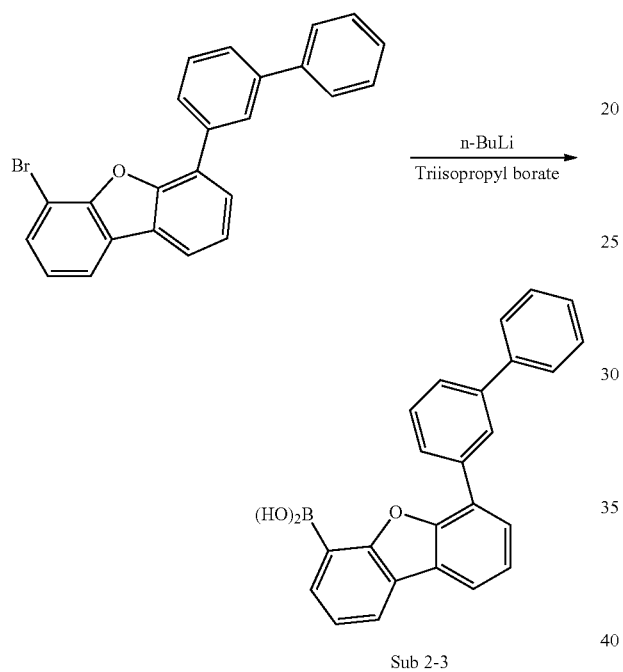

Sub 2-3

After 4-([1,1'-biphenyl]-3-yl)-6-bromodibenzo[b,d]furan (CAS Registry Number: 1010068-89-9) (50 g, 125.22 mmol) were dissolved in THF (522 ml), the temperature of the reactant was lowered to −78° C. Thereafter, n-BuLi (2.5M in hexane) (12.03 g, 187.83 mmol) was added slowly thereto and the mixture was stirred at 0° C. for 1 hour. Thereafter, the temperature of the reactant was lowered to −78° C., triisopropyl borate (28.26 g, 150.27 mmol) and water (261 ml) were added thereto and the mixture was stirred at room temperature for 12 hour. When reaction was completed, the product was extracted with ether and water. Then, the organic layer was dried with MgSO₄ and concentrated. The concentrate was applied to silica gel column and recrystallized to obtain 36.49 g (yield: 80%) of the product.

Synthesis of Sub 2-7

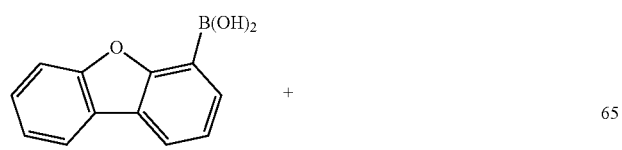

+

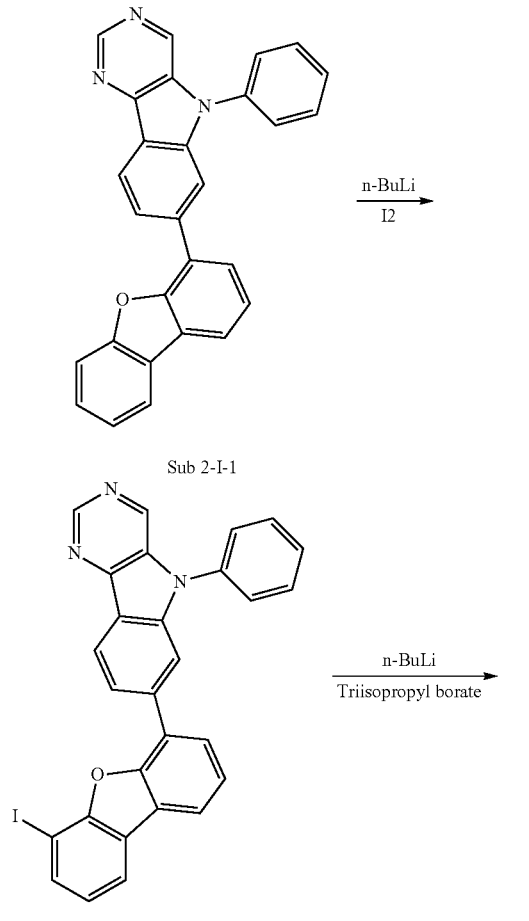

Sub 2-I-2

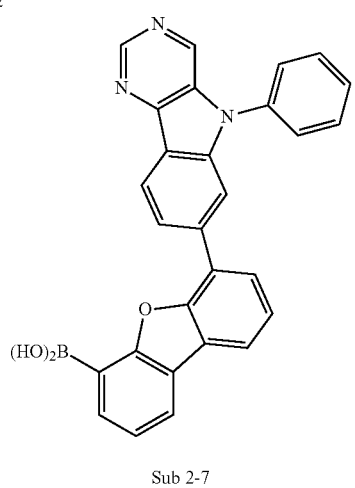

Sub 2-7

(1) Synthesis of Sub 2-I-1

After dibenzo[b,d]furan-4-ylboronic acid (50 g, 235.84 mmol) and 7-bromo-5-phenyl-5H-pyrimido[5,4-b]indole (91.74 g, 283.01 mmol) were dissolved in THF (865 mL), Pd(PPh$_3$)$_4$ (10.90 g, 9.43 mmol), K$_2$CO$_3$ (97.79 g, 707.51 mmol) and water (432 ml) were added thereto and the mixture was stirred under reflux. When reaction was completed, the product was extracted with ether and water. Then, the organic layer was concentrated and dried with MgSO$_4$ and concentrated. Thereafter, concentrate was applied to silica gel column and recrystallized to obtain 53.37 g (yield: 55%) of the product.

(2) Synthesis of Sub 2-I-2

After 7-(dibenzo[b,d]furan-4-yl)-5-phenyl-5H-pyrimido[5,4-b]indole (53.37 g, 129.71 mmol) were dissolved in THF (476 mL), the temperature of the reactant was lowered to −75° C. Thereafter, n-BuLi (2.5M in hexane) (9.97 g, 155.65 mmol) was added slowly thereto and the solution was stirred at room temperature for 1 hour. Thereafter, the temperature of the reactant was lowered to −75° C., I$_2$ (49.38 g, 194.56 mmol) and water (238 mL) were added thereto and the mixture was stirred at room temperature for 17 hour. Thereafter, aqueous solution of sodium thiosulfate was added thereto and the mixture was stirred for 1 hour. When reaction was completed, the product was extracted with ether and water. Then, the organic layer was dried with MgSO$_4$ and concentrated. The concentrate was applied to silica gel column and recrystallized to 41.82 g (yield: 60%) of the product.

(3) Synthesis of Sub 2-7

THF (324 mL), n-BuLi (2.5M in hexane) (7.48 g, 116.74 mmol), triisopropyl borate (17.56 g, 93.39 mmol) and water (162 mL) were added to 6-(5-phenyl-5H-pyrimido[5,4-b]indol-7-yl)dibenzo[b,d]furan-4-yl)boronic acid (41.82 g, 77.82 mmol), and then, 24.80 g (yield: 70%) of the product was obtained by the same method as in synthesis of Sub 2-3.

Synthesis of Sub 2-50

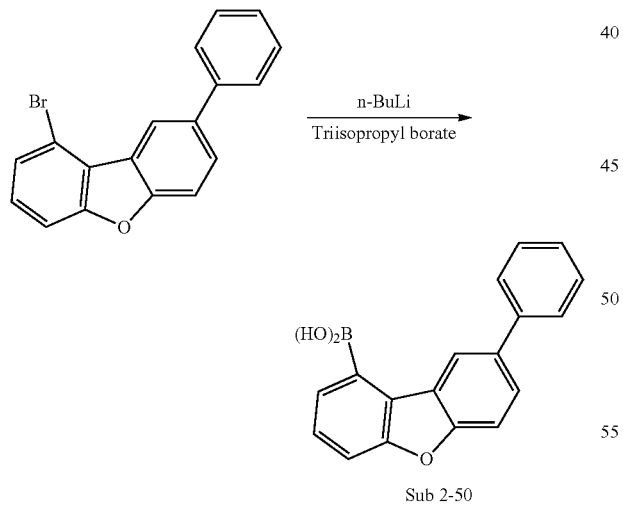

Sub 2-50

After dibenzofuran, 1-bromo-8-phenyl- (CAS Registry Number: 1822310-20-2) (45 g, 139.24 mmol) were dissolved in THF (580 ml), the temperature of the reactant was lowered to −78° C. Thereafter, n-BuLi (2.5M in hexane) (13.38 g, 208.86 mmol) was added slowly thereto and the mixture was stirred at 0° C. for 1 hour. Thereafter, the temperature of the reactant was lowered to −78° C., triisopropyl borate (31.42 g, 167.08 mmol) and water (290 ml) were added thereto and the mixture was stirred at room temperature for 12 hour. When reaction was completed, the organic layer was dried with MgSO$_4$ and concentrated. The concentrate was applied to silica gel column and recrystallized to obtain 26.88 g (yield: 67%) of the product.

The compound belonging to Sub 2 may be, but not limited to, the following compounds, and Table 2 shows FD-MS values of compounds belonging to Sub 2.

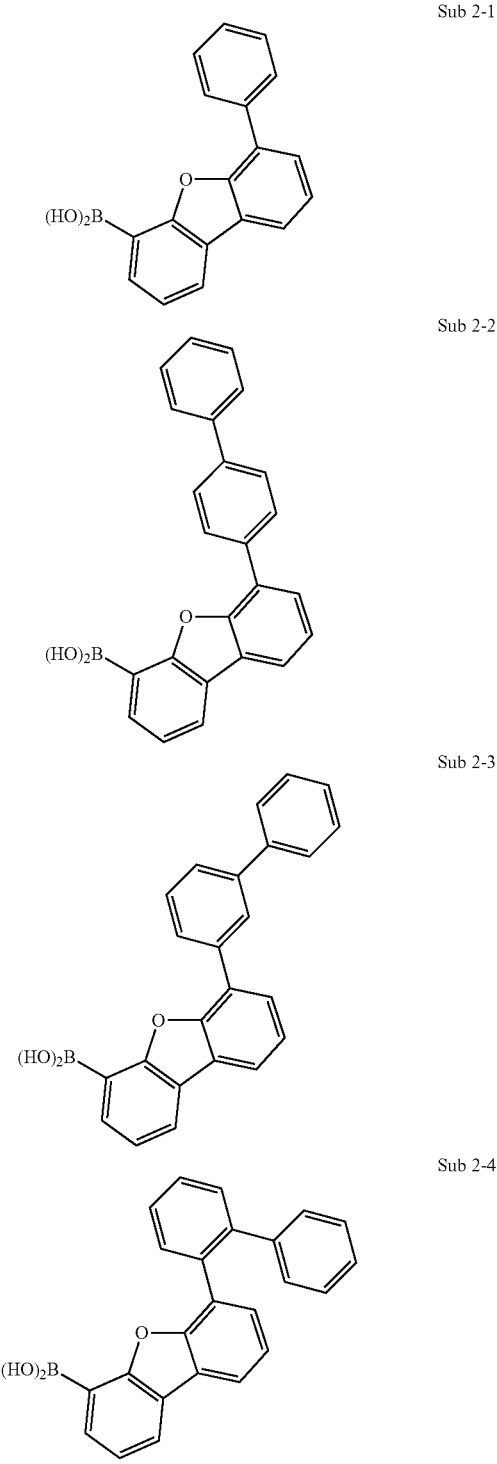

Sub 2-5
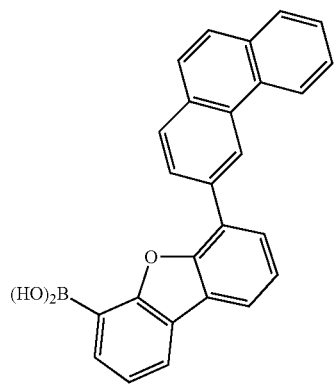
Sub 2-6
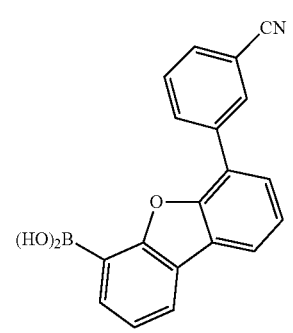
Sub 2-7
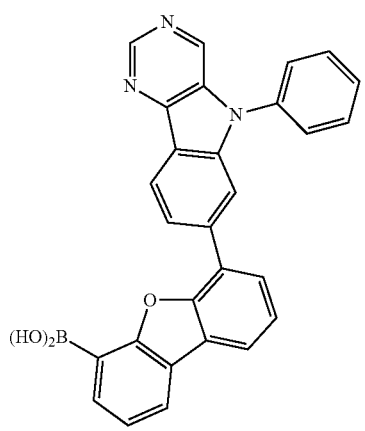
Sub 2-8
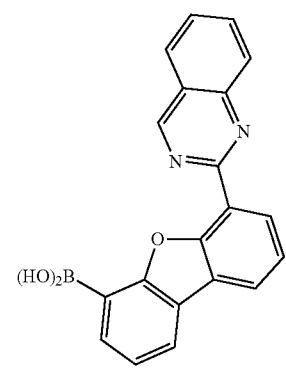
Sub 2-9
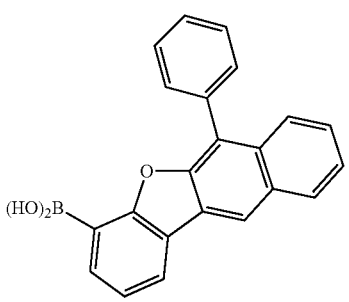
Sub 2-10
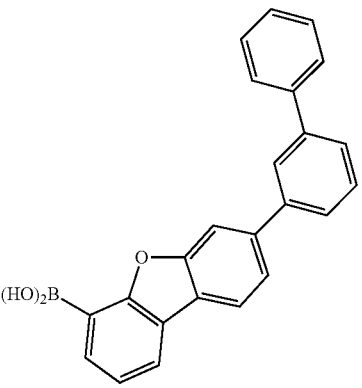
Sub 2-11
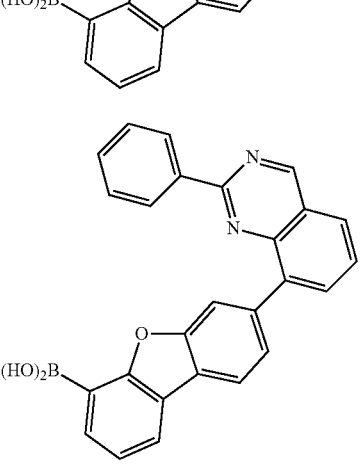
Sub 2-12
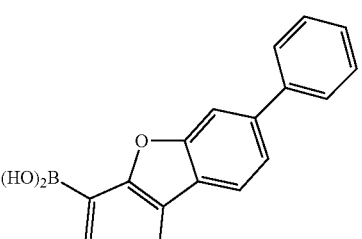
Sub 2-13
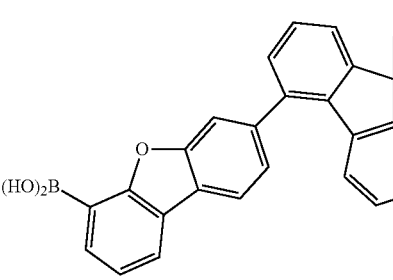

Sub 2-14
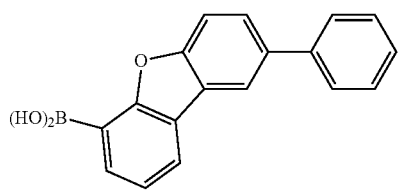
Sub 2-19
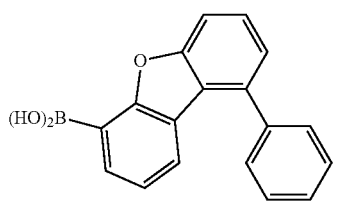
Sub 2-15
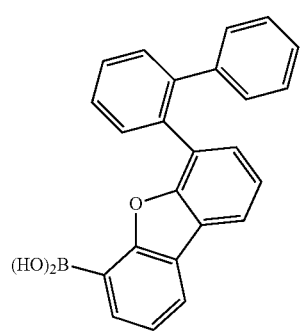
Sub 2-20
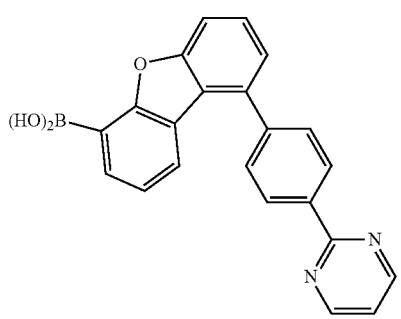
Sub 2-16
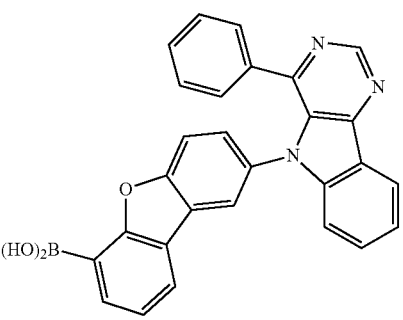
Sub 2-21
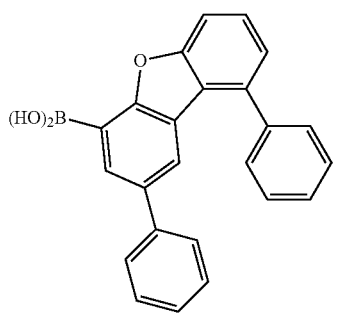
Sub 2-17
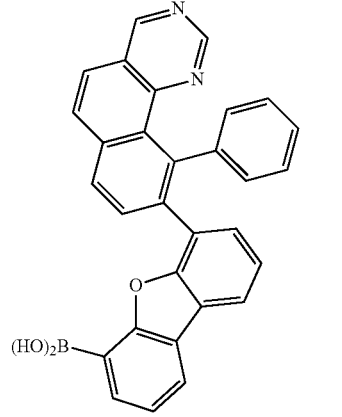
Sub 2-22
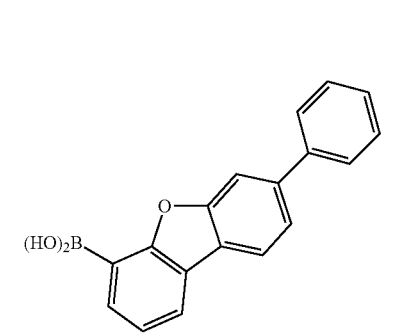
Sub 2-18
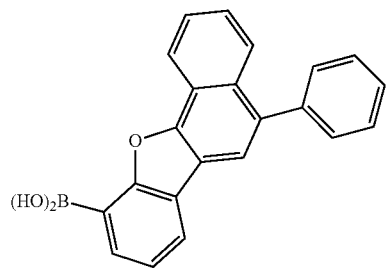
Sub 2-23
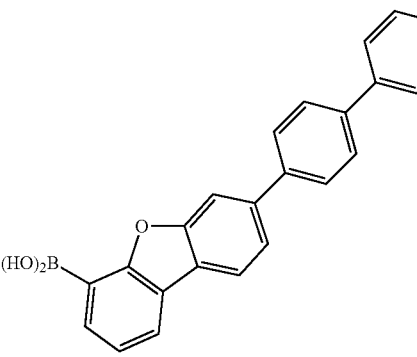

Sub 2-24
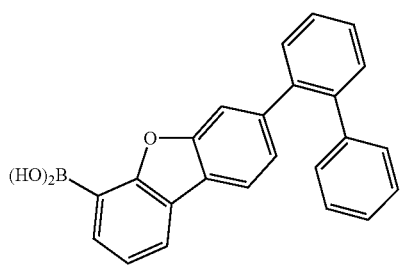
Sub 2-25
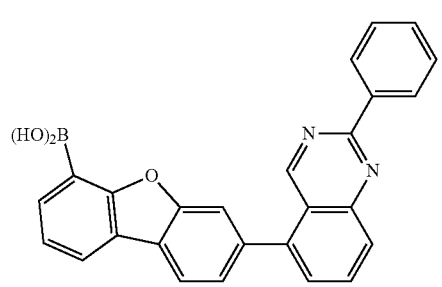
Sub 2-26
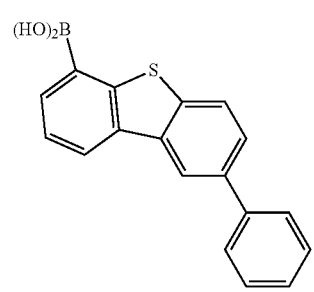
Sub 2-27
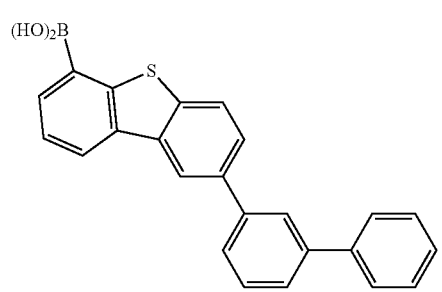
Sub 2-28
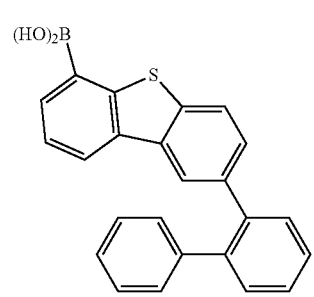
Sub 2-29
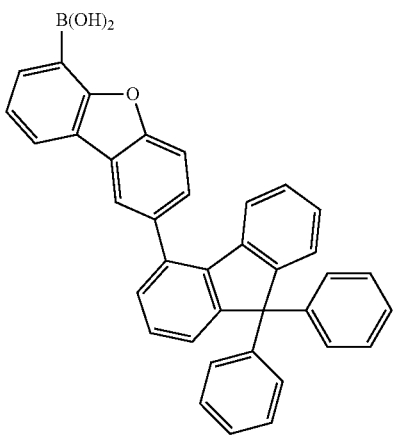
Sub 2-30
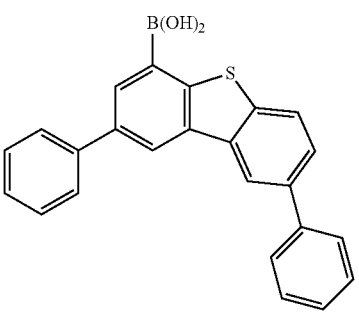
Sub 2-31
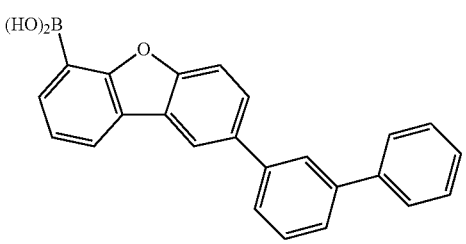
Sub 2-32
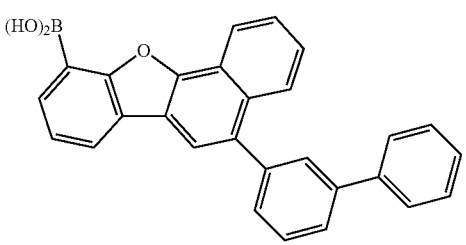
Sub 2-33
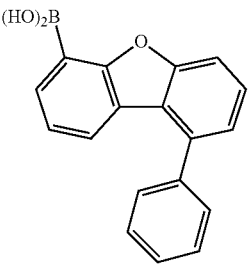

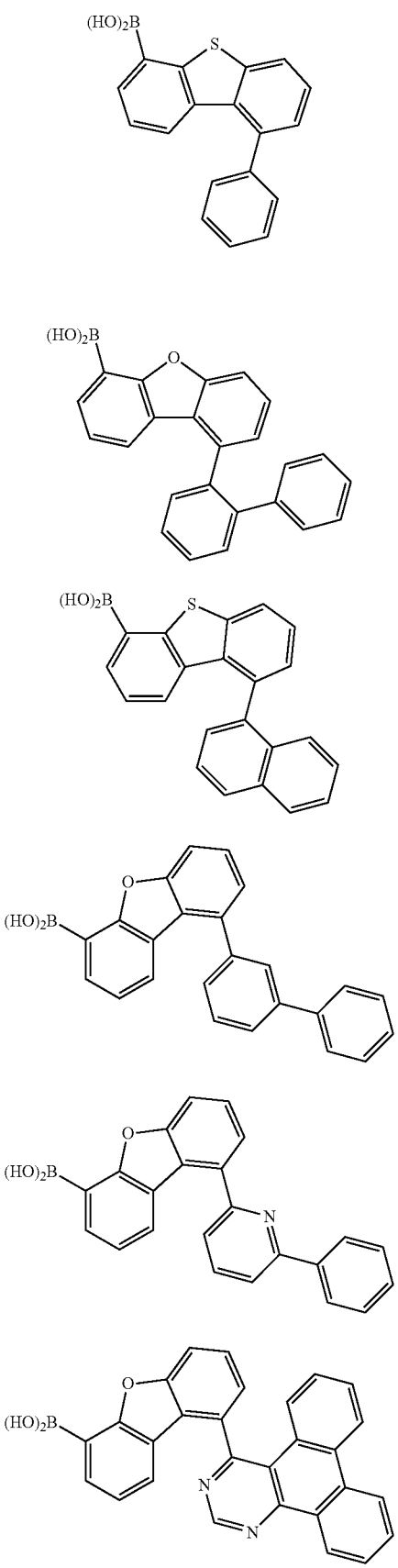
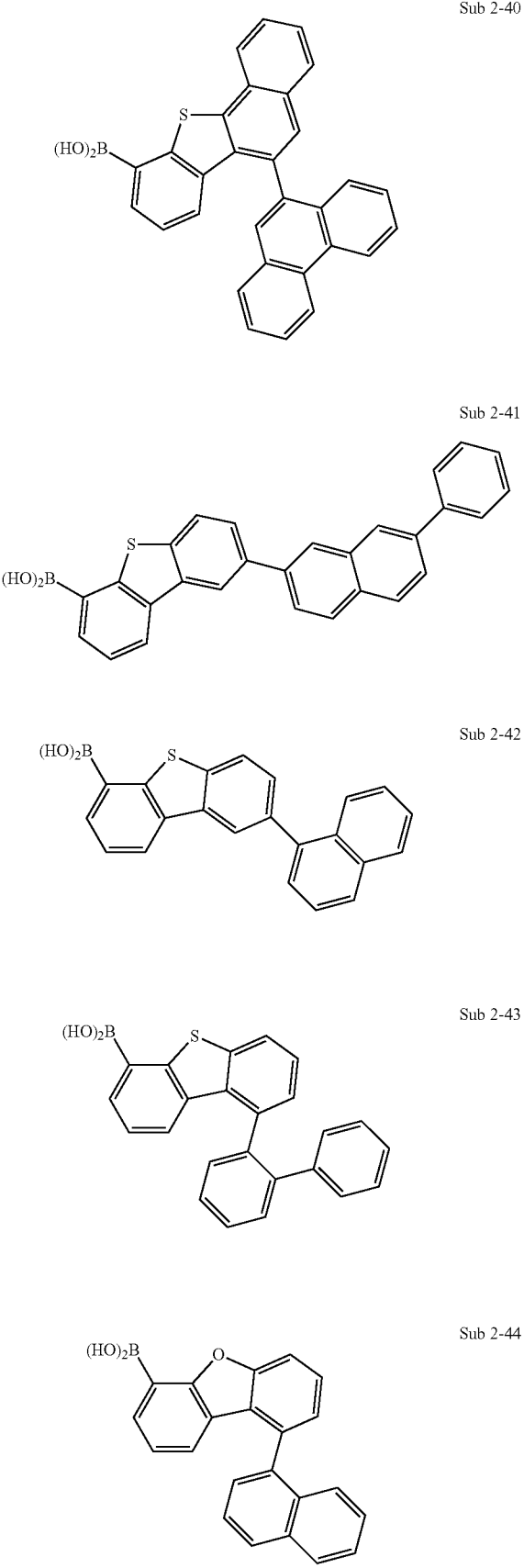

Sub 2-45
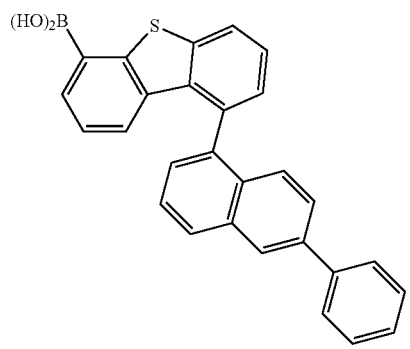
Sub 2-46
Sub 2-47
Sub 2-48
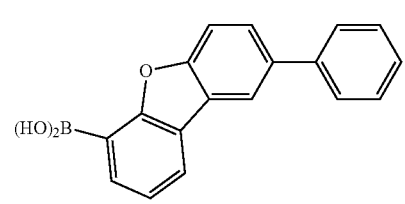
Sub 2-49
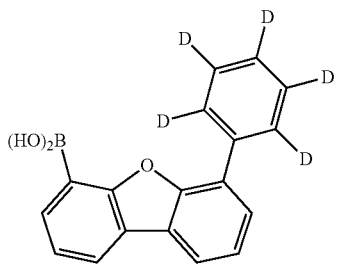
Sub 2-50
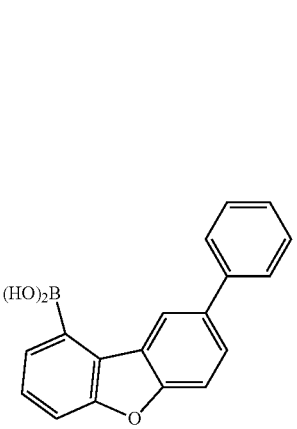
Sub 2-51
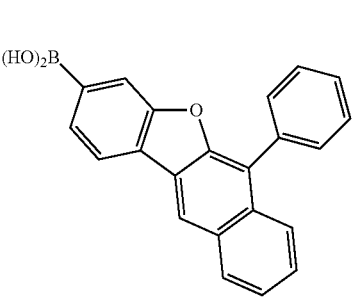
Sub 2-52
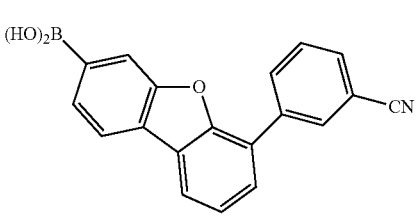

TABLE 2

| Compound | FD-MS | Compound | FD-MS |
|---|---|---|---|
| Sub 2-1 | m/z = 288.10 ($C_{18}H_{13}BO_3$ = 288.11) | Sub 2-3 | m/z = 364.13 ($C_{24}H_{17}BO_3$ = 364.21) |
| Sub 2-5 | m/z = 388.13 ($C_{26}H_{17}BO_3$ = 388.23) | Sub 2-6 | m/z = 313.09 ($C_{19}H_{12}BNO_3$ = 313.12) |
| Sub 2-7 | m/z = 455.14 ($C_{28}H_{18}BN_3O_3$ = 455.28) | Sub 2-8 | m/z = 340.10 ($C_{20}H_{13}BN_2O_3$ = 340.15) |
| Sub 2-9 | m/z = 338.11 ($C_{22}H_{15}BO_3$ = 338.17) | Sub 2-11 | m/z = 416.13 ($C_{26}H_{17}BN_2O_3$ = 416.24) |
| Sub 2-13 | m/z = 404.16 ($C_{27}H_{21}BO_3$ = 404.27) | Sub 2-17 | m/z = 466.15 ($C_{30}H_{19}BN_2O_3$ = 466.30) |
| Sub 2-20 | m/z = 366.12 ($C_{22}H_{15}BN_2O_3$ = 366.18) | Sub 2-30 | m/z = 380.10 ($C_{24}H_{17}BO_2S$ = 380.27) |
| Sub 2-38 | m/z = 365.12 ($C_{23}H_{16}BNO_3$ = 365.20) | Sub 2-39 | m/z = 440.13 ($C_{28}H_{17}BN_2O_3$ = 440.27) |
| Sub 2-40 | m/z = 454.12 ($C_{30}H_{19}BO_2S$ = 454.35) | Sub 2-42 | m/z = 354.09 ($C_{22}H_{15}BO_2S$ = 354.23) |
| Sub 2-45 | m/z = 430.12 ($C_{28}H_{19}BO_2S$ = 430.33) | Sub 2-46 | m/z = 388.13 ($C_{26}H_{17}BO_3$ = 388.23) |
| Sub 2-47 | m/z = 365.12 ($C_{23}H_{16}BNO_3$ = 365.20) | Sub 2-49 | m/z = 293.13 ($C_{18}H_8D_5BO_3$ = 293.14) |

3. Synthesis Example of Final Product

Synthesis of Compound 1-3

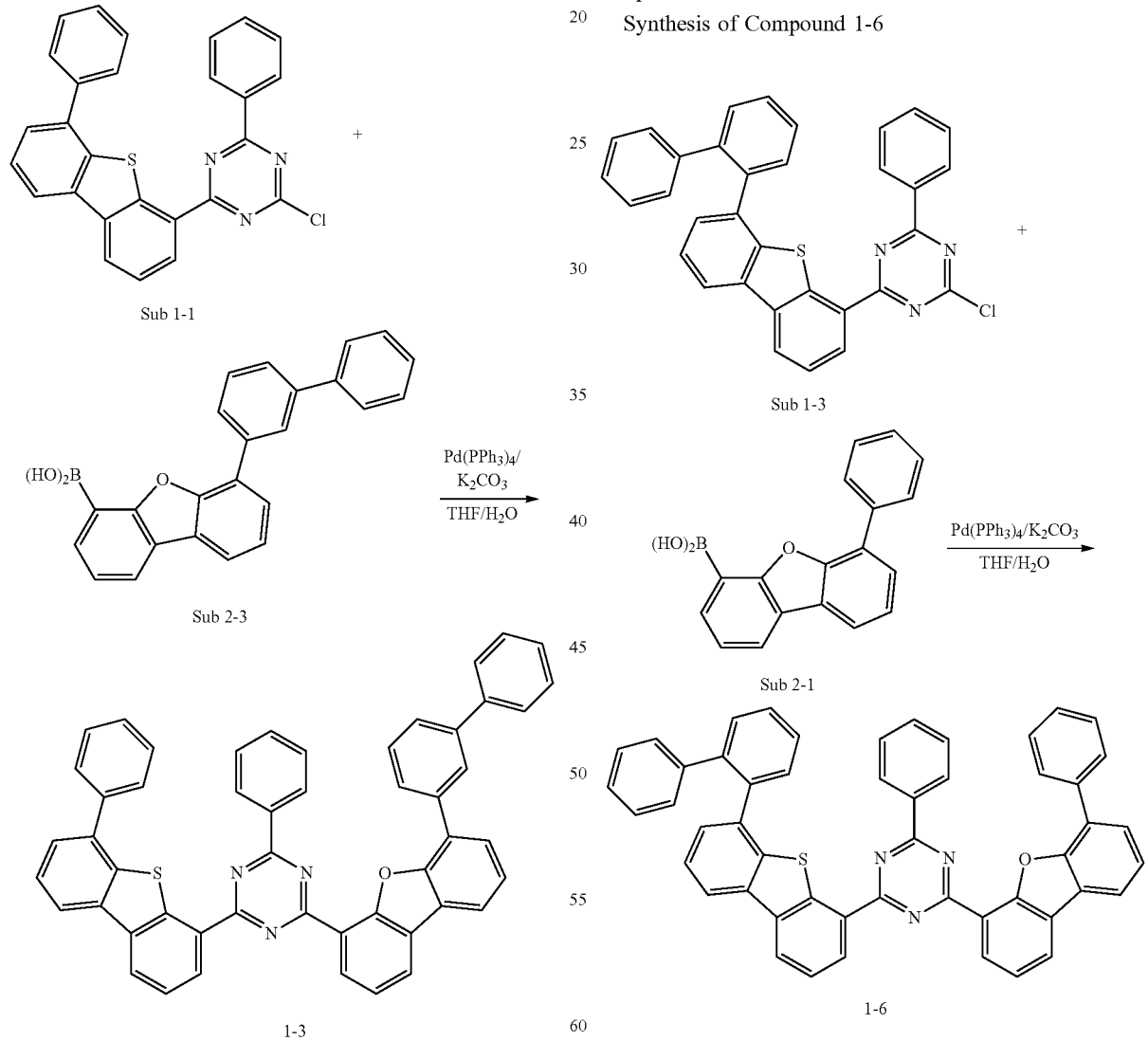

After Sub 1-1 (60 g, 133.35 mmol) in a round bottom flask was dissolved in THF (489 mL), Sub 2-3 (58.28 g, 160.01 mmol), Pd(PPh₃)₄ (6.16 g, 5.33 mmol), K₂CO₃ (55.29 g, 400.04 mmol) and water (244 mL) were added thereto and the mixture was stirred under reflux. When reaction was completed, the product was extracted with ether and water. Thereafter, the organic layer was dried with MgSO₄ and concentrated. The concentrate was applied to silica gel column and recrystallized to obtain 73.40 g (yield: 75%) of the product.

Synthesis of Compound 1-6

THF (418 mL), Sub 2-1 (39.43 g, 136.87 mmol), Pd(PPh₃)₄ (5.27 g, 4.56 mmol), K₂CO₃ (47.29 g, 342.17 mmol), water (209 mL) were added to Sub 1-3 (60 g, 114.06 mmol), and then 61.11 g (yield: 73%) of the product was obtained by the same method as in synthesis of 1-3.

Synthesis of Compound 1-11

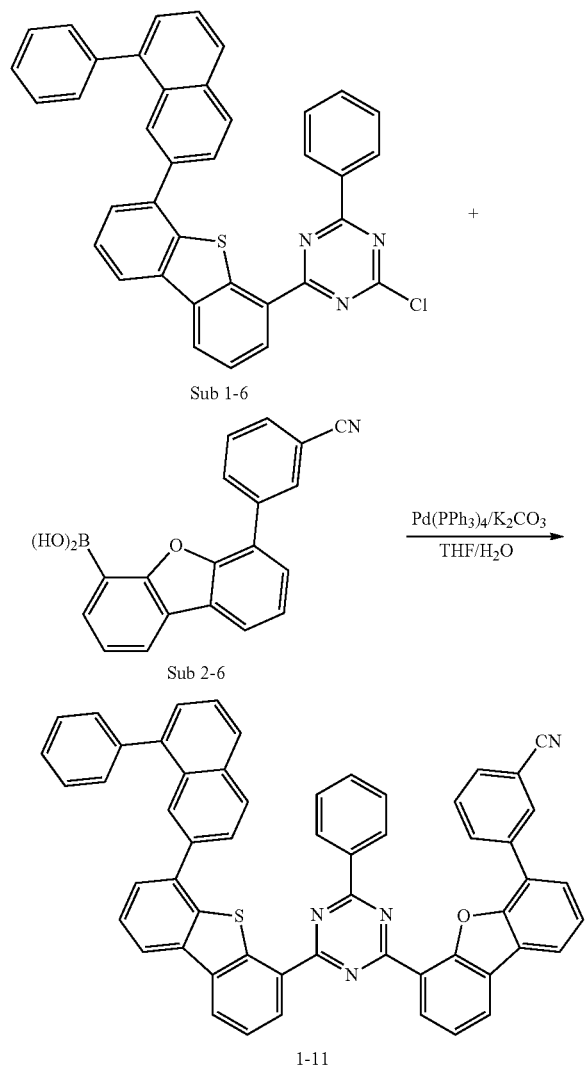

THF (382 mL), Sub 2-6 (39.13 g, 124.98 mmol), Pd(PPh$_3$)$_4$ (4.81 g, 4.17 mmol), K$_2$CO$_3$ (43.18 g, 312.44 mmol) and water (191 mL) were added to Sub 1-6 (60 g, 104.15 mmol), and then 54.76 g (yield: 65%) of the product was obtained by the same method as in synthesis of 1-3.

Synthesis of Compound 1-14

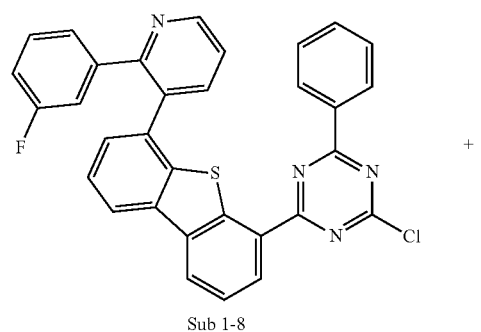

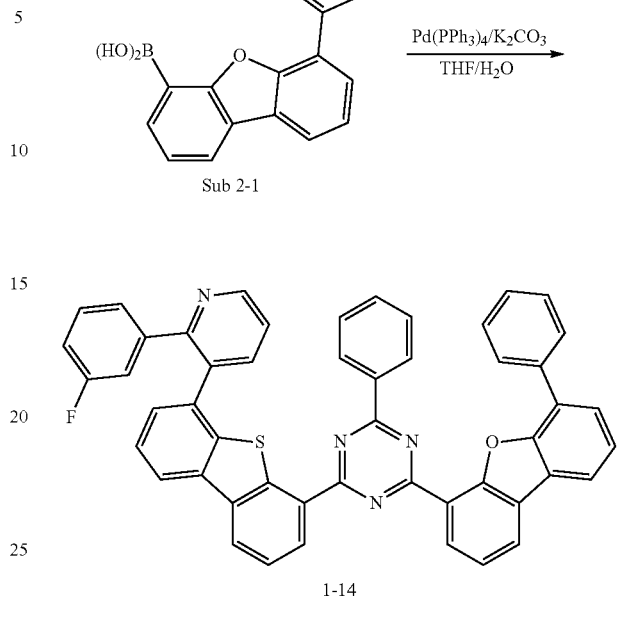

THF (404 mL), Sub 2-1 (288.11 g, 132.10 mmol), Pd(PPh$_3$)$_4$ (5.09 g, 4.40 mmol), K$_2$CO$_3$ (45.64 g, 330.26 mmol) and water (202 mL) were added to Sub 1-8 (60 g, 110.09 mmol), and then 52.21 g (yield: 63%) of the product was obtained by the same method as in synthesis of 1-3.

Synthesis of Compound 1-22

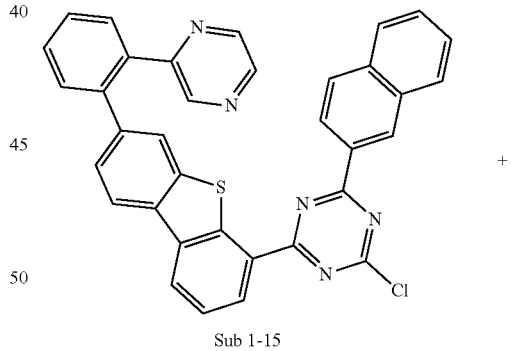

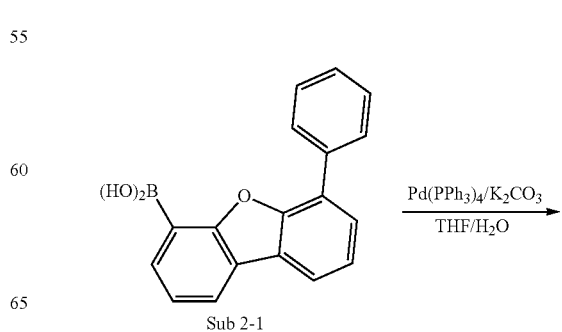

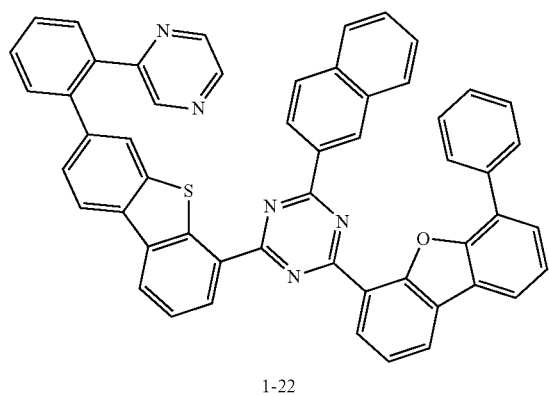

1-22

THF (381 mL), Sub 2-1 (35.88 g, 124.55 mmol), Pd(PPh₃)₄ (4.80 g, 4.15 mmol), K₂CO₃ (43.03 g, 311.37 mmol) and water (190 mL) were added to Sub 1-15 (60 g, 103.79 mmol), and then 55.47 g (yield: 68%) of the product was obtained by the same method as in synthesis of 1-3.

Synthesis of Compound 1-44

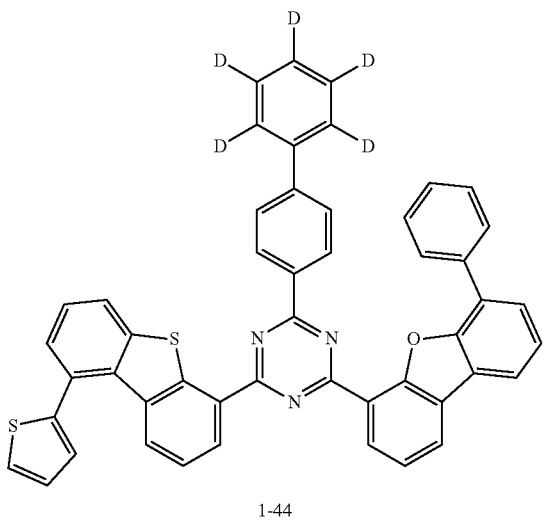

1-44

THF (410 mL), Sub 2-1 (38.62 g, 134.05 mmol), Pd(PPh₃)₄ (5.16 g, 4.47 mmol), K₂CO₃ (46.32 g, 335.13 mmol) and water (205 mL) were added to Sub 1-27 (60 g, 111.71 mmol), and then 49.93 g (yield: 60%) of the product was obtained by the same method as in synthesis of 1-3.

Synthesis of Compound 1-74

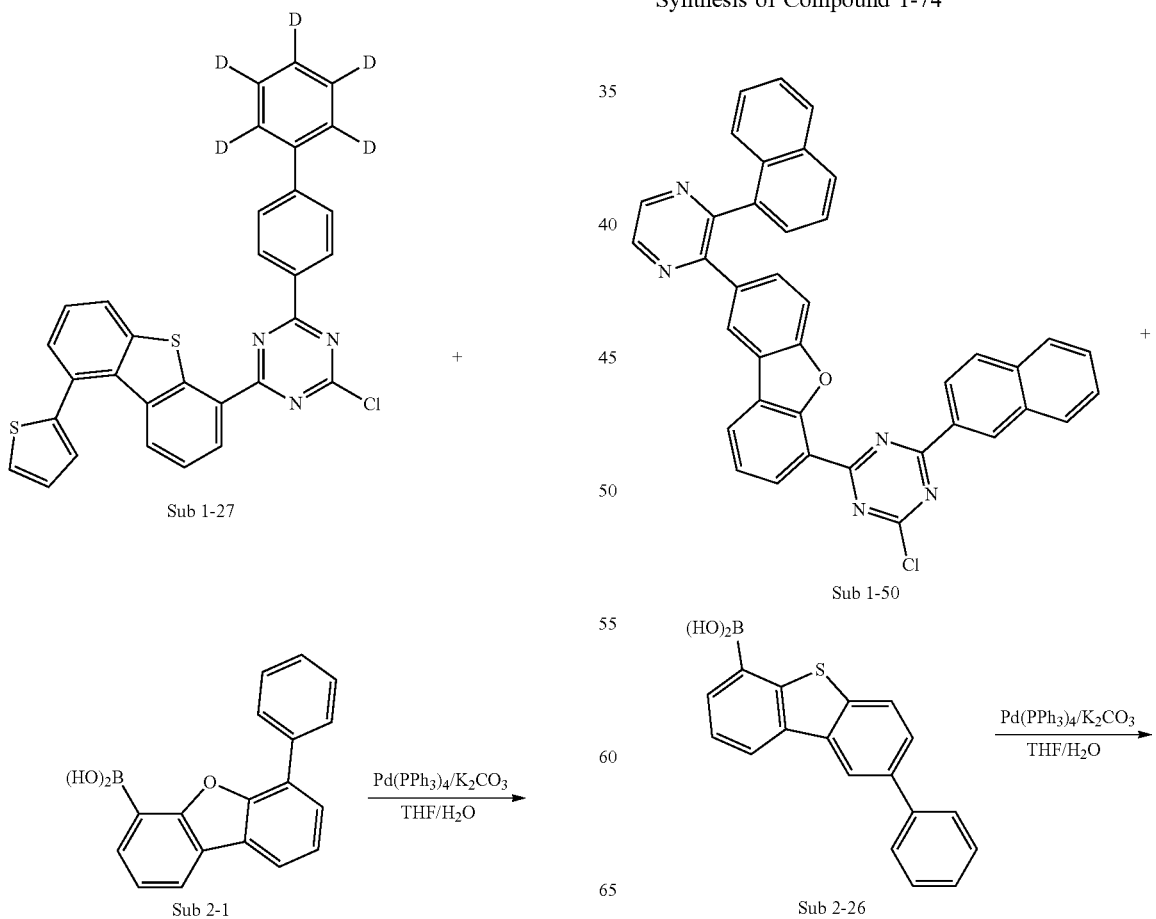

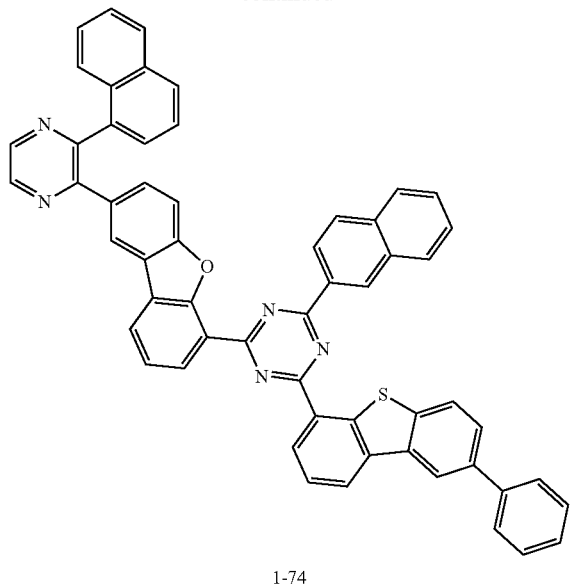

1-74

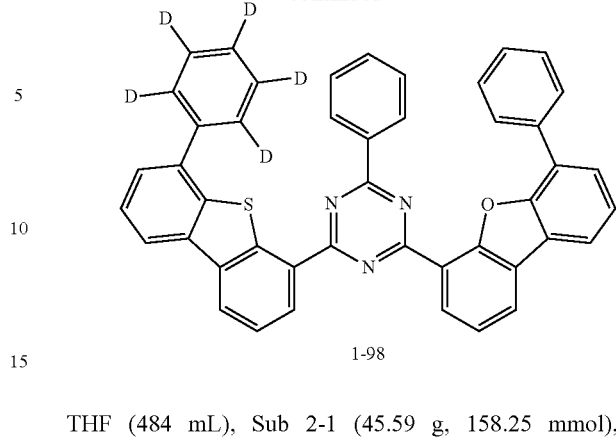

1-98

THF (484 mL), Sub 2-1 (45.59 g, 158.25 mmol), Pd(PPh$_3$)$_4$ (6.10 g, 5.27 mmol), K$_2$CO$_3$ (54.68 g, 395.61 mmol) and water (242 mL) were added to Sub 1-67 (60 g, 131.87 mmol), and then 70.80 g (yield: 81%) of the product was obtained by the same method as in synthesis of 1-3.

Synthesis of Compound 2-15

THF (359 mL), Sub 2-26 (35.78 g, 117.63 mmol), Pd(PPh$_3$)$_4$ (4.53 g, 3.92 mmol), K$_2$CO$_3$ (40.64 g, 294.07 mmol) and water (180 mL) were added to Sub 1-50 (60 g, 98.02 mmol), and then 46.71 g (yield: 57%) of the product was obtained by the same method as in synthesis of 1-3.

Synthesis of Compound 1-98

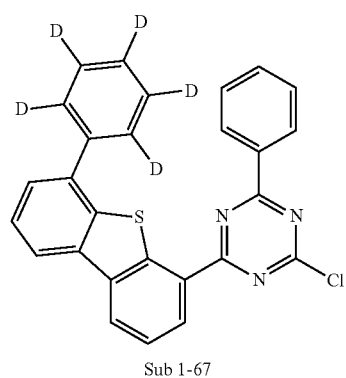

Sub 1-67

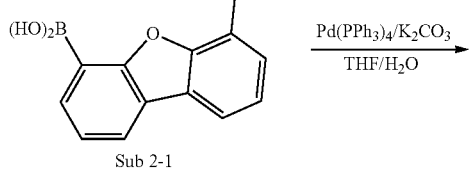

Sub 2-1

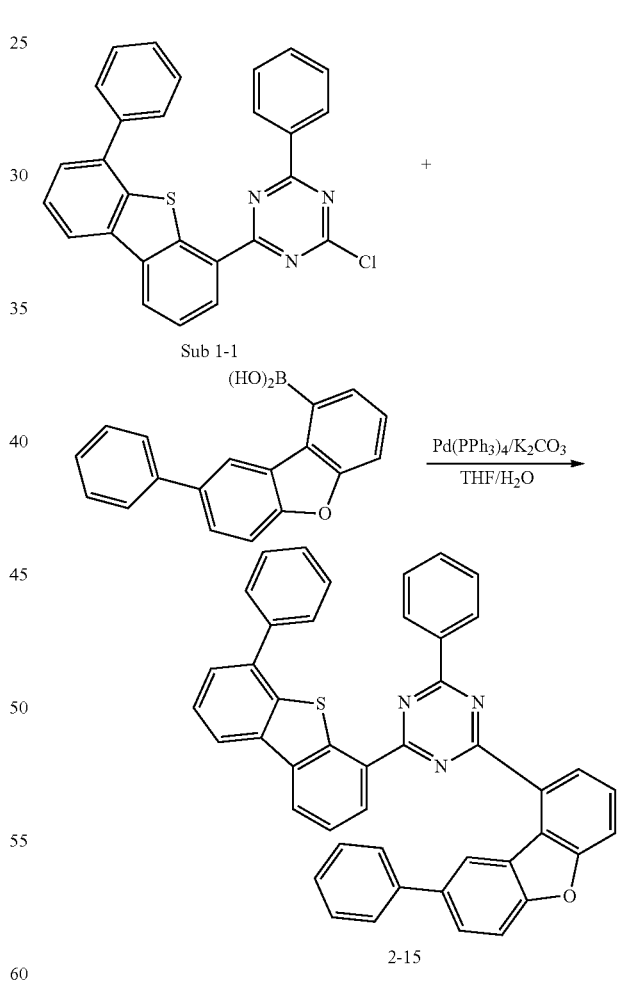

2-15

THF (489 mL), (8-phenyldibenzo[b,d]furan-1-yl)boronic acid (46.10 g, 160.01 mmol), Pd(PPh$_3$)$_4$ (6.16 g, 5.33 mmol), K$_2$CO$_3$ (55.29 g, 400.04 mmol) and water (244 mL) were added to Sub 1-1 (60 g, 133.35 mmol), and then 58.77 g (yield: 67%) of the product was obtained by the same method as in synthesis of 1-3.

Synthesis of Compound 3-22

Synthesis of Compound 4-11

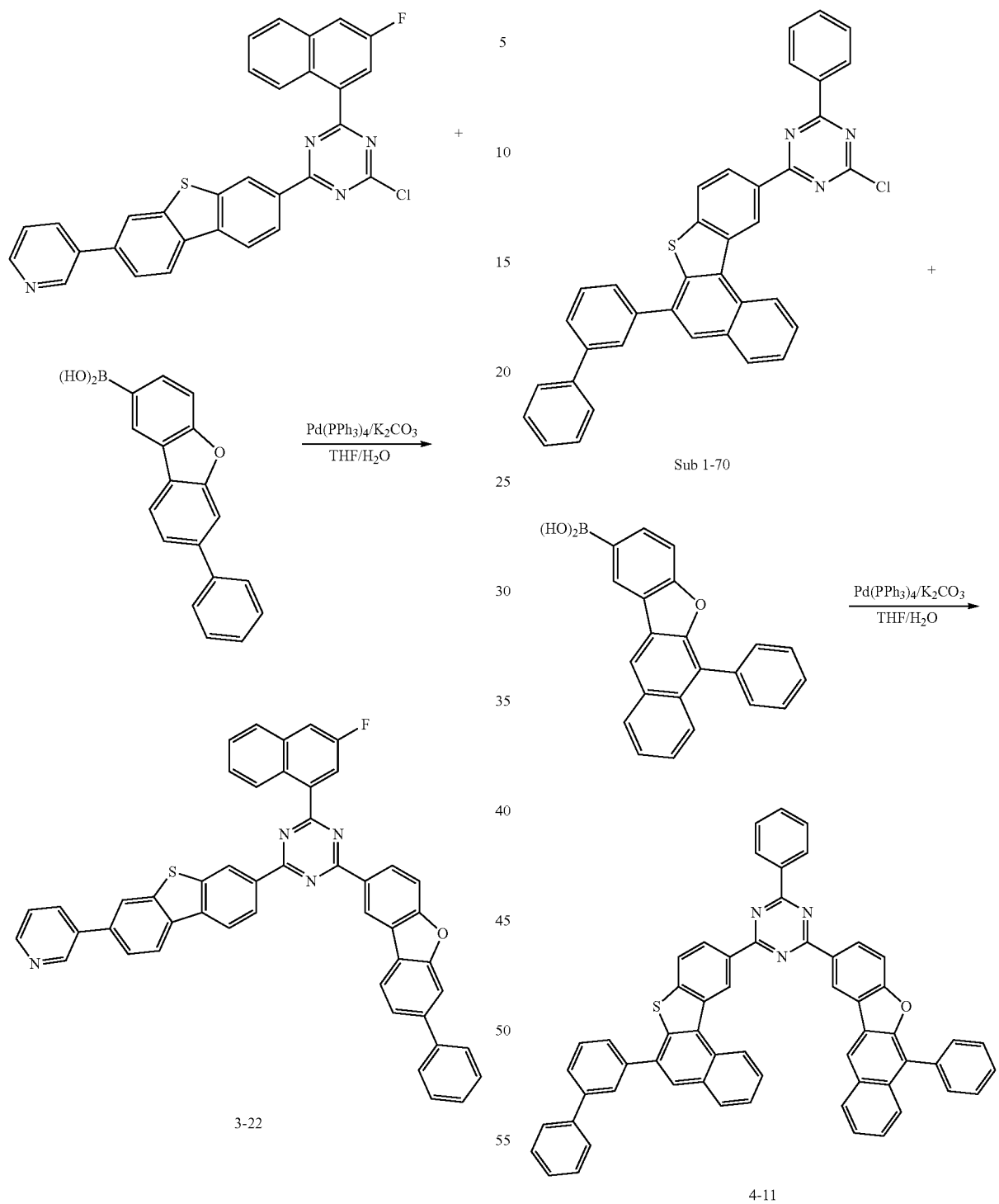

THF (424 mL), (7-phenyldibenzo[b,d]furan-2-yl)boronic acid (39.97 g, 138.73 mmol), Pd(PPh$_3$)$_4$ (5.34 g, 4.62 mmol), K$_2$CO$_3$ (47.94 g, 346.83 mmol) and water (212 mL) were added to 2-chloro-4-(3-fluoronaphthalen-1-yl)-6-(7-(pyridin-3-yl)dibenzo[b,d]thiophen-3-yl)-1,3,5-triazine (60 g, 115.61 mmol), and then 51.26 g (yield: 61%) of the product was obtained by the same method as in synthesis of 1-3.

THF (382 mL), (6-phenylnaphtho[2,3-b]benzofuran-2-yl) boronic acid (42.26 g, 124.98 mmol), Pd(PPh$_3$)$_4$ (4.81 g, 4.17 mmol), K$_2$CO$_3$ (43.18 g, 312.44 mmol) and water (191 mL) were added to Sub 1-70 (60 g, 104.15 mmol), and then 50.38 g (yield: 58%) of the product was obtained by the same method as in synthesis of 1-3.

Synthesis of Compound 4-38

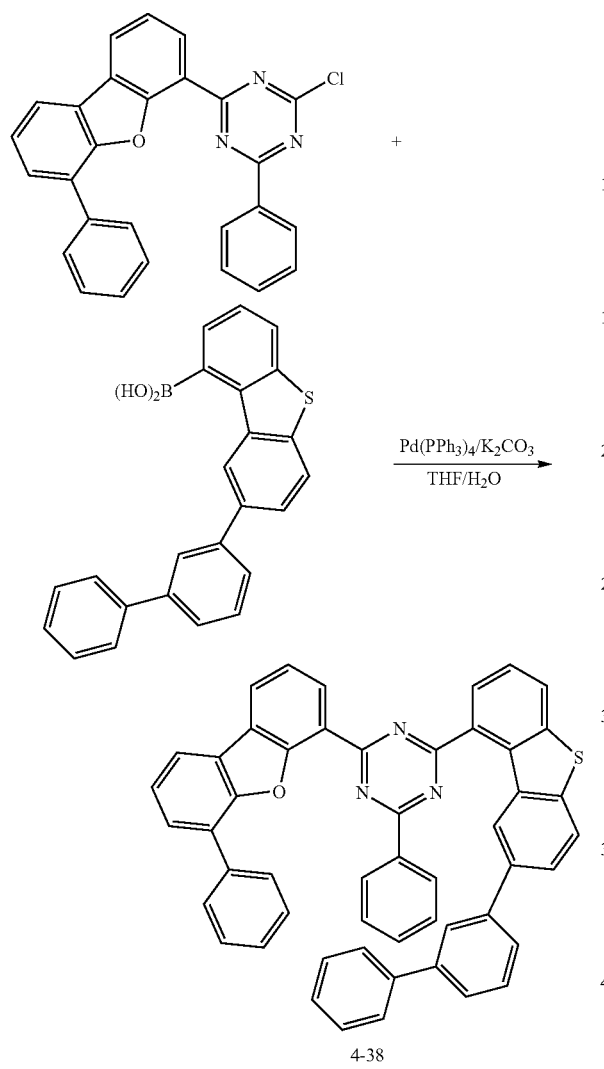

4-38

THF (85 mL), (8-([1,1'-biphenyl]-3-yl)dibenzo[b,d]thiophen-1-yl)boronic acid (10.52 g, 27.7 mmol), Pd(PPh₃)₄ (1.33 g, 1.2 mmol), K₂CO₃ (9.56 g, 69.1 mmol) and water (42 mL) were added to 2-chloro-4-phenyl-6-(6-phenyldibenzo[b,d]furan-4-yl)-1,3,5-triazine (10 g, 23.0 mmol), and then 14.38 g (yield: 85%) of the product was obtained by the same method as in synthesis of 1-3.

Synthesis of Compound 4-41

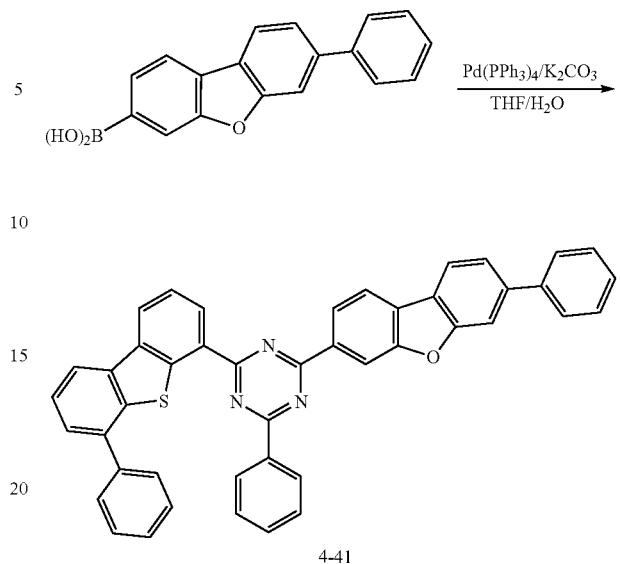

4-41

THF (180 mL), (7-phenyldibenzo[b,d]furan-3-yl)boronic acid (16.9 g, 58.7 mmol), Pd(PPh₃)₄ (2.82 g, 2.4 mmol), K₂CO₃ (20.27 g, 146.7 mmol) and water (90 mL) were added to 2-chloro-4-phenyl-6-(6-phenyldibenzo[b,d]thiophen-4-yl)-1,3,5-triazine (22 g, 48.9 mmol), and then 25.73 g (yield: 80%) of the product was obtained by the same method as in synthesis of 1-3.

Synthesis of Compound 4-43

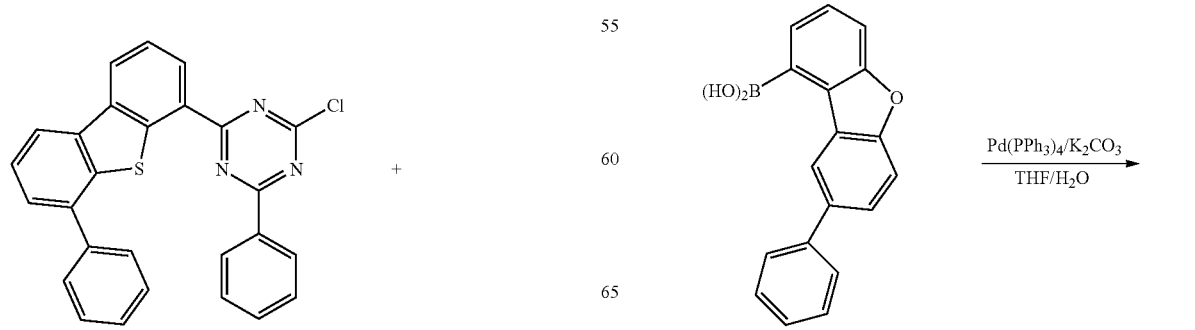

305

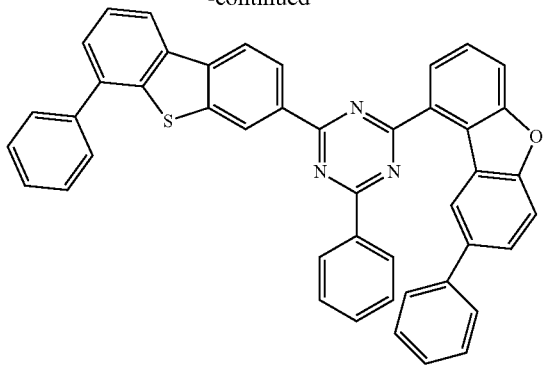

4-43

THF (285 mL), (8-phenyldibenzo[b,d]furan-1-yl)boronic acid (26.89 g, 93.3 mmol), Pd(PPh$_3$)$_4$ (4.49 g, 3.9 mmol), K$_2$CO$_3$ (32.25 g, 233.4 mmol) and water (143 mL) were added to 2-chloro-4-phenyl-6-(6-phenyldibenzo[b,d]thiophen-3-yl)-1,3,5-triazine (35 g, 77.8 mmol), and then 36.84 g (yield: 72%) of the product was obtained by the same method as in synthesis of 1-3.

The FD-MS values of the compounds represented by Formula 1 of the present invention prepared according to the above synthesis examples are shown in Table 3 below.

306

Synthesis Example 2

As shown in Reaction Schemes 4-1 and 4-2 below, the compound represented by Formula 12 according to the present invention can be synthesized by reacting Sub 3 with Sub 4-1, but there is no limitation thereto.

<Reaction Scheme 4-1> (where L$^2$ in Formula 12 is not a single bond)

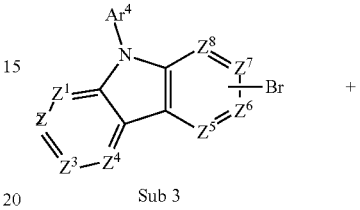

Sub 3

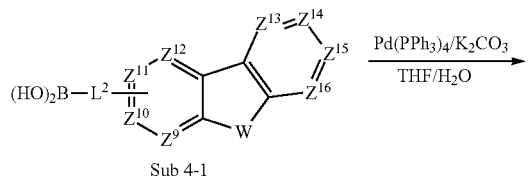

Sub 4-1

TABLE 3

| Compound | FD-MS | Compound | FD-MS |
|---|---|---|---|
| 1-1 | m/z = 657.19 (C$_{45}$H$_{27}$N$_3$OS = 657.79) | 1-2 | m/z = 733.22 (C$_{51}$H$_{31}$N$_3$OS = 733.89) |
| 1-3 | m/z = 733.22 (C$_{51}$H$_{31}$N$_3$OS = 733.89) | 1-4 | m/z = 733.22 (C$_{51}$H$_{31}$N$_3$OS = 733.89) |
| 1-7 | m/z = 707.20 (C$_{49}$H$_{29}$N$_3$OS = 707.85) | 1-8 | m/z = 757.22 (C$_{53}$H$_{31}$N$_3$OS = 757.91) |
| 1-9 | m/z = 859.27 (C$_{61}$H$_{37}$N$_3$OS = 860.05) | 1-10 | m/z = 707.20 (C$_{49}$H$_{29}$N$_3$OS = 707.85) |
| 1-11 | m/z = 808.23 (C$_{56}$H$_{32}$N$_4$OS = 808.96) | 1-12 | m/z = 890.31 (C$_{63}$H$_{34}$D$_5$N$_3$OS = 891.12) |
| 1-13 | m/z = 824.24 (C$_{35}$H$_{32}$N$_6$OS = 824.96) | 1-14 | m/z = 752.20 (C$_{50}$H$_{29}$FN$_4$OS = 752.87) |
| 1-15 | m/z = 765.26 (C$_{51}$H$_{35}$N$_5$OS = 765.94) | 1-16 | m/z = 765.17 (C$_{49}$H$_{27}$N$_5$OS$_2$ = 765.91) |
| 1-17 | m/z = 807.23 (C$_{57}$H$_{33}$N$_3$OS = 807.97) | 1-18 | m/z = 833.25 (C$_{59}$H$_{35}$N$_3$OS = 834.01) |
| 1-19 | m/z = 733.22 (C$_{51}$H$_{31}$N$_3$OS = 733.89) | 1-20 | m/z = 733.22 (C$_{51}$H$_{31}$N$_3$OS = 733.89) |
| 1-21 | m/z = 783.23 (C$_{55}$H$_{33}$N$_3$OS = 783.95) | 1-22 | m/z = 785.22 (C$_{53}$H$_{31}$N$_5$OS = 785.93) |
| 1-23 | m/z = 859.27 (C$_{61}$H$_{37}$N$_3$OS = 860.05) | 1-24 | m/z = 785.22 (C$_{53}$H$_{31}$N$_5$OS = 785.93) |
| 1-25 | m/z = 809.22 (C$_{55}$H$_{31}$N$_5$OS = 809.95) | 1-26 | m/z = 849.28 (C$_{60}$H$_{39}$N$_3$OS = 850.05) |
| 1-27 | m/z = 783.23 (C$_{55}$H$_{33}$N$_3$OS = 783.95) | 1-28 | m/z = 657.19 (C$_{45}$H$_{27}$N$_3$OS = 657.79) |
| 1-29 | m/z = 809.25 (C$_{57}$H$_{35}$N$_3$OS = 809.99) | 1-32 | m/z = 900.27 (C$_{61}$H$_{36}$N$_6$OS = 901.06) |
| 1-33 | m/z = 835.24 (C$_{57}$H$_{33}$N$_5$OS = 835.99) | 1-34 | m/z = 901.25 (C$_{61}$H$_{35}$N$_5$O2S = 902.04) |
| 1-35 | m/z = 809.25 (C$_{37}$H$_{33}$N$_3$OS = 809.99) | 1-36 | m/z = 938.21 (C$_{59}$H$_{31}$F$_5$N$_4$OS = 938.98) |
| 1-37 | m/z = 783.23 (C$_{55}$H$_{33}$N$_3$OS = 783.95) | 1-42 | m/z = 812.24 (C$_{54}$H$_{32}$N$_6$OS = 812.95) |
| 1-43 | m/z = 950.31 (C$_{67}$H$_{42}$N$_4$OS = 951.16) | 1-44 | m/z = 744.21 (C$_{49}$H$_{24}$D$_5$N$_3$OS$_2$ = 744.94) |
| 1-50 | m/z = 726.19 (C$_{48}$H$_{27}$FN$_4$OS = 726.83) | 1-51 | m/z = 791.27 (C$_{53}$H$_{37}$N$_5$OS = 791.97) |
| 1-58 | m/z = 897.28 (C$_{64}$H$_{39}$N$_3$OS = 898.10) | 1-59 | m/z = 822.25 (C$_{57}$H$_{34}$N$_4$OS = 822.99) |
| 1-60 | m/z = 887.27 (C$_{61}$H$_{37}$N$_5$OS = 888.06) | 1-64 | m/z = 885.28 (C$_{63}$H$_{39}$N$_3$OS = 886.09) |
| 1-68 | m/z = 911.27 (C$_{63}$H$_{37}$N$_5$OS = 912.08) | 1-69 | m/z = 885.26 (C$_{61}$H$_{35}$N$_5$OS = 886.05) |
| 1-70 | m/z = 989.25 (C$_{69}$H$_{39}$N$_3$OS$_2$ = 990.21) | 1-75 | m/z = 909.28 (C$_{65}$H$_{39}$N$_3$OS = 910.11) |
| 1-76 | m/z = 856.23 (C$_{57}$H$_{36}$N$_4$OS$_2$ = 857.06) | 1-78 | m/z = 929.32 (C$_{65}$H$_{35}$D$_5$N$_4$OS = 930.15) |
| 1-79 | m/z = 735.21 (C$_{49}$H$_{29}$N5OS = 735.87) | 1-90 | m/z = 784.23 (C$_{54}$H$_{32}$N$_4$OS = 784.94) |
| 1-92 | m/z = 889.28 (C$_{62}$H$_{39}$N$_3$O$_2$S = 890.07) | 1-96 | m/z = 888.27 (C$_{60}$H$_{36}$N$_6$OS = 889.05) |
| 1-98 | m/z = 662.22 (C$_{45}$H$_{22}$D$_5$N$_3$OS = 662.82) | 1-99 | m/z = 667.25 (C$_{45}$H$_{17}$D$_{10}$N$_3$OS = 667.85) |
| 1-100 | m/z = 733.22 (C$_{51}$H$_{31}$N$_3$OS = 733.89) | 2-15 | m/z = 657.19 (C$_{45}$H$_{27}$N$_3$OS = 657.79) |

-continued

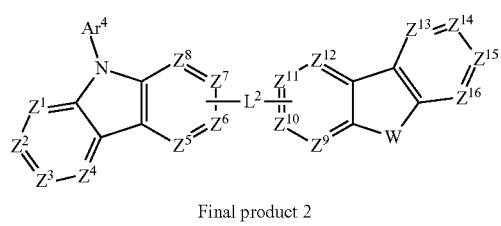

Final product 2

<Reaction Scheme 4-2> (where L² in Formula 12 is a single bond)

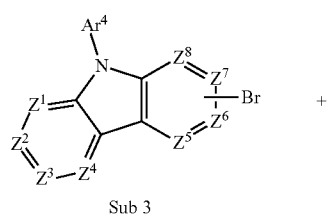

Sub 3

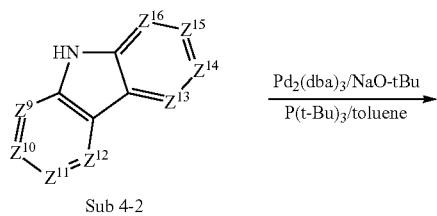

Sub 4-2

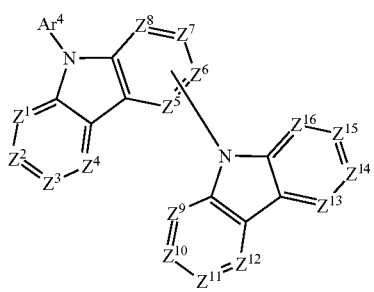

Final product 2

Synthesis of compound 5-1

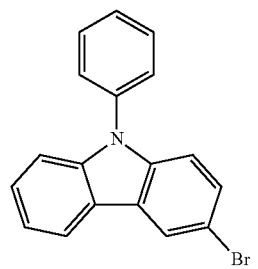

-continued

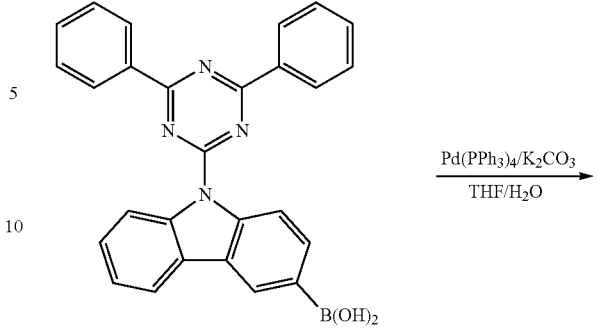

5-1

After 3-bromo-9-phenyl-9H-carbazole (6.4 g, 20 mmol) was dissolved in THF, (9-(4,6-diphenyl-1,3,5-triazin-2-yl)-9H-carbazol-3-yl)boronic acid (8.8 g, 20 mmol), Pd(PPh₃)₄ (0.03 eq.), K₂CO₃ (3 eq.) and water were added thereto and the mixture was stirred under reflux. When reaction was completed, the product was extracted with ether and water. Thereafter, the organic layer was dried with MgSO₄ and concentrated. The concentrate was applied to silica gel column and recrystallized to obtain 9.2 g (yield: 72%) of the product.

Synthesis of Compound 5-21

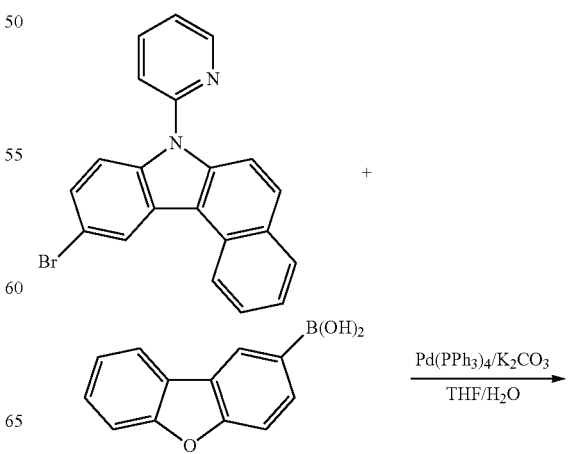

309
-continued

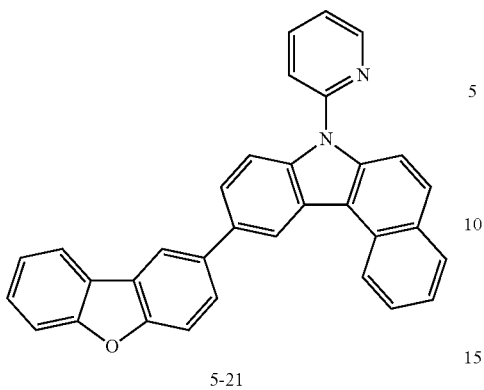

5-21

Dibenzo[b,d]furan-2-ylboronic acid (4.2 g, 20 mmol) were added to 10-bromo-7-(pyridin-2-yl)-7H-benzo[c]carbazole (7.5 g, 20 mmol), and then 6.5 g (yield: 71%) of the product was obtained by the same method as in synthesis of 5-1.

Synthesis of Compound 5-25

310
-continued

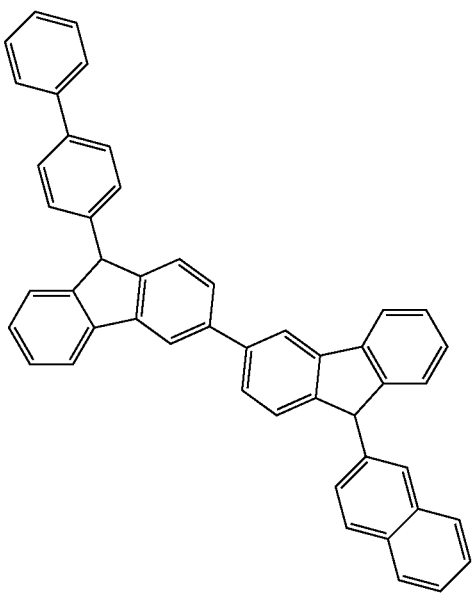

5-25

(9-(naphthalen-2-yl)-9H-carbazol-3-yl)boronic acid (6.7 g, 20 mmol) were added to 9-([1,1'-biphenyl]-4-yl)-3-bromo-9H-carbazole (8.0 g, 20 mmol), and then 9.2 g (yield: 75%) of the product was obtained by the same method as in synthesis of 5-1.

Synthesis of Compound 5-31

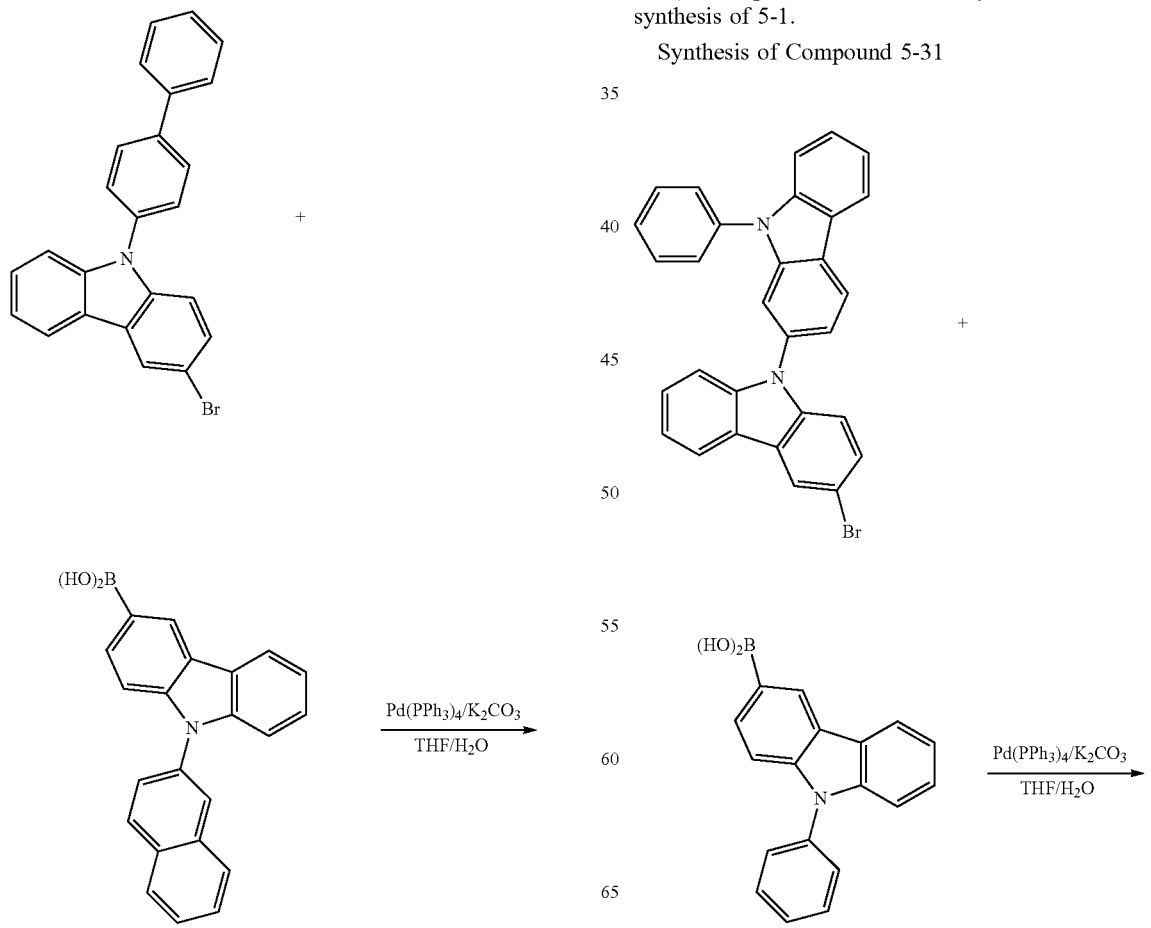

311
-continued

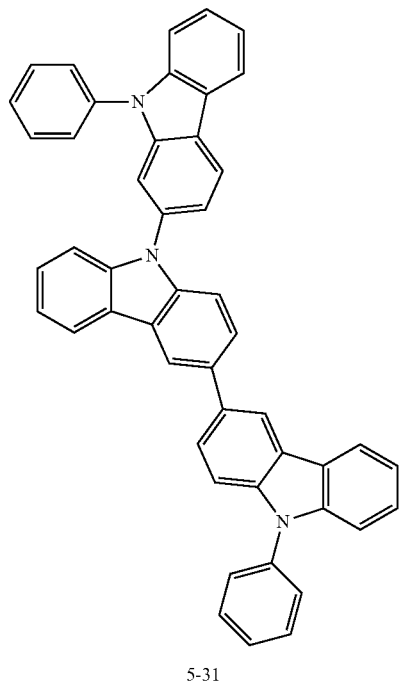

5-31

(9-phenyl-9H-carbazol-3-yl)boronic acid (5.7 g, 20 mmol) were added to 3'-bromo-9-phenyl-9H-2,9'-bicarbazole (9.7 g, 20 mmol), and then 9.5 g (yield: 73%) of the product was obtained by the same method as in synthesis of 5-1.

Synthesis of Compound 5-32

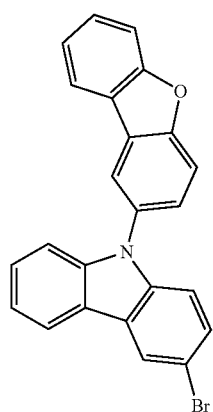

+

312
-continued

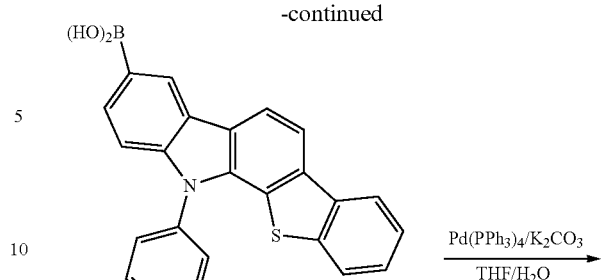

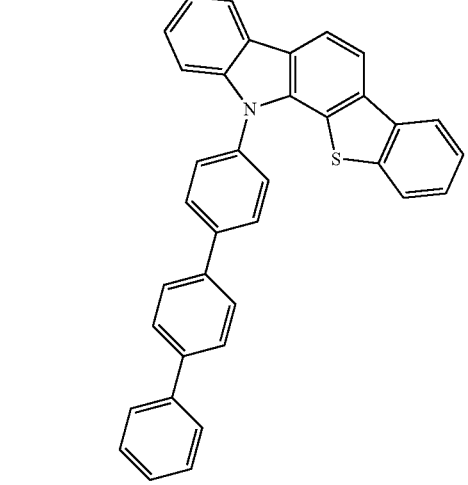

5-32

(12-([1,1':4',1''-terphenyl]-4-yl)-12H-benzo[4,5]thieno[2,3-a]carbazol-3-yl)boronic acid (10.9 g, 20 mmol) were added to 3-bromo-9-(dibenzo[b,d]furan-2-yl)-9H-carbazole (8.2 g, 20 mmol), and then 11.5 g (yield: 69%) of the product was obtained by the same method as in synthesis of 5-1.

Synthesis of Compound 5-34

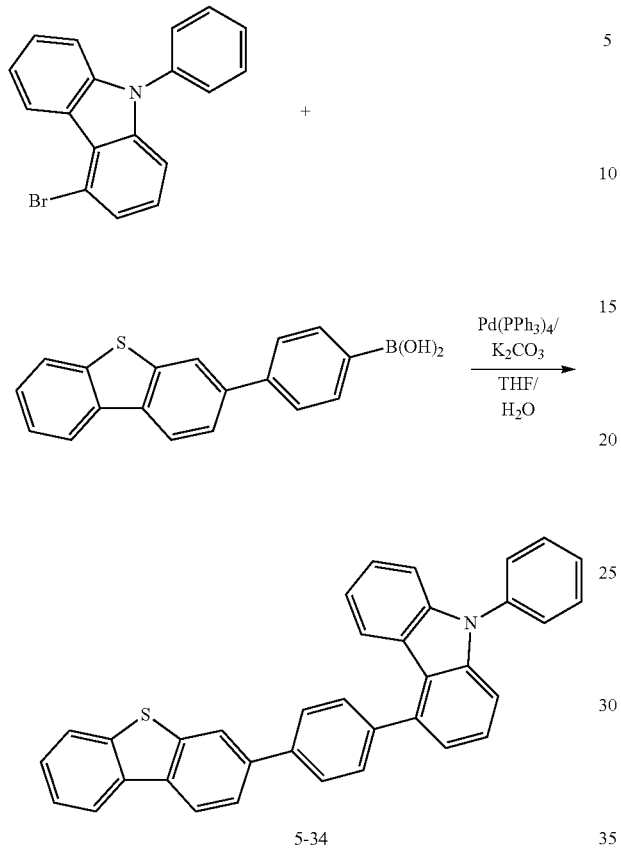

5-34

(4-(dibenzo[b,d]thiophen-3-yl)phenyl)boronic acid (6.1 g, 20 mmol) were added to 4-bromo-9-phenyl-9H-carbazole (6.4 g, 20 mmol), and then 6.7 g (yield: 67%) of the product was obtained by the same method as in synthesis of 5-1.

Synthesis of Compound 5-35

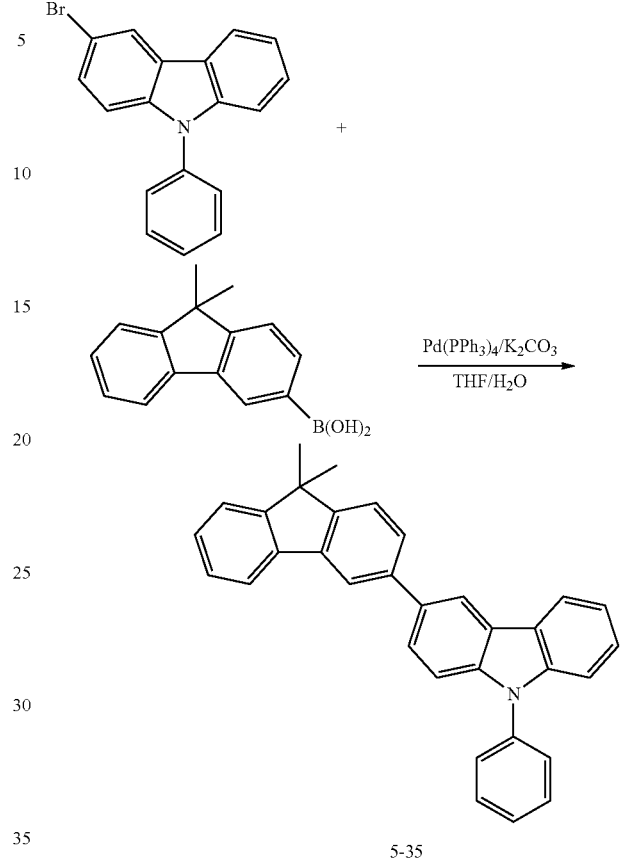

5-35

9(9,9-dimethyl-9H-fluoren-3-yl)boronic acid (4.8 g, 20 mmol) were added to 3-bromo-9-phenyl-9H-carbazole (6.4 g, 20 mmol), and then 6.1 g (yield: 70%) of the product was obtained by the same method as in synthesis of 5-1.

The ED-MS values of the compounds according to Formula 1 of the present invention prepared according to the above synthesis examples are shown in the following Table 4.

TABLE 4

| Compound | FD-MS | Compound | FD-MS |
|---|---|---|---|
| 5-1 | m/z = 639.24 ($C_{45}H_{29}N_5$ = 639.75) | 5-2 | m/z = 715.27 ($C_{51}H_{33}N_5$ = 715.84) |
| 5-3 | m/z = 780.33 ($C_{57}H_{40}N_4$ = 780.95) | 5-4 | m/z = 639.24 ($C_{45}H_{29}N_5$ = 639.75) |
| 5-5 | m/z = 715.27 ($C_{51}H_{33}N_5$ = 715.84) | 5-6 | m/z = 780.33 ($C_{57}H_{40}N_4$ = 780.95) |
| 5-7 | m/z = 612.23 ($C_{44}H_{28}N_4$ = 612.72) | 5-8 | m/z = 612.23 ($C_{44}H_{28}N_4$ = 612.72) |
| 5-9 | m/z = 662.25 ($C_{48}H_{30}N_4$ = 662.78) | 5-10 | m/z = 484.19 ($C_{36}H_{24}N_2$ = 484.59) |
| 5-11 | m/z = 639.24 ($C_{45}H_{29}N_5$ = 639.75) | 5-12 | m/z = 715.27 ($C_{51}H_{33}N_5$ = 715.84) |
| 5-13 | m/z = 715.27 ($C_{51}H_{33}N_5$ = 715.84) | 5-14 | m/z = 638.25 ($C_{46}H_{30}N_4$ = 638.76) |
| 5-15 | m/z = 579.18 ($C_{40}H_{25}N_3S$ = 579.71) | 5-16 | m/z = 410.14 ($C_{29}H_{18}N_2S$ = 410.47) |
| 5-17 | m/z = 486.17 ($C_{35}H_{22}N_2O$ = 486.56) | 5-18 | m/z = 486.17 ($C_{35}H_{22}N_2O$ = 486.56) |
| 5-19 | m/z = 486.17 ($C_{35}H_{22}N_2O$ = 486.56) | 5-20 | m/z = 563.20 ($C_{40}H_{25}N_3O$ = 563.65) |
| 5-21 | m/z = 460.16 ($C_{33}H_{20}N_2O$ = 460.52) | 5-22 | m/z = 536.19 ($C_{39}H_{24}N_2O$ = 536.62) |
| 5-23 | m/z = 689.26 ($C_{49}H_{31}N_5$ = 689.80) | 5-24 | m/z = 585.22 ($C_{43}H_{27}N_3$ = 585.69) |
| 5-25 | m/z = 610.24 ($C_{46}H_{30}N_2$ = 610.76) | 5-26 | m/z = 610.24 ($C_{46}H_{30}N_2$ = 610.76) |
| 5-27 | m/z = 636.26 ($C_{48}H_{32}N_2$ = 636.80) | 5-28 | m/z = 636.26 ($C_{48}H_{32}N_2$ = 636.80) |
| 5-29 | m/z = 610.24 ($C_{46}H_{30}N_2$ = 610.76) | 5-30 | m/z = 610.24 ($C_{46}H_{30}N_2$ = 610.76) |
| 5-31 | m/z = 649.25 ($C_{48}H_{31}N_3$ = 649.80) | 5-32 | m/z = 832.25 ($C_{60}H_{36}N_2OS$ = 833.02) |
| 5-33 | m/z = 560.23 ($C_{42}H_{28}N_2$ = 560.70) | 5-34 | m/z = 501.16 ($C_{36}H_{23}NS$ = 501.65) |
| 5-35 | m/z = 435.20 ($C_{33}H_{25}N$ = 435.57) | 5-36 | m/z = 725.28 ($C_{54}H_{35}N_3$ = 725.90) |
| 5-37 | m/z = 650.24 ($C_{48}H_{30}N_2O$ = 650.78) | 5-38 | m/z = 650.24 ($C_{48}H_{30}N_2O$ = 650.78) |
| 5-39 | m/z = 650.24 ($C_{48}H_{30}N_2O$ = 650.78) | 5-40 | m/z = 650.24 ($C_{48}H_{30}N_2O$ = 650.78) |
| 5-41 | m/z = 666.21 ($C_{48}H_{30}N_2S$ = 666.84) | 5-42 | m/z = 666.21 ($C_{48}H_{30}N_2S$ = 666.84) |

TABLE 4-continued

| Compound | FD-MS | Compound | FD-MS |
|---|---|---|---|
| 5-43 | m/z = 666.21 ($C_{48}H_{30}N_2S$ = 666.84) | 5-44 | m/z = 666.21 ($C_{48}H_{30}N_2S$ = 666.84) |
| 5-45 | m/z = 650.24 ($C_{48}H_{30}N_2O$ = 650.78) | 5-46 | m/z = 650.24 ($C_{48}H_{30}N_2O$ = 650.78) |
| 5-47 | m/z = 650.24 ($C_{48}H_{30}N_2O$ = 650.78) | 5-48 | m/z = 650.24 ($C_{48}H_{30}N_2O$ = 650.78) |
| 5-49 | m/z = 666.21 ($C_{48}H_{30}N_2S$ = 666.84) | 5-50 | m/z = 666.21 ($C_{48}H_{30}N_2S$ = 666.84) |
| 5-51 | m/z = 666.21 ($C_{48}H_{30}N_2S$ = 666.84) | 5-52 | m/z = 666.21 ($C_{48}H_{30}N_2S$ = 666.84) |
| 5-57 | m/z = 636.26 ($C_{48}H_{32}N_2$ = 636.80) | 5-58 | m/z = 725.28 ($C_{54}H_{35}N_3$ = 725.90) |

Synthesis Example 3

The compound represented by Formula 20 according to the present invention can be synthesized as follows, but is not limited thereto.

Synthesis of Compound 13-17

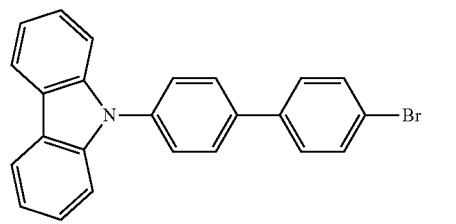

+

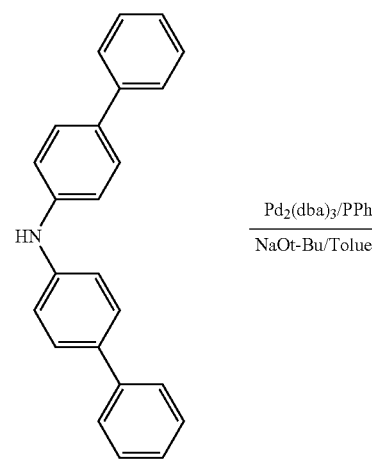

$\xrightarrow{\text{Pd}_2(\text{dba})_3/\text{PPh}_3}{\text{NaOt-Bu/Toluene}}$

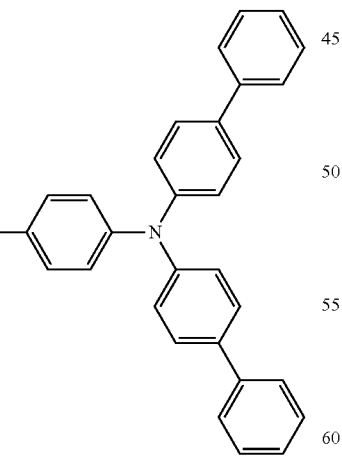

13-17 mixture was stirred under reflux at 100° C. for 24. When reaction was completed, the product was extracted with ether and water. Thereafter, the organic layer was dried with MgSO₄ and concentrated. The concentrate was applied to silica gel column and recrystallized to obtain 12.9 g (yield: 84%) of the product.

Synthesis of Compound 13-32

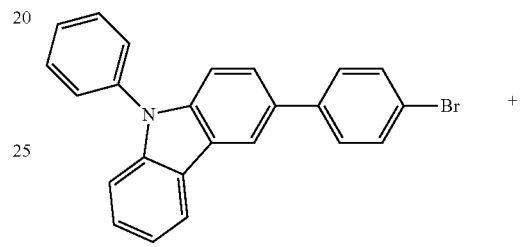

+

$\xrightarrow{\text{Pd}_2(\text{dba})_3/\text{PPh}_3}{\text{NaOt-Bu/Toluene}}$

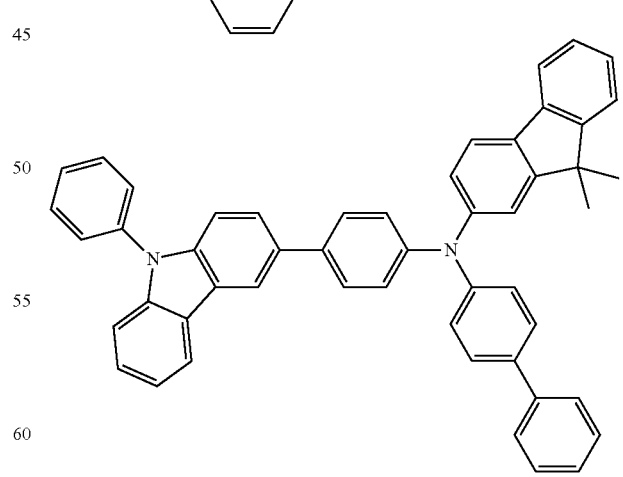

13-32

After 9-(4'-bromo-[1,1'-biphenyl]-4-yl)-9H-carbazole (9.6 g, 24 mmol) was dissolved in toluene, di([1,1'-biphenyl]-4-yl)amine (6.4 g, 20 mmol), Pd₂(dba)₃ (0.05 eq.), PPh₃ (0.1 eq.) and NaOt-Bu (3 eq.) were added thereto and the After 3-(4-bromophenyl)-9-phenyl-9H-carbazole (9.6 g, 24 mmol) was dissolved in toluene, N-([1,1'-biphenyl]-4-yl)-9,9-dimethyl-9H-fluoren-2-amine (7.2 g, 20 mmol), Pd$_2$(dba)$_3$ (0.05 eq.), PPh$_3$ (0.1 eq.) and NaOt-Bu (3 eq.) were added thereto and then 13.8 g (yield: 85%) of the product was obtained by the same method as in synthesis of 13-17.

Synthesis of Compound 14-34

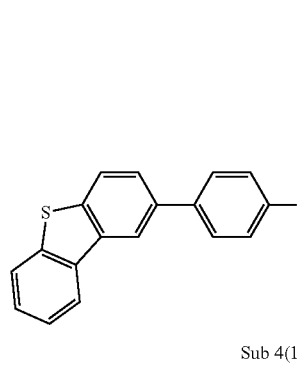

Sub 4(19)

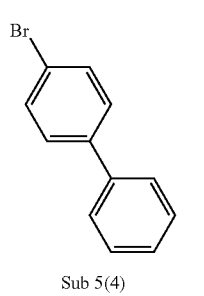

Sub 5(4)

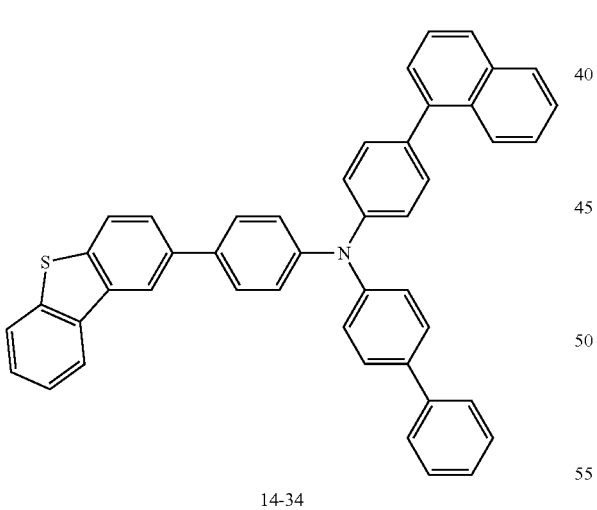

14-34

After Sub 5(4) (4.7 g, 20 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were added to Sub 4(19) (9.5 g, 20 mmol) and the reaction was carried out at 100° C. When reaction was completed, the product was extracted with CH$_2$Cl$_2$ and water. Thereafter, the organic layer was dried with MgSO$_4$ and concentrated. The concentrate was applied to silica gel column and recrystallized to obtain 9.8 g (yield: 78%) of the product.

Synthesis of Compound 14-58

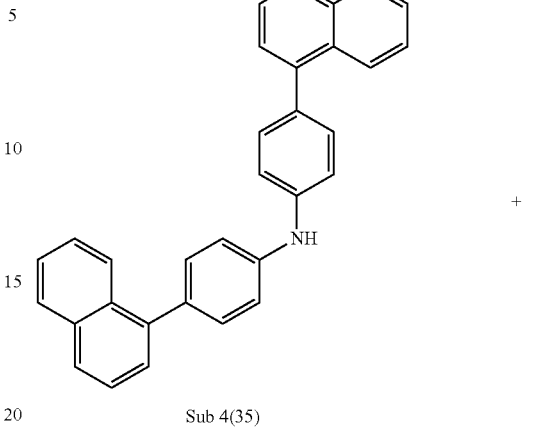

Sub 4(35)

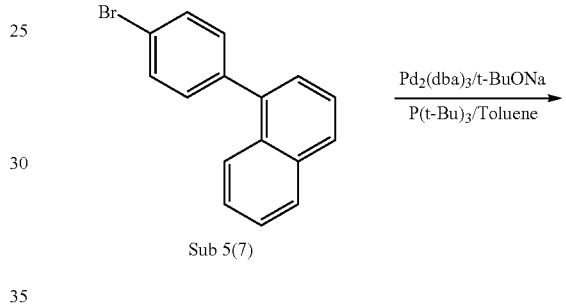

Sub 5(7)

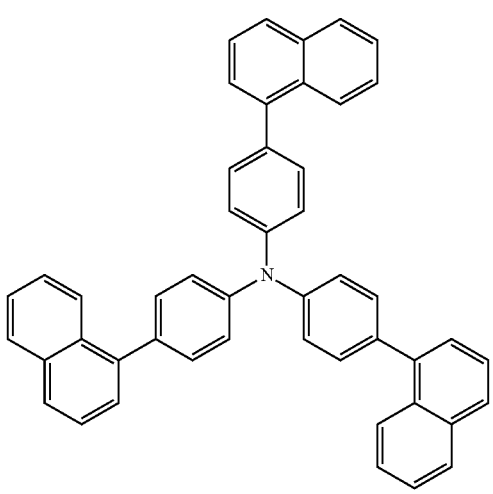

14-58

Sub 5(7) (5.7 g, 20 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were added to Sub 4(35) (8.4 g, 20 mmol), and then 10.4 g (yield: 83%) of the product was obtained by the same method as in synthesis of 14-34.

Synthesis of Compound 14-59

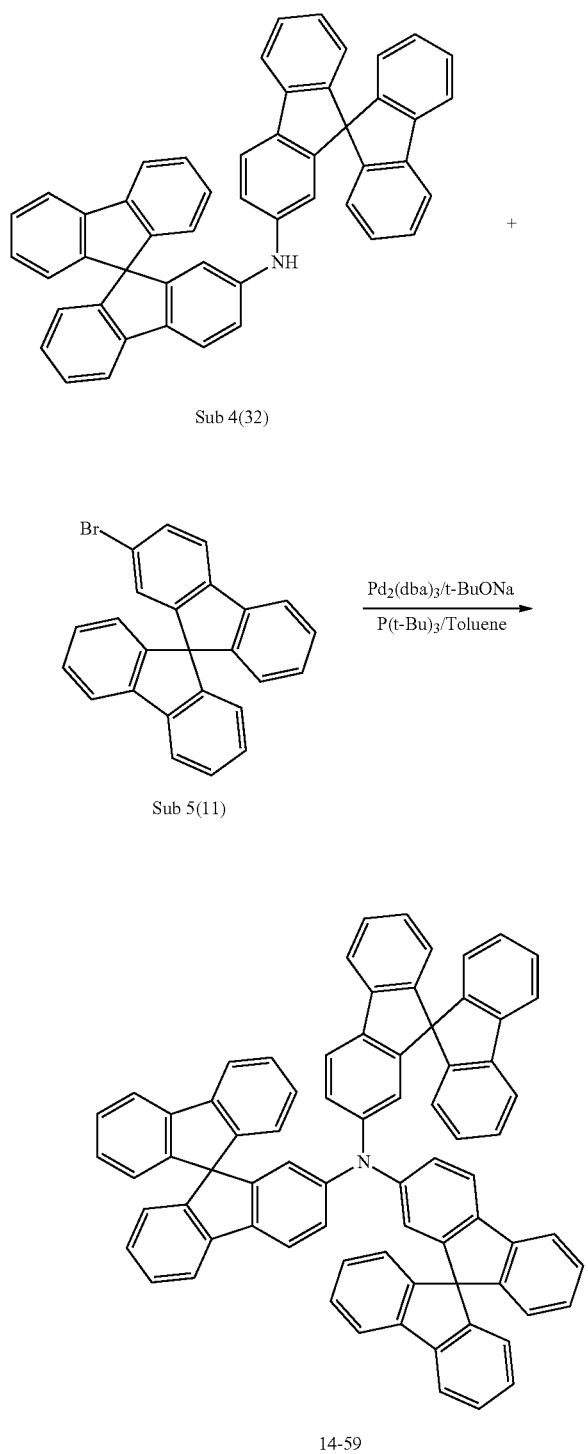

14-59

Sub 5(11) (7.9 g, 20 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were added to Sub 4(32) (12.9 g, 20 mmol), and then 5.2 g (yield: 79%) of the product was obtained by the same method as in synthesis of 14-34.

Synthesis of Compound 14-69

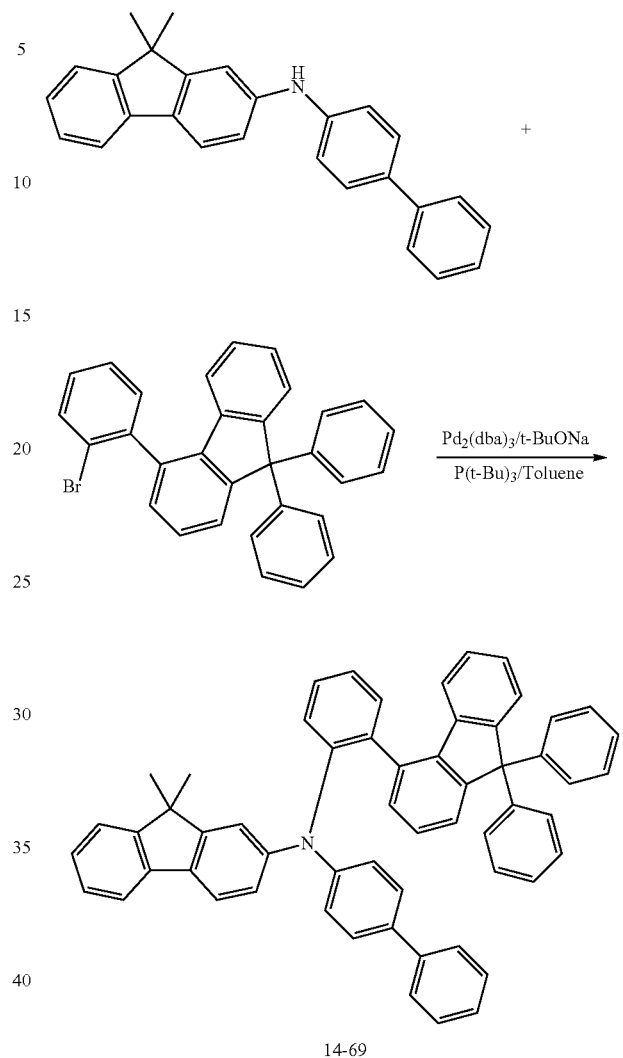

14-69

4-(O-∥p (0.5 g, 0.6 mmol), P(t-Bu)$_3$ (0.2 g, 2 mmol), t-BuONa (5.8 g, 60 mmol) and toluene (300 mL) were added to N-([1,1'-biphenyl]-4-yl)-9,9-dimethyl-9H-fluoren-2-amine (7.2 g, 20 mmol), and then 12.2 g (yield: 81%) of the product was obtained by the same method as in synthesis of 14-34.

Synthesis of Compound 14-71

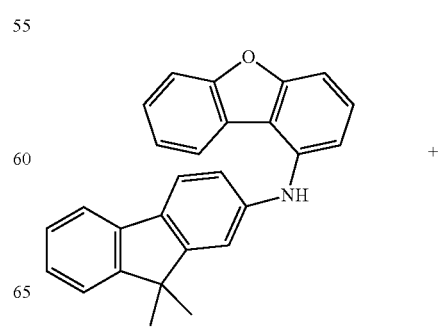

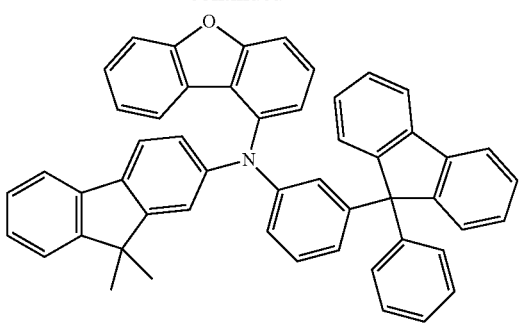

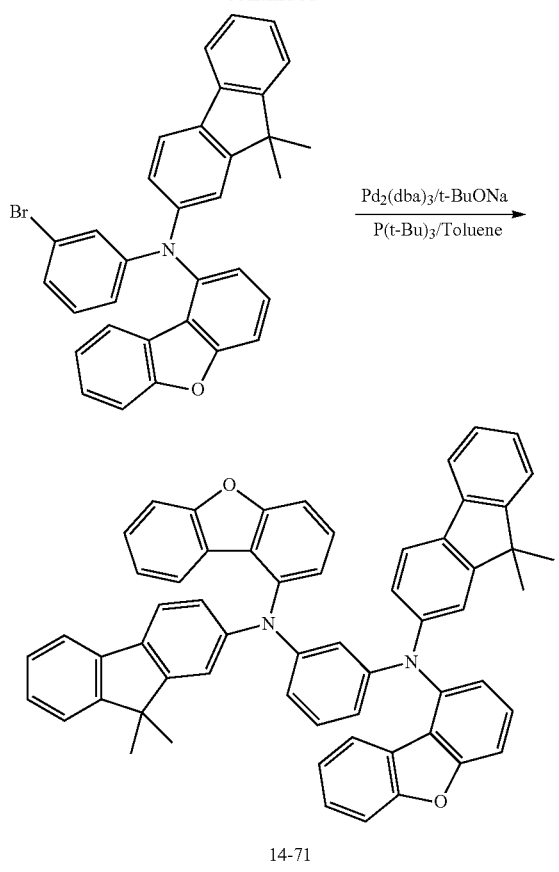

14-71

N-(3-bromophenyl)-N-(9,9-dimethyl-9H-fluoren-2-yl)dibenzo[b,d]furan-1-amine (10.6 g, 20 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were added to N-(9,9-dimethyl-9H-fluoren-2-yl)dibenzo[b,d]furan-1-amine (7.5 g, 20 mmol), and then 12.9 g (yield: 78%) of the product was obtained by the same method as in synthesis of 14-34.

Synthesis of Compound 14-72

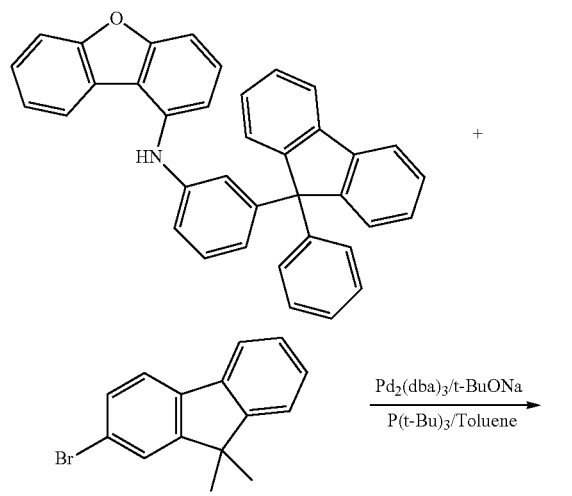

14-72

2-bromo-9,9-dimethyl-9H-fluorene (5.5 g, 20 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were added to N-(3-(9-phenyl-9H-fluoren-9-yl)phenyl)dibenzo[b,d]furan-1-amine (10.0 g, 20 mmol), and then 11.1 g (yield: 80%) of the product was obtained by the same method as in synthesis of 14-34.

Synthesis Example 4

As shown in Reaction Scheme 5 below, the compound represented by Formula A according to the present invention can be synthesized by reacting Sub a with Sub b, but there is no limitation thereto.

<Reaction Scheme 5>

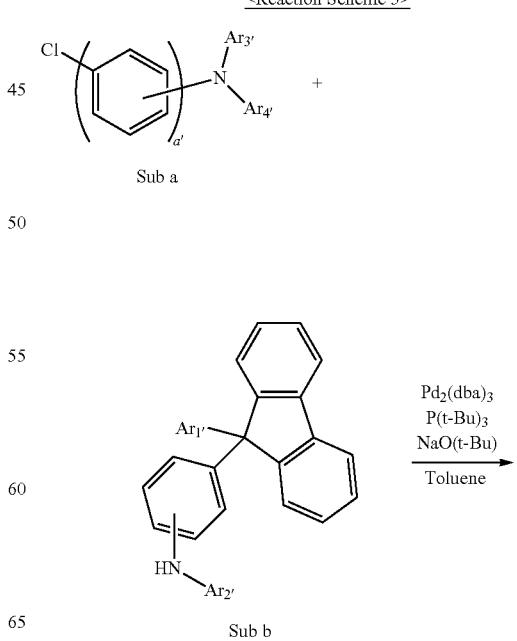

Sub a

Sub b

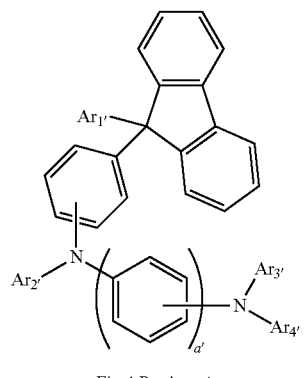

Final Product A

Synthesis Example of Sub a

Sub a of the Reaction Scheme 5 can be synthesized according to the reaction route of the following Reaction Scheme 5-1, but there is no limitation thereto.

<Reaction Scheme 5-1>

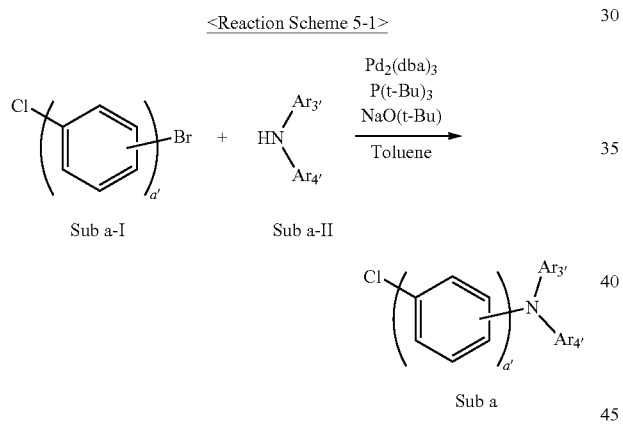

Synthesis of Sub a-3

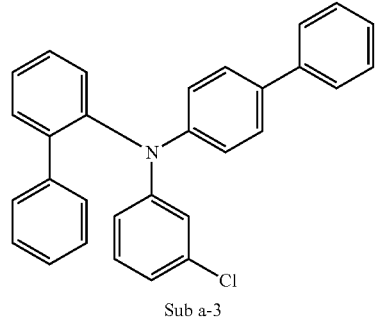

Sub a-3

1-bromo-3-chlorobenzene (50 g, 261.2 mmol), N-([1,1'-biphenyl]-4-yl)-[1,1'-biphenyl]-2-amine (125.92 g, 391.7 mmol), $Pd_2(dba)_3$ (7.17 g, 7.8 mmol), P(t-Bu)$_3$ (4.23 g, 20.9 mmol), NaO(t-Bu) (75.30 g, 783.5 mmol) and toluene (3200 mL) were placed in a round bottom flask and then the mixture was heated under reflux at 80° C. for 4 hours.

When the reaction is completed, the resultant was diluted with distilled water at room temperature and was extracted with $CH_2Cl_2$ and water. Thereafter, the organic layer was dried with $MgSO_4$ and concentrated. The concentrate was recrystallized with methylene chloride and hexane to obtain Sub a-3 (93.63 g, 83%) of the product.

Synthesis of Sub a-29

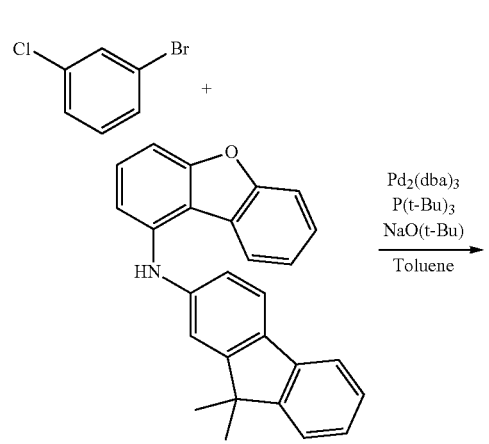

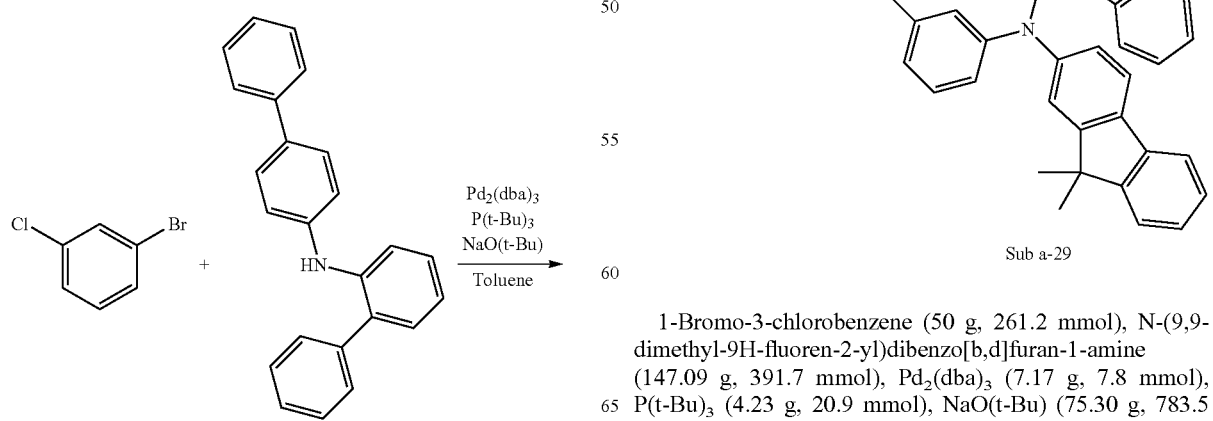

Sub a-29

1-Bromo-3-chlorobenzene (50 g, 261.2 mmol), N-(9,9-dimethyl-9H-fluoren-2-yl)dibenzo[b,d]furan-1-amine (147.09 g, 391.7 mmol), $Pd_2(dba)_3$ (7.17 g, 7.8 mmol), P(t-Bu)$_3$ (4.23 g, 20.9 mmol), NaO(t-Bu) (75.30 g, 783.5 mmol) and toluene (3200 mL) were placed in a round bottom flask and then the mixture was heated under reflux at 80° C. for 4 hours. When the reaction is completed, the resultant was diluted with distilled water at room temperature and was extracted with CH$_2$Cl$_2$ and water. Thereafter, the organic layer was dried with MgSO$_4$ and concentrated. The concentrate was recrystallized with methylene chloride and hexane to obtain Sub a-29 (107.89 g, 85%) of the product.

Synthesis of Sub a-39

The concentrate was recrystallized with methylene chloride and hexane to obtain Sub a-39 (87.19 g, 83%) of the product.

The example of the compound belonging to Sub a may be, but not limited to, the following compounds, and Table 5 shows FD-MS values of the following compounds.

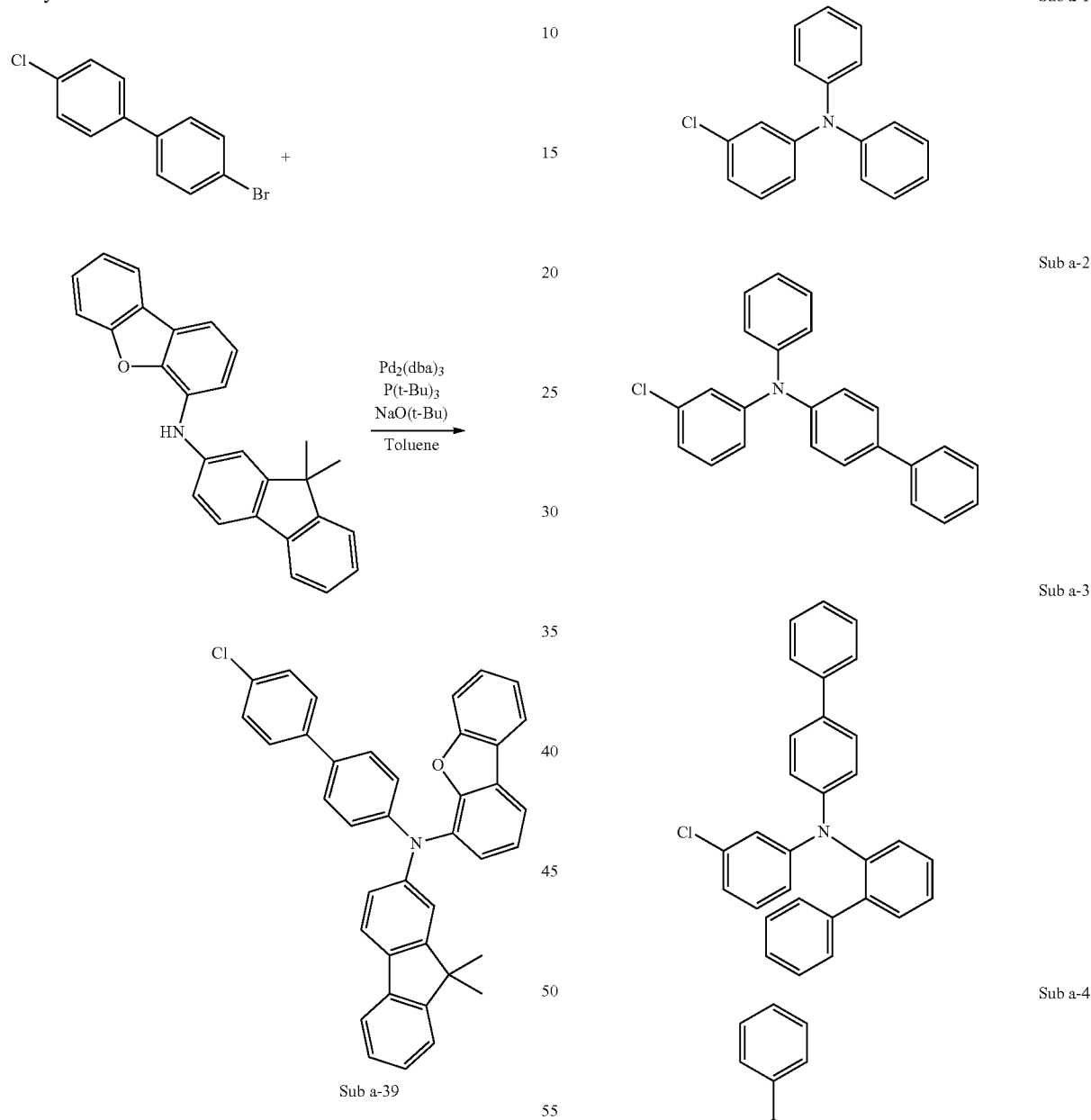

4-Bromo-4'-chloro-1,1'-biphenyl (50 g, 186.9 mmol), N-(9,9-dimethyl-9H-fluoren-2-yl)dibenzo[b,d]furan-4-amine (105.25 g, 280.3 mmol), Pd$_2$(dba)$_3$ (5.13 g, 5.6 mmol), P(t-Bu)$_3$ (3.02 g, 15.0 mmol), NaO(t-Bu) (53.88 g, 560.6 mmol) and toluene (2300 mL) were placed in a round bottom flask and then the mixture was heated under reflux at 80° C. for 4 hours. When the reaction is completed, the resultant was diluted with distilled water at room temperature and was extracted with CH$_2$Cl$_2$ and water. Thereafter, the organic layer was dried with MgSO$_4$ and concentrated.

Sub a-5
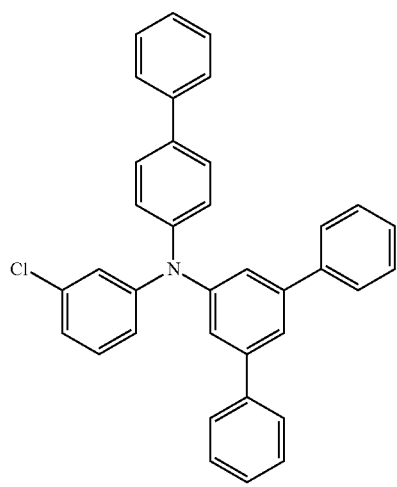
Sub a-6
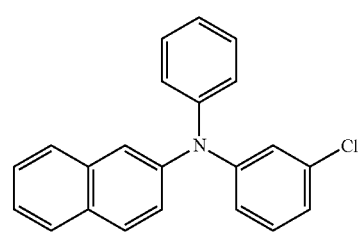
Sub a-7
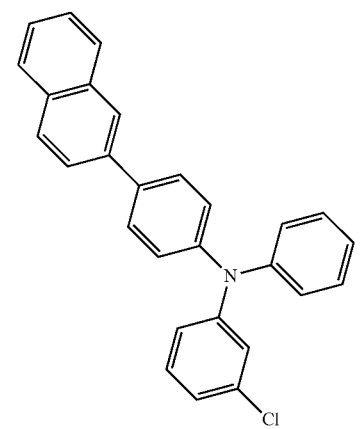
Sub a-8
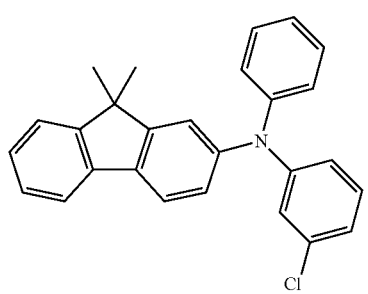
Sub a-9
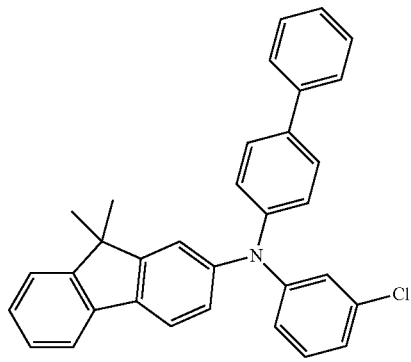
Sub a-10
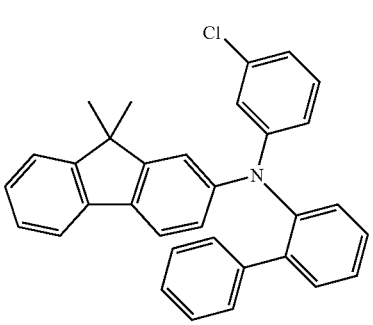
Sub a-11
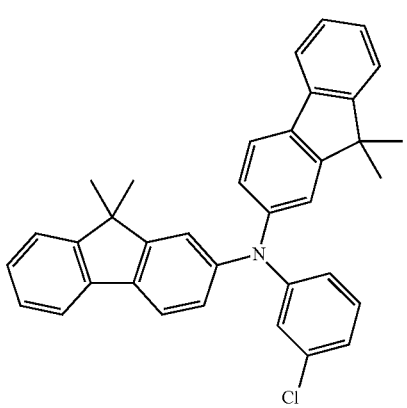
Sub a-12
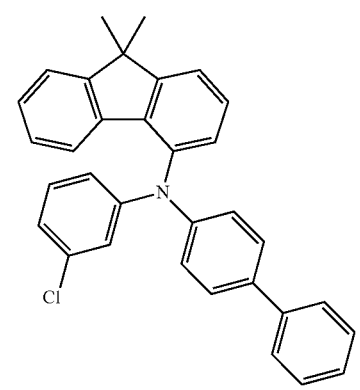

-continued
Sub a-13
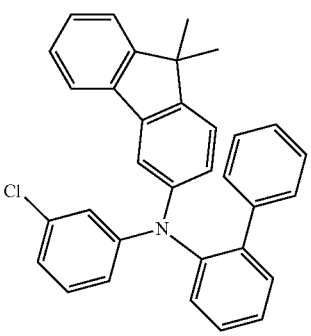
Sub a-14
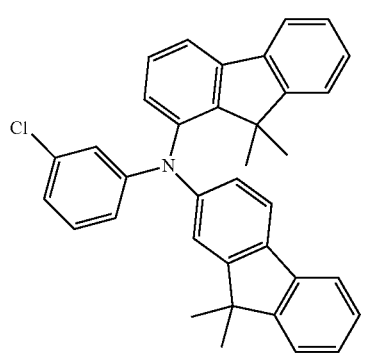
Sub a-15
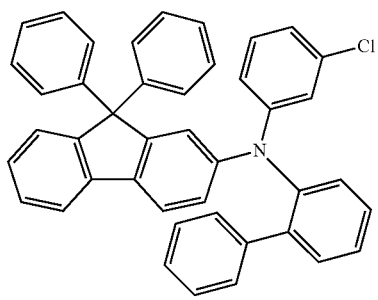
Sub a-16
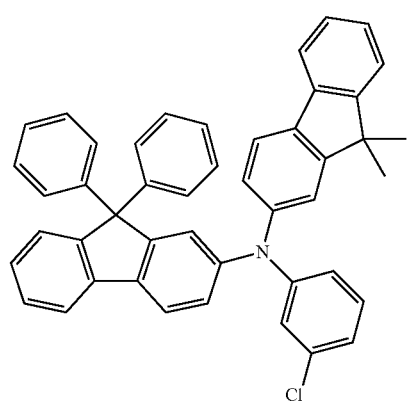
-continued
Sub a-17
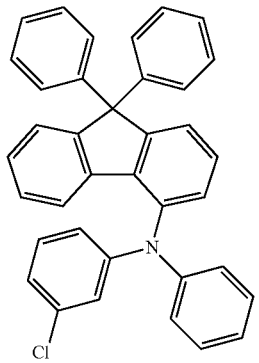
Sub a-18
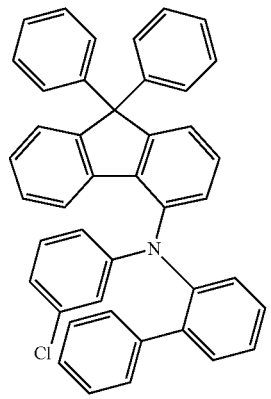
Sub a-19
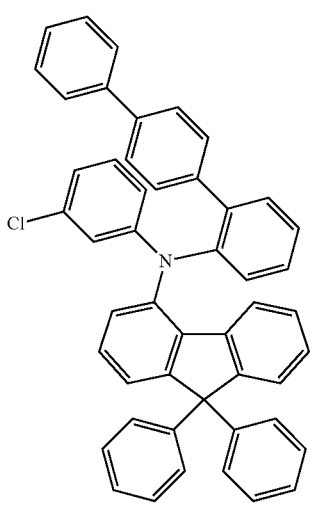
Sub a-20
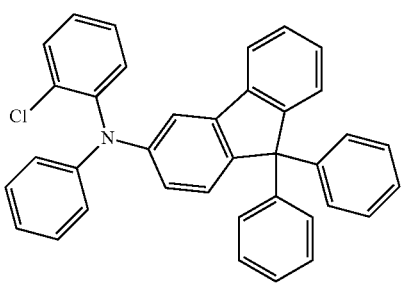

Sub a-21
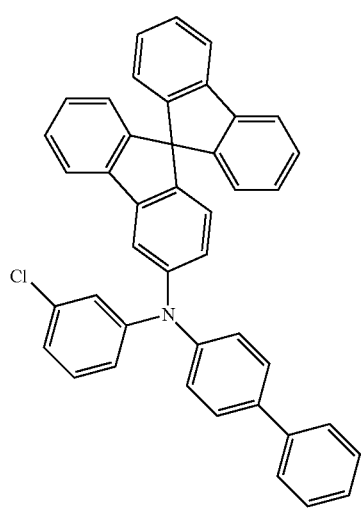
Sub a-22
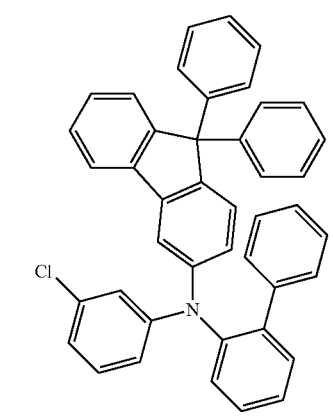
Sub a-23
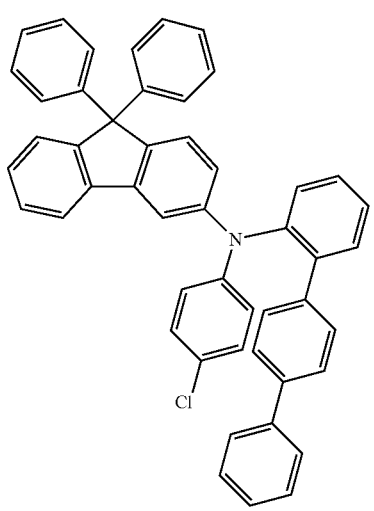
Sub a-24
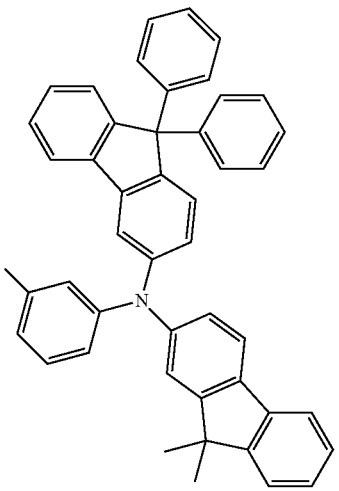
Sub a-25
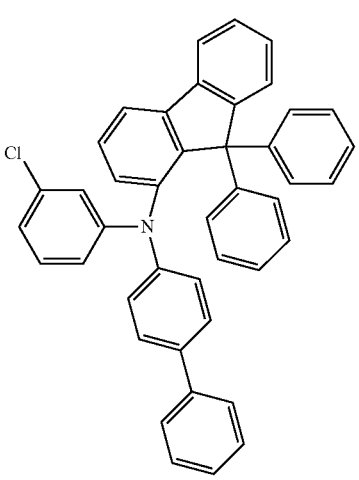
Sub a-26
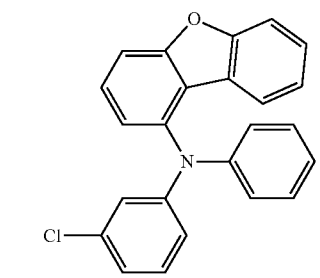
Sub a-27
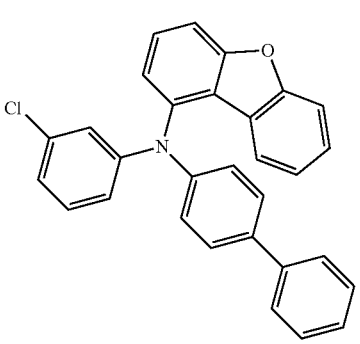

Sub a-28
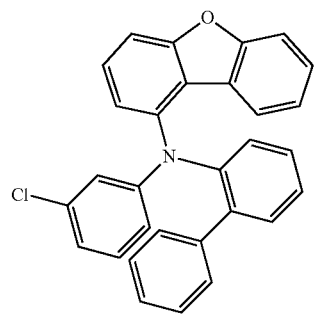
Sub a-29
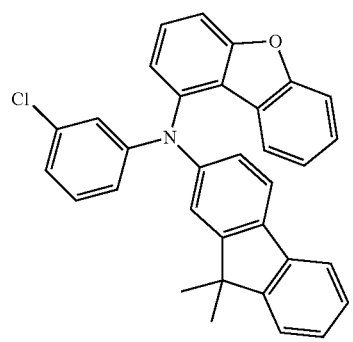
Sub a-30
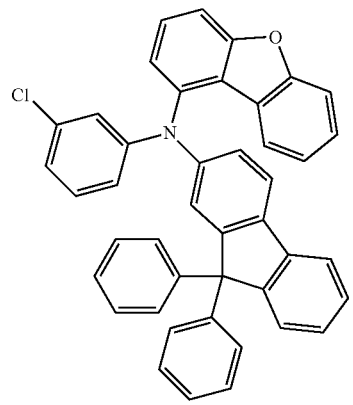
Sub a-31
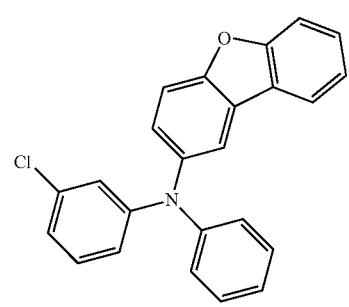
Sub a-32
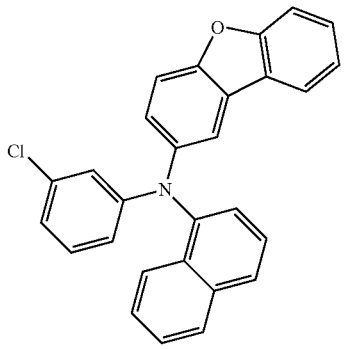
Sub a-33
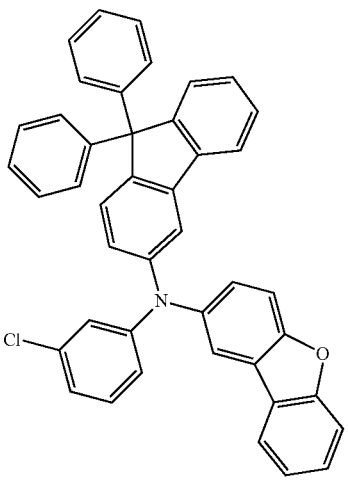
Sub a-34
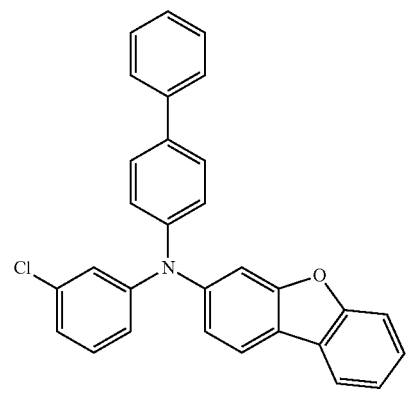
Sub a-35
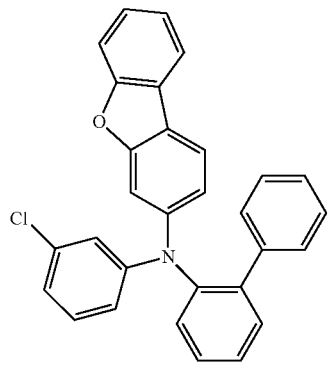

Sub a-36
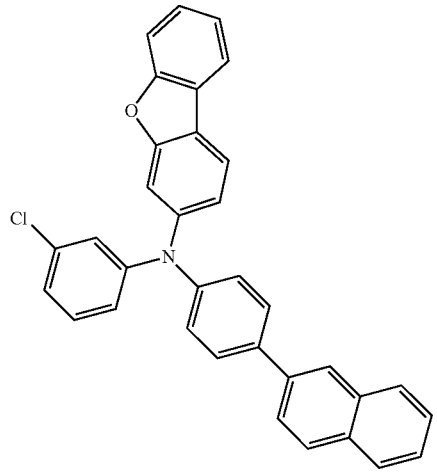
Sub a-37
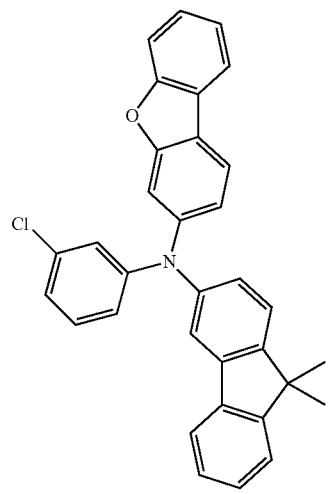
Sub a-38
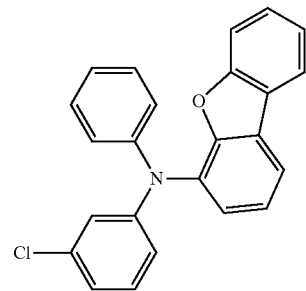
Sub a-39
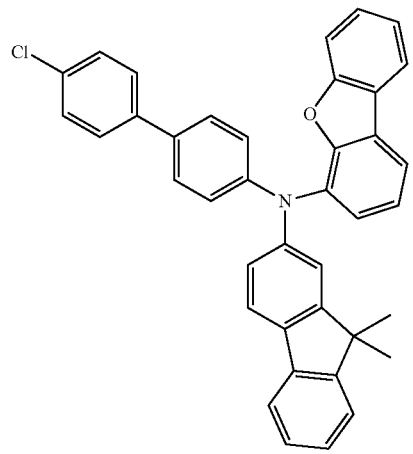
Sub a-40
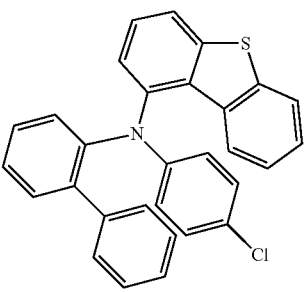
Sub a-41
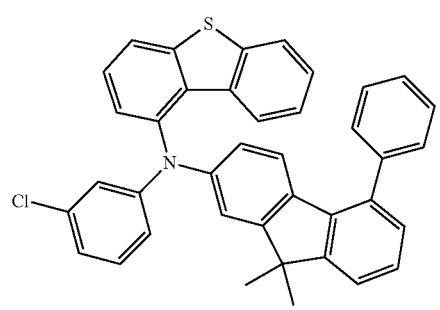
Sub a-42
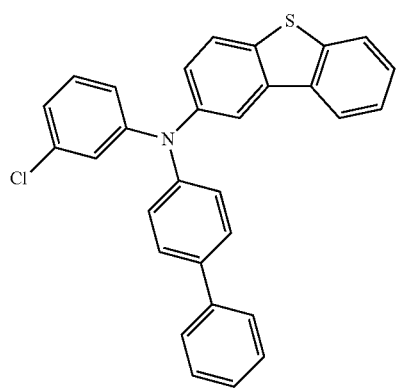

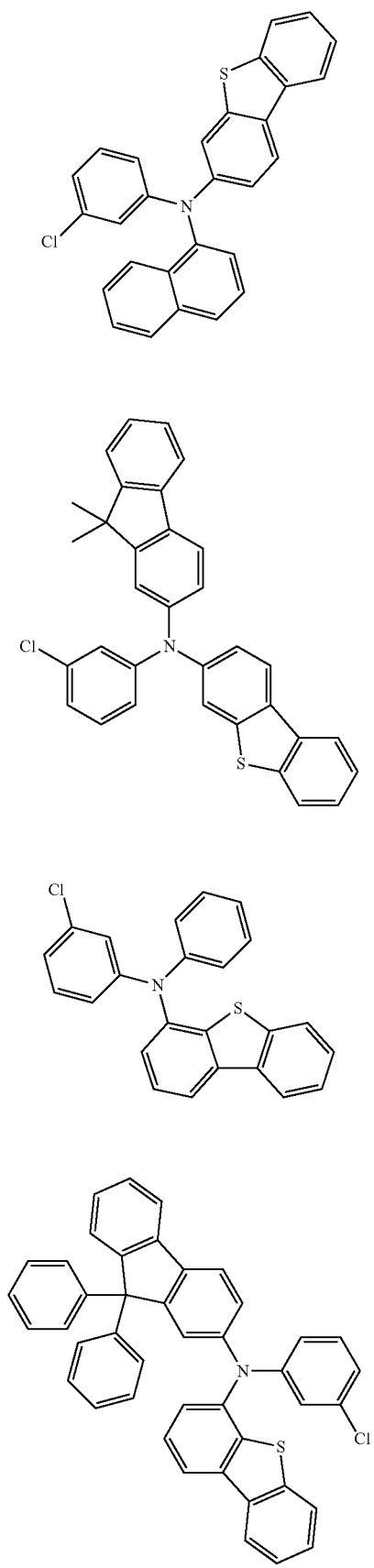
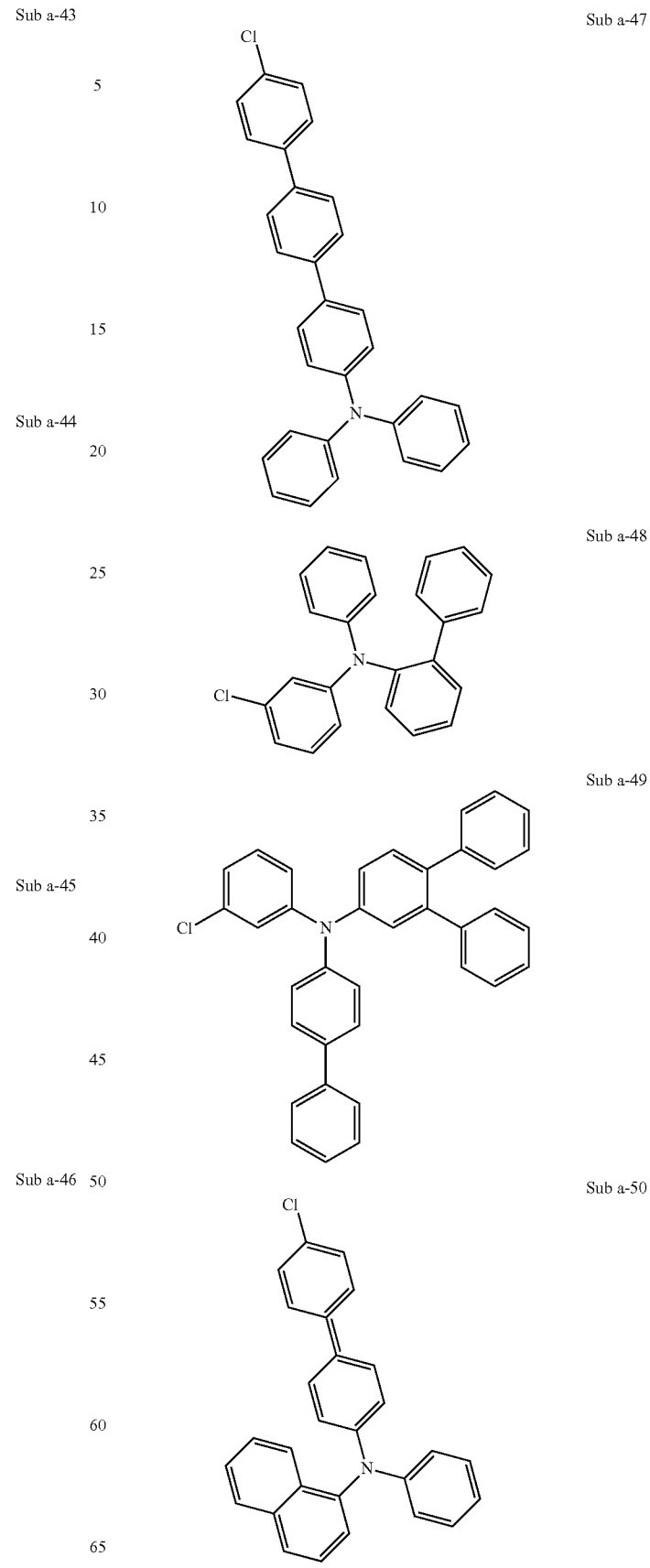

Sub a-51
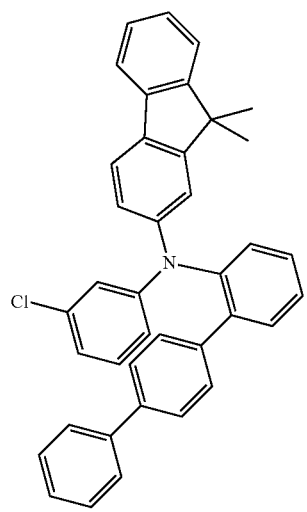
Sub a-52
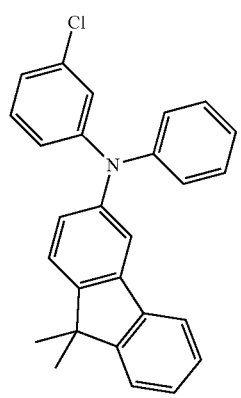
Sub a-53
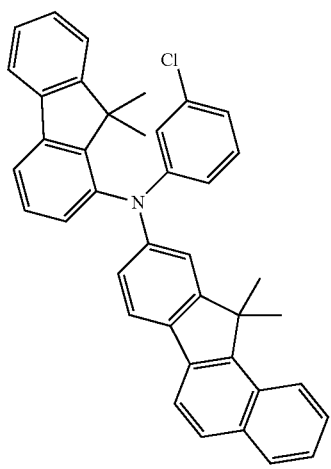
Sub a-54
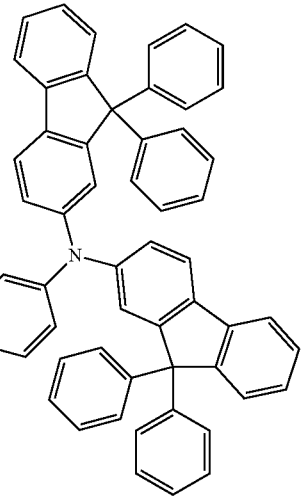
Sub a-55
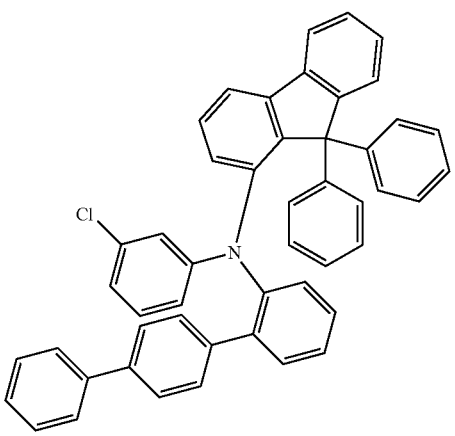
Sub a-56
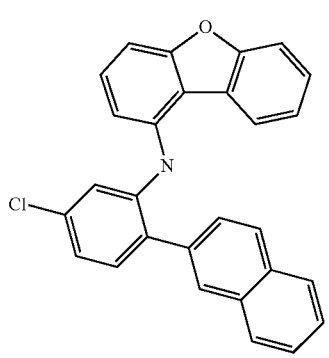

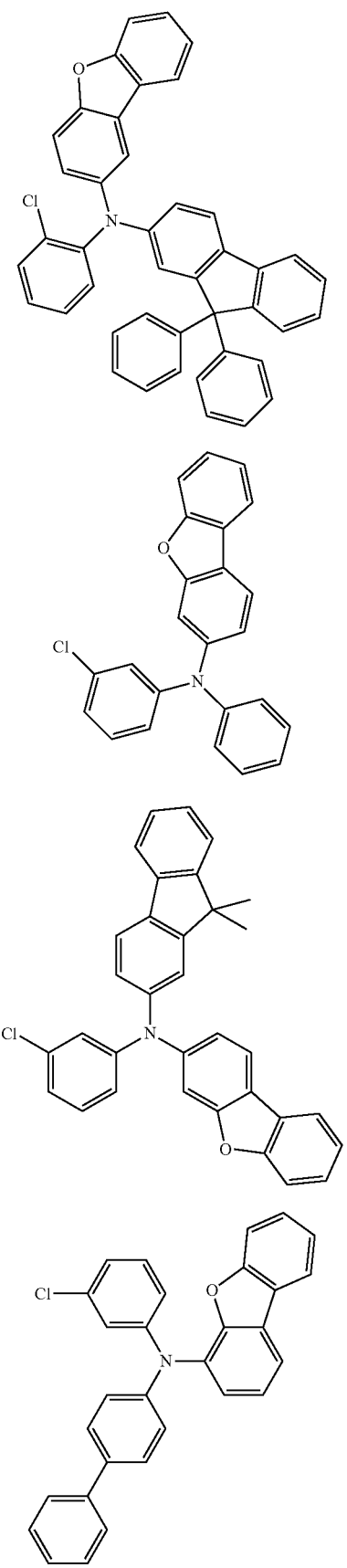
Sub a-57
Sub a-58
Sub a-59
Sub a-60
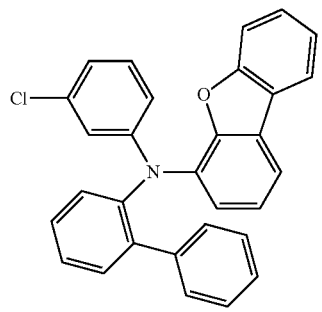
Sub a-61
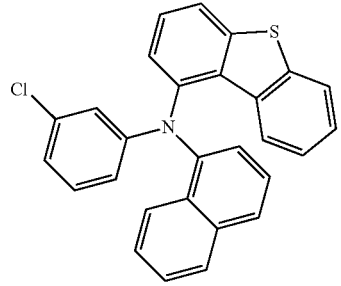
Sub a-62
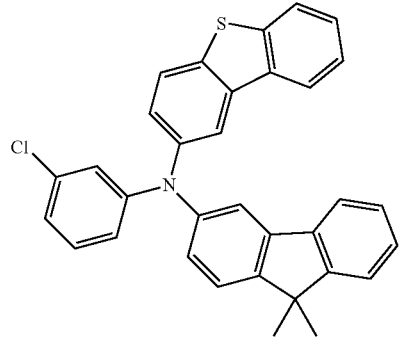
Sub a-63
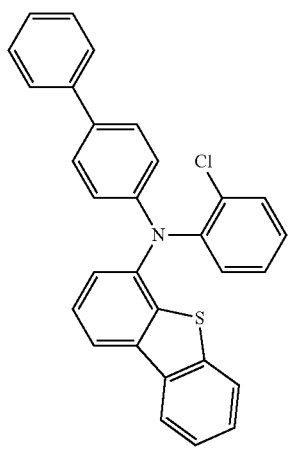
Sub a-64

Sub a-65
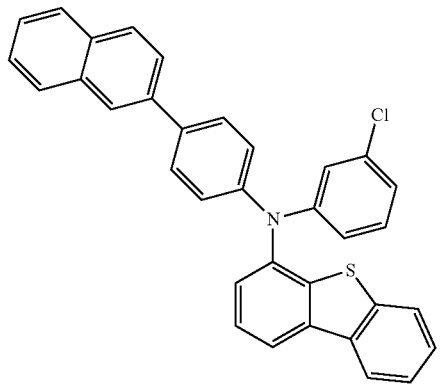
Sub a-66
Sub a-67
Sub a-68
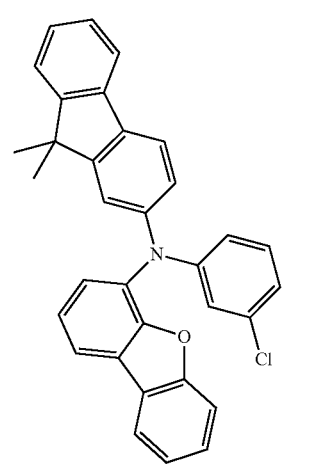
Sub a-69
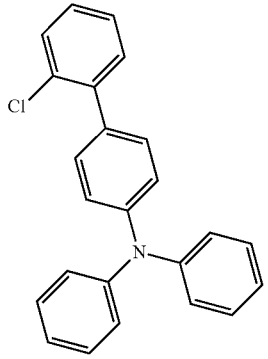
Sub a-70
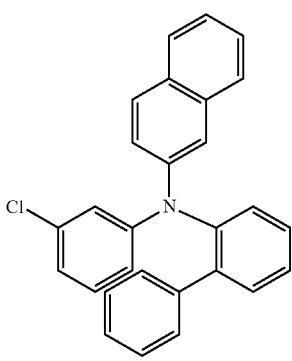
Sub a-71
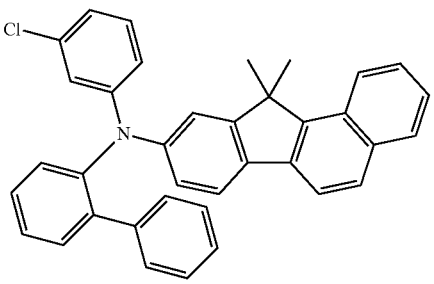
Sub a-72
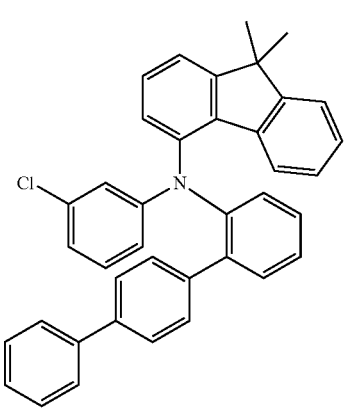

Sub a-73
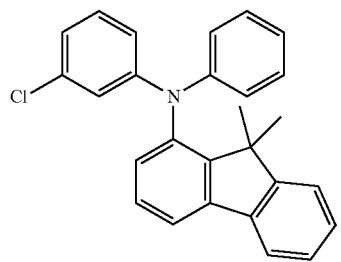
Sub a-77
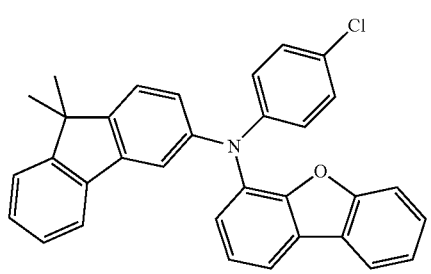
Sub a-74
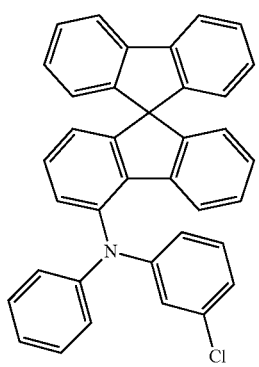
Sub a-78
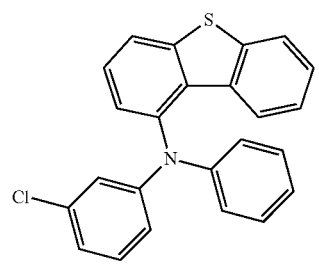
Sub a-75
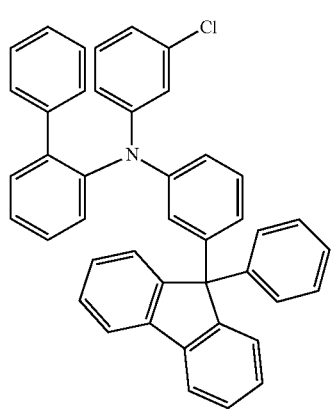
Sub a-79
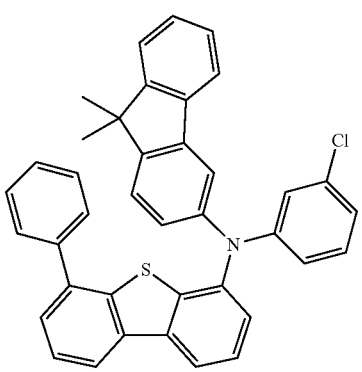
Sub a-80
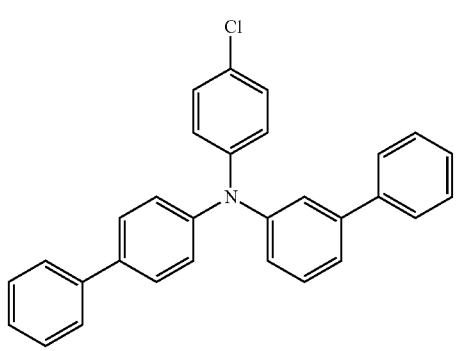
Sub a-76
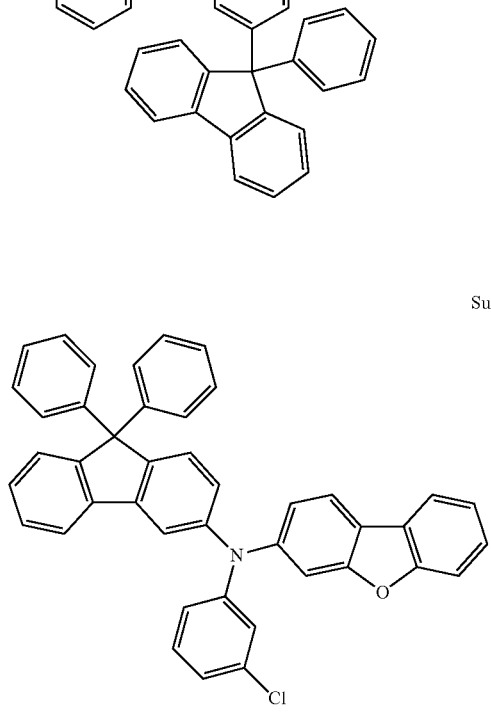
Sub a-81
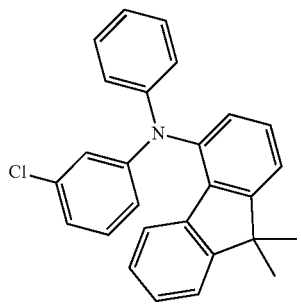

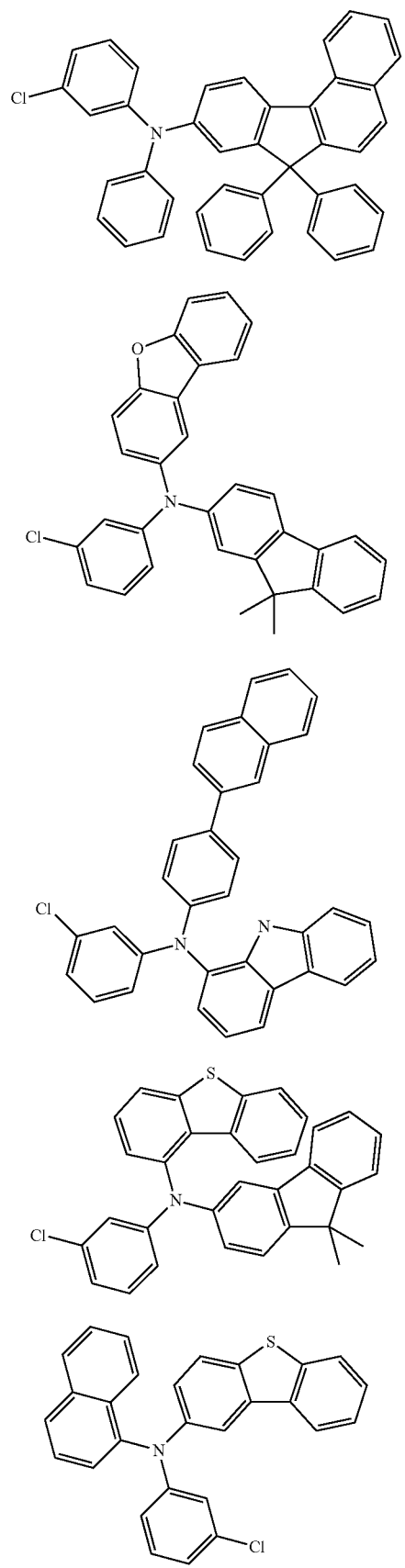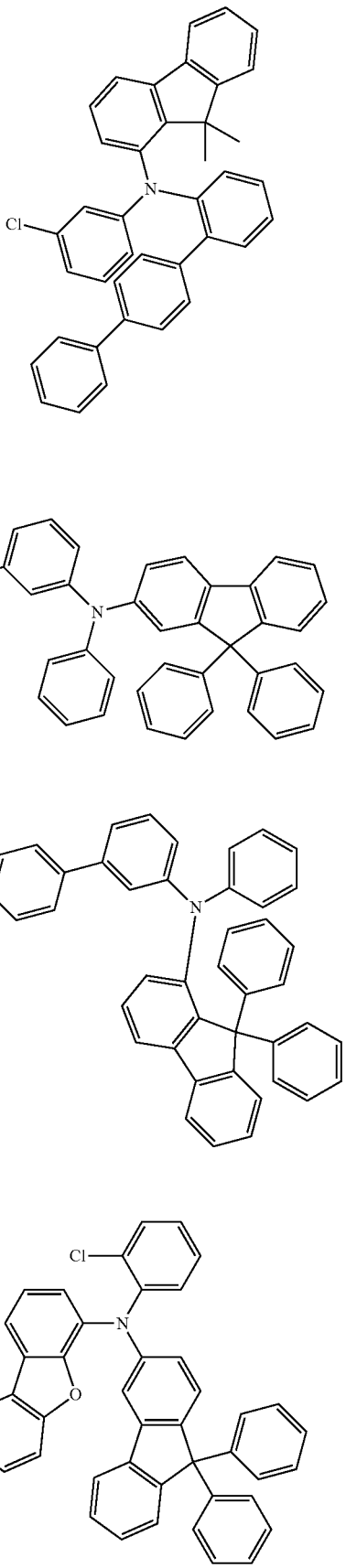

Sub a-91
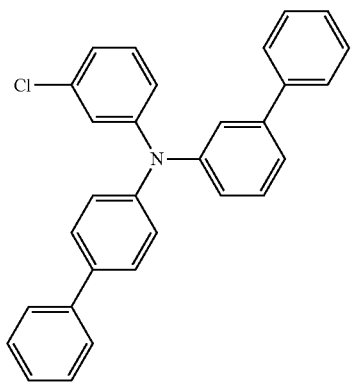
Sub a-92
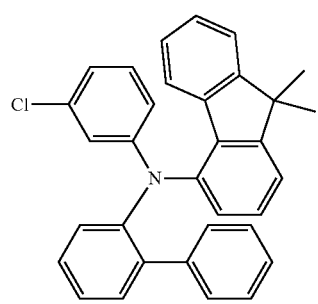
Sub a-93
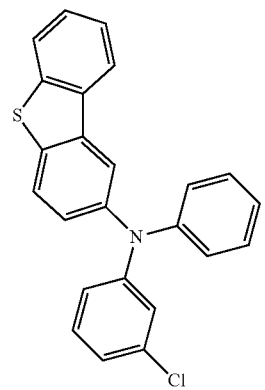
Sub a-94
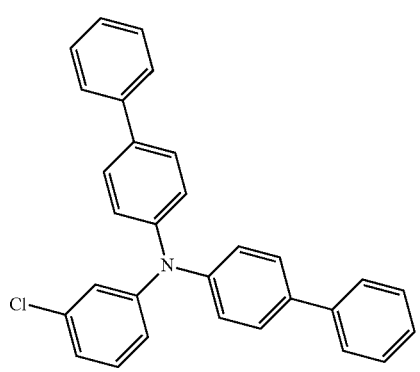
Sub a-95
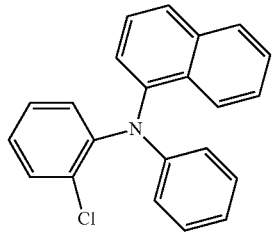
Sub a-96
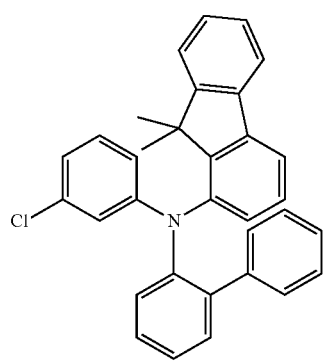
Sub a-97
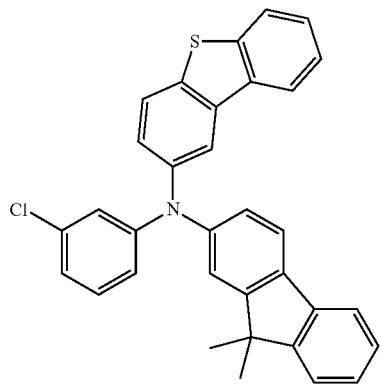
Sub a-98
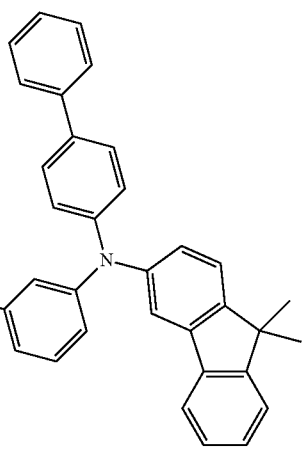

Sub a-99
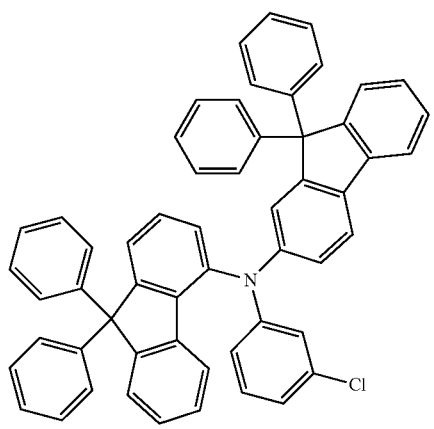
Sub a-100
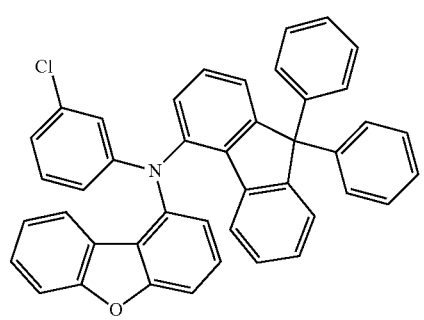
Sub a-101
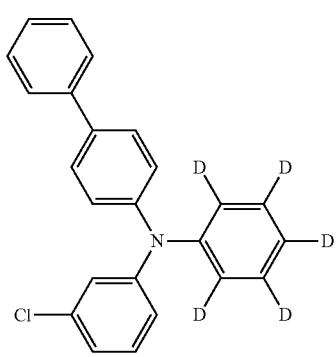
Sub a-102
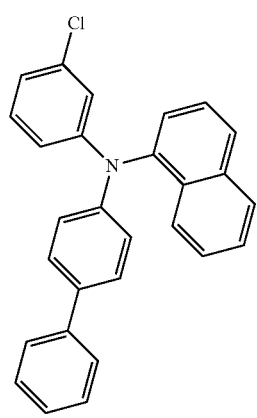
Sub a-103
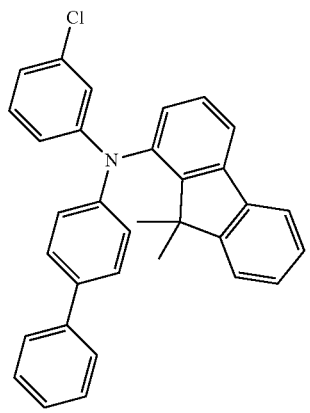
Sub a-104
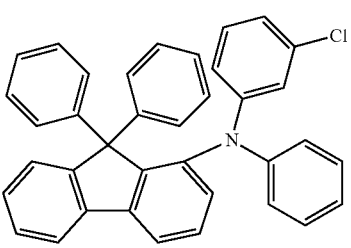
Sub a-105
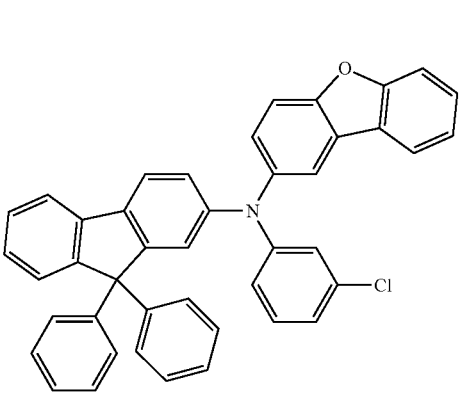
Sub a-106
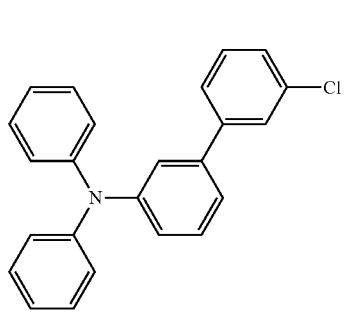

Sub a-107
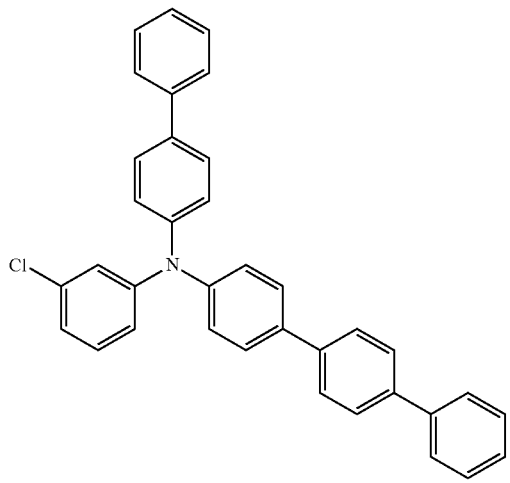
Sub a-108
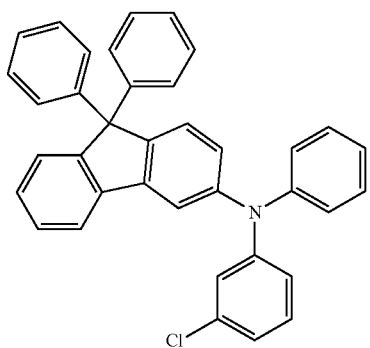
Sub a-109
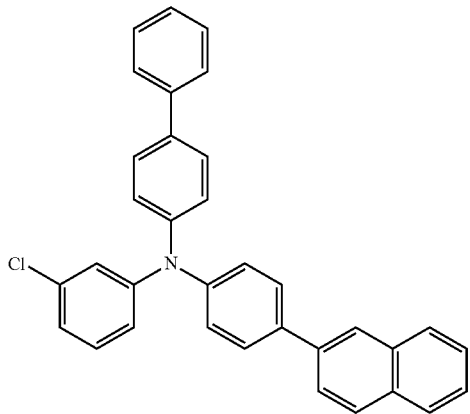
Sub a-110
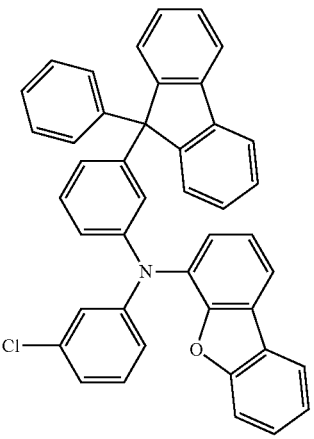
Sub a-111
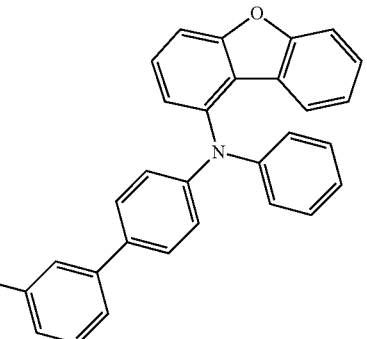
Sub a-112
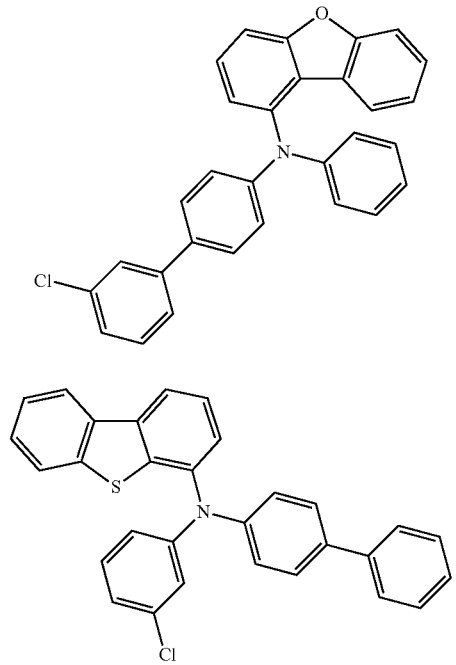
Sub a-113
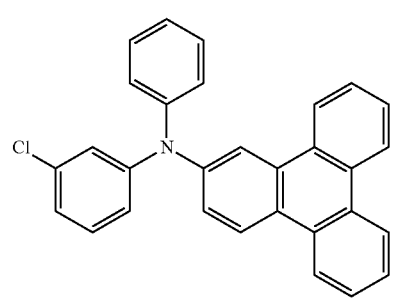
Sub a-114
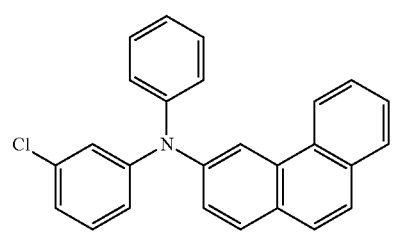

Sub a-115

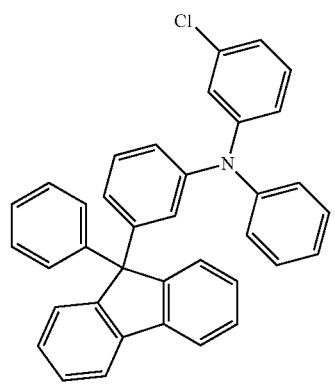

Sub a-116

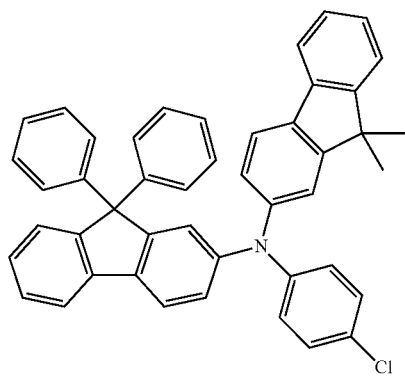

Sub a-117

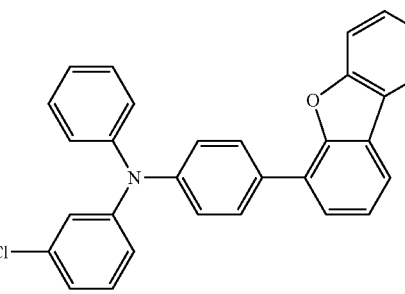

Sub a-118

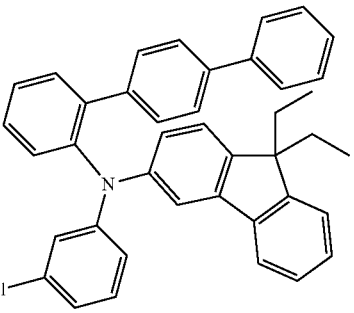

Sub a-119

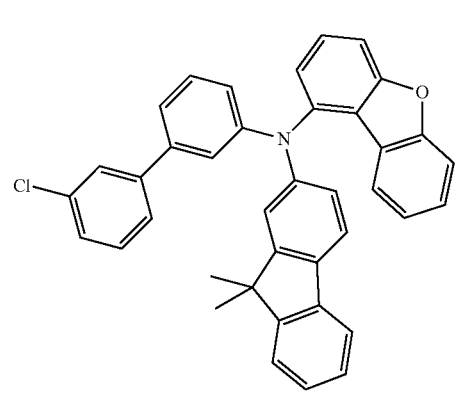

TABLE 5

| Compound | FD-MS | Compound | FD-MS |
|---|---|---|---|
| Sub a-1 | m/z = 279.08 ($C_{18}H_{14}ClN$ = 279.77) | Sub a-2 | m/z = 355.11 ($C_{24}H_{18}ClN$ = 355.87) |
| Sub a-3 | m/z = 431.14 ($C_{30}H_{22}ClN$ = 431.96) | Sub a-4 | m/z = 507.18 ($C_{36}H_{26}ClN$ = 508.06) |
| Sub a-5 | m/z = 507.18 ($C_{36}H_{26}ClN$ = 508.06) | Sub a-6 | m/z = 329.10 ($C_{22}H_{16}ClN$ = 329.83) |
| Sub a-7 | m/z = 405.13 ($C_{28}H_{20}ClN$ = 405.93) | Sub a-8 | m/z = 395.14 ($C_{27}H_{22}ClN$ = 395.93) |
| Sub a-9 | m/z = 471.18 ($C_{33}H_{26}ClN$ = 472.03) | Sub a-10 | m/z = 471.18 ($C_{33}H_{26}ClN$ = 472.03) |
| Sub a-11 | m/z = 511.21 ($C_{36}H_{30}ClN$ = 512.09) | Sub a-12 | m/z = 471.18 ($C_{33}H_{26}ClN$ = 472.03) |
| Sub a-13 | m/z = 471.18 ($C_{33}H_{26}ClN$ = 472.03) | Sub a-14 | m/z = 511.21 ($C_{36}H_{30}ClN$ = 512.09) |
| Sub a-15 | m/z = 595.21 ($C_{43}H_{30}ClN$ = 596.17) | Sub a-16 | m/z = 635.24 ($C_{46}H_{34}ClN$ = 636.24) |
| Sub a-17 | m/z = 519.18 ($C_{37}H_{26}ClN$ = 520.07) | Sub a-18 | m/z = 595.21 ($C_{43}H_{30}ClN$ = 596.17) |
| Sub a-19 | m/z = 671.24 ($C_{49}H_{34}ClN$ = 672.27) | Sub a-20 | m/z = 519.18 ($C_{37}H_{26}ClN$ = 520.07) |
| Sub a-21 | m/z = 593.19 ($C_{43}H_{28}ClN$ = 594.15) | Sub a-22 | m/z = 595.21 ($C_{43}H_{30}ClN$ = 596.17) |
| Sub a-23 | m/z = 671.24 ($C_{49}H_{34}ClN$ = 672.27) | Sub a-24 | m/z = 635.24 ($C_{46}H_{34}ClN$ = 636.24) |
| Sub a-25 | m/z = 595.21 ($C_{43}H_{30}ClN$ = 596.17) | Sub a-26 | m/z = 369.09 ($C_{24}H_{16}ClNO$ = 369.85) |
| Sub a-27 | m/z = 445.12 ($C_{30}H_{20}ClNO$ = 445.95) | Sub a-28 | m/z = 445.12 ($C_{30}H_{20}ClNO$ = 445.95) |
| Sub a-29 | m/z = 485.15 ($C_{33}H_{24}ClNO$ = 486.01) | Sub a-30 | m/z = 609.19 ($C_{43}H_{28}ClNO$ = 610.15) |
| Sub a-31 | m/z = 369.09 ($C_{24}H_{16}ClNO$ = 369.85) | Sub a-32 | m/z = 419.11 ($C_{28}H_{18}ClNO$ = 419.91) |
| Sub a-33 | m/z = 609.19 ($C_{43}H_{28}ClNO$ = 610.15) | Sub a-34 | m/z = 445.12 ($C_{30}H_{20}ClNO$ = 445.95) |
| Sub a-35 | m/z = 445.12 ($C_{30}H_{20}ClNO$ = 445.95) | Sub a-36 | m/z = 495.14 ($C_{34}H_{22}ClNO$ = 496.01) |
| Sub a-37 | m/z = 485.15 ($C_{33}H_{24}ClNO$ = 486.01) | Sub a-38 | m/z = 369.09 ($C_{24}H_{16}ClNO$ = 369.85) |
| Sub a-39 | m/z = 561.1 ($C_{39}H_{28}ClNO$ = 562.11) | Sub a-40 | m/z = 461.10 ($C_{30}H_{20}ClNS$ = 462.01) |
| Sub a-41 | m/z = 577.16 ($C_{39}H_{28}ClNS$ = 578.17) | Sub a-42 | m/z = 461.10 ($C_{30}H_{20}ClNS$ = 462.01) |

TABLE 5-continued

| Compound | FD-MS | Compound | FD-MS |
|---|---|---|---|
| Sub a-43 | m/z = 435.08 ($C_{28}H_{18}ClNS$ = 435.97) | Sub a-44 | m/z = 501.13 ($C_{33}H_{24}ClNS$ = 502.07) |
| Sub a-45 | m/z = 385.07 ($C_{24}H_{16}ClNS$ = 385.91) | Sub a-46 | m/z = 625.16 ($C_{43}H_{28}ClNS$ = 626.21) |
| Sub a-47 | m/z = 431.14 ($C_{30}H_{22}ClN$ = 431.96) | Sub a-48 | m/z = 355.11 ($C_{24}H_{18}ClN$ = 355.87) |
| Sub a-49 | m/z = 507.18 ($C_{36}H_{26}ClN$ = 508.06) | Sub a-50 | m/z = 405.13 ($C_{28}H_{20}ClN$ = 405.93) |
| Sub a-51 | m/z = 547.21 ($C_{39}H_{30}ClN$ = 548.13) | Sub a-52 | m/z = 395.14 ($C_{27}H_{22}ClN$ = 395.93) |
| Sub a-53 | m/z = 561.22 ($C_{40}H_{32}ClN$ = 562.15) | Sub a-54 | m/z = 759.27 ($C_{56}H_{38}ClN$ = 760.38) |
| Sub a-55 | m/z = 671.24 ($C_{49}H_{34}ClN$ = 672.27) | Sub a-56 | m/z = 419.11 ($C_{28}H_{18}ClNO$ = 419.91) |
| Sub a-57 | m/z = 609.19 ($C_{43}H_{28}ClNO$ = 610.15) | Sub a-58 | m/z = 369.09 ($C_{24}H_{16}ClNO$ = 369.85) |
| Sub a-59 | m/z = 485.15 ($C_{33}H_{24}ClNO$ = 486.01) | Sub a-60 | m/z = 445.12 ($C_{30}H_{20}ClNO$ = 445.95) |
| Sub a-61 | m/z = 445.12 ($C_{30}H_{20}ClNO$ = 445.95) | Sub a-62 | m/z = 435.08 ($C_{28}H_{18}ClNS$ = 435.97) |
| Sub a-63 | m/z = 501.13 ($C_{33}H_{24}ClNS$ = 502.07) | Sub a-64 | m/z = 461.10 ($C_{30}H_{20}ClNS$ = 462.01) |
| Sub a-65 | m/z = 511.12 ($C_{34}H_{22}ClNS$ = 512.07) | Sub a-66 | m/z = 431.14 ($C_{30}H_{22}ClN$ = 431.96) |
| Sub a-67 | m/z = 569.19 ($C_{41}H_{28}ClN$ = 570.13) | Sub a-68 | m/z = 485.15 ($C_{33}H_{24}ClNO$ = 486.01) |
| Sub a-69 | m/z = 355.11 ($C_{24}H_{18}ClN$ = 355.87) | Sub a-70 | m/z = 405.13 ($C_{28}H_{20}ClN$ = 405.93) |
| Sub a-71 | m/z = 521.19 ($C_{37}H_{28}ClN$ = 522.09) | Sub a-72 | m/z = 547.21 ($C_{39}H_{30}ClN$ = 548.13) |
| Sub a-73 | m/z = 395.14 ($C_{27}H_{22}ClN$ = 395.93) | Sub a-74 | m/z = 517.16 ($C_{37}H_{24}ClN$ = 518.06) |
| Sub a-75 | m/z = 595.21 ($C_{43}H_{30}ClN$ = 596.17) | Sub a-76 | m/z = 609.19 ($C_{43}H_{28}ClNO$ = 610.15) |
| Sub a-77 | m/z = 485.15 ($C_{33}H_{24}ClNO$ = 486.01) | Sub a-78 | m/z = 385.07 ($C_{24}H_{16}ClNS$ = 385.91) |
| Sub a-79 | m/z = 577.16 ($C_{39}H_{28}ClNS$ = 578.17) | Sub a-80 | m/z = 431.14 ($C_{30}H_{22}ClN$ = 431.96) |
| Sub a-81 | m/z = 395.14 ($C_{27}H_{22}ClN$ = 395.93) | Sub a-82 | m/z = 569.19 ($C_{41}H_{28}ClN$ = 570.13) |
| Sub a-83 | m/z = : 485.15 ($C_{33}H_{24}ClNO$ = 486.01) | Sub a-84 | m/z = 495.14 ($C_{34}H_{22}ClNO$ = 496.01) |
| Sub a-85 | m/z = 501.13 ($C_{33}H_{24}ClNS$ = 502.07) | Sub a-86 | m/z = 435.08 ($C_{28}H_{18}ClNS$ = 435.97) |
| Sub a-87 | m/z = 547.21 ($C_{39}H_{30}ClN$ = 548.13) | Sub a-88 | m/z = 519.18 ($C_{37}H_{26}ClN$ = 520.07) |
| Sub a-89 | m/z = 595.21 ($C_{43}H_{30}ClN$ = 596.17) | Sub a-90 | m/z = 609.19 ($C_{43}H_{28}ClNO$ = 610.15) |
| Sub a-91 | m/z = 431.14 ($C_{30}H_{22}ClN$ = 431.96) | Sub a-92 | m/z = 471.18 ($C_{33}H_{26}ClN$ = 472.03) |
| Sub a-93 | m/z = 385.07 ($C_{24}H_{16}ClNS$ = 385.91) | Sub a-94 | m/z = 431.14 ($C_{30}H_{22}ClN$ = 431.96) |
| Sub a-95 | m/z = 329.10 ($C_{22}H_{16}ClN$ = 329.83) | Sub a-96 | m/z = 471.18 ($C_{33}H_{26}ClN$ = 472.03) |
| Sub a-97 | m/z = 501.13 ($C_{33}H_{24}ClNS$ = 502.07) | Sub a-98 | m/z = 471.18 ($C_{33}H_{26}ClN$ = 472.03) |
| Sub a-99 | m/z = 759.27 ($C_{56}H_{38}ClN$ = 760.38) | Sub a-100 | m/z = 609.19 ($C_{43}H_{28}ClNO$ = 610.15) |
| Sub a-101 | m/z = 360.14 ($C_{24}H_{13}D_5ClN$ = 360.90) | Sub a-102 | m/z = 405.13 ($C_{28}H_{20}ClN$ = 405.93) |
| Sub a-103 | m/z = 471.18 ($C_{33}H_{26}ClN$ = 472.03) | Sub a-104 | m/z = 519.18 ($C_{37}H_{26}ClN$ = 520.07) |
| Sub a-105 | m/z = 609.19 ($C_{43}H_{28}ClNO$ = 610.15) | Sub a-106 | m/z = 355.11 ($C_{24}H_{18}ClN$ = 355.87) |
| Sub a-107 | m/z = 507.18 ($C_{36}H_{26}ClN$ = 508.06) | Sub a-108 | m/z = 519.18 ($C_{37}H_{26}ClN$ = 520.07) |
| Sub a-109 | m/z = 481.16 ($C_{34}H_{24}ClN$ = 482.02) | Sub a-110 | m/z = 609.19 ($C_{43}H_{28}ClNO$ = 610.15) |
| Sub a-111 | m/z = 445.12 ($C_{30}H_{20}ClNO$ = 445.95) | Sub a-112 | m/z = 461.10 ($C_{30}H_{20}ClNS$ = 462.01) |
| Sub a-113 | m/z = 429.13 ($C_{30}H_{20}ClN$ = 429.95) | Sub a-114 | m/z = 379.11 ($C_{26}H_{18}ClN$ = 379.89) |
| Sub a-115 | m/z = 519.18 ($C_{37}H_{26}ClN$ = 520.07) | Sub a-116 | m/z = 635.24 ($C_{46}H_{34}ClN$ = 636.24) |
| Sub a-117 | m/z = 445.12 ($C_{30}H_{20}ClNO$ = 445.95) | Sub a-118 | m/z = 575.24 ($C_{44}H_{23}ClN$ = 576.18) |
| Sub a-119 | m/z = 561.19 ($C_{39}H_{28}ClNO$ = 562.11) | | |

Synthesis Example of Sub b

Sub b of the Reaction Scheme 5 can be synthesized according to the reaction route of the following Reaction Scheme 5-2, but there is no limitation thereto.

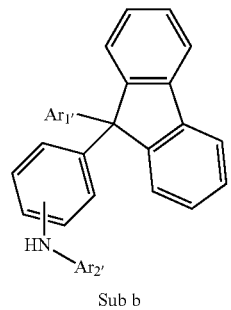

Sub b

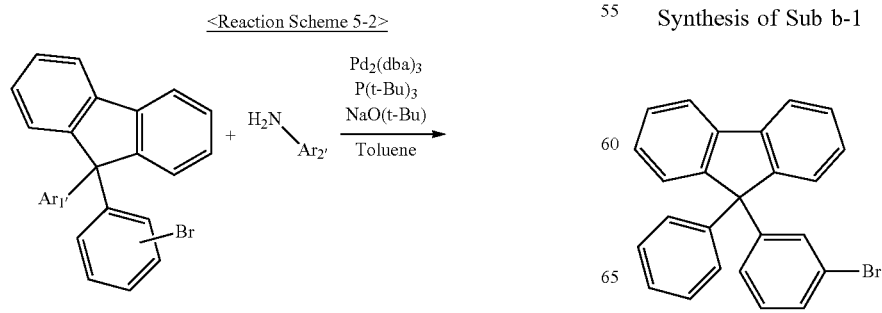

<Reaction Scheme 5-2>

Synthesis of Sub b-1

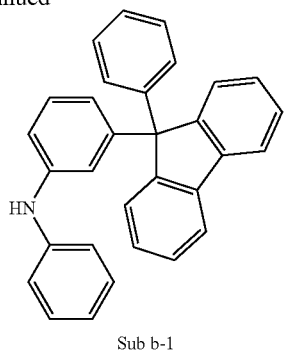

Sub b-1

9-(3-bromophenyl)-9-phenyl-9H-fluorene (100 g, 251.7 mmol), aniline (35.16 g, 377.5 mmol), Pd$_2$(dba)$_3$ (6.91 g, 7.6 mmol), P(t-Bu)$_3$ (4.07 g, 20.1 mmol), NaO(t-Bu) (72.57 g, 755.1 mmol) and toluene (3150 mL) were placed in a round bottom flask and then the mixture was heated under reflux at 60° C. for 4 hours. When the reaction is completed, the resultant was diluted with distilled water at room temperature and was extracted with CH$_2$Cl$_2$ and water. Thereafter, the organic layer was dried with MgSO$_4$ and concentrated. The concentrate was recrystallized with methylene chloride and hexane to obtain Sub b-1 (82.46 g, 80%) of the product.

Synthesis of Sub b-17

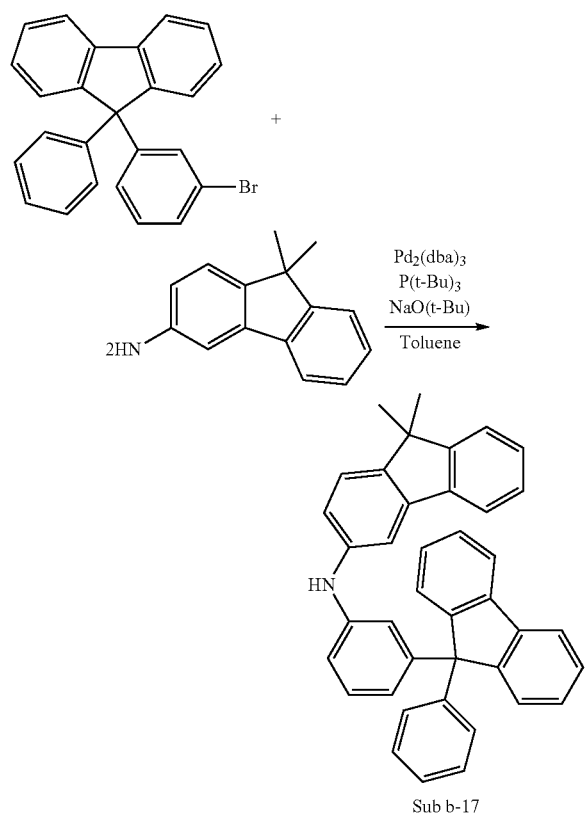

Sub b-17

9-(3-bromophenyl)-9-phenyl-9H-fluorene (100 g, 251.7 mmol), 9,9-dimethyl-9H-fluoren-3-amine (79.01 g, 377.5 mmol), Pd$_2$(dba)$_3$ (6.91 g, 7.6 mmol), P(t-Bu)$_3$ (4.07 g, 20.1 mmol), NaO(t-Bu) (72.57 g, 755.1 mmol) and toluene (3150 mL) were placed in a round bottom flask and then the mixture was heated under reflux at 60° C. for 4 hours. When the reaction is completed, the resultant was diluted with distilled water at room temperature and was extracted with CH$_2$Cl$_2$ and water. Thereafter, the organic layer was dried with MgSO$_4$ and concentrated. The concentrate was recrystallized with methylene chloride and hexane to obtain Sub b-17 (101.88 g, 77%) of the product.

Synthesis of Sub b-26

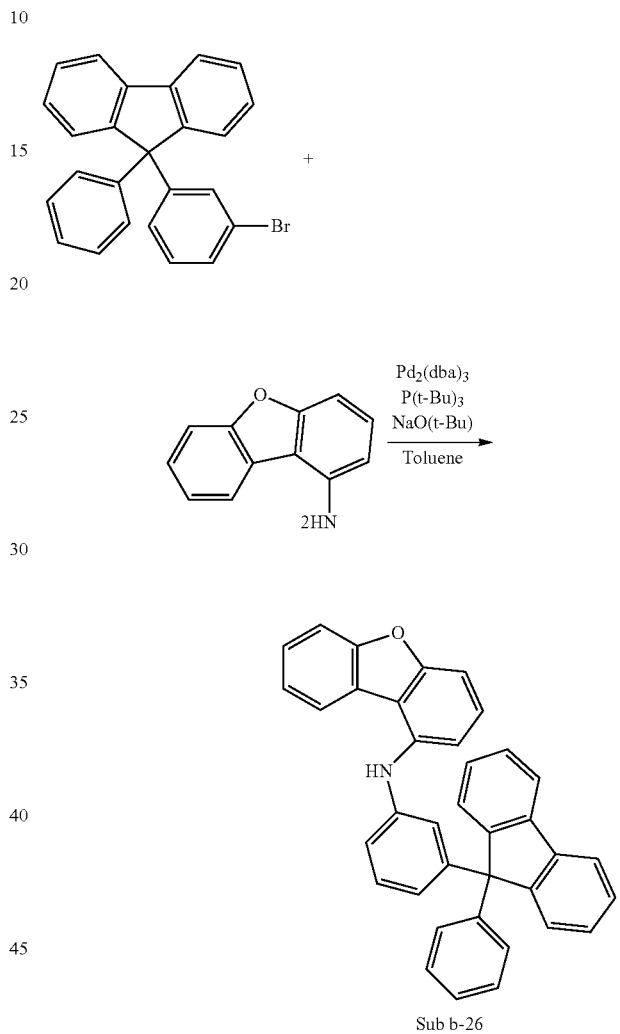

Sub b-26

9-(3-bromophenyl)-9-phenyl-9H-fluorene (100 g, 251.7 mmol), 9,9-dimethyl-9H-fluoren-4-amine (69.17 g, 377.5 mmol), Pd$_2$(dba)$_3$ (6.91 g, 7.6 mmol), P(t-Bu)$_3$ (4.07 g, 20.1 mmol), NaO(t-Bu) (72.57 g, 755.1 mmol) and toluene (3150 mL) were placed in a round bottom flask and then the mixture was heated under reflux at 60° C. for 4 hours. When the reaction is completed, the resultant was diluted with distilled water at room temperature and was extracted with CH$_2$Cl$_2$ and water. Thereafter, the organic layer was dried with MgSO$_4$ and concentrated. The concentrate was recrystallized with methylene chloride and hexane to obtain Sub b-26 (99.34 g, 79%) of the product.

Example of the compounds belonging to Sub b may be, but not limited to, the following compounds, and Table 6 shows the FD-MS values of the following compounds.

Sub b-1
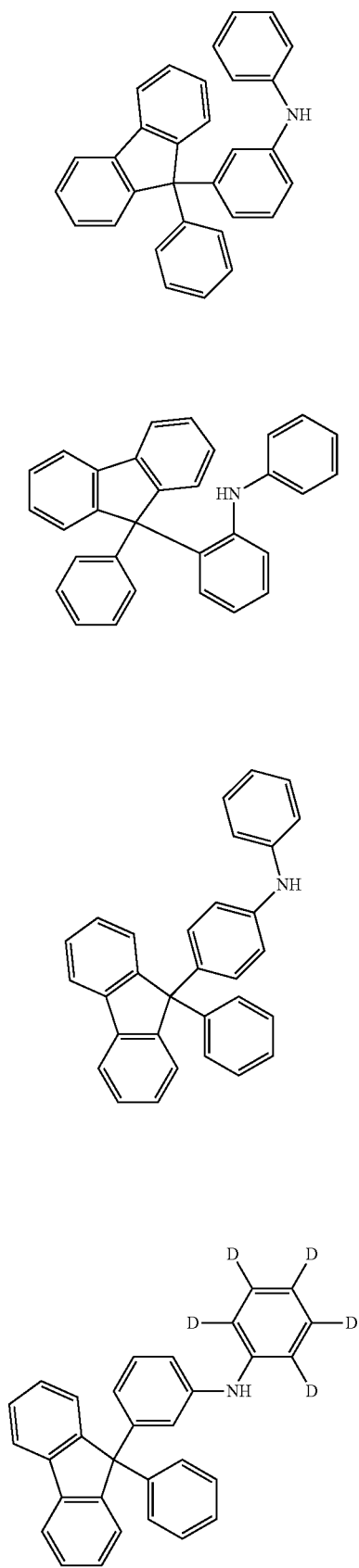
Sub b-2
Sub b-3
Sub b-4
Sub b-5
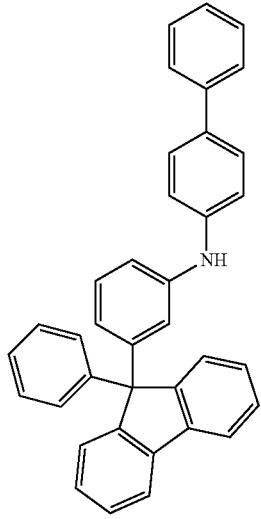
Sub b-6
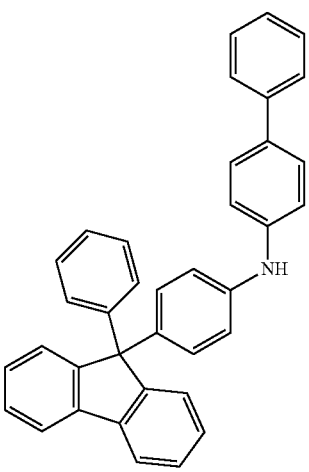
Sub b-7
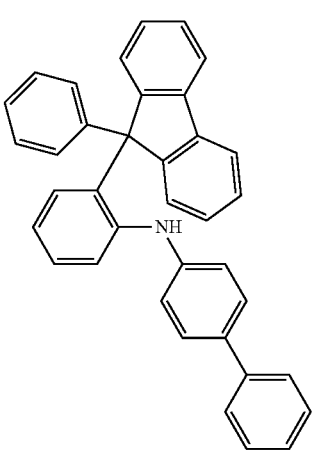

Sub b-8
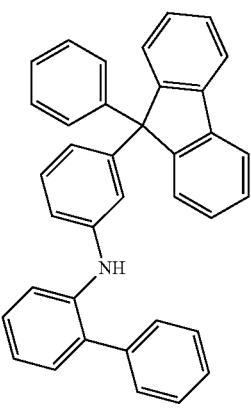
Sub b-9
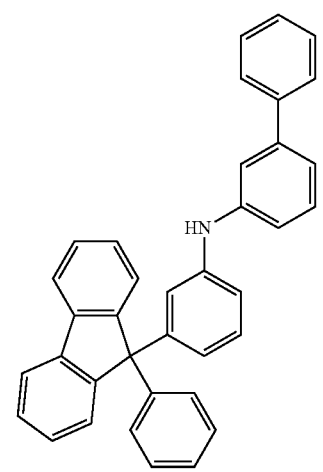
Sub b-10
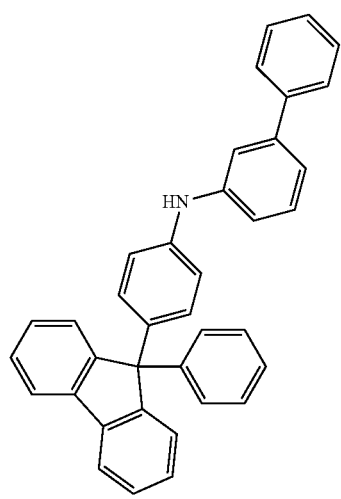
Sub b-11
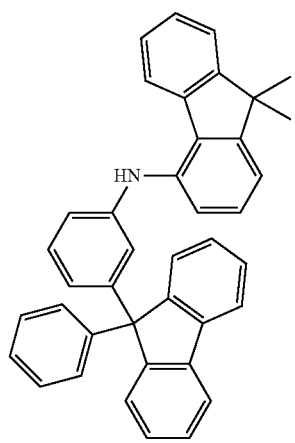
Sub b-12
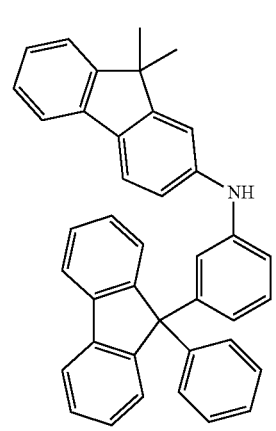
Sub b-13
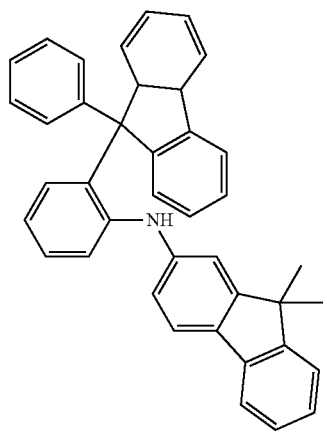

Sub b-14
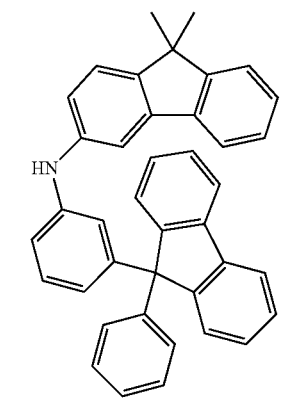
Sub b-15
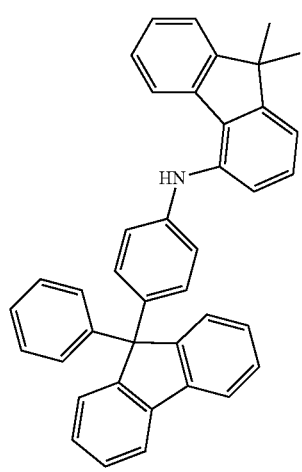
Sub b-16
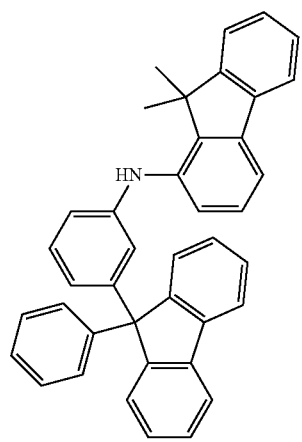
Sub b-17
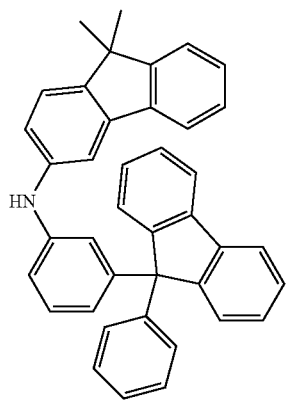
Sub b-18
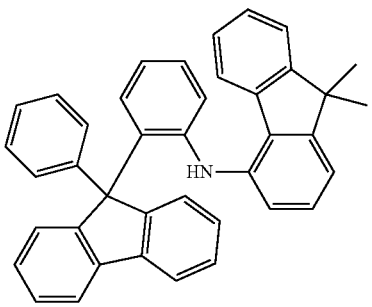
Sub b-19
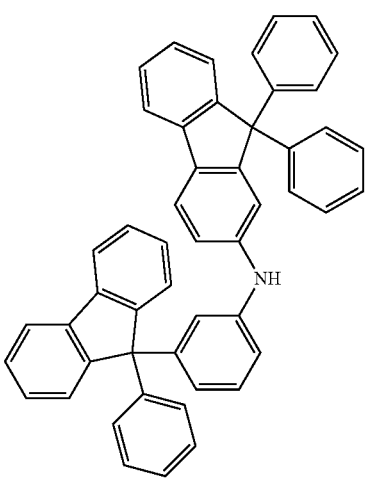
Sub b-20
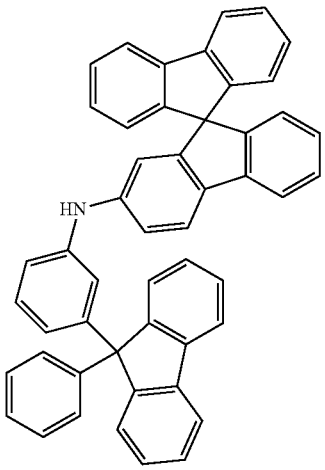

Sub b-21
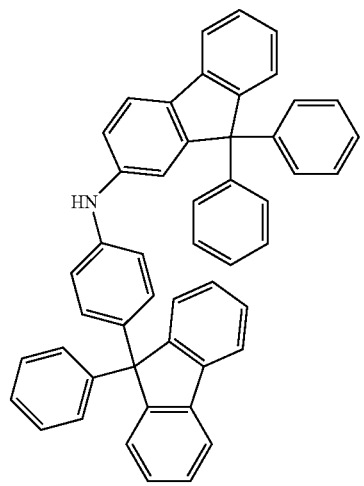
Sub b-22
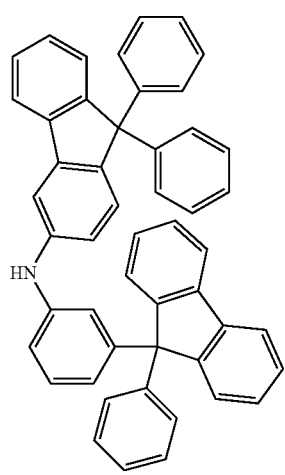
Sub b-23
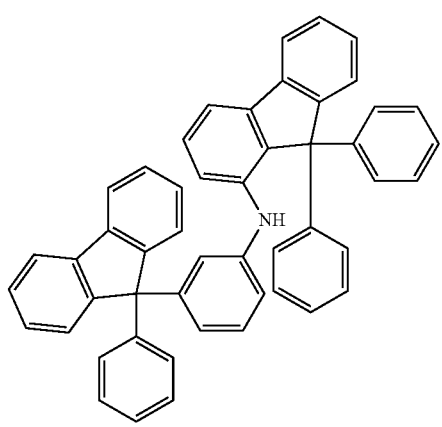
Sub b-24
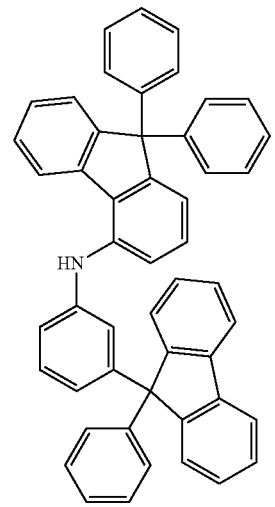
Sub b-25
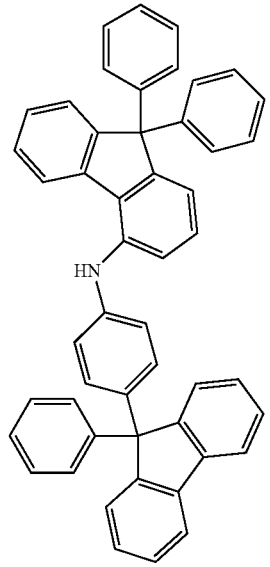
Sub b-26
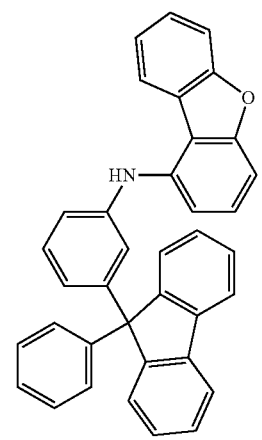

Sub b-27
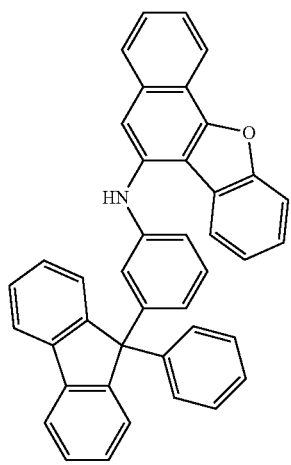
Sub b-28
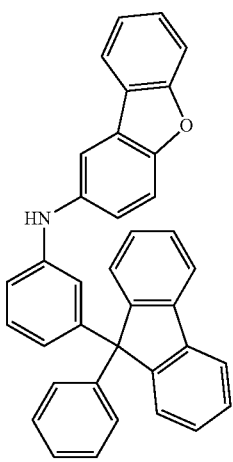
Sub b-29
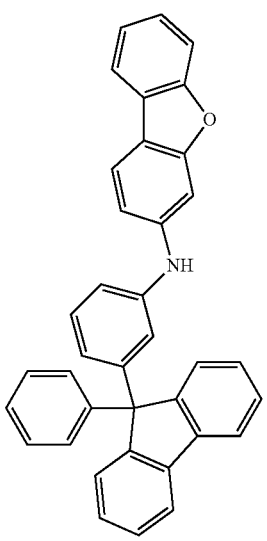
Sub b-30
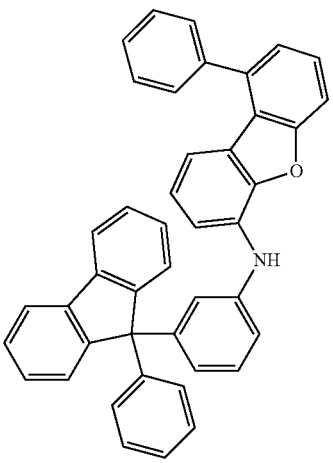
Sub b-31
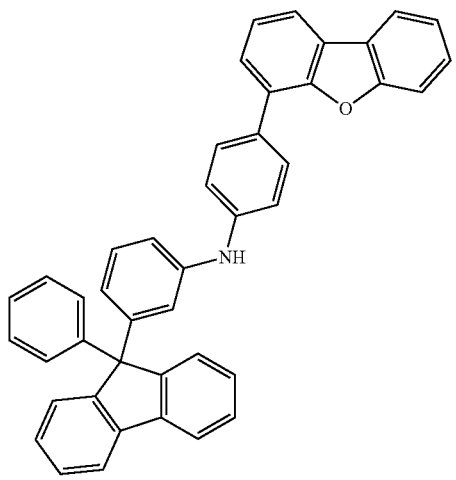
Sub b-32
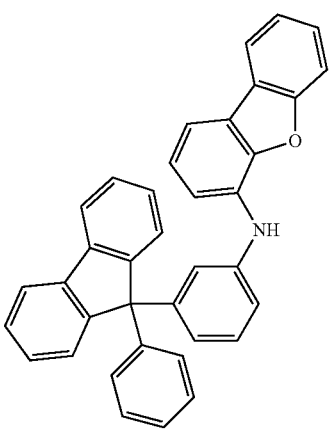

Sub b-33

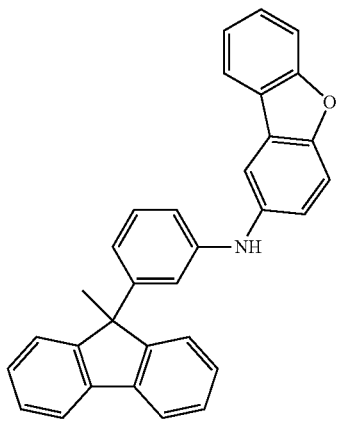

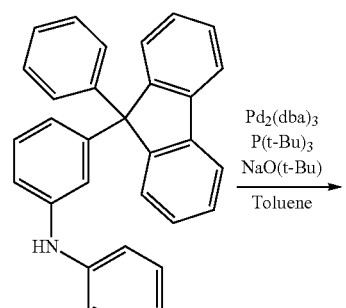

Sub b-1

TABLE 6

| Compound | FD-MS | Compound | FD-MS |
| --- | --- | --- | --- |
| Sub b-1 | m/z = 409.18 ($C_{31}H_{23}N$ = 409.53) | Sub b-2 | m/z = 409.18 ($C_{31}H_{23}N$ = 409.53) |
| Sub b-3 | m/z = 409.18 ($C_{31}H_{23}N$ = 409.53) | Sub b-4 | m/z = 414.21 ($C_{31}H_{18}D_5N$ = 414.56) |
| Sub b-5 | m/z = 485.21 ($C_{37}H_{27}N$ = 485.63) | Sub b-6 | m/z = 485.21 ($C_{37}H_{27}N$ = 485.63) |
| Sub b-7 | m/z = 485.21 ($C_{37}H_{27}N$ = 485.63) | Sub b-8 | m/z = 485.21 ($C_{37}H_{27}N$ = 485.63) |
| Sub b-9 | m/z = 485.21 ($C_{37}H_{27}N$ = 485.63) | Sub b-10 | m/z = 485.21 ($C_{37}H_{27}N$ = 485.63) |
| Sub b-11 | m/z = 525.25 ($C_{40}H_{31}N$ = 525.70) | Sub b-12 | m/z = 525.25 ($C_{40}H_{31}N$ = 525.70) |
| Sub b-13 | m/z = 527.26 ($C_{40}H_{33}N$ = 527.71) | Sub b-14 | m/z = 525.25 ($C_{40}H_{31}N$ = 525.70) |
| Sub b-15 | m/z = 525.25 ($C_{40}H_{31}N$ = 525.70) | Sub b-16 | m/z = 525.25 ($C_{40}H_{31}N$ = 525.70) |
| Sub b-17 | m/z = 525.25 ($C_{40}H_{31}N$ = 525.70) | Sub b-18 | m/z = 525.25 ($C_{40}H_{31}N$ = 525.70) |
| Sub b-19 | m/z = 649.28 ($C_{50}H_{35}N$ = 649.84) | Sub b-20 | m/z = 647.26 ($C_{50}H_{33}N$ = 647.82) |
| Sub b-21 | m/z = 649.28 ($C_{50}H_{35}N$ = 649.84) | Sub b-22 | m/z = 649.28 ($C_{50}H_{35}N$ = 649.84) |
| Sub b-23 | m/z = 649.28 ($C_{50}H_{35}N$ = 649.84) | Sub b-24 | m/z = 649.28 ($C_{50}H_{35}N$ = 649.84) |
| Sub b-25 | m/z = 649.28 ($C_{50}H_{35}N$ = 649.84) | Sub b-26 | m/z = 499.19 ($C_{37}H_{25}NO$ = 499.61) |
| Sub b-27 | m/z = 549.21 ($C_{41}H_{27}NO$ = 549.67) | Sub b-28 | m/z = 499.19 ($C_{37}H_{25}NO$ = 499.61) |
| Sub b-29 | m/z = 499.19 ($C_{37}H_{25}NO$ = 499.61) | Sub b-30 | m/z = 575.22 ($C_{43}H_{29}NO$ = 575.71) |
| Sub b-31 | m/z = 575.22 ($C_{43}H_{29}NO$ = 575.71) | Sub b-32 | m/z = 499.19 ($C_{37}H_{25}NO$ = 499.61) |
| Sub b-33 | m/z = 437.18 ($C_{32}H_{23}NO$ = 437.54) | | |

Synthesis Example of Final Product

Synthesis of Compound G-3

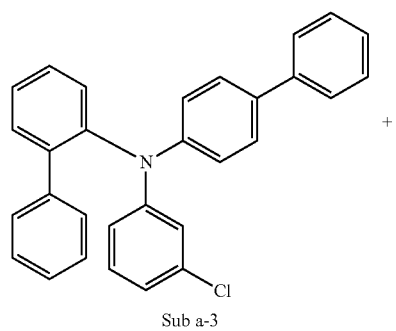

Sub a-3

+

-continued

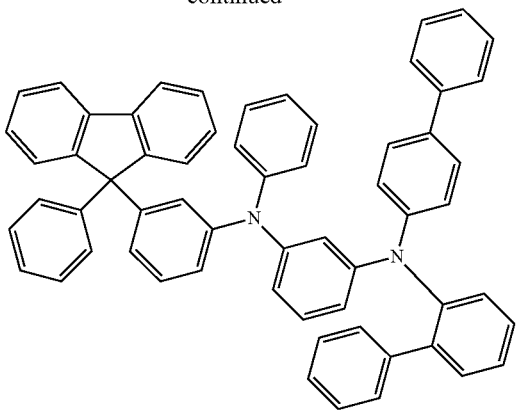

G-3

Sub a-3 (10 g, 23.2 mmol), Sub b-1 (9.48 g, 23.2 mmol), $Pd_2(dba)_3$ (0.64 g, 0.7 mmol), $P(t-Bu)_3$ (0.37 g, 1.9 mmol), NaO(t-Bu) (6.67 g, 69.5 mmol) and toluene (230 mL) were placed in a round bottom flask and then the mixture was heated under reflux at 110° C. for 3 hours. When the reaction is completed, the resultant was diluted with distilled water at room temperature and was extracted with $CH_2Cl_2$ and water. Thereafter, the organic layer was dried with $MgSO_4$ and concentrated. The concentrate was dissolved in toluene and filtered with a silica gel filter. After concentrating the filtered solution, the concentrate was recrystallized with toluene and acetone to obtain G-3 (17.0 g, 89%) of the product.

Synthesis of Compound G-29

Synthesis of Compound G-81

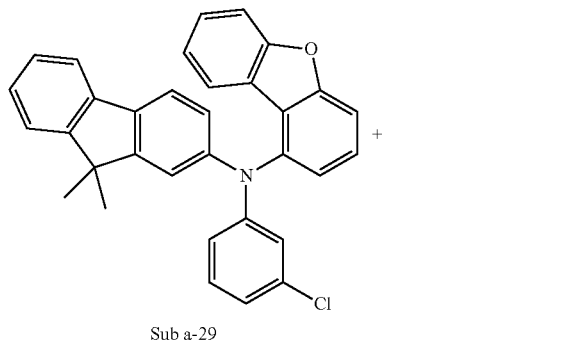

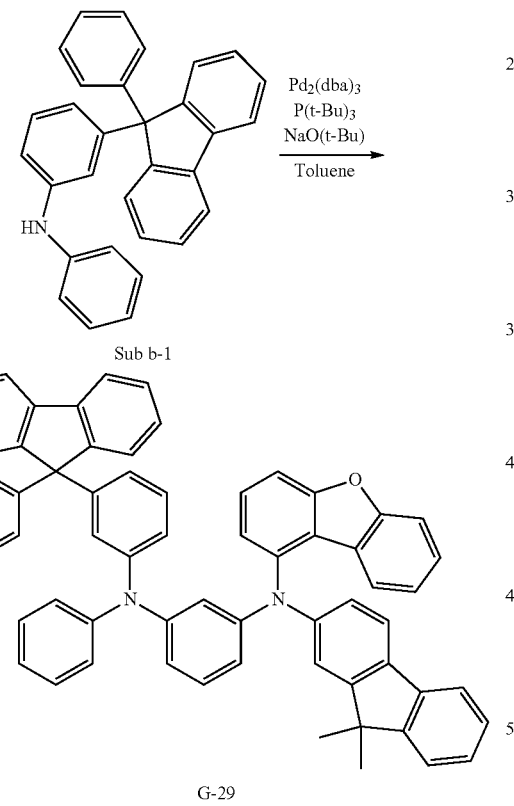

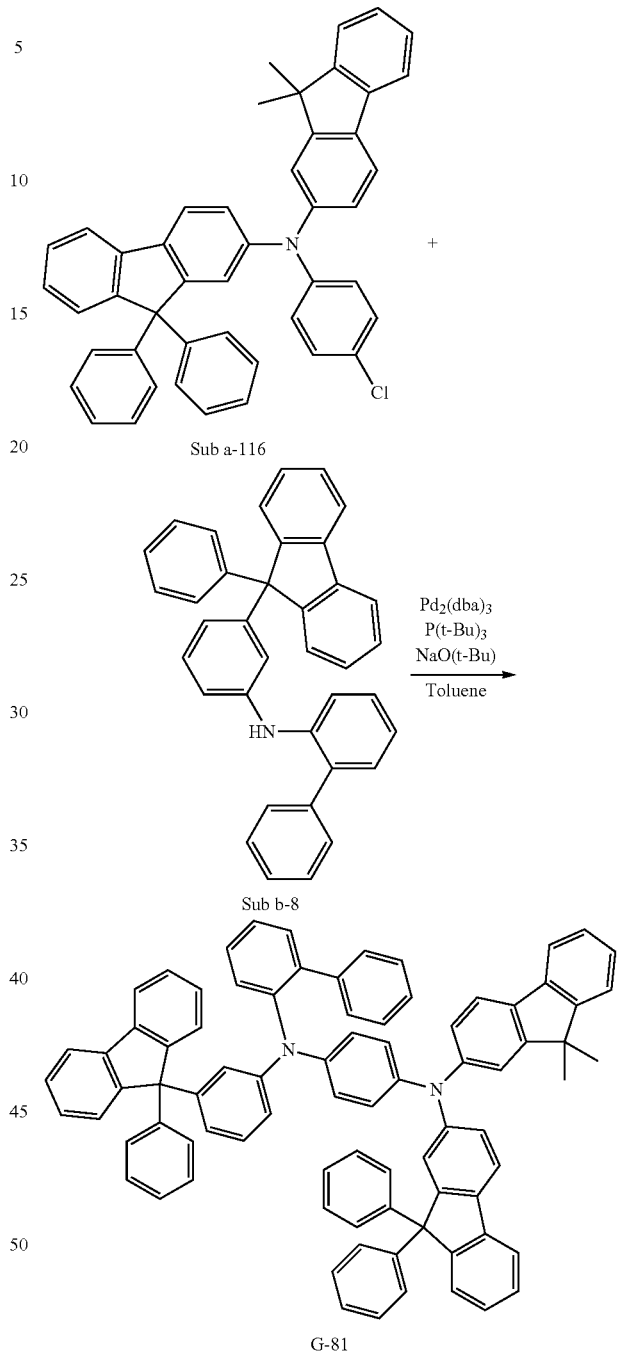

Sub a-29 (10 g, 20.6 mmol), Sub b-1 (8.43 g, 20.6 mmol), Pd$_2$(dba)$_3$ (0.57 g, 0.6 mmol), P(t-Bu)$_3$ (0.33 g, 1.6 mmol), NaO(t-Bu) (5.93 g, 61.7 mmol) and toluene (210 mL) were placed in a round bottom flask and then the mixture was heated under reflux at 110° C. for 3 hours. When the reaction is completed, the resultant was diluted with distilled water at room temperature and was extracted with CH$_2$Cl$_2$ and water. Thereafter, the organic layer was dried with MgSO$_4$ and concentrated. The concentrate was dissolved in toluene and filtered with a silica gel filter. After concentrating the filtered solution, the concentrate was recrystallized with toluene and acetone to obtain G-29 (15.20 g, 86%) of the product.

Sub a-116 (10 g, 15.7 mmol), Sub b-8 (7.63 g, 15.7 mmol), Pd$_2$(dba)$_3$ (0.43 g, 0.5 mmol), P(t-Bu)$_3$ (0.25 g, 1.3 mmol), NaO(t-Bu) (4.53 g, 47.2 mmol) and toluene (160 mL) were placed in a round bottom flask and then the mixture was heated under reflux at 110° C. for 3 hours. When the reaction is completed, the resultant was diluted with distilled water at room temperature and was extracted with CH$_2$Cl$_2$ and water. Thereafter, the organic layer was dried with MgSO$_4$ and concentrated. The concentrate was dissolved in toluene and filtered with a silica gel filter. After concentrating the filtered solution, the concentrate was recrystallized with toluene and acetone to obtain G-81 (13.99 g, 82%) of the product.

Synthesis of Compound G-88

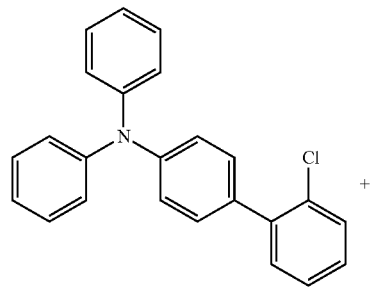

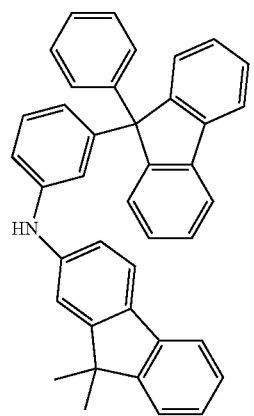

Synthesis of Compound G-137

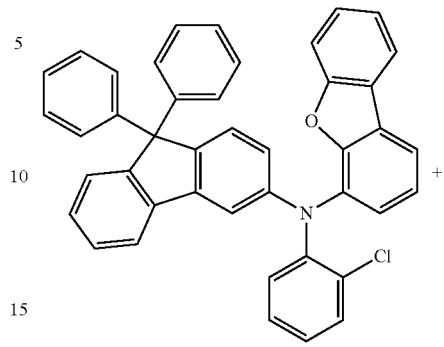

Sub a-69 (10 g, 28.1 mmol), Sub b-12 (14.77 g, 28.1 mmol), Pd$_2$(dba)$_3$ (0.77 g, 0.8 mmol), P(t-Bu)$_3$ (0.45 g, 2.2 mmol), NaO(t-Bu) (8.10 g, 84.3 mmol) and toluene (280 mL) were placed in a round bottom flask and then the mixture was heated under reflux at 110° C. for 3 hours. When the reaction is completed, the resultant was diluted with distilled water at room temperature and was extracted with CH$_2$Cl$_2$ and water. Thereafter, the organic layer was dried with MgSO$_4$ and concentrated. The concentrate was dissolved in toluene and filtered with a silica gel filter. After concentrating the filtered solution, the concentrate was recrystallized with toluene and acetone to obtain G-88 (19.47 g, 82%) of the product.

Sub a-90 (10 g, 16.4 mmol), Sub b-21 (10.65 g, 16.4 mmol), Pd$_2$(dba)$_3$ (0.45 g, 0.5 mmol), P(t-Bu)$_3$ (0.27 g, 1.3 mmol), NaO(t-Bu) (4.73 g, 49.2 mmol) and toluene (170 mL) were placed in a round bottom flask and then the mixture was heated under reflux at 110° C. for 3 hours. When the reaction is completed, the resultant was diluted with distilled water at room temperature and was extracted with CH$_2$Cl$_2$ and water. Thereafter, the organic layer was dried with MgSO$_4$ and concentrated. The concentrate was dissolved in toluene and filtered with a silica gel filter. After concentrating the filtered solution, the concentrate was recrystallized with toluene and acetone to obtain G-137 (16.24 g, 81%) of the product.

Synthesis of Compound G-168

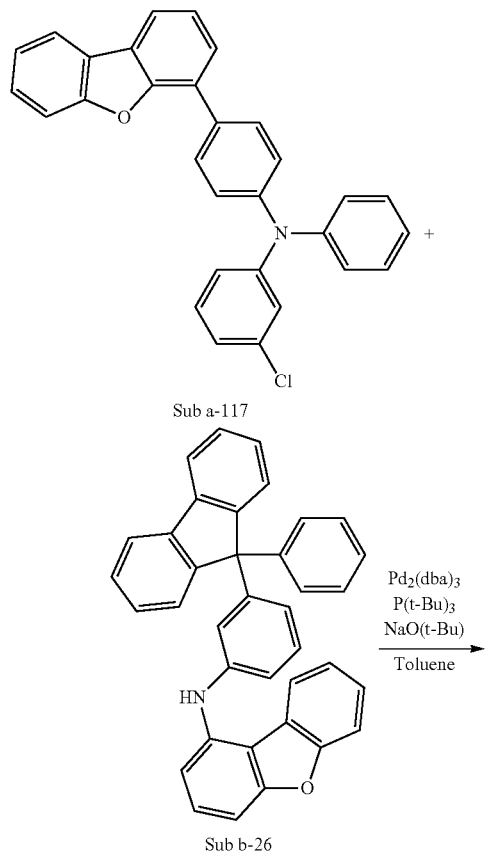

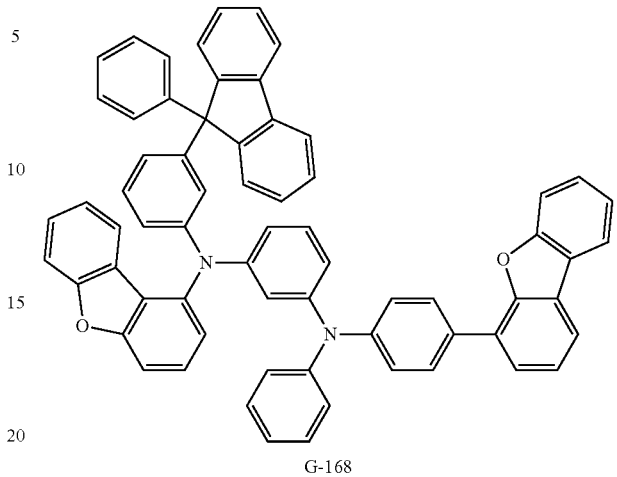

G-168

Sub a-117 (10 g, 22.4 mmol), Sub b-26 (11.20 g, 22.4 mmol), Pd$_2$(dba)$_3$ (0.62 g, 0.7 mmol), P(t-Bu)$_3$ (0.36 g, 1.8 mmol), NaO(t-Bu) (6.47 g, 67.3 mmol) and toluene (230 mL) were placed in a round bottom flask and then the mixture was heated under reflux at 110° C. for 3 hours. When the reaction is completed, the resultant was diluted with distilled water at room temperature and was extracted with CH$_2$Cl$_2$ and water. Thereafter, the organic layer was dried with MgSO$_4$ and concentrated. The concentrate was dissolved in toluene and filtered with a silica gel filter. After concentrating the filtered solution, the concentrate was recrystallized with toluene and acetone to obtain G-168 (16.92 g, 83%) of the product.

The FD-MS values of the compounds according to Formula A of the present invention prepared according to the above synthesis examples are shown in the following Table 7.

TABLE 7

| Compound | FD-MS | Compound | FD-MS |
|---|---|---|---|
| G-1 | m/z = 652.29 (C$_{49}$H$_{36}$N$_2$ = 652.84) | G-2 | m/z = 728.32 (C$_{55}$H$_{40}$N$_2$ = 728.94) |
| G-3 | m/z = 804.35 (C$_{61}$H$_{44}$N$_2$ = 805.04) | G-4 | m/z = 880.38 (C$_{67}$H$_{48}$N$_2$ = 881.14) |
| G-5 | m/z = 880.38 (C$_{67}$H$_{48}$N$_2$ = 881.14) | G-6 | m/z = 702.30 (C$_{53}$H$_{38}$N$_2$ = 702.90) |
| G-7 | m/z = 778.33 (C$_{59}$H$_{42}$N$_2$ = 779.00) | G-8 | m/z = 768.35 (C$_{58}$H$_{44}$N$_2$ = 769.00) |
| G-9 | m/z = 844.38 (C$_{64}$H$_{48}$N$_2$ = 845.10) | G-10 | m/z = 844.38 (C$_{64}$H$_{48}$N$_2$ = 845.10) |
| G-11 | m/z = 884.41 (C$_{67}$H$_{52}$N$_2$ = 885.17) | G-12 | m/z = 844.38 (C$_{64}$H$_{48}$N$_2$ = 845.10) |
| G-13 | m/z = 844.38 (C$_{64}$H$_{48}$N$_2$ = 845.10) | G-14 | m/z = 884.41 (C$_{67}$H$_{52}$N$_2$ = 885.17) |
| G-15 | m/z = 968.41 (C$_{74}$H$_{52}$N$_2$ = 969.24) | G-16 | m/z = 1008.44 (C$_{77}$H$_{56}$N$_2$ = 1009.31) |
| G-17 | m/z = 892.38 (C$_{68}$H$_{48}$N$_2$ = 893.15) | G-18 | m/z = 968.41 (C$_{74}$H$_{52}$N$_2$ = 969.24) |
| G-19 | m/z = 1044.44 (C$_{80}$H$_{56}$N$_2$ = 1045.34) | G-20 | m/z = 892.38 (C$_{68}$H$_{48}$N$_2$ = 893.15) |
| G-21 | m/z = 966.40 (C$_{74}$H$_{50}$N$_2$ = 967.23) | G-22 | m/z = 968.41 (C$_{74}$H$_{52}$N$_2$ = 969.24) |
| G-23 | m/z = 1044.44 (C$_{80}$H$_{56}$N$_2$ = 1045.34) | G-24 | m/z = 1008.44 (C$_{77}$H$_{56}$N$_2$ = 1009.31) |
| G-25 | m/z = 968.41 (C$_{74}$H$_{52}$N$_2$ = 969.24) | G-26 | m/z = 742.30 (C$_{55}$H$_{38}$N$_2$O = 742.92) |
| G-27 | m/z = 823.36 (C$_{61}$H$_{37}$D$_5$N$_2$O = 824.05) | G-28 | m/z = 818.33 (C$_{61}$H$_{42}$N$_2$O = 819.02) |
| G-29 | m/z = 858.36 (C$_{64}$H$_{46}$N$_2$O = 859.09) | G-30 | m/z = 982.39 (C$_{74}$H$_{50}$N$_2$O = 983.23) |
| G-31 | m/z = 742.30 (C$_{55}$H$_{38}$N$_2$O = 742.92) | G-32 | m/z = 792.31 (C$_{59}$H$_{40}$N$_2$O = 792.98) |
| G-33 | m/z = 982.39 (C$_{74}$H$_{50}$N$_2$O = 983.23) | G-34 | m/z = 818.33 (C$_{61}$H$_{42}$N$_2$O = 819.02) |
| G-35 | m/z = 818.33 (C$_{61}$H$_{42}$N$_2$O = 819.02) | G-36 | m/z = 868.35 (C$_{65}$H$_{44}$N$_2$O = 869.08) |

TABLE 7-continued

| Compound | FD-MS | Compound | FD-MS |
|---|---|---|---|
| G-37 | m/z = 858.36 ($C_{64}H_{46}N_2O$ = 859.09) | G-38 | m/z = 742.30 ($C_{55}H_{38}N_2O$ = 742.92) |
| G-39 | m/z = 934.39 ($C_{70}H_{50}N_2O$ = 935.18) | G-40 | m/z = 834.31 ($C_{61}H_{42}N_2S$ = 835.08) |
| G-41 | m/z = 950.37 ($C_{70}H_{50}N_2S$ = 951.24) | G-42 | m/z = 834.31 ($C_{61}H_{42}N_2S$ = 835.08) |
| G-43 | m/z = 808.29 ($C_{59}H_{40}N_2S$ = 809.04) | G-44 | m/z = 874.34 ($C_{64}H_{46}N_2S$ = 875.15) |
| G-45 | m/z = 758.28 ($C_{55}H_{38}N_2S$ = 758.98) | G-46 | m/z = 998.37 ($C_{74}H_{50}N_2S$ = 999.29) |
| G-47 | m/z = 880.38 ($C_{67}H_{48}N_2$ = 881.14) | G-48 | m/z = 804.35 ($C_{61}H_{44}N_2$ = 805.04) |
| G-49 | m/z = 804.35 ($C_{61}H_{44}N_2$ = 805.04) | G-50 | m/z = 880.38 ($C_{67}H_{48}N_2$ = 881.14) |
| G-51 | m/z = 854.37 ($C_{65}H_{46}N_2$ = 855.10) | G-52 | m/z = 844.38 ($C_{64}H_{48}N_2$ = 845.10) |
| G-53 | m/z = 996.44 ($C_{76}H_{56}N_2$ = 997.30) | G-54 | m/z = 920.41 ($C_{70}H_{52}N_2$ = 921.20) |
| G-55 | m/z = 844.38 ($C_{64}H_{48}N_2$ = 845.10) | G-56 | m/z = 920.41 ($C_{70}H_{52}N_2$ = 921.20) |
| G-57 | m/z = 1010.46 ($C_{77}H_{58}N_2$ = 1011.33) | G-58 | m/z = 1044.44 ($C_{80}H_{56}N_2$ = 1045.34) |
| G-59 | m/z = 1208.51 ($C_{93}H_{64}N_2$ = 1209.55) | G-60 | m/z = 1118.46 ($C_{86}H_{58}N_2$ = 1119.42) |
| G-61 | m/z = 968.41 ($C_{74}H_{52}N_2$ = 969.24) | G-62 | m/z = 1120.48 ($C_{86}H_{60}N_2$ = 1121.44) |
| G-63 | m/z = 868.35 ($C_{65}H_{44}N_2O$ = 869.08) | G-64 | m/z = 1058.42 ($C_{80}H_{54}N_2O$ = 1059.33) |
| G-65 | m/z = 818.33 ($C_{61}H_{42}N_2O$ = 819.02) | G-66 | m/z = 934.39 ($C_{70}H_{50}N_2O$ = 935.18) |
| G-67 | m/z = 894.36 ($C_{67}H_{46}N_2O$ = 895.12) | G-68 | m/z = 894.36 ($C_{67}H_{46}N_2O$ = 895.12) |
| G-69 | m/z = 884.32 ($C_{65}H_{44}N_2S$ = 885.14) | G-70 | m/z = 950.37 ($C_{70}H_{50}N_2S$ = 951.24) |
| G-71 | m/z = 910.34 ($C_{67}H_{46}N_2S$ = 911.18) | G-72 | m/z = 960.35 ($C_{71}H_{48}N_2S$ = 961.24) |
| G-73 | m/z = 1074.40 ($C_{80}H_{54}N_2S$ = 1075.39) | G-74 | m/z = 652.29 ($C_{49}H_{44}N_2$ = 652.84) |
| G-75 | m/z = 880.38 ($C_{67}H_{48}N_2$ = 881.14) | G-76 | m/z = 880.38 ($C_{67}H_{48}N_2$ = 881.14) |
| G-77 | m/z = 844.38 ($C_{64}H_{48}N_2$ = 845.10) | G-78 | m/z = 920.41 ($C_{70}H_{52}N_2$ = 921.20) |
| G-79 | m/z = 920.41 ($C_{70}H_{52}N_2$ = 921.20) | G-80 | m/z = 960.44 ($C_{73}H_{56}N_2$ = 961.27) |
| G-81 | m/z = 1084.48 ($C_{83}H_{60}N_2$ = 1085.41) | G-82 | m/z = 1018.43 ($C_{78}H_{54}N_2$ = 1019.30) |
| G-83 | m/z = 1044.44 ($C_{80}H_{56}N_2$ = 1045.34) | G-84 | m/z = 894.36 ($C_{67}H_{46}N_2O$ = 895.12) |
| G-85 | m/z = 818.33 ($C_{61}H_{42}N_2O$ = 819.02) | G-86 | m/z = 1058.42 ($C_{80}H_{54}N_2O$ = 1059.33) |
| G-87 | m/z = 934.39 ($C_{70}H_{50}N_2O$ = 935.18) | G-88 | m/z = 844.38 ($C_{64}H_{48}N_2$ = 845.10) |
| G-89 | m/z = 844.38 ($C_{64}H_{48}N_2$ = 845.10) | G-90 | m/z = 920.41 ($C_{70}H_{52}N_2$ = 921.20) |
| G-91 | m/z = 896.41 ($C_{68}H_{52}N_2$ = 897.18) | G-92 | m/z = 1010.46 ($C_{77}H_{58}N_2$ = 1011.33) |
| G-93 | m/z = 1036.48 ($C_{79}H_{60}N_2$ = 1037.36) | G-94 | m/z = 884.41 ($C_{67}H_{52}N_2$ = 885.17) |
| G-95 | m/z = 1006.43 ($C_{77}H_{54}N_2$ = 1007.29) | G-96 | m/z = 1084.48 ($C_{83}H_{60}N_2$ = 1085.41) |
| G-97 | m/z = 1084.48 ($C_{83}H_{60}N_2$ = 1085.41) | G-98 | m/z = 858.36 ($C_{64}H_{46}N_2O$ = 859.09) |
| G-99 | m/z = 974.42 ($C_{73}H_{54}N_2O$ = 975.25) | G-100 | m/z = 908.38 ($C_{68}H_{48}N_2O$ = 909.15) |
| G-101 | m/z = 934.39 ($C_{70}H_{50}N_2O$ = 935.18) | G-102 | m/z = 1098.45 ($C_{83}H_{58}N_2O$ = 1099.39) |
| G-103 | m/z = 974.42 ($C_{73}H_{54}N_2O$ = 975.25) | G-104 | m/z = 874.34 ($C_{64}H_{46}N_2S$ = 875.15) |
| G-105 | m/z = 1066.43 ($C_{79}H_{58}N_2S$ = 1067.41) | G-106 | m/z = 768.35 ($C_{58}H_{44}N_2$ = 769.00) |
| G-107 | m/z = 844.38 ($C_{64}H_{48}N_2$ = 845.10) | G-108 | m/z = 920.41 ($C_{70}H_{52}N_2$ = 921.20) |
| G-109 | m/z = 996.44 ($C_{76}H_{56}N_2$ = 997.30) | G-110 | m/z = 818.37 ($C_{62}H_{46}N_2$ = 819.06) |
| G-111 | m/z = 894.40 ($C_{68}H_{50}N_2$ = 895.16) | G-112 | m/z = 960.44 ($C_{73}H_{56}N_2$ = 961.27) |
| G-113 | m/z = 884.41 ($C_{67}H_{52}N_2$ = 885.17) | G-114 | m/z = 960.44 ($C_{73}H_{56}N_2$ = 961.27) |
| G-115 | m/z = 1058.46 ($C_{81}H_{58}N_2$ = 1059.37) | G-116 | m/z = 1084.48 ($C_{83}H_{60}N_2$ = 1085.41) |
| G-117 | m/z = 1160.51 ($C_{89}H_{64}N_2$ = 1161.51) | G-118 | m/z = 1084.48 ($C_{83}H_{60}N_2$ = 1085.41) |
| G-119 | m/z = 934.39 ($C_{70}H_{50}N_2O$ = 935.18) | G-120 | m/z = 974.42 ($C_{73}H_{54}N_2O$ = 975.25) |
| G-121 | m/z = 934.39 ($C_{70}H_{50}N_2O$ = 935.18) | G-122 | m/z = 984.41 ($C_{74}H_{52}N_2O$ = 985.24) |
| G-123 | m/z = 990.40 ($C_{73}H_{54}N_2S$ = 991.31) | G-124 | m/z = 924.35 ($C_{68}H_{48}N_2S$ = 925.21) |
| G-125 | m/z = 874.34 ($C_{64}H_{46}N_2S$ = 875.15) | G-126 | m/z = 968.41 ($C_{74}H_{52}N_2$ = 969.24) |
| G-127 | m/z = 1044.44 ($C_{80}H_{56}N_2$ = 1045.34) | G-128 | m/z = 940.38 ($C_{72}H_{48}N_2$ = 941.19) |
| G-129 | m/z = 1008.44 ($C_{77}H_{56}N_2$ = 1009.31) | G-130 | m/z = 1084.48 ($C_{83}H_{60}N_2$ = 1085.41) |
| G-131 | m/z = 1160.51 ($C_{89}H_{64}N_2$ = 1161.51) | G-132 | m/z = 1132.48 ($C_{87}H_{60}N_2$ = 1133.45) |
| G-133 | m/z = 1208.51 ($C_{93}H_{64}N_2$ = 1209.55) | G-134 | m/z = 1208.51 ($C_{93}H_{64}N_2$ = 1209.55) |
| G-135 | m/z = 1098.45 ($C_{83}H_{58}N_2O$ = 1099.39) | G-136 | m/z = 982.39 ($C_{74}H_{50}N_2O$ = 983.23) |
| G-137 | m/z = 1222.49 ($C_{93}H_{62}N_2O$ = 1223.53) | G-138 | m/z = 1048.39 ($C_{78}H_{52}N_2S$ = 1049.35) |
| G-139 | m/z = 892.38 ($C_{68}H_{48}N_2$ = 893.15) | G-140 | m/z = 1044.44 ($C_{80}H_{56}N_2$ = 1045.34) |
| G-141 | m/z = 1084.48 ($C_{83}H_{60}N_2$ = 1085.41) | G-142 | m/z = 982.39 ($C_{74}H_{50}N_2O$ = 983.23) |
| G-143 | m/z = 1058.42 ($C_{80}H_{54}N_2O$ = 1059.33) | G-144 | m/z = 998.37 ($C_{74}H_{50}N_2S$ = 999.29) |
| G-145 | m/z = 1044.44 ($C_{80}H_{56}N_2$ = 1045.34) | G-146 | m/z = 1120.48 ($C_{86}H_{60}N_2$ = 1121.44) |
| G-147 | m/z = 942.40 ($C_{72}H_{50}N_2$ = 943.21) | G-148 | m/z = 1084.48 ($C_{83}H_{60}N_2$ = 1085.41) |
| G-149 | m/z = 1084.48 ($C_{83}H_{60}N_2$ = 1085.41) | G-150 | m/z = 1132.48 ($C_{87}H_{60}N_2$ = 1133.45) |
| G-151 | m/z = 1248.54 ($C_{96}H_{68}N_2$ = 1249.61) | G-152 | m/z = 982.39 ($C_{74}H_{50}N_2O$ = 983.23) |
| G-153 | m/z = 1058.42 ($C_{80}H_{54}N_2O$ = 1059.33) | G-154 | m/z = 1112.42 ($C_{83}H_{56}N_2S$ = 1113.44) |
| G-155 | m/z = 998.37 ($C_{74}H_{50}N_2S$ = 999.29) | G-156 | m/z = 742.30 ($C_{55}H_{38}N_2O$ = 742.92) |
| G-157 | m/z = 818.33 ($C_{61}H_{42}N_2O$ = 819.02) | G-158 | m/z = 868.35 ($C_{65}H_{44}N_2O$ = 869.08) |
| G-159 | m/z = 1010.42 ($C_{76}H_{54}N_2O$ = 1011.28) | G-160 | m/z = 934.39 ($C_{70}H_{50}N_2O$ = 935.18) |
| G-161 | m/z = 984.41 ($C_{74}H_{52}N_2O$ = 985.24) | G-162 | m/z = 982.39 ($C_{74}H_{50}N_2O$ = 983.23) |
| G-163 | m/z = 1222.49 ($C_{93}H_{62}N_2O$ = 1223.53) | G-164 | m/z = 908.34 ($C_{67}H_{44}N_2O_2$ = 909.10) |
| G-165 | m/z = 1072.40 ($C_{80}H_{52}N_2O_2$ = 1073.31) | G-166 | m/z = 832.30 ($C_{61}H_{40}N_2O_2$ = 833.00) |
| G-167 | m/z = 948.37 ($C_{70}H_{48}N_2O_2$ = 949.17) | G-168 | m/z = 908.34 ($C_{67}H_{44}N_2O_2$ = 909.10) |
| G-169 | m/z = 823.36 ($C_{61}H_{37}D_5N_2O$ = 824.05) | G-170 | m/z = 894.36 ($C_{67}H_{46}N_2O$ = 895.12) |
| G-171 | m/z = 970.39 ($C_{73}H_{50}N_2O$ = 971.22) | G-172 | m/z = 868.35 ($C_{65}H_{44}N_2O$ = 869.08) |
| G-173 | m/z = 858.36 ($C_{64}H_{46}N_2O$ = 859.09) | G-174 | m/z = 934.39 ($C_{70}H_{50}N_2O$ = 935.18) |
| G-175 | m/z = 934.39 ($C_{70}H_{50}N_2O$ = 935.18) | G-176 | m/z = 1058.42 ($C_{80}H_{54}N_2O$ = 1059.33) |
| G-177 | m/z = 982.39 ($C_{74}H_{50}N_2O$ = 983.23) | G-178 | m/z = 908.34 ($C_{67}H_{44}N_2O_2$ = 909.10) |
| G-179 | m/z = 1072.40 ($C_{80}H_{52}N_2O_2$ = 1073.31) | G-180 | m/z = 908.34 ($C_{67}H_{44}N_2O_2$ = 909.10) |
| G-181 | m/z = 818.33 ($C_{61}H_{42}N_2O$ = 819.02) | G-182 | m/z = 970.39 ($C_{73}H_{50}N_2O$ = 971.22) |
| G-183 | m/z = 858.36 ($C_{64}H_{46}N_2O$ = 859.09) | G-184 | m/z = 1058.42 ($C_{80}H_{54}N_2O$ = 1059.33) |
| G-185 | m/z = 982.39 ($C_{74}H_{50}N_2O$ = 983.23) | G-186 | m/z = 882.32 ($C_{65}H_{42}N_2O_2$ = 883.06) |
| G-187 | m/z = 908.34 ($C_{67}H_{44}N_2O_2$ = 909.10) | G-188 | m/z = 970.39 ($C_{73}H_{50}N_2O$ = 971.22) |
| G-189 | m/z = 1020.41 ($C_{77}H_{52}N_2O$ = 1021.28) | G-190 | m/z = 1010.42 ($C_{76}H_{54}N_2O$ = 1011.28) |
| G-191 | m/z = 974.42 ($C_{73}H_{54}N_2O$ = 975.25) | G-192 | m/z = 982.39 ($C_{74}H_{50}N_2O$ = 983.23) |

TABLE 7-continued

| Compound | FD-MS | Compound | FD-MS |
|---|---|---|---|
| G-193 | m/z = 1134.45 ($C_{86}H_{58}N_2O$ = 1135.42) | G-194 | m/z = 982.39 ($C_{74}H_{50}N_2O$ = 983.23) |
| G-195 | m/z = 908.34 ($C_{67}H_{44}N_2O_2$ = 909.10) | G-196 | m/z = 948.37 ($C_{70}H_{48}N_2O_2$ = 949.17) |
| G-197 | m/z = 924.32 ($C_{67}H_{44}N_2OS$ = 925.16) | G-198 | m/z = 802.33 ($C_{61}H_{42}N_2$ = 803.02) |
| G-199 | m/z = 752.32 ($CS_7H_{40}N_2$ = 752.96) | G-200 | m/z = 892.38 ($C_{68}H_{48}N_2$ = 893.15) |
| G-204 | m/z = 934.39 ($C_{70}H_{50}N_2O$ = 935.18) | | |

Fabrication and Evaluation of Organic Electronic Element

[Example 1] Green OLED (a Phosphorescent Host)

$N^1$-(naphthalen-2-yl)-$N^4$,$N^4$-bis(4-(naphthalen-2-yl(phenyl)amino)phenyl)-$N^1$-phenylbenzene-1,4-diamine (hereinafter, "2-TNATA") was vacuum-deposited on the ITO layer formed on a glass substrate to form a hole injection layer with a thickness of 60 nm.

Next, 4,4'-bis[N-(1-naphthyl)-N-phenylamino]biphenyl (hereinafter, "NPD") was vacuum-deposited on the hole injection layer to form a hole transport layer with a thickness of 60 nm.

Subsequently, a light emitting layer with a thickness of 30 nm was vacuum-deposited on the hole transport layer by using compound 1-1 of the present invention as a host material and tris(2-phenylpyridine)-iridium (hereinafter, "Ir(ppy)$_3$") as a dopant material in a weight ratio of 95:5.

Subsequently, (1,1'-biphenyl-4-olato)bis(2-methyl-8-quinolinolato)aluminum (hereinafter, "BAlq") was vacuum-deposited with a thickness of 10 nm on the light emitting layer to form a hole blocking layer, and tris-(8-hydroxyquinoline)aluminum (hereinafter, "Alq$_3$") was vacuum-deposited with a thickness of 40 nm on the hole blocking layer to form an electron transport layer.

Next, LiF was deposited with a thickness of 0.2 nm on the electron transport layer to form an electron injection layer, and then Al was deposited with a thickness of 150 nm on the electron injection layer to form a cathode.

[Example 2] to [Example 15]

The OLED was fabricated in the same manner as described in Example 1 except that compounds of the present invention described in Table 5 instead of the compound 1-1 of the present invention was used as host material of a light emitting layer.

[Comparative Example 1] to [Comparative Example 3]

The OLEDs were fabricated in the same manner as described in Example 1 except that one of the comparative compounds 1 to 3 instead of compound 1-1 of the present invention was used as host material of a light emitting layer.

<Comp.compd 1>

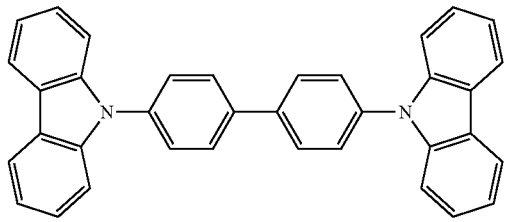

<Comp.compd 2>

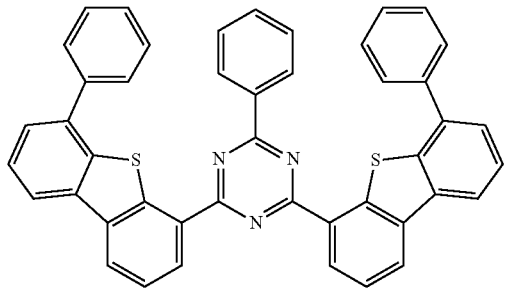

<Comp.compd 3>

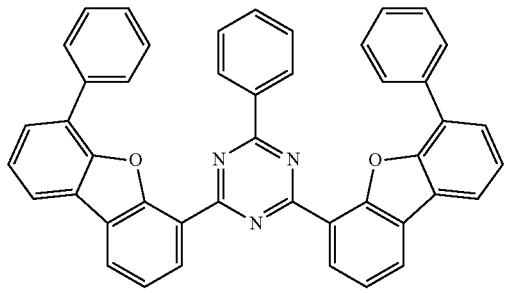

Electroluminescence (EL) characteristics were measured with PR-650 (Photoresearch) by applying a forward bias DC voltage to the OLEDs prepared in Examples 1 to 15 of the present invention and Comparative Examples 1 to 3. And, the T95 life time was measured using a life time measuring apparatus manufactured by Mcscience Inc. at reference brightness of 5000 cd/m$^2$. The measurement results are shown in Tables 8 below.

TABLE 8

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex(1) | comp. Com 1 | 5.9 | 21.2 | 5000 | 23.6 | 56.1 | 0.33 | 0.61 |
| comp. Ex(2) | comp. Com 2 | 5.8 | 15.9 | 5000 | 31.5 | 75.4 | 0.33 | 0.61 |
| comp. Ex(3) | comp. Com 3 | 5.8 | 15.1 | 5000 | 33.2 | 77.1 | 0.33 | 0.61 |
| Ex. (1) | Com. 1-1 | 5.7 | 13.8 | 5000 | 36.2 | 84.3 | 0.33 | 0.62 |
| Ex. (2) | Com. 1-2 | 5.6 | 14.1 | 5000 | 35.4 | 85.1 | 0.33 | 0.61 |
| Ex. (3) | Com. 1-98 | 5.6 | 13.7 | 5000 | 36.4 | 84.8 | 0.33 | 0.62 |
| Ex. (4) | Com. 1-100 | 5.7 | 14.2 | 5000 | 35.2 | 82.1 | 0.33 | 0.62 |
| Ex. (5) | Com. 2-1 | 5.6 | 13.3 | 5000 | 37.6 | 85.6 | 0.33 | 0.61 |
| Ex. (6) | Com. 2-3 | 5.5 | 13.4 | 5000 | 37.2 | 86.6 | 0.33 | 0.61 |
| Ex. (7) | Com. 2-15 | 5.5 | 12.9 | 5000 | 38.9 | 87.5 | 0.33 | 0.62 |
| Ex. (8) | Com. 2-35 | 5.5 | 13.3 | 5000 | 37.7 | 87.2 | 0.33 | 0.62 |
| Ex. (9) | Com. 3-6 | 5.5 | 13.7 | 5000 | 36.5 | 85.9 | 0.33 | 0.61 |
| Ex. (10) | Com. 4-33 | 5.7 | 14.2 | 5000 | 35.1 | 80.7 | 0.33 | 0.62 |
| Ex. (11) | Com. 4-37 | 5.5 | 13.1 | 5000 | 38.2 | 87.8 | 0.33 | 0.61 |
| Ex. (12) | Com. 4-39 | 5.7 | 14.2 | 5000 | 35.3 | 81.5 | 0.33 | 0.61 |
| Ex. (13) | Com. 4-42 | 5.7 | 14.2 | 5000 | 35.2 | 81.0 | 0.33 | 0.61 |
| Ex. (14) | Com. 4-43 | 5.7 | 14.2 | 5000 | 35.1 | 81.2 | 0.33 | 0.61 |
| Ex. (15) | Com. 4-45 | 5.7 | 14.1 | 5000 | 35.4 | 80.9 | 0.33 | 0.61 |

[Example 16] to [Example 55]

The OLED was fabricated in the same manner as described in Example 1 except that a mixture of the compound represented by Formula 1 and the compound represented by Formula 12 of the present invention described in Table 6 instead of compound 1-1 of the present invention was used as host material of a light emitting layer.

[Comparative Example 4] and [Comparative Example 6]

The OLEDs were fabricated in the same manner as described in Example 1 except that a mixture of comparative compound 2 and compound 5-27 of the present invention (Comparative Example 4), or a mixture of comparative compound 3 and compound 5-27 of the present invention instead of compound 1-1 of the present invention was used as host material of a light emitting layer.

Electroluminescence (EL) characteristics were measured with PR-650 (Photoresearch) by applying a forward bias DC voltage to the OLEDs prepared in Examples 16 to 55 of the present invention and Comparative Examples 4 and 5. And, the T95 life time was measured using a life time measuring apparatus manufactured by Mcscience Inc. at reference brightness of 5000 cd/m$^2$. The measurement results are shown in Tables 9 below.

TABLE 9

| | Host 1 | Host 2 | Voltage (V) | Current Density (mA/cm$^2$) | Brightness (cd/m$^2$) | Efficiency (cd/A) | Lifetime T(95) |
|---|---|---|---|---|---|---|---|
| comp. Ex(4) | comp. Com 2 | Com. 5-27 | 5.6 | 14.8 | 5000 | 33.8 | 83.7 |
| comp. Ex(5) | comp. Com 3 | Com. 5-27 | 5.6 | 14.0 | 5000 | 35.7 | 86.3 |
| Ex. (16) | Com. 1-1 | Com. 5-27 | 5.0 | 11.9 | 5000 | 42.1 | 105.3 |
| Ex. (17) | Com. 1-2 | | 5.0 | 11.9 | 5000 | 41.9 | 106.4 |
| Ex. (18) | Com. 1-98 | | 5.0 | 11.9 | 5000 | 42.0 | 106.0 |
| Ex. (19) | Com. 1-100 | | 5.1 | 12.0 | 5000 | 41.8 | 105.1 |
| Ex. (20) | Com. 2-3 | | 5.0 | 11.8 | 5000 | 42.4 | 106.9 |
| Ex. (21) | Com. 2-15 | | 5.0 | 11.7 | 5000 | 42.9 | 107.0 |
| Ex. (22) | Com. 2-35 | | 5.0 | 11.7 | 5000 | 42.6 | 106.7 |
| Ex. (23) | Com. 3-6 | | 5.0 | 11.9 | 5000 | 42.0 | 106.5 |
| Ex. (24) | Com. 4-33 | | 5.1 | 12.0 | 5000 | 41.8 | 104.9 |
| Ex. (25) | Com. 4-37 | | 5.0 | 11.7 | 5000 | 42.7 | 107.2 |
| Ex. (26) | Com. 1-1 | Com. 5-25 | 5.1 | 12.3 | 5000 | 40.6 | 103.2 |
| Ex. (27) | Com. 1-2 | | 5.1 | 12.3 | 5000 | 40.7 | 103.9 |
| Ex. (28) | Com. 1-98 | | 5.1 | 12.1 | 5000 | 41.2 | 103.5 |
| Ex. (29) | Com. 1-100 | | 5.2 | 12.2 | 5000 | 40.9 | 102.8 |
| Ex. (30) | Com. 2-3 | | 5.1 | 12.0 | 5000 | 41.5 | 104.6 |
| Ex. (31) | Com. 2-15 | | 5.1 | 12.0 | 5000 | 41.7 | 104.7 |
| Ex. (32) | Com. 2-35 | | 5.1 | 12.1 | 5000 | 41.2 | 104.2 |
| Ex. (33) | Com. 3-6 | | 5.1 | 12.2 | 5000 | 41.1 | 104.0 |
| Ex. (34) | Com. 4-33 | | 5.2 | 12.3 | 5000 | 40.6 | 102.5 |
| Ex. (35) | Com. 4-37 | | 5.1 | 12.0 | 5000 | 41.6 | 104.8 |
| Ex. (36) | Com. 1-1 | Com. 5-31 | 4.9 | 11.5 | 5000 | 43.6 | 107.7 |
| Ex. (37) | Com. 1-2 | | 4.9 | 11.5 | 5000 | 43.3 | 108.2 |
| Ex. (38) | Com. 1-98 | | 4.9 | 11.5 | 5000 | 43.5 | 107.9 |
| Ex. (39) | Com. 1-100 | | 5.0 | 11.6 | 5000 | 43.1 | 107.2 |
| Ex. (40) | Com. 2-3 | | 4.9 | 11.4 | 5000 | 43.9 | 109.0 |
| Ex. (41) | Com. 2-15 | | 4.9 | 11.3 | 5000 | 44.2 | 109.2 |
| Ex. (42) | Com. 2-35 | | 4.9 | 11.4 | 5000 | 44.0 | 108.8 |
| Ex. (43) | Com. 3-6 | | 4.9 | 11.4 | 5000 | 43.8 | 108.5 |

TABLE 9-continued

|  | Host 1 | Host 2 | Voltage (V) | Current Density (mA/cm$^2$) | Brightness (cd/m$^2$) | Efficiency (cd/A) | Lifetime T(95) |
|---|---|---|---|---|---|---|---|
| Ex. (44) | Com. 4-33 |  | 5.0 | 11.6 | 5000 | 43.0 | 107.1 |
| Ex. (45) | Com. 4-37 |  | 4.9 | 11.4 | 5000 | 44.0 | 109.3 |
| Ex. (46) | Com. 1-1 | Com. 5-42 | 5.2 | 12.7 | 5000 | 39.5 | 101.0 |
| Ex. (47) | Com. 1-2 |  | 5.2 | 12.5 | 5000 | 40.0 | 101.5 |
| Ex. (48) | Com. 1-98 |  | 5.2 | 12.5 | 5000 | 39.9 | 101.2 |
| Ex. (49) | Com. 1-100 |  | 5.2 | 12.7 | 5000 | 39.4 | 100.7 |
| Ex. (50) | Com. 2-3 |  | 5.2 | 12.6 | 5000 | 39.7 | 102.1 |
| Ex. (51) | Com. 2-15 |  | 5.2 | 12.4 | 5000 | 40.3 | 102.4 |
| Ex. (52) | Com. 2-35 |  | 5.2 | 12.5 | 5000 | 40.1 | 102.0 |
| Ex. (53) | Com. 3-6 |  | 5.2 | 12.6 | 5000 | 39.6 | 101.7 |
| Ex. (54) | Com. 4-33 |  | 5.2 | 12.7 | 5000 | 39.4 | 100.5 |
| Ex. (55) | Com. 4-37 |  | 5.2 | 12.5 | 5000 | 40.0 | 102.4 |

Example 56

After 2-TNATA was vacuum-deposited on the ITO layer formed on a glass substrate to form a hole injection layer with a thickness of 60 nm, NPD was vacuum-deposited on the hole injection layer to form a hole transport layer with a thickness of 60 nm.

Next, compound 14-69 of the present invention was vacuum-deposited to a thickness of 20 nm on the hole transport layer to form an emission-auxiliary layer, and a light emitting layer with a thickness of 30 nm was vacuum-deposited on the hole transport layer by using a mixture of compound 1-1 (the first host) and compound 5-27 (the second host) of the present invention in the ratio of 6:4 as a host material and Ir(ppy)$_3$ as a dopant material in a weight ratio of 95:5.

Subsequently, BAlq was vacuum-deposited with a thickness of 10 nm on the light emitting layer to form a hole blocking layer, Alq$_3$ was vacuum-deposited with a thickness of 40 nm on the hole blocking layer to form an electron transport layer. Next, LiF was deposited with a thickness of 0.2 nm on the electron transport layer to form an electron injection layer, and then Al was deposited with a thickness of 150 nm on the electron injection layer to form a cathode.

[Example 57] to [Example 73]

The OLEDs were fabricated in the same manner as described in Example 56 except that the compounds of the present invention described in the following Table 7 were used as an emission-auxiliary layer material and the first host material.

[Comparative Example 6] and [Comparative Example 7]

The OLEDs were fabricated in the same manner as described in Example 56 except that Comparative compound 2 or 3 was used as the first host material.

Electroluminescence (EL) characteristics were measured with a PR-650 (Photoresearch) by applying a forward bias DC voltage to the OLEDs prepared in Examples 56 to 73 of the present invention and Comparative Examples 6 and 7. And, the T95 life time was measured using a life time measuring apparatus manufactured by Mcscience Inc. at reference brightness of 5000 cd/m$^2$. The measurement results are shown in Tables 10 below.

TABLE 10

|  | EAL | Host 1 | Host 2 | Voltage (V) | Current Density (mA/cm$^2$) | Brightness (cd/m$^2$) | Efficiency (cd/A) | Lifetime T(95) |
|---|---|---|---|---|---|---|---|---|
| comp. Ex(6) | 14-69 | comp. Com 2 | 5-27 | 5.4 | 13.6 | 5000 | 36.8 | 88.4 |
| comp. Ex(7) |  | comp. Com 3 |  | 5.4 | 13.1 | 5000 | 38.1 | 91.5 |
| Ex. (56) |  | Com. 1-1 |  | 5.1 | 9.8 | 5000 | 51.0 | 123.5 |
| Ex. (57) |  | Com. 1-2 |  | 5.1 | 9.3 | 5000 | 53.6 | 125.6 |
| Ex. (58) |  | Com. 1-98 |  | 5.1 | 9.5 | 5000 | 52.6 | 124.4 |
| Ex. (59) |  | Com. 2-3 |  | 5.0 | 9.2 | 5000 | 54.1 | 127.4 |
| Ex. (60) |  | Com. 2-15 |  | 4.9 | 9.1 | 5000 | 54.7 | 128.0 |
| Ex. (61) |  | Com. 4-37 |  | 4.9 | 9.2 | 5000 | 54.5 | 128.2 |
| comp. Ex(8) | 14-72 | comp. Com 2 |  | 5.4 | 12.6 | 5000 | 39.6 | 92.6 |
| comp. Ex(9) |  | comp. Com 3 |  | 5.3 | 12.0 | 5000 | 41.6 | 95.1 |
| Ex. (62) |  | Com. 1-1 |  | 4.9 | 9.0 | 5000 | 55.8 | 128.8 |
| Ex. (63) |  | Com. 1-2 |  | 4.9 | 8.8 | 5000 | 56.7 | 130.2 |
| Ex. (64) |  | Com. 1-98 |  | 4.9 | 8.9 | 5000 | 56.4 | 129.7 |
| Ex. (65) |  | Com. 2-3 |  | 4.8 | 8.4 | 5000 | 59.7 | 131.6 |
| Ex. (66) |  | Com. 2-15 |  | 4.8 | 8.3 | 5000 | 60.5 | 133.8 |
| Ex. (67) |  | Com. 4-37 |  | 4.8 | 8.3 | 5000 | 60.1 | 134.0 |
| comp. Ex(10) | 14-74 | comp. Com 2 |  | 5.3 | 11.6 | 5000 | 43.1 | 96.7 |
| comp. Ex(11) |  | comp. Com 3 |  | 5.3 | 10.8 | 5000 | 46.3 | 99.2 |
| Ex. (68) |  | Com. 1-1 |  | 4.8 | 8.1 | 5000 | 61.7 | 134.2 |
| Ex. (69) |  | Com. 1-2 |  | 4.8 | 8.0 | 5000 | 62.4 | 137.6 |
| Ex. (70) |  | Com. 1-98 |  | 4.8 | 8.1 | 5000 | 62.0 | 135.2 |
| Ex. (71) |  | Com. 2-3 |  | 4.7 | 7.9 | 5000 | 63.2 | 138.1 |
| Ex. (72) |  | Com. 2-15 |  | 4.7 | 7.8 | 5000 | 64.1 | 138.8 |
| Ex. (73) |  | Com. 4-37 |  | 4.7 | 7.8 | 5000 | 63.9 | 139.6 |

Example 74

After 2-TNATA was vacuum-deposited on the ITO layer formed on a glass substrate to form a hole injection layer with a thickness of 60 nm, the compound 14-69 of the present invention was vacuum-deposited on the hole injection layer to form a hole transport layer with a thickness of 60 nm. Next, the compound 14-72 of the present invention was vacuum-deposited to a thickness of 20 nm on the hole transport layer to form an emission-auxiliary layer and a light emitting layer with a thickness of 30 nm was vacuum-deposited on the hole transport layer by using a mixture of the compound 1-1 (the first host) and the compound 5-27 (the second host) of the present invention at 6:4 as a host material and Ir(ppy)$_3$ as a dopant material in a weight ratio of 95:5.

Subsequently, BAlq was vacuum-deposited with a thickness of 10 nm on the light emitting layer to form a hole blocking layer, Alq$_3$ was vacuum-deposited with a thickness of 40 nm on the hole blocking layer to form an electron transport layer. Next, LiF was deposited with a thickness of 0.2 nm on the electron transport layer to form an electron injection layer, and then Al was deposited with a thickness of 150 nm on the electron injection layer to form a cathode.

[Example 75] to [Example 85]

The OLEDs were fabricated in the same manner as described in Example 74 except that the compounds of the present invention described in the following Table 8 were used as an emission-auxiliary layer material and the first host material.

Electroluminescence (EL) characteristics were measured with a PR-650 (Photoresearch) by applying a forward bias DC voltage to the OLEDs prepared in Examples 74 to 85 of the present invention. And, the T95 life time was measured using a life time measuring apparatus manufactured by Mcscience Inc. at reference brightness of 5000 cd/m$^2$. The measurement results are shown in Tables 11 below.

These results can be explained by the LUMO value of Compound 1-1 of the present invention. Referring to Table 9A below, it can be seen that the LUMO level of Comparative Compound 2 is the highest, the LUMO level of Comparative Compound 3 is the lowest, and the LUMO level of Compound 1-1 of the present invention is located in the middle.

TABLE 9A

|  | comp. Com2 | comp. Com3 | Com. 1-1 |
|---|---|---|---|
| LUMO | 1.939 | 1.839 | 1.877 |

When comparing Comparative Compounds 2 and 3, Comparative Compound 2 is different in that the heteroatom of both heterocycles attached to the triazine is S, while in case of Comparative Compound 3, the heteroatom is O. From Table 9 above, it can be seen that when heteroatoms S are introduced into both heterocycles, the LUMO value is highest (comparative compound 2), and when O is introduced, the LUMO value is lowest (comparative compound 3), the LUMO value is located in the middle when S as a heteroatom is introduced into one heterocycle and O is introduced into the other heterocycle as the compound of the present invention.

When comparative compound 2 having the highest LUMO level is used as the phosphorescent host material, the LUMO level is too high, and thus the LUMO level acts as a barrier to electron movement. Therefore, the electron transfer from the electron transport layer to the light emitting layer is not easy, and the charge balance in the light emitting layer is reduced.

In addition, when comparative compound 3 having the lowest LUMO level is used as a phosphorescent host material, the energy gap between the electron transport layer and the LUMO level becomes too large, so that electrons cannot be smoothly transferred from the electron transport layer to

TABLE 11

|  | HTL | EAE | Host 1 | Host 2 | Voltage (V) | Current Density (mA/cm$^2$) | Brightness (cd/m$^2$) | Efficiency (cd/A) | Lifetime T(95) |
|---|---|---|---|---|---|---|---|---|---|
| Ex. (74) | 14-69 | 14-72 | Com. 1-1 | 5-27 | 4.6 | 7.9 | 5000 | 63.2 | 135.2 |
| Ex. (75) |  |  | Com. 1-2 |  | 4.5 | 7.6 | 5000 | 65.6 | 138.4 |
| Ex. (76) |  |  | Com. 1-98 |  | 4.5 | 7.7 | 5000 | 65.2 | 137.1 |
| Ex. (77) |  |  | Com. 2-3 |  | 4.4 | 7.4 | 5000 | 67.6 | 139.4 |
| Ex. (78) |  |  | Com. 2-15 |  | 4.4 | 7.3 | 5000 | 68.2 | 140.0 |
| Ex. (79) |  |  | Com. 4-37 |  | 4.3 | 7.4 | 5000 | 68.0 | 140.6 |
| Ex. (80) |  | 14-74 | Com. 1-1 |  | 4.5 | 7.7 | 5000 | 65.3 | 141.2 |
| Ex. (81) |  |  | Com. 1-2 |  | 4.4 | 7.4 | 5000 | 67.8 | 145.2 |
| Ex. (82) |  |  | Com. 1-98 |  | 4.4 | 7.5 | 5000 | 67.1 | 144.0 |
| Ex. (83) |  |  | Com. 2-3 |  | 4.3 | 7.3 | 5000 | 68.4 | 146.4 |
| Ex. (84) |  |  | Com. 2-15 |  | 4.3 | 7.2 | 5000 | 69.0 | 147.0 |
| Ex. (85) |  |  | Com. 4-37 |  | 4.2 | 7.3 | 5000 | 68.7 | 147.3 |

From Tables 5 to 8, it can be seen that the driving voltage of the organic electroluminescent device can be lowered and the luminous efficiency and lifespan are significantly improved when the material for an organic electroluminescent device of the present invention is used as a phosphorescent host material.

In particular, referring to Table 5, it can be seen that even when the compound represented by Formula 1 of the present invention is used as a single host, device characteristics are superior to that using a comparative compound.

the light emitting layer, as a result, the charge balance within the light emitting layer is reduced.

On the other hand, when the compound of the present invention in which the LUMO level is located in the middle of the LUMO level of the comparative compounds is used as a phosphorescent host material, it has an appropriate LUMO level for electron transfer, so the biased electron transfer characteristics of Comparative Compound 2 and Comparative Compound 3 can be complemented. Therefore, when the compound of the present invention is used as a phosphorescent host material, the charge balance in the light-emitting layer increases, so that the luminous efficiency and lifetime of the organic electroluminescent device are improved.

In Table 9A, compound 1-1 of the present invention is used as an example, but the same conclusion can be reached with the compounds of the present invention used in Examples 2 to 15 as a phosphorescent host material.

On the other hand, referring to the device results of the embodiments of the present invention, it can be seen that performance is improved in all aspects of driving voltage, efficiency, and lifetime when 1-dibenzofuran is substituted rather than 4-dibenzofuran, and when 2-position of 1-dibenzofuran is substituted rather than 4-position.

In more detail, it can be seen that the device result of Example 5 in which 1-dibenzofuran is substituted in triazine is better than Example 1 in which 4-dibenzofuran is substituted in triazine, and the electrical properties of the device of Example 7 in which a substituent is attached at 2-position in benzene of 1-dibenzofuran instead of 4-position are improved.

This suggests that the energy level of the compound (HOMO, LUMO, T1, etc.) and deposition conditions (for example, $T_d$, etc.) are changed because the physical properties of the compound change depending on the substitution position, and this acts as a major factor (e.g. energy balance) in improving device performance, which can lead to different device results.

The above description can be equally applied to the case of using one compound of the present invention as a host, as well as when using two or more hosts and even when used in combination with other layers.

In addition, as can be seen from the device measurement results of Examples 1, 2, 5 and 6 of the present invention, it can be seen that when a substituent ($Ar_2$, $Ar_3$) attached to a heterocycle (dibenzofuran, dibenzothiophene) attached to a triazine is mutually asymmetric, device performance is further improved. It is believed that when $Ar_2$ and $Ar_3$ are mutually asymmetric, due to the non-planarity of the compound, charges are appropriately localized and the flow of the conjugate system is effectively controlled to improve the lifetime of the device.

[Example 86] Green OLED (an Emission-Auxiliary Layer)

After 2-TNATA was vacuum-deposited on the ITO(anode) layer formed on a glass substrate to form a hole injection layer with a thickness of 60 nm, NPD was vacuum-deposited on the hole injection layer to form a hole transport layer with a thickness of 60 nm. Next, compound G-1 of the present invention was vacuum-deposited to a thickness of 20 nm on the hole transport layer to form an emission-auxiliary layer and a light emitting layer with a thickness of 30 nm was vacuum-deposited on the hole transport layer by using 4,4'-N,N'-dicarbazole-biphenyl (hereinafter, "CBP") and Ir(ppy)$_3$) as adopant material in a weight ratio of 95:5. Subsequently, BAlq was vacuum-deposited with a thickness of 10 nm on the light emitting layer to form a hole blocking layer, Alq$_3$ was vacuum-deposited with a thickness of 40 nm on the hole blocking layer to form an electron transport layer. Next, LiF was deposited with a thickness of 0.2 nm on the electron transport layer to form an electron injection layer, and then Al was deposited with a thickness of 150 nm on the electron injection layer to form a cathode.

[Example 87] to [Example 116]

The OLEDs were fabricated in the same manner as described in Example 86 except that the compounds of the present invention described in the following Table 12, instead of compound G-1 of the present invention, were used as an emission-auxiliary layer material.

Comparative Example 12

The OLED was fabricated in the same manner as described in Example 86 except that an emission-auxiliary layer was not formed.

[Comparative Example 13] to [Comparative Example 16]

The OLEDs were fabricated in the same manner as described in Example 86 except that the following Comparative compounds ref 1 to ref 4, respectively, instead of compound P-1 of the present invention, were used as an emission-auxiliary layer material.

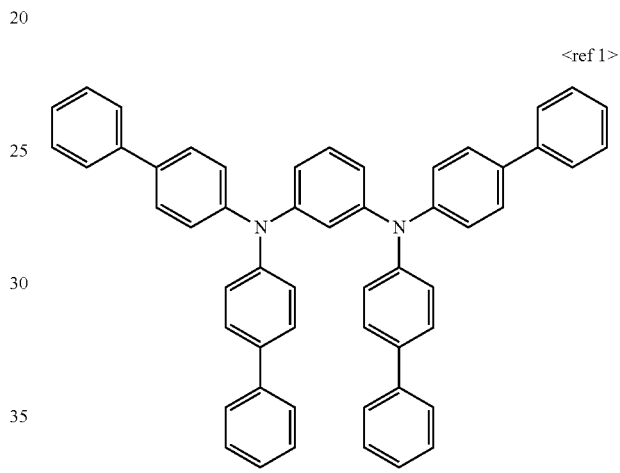

<ref 1>

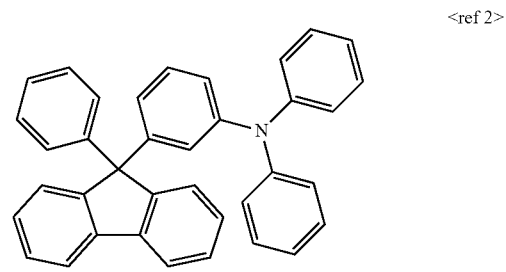

<ref 2>

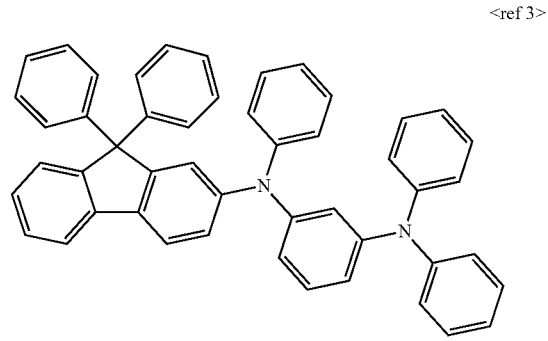

<ref 3>

<ref 4>

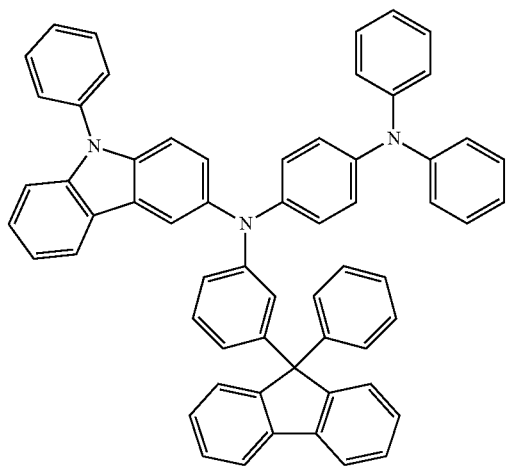

Electroluminescence (EL) characteristics were measured with PR-650 (Photoresearch) by applying a forward bias DC voltage to the OLEDs prepared in Examples 86 to 116 of the present invention and Comparative Examples 12 to 16. And, the T95 life time was measured using a life time measuring apparatus manufactured by Mcscience Inc. at reference brightness of 5000 cd/m$^2$. The measurement results are shown in Tables 12 below.

As can be seen from the results of Table 12, when a green organic electroluminescent device was manufactured by using the compounds of the present invention as material for an emission-auxiliary layer, the driving voltage of the organic electroluminescent device is lowered, and luminous efficiency and lifetime can be improved, compared to the comparative examples not forming an emission-auxiliary layer, or using Ref 1 to Ref 4 as material of an emission-auxiliary layer. That is, in the case of Comparative Examples 13 to 16 in which the emission-auxiliary layer was formed using one of the comparative compounds ref 1 to ref 4 rather than Comparative Example 12 in which an emission-auxiliary layer was not formed, the driving voltage, efficiency, and lifetime of the device were improved.

Ref 1, Ref 3 and Ref 4 differ in the substituents connected to the nitrogen atom of the amine group in the NPB type. A phenyl derivative (biphenyl) is attached to the nitrogen atom of the amine group in Ref 1, while diphenyl fluorene is attached to the nitrogen atom in Ref 3 and Ref 4. Looking at the device characteristics of Comparative Example 13, 15, and 16 using these compounds as material of an emission-auxiliary layer, it can be seen that the device characteristics of Comparative Example 15 and 16 are superior to those of Comparative Example 13.

In addition, comparing Ref 2 and Ref 4, Ref 4 contains one additional amine group and carbazole is bound to the additional amine group, compared to Ref 2. Looking at the device characteristics of Comparative Example 14 and 16 using these compounds as material of an emission-auxiliary

TABLE 12

| | Compound | Voltage (V) | Current Density (mA/cm$^2$) | Brightness (cd/m$^2$) | Efficiency (cd/A) | Lifetime T(95) | CIE X | CIE Y |
|---|---|---|---|---|---|---|---|---|
| comp. Ex(12) | — | 5.9 | 13.6 | 5000 | 36.8 | 116.9 | 0.33 | 0.61 |
| comp. Ex(13) | ref 1 | 5.8 | 12.9 | 5000 | 38.9 | 119.2 | 0.33 | 0.61 |
| comp. Ex(14) | ref 2 | 5.6 | 11.3 | 5000 | 44.2 | 121.3 | 0.33 | 0.61 |
| comp. Ex(15) | ref 3 | 5.5 | 9.8 | 5000 | 50.8 | 125.4 | 0.33 | 0.60 |
| comp. Ex(16) | ref 4 | 5.7 | 11.4 | 5000 | 43.9 | 121.8 | 0.33 | 0.61 |
| Ex. (86) | Com. G-1 | 4.8 | 7.0 | 5000 | 71.9 | 143.0 | 0.33 | 0.63 |
| Ex. (87) | Com. G-9 | 4.9 | 7.3 | 5000 | 68.5 | 139.7 | 0.33 | 0.62 |
| Ex. (88) | Com. G-14 | 4.8 | 6.9 | 5000 | 72.3 | 143.4 | 0.33 | 0.63 |
| Ex. (89) | Com. G-15 | 5.0 | 7.4 | 5000 | 67.5 | 137.8 | 0.33 | 0.63 |
| Ex. (90) | Com. G-27 | 4.6 | 6.6 | 5000 | 75.3 | 144.7 | 0.33 | 0.62 |
| Ex. (91) | Com. G-29 | 4.5 | 6.6 | 5000 | 76.3 | 145.5 | 0.33 | 0.63 |
| Ex. (92) | Com. G-39 | 4.9 | 7.2 | 5000 | 69.8 | 141.9 | 0.33 | 0.63 |
| Ex. (93) | Com. G-42 | 4.6 | 6.6 | 5000 | 75.6 | 144.5 | 0.33 | 0.63 |
| Ex. (94) | Com. G-47 | 5.1 | 7.5 | 5000 | 67.0 | 137.5 | 0.33 | 0.63 |
| Ex. (95) | Com. G-50 | 4.8 | 7.0 | 5000 | 71.1 | 142.8 | 0.33 | 0.63 |
| Ex. (96) | Com. G-51 | 4.9 | 7.4 | 5000 | 67.7 | 138.3 | 0.33 | 0.62 |
| Ex. (97) | Com. G-52 | 4.5 | 6.7 | 5000 | 74.9 | 144.9 | 0.33 | 0.62 |
| Ex. (98) | Com. G-55 | 4.9 | 7.3 | 5000 | 68.4 | 139.5 | 0.33 | 0.62 |
| Ex. (99) | Com. G-58 | 5.2 | 7.6 | 5000 | 65.8 | 136.8 | 0.33 | 0.63 |
| Ex. (100) | Com. G-66 | 4.5 | 6.6 | 5000 | 76.0 | 145.1 | 0.33 | 0.63 |
| Ex. (101) | Com. G-71 | 5.2 | 7.7 | 5000 | 65.1 | 135.3 | 0.33 | 0.62 |
| Ex. (102) | Com. G-74 | 4.9 | 7.3 | 5000 | 68.8 | 141.2 | 0.33 | 0.62 |
| Ex. (103) | Com. G-82 | 5.1 | 7.5 | 5000 | 66.4 | 137.3 | 0.33 | 0.63 |
| Ex. (104) | Com. G-99 | 5.2 | 7.6 | 5000 | 66.1 | 135.6 | 0.33 | 0.63 |
| Ex. (105) | Com. G-101 | 4.9 | 7.2 | 5000 | 69.3 | 141.6 | 0.33 | 0.63 |
| Ex. (106) | Com. G-115 | 5.2 | 7.7 | 5000 | 64.9 | 137.0 | 0.33 | 0.62 |
| Ex. (107) | Com. G-176 | 5.2 | 7.7 | 5000 | 65.3 | 135.0 | 0.33 | 0.63 |
| Ex. (108) | Com. G-190 | 5.0 | 7.4 | 5000 | 68.0 | 138.6 | 0.33 | 0.63 |
| Ex. (109) | Com. G-193 | 5.2 | 7.7 | 5000 | 65.0 | 136.0 | 0.33 | 0.63 |
| Ex. (110) | Com. G-198 | 4.8 | 7.1 | 5000 | 70.7 | 142.4 | 0.33 | 0.63 |
| Ex. (111) | Com. G-199 | 4.8 | 7.1 | 5000 | 70.3 | 142.1 | 0.33 | 0.62 |
| Ex. (112) | Com. G-200 | 4.9 | 7.3 | 5000 | 68.2 | 139.0 | 0.33 | 0.62 |
| Ex. (113) | Com. G-201 | 4.7 | 6.7 | 5000 | 74.3 | 144.3 | 0.33 | 0.62 |
| Ex. (114) | Com. G-202 | 4.7 | 6.8 | 5000 | 73.8 | 144.1 | 0.33 | 0.62 |
| Ex. (115) | Com. G-203 | 4.7 | 6.8 | 5000 | 73.1 | 143.8 | 0.33 | 0.62 |
| Ex. (116) | Com. G-204 | 4.7 | 6.9 | 5000 | 72.6 | 143.6 | 0.33 | 0.63 | layer, it can be seen that efficiency and lifetime are similar, but the driving voltage is better in Comparative Example 14.

From these results, it can be seen that even if compounds having similar structures are used for devices, the characteristics of the devices may vary depending on the substitution position of the substituent and the type of the substituent. This seems to be due to differences in the properties of the compounds when they have different types of substituents and the position substituted, and due to these differences, the physical properties of the compound act as a major factor in improving device performance (eg, energy balance) when depositing the compound in the device manufacturing process.

Comparing the compound of the present invention and Ref 3, it is the same in that the two amine groups are bonded through an arylene linking group, and diphenylfluorene is bonded to the nitrogen atom of the amine group, but there is a difference in that the position where the nitrogen of the amine group is bonded is reverse phenyl(i.e, refers to the phenyl of the diphenyl position rather than the fluorene backbone of the 9,9-diphenylfluorene structure) in case of the present invention, while the position is the backbone benzene in case of Ref 3. Due to this difference, it can be seen that the driving voltage, lifetime, and efficiency are significantly improved when the compound of the present invention is used as material of an emission-auxiliary layer, compared to Comparative Example 15 using Ref 3.

It appears that this is because the physical properties of the compound including LUMO, HOMO, band gap and $T_1$ value are changed depending on where the amine group is attached to the diphenylfluorene and this difference in physical properties serves as a major factor influencing device characteristics when depositing a compound for forming an emission-auxiliary layer in a device manufacturing process.

In addition, comparing the device results of Examples 86, 90, 91, and 97 of the present invention, it can be seen that the driving voltage, efficiency, and lifetime of the device when a specific substituent other than a simple aryl group is substituted with a substituent of an amine group. That is, the device results of Examples 90 and 97 showed better values than Example 86, wherein a compound (G-27 or G-52) substituted with dibenzofuran or fluorene containing a hetero atom is used in Examples 90 and 97 and Compound G-1 in which a simple phenyl group was substituted with a substituent of an amine group was used as material of an emission-auxiliary layer in Example 86, and the device results of Examples 91 showed better values than Examples 90 and 97, wherein a compound G-29 in which fluorene and dibenzofuran are linked to one nitrogen atom of the amine group is used in Example 91.

Further, comparing Examples 100 and 106 of the present invention, it can be seen that the device results of Example 100 are further improved than Example 105, wherein fluorene-substituted compound G-101 at a nitrogen atom connected to diphenylfluorene is used as material of an emission-auxiliary layer in Example 105, and compound G-66 in which fluorene is substituted at a nitrogen atom of another amine group other than the nitrogen atom connected to diphenylfluorene is used as material of an emission-auxiliary layer in Example 100.

In addition, comparing Examples 86 and 102 of the present invention, it can be seen that the device results of Example 86 are further improved than Example 102 when two amine groups of the compound of the present invention are linked to each other through a phenyl linker, wherein a compound G-1 in which two amine groups are linked to the linker phenyl in a meta position is used as material of an emission-auxiliary layer in Example 86 and compound G-74 in which two amine groups are para-linked to phenyl is used as material of an emission-auxiliary layer in Example 102.

It appears that this is because when the structure of the compound is changed according to the type of substituent, the position of substitution and the method of substitution, the physical properties of the compound are changed, and as a result, physical properties are changed to improve the properties of the device when an emission-auxiliary layer is formed.

Although exemplary embodiments of the present invention have been described for illustrative purposes, those skilled in the art will appreciate that various modifications can be made without departing from the essential characteristics of the present invention. Therefore, the embodiments disclosed in the present invention are intended to illustrate the present invention, and the scope of the present invention is not limited by the embodiments. The scope of the present invention shall be construed on the basis of the accompanying claims, and it shall be construed that all of the technical ideas included within the scope equivalent to the claims belong to the present invention.

The invention claimed is:

1. A compound of Formula 1:

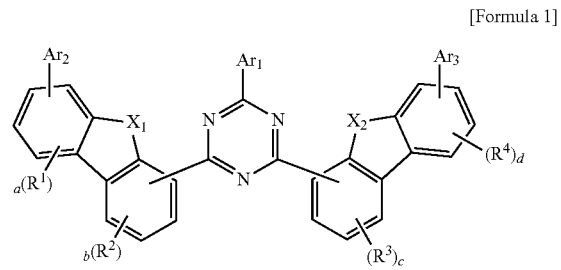

[Formula 1]

wherein:

$X_1$ and $X_2$ are each independently O or S, with the proviso that $X_1$ and $X_2$ are different from each other, $Ar_1$ to $Ar_3$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{60}$ aryloxy group and -L'-N($R_a$)($R_b$), $R^1$ to $R^4$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{60}$ aryloxy group and -L'-N($R_a$)($R_b$), and adjacent groups may be optionally linked to each other to form a $C_6$-$C_{60}$ aromatic ring, a $C_2$-$C_{60}$ heterocyclic group, a $C_3$-$C_{60}$ aliphatic ring, or a fused ring group formed by a $C_3$-$C_{60}$ aliphatic ring with a $C_6$-$C_{60}$ aromatic ring, a to d are each an integer of 0 to 3, where each of these is an integer of 2 or more, each of $R^1$s, each of $R^2$s, each of $R^3$s or each of $R^4$s is the same or different from each other, L' is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, $R_a$ and $R_b$ are each independently selected from the group consisting of hydrogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, and $Ar_1$ to $Ar_3$, $R^1$ to $R^4$, L', $R_a$, $R_b$, and the ring formed by any adjacent groups of neighboring $R^1$s to neighboring $R^4$s may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, and a $C_8$-$C_{20}$ arylalkenyl group.

2. The compound of claim 1, wherein Formula 1 is represented by one of Formula 2 to Formula 11:

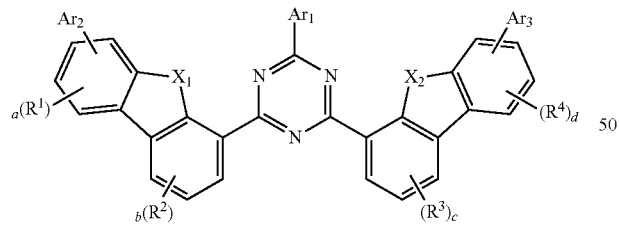

<Formula 2>

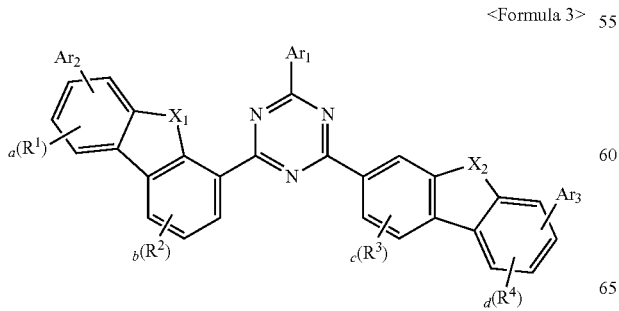

<Formula 3>

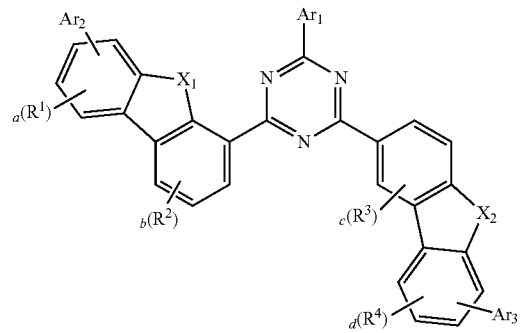

<Formula 4>

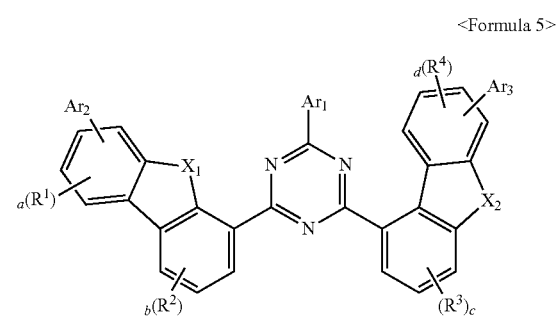

<Formula 5>

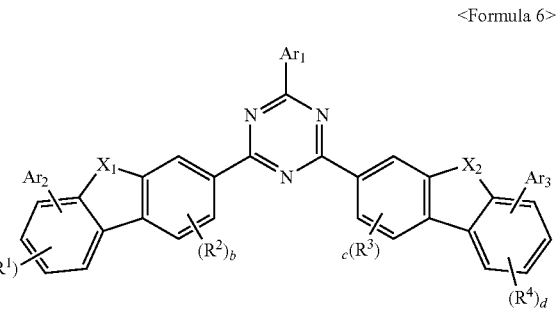

<Formula 6>

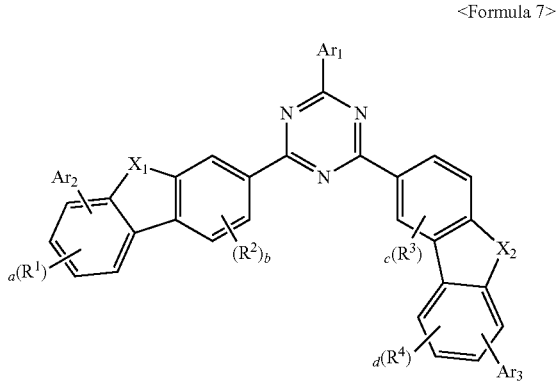

<Formula 7>

-continued

<Formula 8>

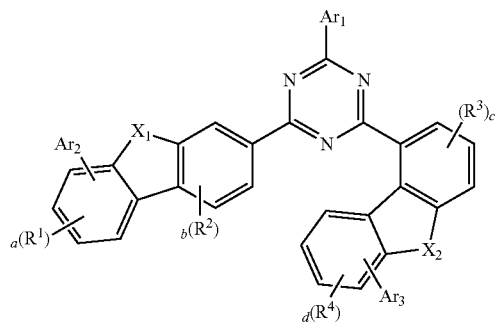

<Formula 9>

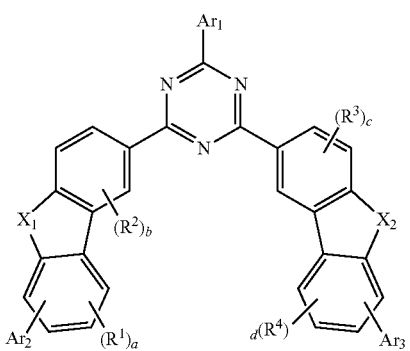

<Formula 10>

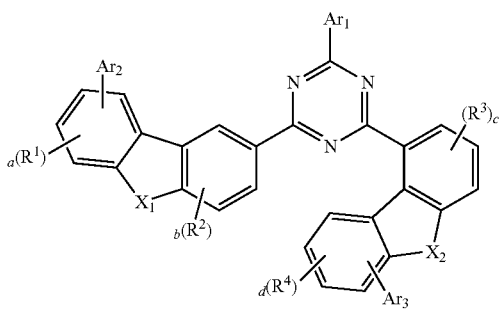

<Formula 11>

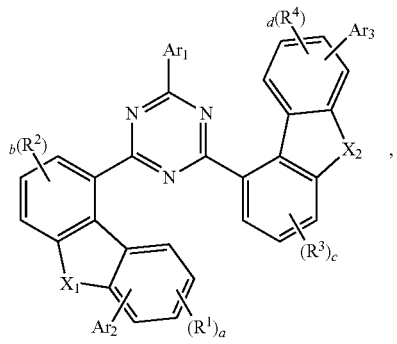

in Formulas 2 to 11, $X_1$, $X_2$, $Ar_1$ to $Ar_3$, $R^1$ to $R^4$, a, b, c and d are the same as defined in claim 1.

3. The compound of claim 1, wherein at least one of $Ar_1$ to $Ar_3$ is a $C_6$ to $C_{24}$ aryl group.

4. The compound of claim 1, wherein at least one of $Ar_1$ to $Ar_3$ is a $C_6$ to $C_{12}$ aryl group.

5. The compound of claim 1, wherein $Ar_2$ and $Ar_3$ are different from each other.

6. The compound of claim 1, wherein the compound represented by Formula 1 is one of the following compounds:

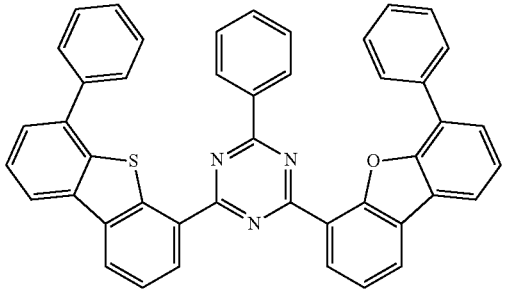
1-1

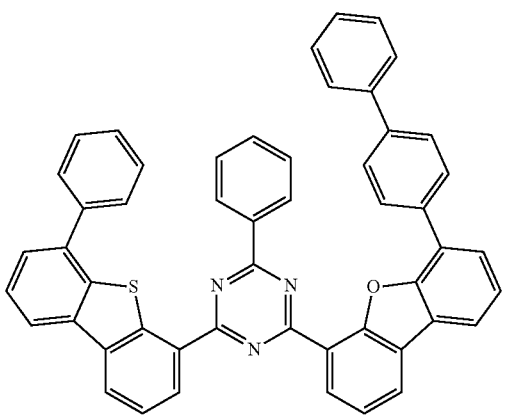
1-2

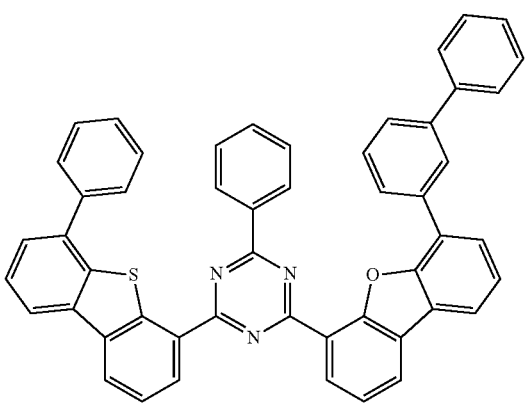
1-3

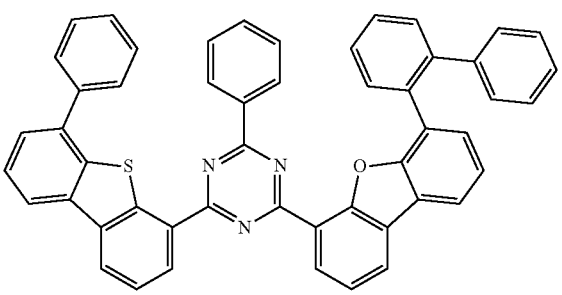
1-4

1-5
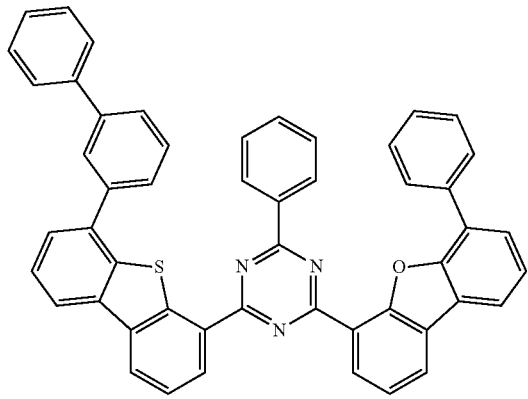
1-6
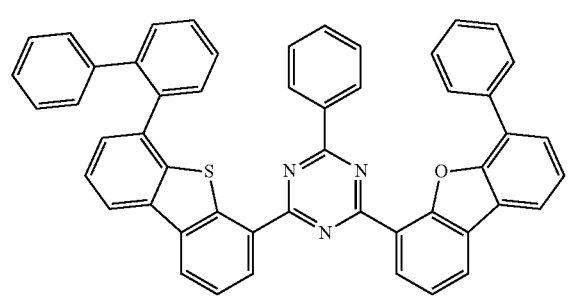
1-7
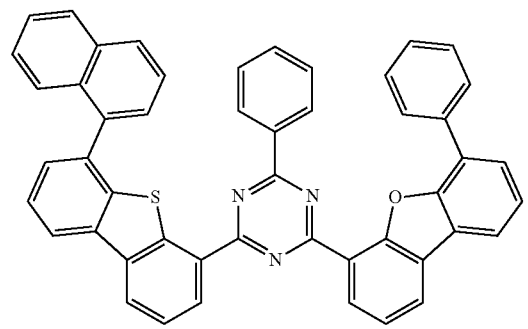
1-8
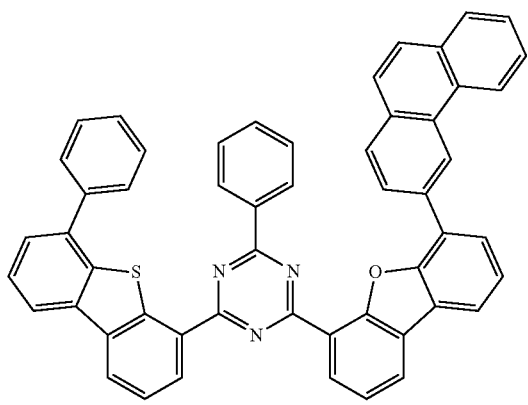
1-9
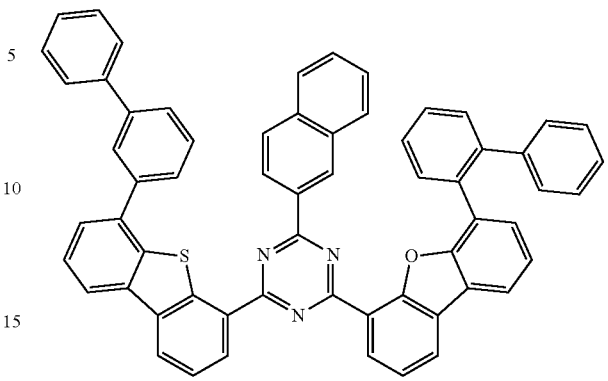
1-10
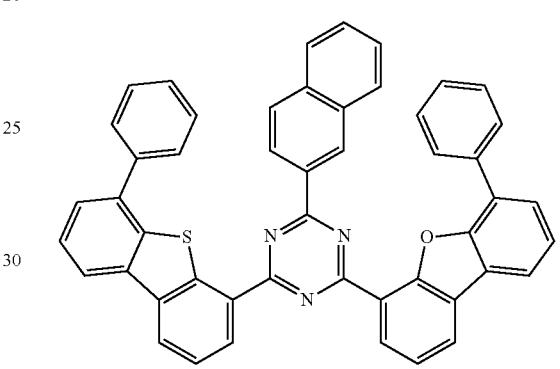
1-11
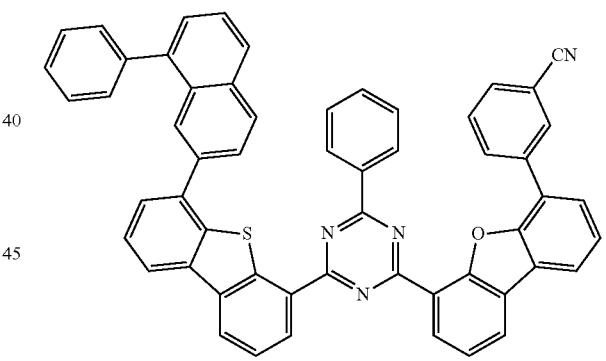
1-12
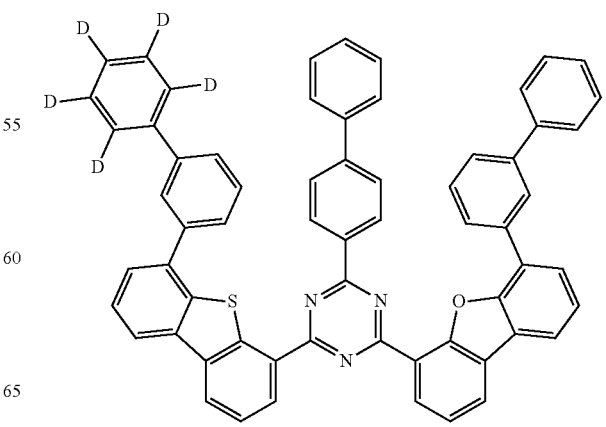

1-13
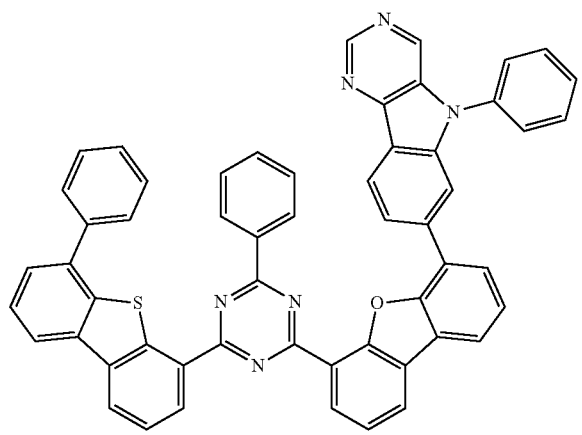
1-14
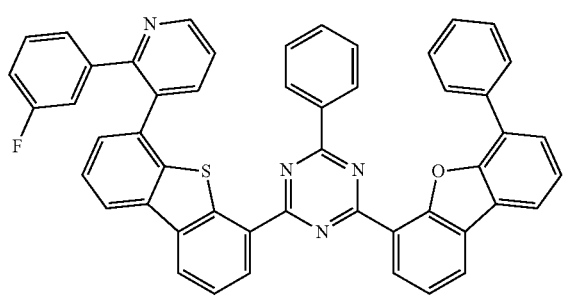
1-15
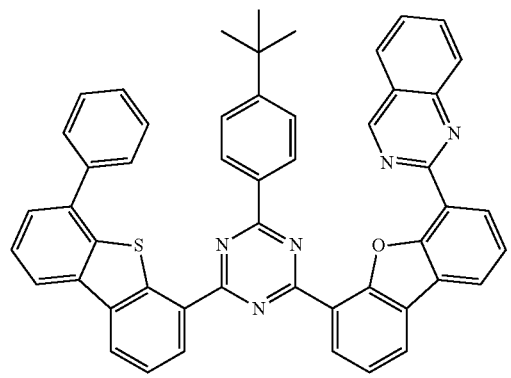
1-16
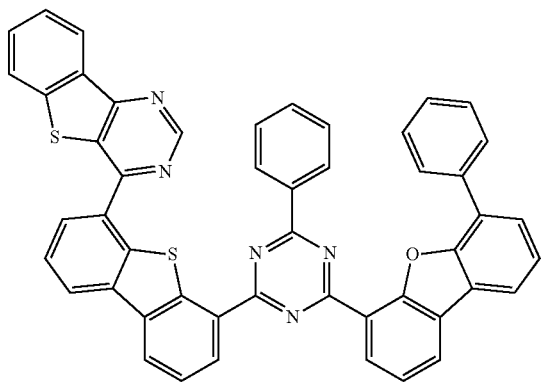
1-17
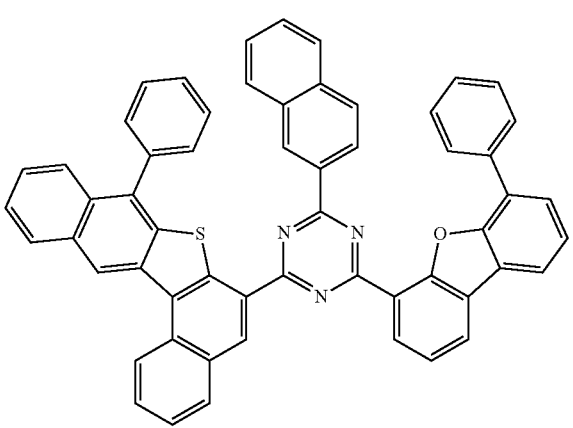
1-18
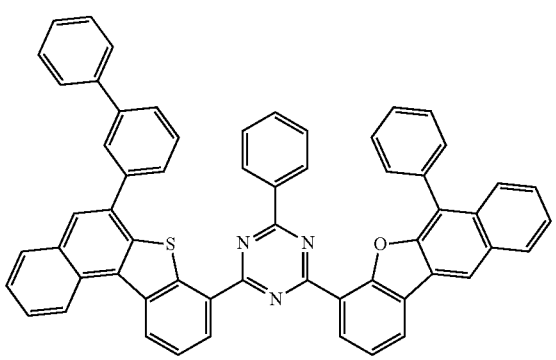
1-19
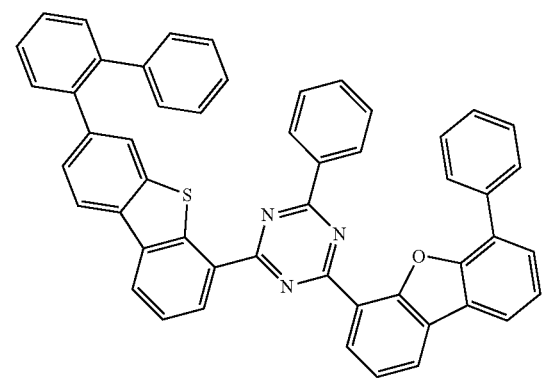
1-20
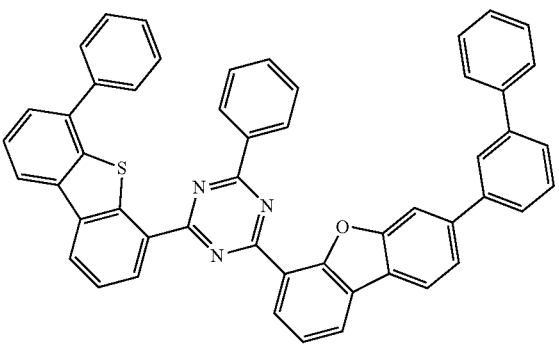

1-21
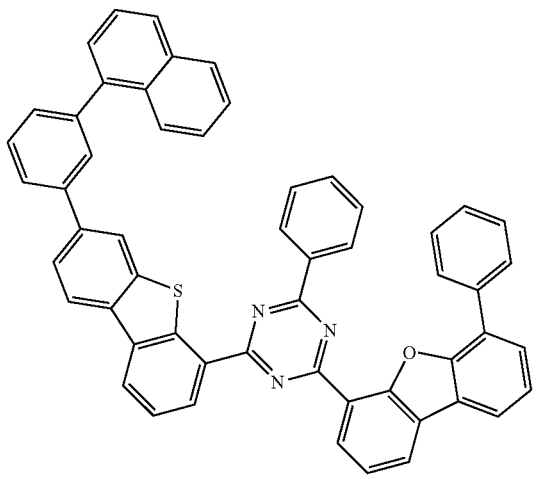
1-22
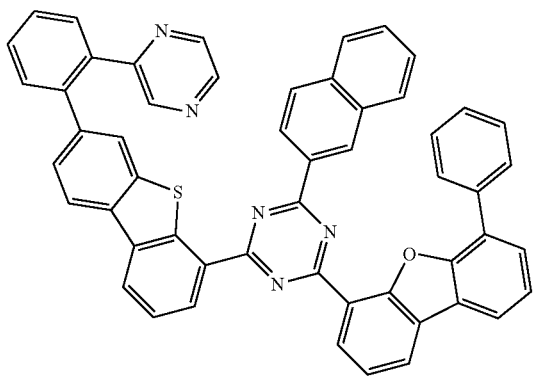
1-23
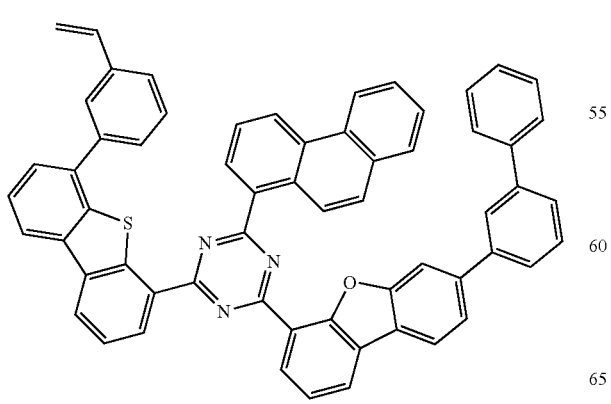
1-24
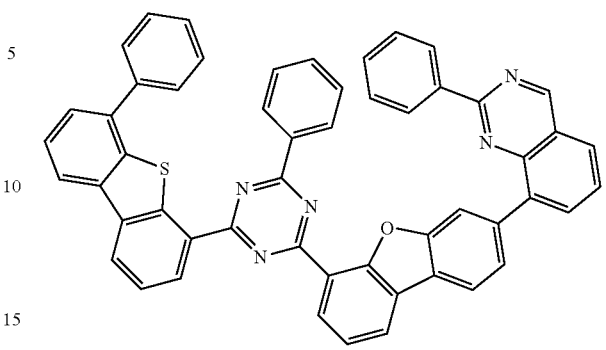
1-25
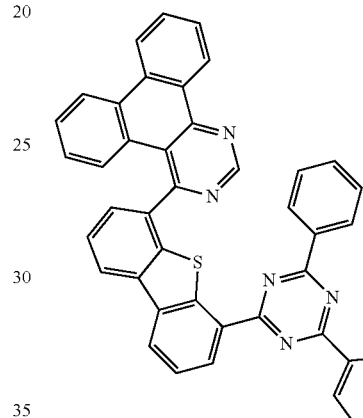
1-26
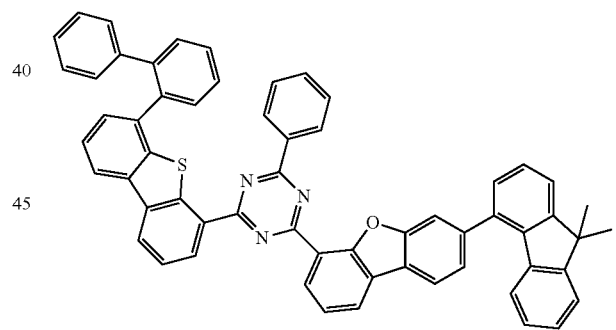
1-27
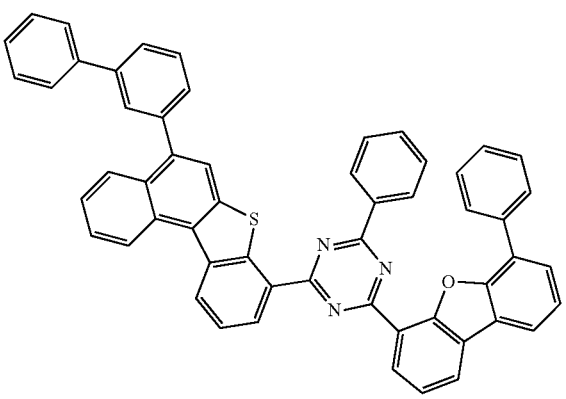

1-28
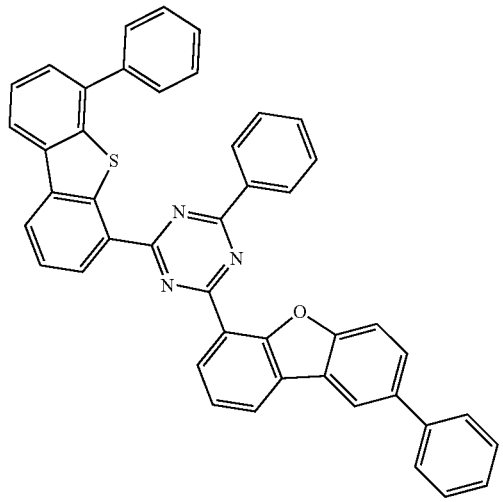
1-29
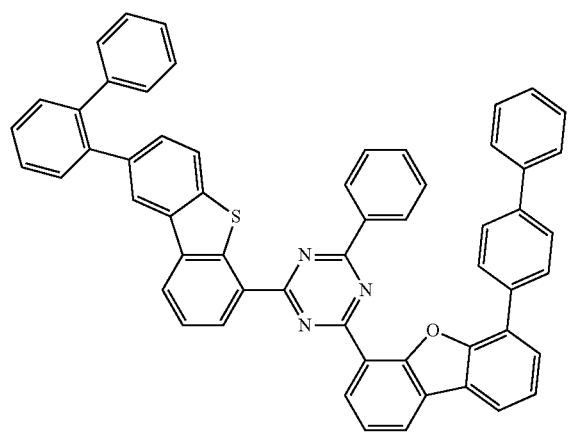
1-30
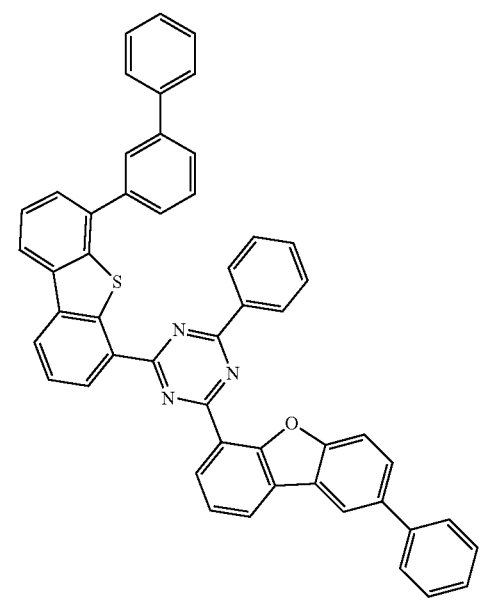
1-31
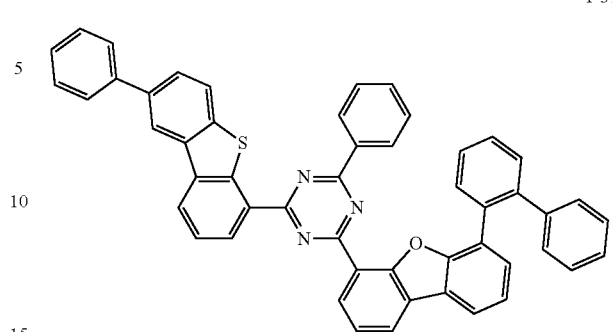
1-32
1-33
1-34
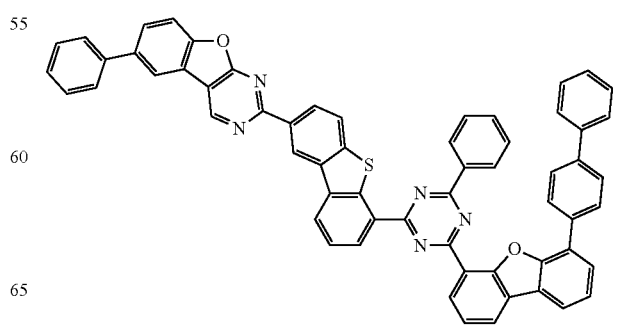

1-35
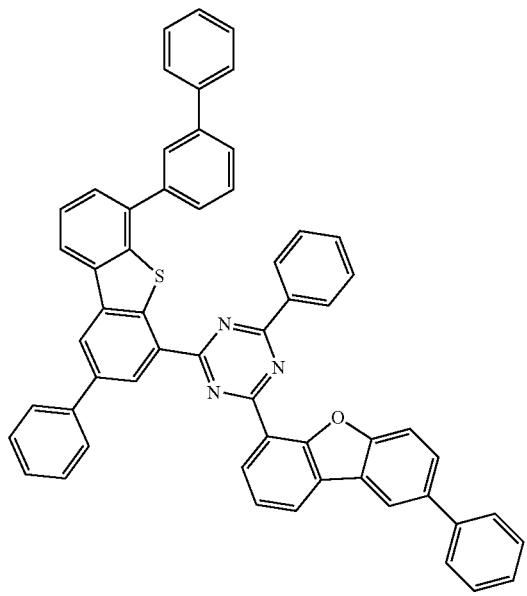
1-36
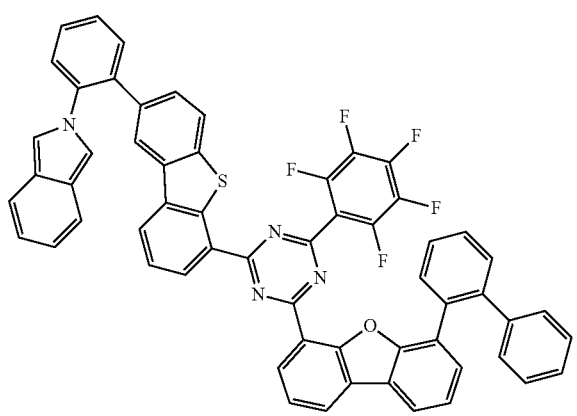
1-37
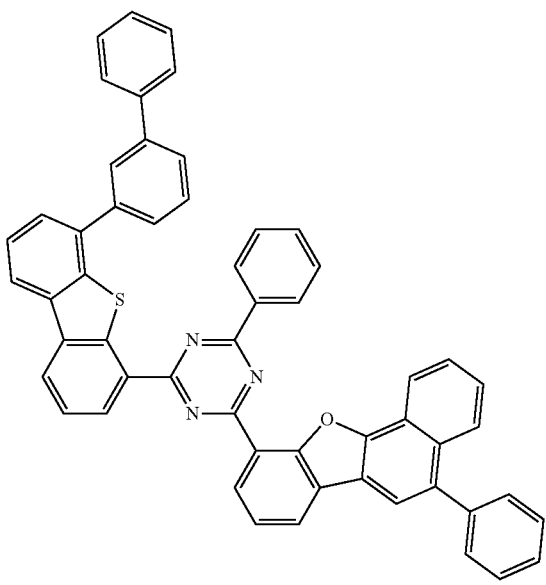
1-38
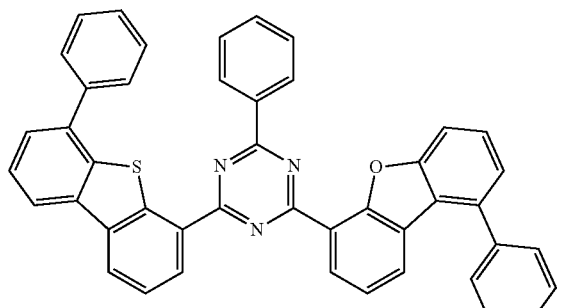
1-39
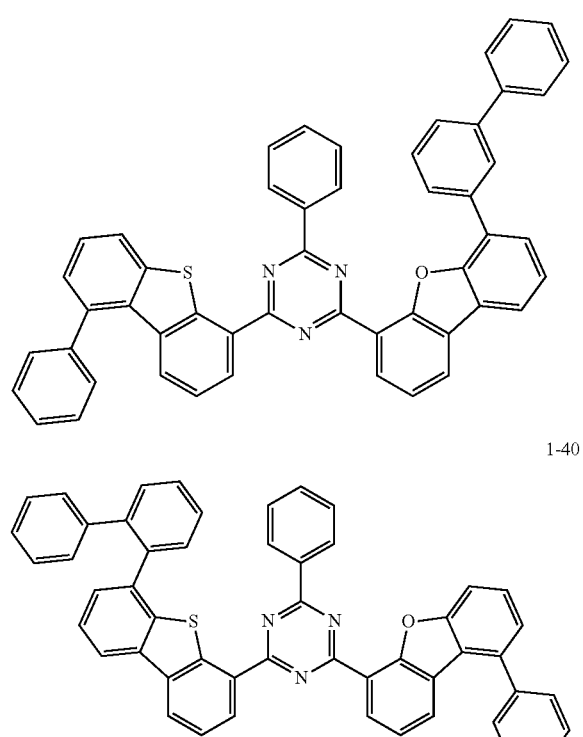
1-40
1-41
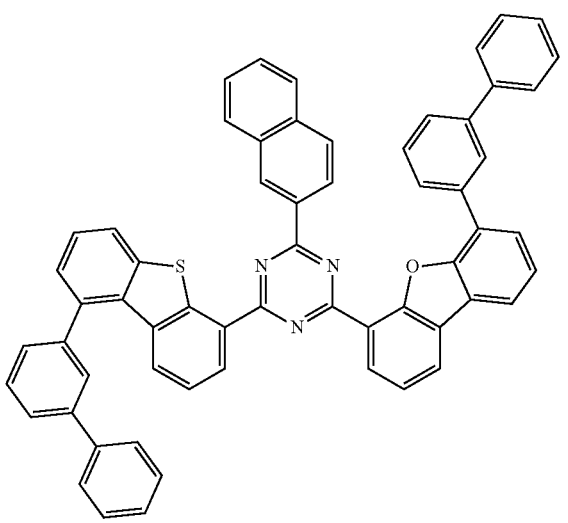

1-42
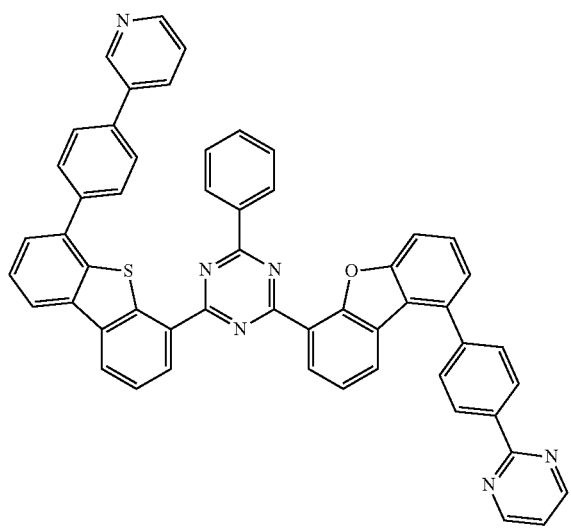
1-43
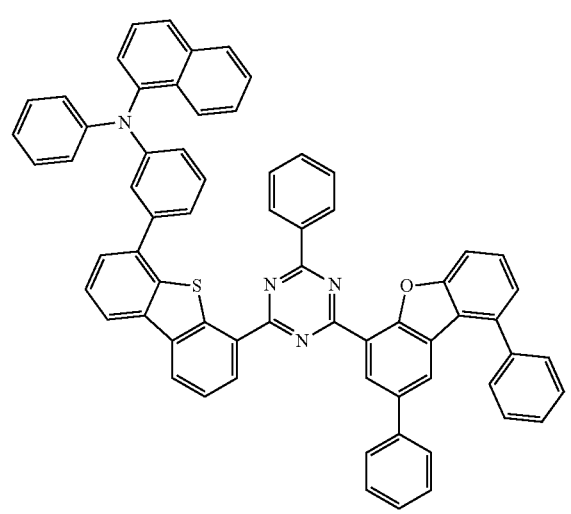
1-44
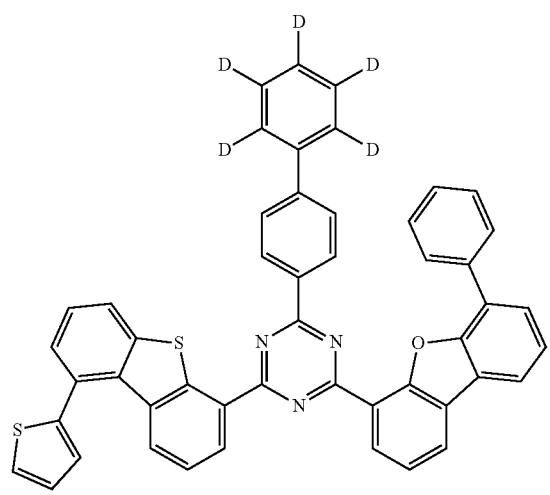
1-45
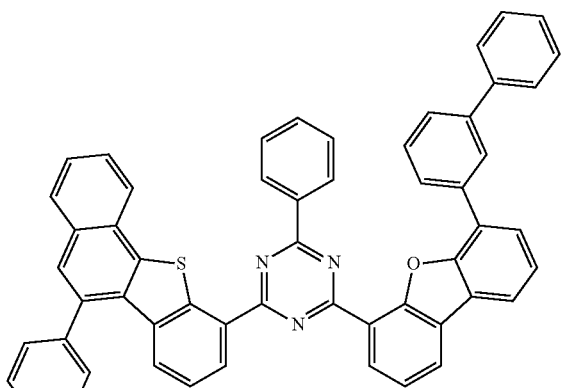
1-46
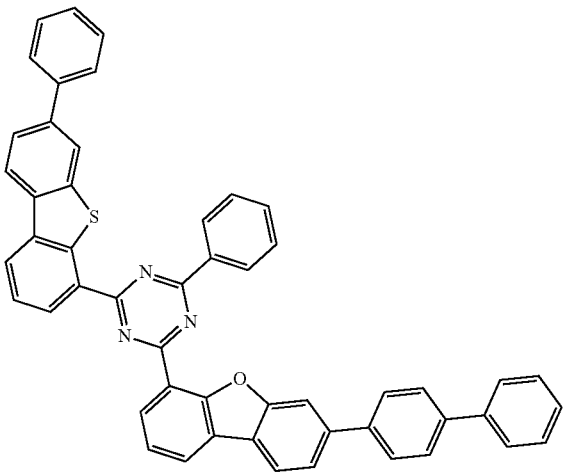
1-47

1-48
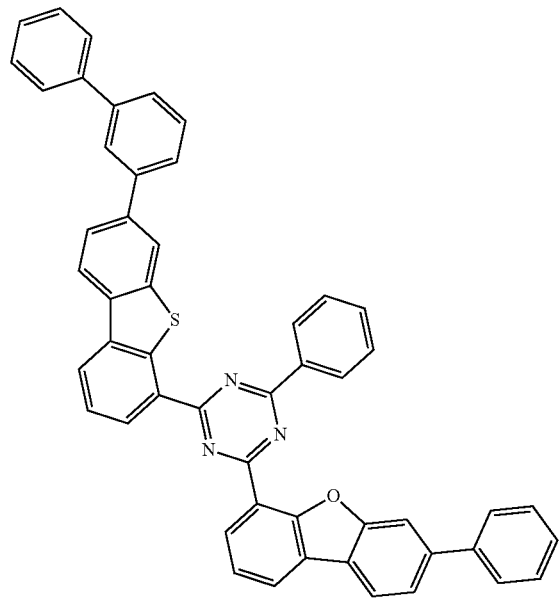
1-49
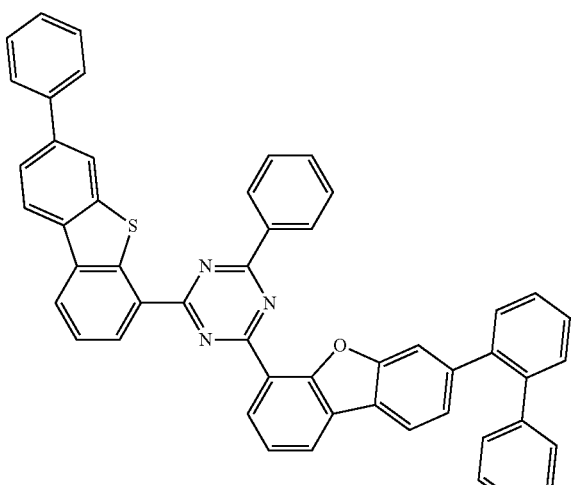
1-50
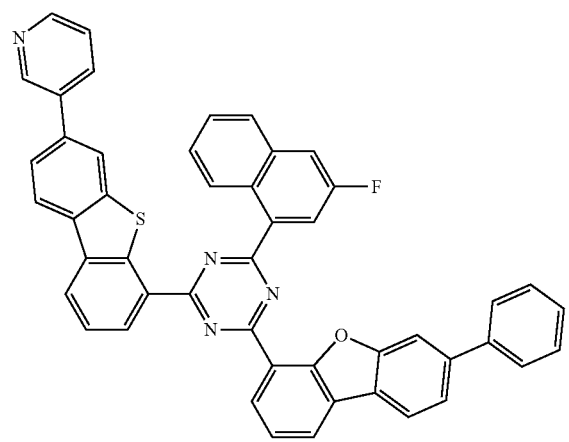
1-51
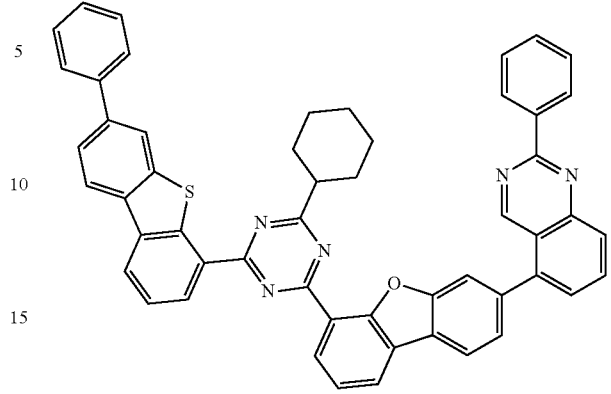
1-52
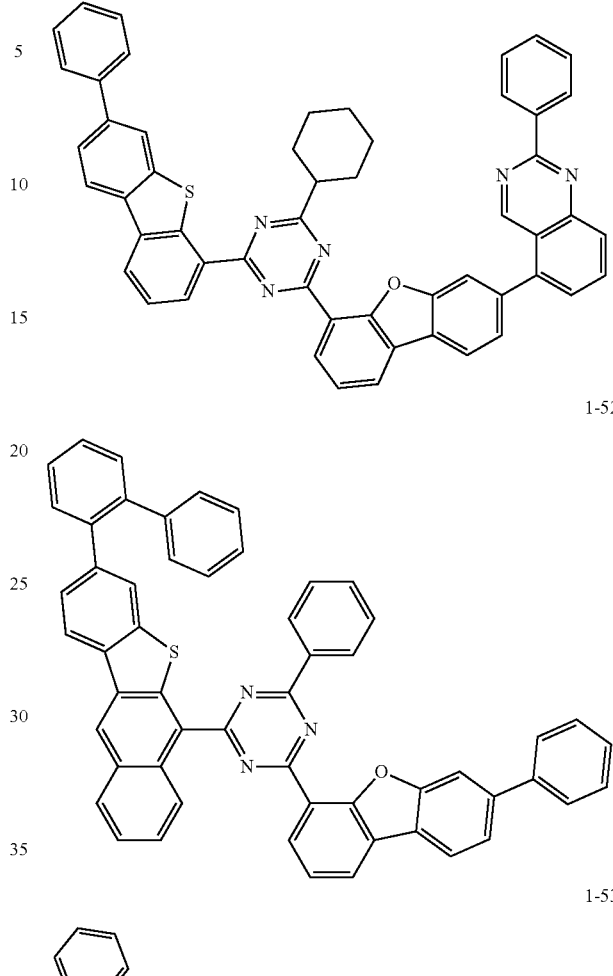
1-53
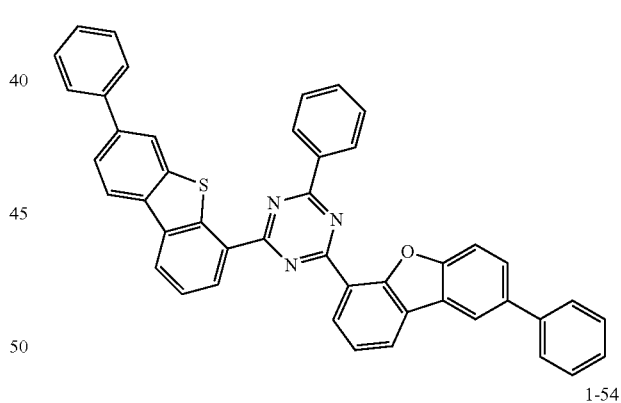
1-54
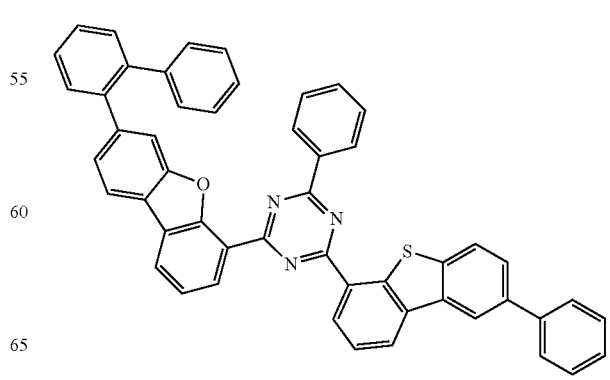

1-55
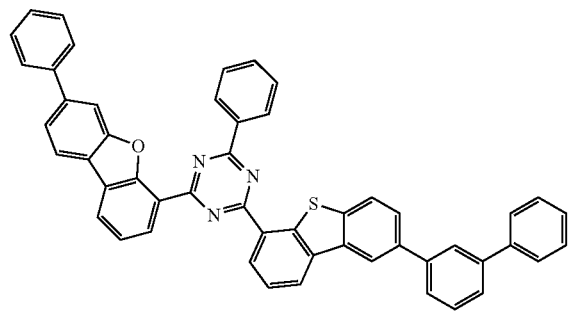
1-56
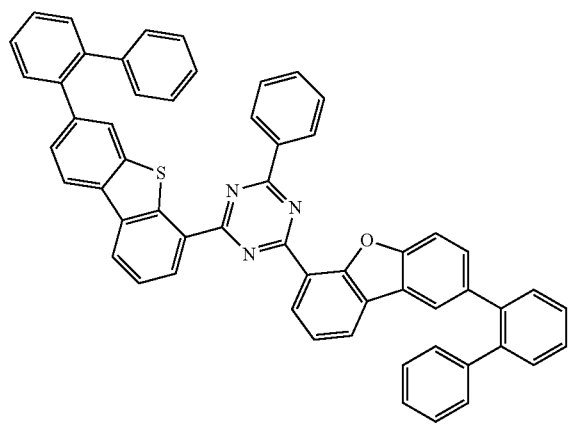
1-57
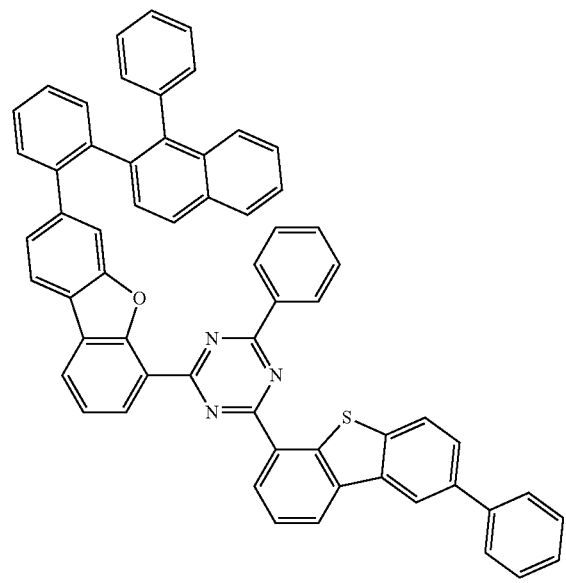
1-58
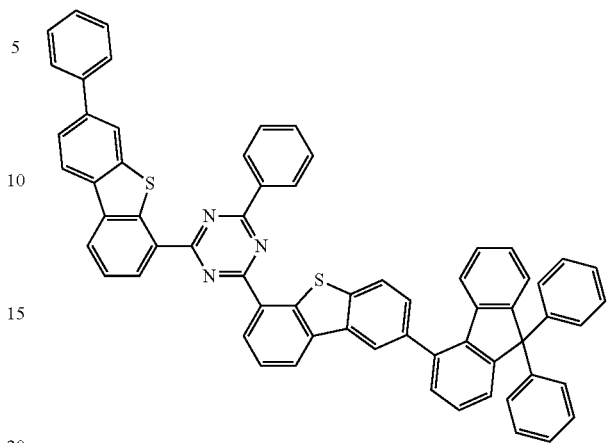
1-59
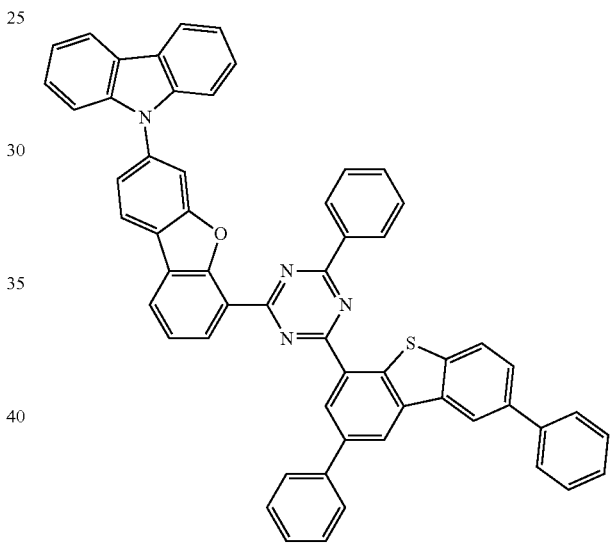
1-60
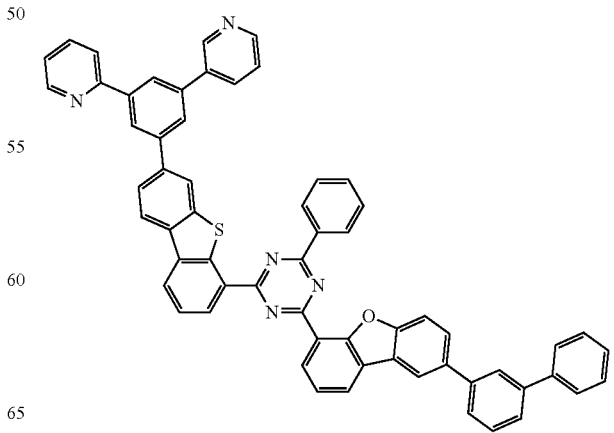

1-61
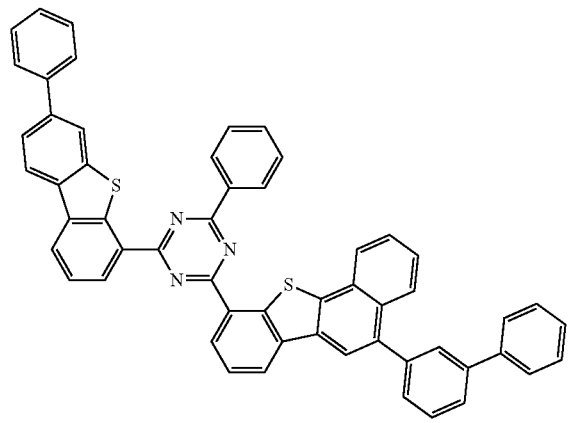
1-62
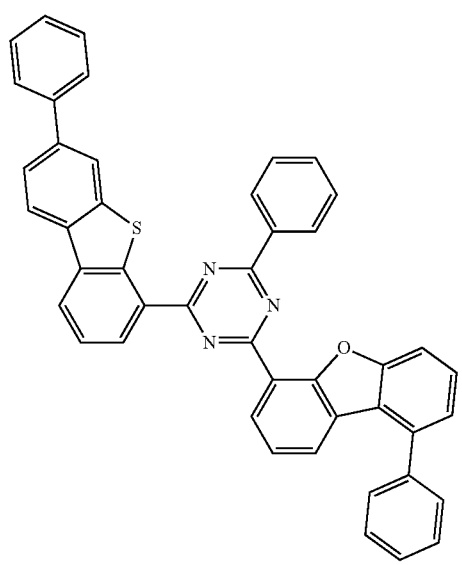
1-63
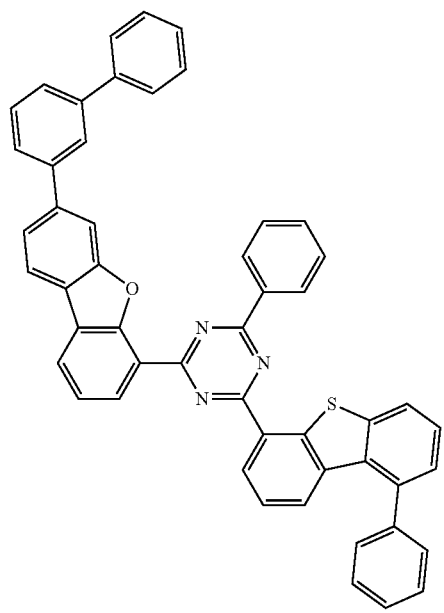
1-64
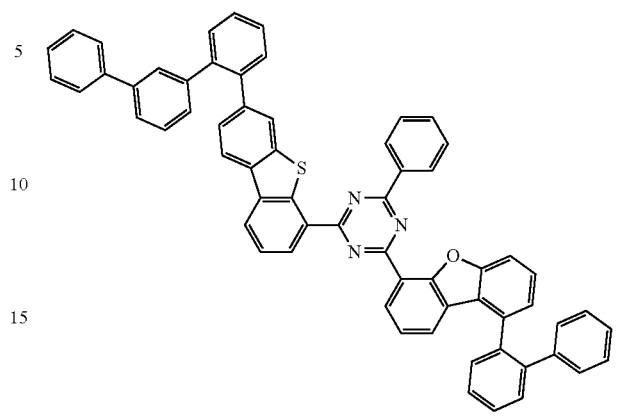
1-65
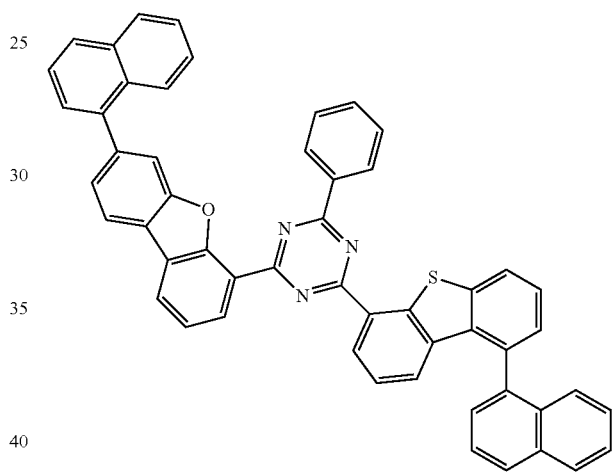
1-66
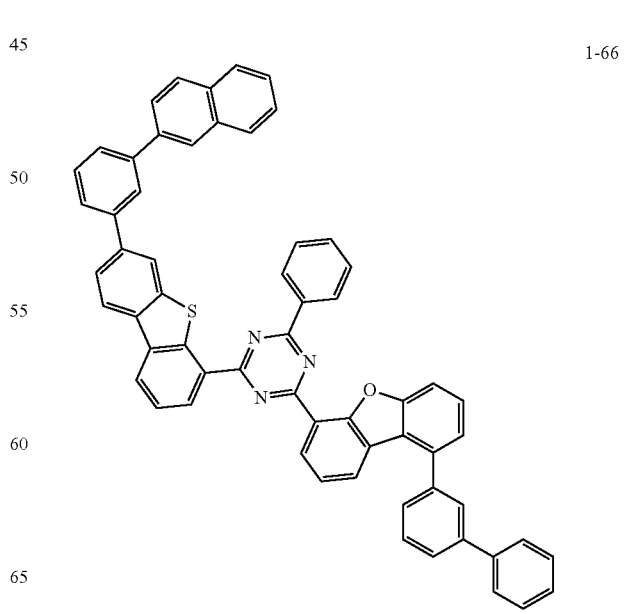

1-67
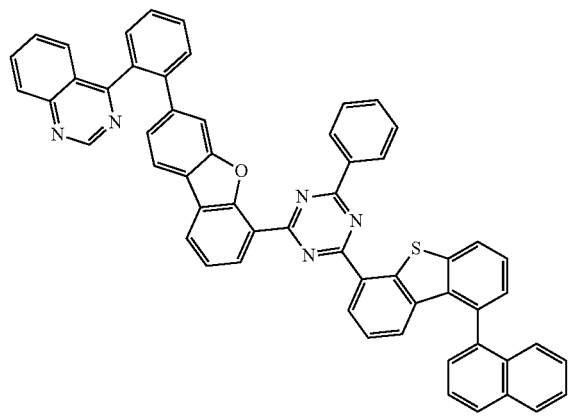
1-70
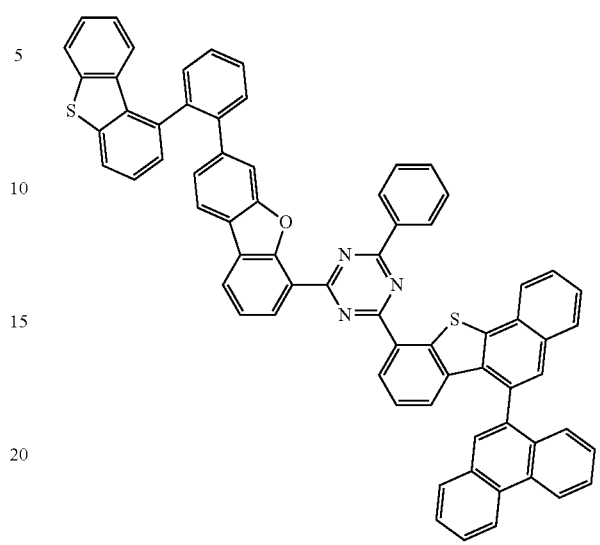
1-68
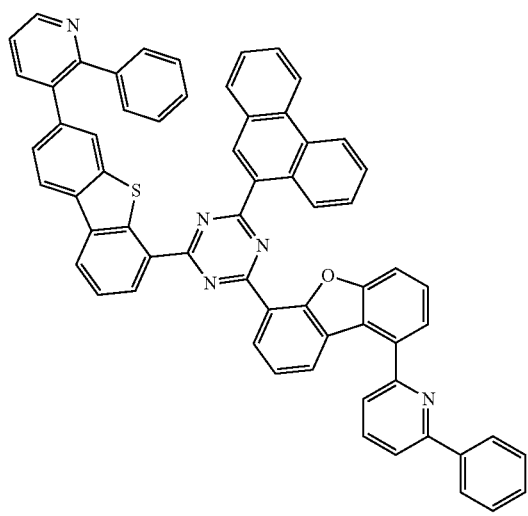
1-71
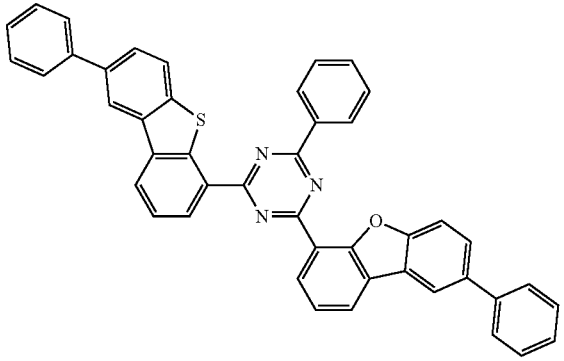
1-69
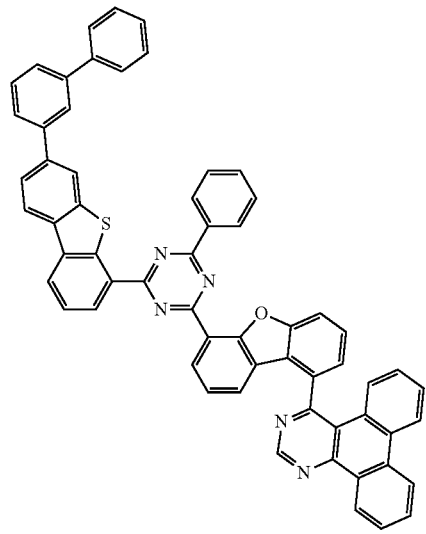
1-72
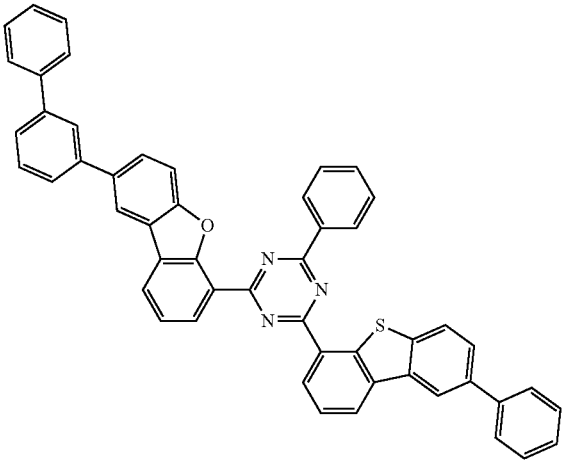

419
-continued
1-73
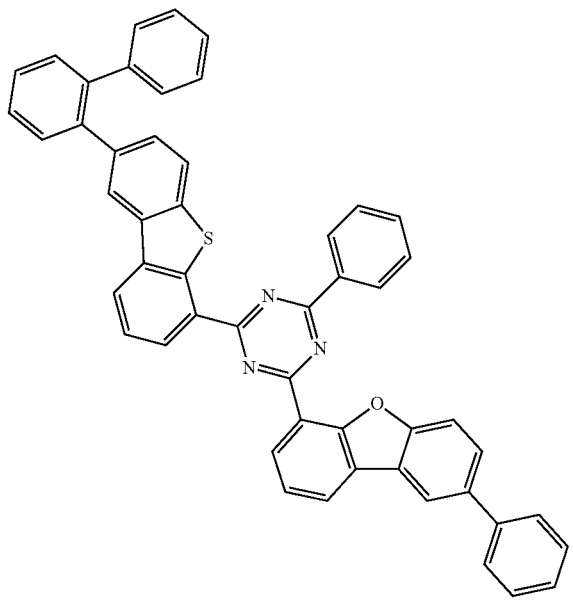
1-74
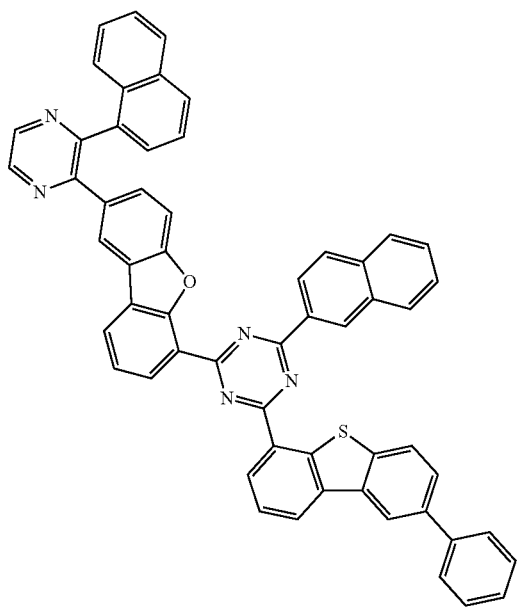
420
-continued
1-75
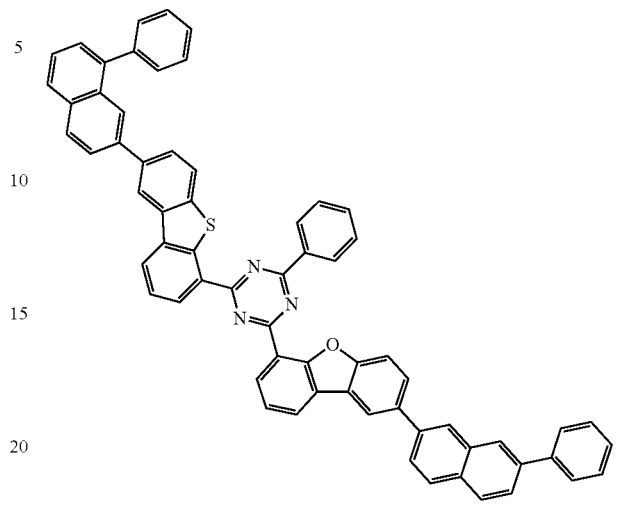
1-76
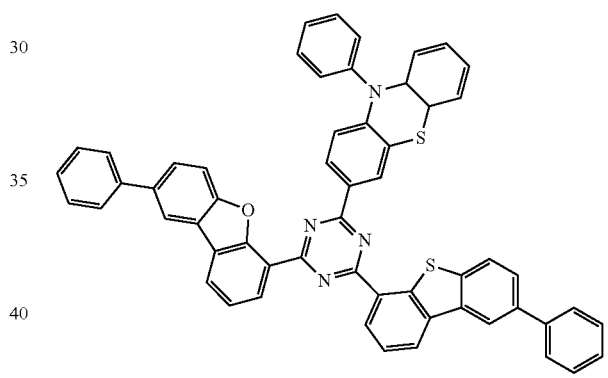
1-77
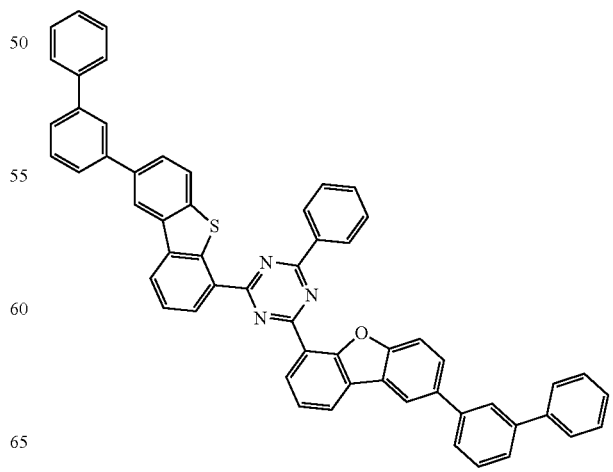

1-78
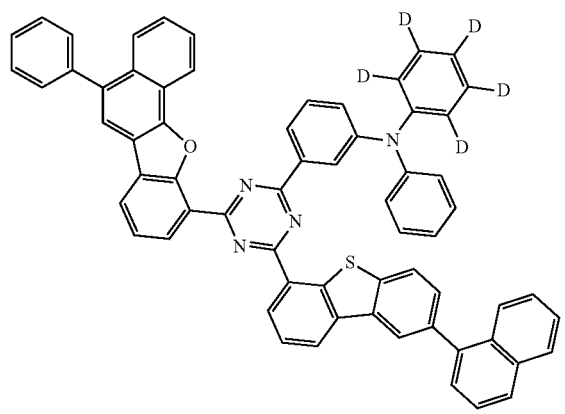
1-79
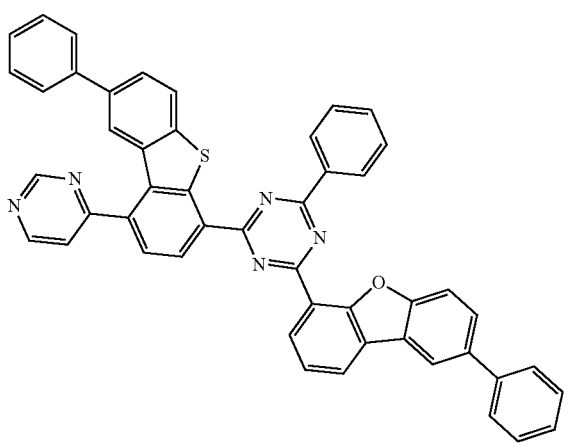
1-80
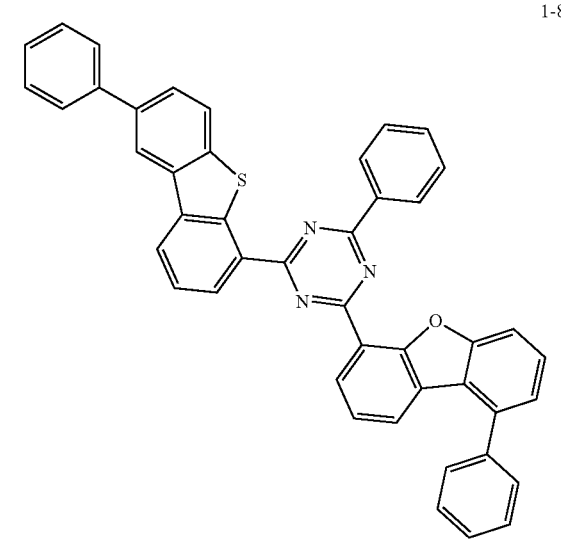
1-81
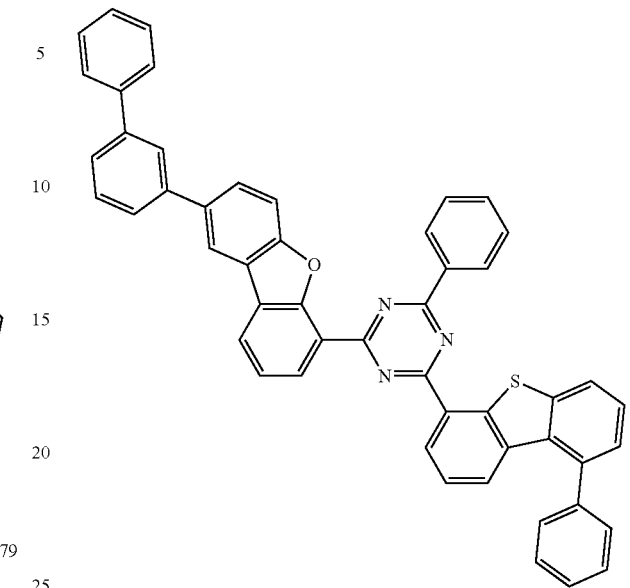
1-82
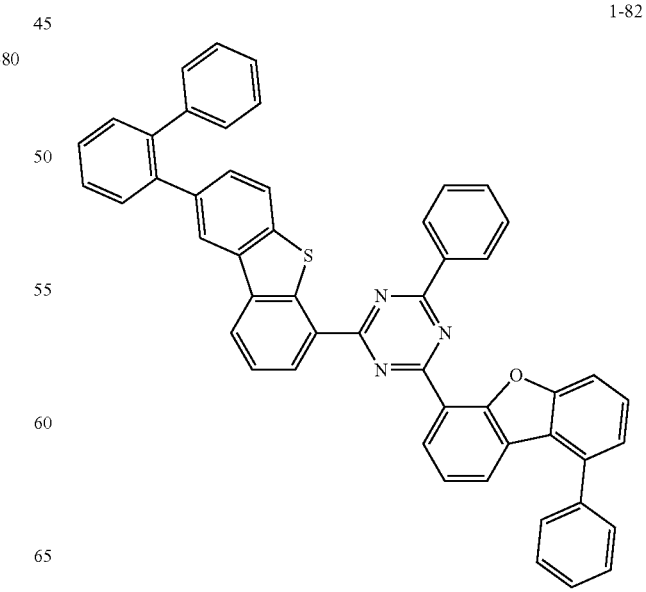

1-83
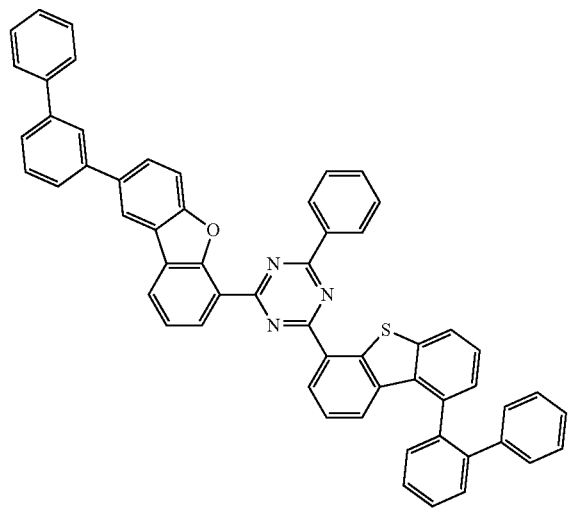
1-85
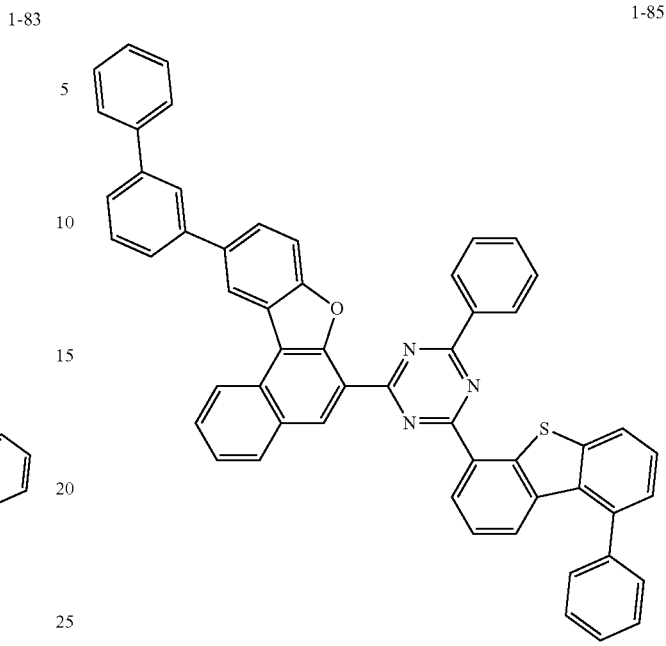
1-84
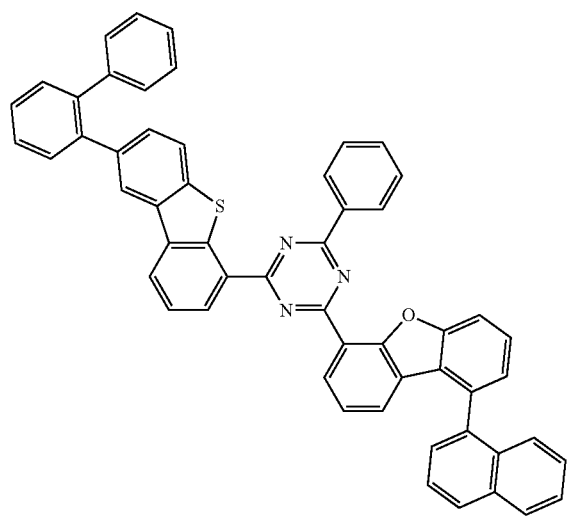
1-86
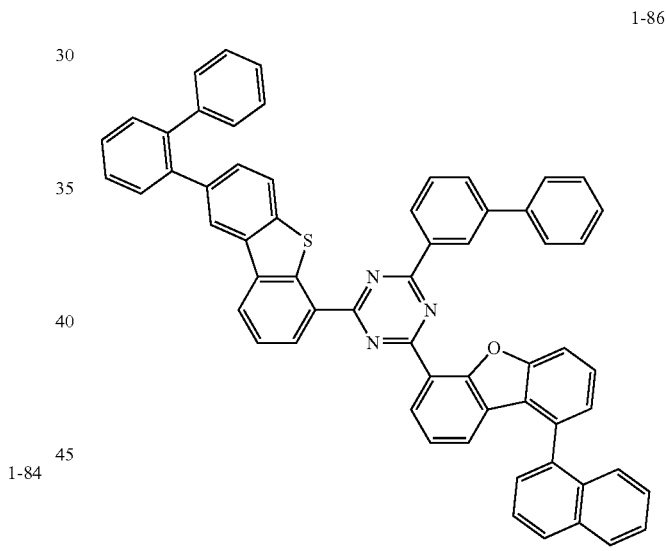
1-87
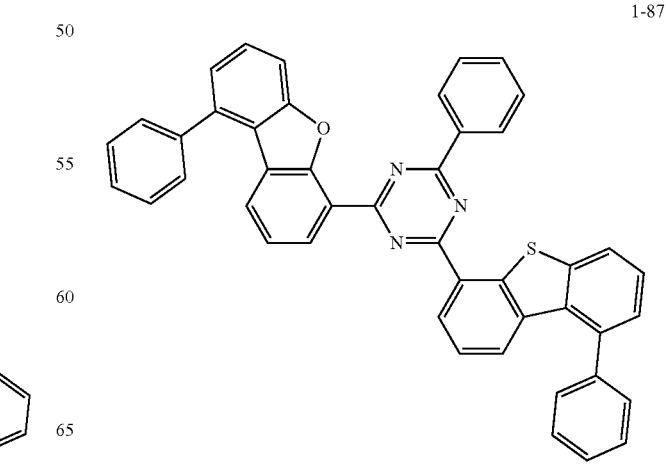

1-88
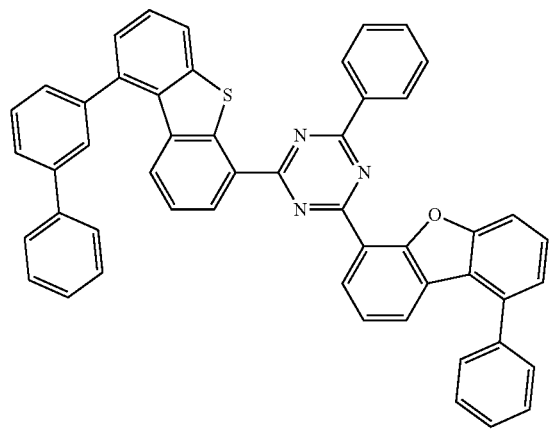
1-89
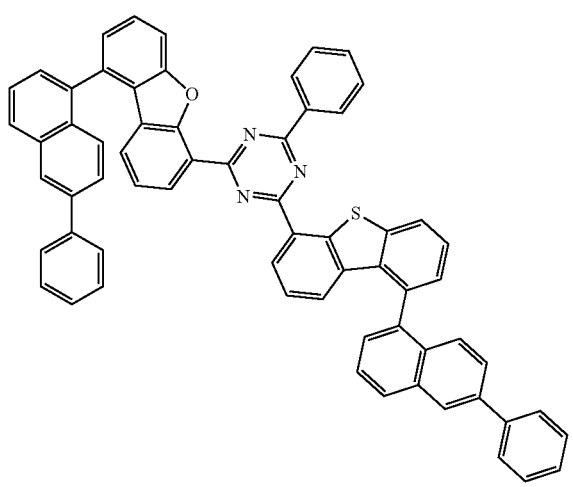
1-90
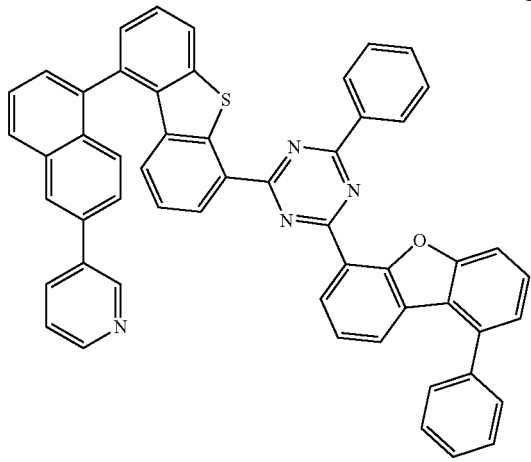
1-91
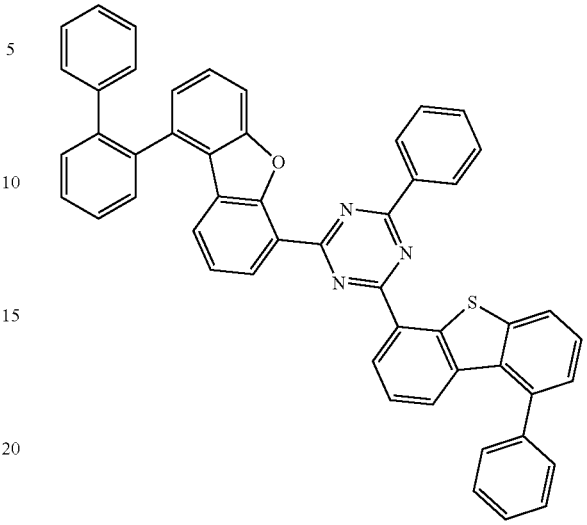
1-92
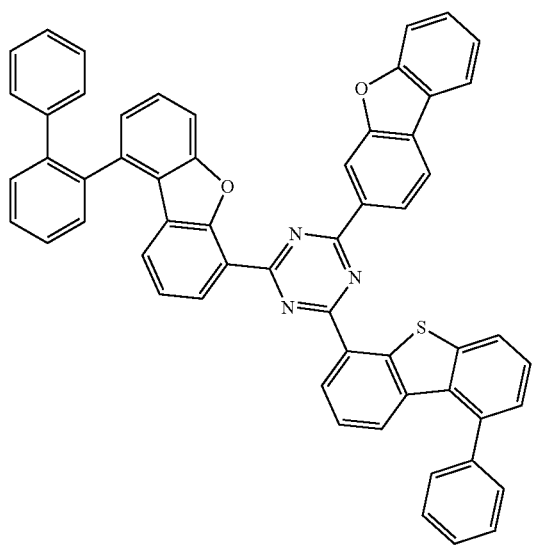
1-93

1-94
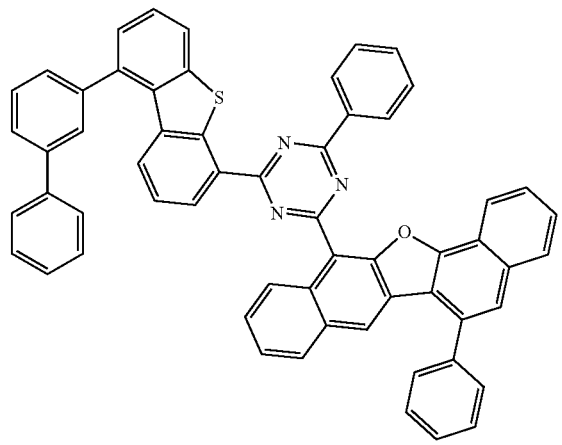
1-95
1-96
1-97
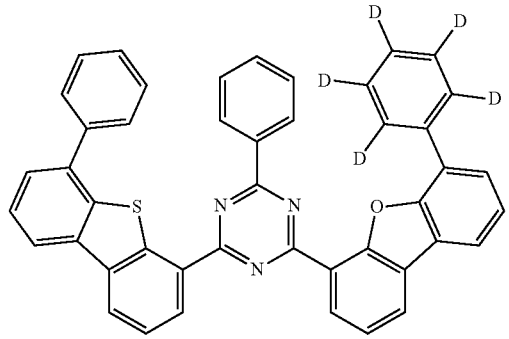
1-98
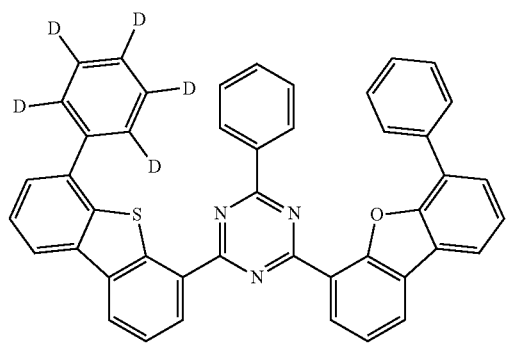
1-99
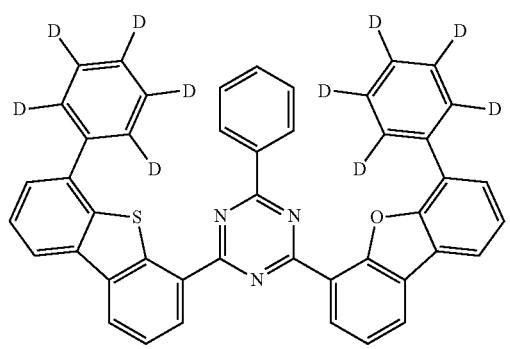
1-100
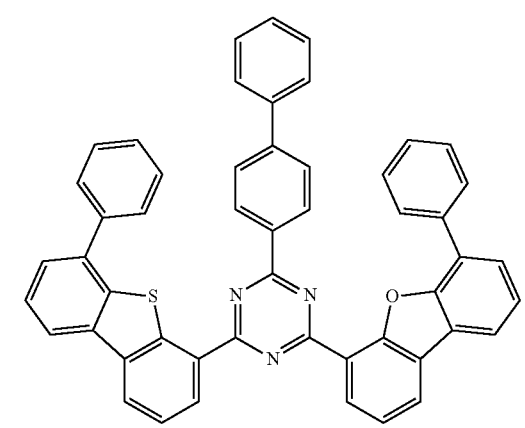

-continued
2-1
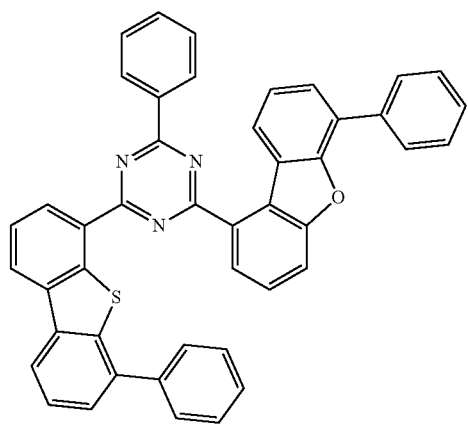
2-2
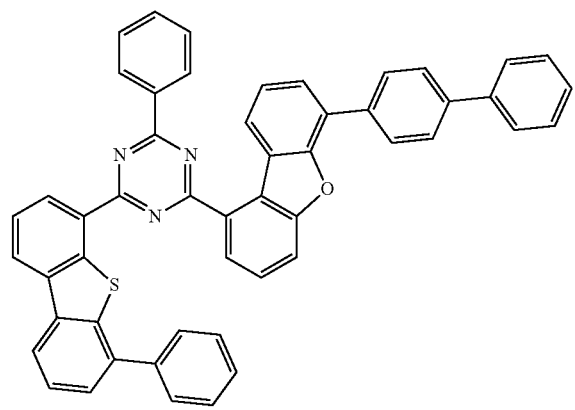
2-3
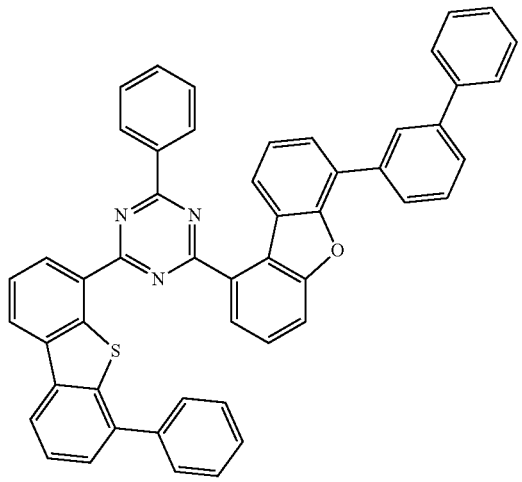
-continued
2-4
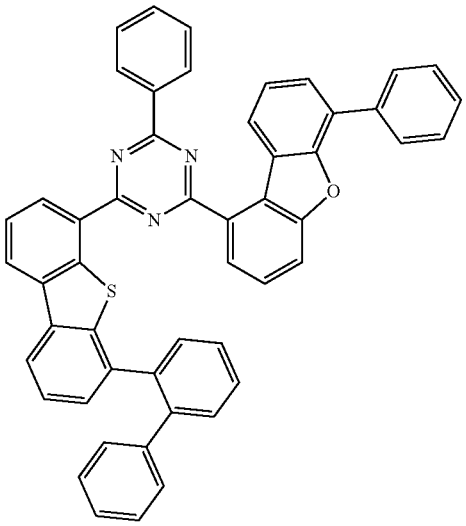
2-5
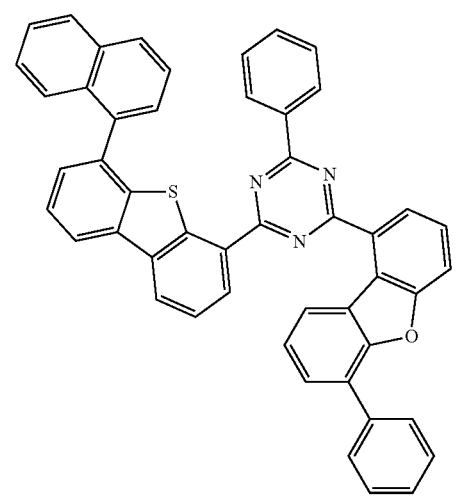
2-6
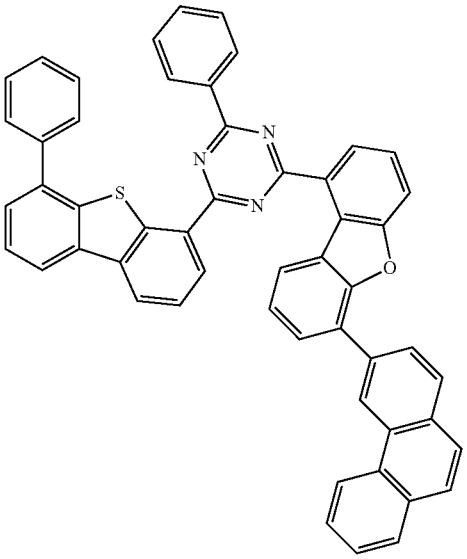

-continued
2-7
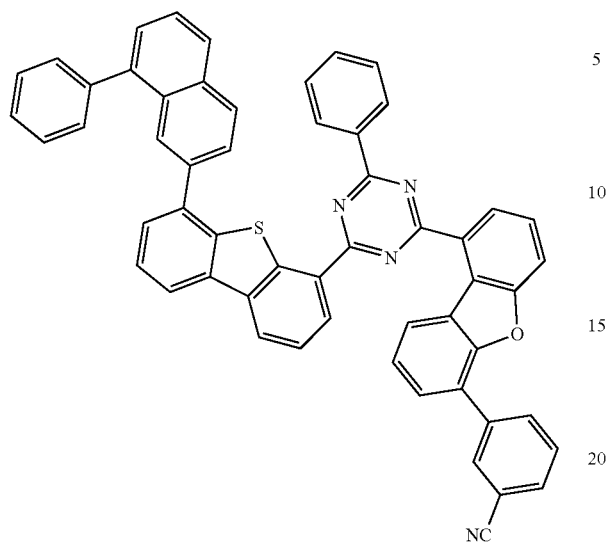
2-8
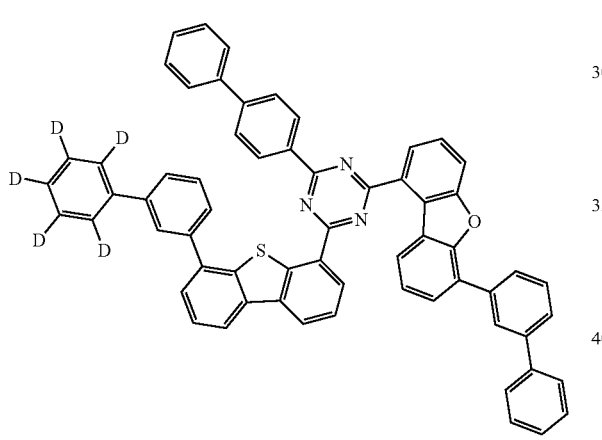
2-9
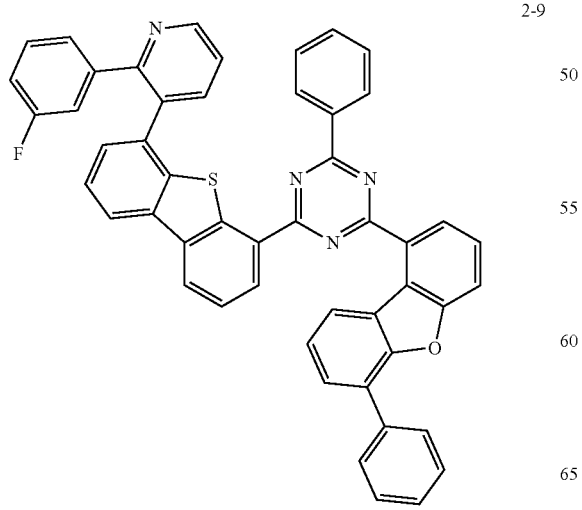
-continued
2-10
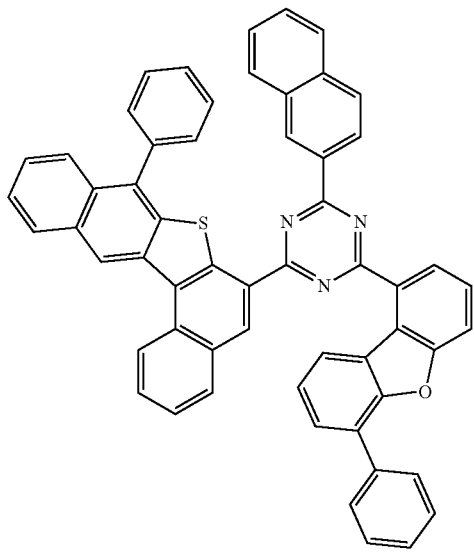
2-11
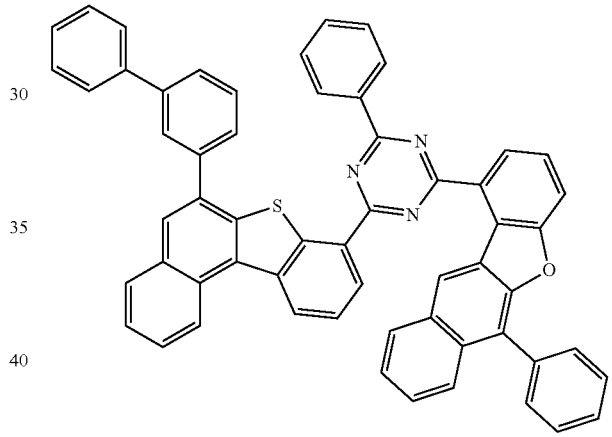
2-12
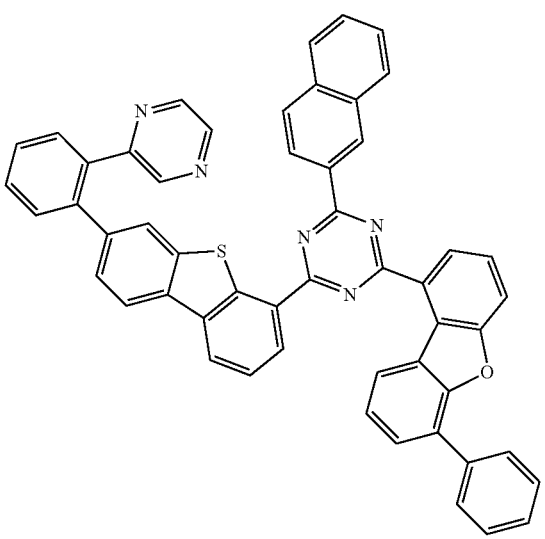

2-13
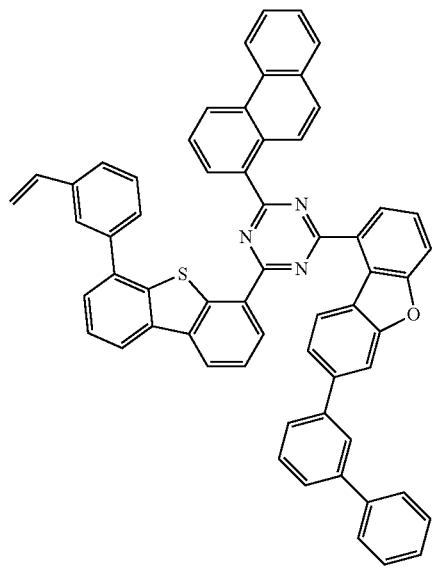
2-16
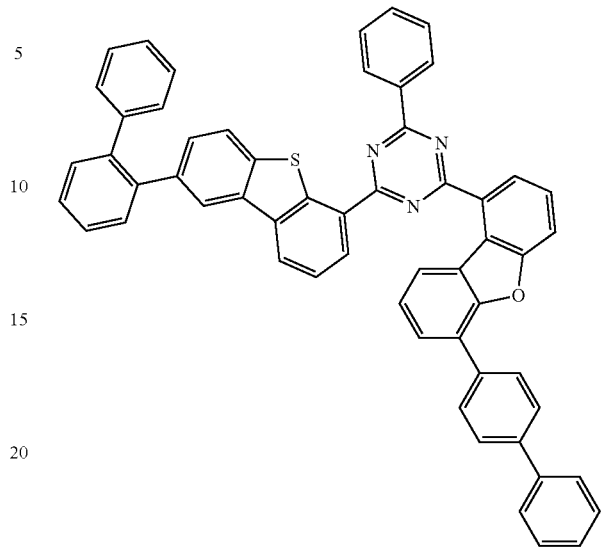
2-14
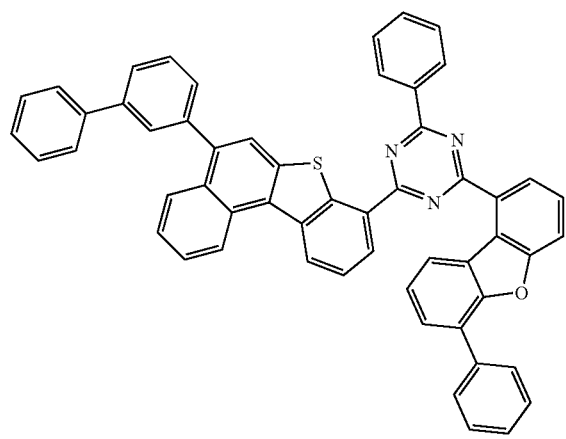
2-17
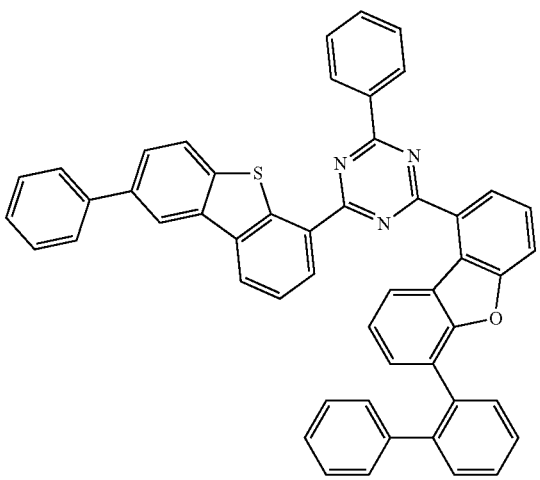
2-15
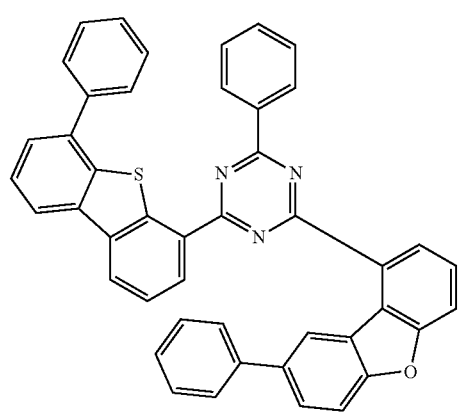
2-18
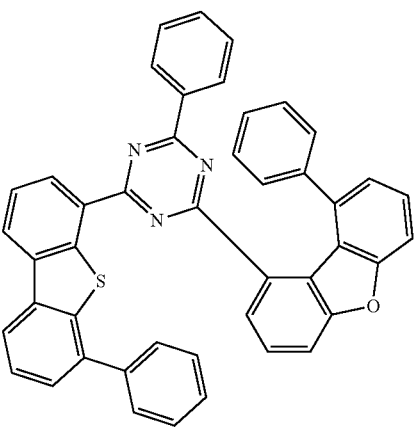

435
-continued
2-19
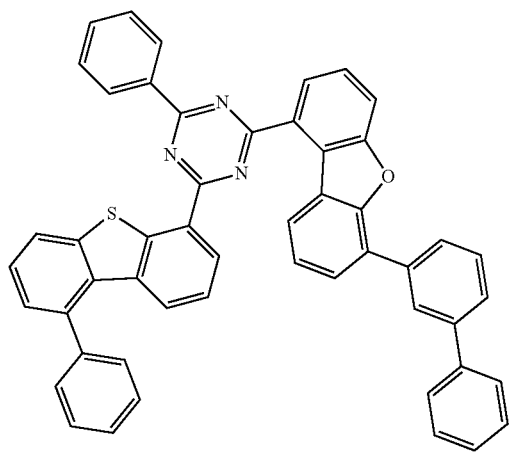
2-20
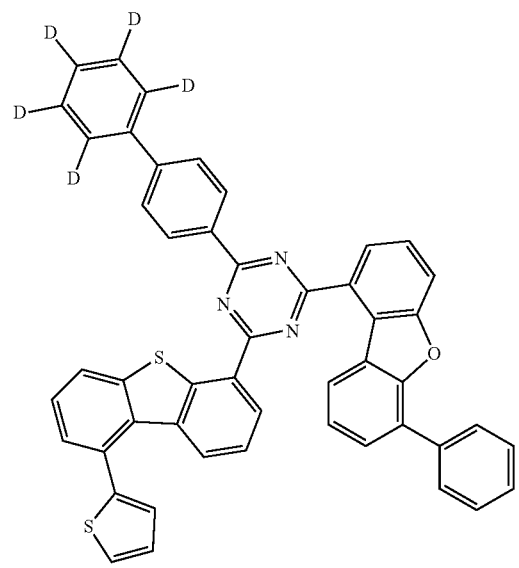
2-21
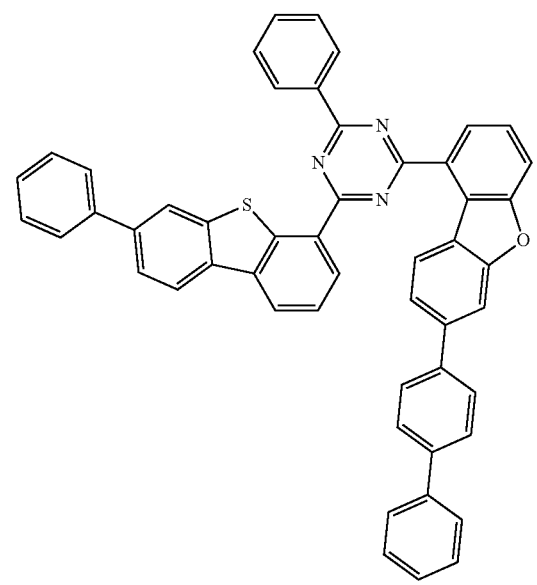
436
-continued
2-22
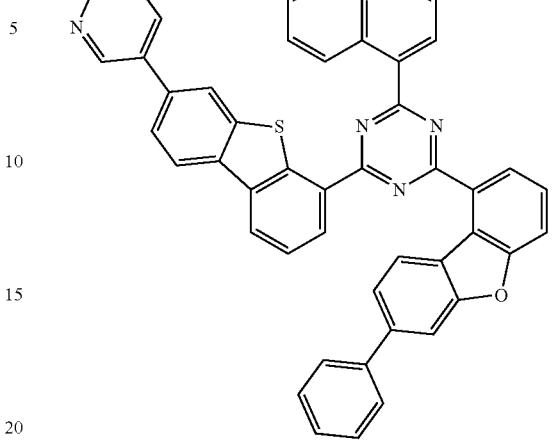
2-23
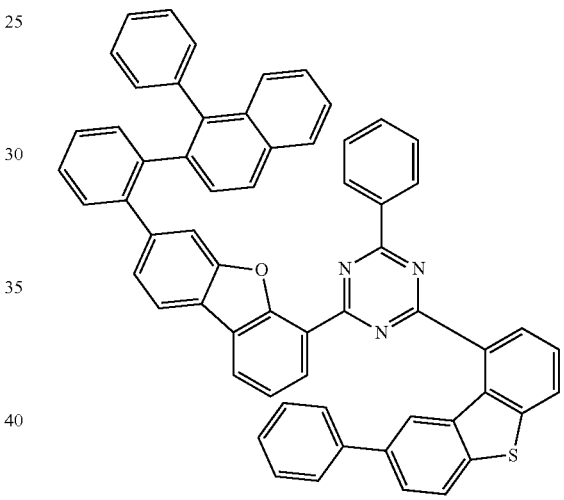
2-24
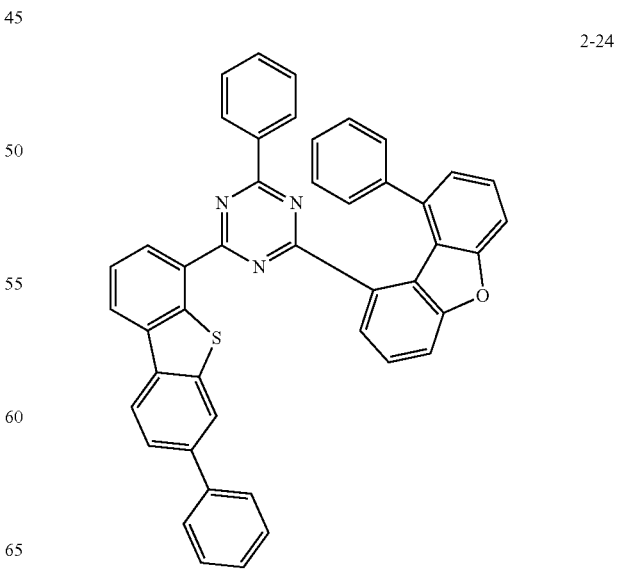

2-25
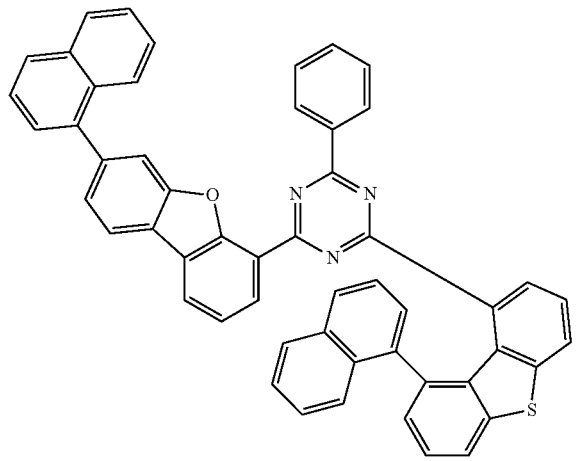
2-26
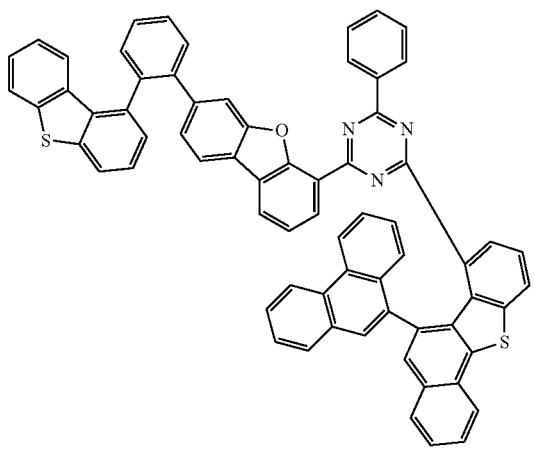
2-27
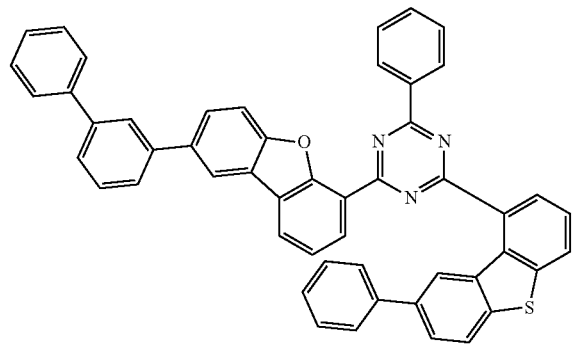
2-28
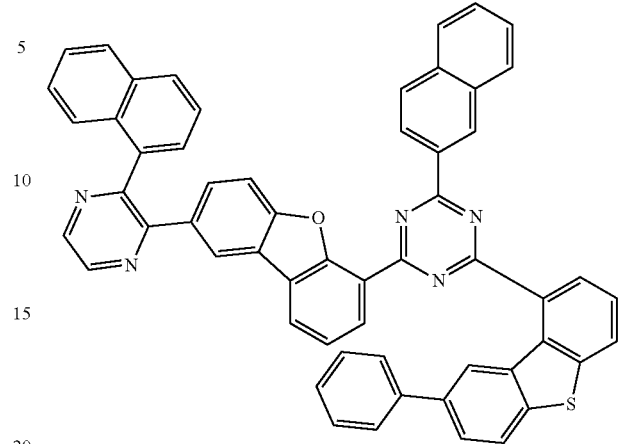
2-29
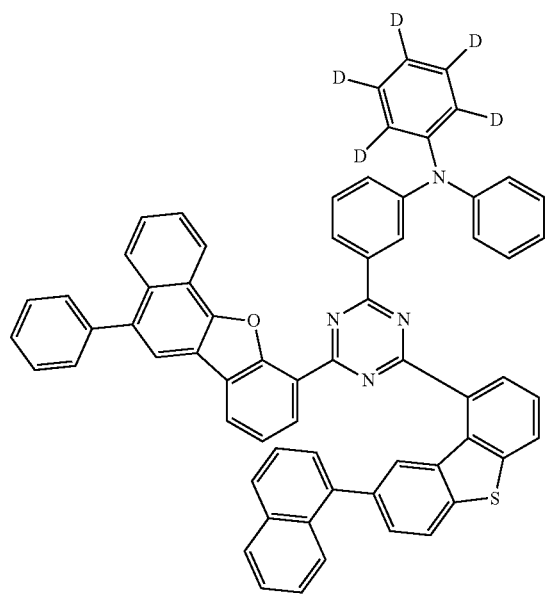
2-30
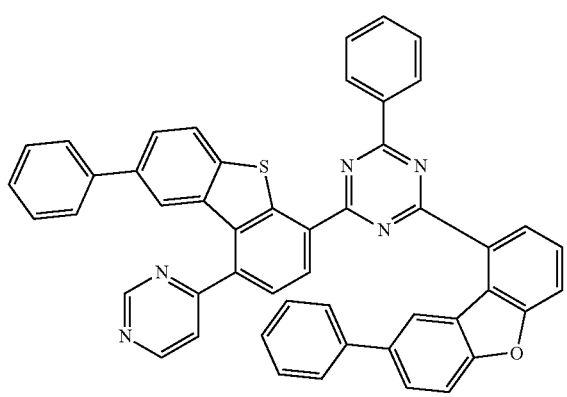

2-31
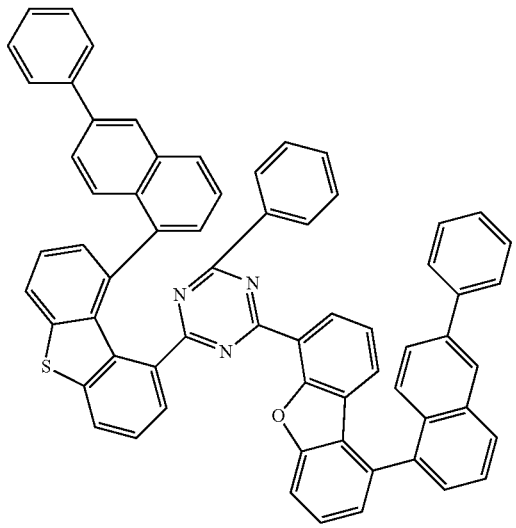
2-32
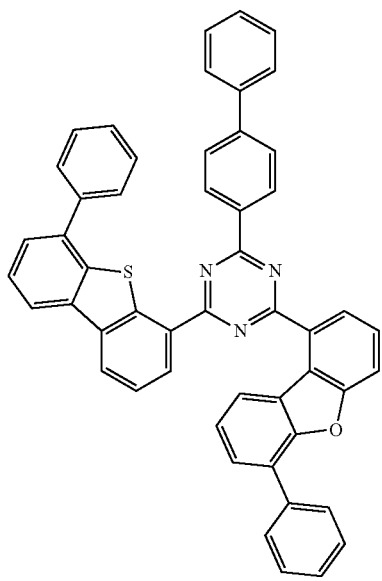
2-33
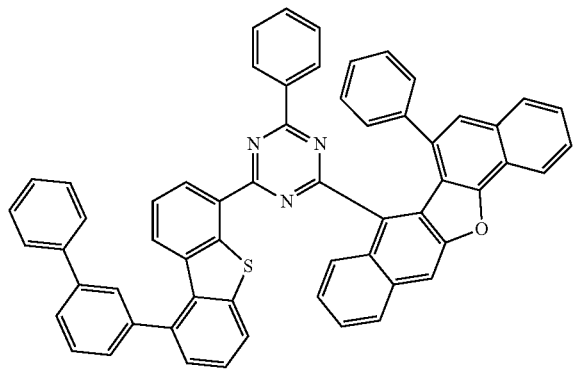
2-34
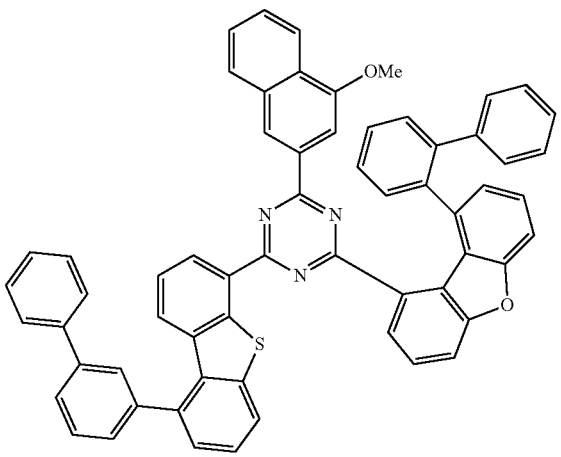
2-35
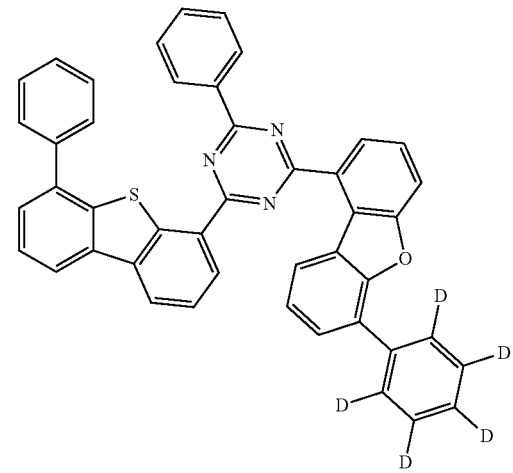
2-36
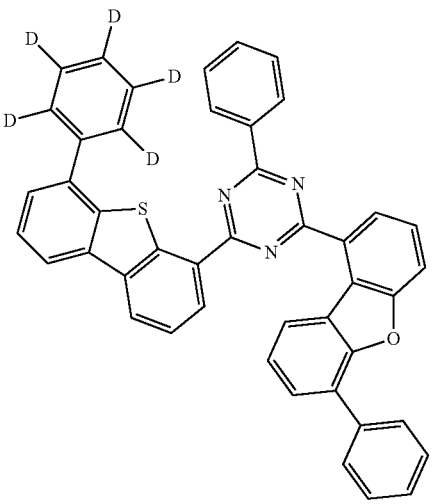

3-1
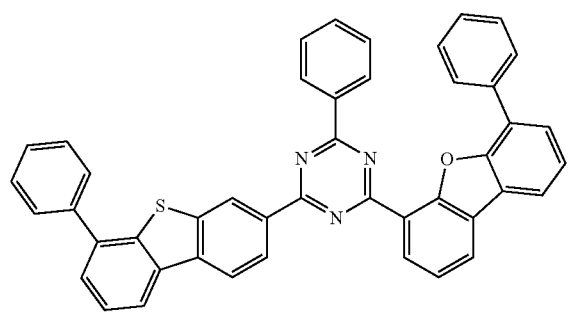
3-2
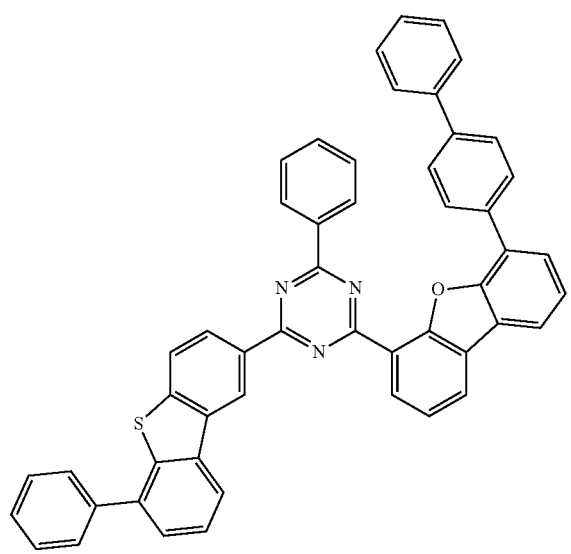
3-3
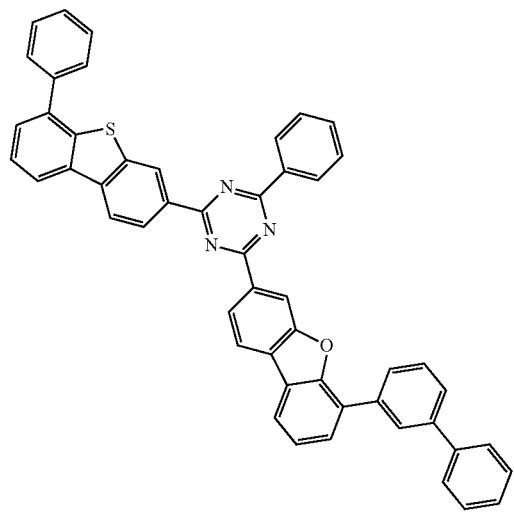
3-4
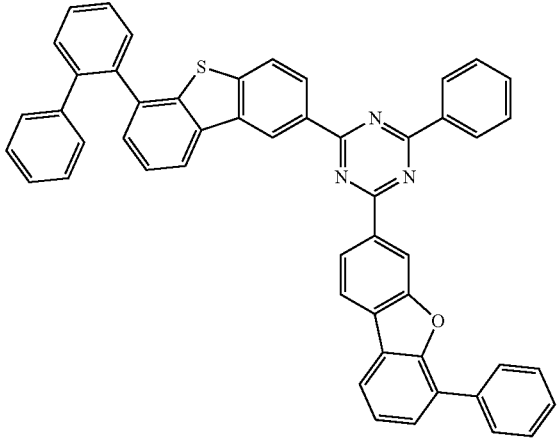
3-5
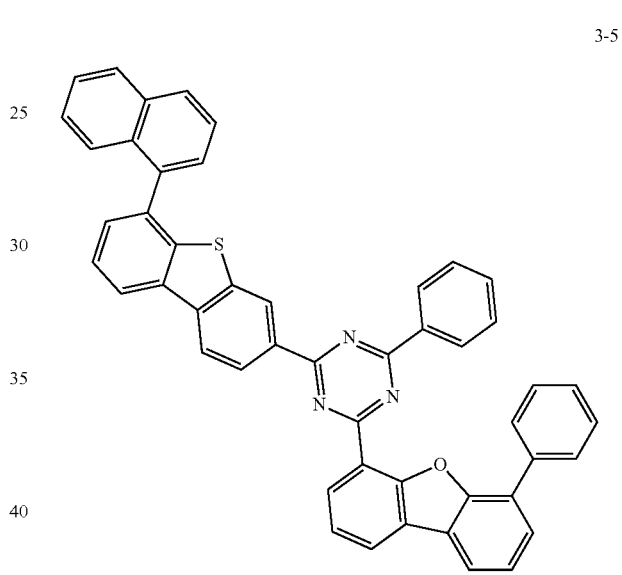
3-6
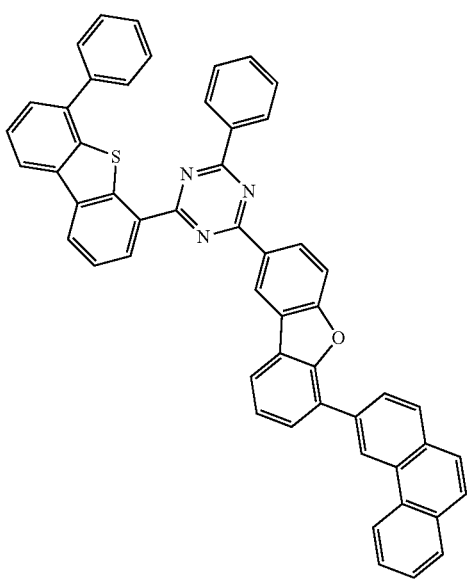

3-7
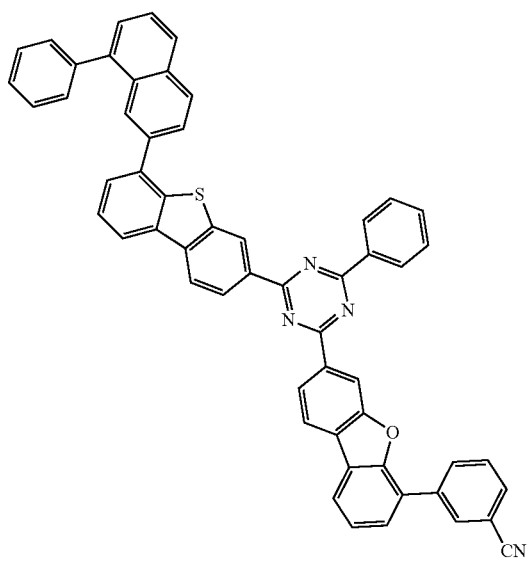
3-8
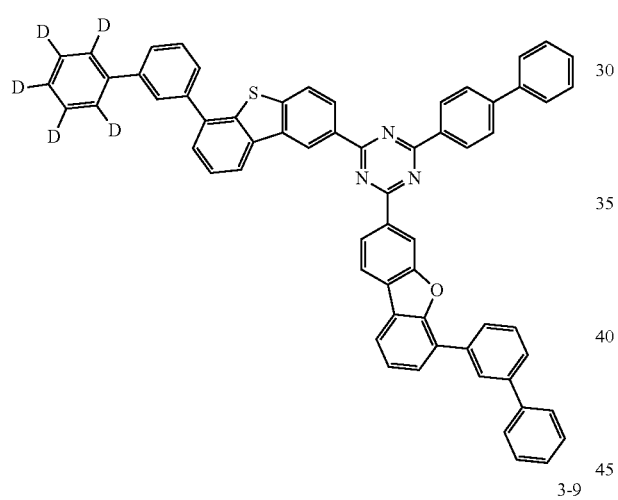
3-9
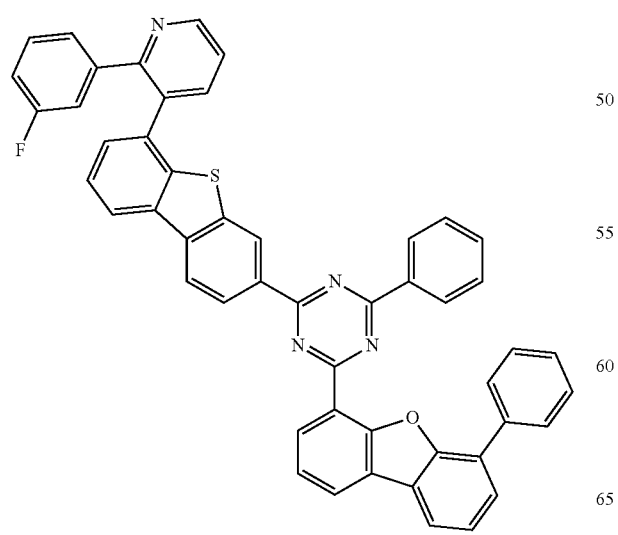
3-10
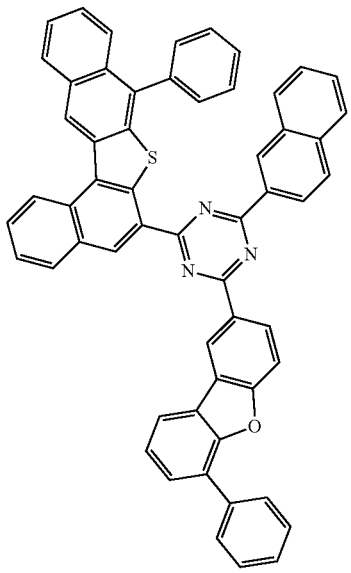
3-11
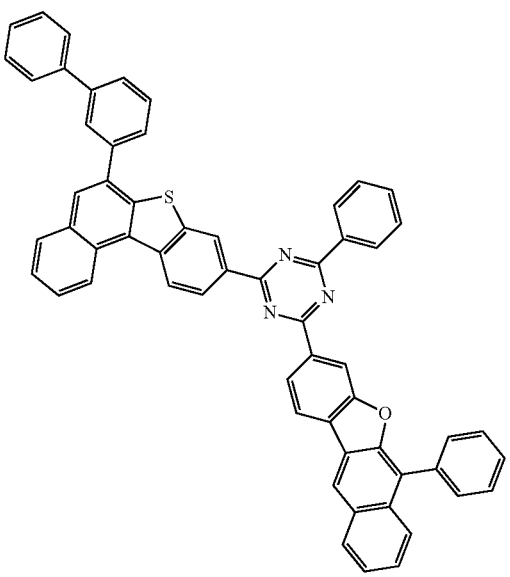
3-12
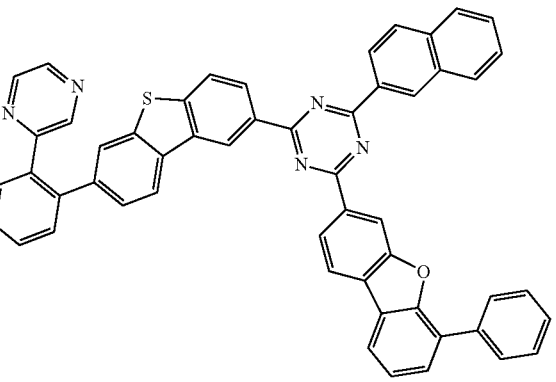

3-13
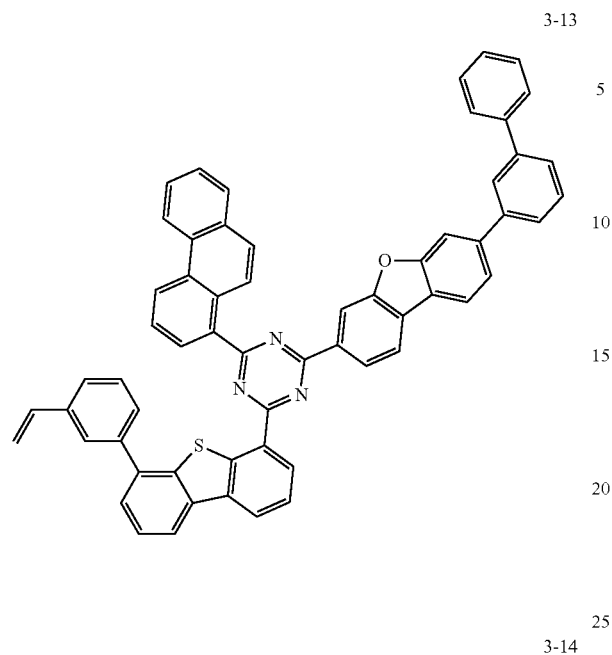
3-16
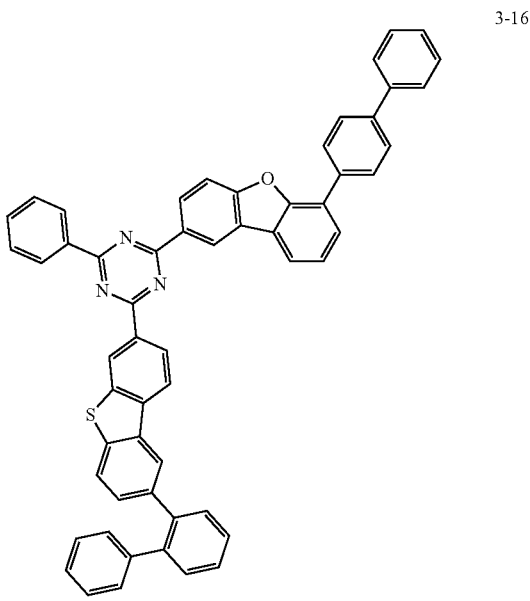
3-14
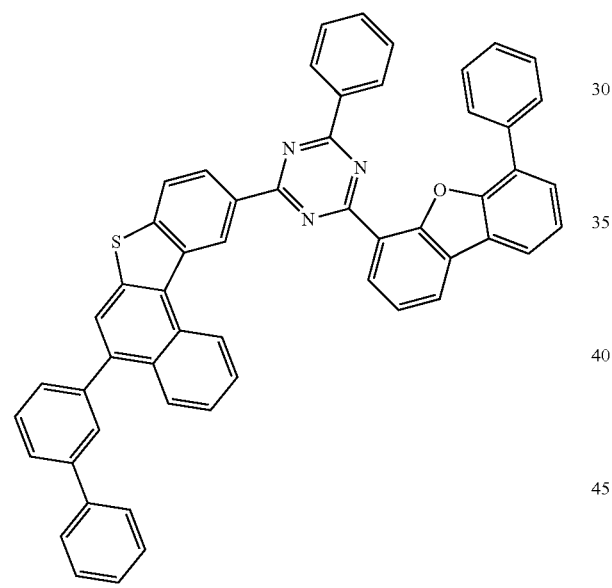
3-15
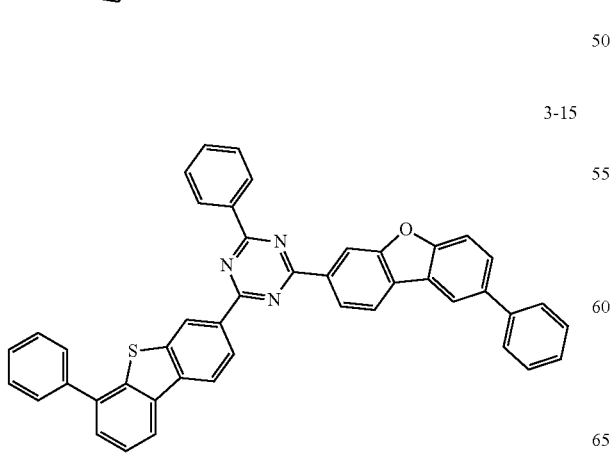
3-17
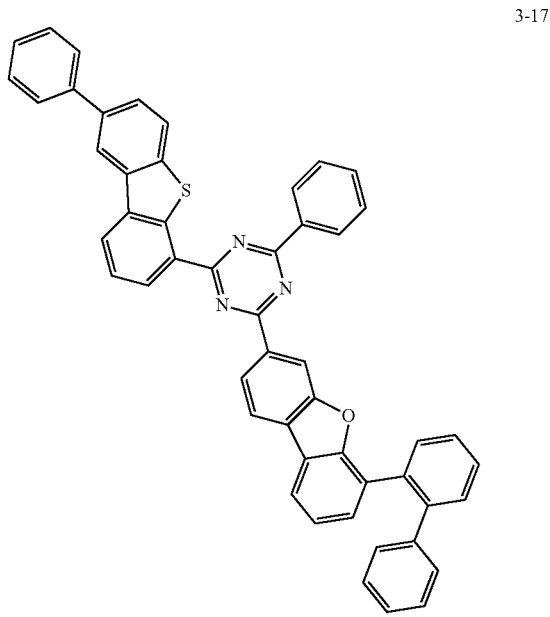

3-18
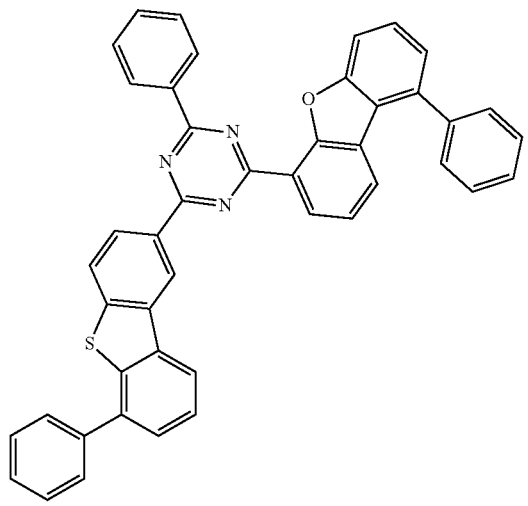
3-19
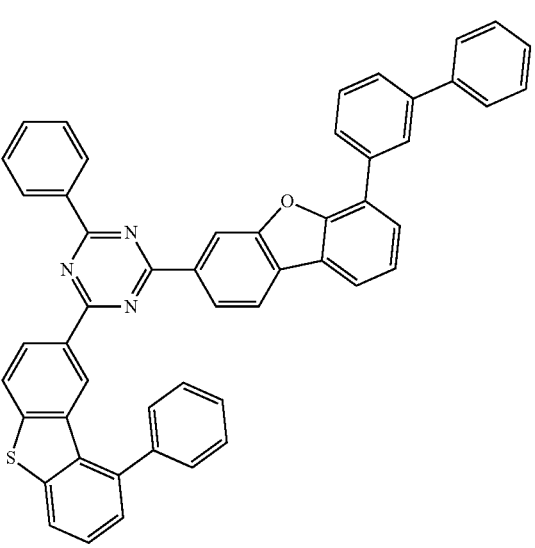
3-20
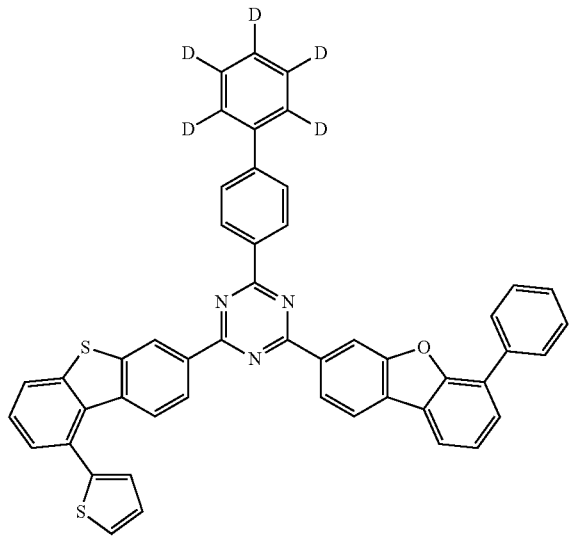
3-21
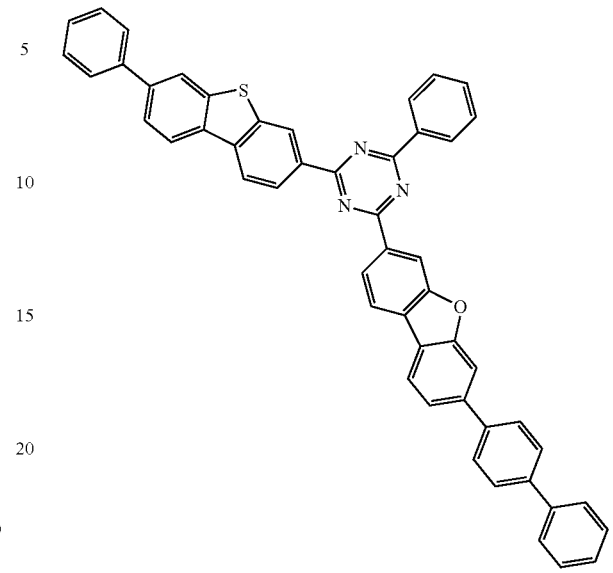
3-22
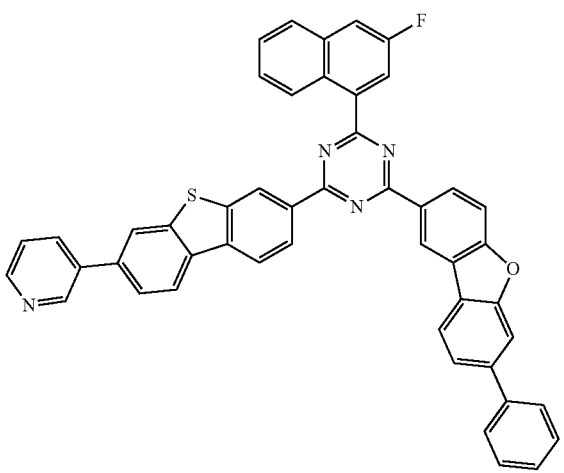

3-23
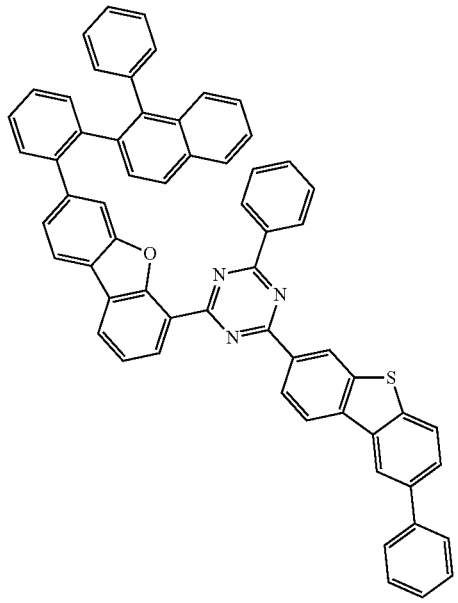
3-24
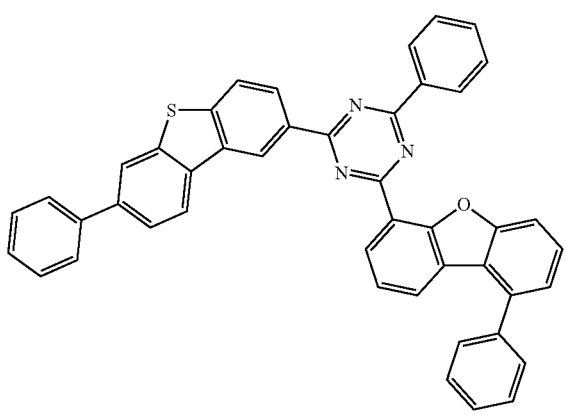
3-25
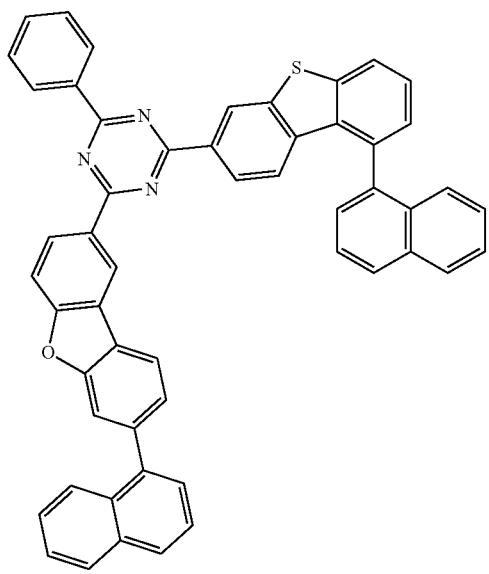
3-26
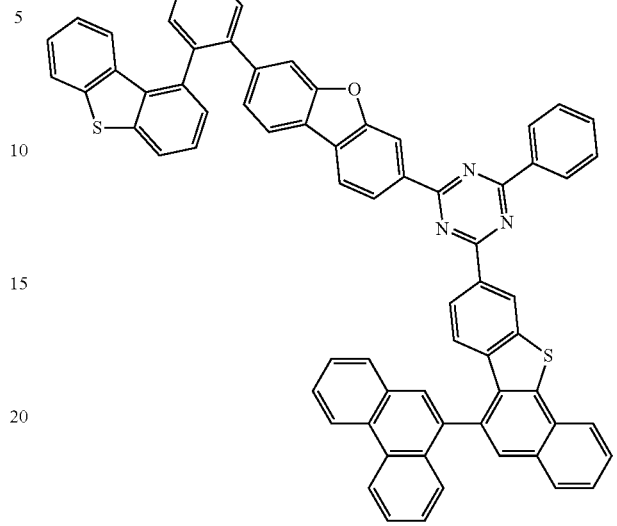
3-27
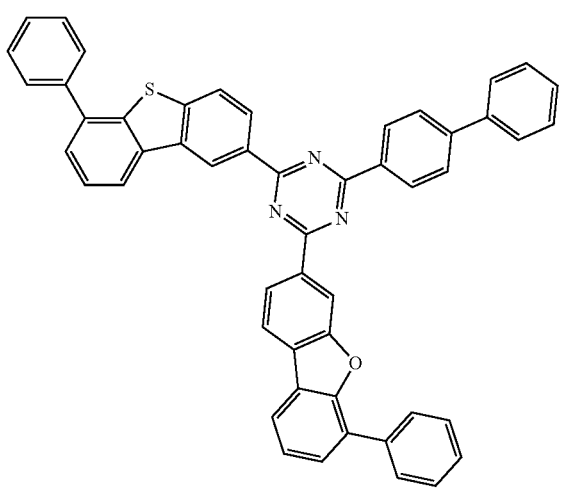
3-28
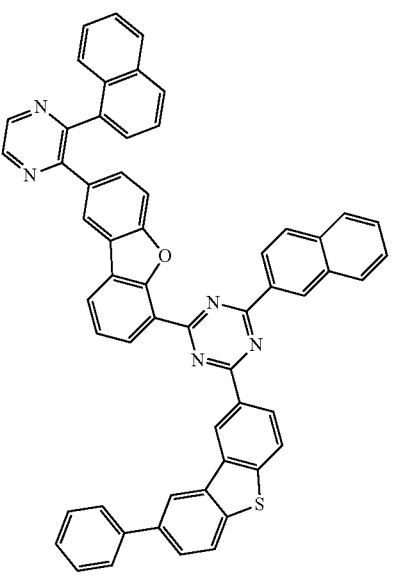

451
-continued
3-29
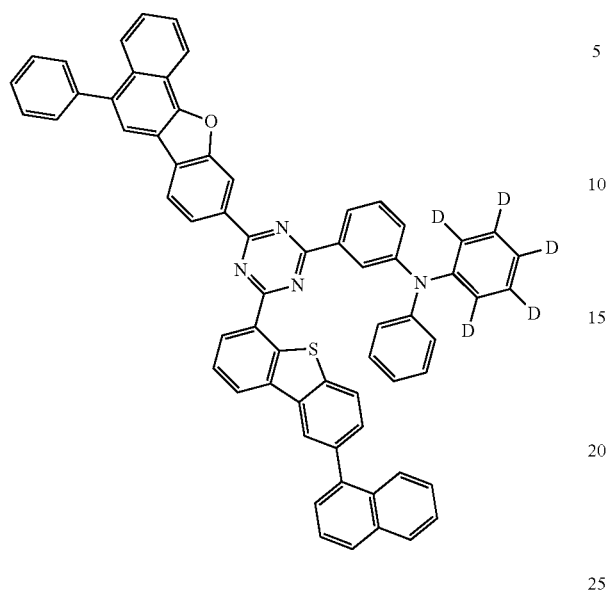
3-30
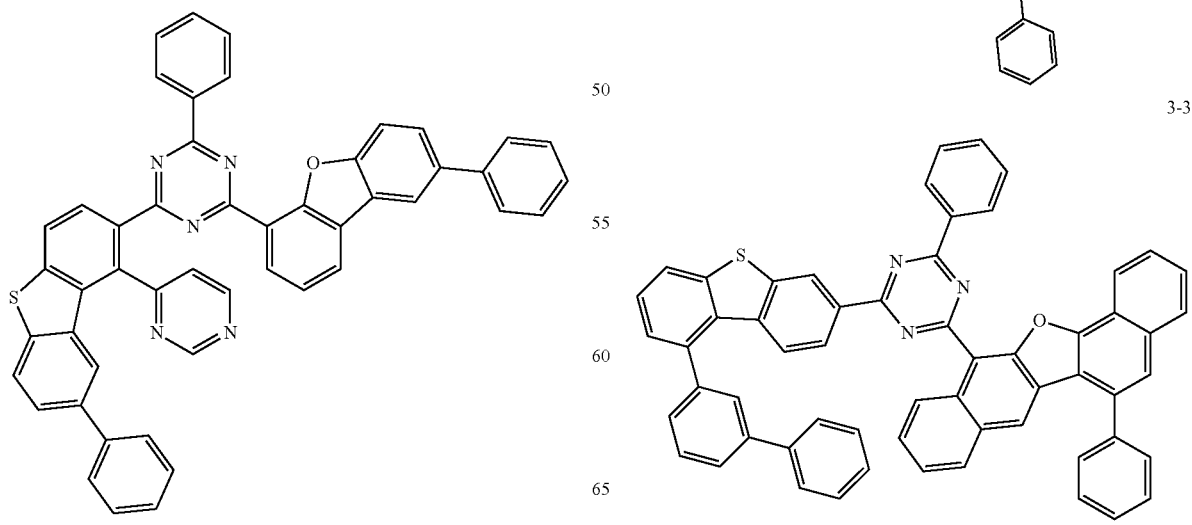
452
-continued
3-31
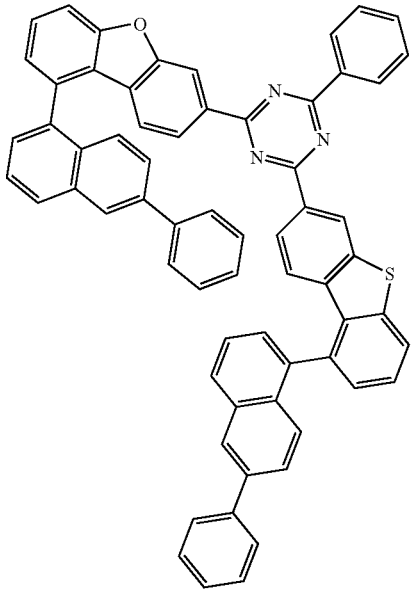
3-32
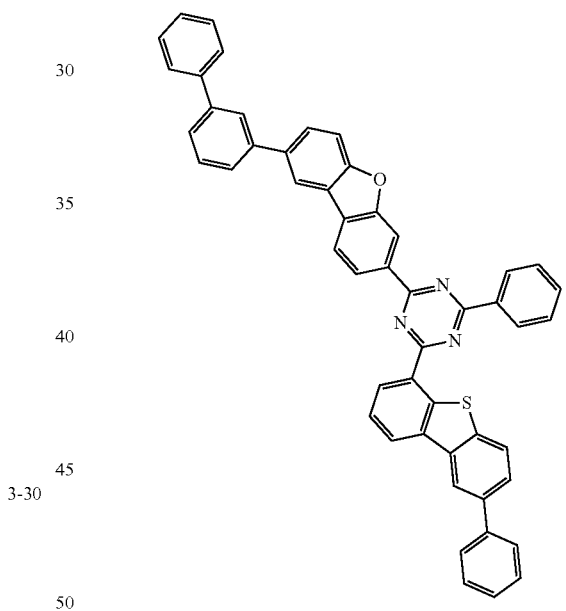
3-33

3-34
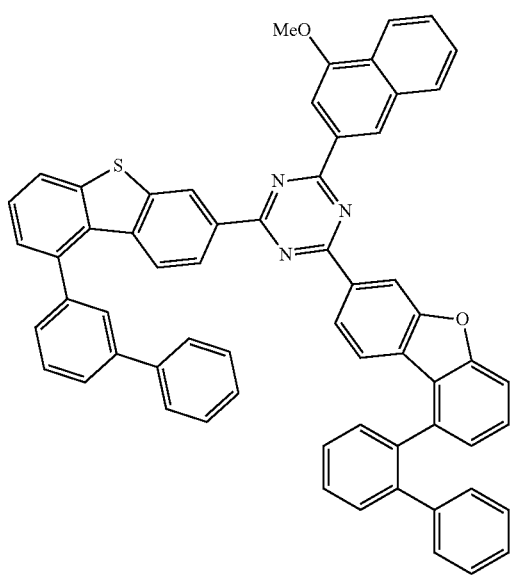
4-1
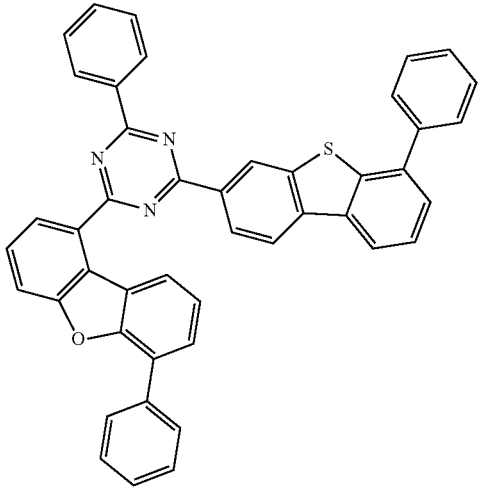
3-35
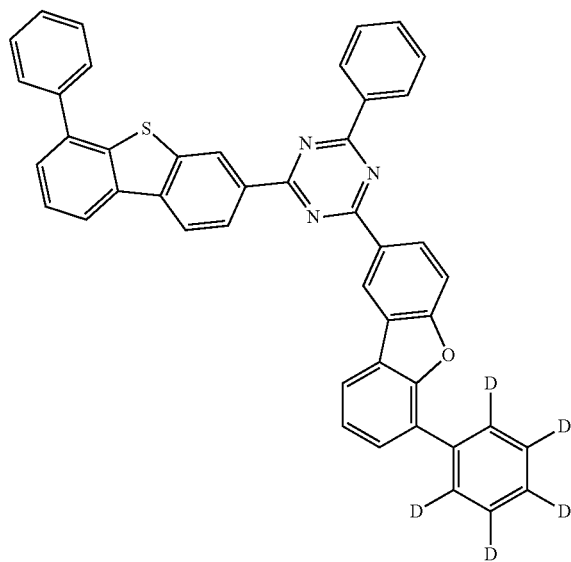
4-2
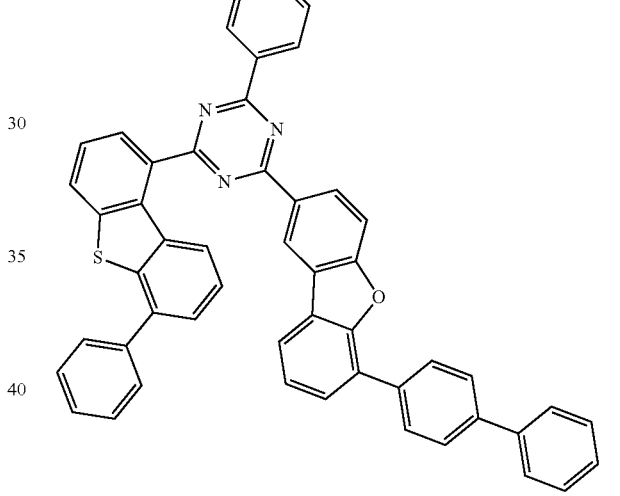
3-36
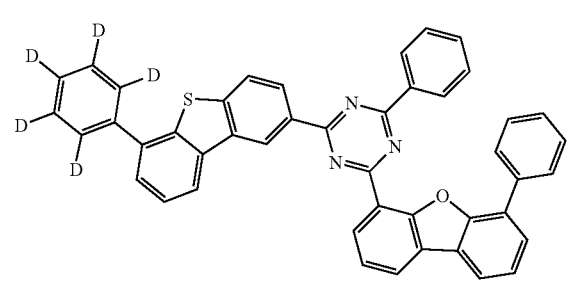
4-3

4-4
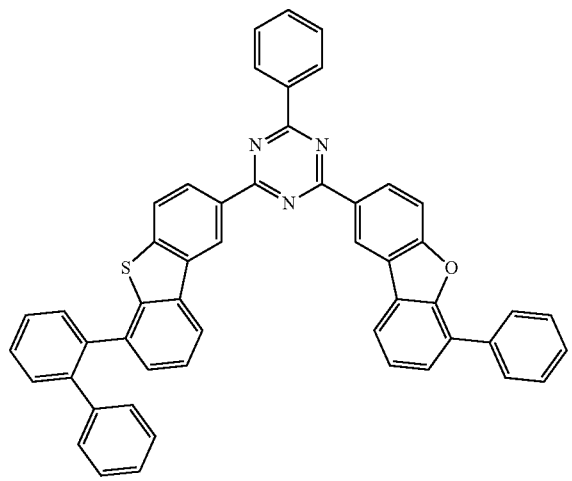
4-5
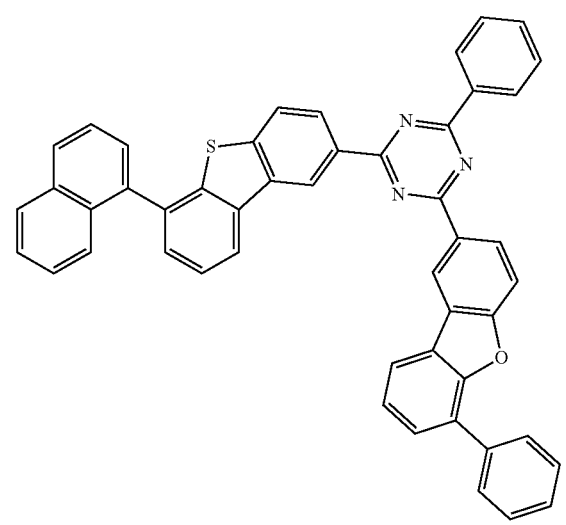
4-6
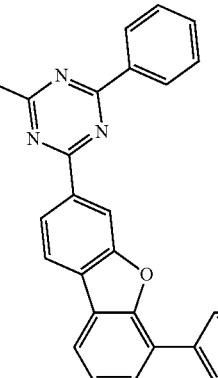
4-7
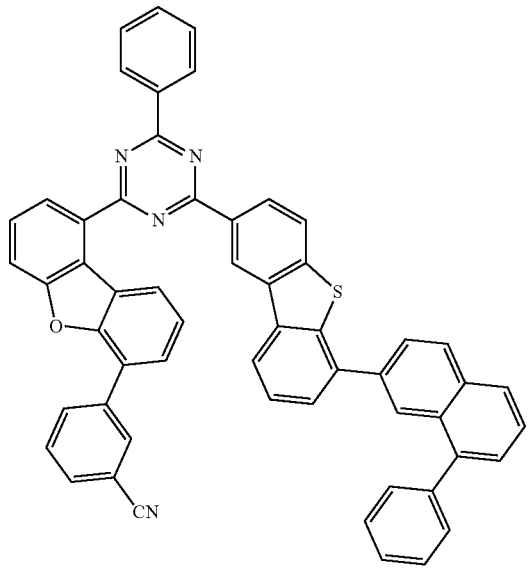
4-8
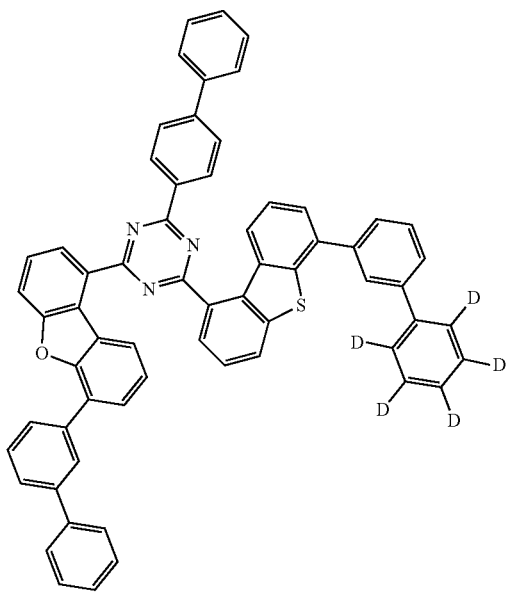
4-9
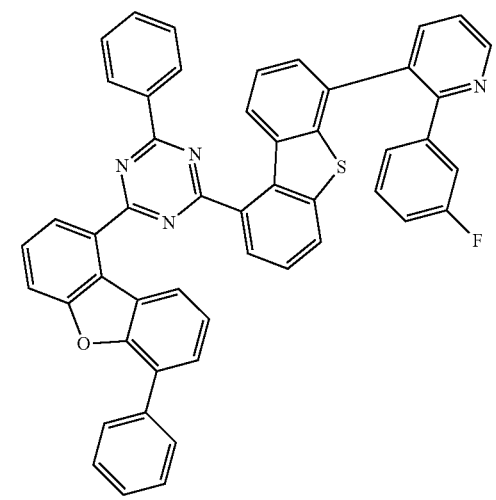

4-10
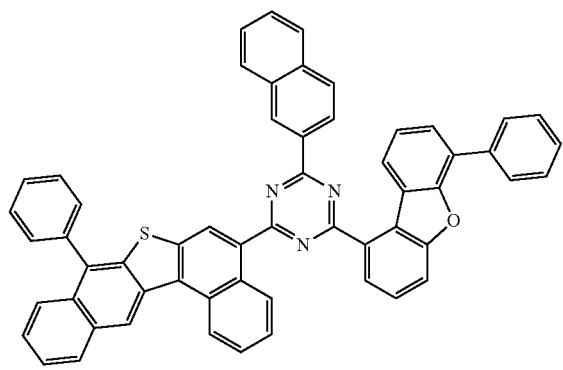
4-11
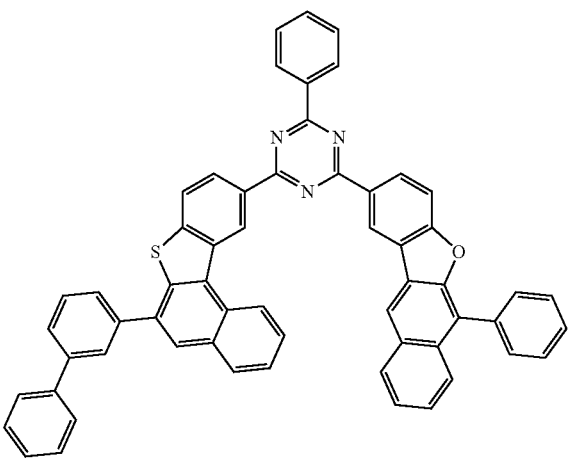
4-12
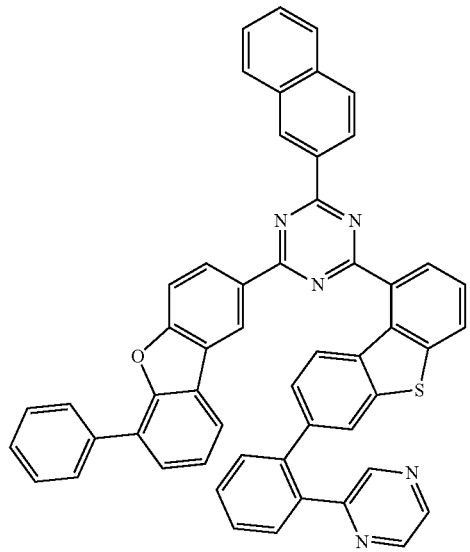
4-13
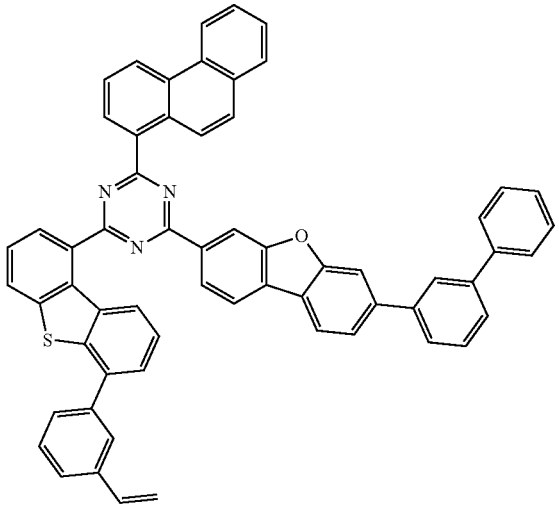
4-14
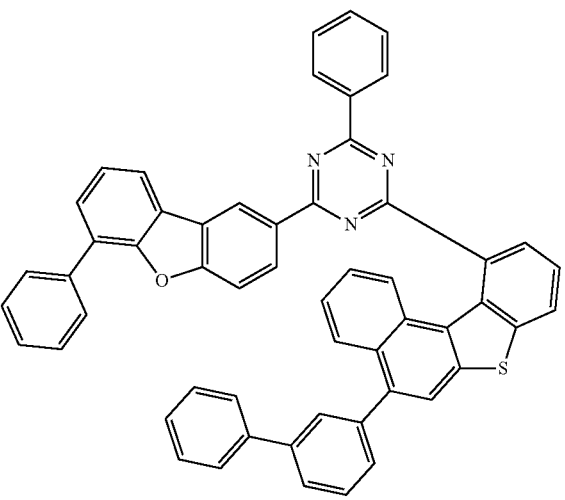
4-15
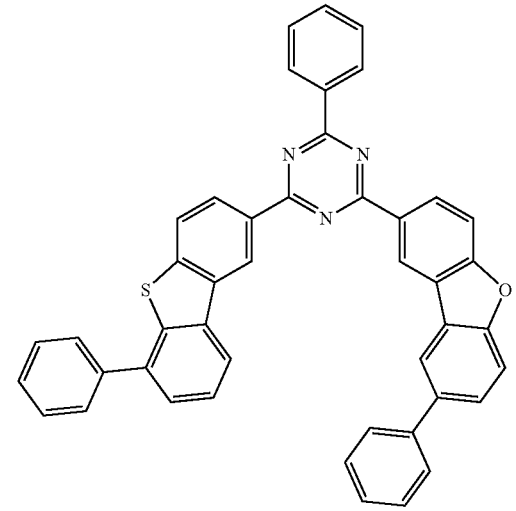

4-16
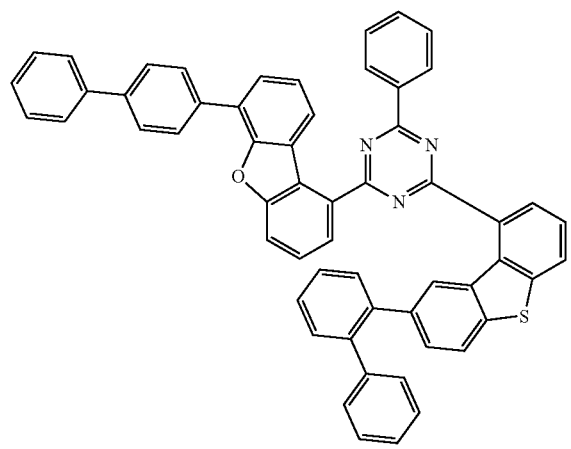
4-19
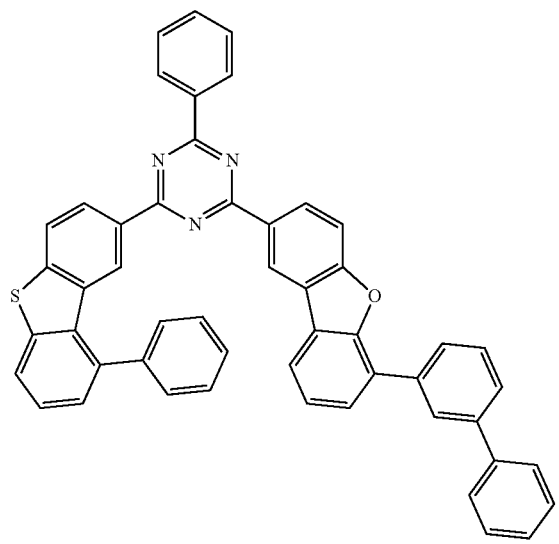
4-17
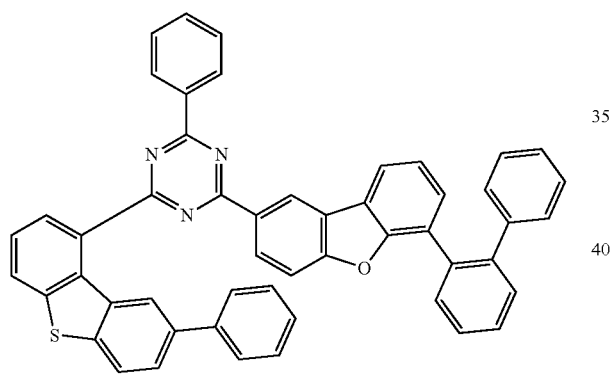
4-18
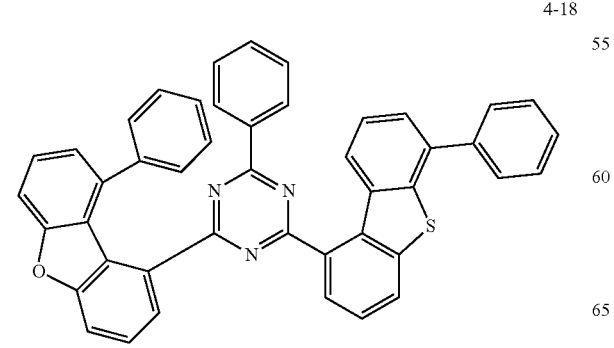
4-20
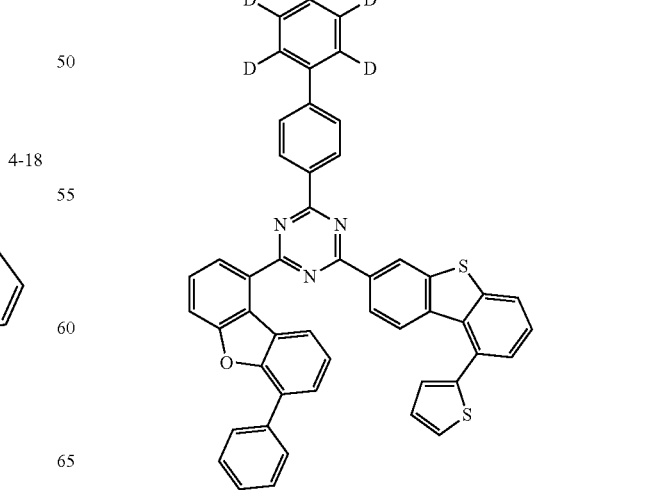

4-21
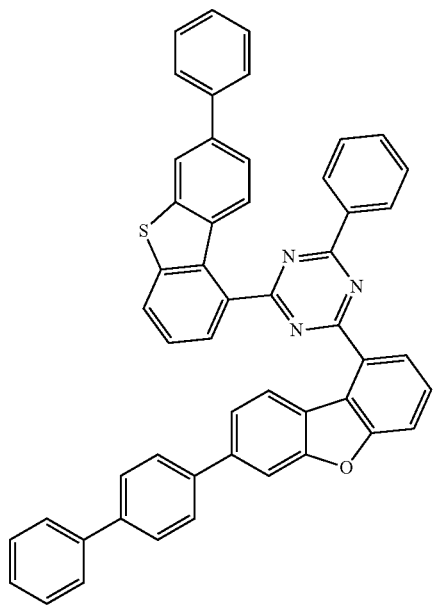
4-22
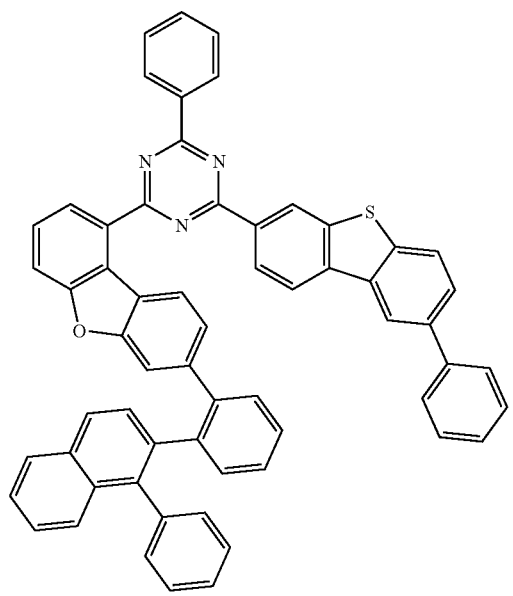
4-23
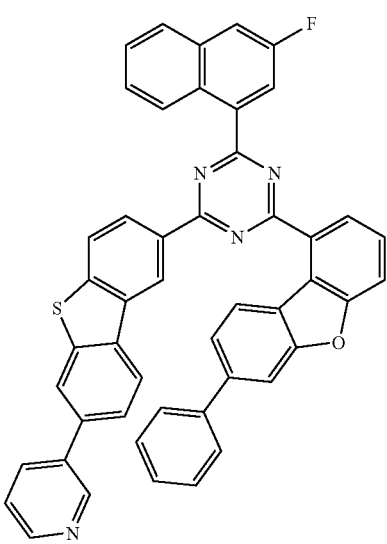
4-24
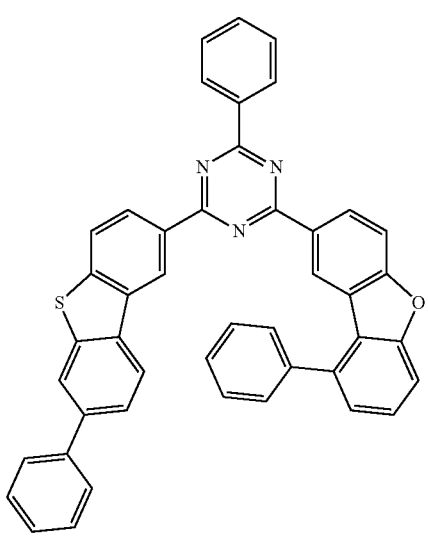
4-25
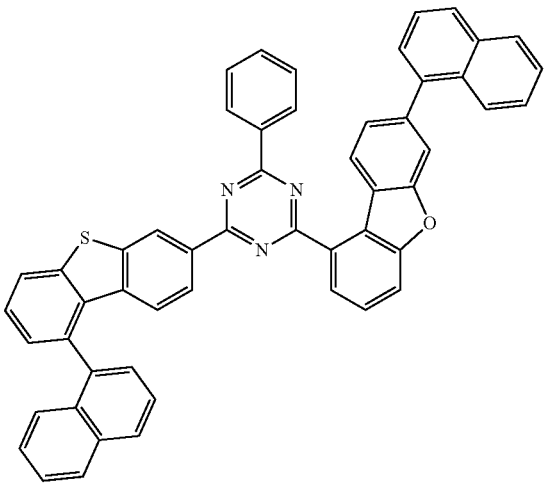

4-26
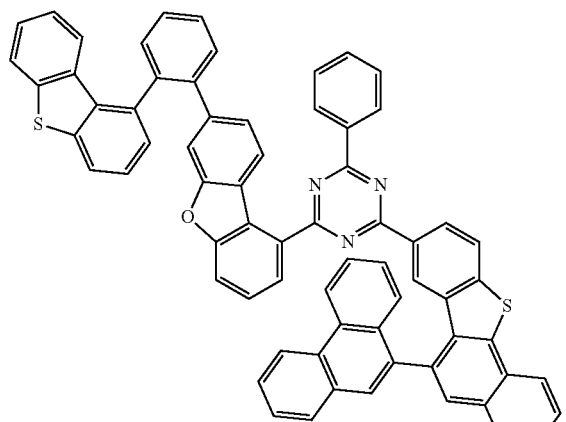
4-27
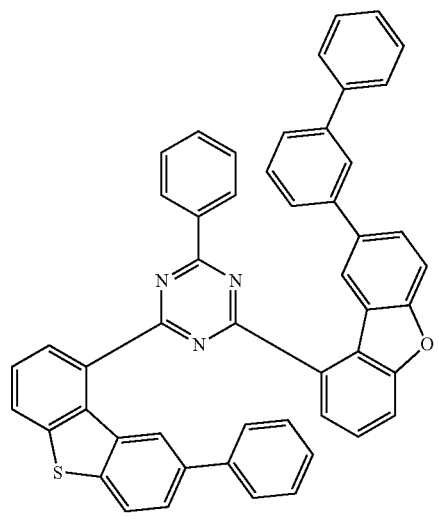
4-28
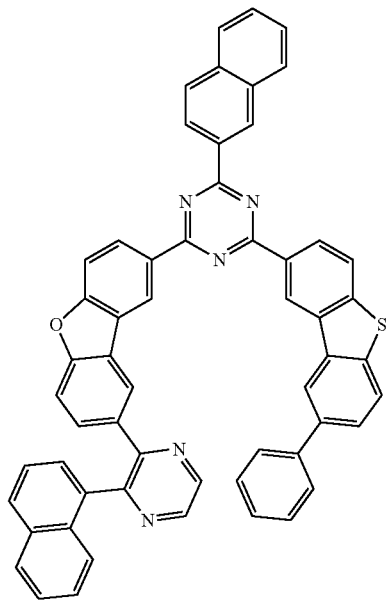
4-29
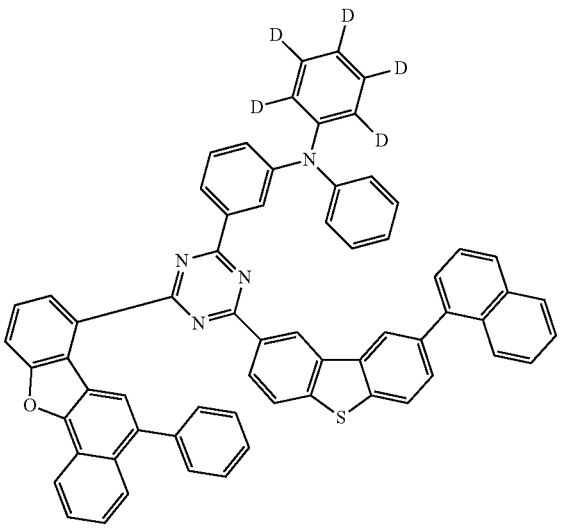
4-30
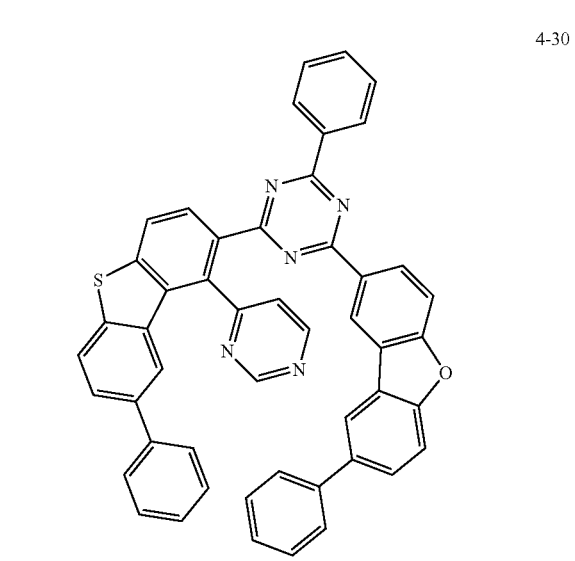
4-31
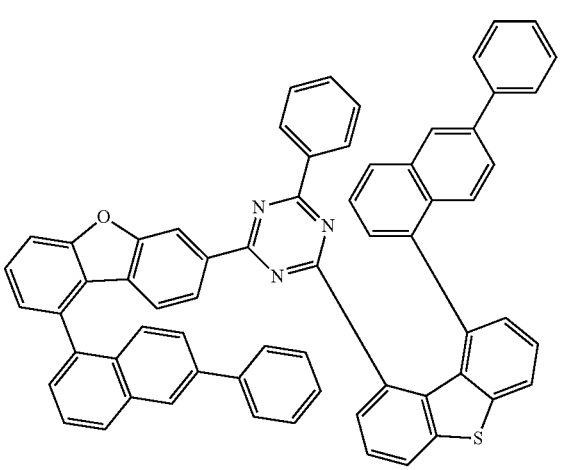

4-32
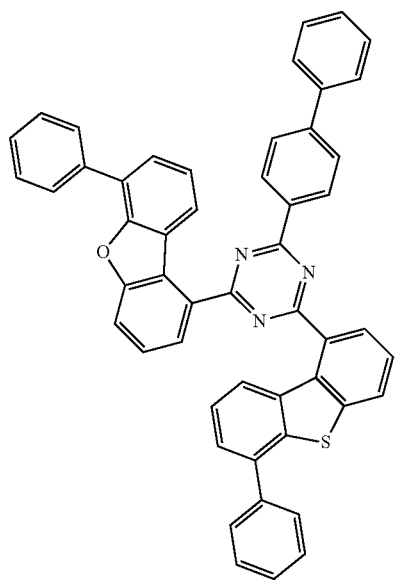
4-35
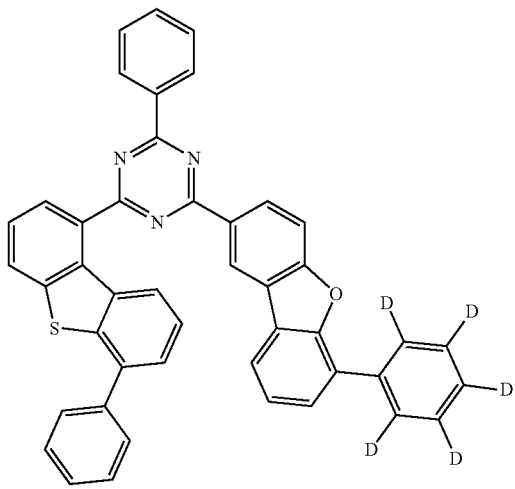
4-33
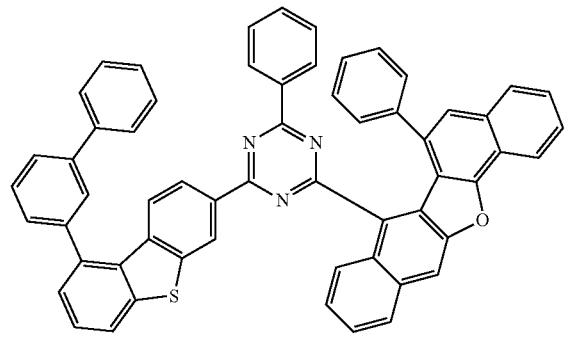
4-36
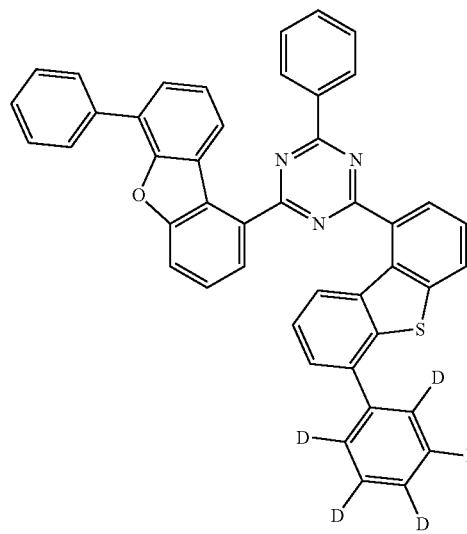
4-34
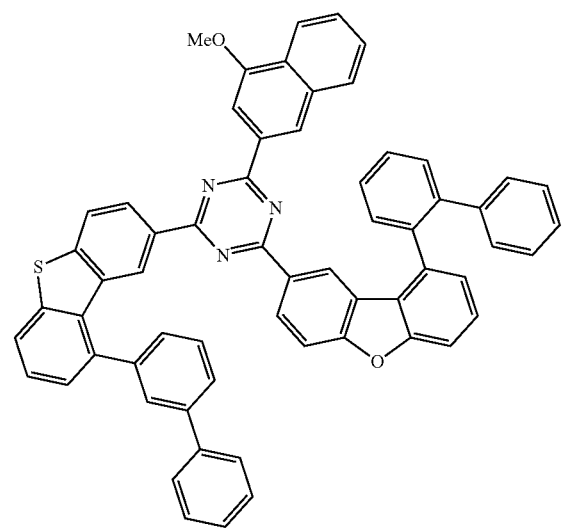
4-37
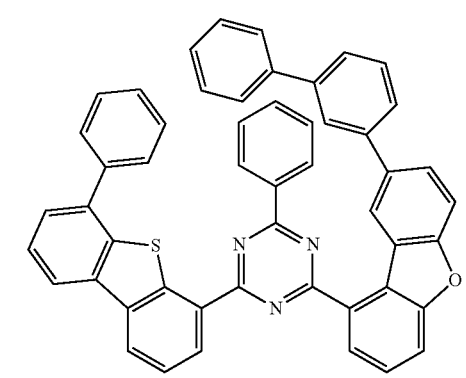

4-38
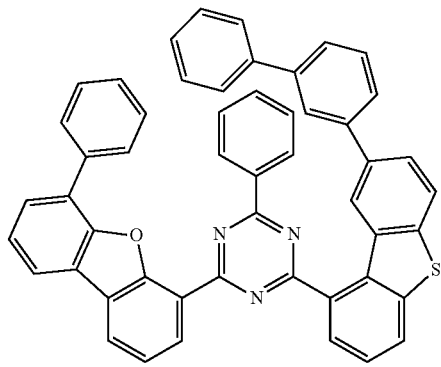
4-39
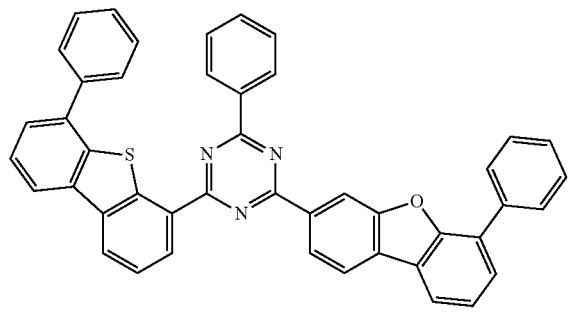
4-40
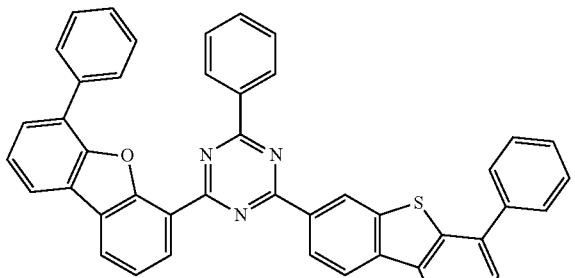
4-41
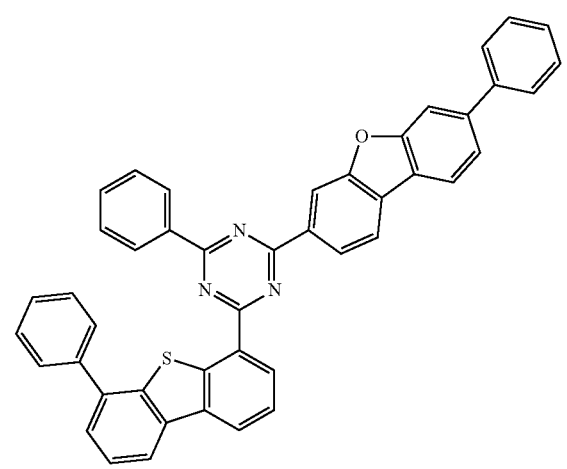
4-42
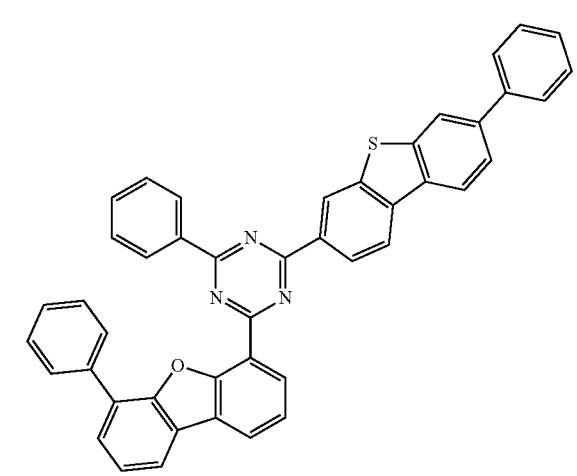
4-43
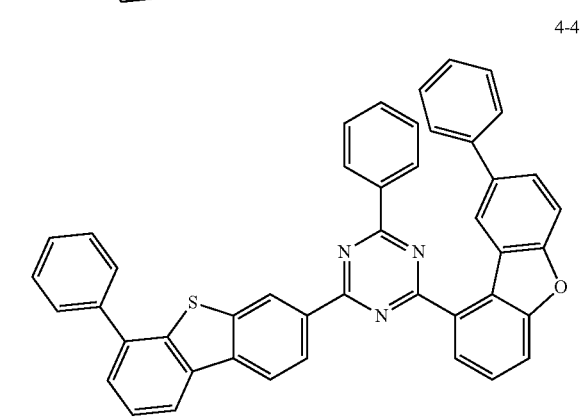
4-44
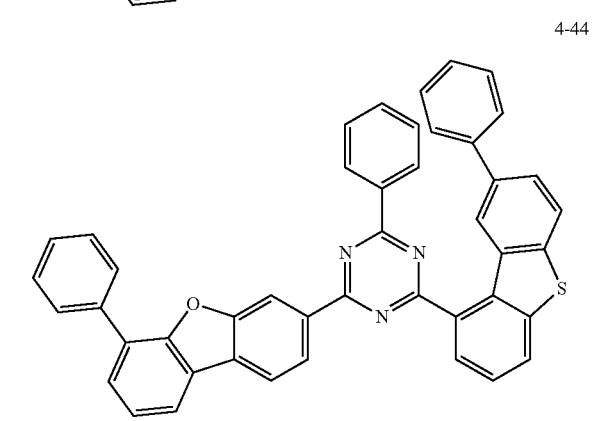
4-45
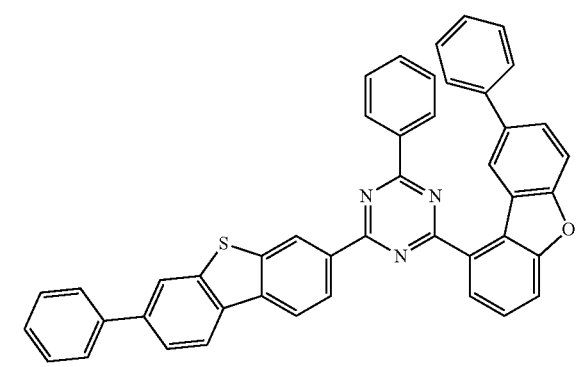

-continued 4-46

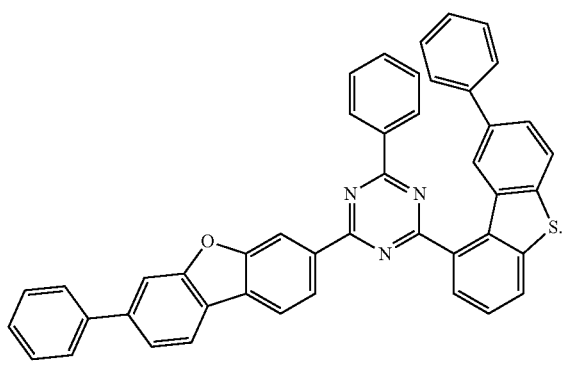

7. An organic electric element comprising a first electrode, a second electrode, and an organic material layer formed between the first electrode and the second electrode, wherein the organic material layer comprises a single compound or a mixture of two or more kinds represented by the Formula 1 of claim 1.

8. The organic electric element of claim 7, wherein the organic material layer comprises at least one layer of a hole injection layer, a hole transport layer, an emission-auxiliary layer, a light emitting layer, an electron transport auxiliary layer, an electron transport layer and an electron injection layer.

9. The organic electric element of claim 8, wherein the light emitting layer comprises a compound represented by Formula 12:

<Formula 12>

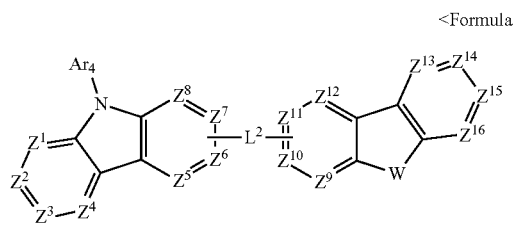

wherein:

$Z^1$ to $Z^4$ and $Z^{13}$ to $Z^{16}$ are each independently C(R) or N, $Z^5$ to $Z^{12}$ are independently C, C(R) or N, $L^2$ is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, W is N(Ar$_5$), N, O, S, C(R') or C(R')(R''), with the proviso that W is N or C(R') where W is combined with $L^2$, Ar$_4$ and Ar$_5$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{60}$ aryloxy group, -L'-N(R$_a$)(R$_b$) and a combination thereof, R, R' and R'' are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{60}$ aryloxy group and -L'-N(R$_a$)(R$_b$), adjacent R groups may be optionally linked to each other to form a ring, and R' and R'' may be optionally linked to each other to form a ring, L' is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, R$_a$ and R$_b$ are each independently selected from the group consisting of hydrogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, $L^2$, Ar$_4$, Ar$_5$, R, R', R'', a ring formed by linking between adjacent R groups, and a ring formed by linking between R' and R'' may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, and a $C_8$-$C_{20}$ arylalkenyl group.

10. The organic electric element of claim 9, wherein Formula 12 is represented by one of Formulas 13 to 17:

<Formula 13>

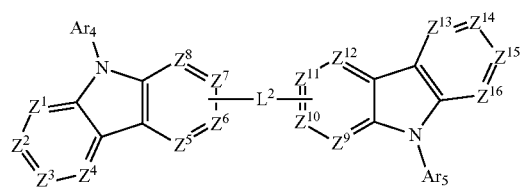

<Formula 14>

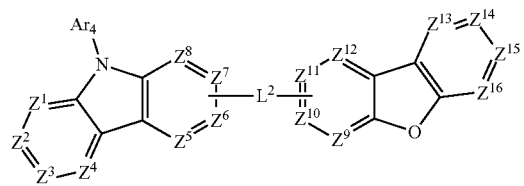

-continued

<Formula 15>

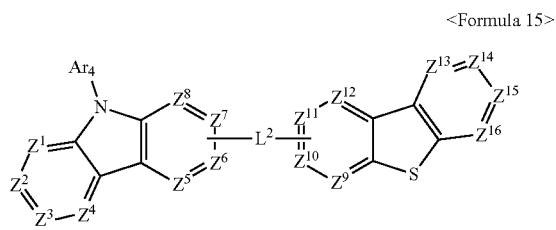

<Formula 16>

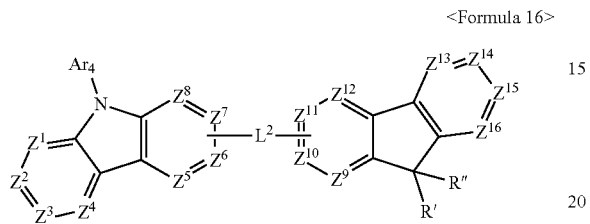

<Formula 17>

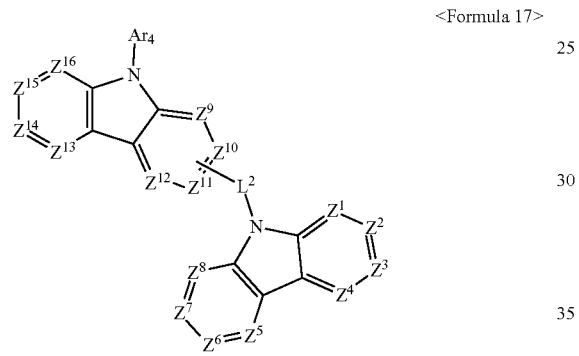

wherein $Ar_4$, $Z^1$ to $Z^{16}$, $L^2$, R' and R" are the same as defined in claim 1.

11. The organic electric element of claim 9, wherein both $Ar_4$ and $Ar_5$ are a $C_6$ to $C_{30}$ aryl group.

12. The organic electric element of claim 9, wherein Formula 12 is represented by Formula 18 or Formula 19:

<Formula 18>

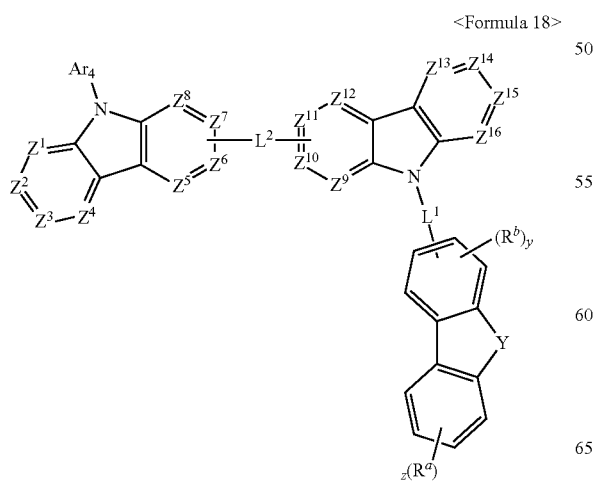

-continued

<Formula 19>

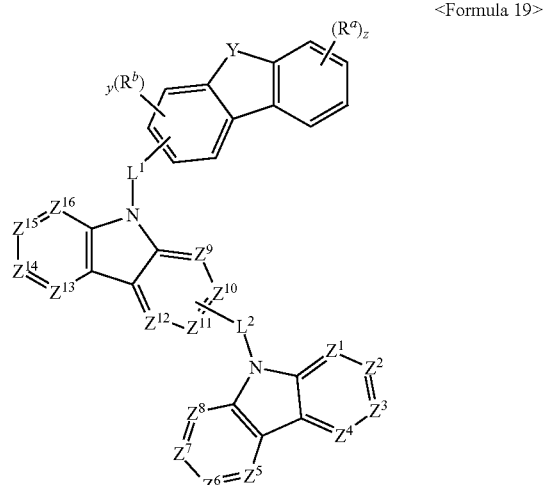

wherein:

$Ar_4$, $Z^1$ to $Z^{16}$, and $L^2$ are the same as defined in claim 9, $L^1$ is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, Y is O, S or N—$Ar_6$, $R_a$ and $R^b$ are each independently selected from the group consisting of hydrogen, deuterium, halogen, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group and a $C_8$-$C_{20}$ arylalkenyl group, and adjacent groups may be optionally linked to each other to form a $C_6$-$C_{60}$ aromatic ring, a $C_2$-$C_{60}$ heterocyclic group, a $C_3$-$C_{60}$ aliphatic ring, or a fused ring group formed by a $C_3$-$C_{60}$ aliphatic ring with a $C_6$-$C_{60}$ aromatic ring, y is an integer of 0 to 3, z is an integer of 0 to 4, where each of these is an integer of 2 or more, each of $R^a$s, each of $R^b$s is the same or different from each other, $Ar_6$ is selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group and a $C_6$-$C_{60}$ aryloxy group.

13. The organic electric element of claim 9, wherein the compound represented by Formula 12 is one of the following compounds:

5-1
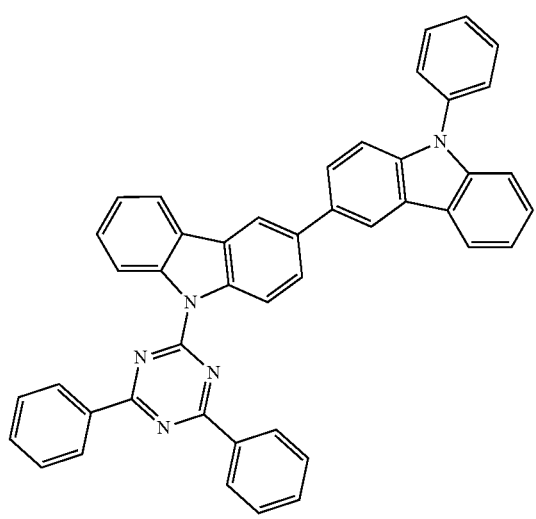
5-2
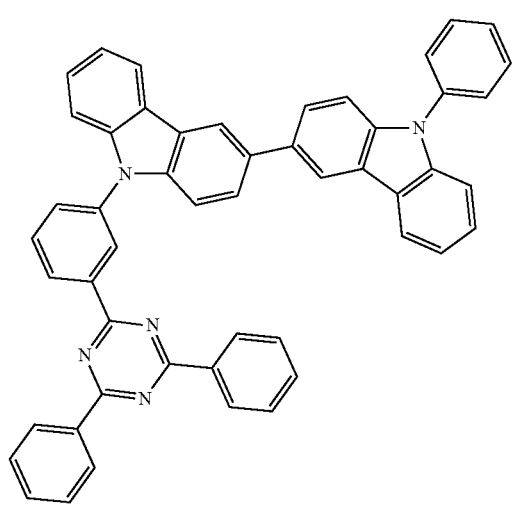
5-3
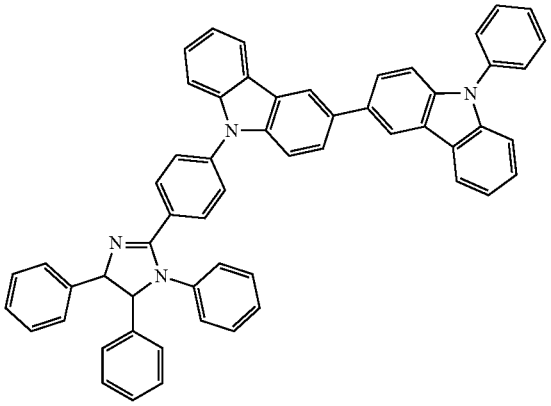
-continued
5-4
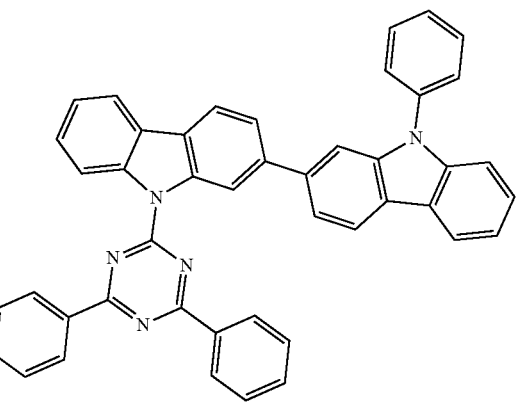
5-5
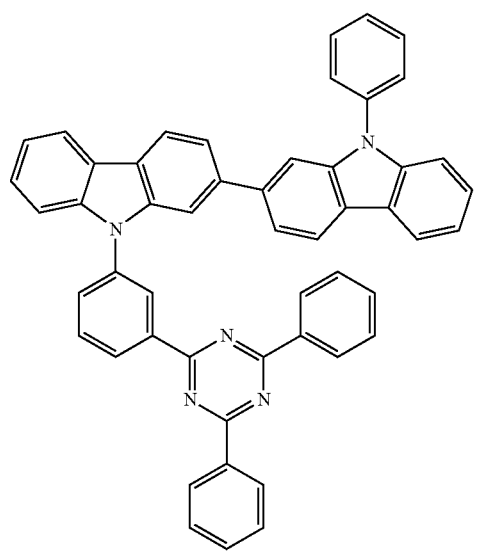
5-6
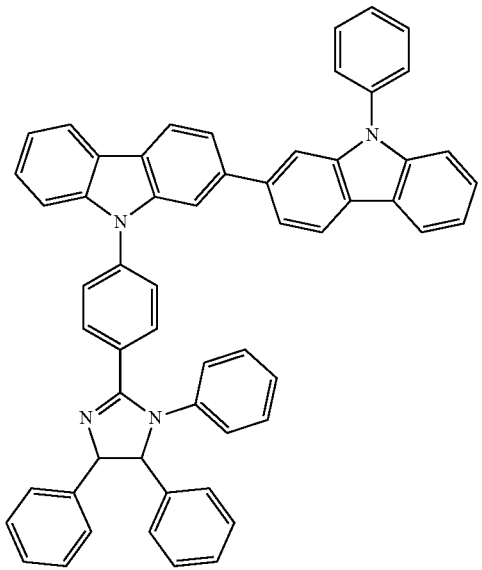

5-7
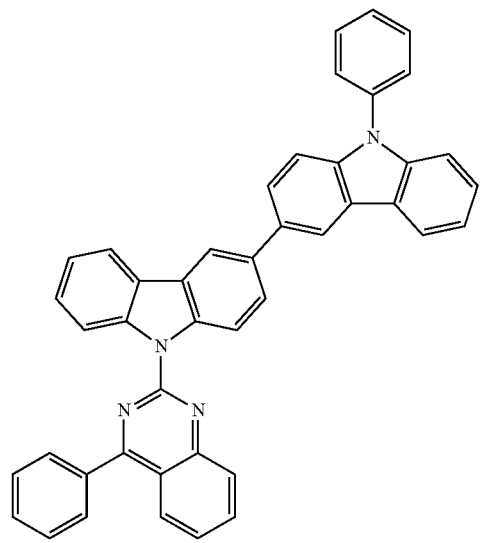
5-8
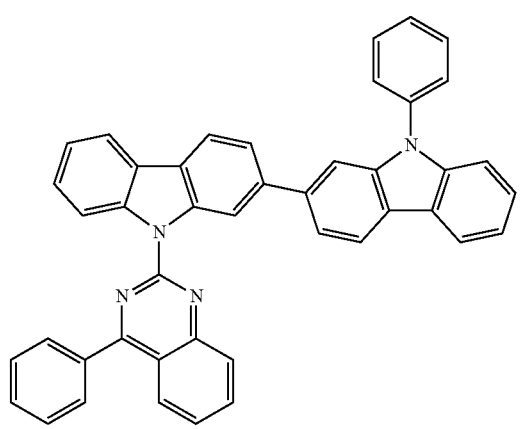
5-9
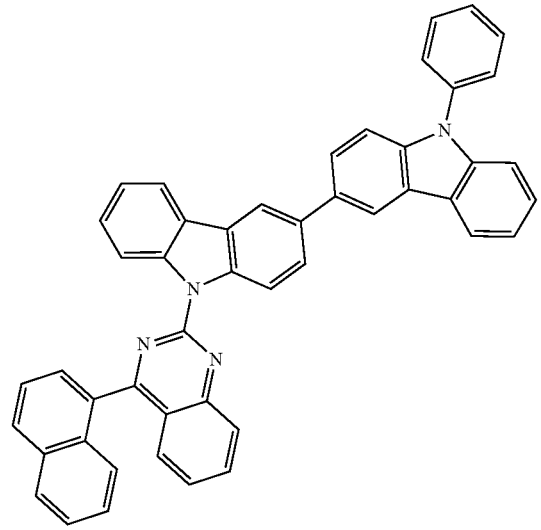
5-10
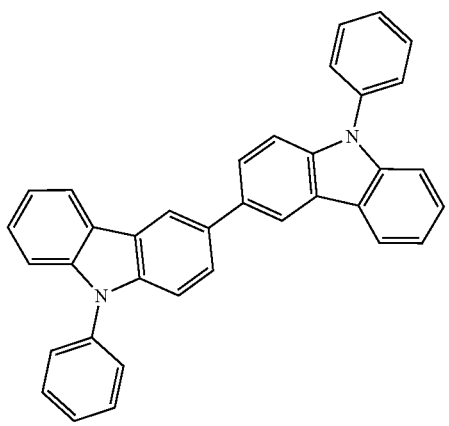
5-11
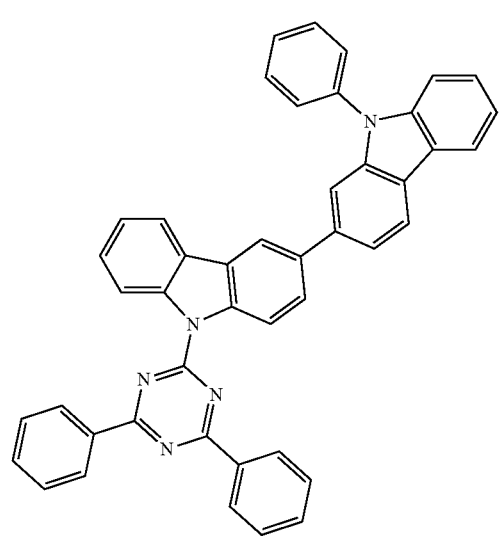
5-12
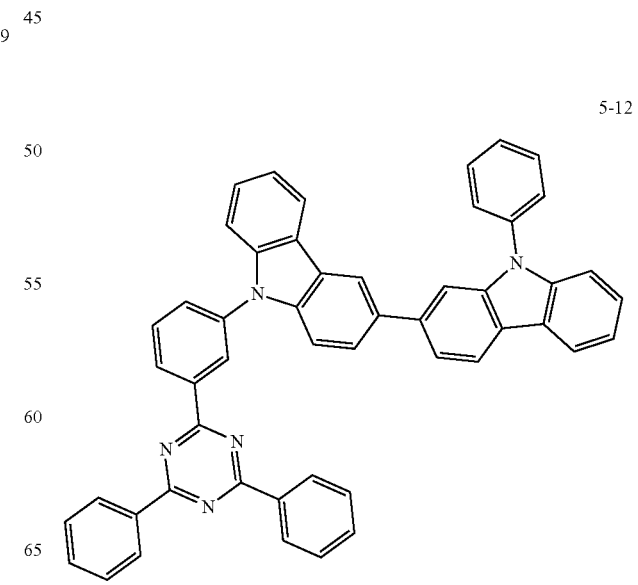

-continued
5-13
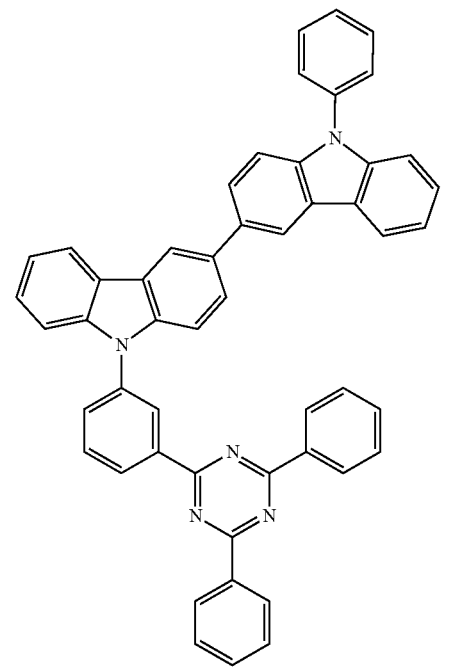
5-14
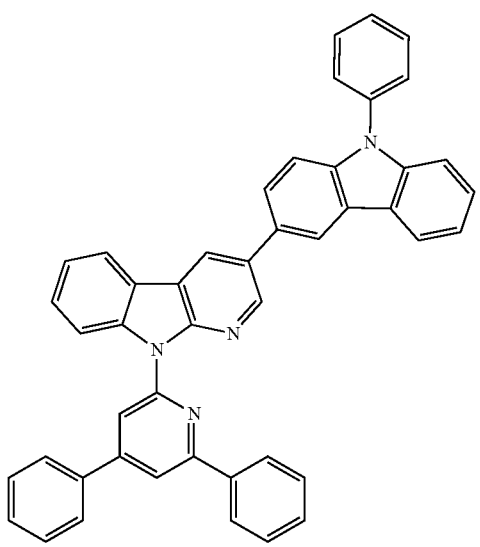
5-15
-continued
5-16
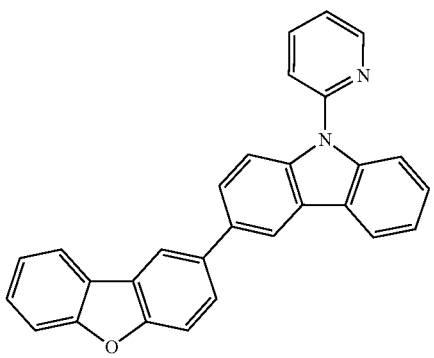
5-17
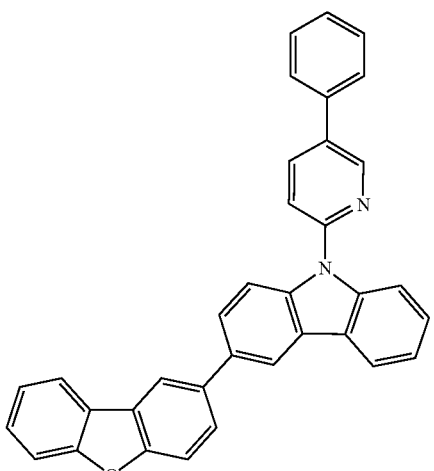
5-18
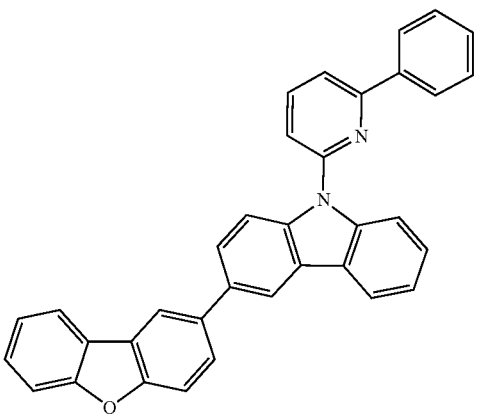

-continued
5-19
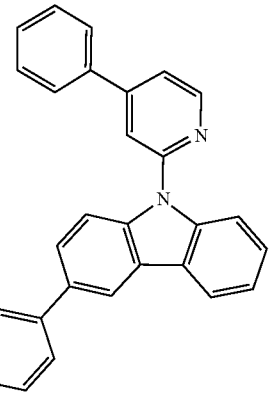
5-20
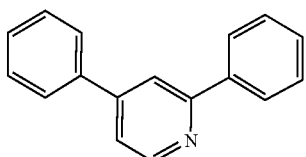
5-21
5-22
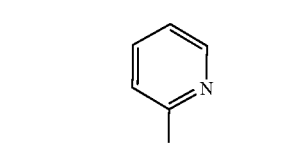
-continued
5-23
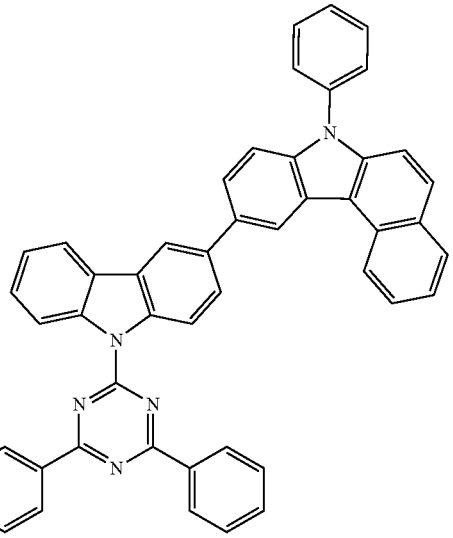
5-24
5-25
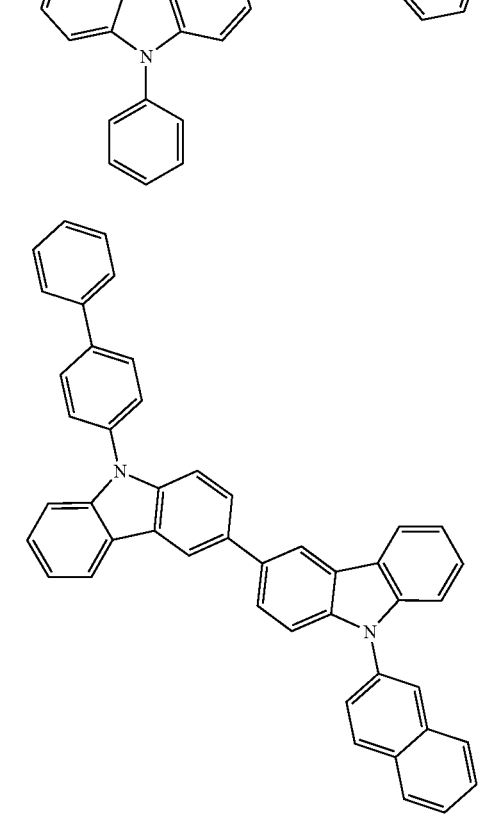

-continued
5-26
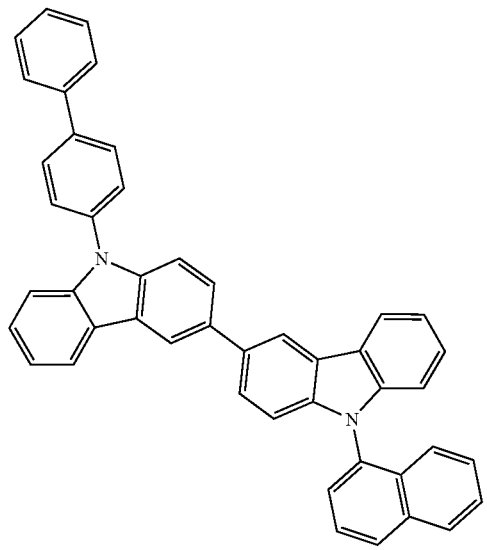
5-28
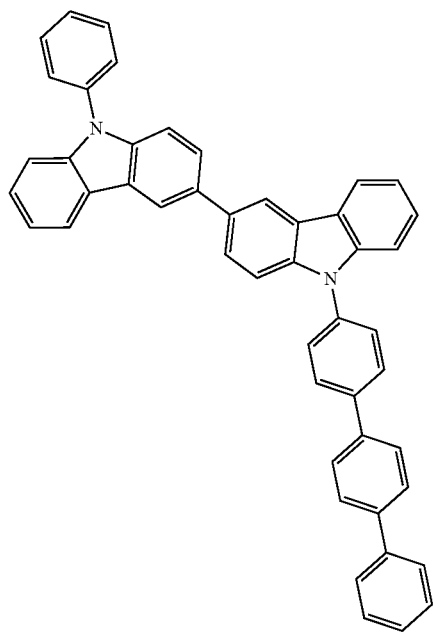
5-27
5-29
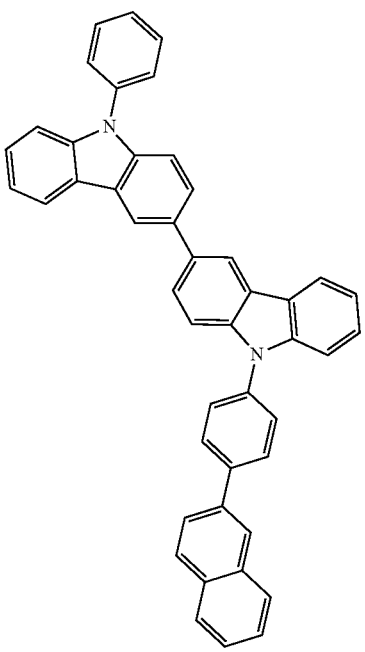

5-30
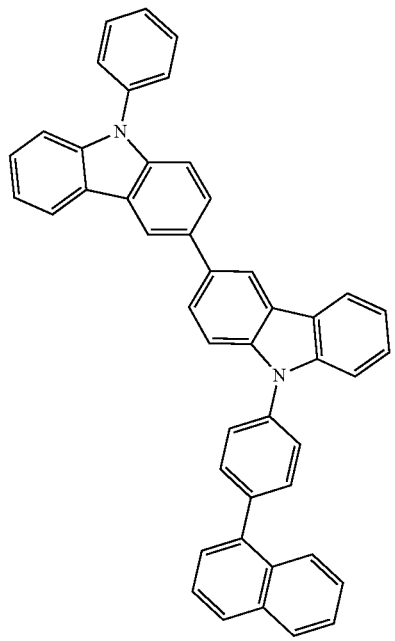
5-32
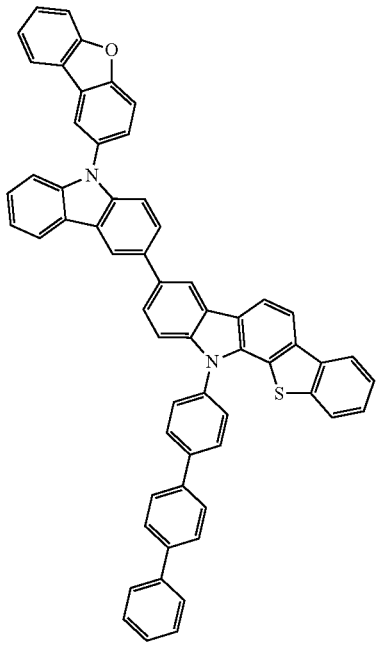
5-31
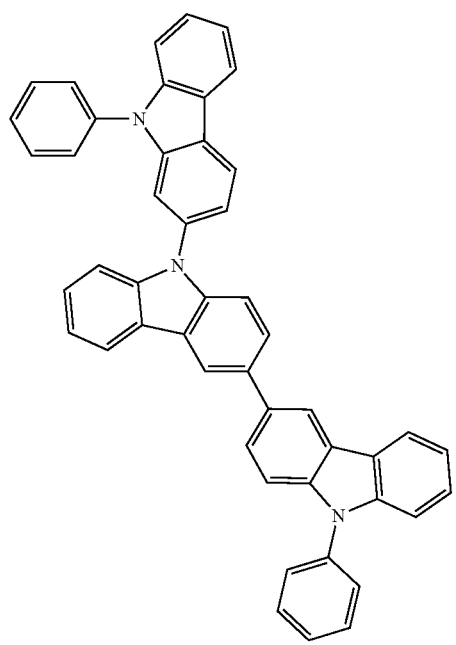
5-33
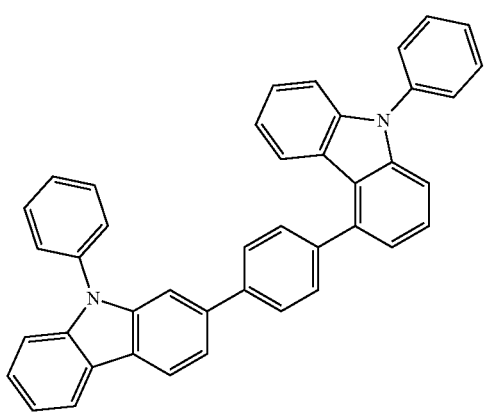
5-34
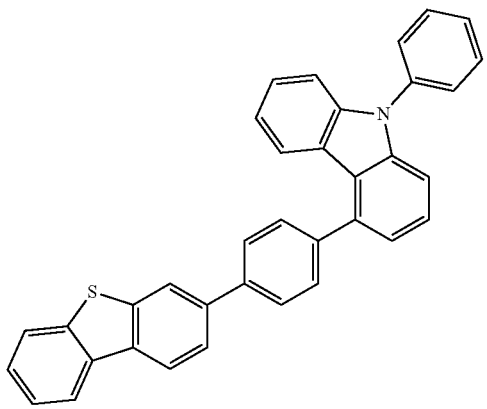

5-35
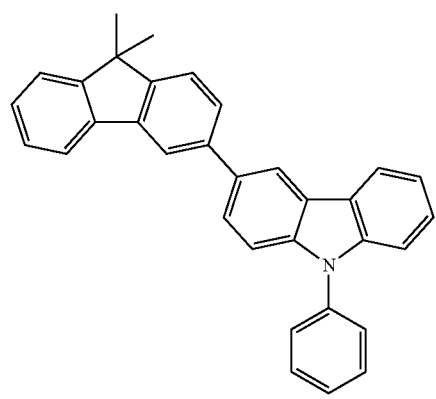
5-36
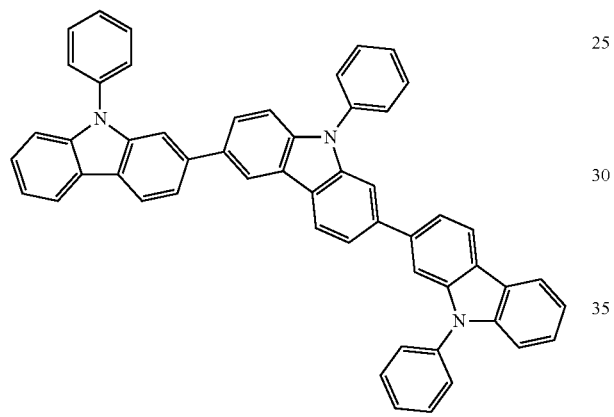
5-37
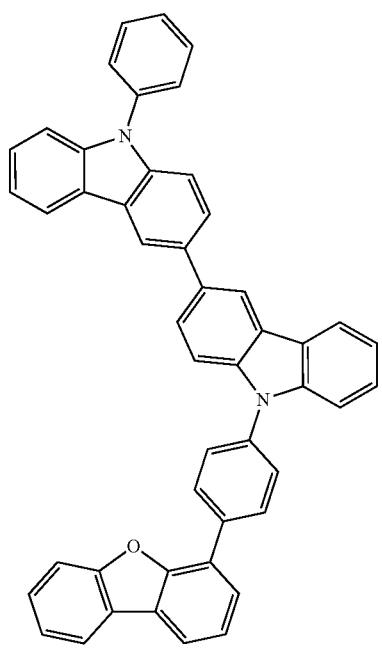
5-38
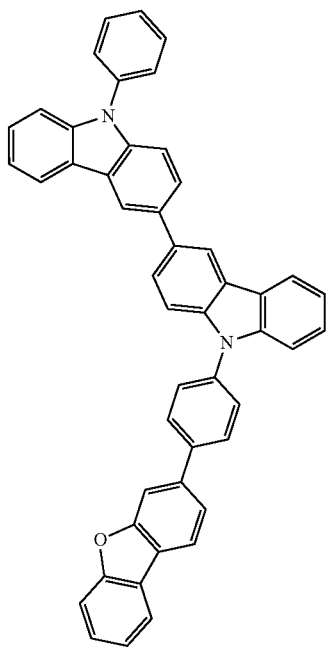
5-39
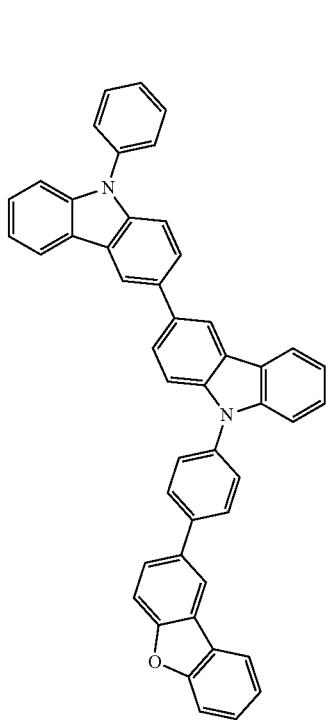

5-40
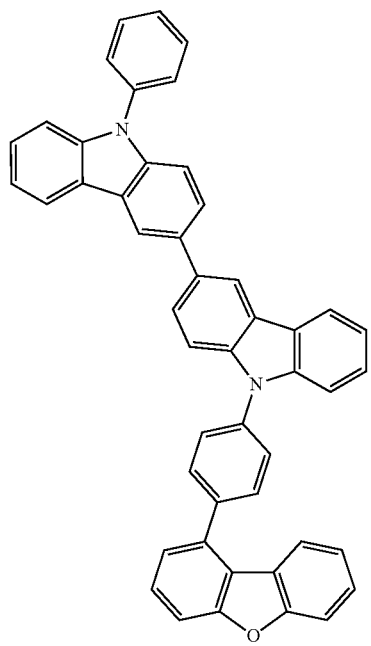
5-41
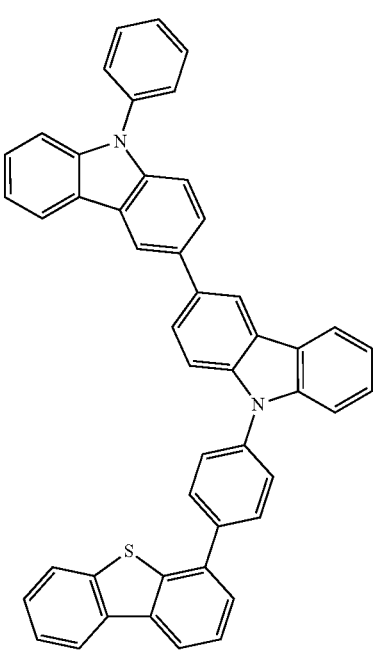
5-42
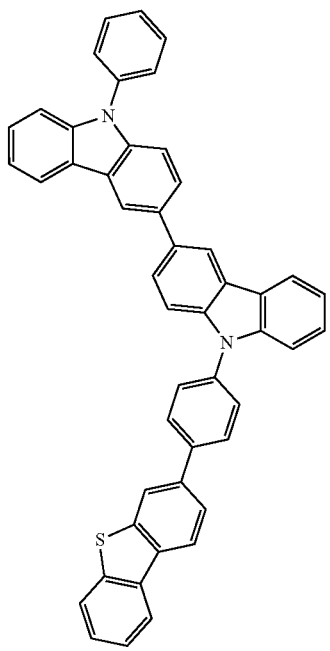
5-43
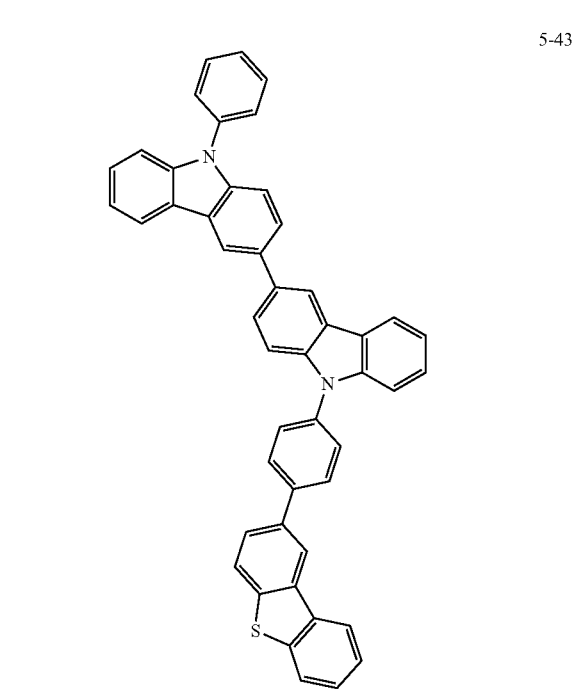

5-44
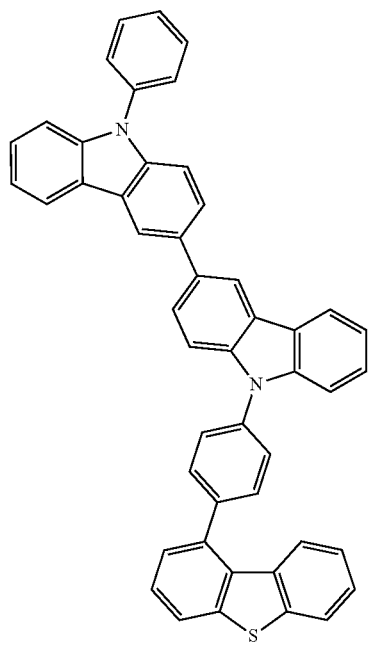
5-45
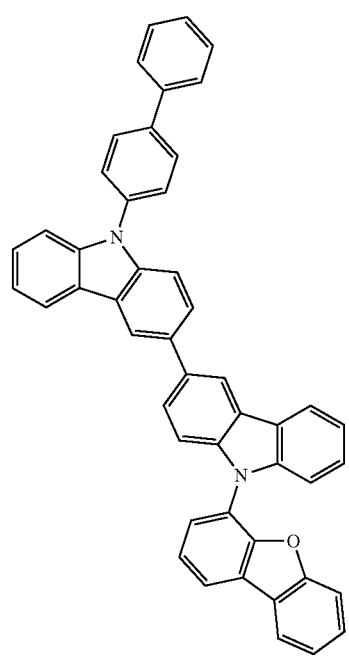
5-46
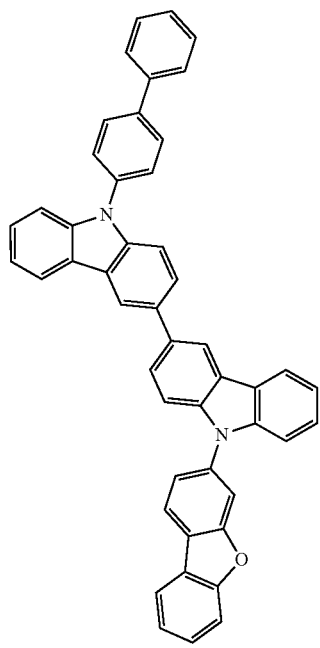
5-47
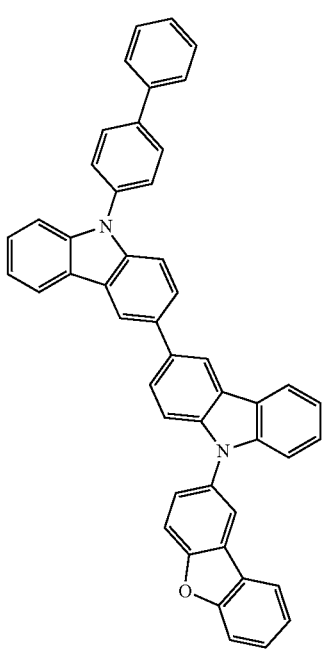

5-48
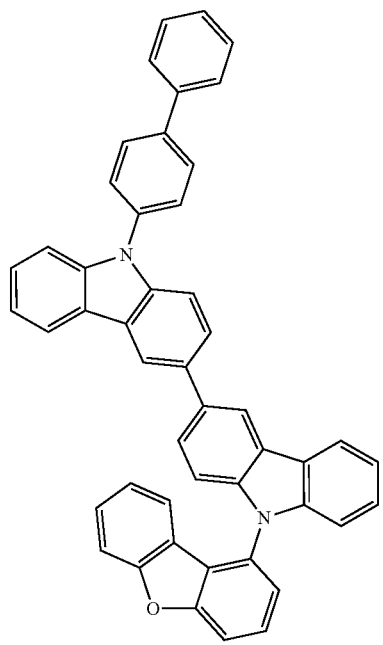
5-49
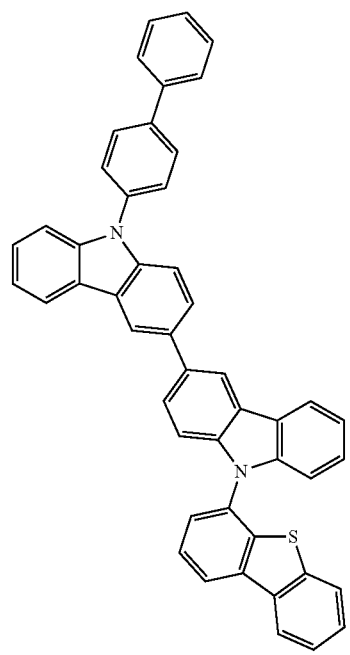
5-50
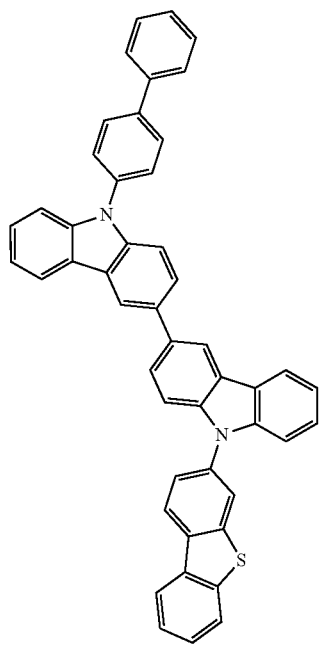
5-51
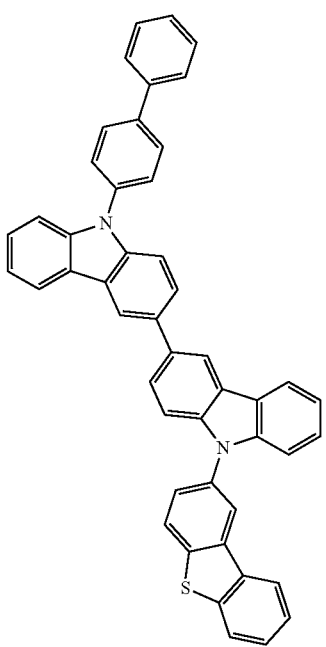

5-52
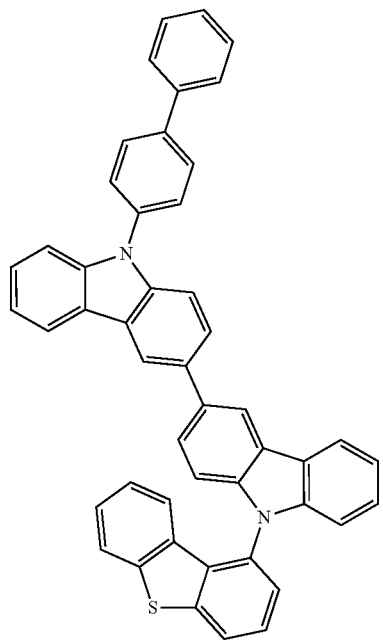
5-53
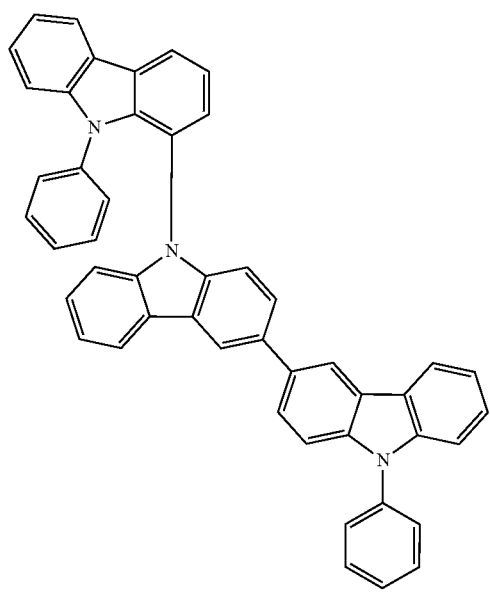
5-54
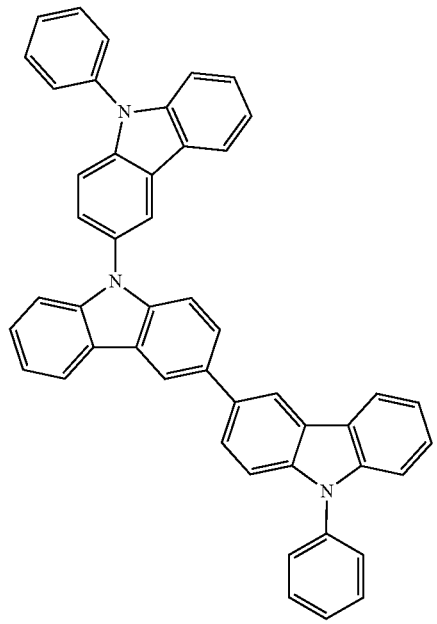
5-55
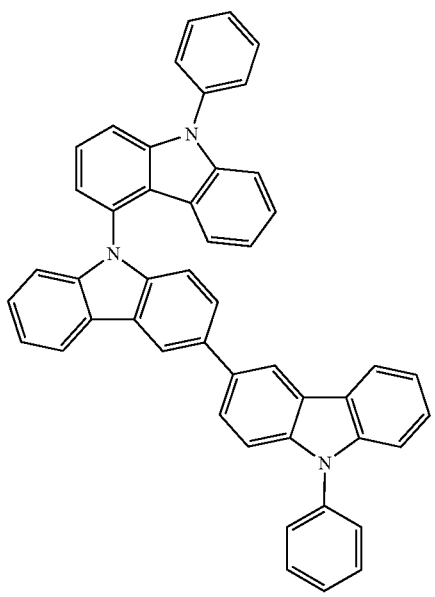

5-56
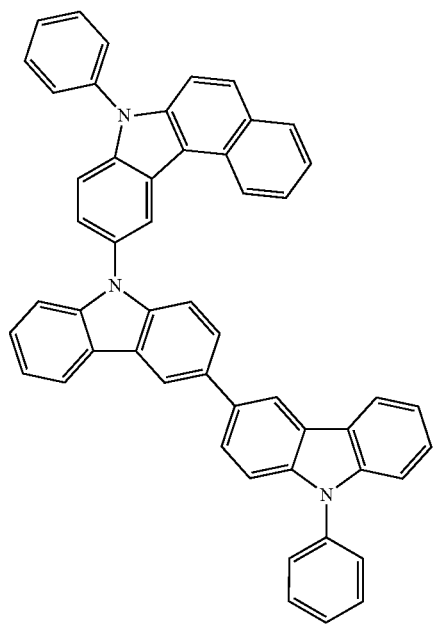
5-57
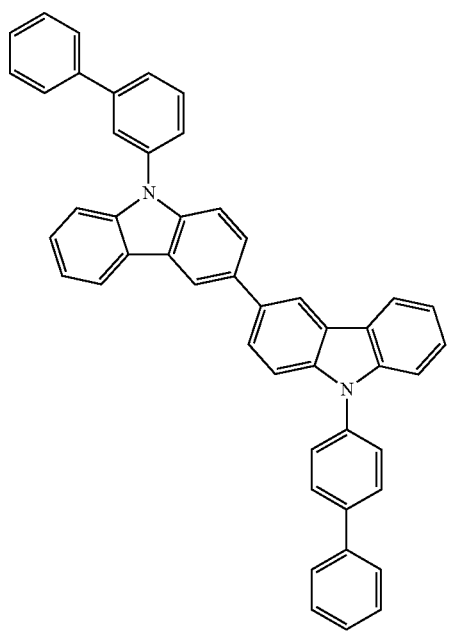
5-58
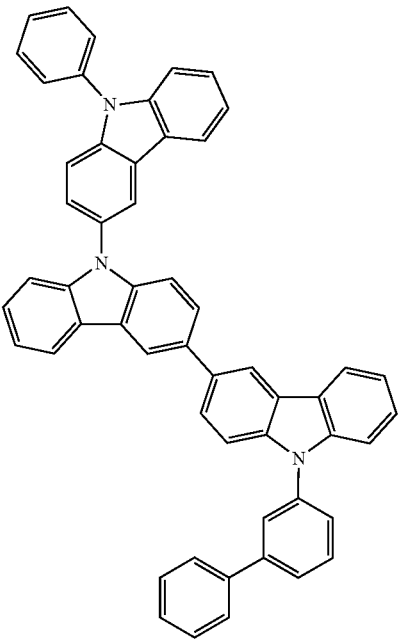
5-59
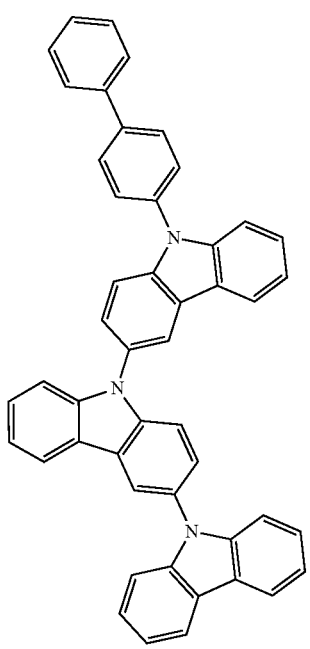

5-60

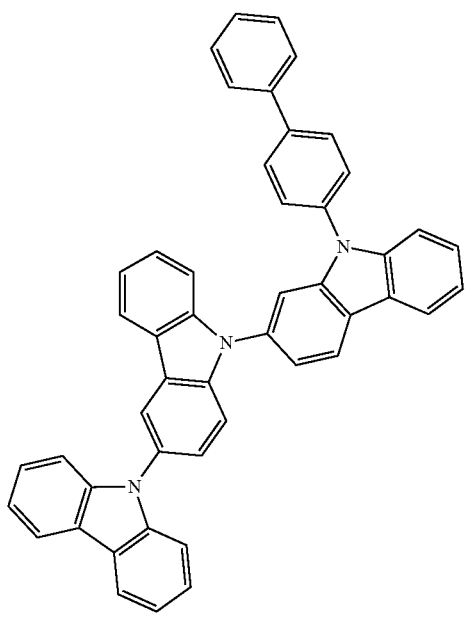

5-61

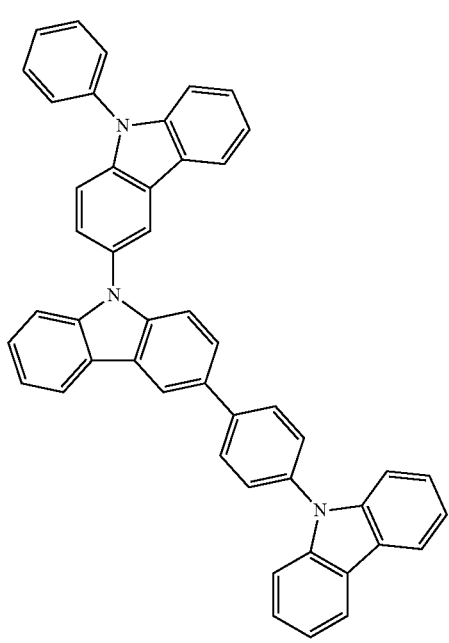

5-62

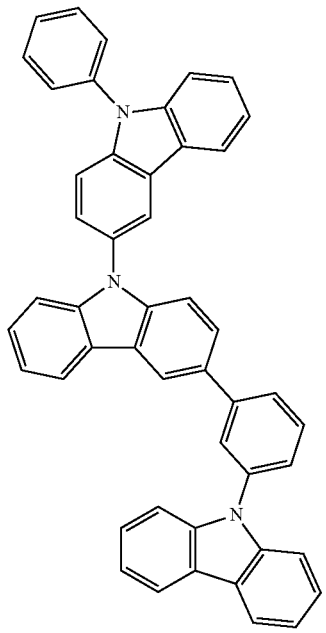

14. The organic electric element of claim 7, wherein the organic material layer comprises a light emitting layer, a hole transport layer formed between the first electrode and the light emitting layer, and an emission-auxiliary layer formed between the light emitting layer and the hole transport layer, and wherein the light emitting layer comprises the compound represented by Formula 1, and the hole transport layer or the emission-auxiliary layer comprises the compound represented by Formula 20:

<Formula 20>

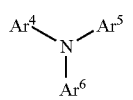

wherein:

Ar$^4$ and Ar$^5$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{60}$ aryloxy group and -L'-N(R$_a$)(R$_b$), and Ar$^4$ and Ar$^5$ may be combined with each other to form a ring, Ar$^6$ is selected from the group consisting of a $C_6$-$C_{60}$ aryl group, a fluorenyl group, and a $C_2$-$C_{60}$ heterocyclic group containing at least one heteroatom selected from the group consisting of O, N, S, Si, and P; or Ar$^6$ is selected from the group consisting of the following Formulas 1-a to 1-c:

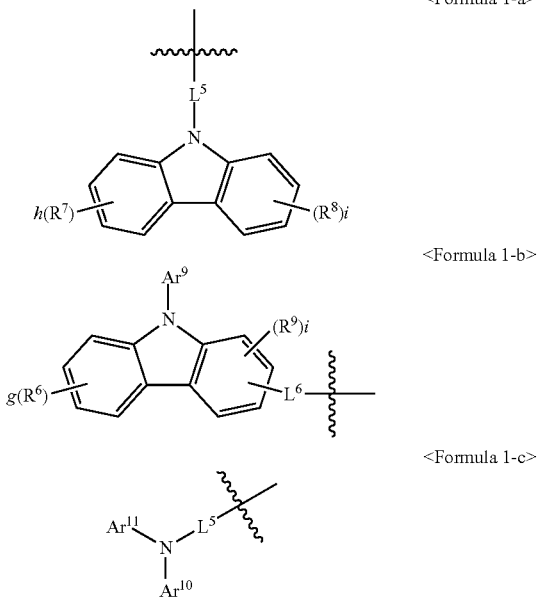

<Formula 1-a>
<Formula 1-b>
<Formula 1-c>

Wherein:

$Ar^9$ to $Ar^{11}$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), $L^5$ is selected from the group consisting of a $C_6$-$C_{60}$ arylene group, a fluorenylene group, and a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, $L^6$ is selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, $R^6$ to $R^9$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{60}$ aryloxy group and -L'-N($R_a$)($R_b$), and adjacent groups may be optionally linked to each other to form a ring, h, i and g are each an integer of 0 to 4, j is an integer of 0 to 3, where each of these is an integer of 2 or more, a plurality of $R^6$s, a plurality of $R^7$s, a plurality of $R^8$s, a plurality of $R^9$s are the same as or different from each other, L' is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, $R_a$ and $R_b$ are each independently selected from the group consisting of hydrogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, $Ar^4$ to $Ar^6$, $Ar^9$ to $Ar^{11}$, $R^6$ to $R^9$, $L^5$, $L^6$, and the ring formed by adjacent groups may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, a $C_8$-$C_{20}$ arylalkenyl group and a combination thereof.

15. The organic electric element of claim 14, wherein the light emitting layer further comprises the compound represented by Formula 12.

16. The organic electric element of claim 14, wherein the hole transport layer comprises the compound represented by the following Formula 21 or 22 and the emission-auxiliary layer comprises the compound represented by the following Formula 23 or 24:

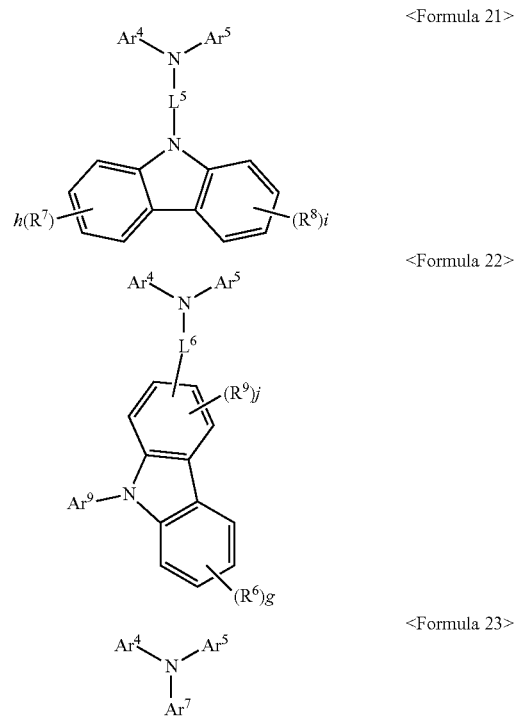

<Formula 21>
<Formula 22>
<Formula 23>

-continued

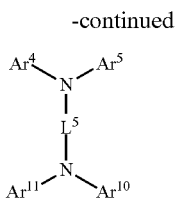

<Formula 24> wherein $Ar^4$, $Ar^5$, $Ar^9$ to $Ar^{11}$, h, i, g, j, $L^5$, $L^6$, $R^6$ to $R^9$ are the same as defined in claim 14, $Ar^7$ is selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, and a $C_3$-$C_{60}$ aliphatic ring.

17. The organic electric element of claim 16, wherein, in Formula 24, at least one of $Ar^4$, $Ar^5$, $Ar^{10}$ and $Ar^{11}$ is a fluorenyl group represented by Formula 24-1, and $L^5$ is a $C_6$ to $C_{60}$ arylene group:

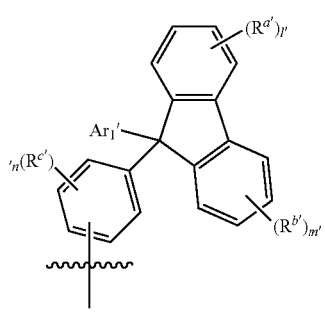

<Formula 24-1> wherein:
$R^{a'}$, $R^{b'}$ and $R^{c'}$ are each independently selected from the group consisting of hydrogen, deuterium, halogen, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom selected from the group consisting of O, N, S, Si, and P, $C_3$-$C_{20}$ cycloalkyl group, and a fused ring group formed by a $C_3$-$C_{60}$ aliphatic ring with a $C_6$-$C_{60}$ aromatic ring, and adjacent groups may be optionally linked to each other to form a ring, l', m' and n' are each an integer of 0 to 4, where each of these is an integer of 2 or more, a plural of $R^{a'}$s, a plural of $R^{b'}$s or a plural of $R^{c'}$s are each the same or different from each other, $Ar_{1'}$ is selected from the group consisting of a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom selected from the group consisting of O, N, S, Si, and P, $C_3$-$C_{20}$ cycloalkyl group, and a fused ring group formed by a $C_3$-$C_{60}$ aliphatic ring with a $C_6$-$C_{60}$ aromatic ring, and $R^{a'}$, $R^{b'}$, $R^{c'}$, $Ar_{1'}$ and the ring formed by adjacent groups may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, a $C_8$-$C_{20}$ arylalkenyl group and a combination thereof.

18. The organic electric element of claim 17, wherein $Ar_{1'}$ and $L^5$ are each independently phenyl, biphenyl, o-terphenyl, m-terphenyl, p-terphenyl or naphthalene.

19. The organic electric element of claim 17, wherein Formula 24 is represented by Formula A:

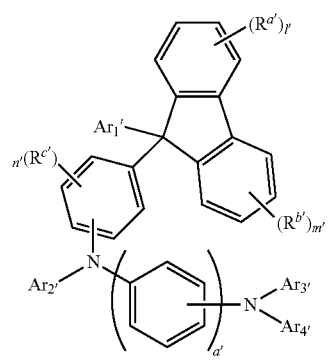

<Formula A> wherein $R^{a'}$, $R^{b'}$, $R^{c'}$, $Ar_{1'}$, l', m' and n' are the same as defined in claim 17, $Ar_{2'}$ is the same as defined for $Ar^{11}$ in Formula 24, $Ar_{3'}$ is the same as defined for $Ar^4$ in Formula 24, $Ar_{4'}$ is the same as defined for $Ar^5$ in Formula 24, and a' is an integer of 1 to 3.

20. The organic electric element of claim 14, wherein the compound represented by Formula 20 is one of the following compounds:

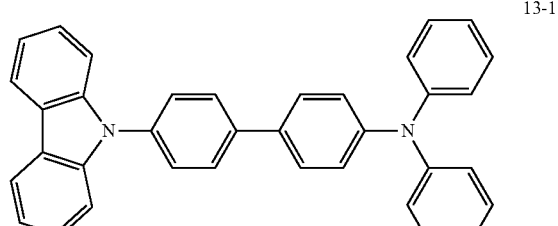

13-1

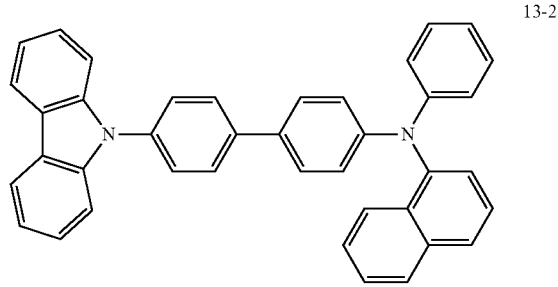

13-2

13-3
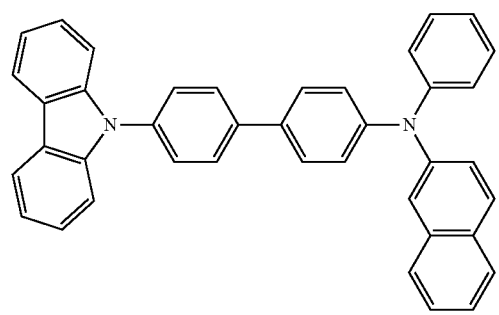
13-4
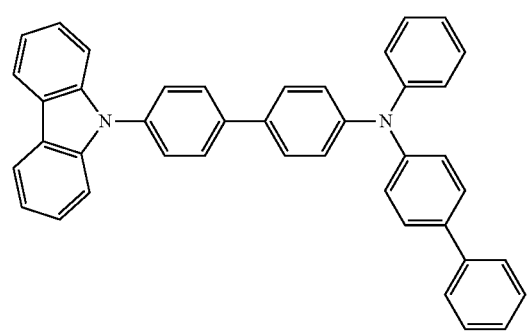
13-5
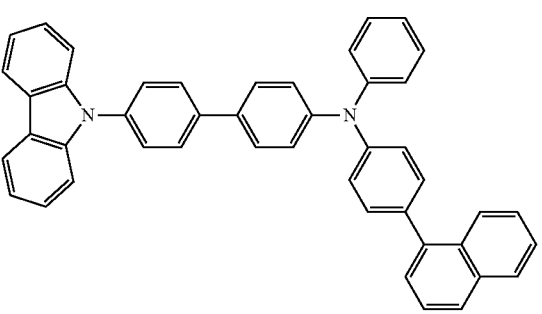
13-6
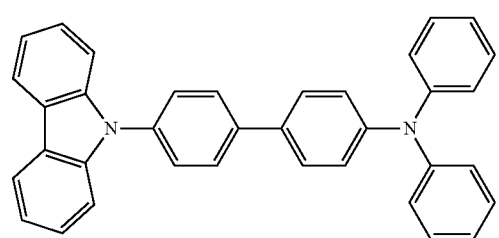
13-7
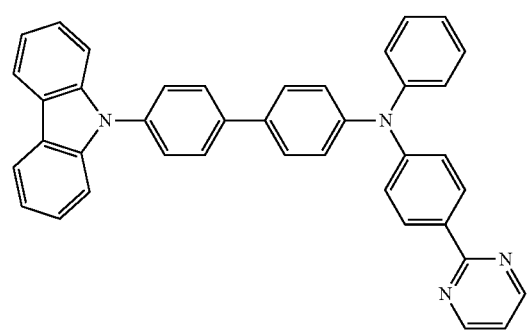
13-8
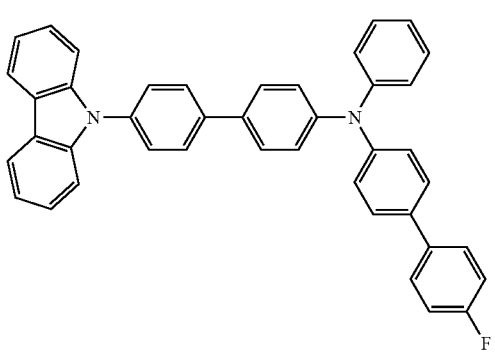
13-9
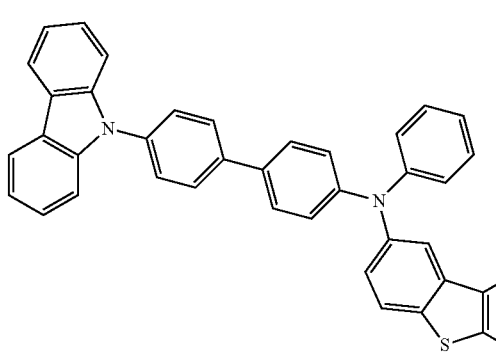
13-10
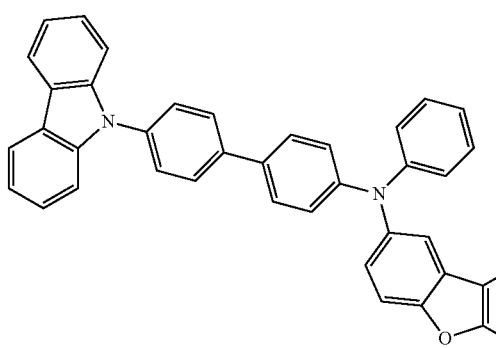
13-11
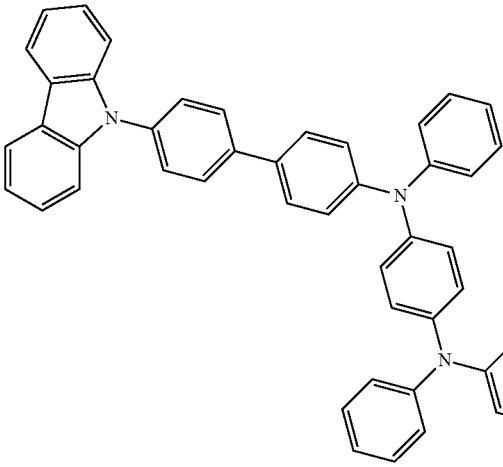

13-12
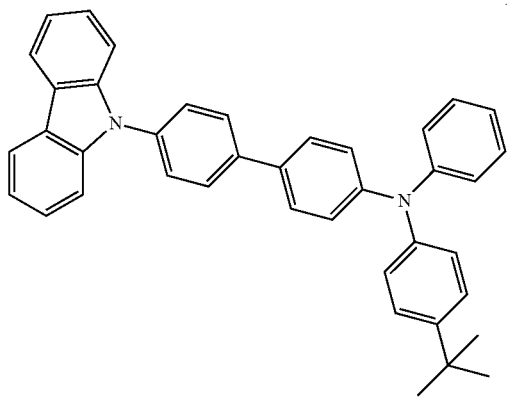
13-16
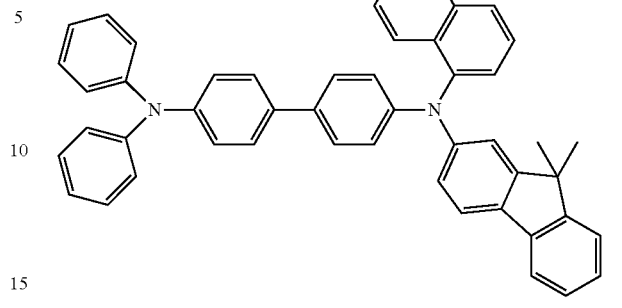
13-13
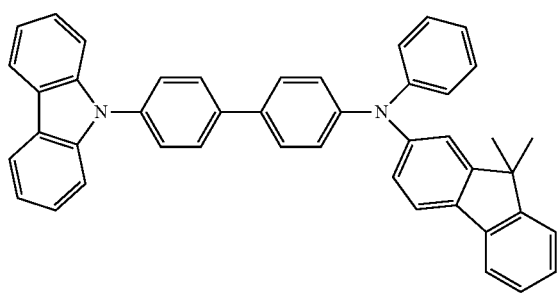
13-17
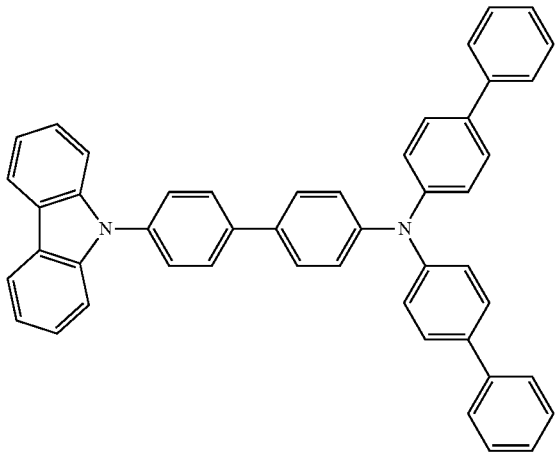
13-14
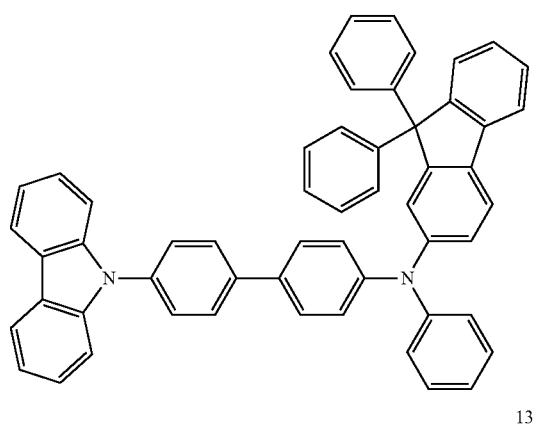
13-18
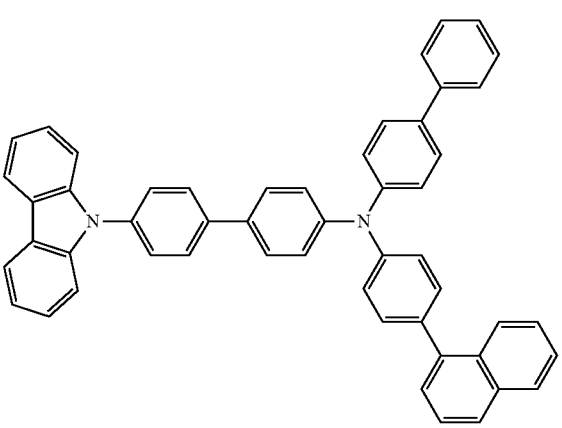
13-15
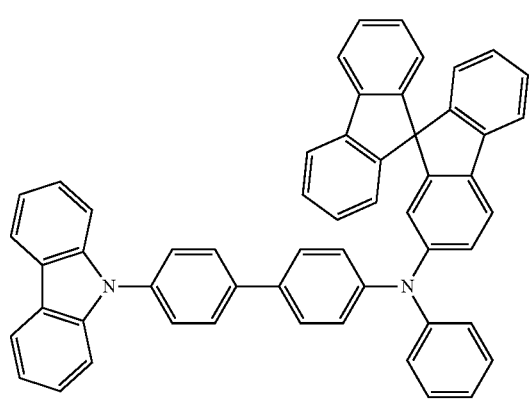
13-19
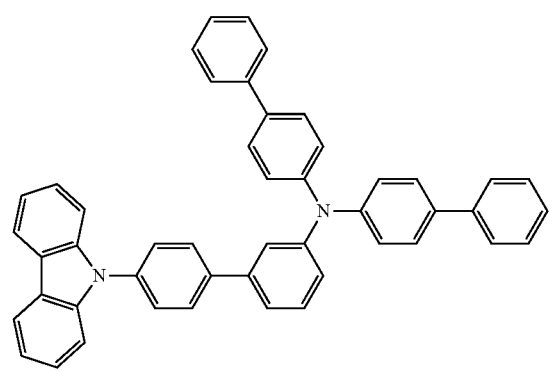

13-20
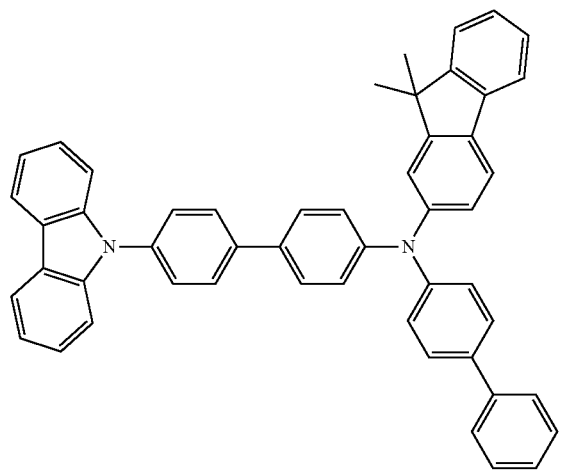
13-21
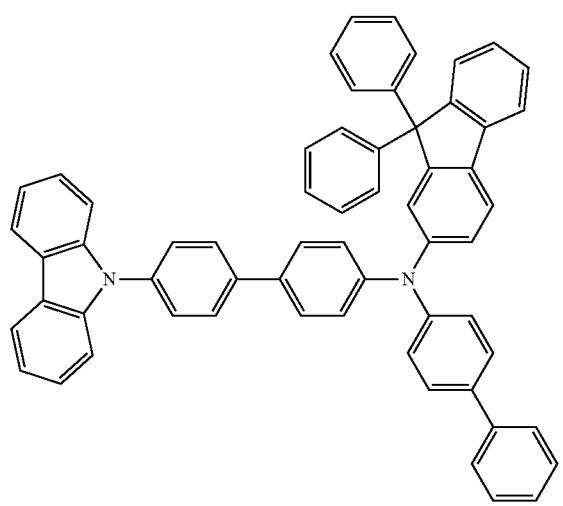
13-22
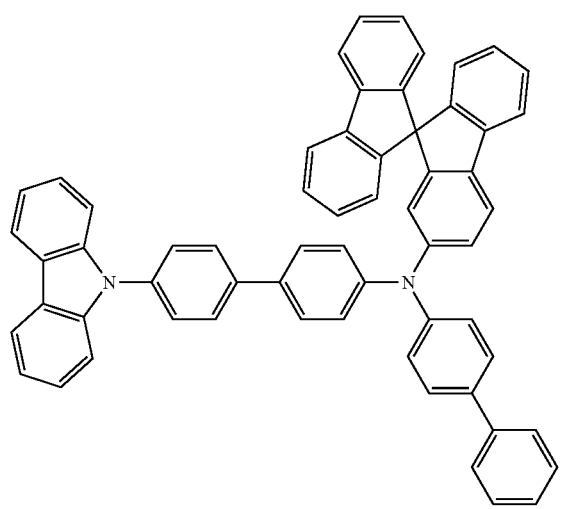
13-23
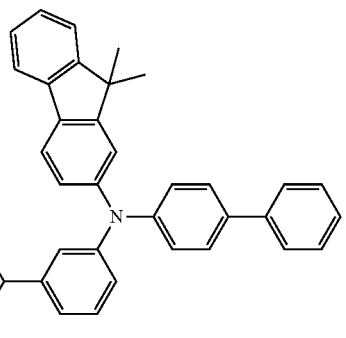
13-24
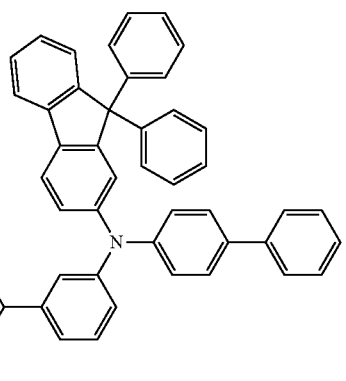
13-25
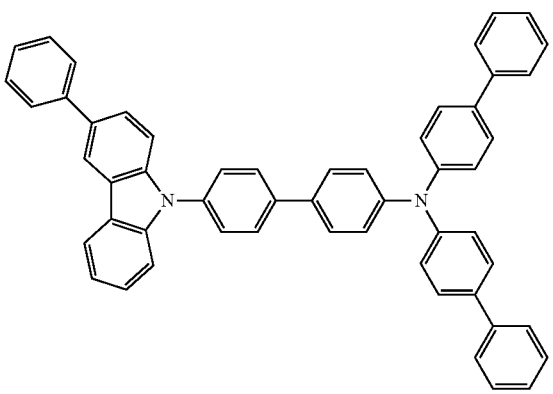
13-26
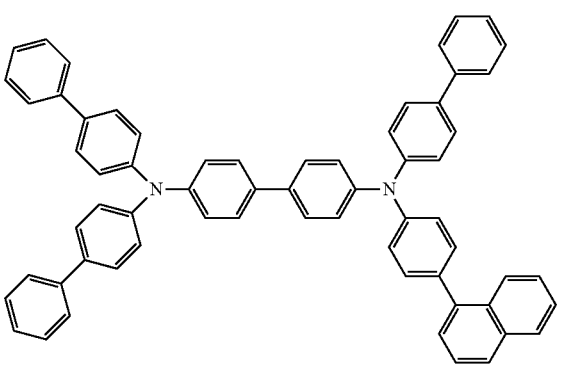

13-27
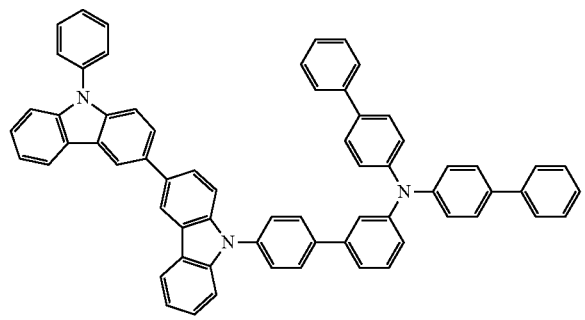
13-28
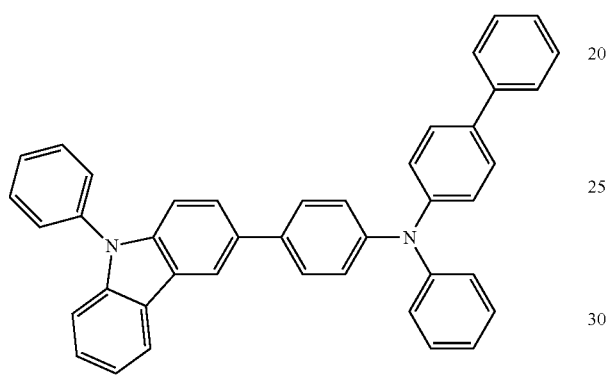
13-29
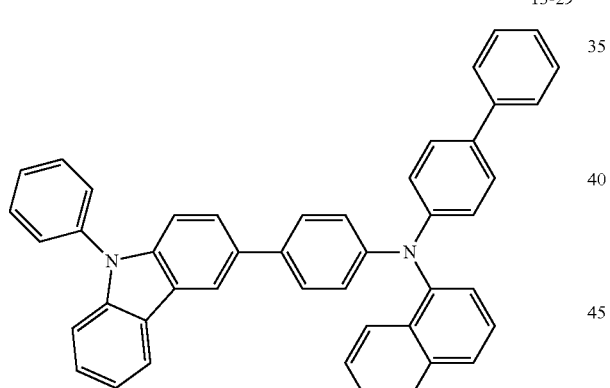
13-30
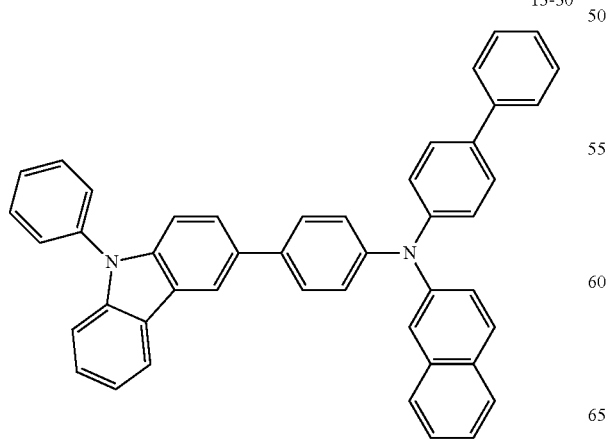
13-31
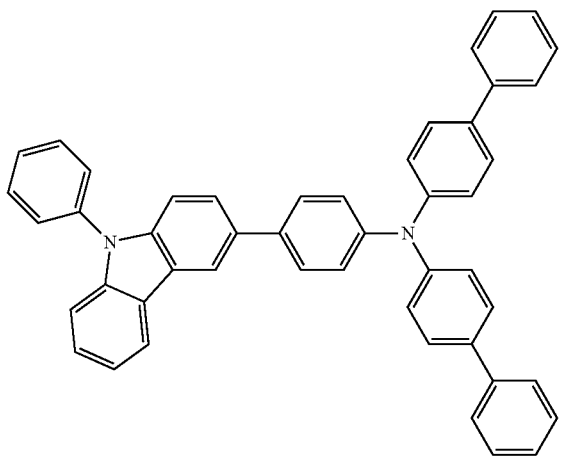
13-32
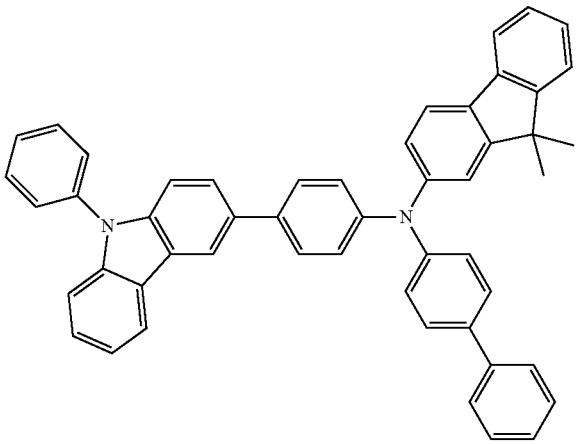
13-33
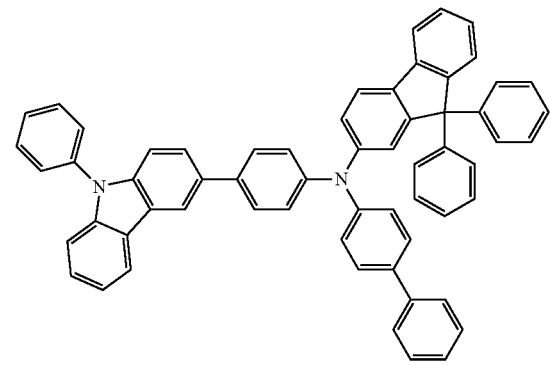

13-34
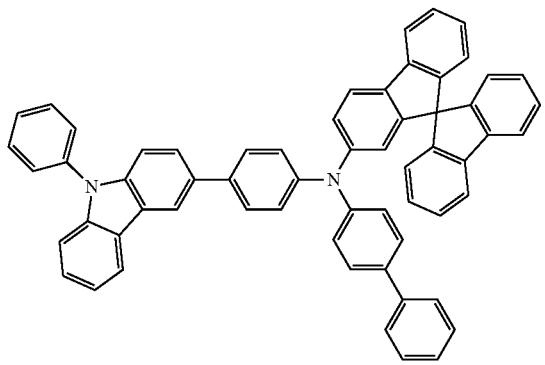
13-35
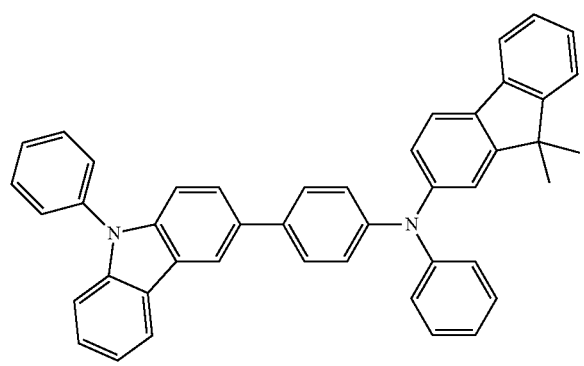
13-36
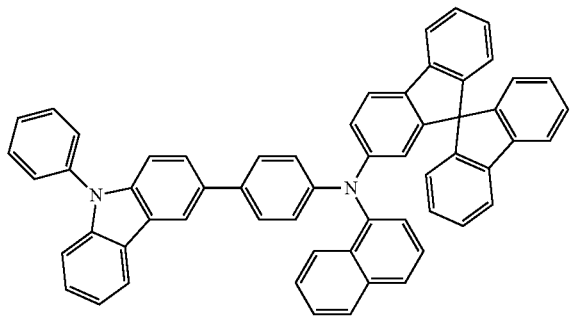
13-37
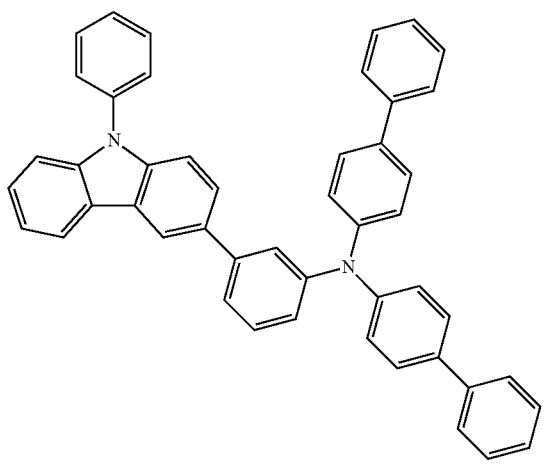
13-38
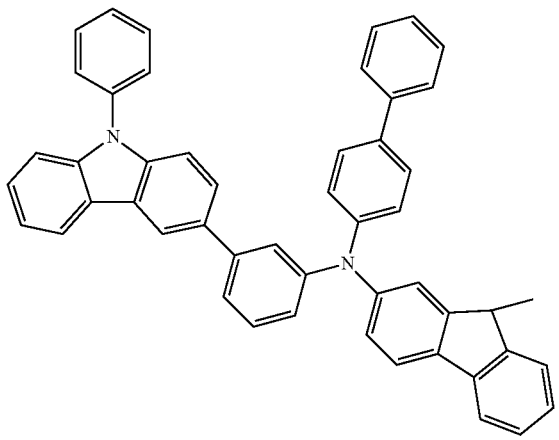
13-39
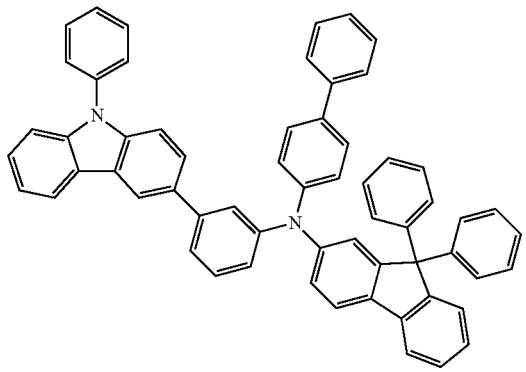
13-40
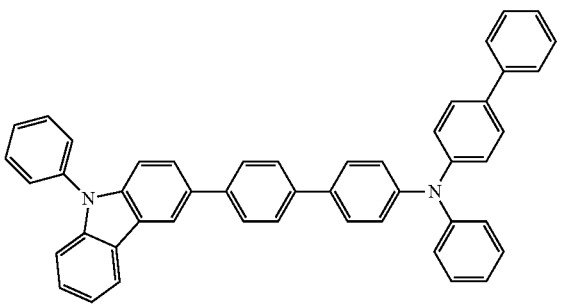
13-41
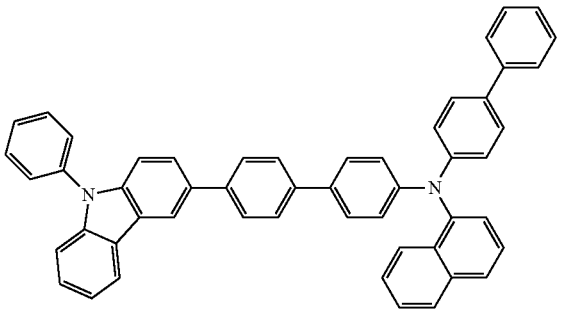

-continued
13-42
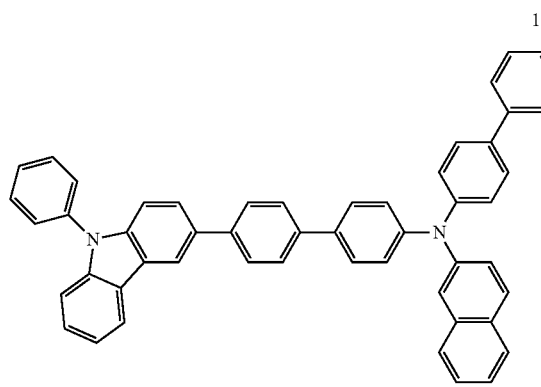
13-43
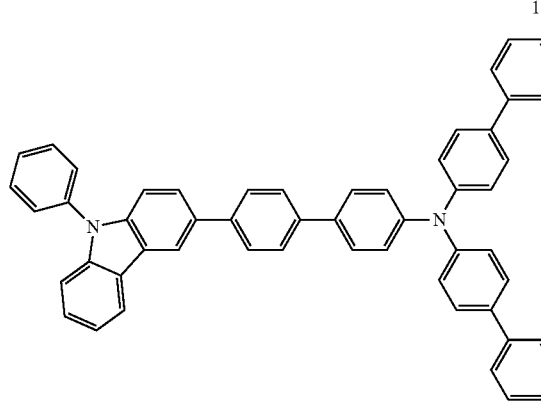
13-44
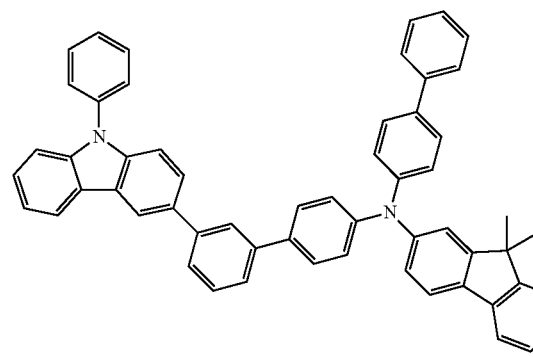
13-45
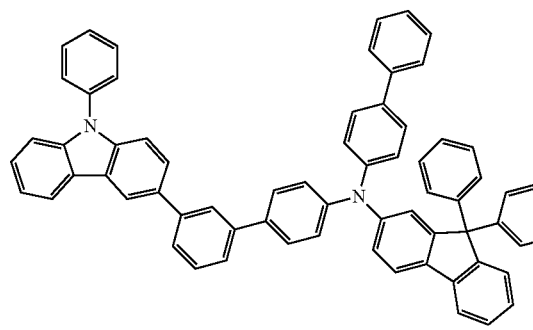
-continued
13-46
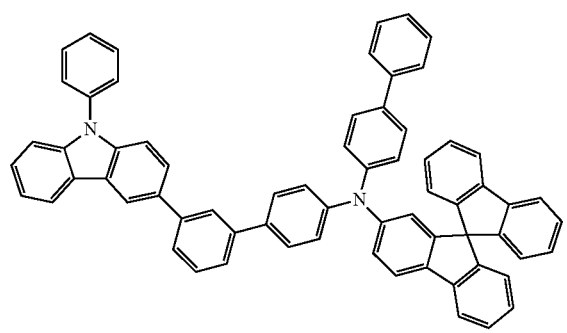
13-47
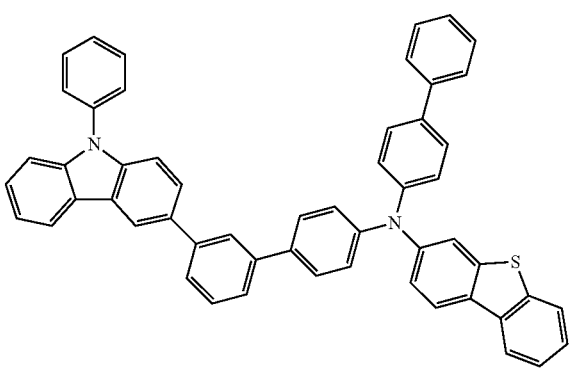
13-48
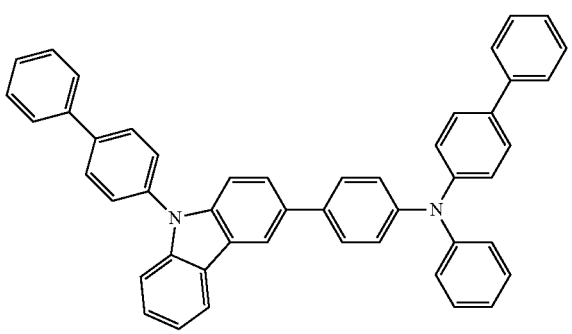
13-49
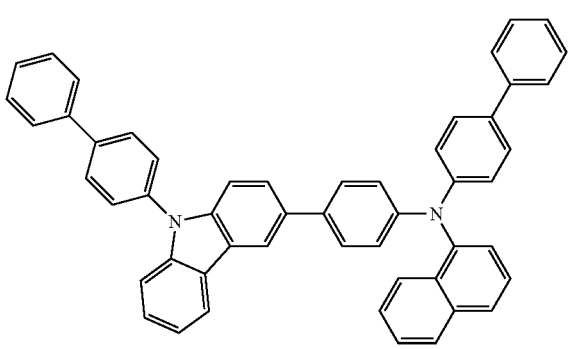

515
-continued
13-50
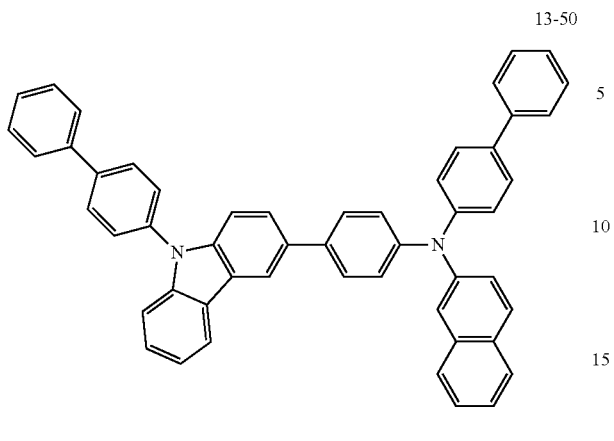
13-51
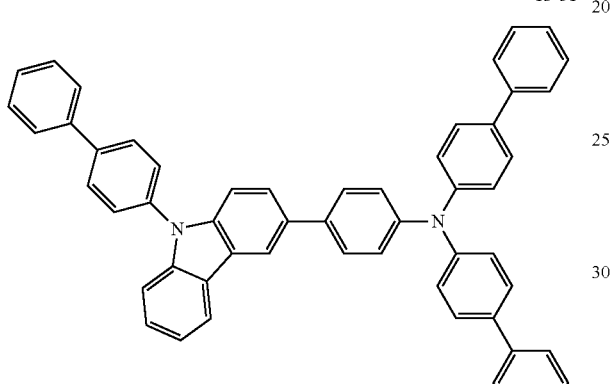
13-52
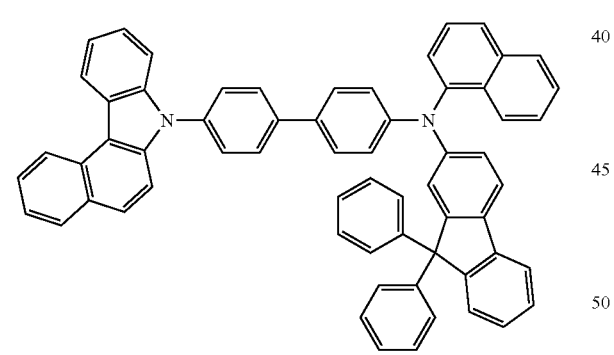
13-53
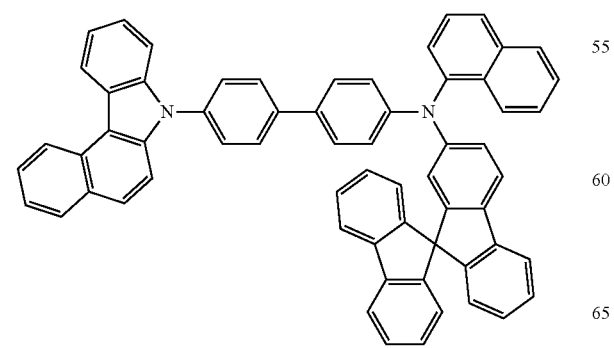
516
-continued
13-54
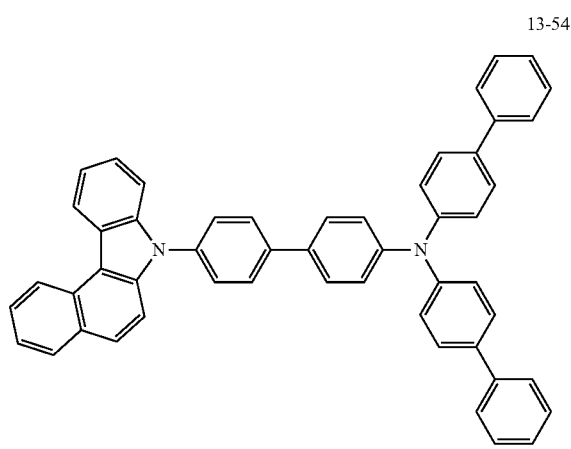
13-55, 13-56
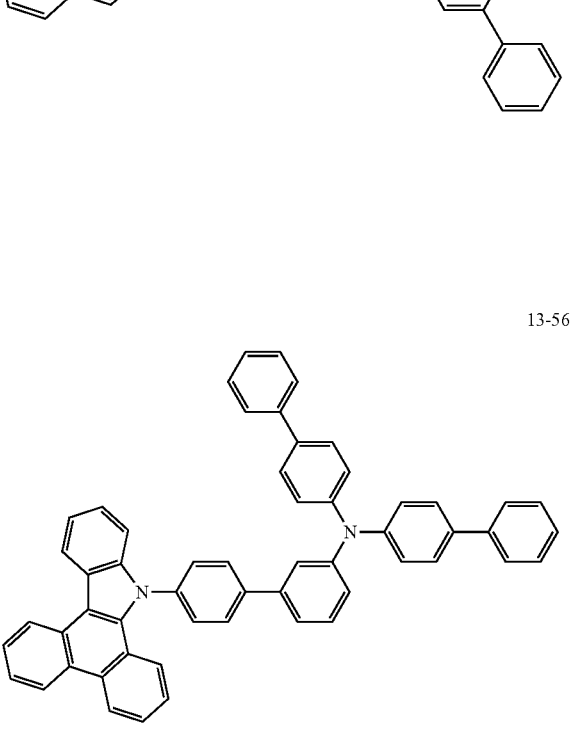

13-57
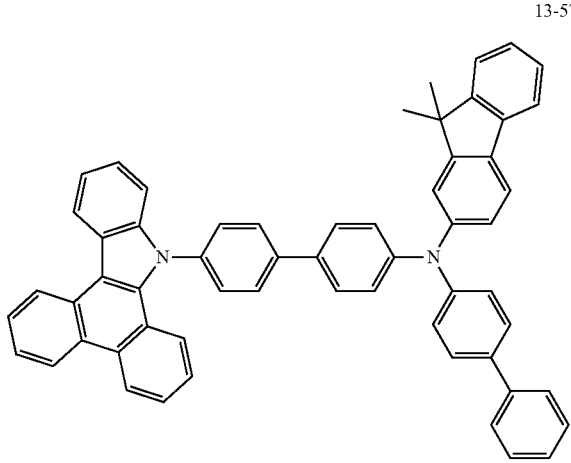
13-58
13-59
13-60
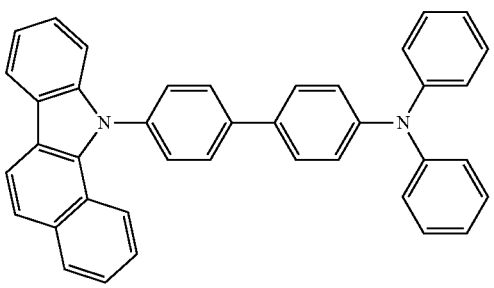
13-61
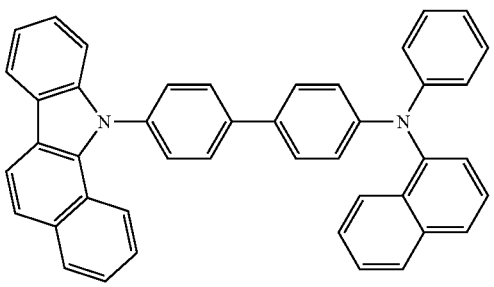
13-62
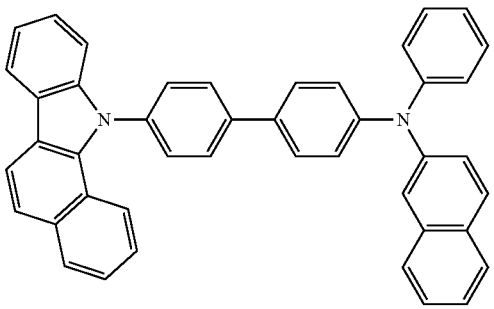
13-63
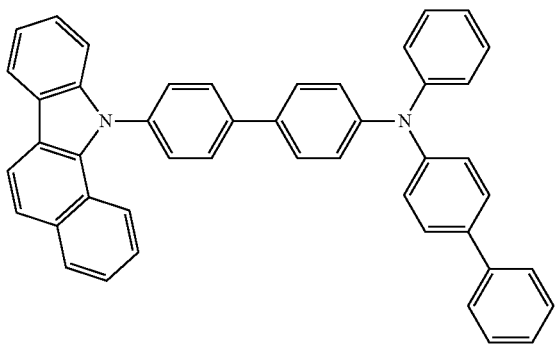

13-64
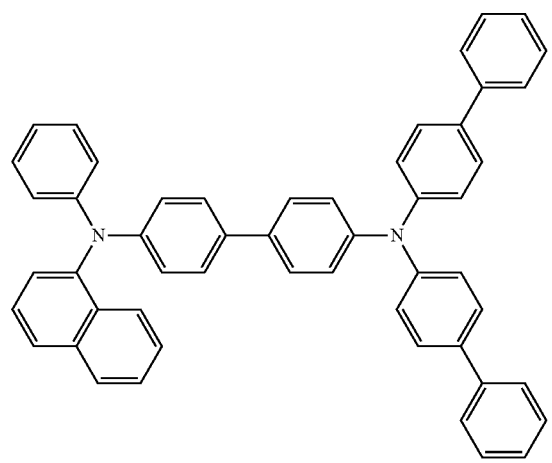
13-65
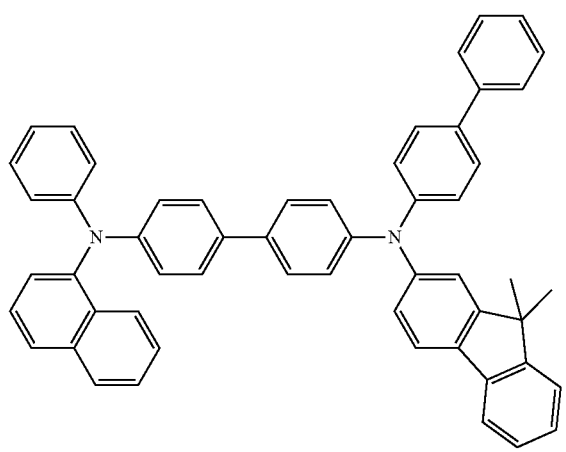
13-66
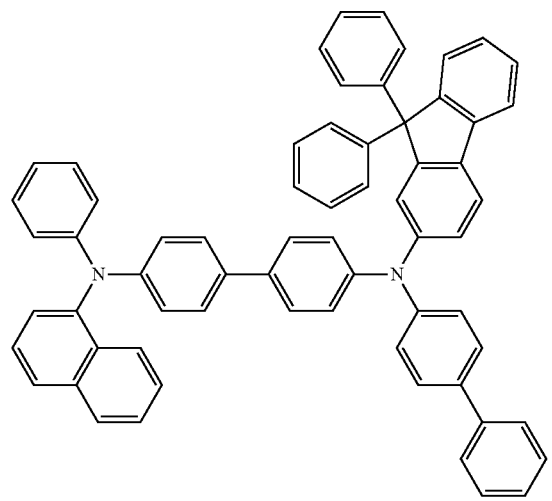
13-67
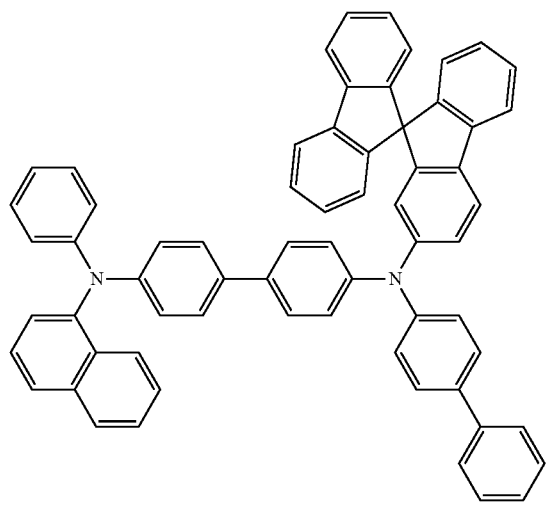
13-68
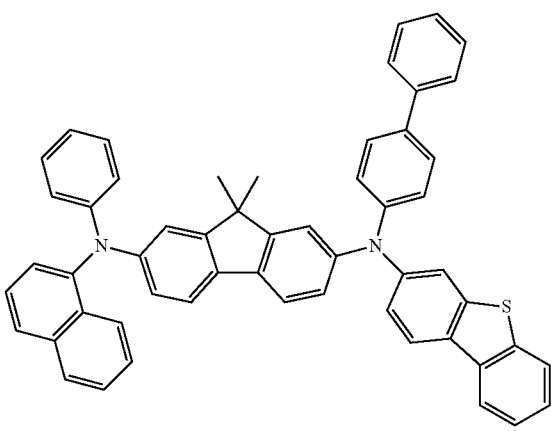
13-69
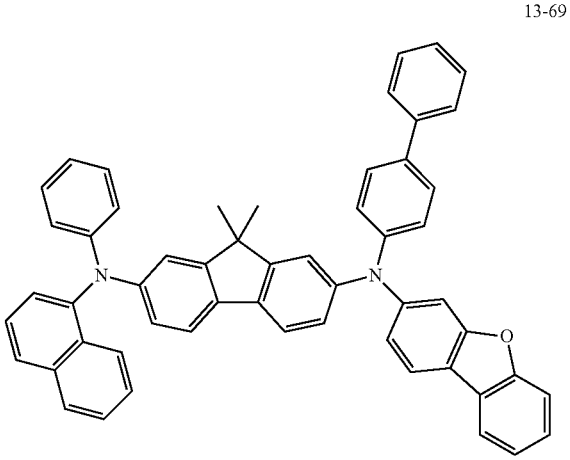

13-70
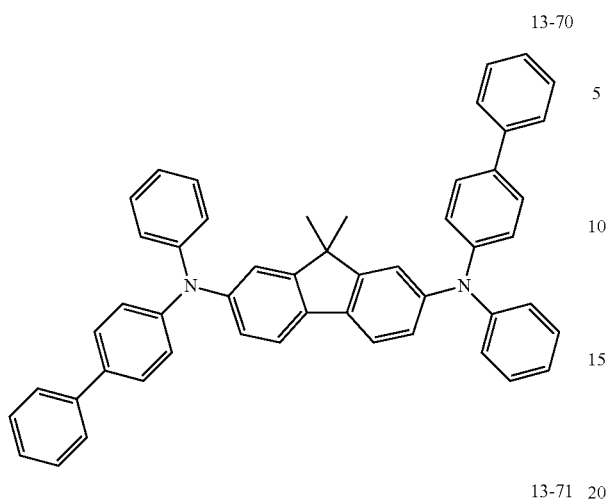
13-71
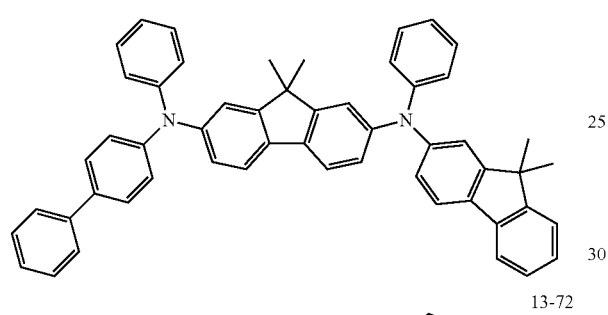
13-72
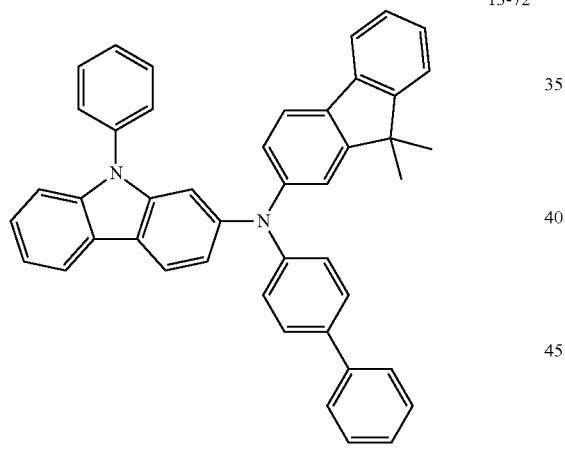
13-73
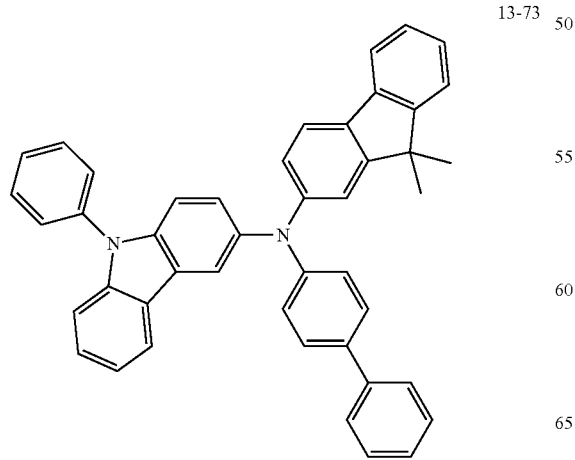
13-74
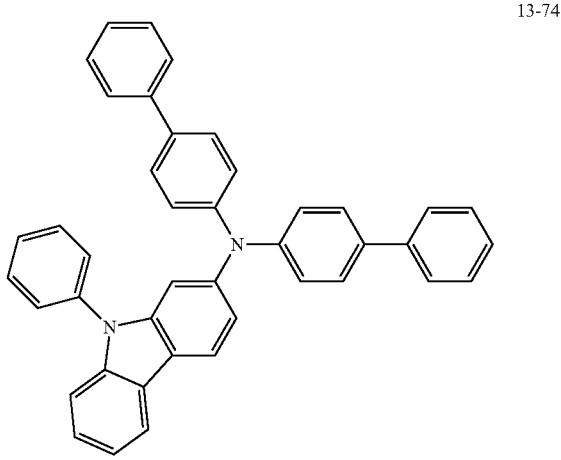
13-75
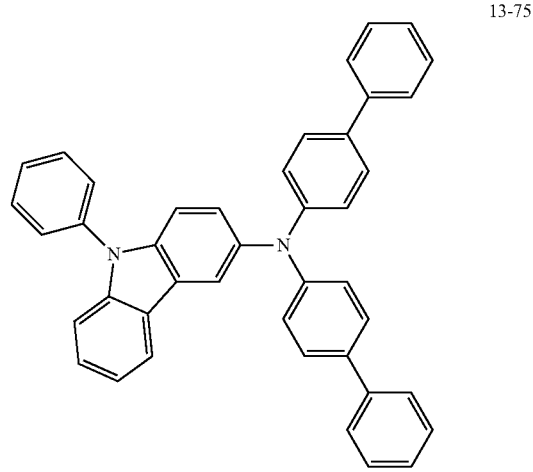
13-76
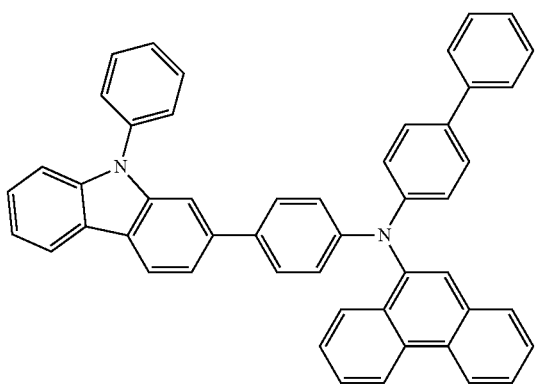

523
-continued
13-77
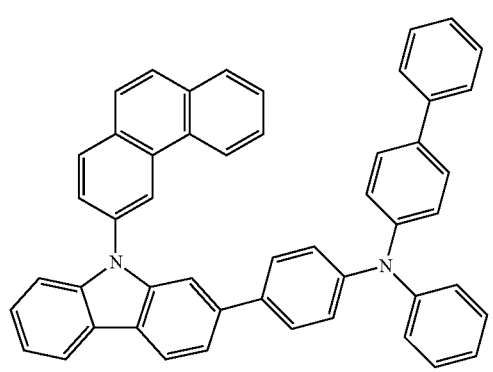
13-78
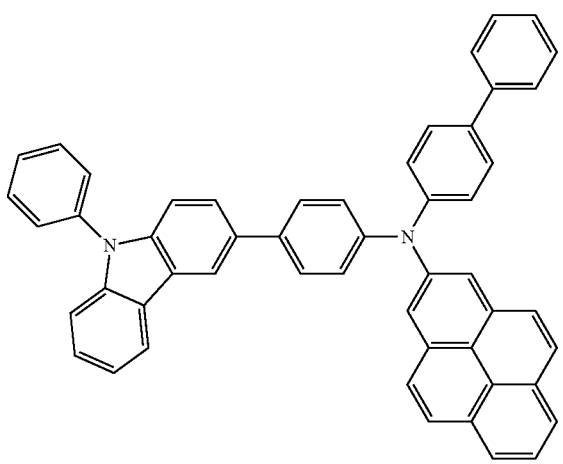
13-79
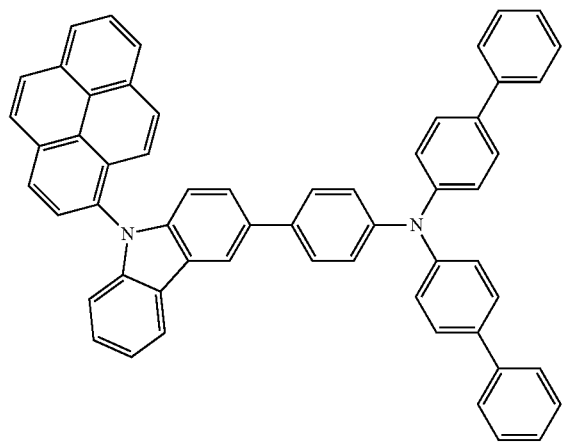
524
-continued
14-1
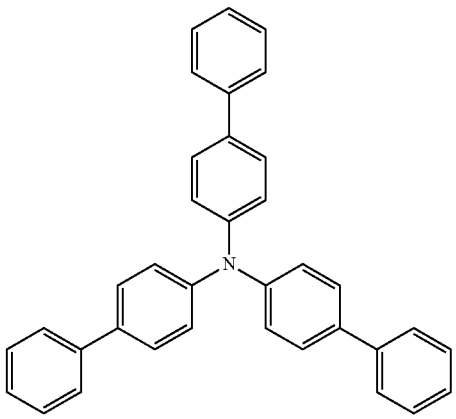
14-2
14-3
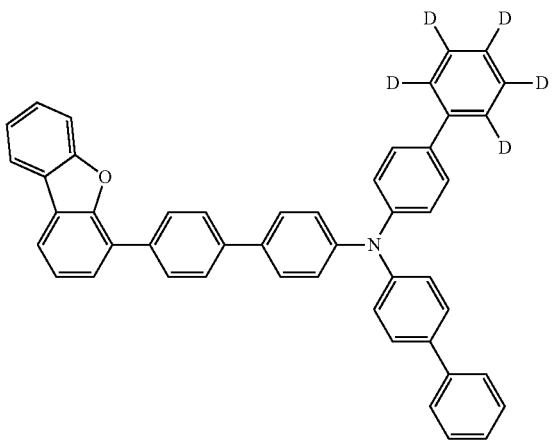

14-4
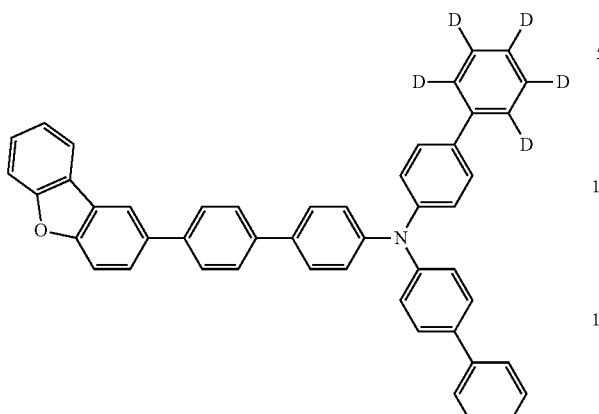
14-5
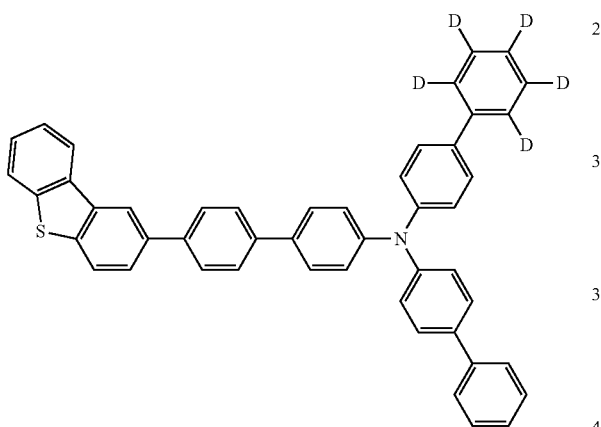
14-6
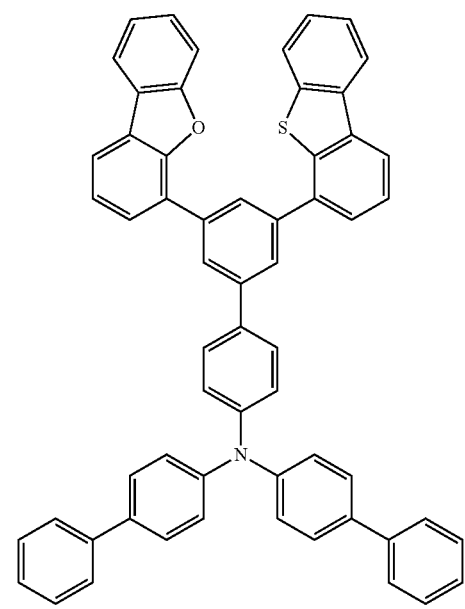
14-7
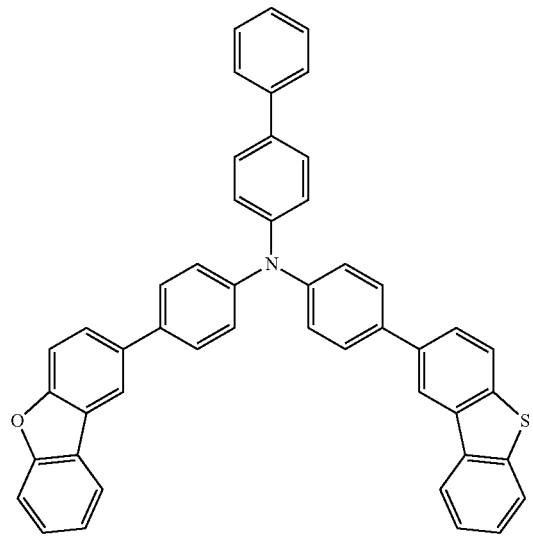
14-8
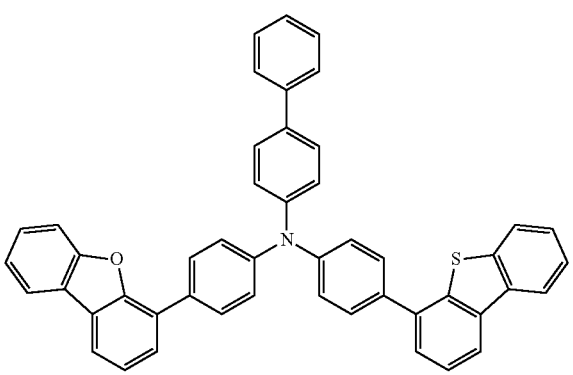
14-9
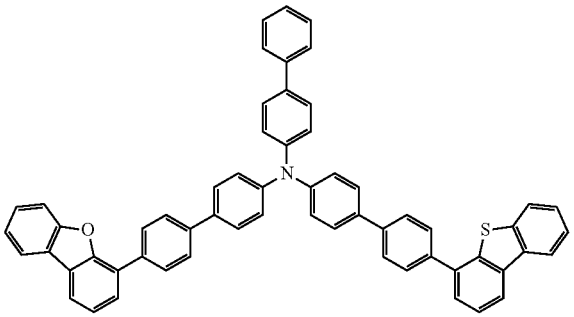

14-10
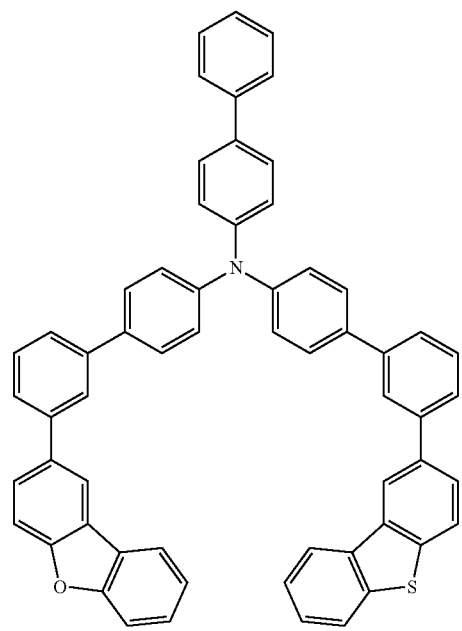
14-12
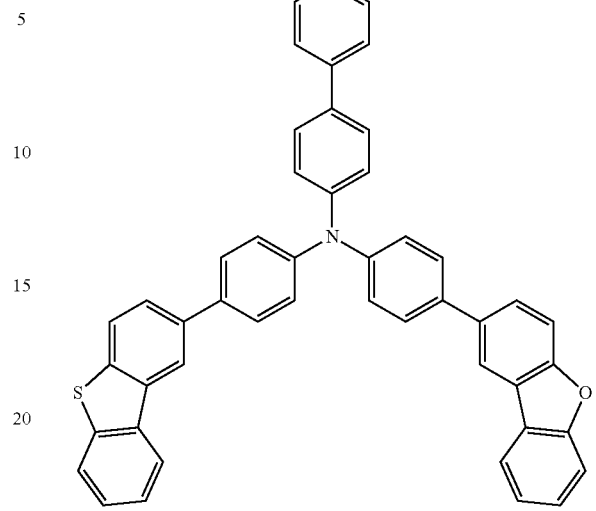
14-13
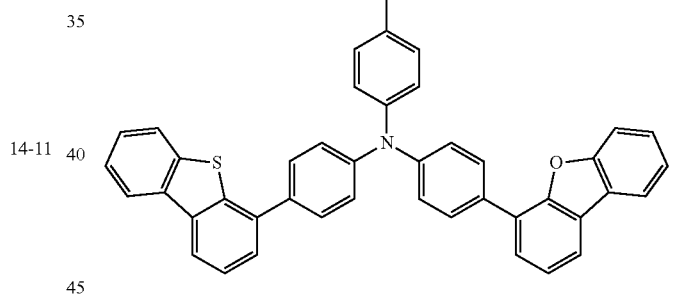
14-11
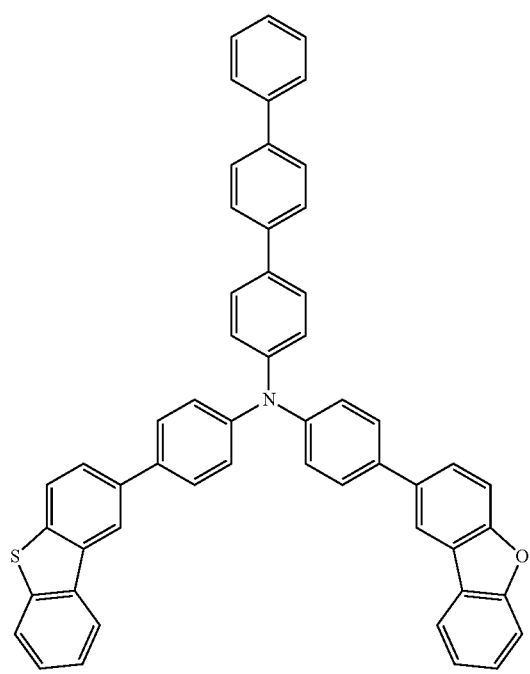
14-14
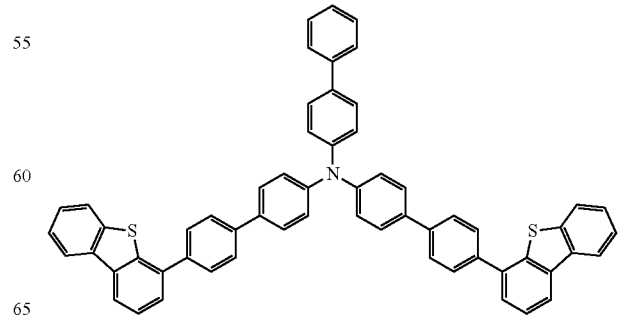

14-15
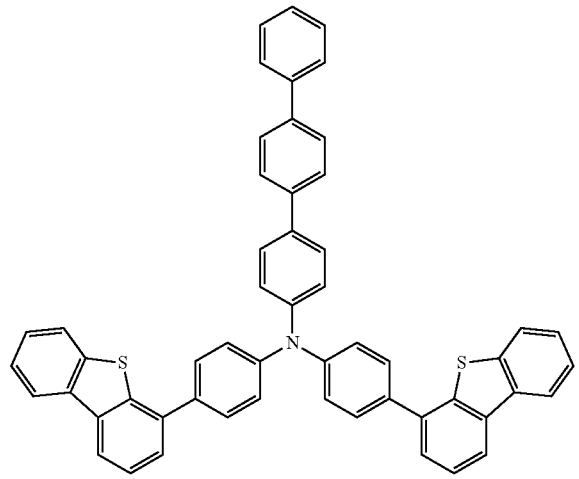
14-16
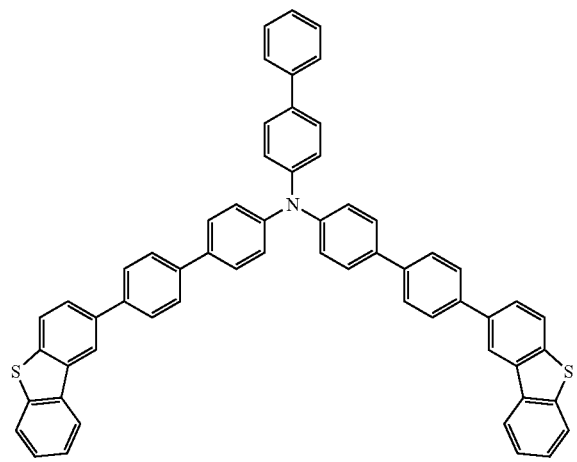
14-17
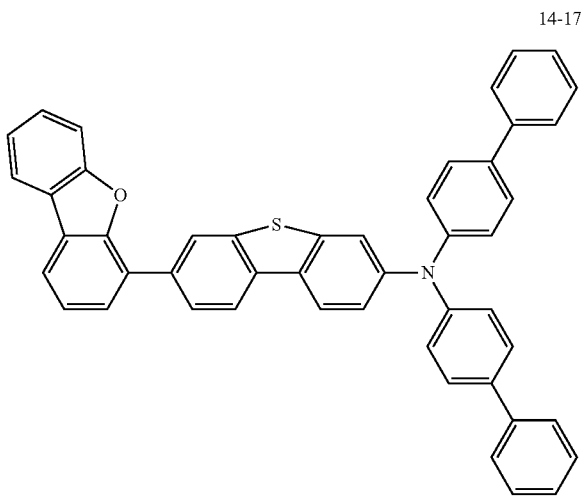
14-18
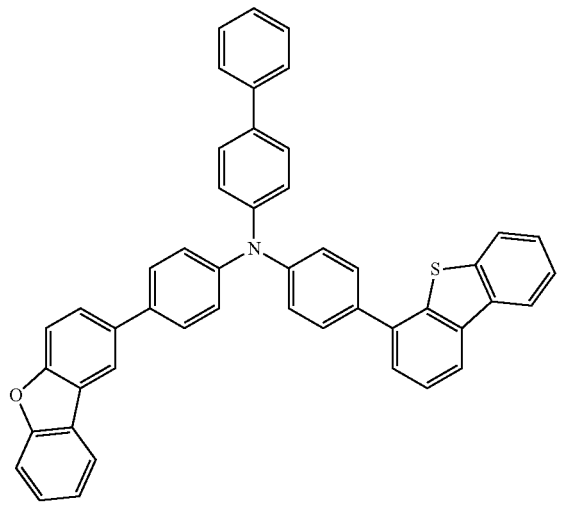
14-19
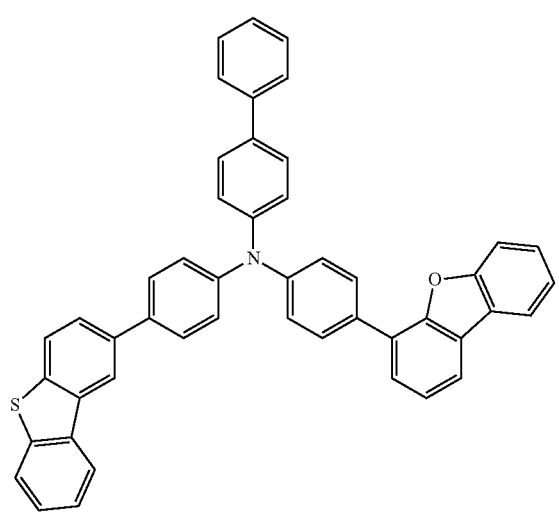
14-20
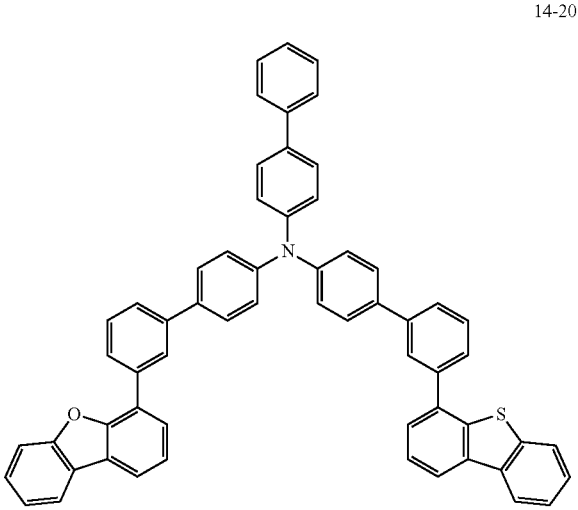

14-21
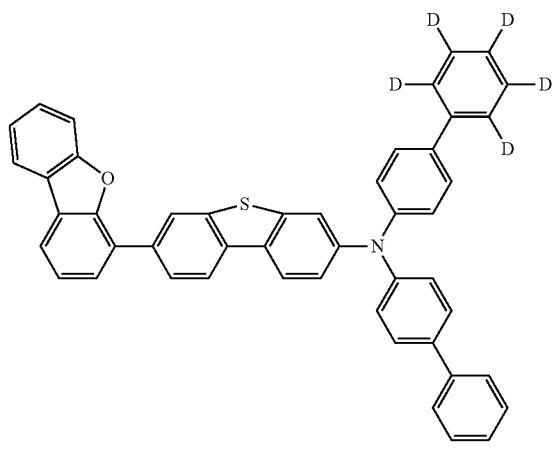
14-24
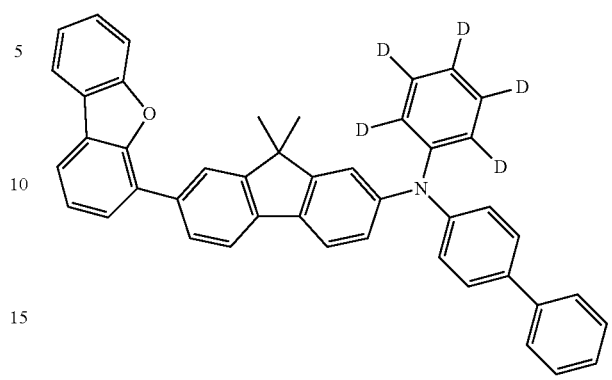
14-22
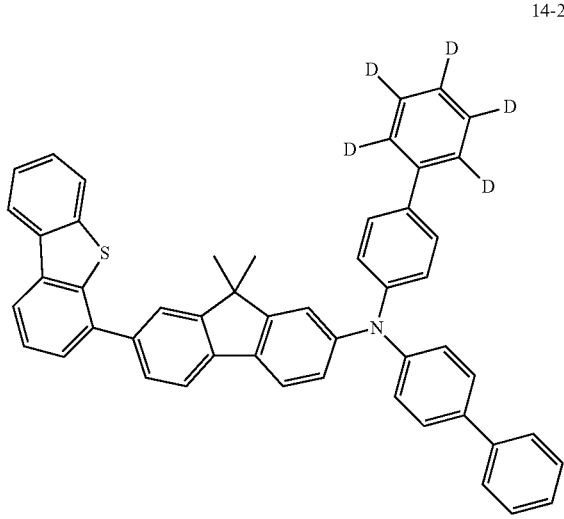
14-25
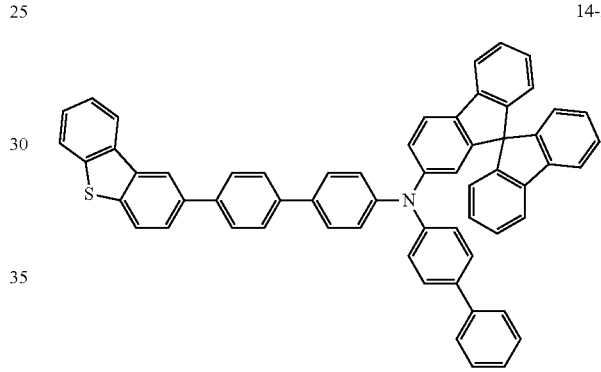
14-23
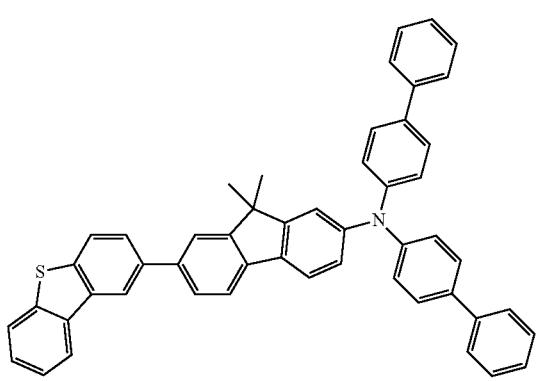
14-26
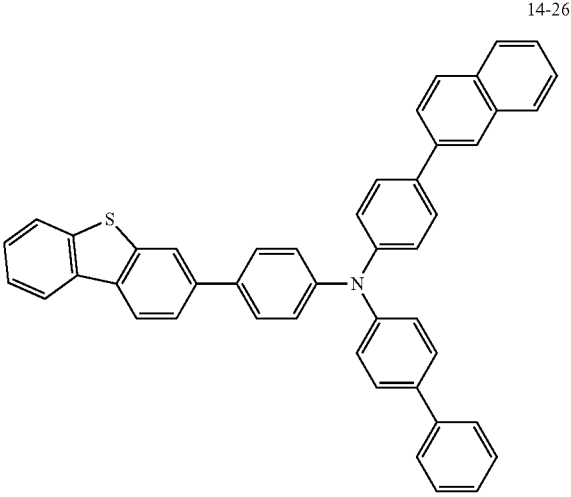

14-27
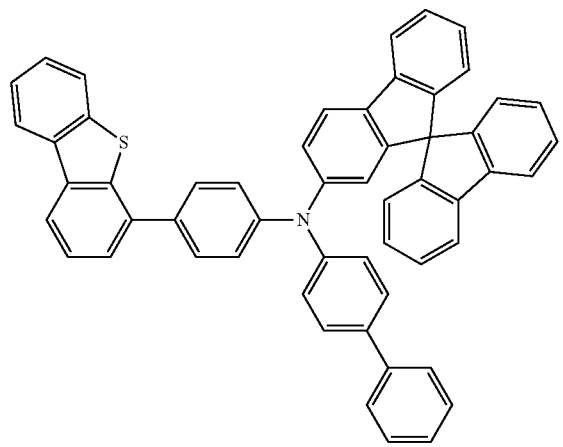
14-28
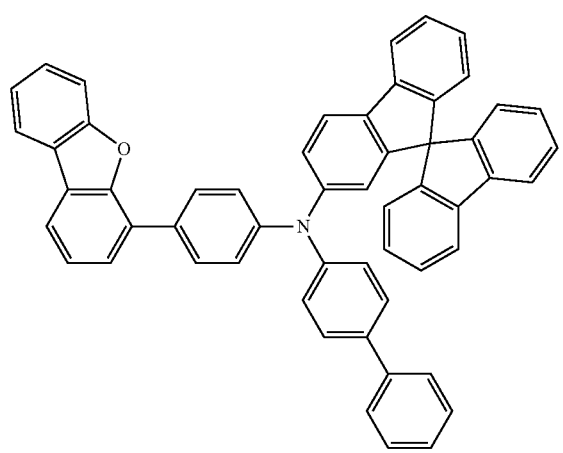
14-29
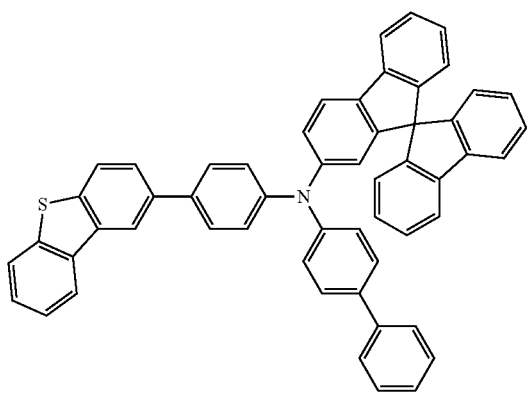
14-30
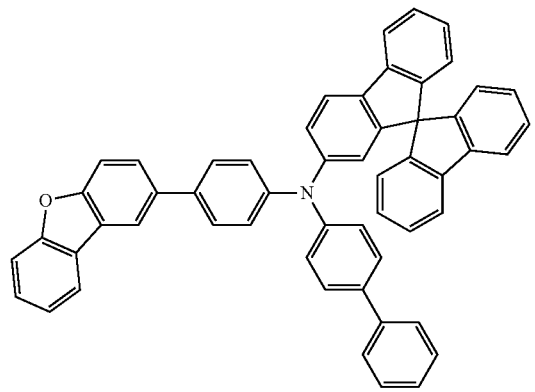
14-31
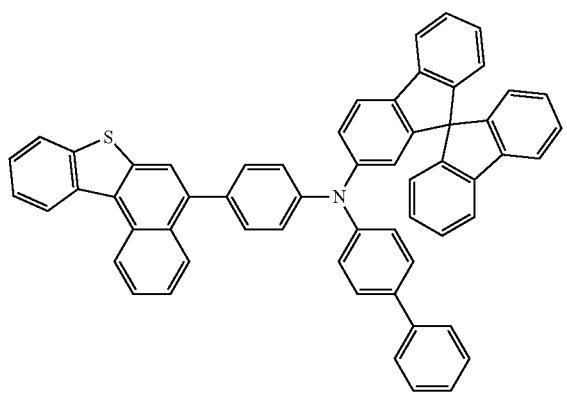
14-32
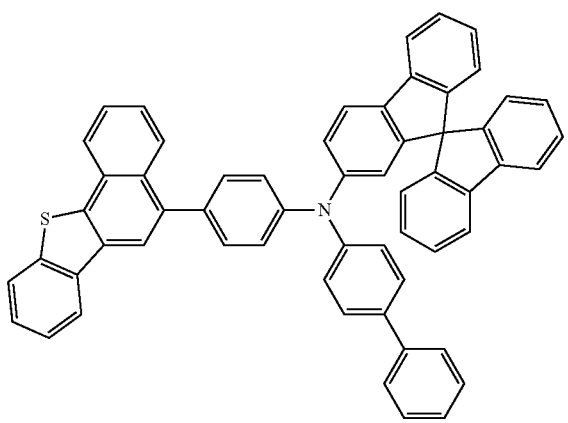

-continued
14-33
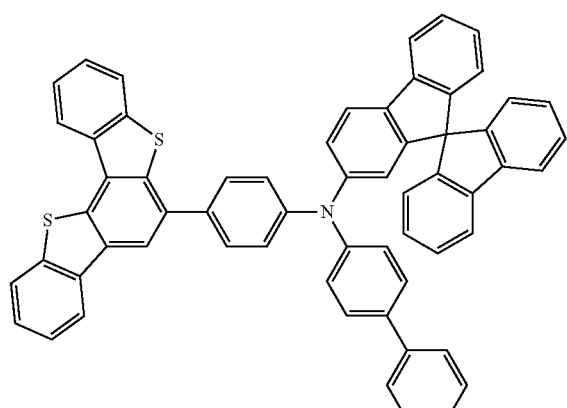
14-34
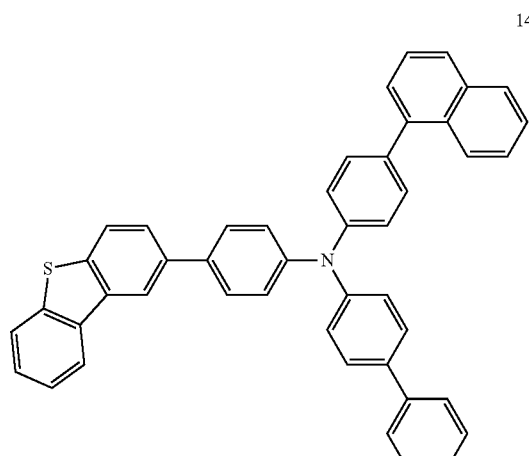
14-35
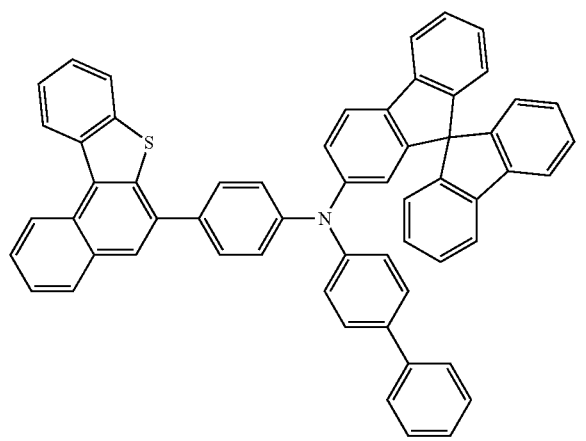
-continued
14-36
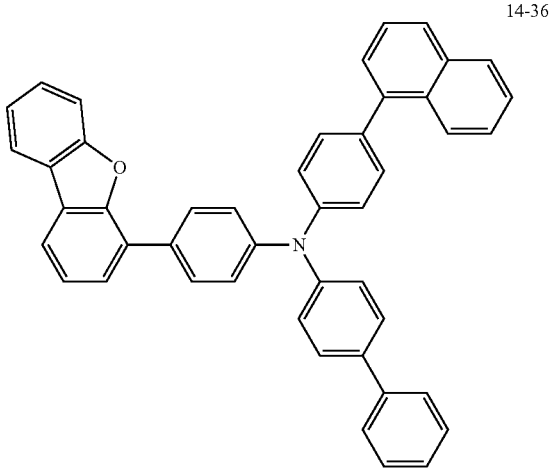
14-37
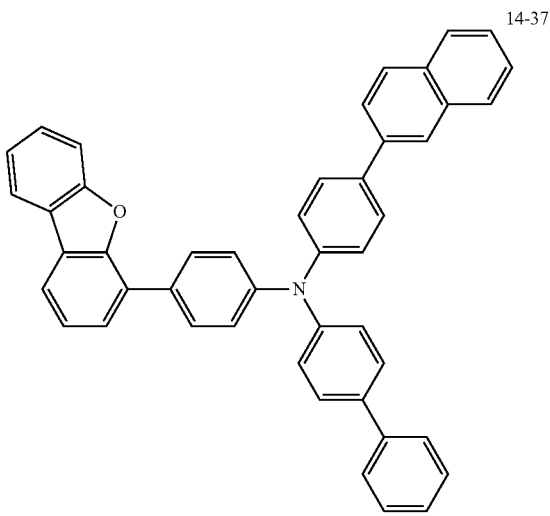
14-38
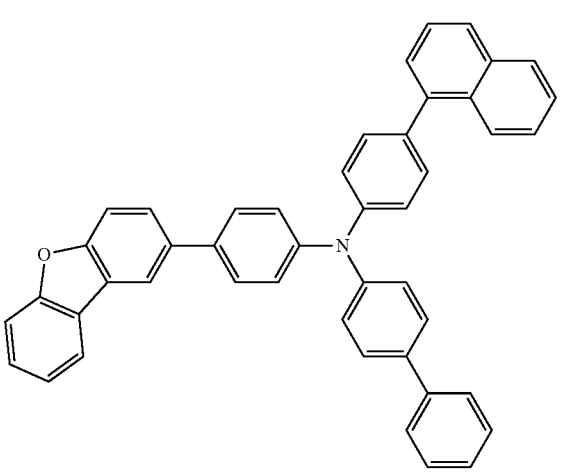

14-39
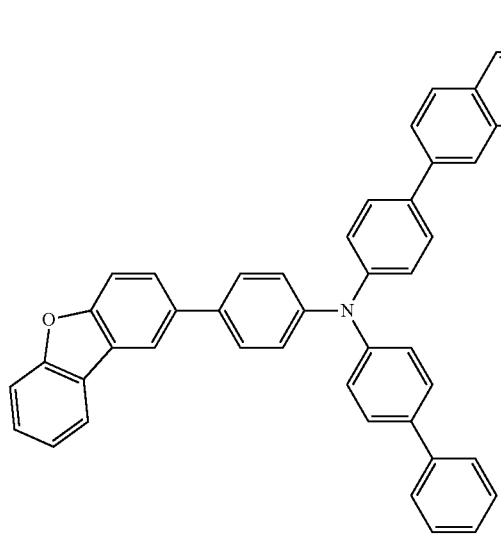
14-42
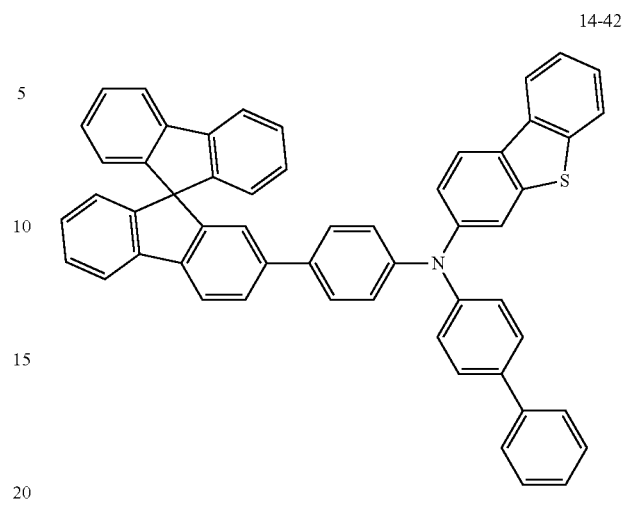
14-40
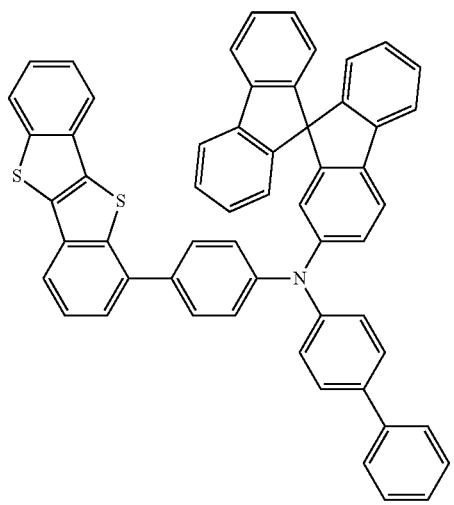
14-43
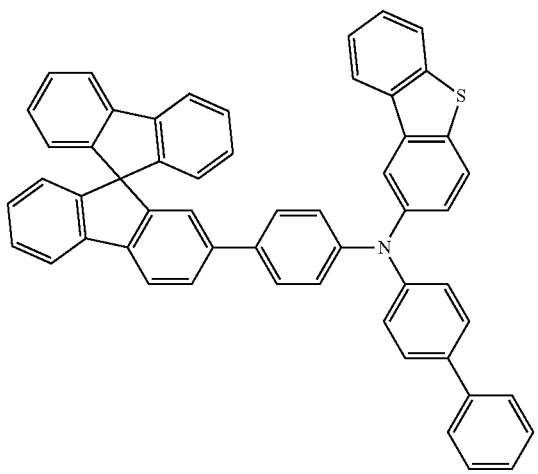
14-41
14-44
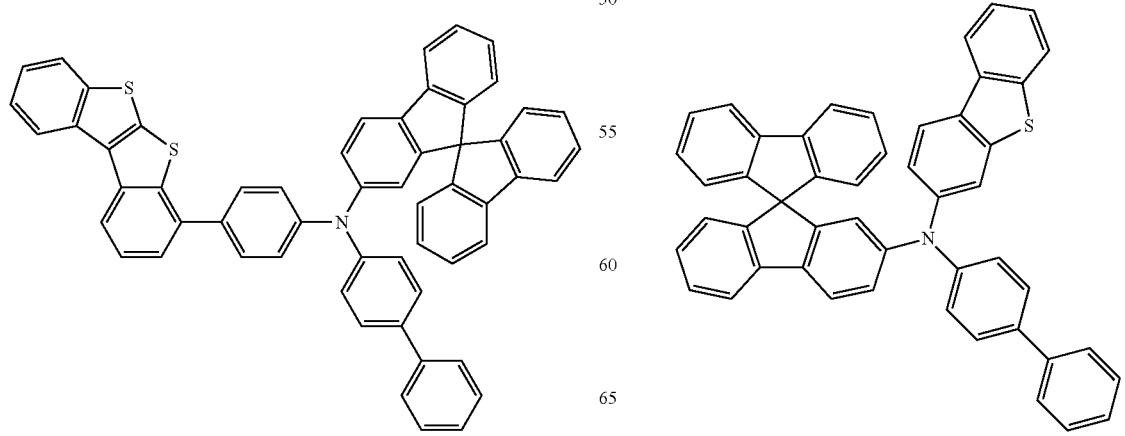

14-45
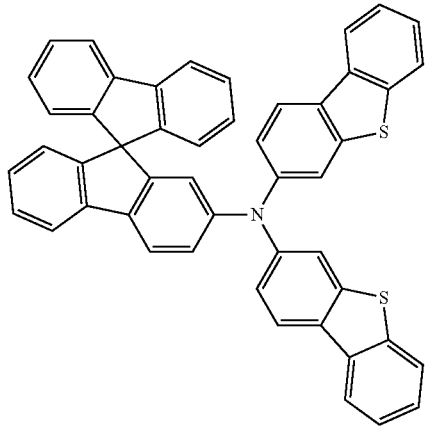
14-46
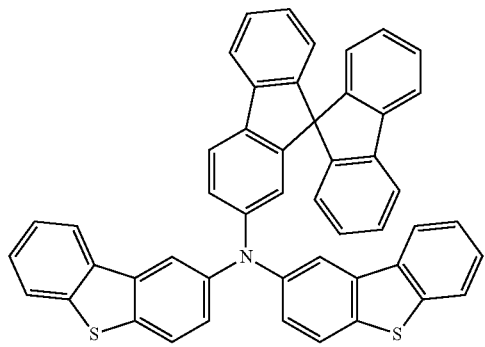
14-47
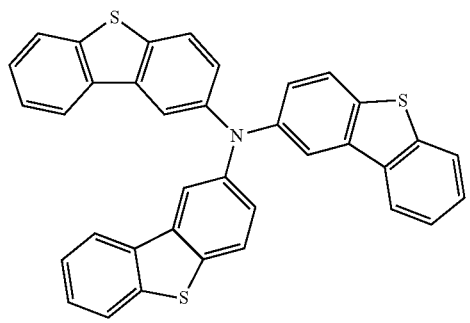
14-48
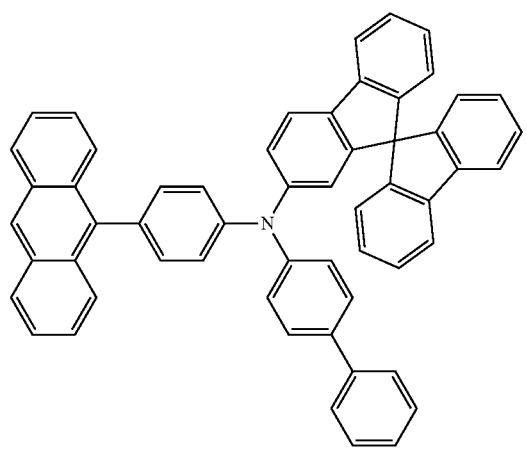
14-49
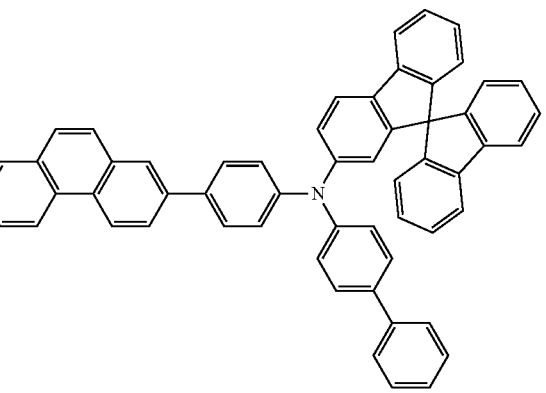
14-50
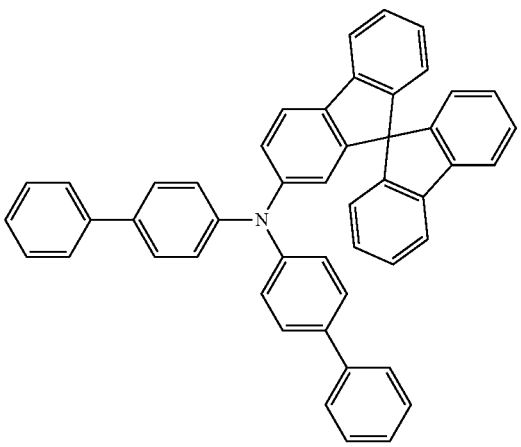
14-51
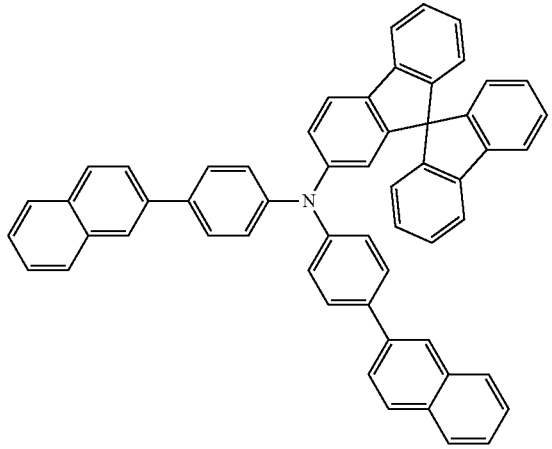

14-52
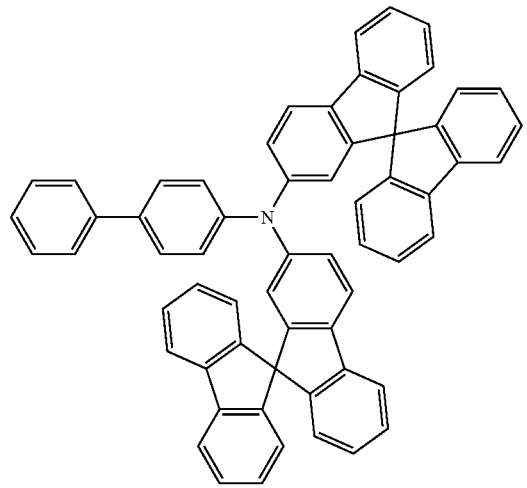
14-55
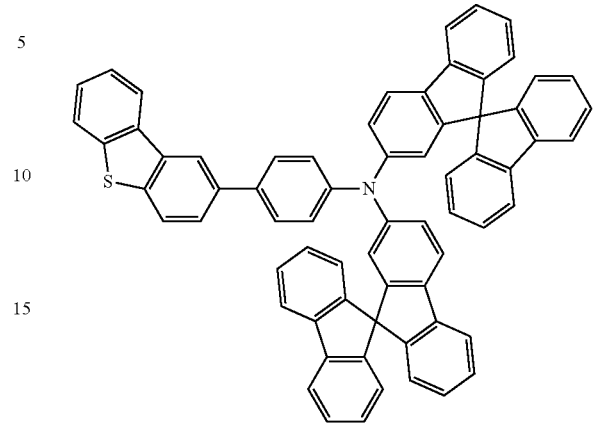
14-53
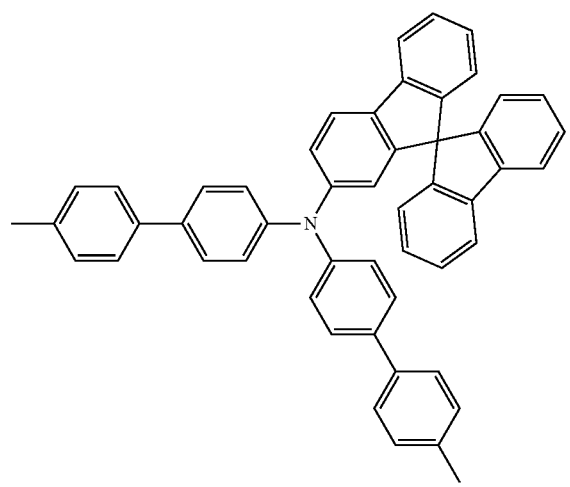
14-56
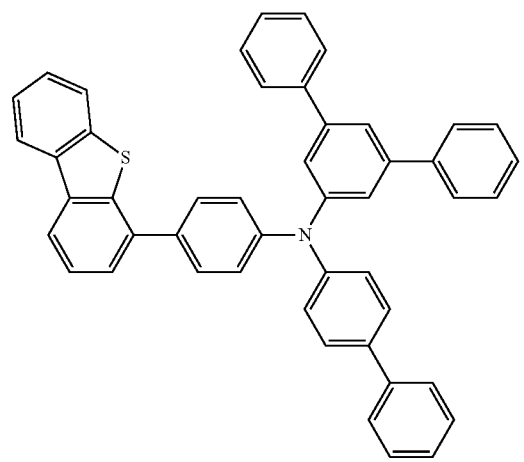
14-54
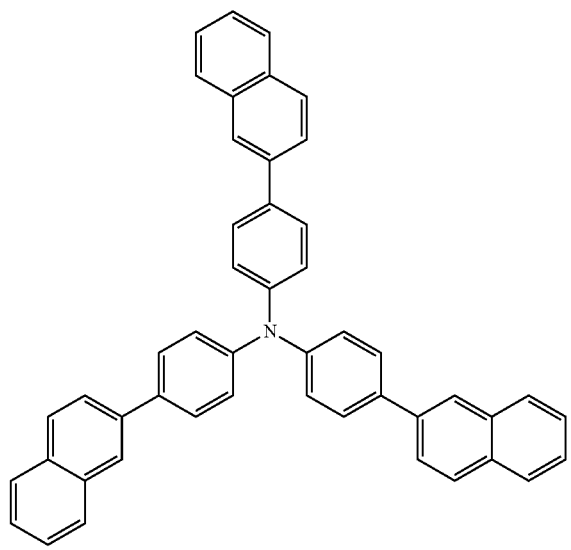
14-57
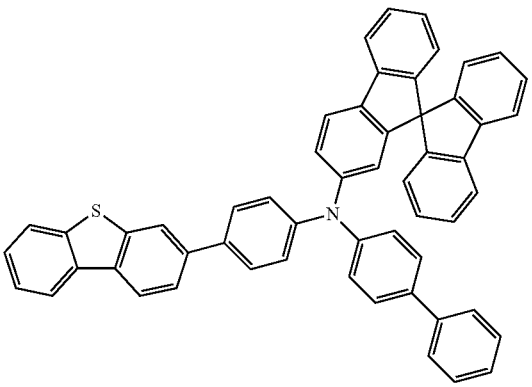

14-58
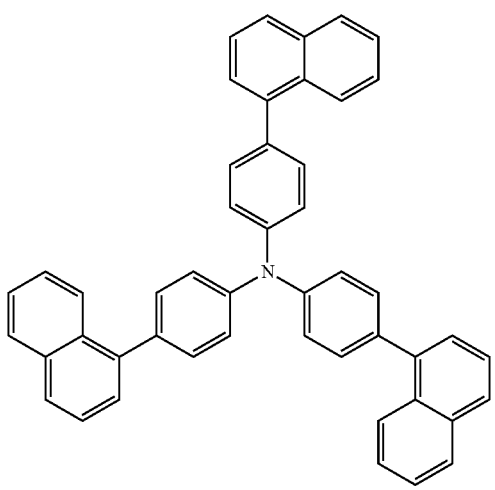
14-61
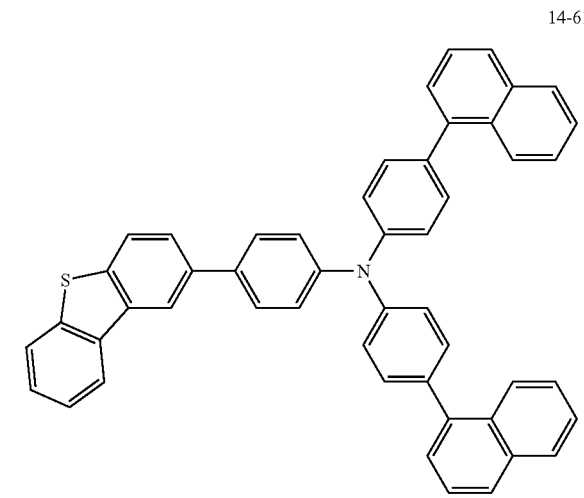
14-59
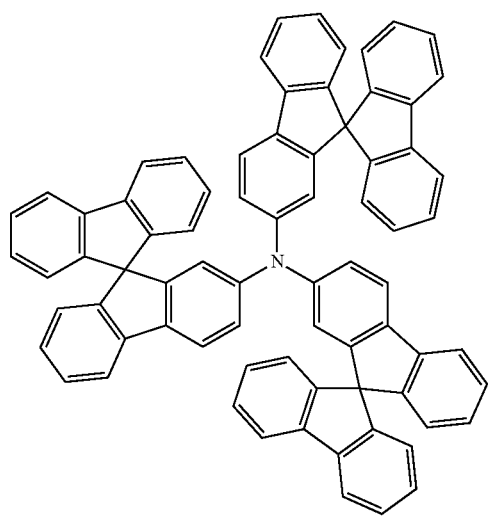
14-62
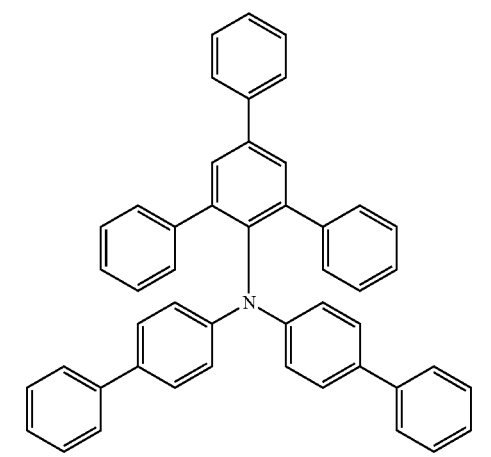
14-60
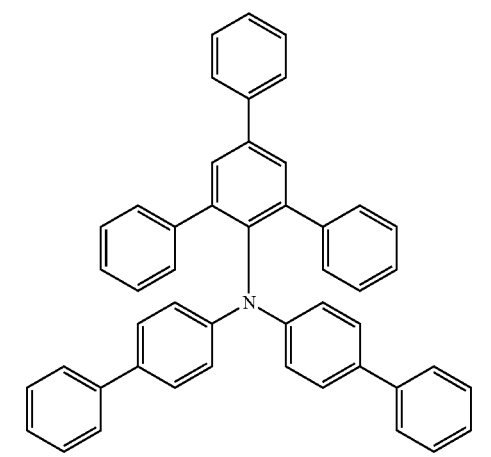
14-63
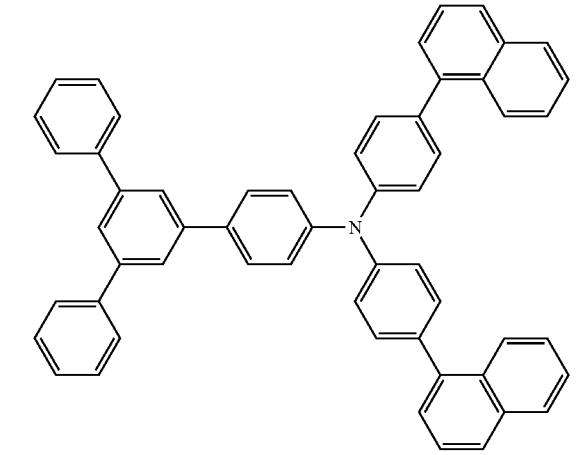

14-64
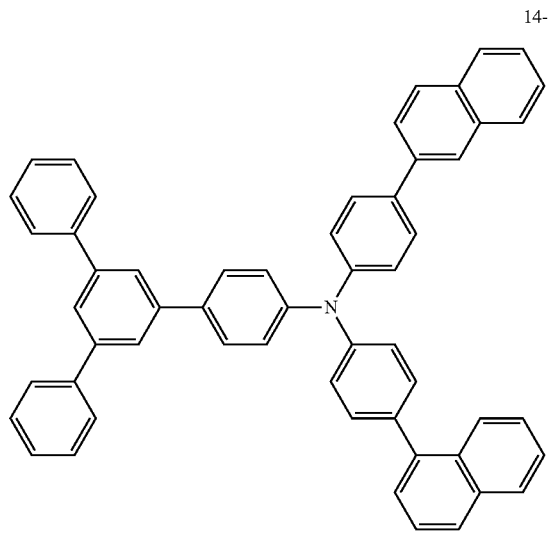
14-67
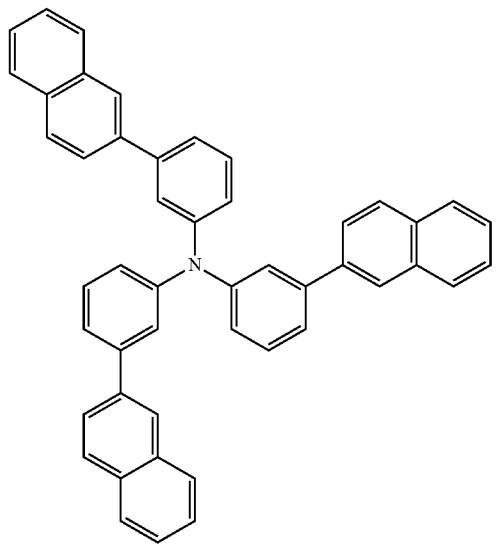
14-65
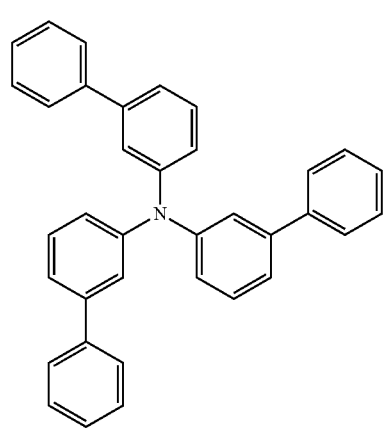
14-68
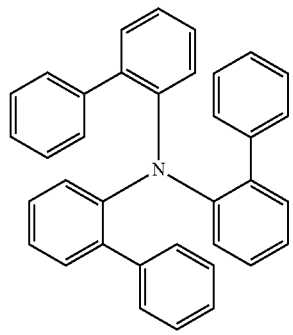
14-66
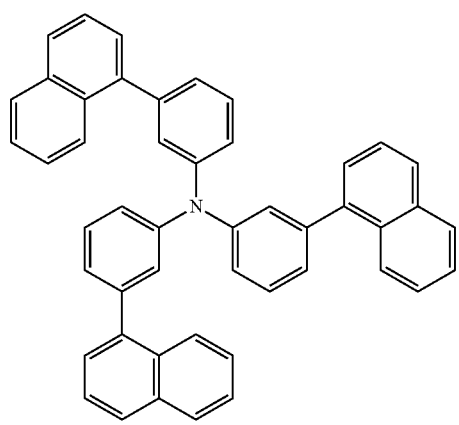
14-69
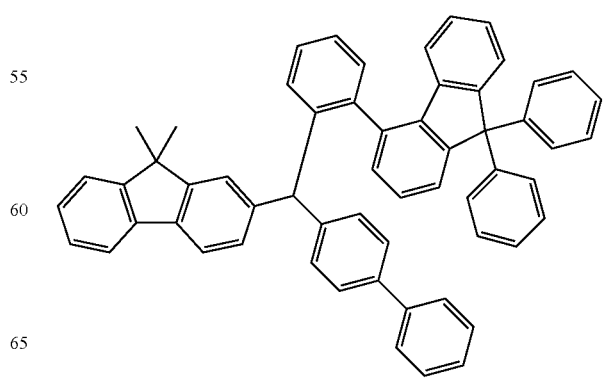

14-70
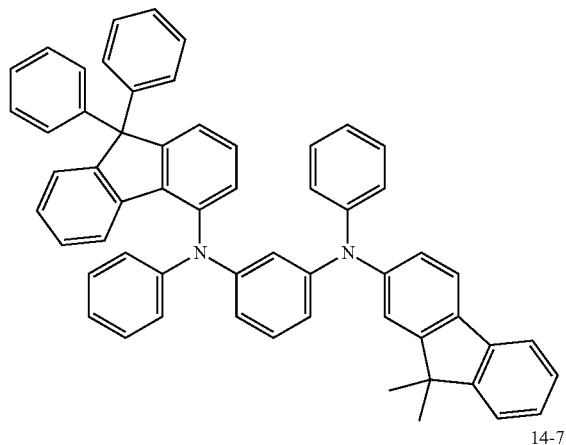
14-71
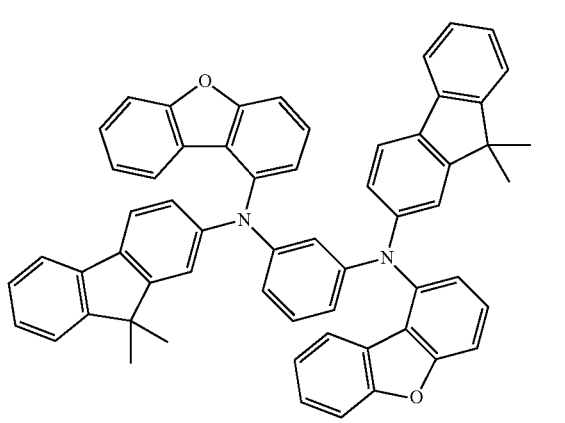
14-72
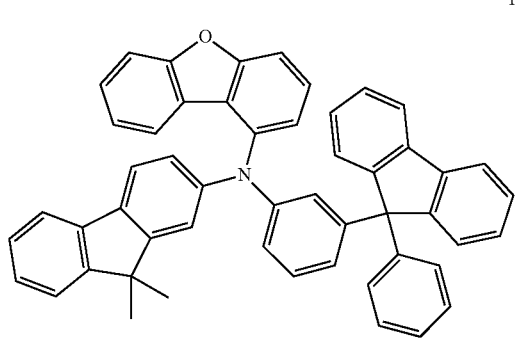
14-73
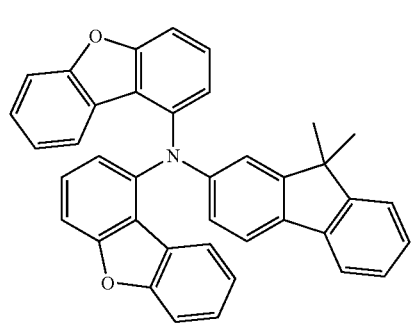
14-74
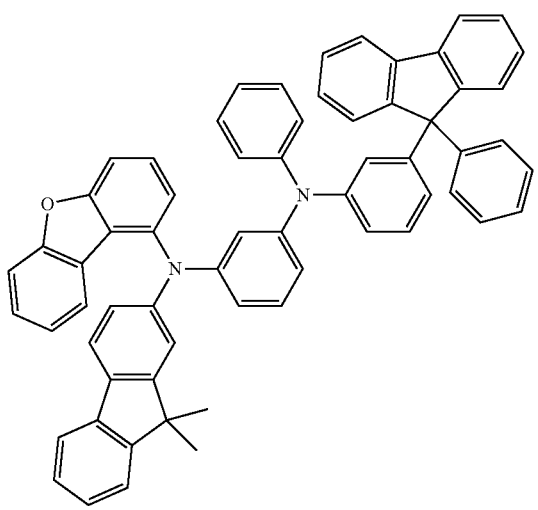
14-75
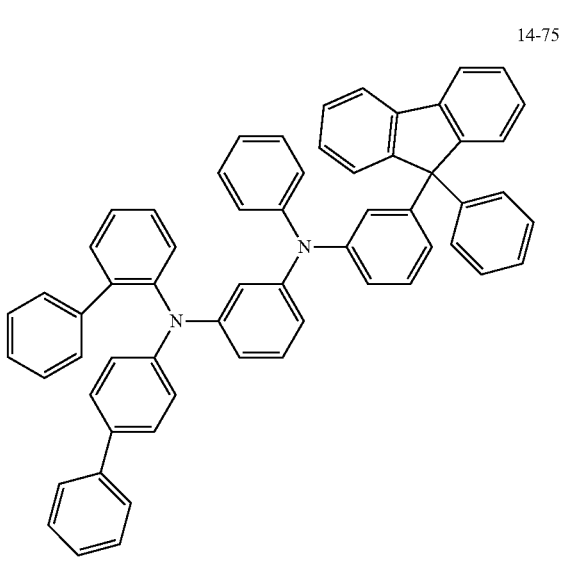
14-76
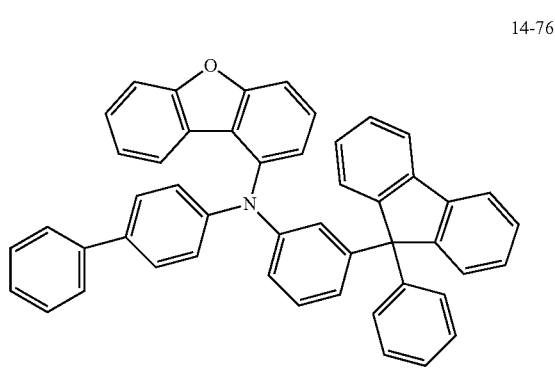

15-1
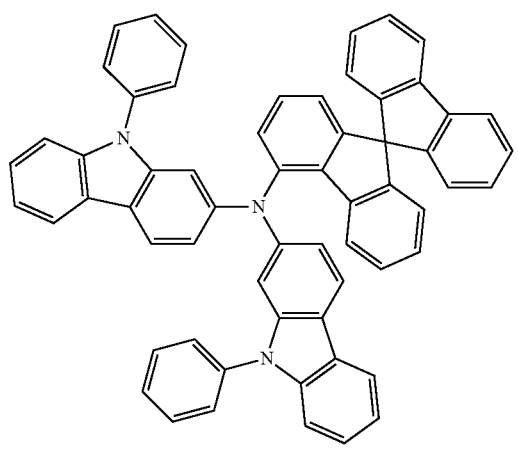
15-4
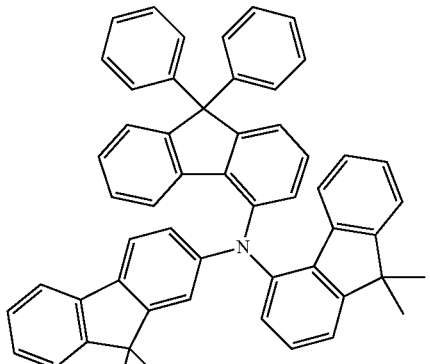
15-2
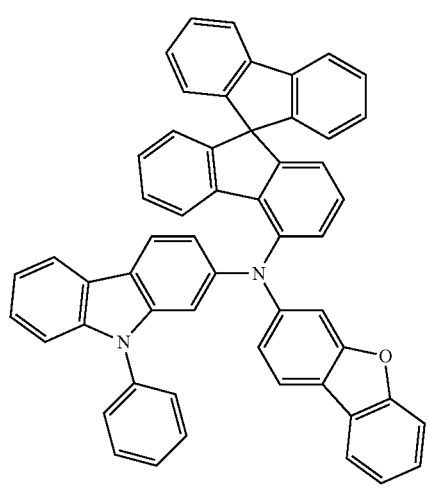
15-5
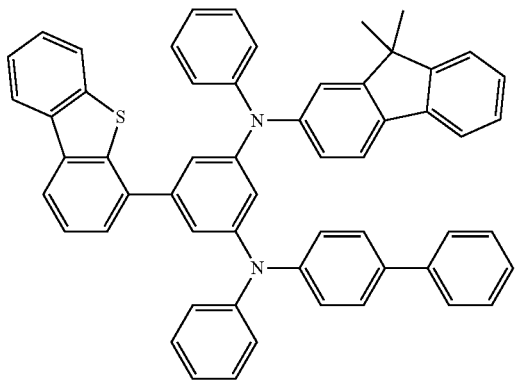
15-3
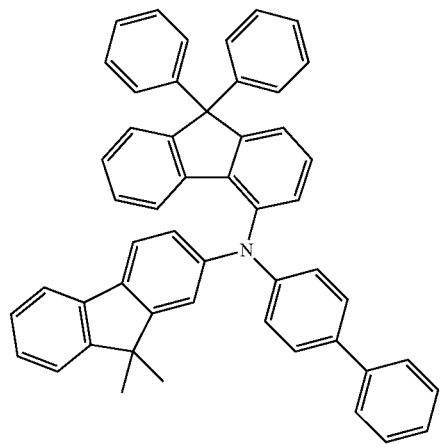
15-6
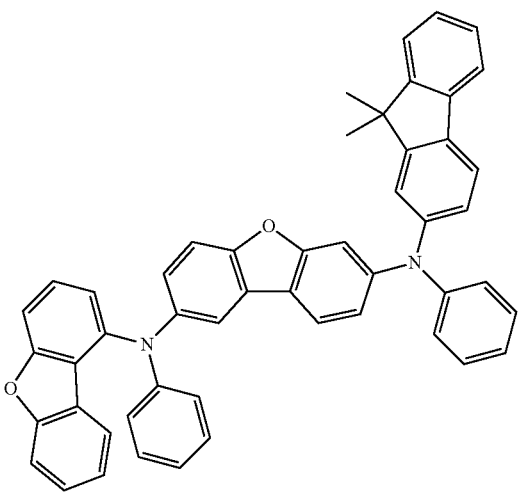

-continued

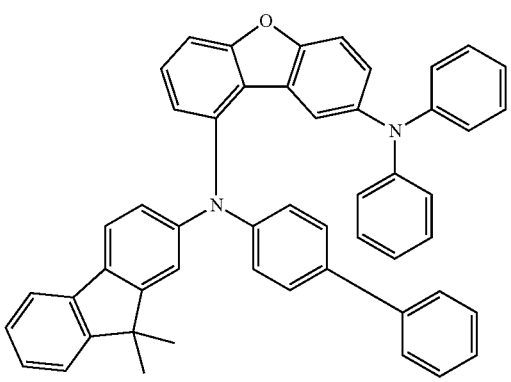
15-7

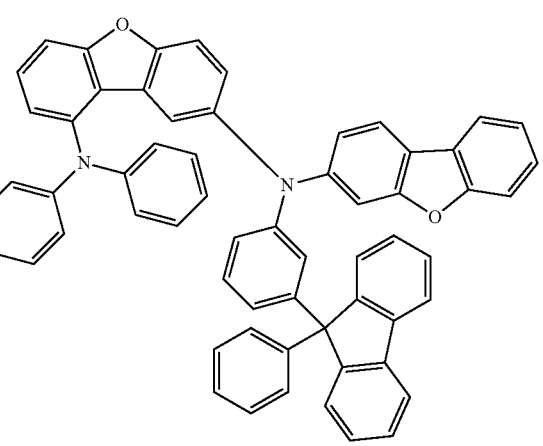
15-10

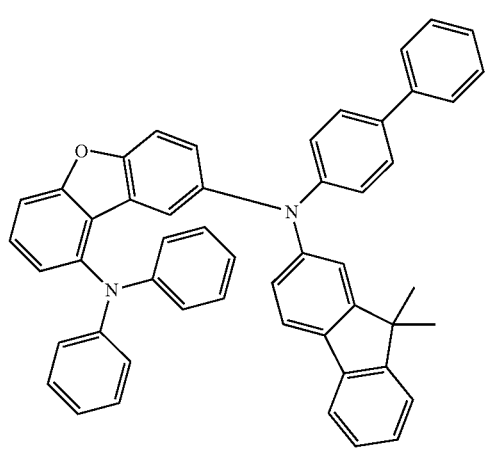
15-8

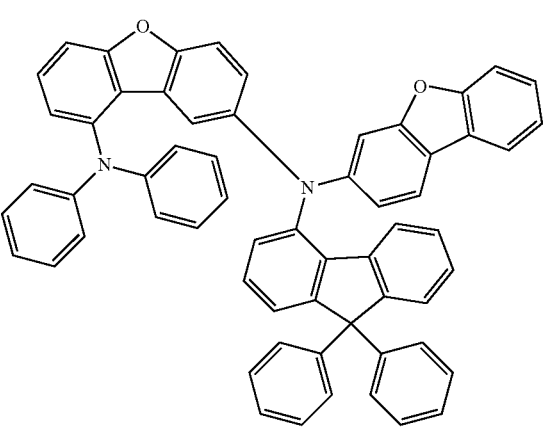
15-11

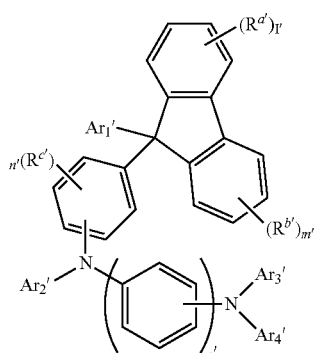
15-9

21. A compound of Formula A

<Formula A> wherein:
a' is an integer of 1 to 3,
$R^{a'}$, $R^{b'}$ and $R^{c'}$ are each independently selected from the group consisting of hydrogen, deuterium, halogen, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom selected from the group consisting of O, N, S, Si, and P, $C_3$-$C_{20}$ cycloalkyl group, and a fused ring group formed by a $C_3$-$C_{60}$ aliphatic ring with a $C_6$-$C_{60}$ aromatic ring, and adjacent groups may be optionally linked to each other to form a ring, l', m' and n' are each an integer of 0 to 4, where each of these is an integer of 2 or more, a plural of $R^{a'}$s, a plural of $R^{b'}$s or a plural of $R^{c'}$s are each the same or different from each other, $Ar_{1'}$ is selected from the group consisting of a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom selected from the group consisting of O, N, S, Si, and P, $C_3$-$C_{20}$ cycloalkyl group, and a fused ring group formed by a $C_3$-$C_{60}$ aliphatic ring with a $C_6$-$C_{60}$ aromatic ring, $Ar_{2'}$, $Ar_{3'}$ and $Ar_{4'}$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{60}$ aryloxy group and -L'-N($R_a$)($R_b$), and $Ar^{3'}$ and $Ar^{4'}$ may be combined with each other to form a ring, and $R^{a'}$, $R^{b'}$, $R^{c'}$, $Ar_{1'}$ to $Ar_{4'}$ and the ring formed by adjacent groups may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{60}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, a $C_8$-$C_{20}$ arylalkenyl group and a combination thereof.

22. The compound of claim 21, wherein Formula A is represented by one of Formula B to Formula D:

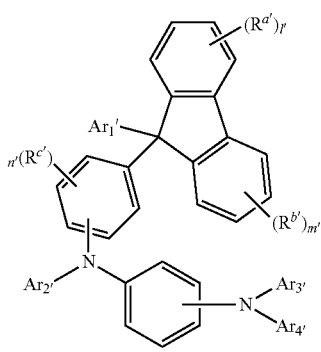

<Formula B>

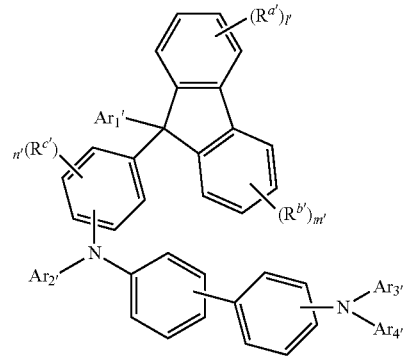

<Formula C>

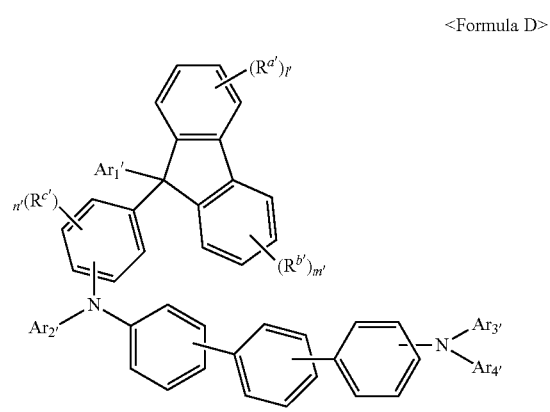

<Formula D> wherein, $R^{a'}$, $R^{b'}$, $R^{c'}$, l', m', n', $Ar_{1'}$ to $Ar_{4'}$ are the same as defined in claim 21.

23. The compound of claim 21, wherein Formula A is represented by one of Formula E to Formula G:

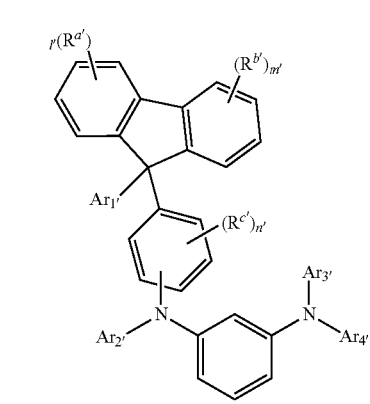

<Formula E>

<Formula F>

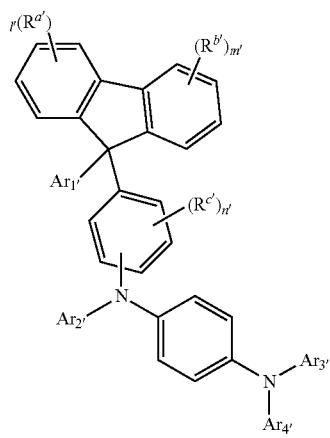

<Formula G>

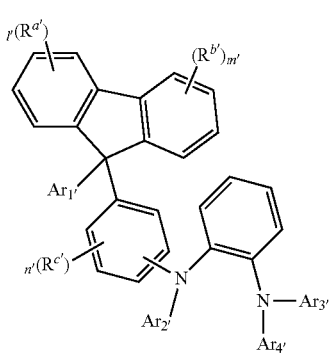

wherein, $R^{a'}$, $R^{b'}$, $R^{c'}$, l', m', n', $Ar_{1'}$ to $Ar_{4'}$ are the same as defined in claim 21.

24. The compound of claim 21, wherein Formula A is represented by one of Formula H to Formula K:

<Formula H>

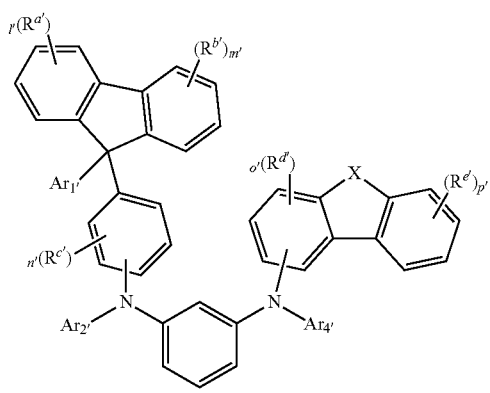

<Formula I>

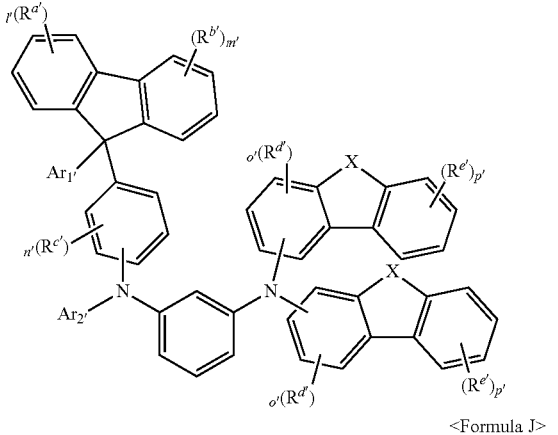

<Formula J>

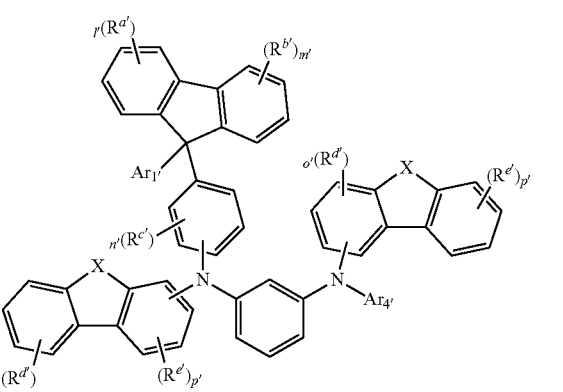

<Formula K> wherein, $R^{a'}$, $R^{b'}$, $R^{c'}$, l', m', n', $Ar_{1'}$ to $Ar_{4'}$ are the same as defined in claim 21, X is independently O, S or C(R')(R"), $R^{d'}$, $R^{e'}$, R' and R" are each independently selected from the group consisting of hydrogen, deuterium, halogen, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom selected from the group consisting of O, N, S, Si, and P, $C_3$-$C_{20}$ cycloalkyl group, and a fused ring group formed by a $C_3$-$C_{60}$ aliphatic ring with a $C_6$-$C_{60}$ aromatic ring, and adjacent groups may be optionally linked to each other to form a ring, o' is independently an integer of 0 to 3, p' is independently an integer of 0 to 4, where o' is an integer of 2 or more, a plural of $R^{d'}$s are each the same or different from each other, where p' is an integer of 2 or more, a plural of $R^{e'}$s are each the same or different from each other, $R^{d'}$, $R^{e'}$, R' and R" may be each further substituted with one or more substituents selected from the group consisting of deuterium, halogen, a silane group unsubstituted or substituted with a $C_1$-$C_{60}$ alkyl group or a $C_6$-$C_{60}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, a $C_8$-$C_{20}$ arylalkenyl group and a combination thereof.

25. The compound of claim 21, wherein Formula A is represented by one of Formula L to Formula O:

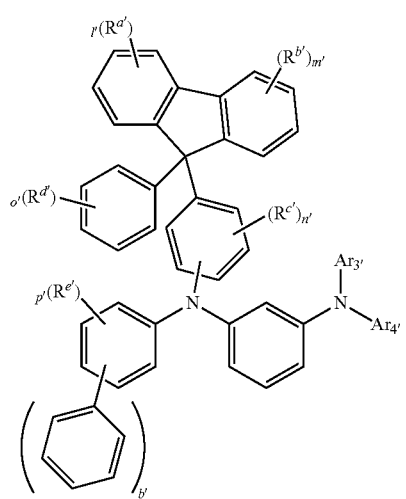

<Formula L>

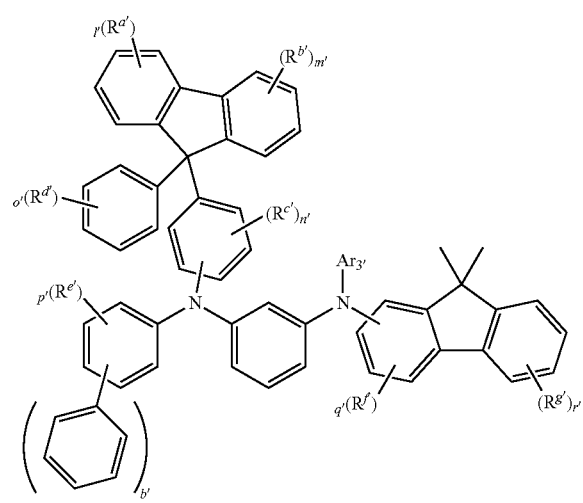

<Formula M>

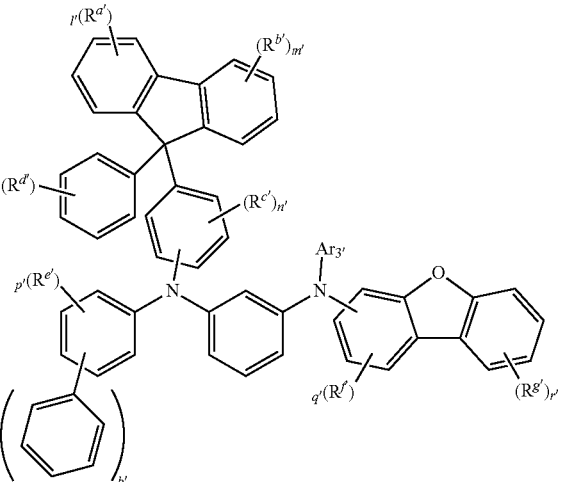

<Formula N>

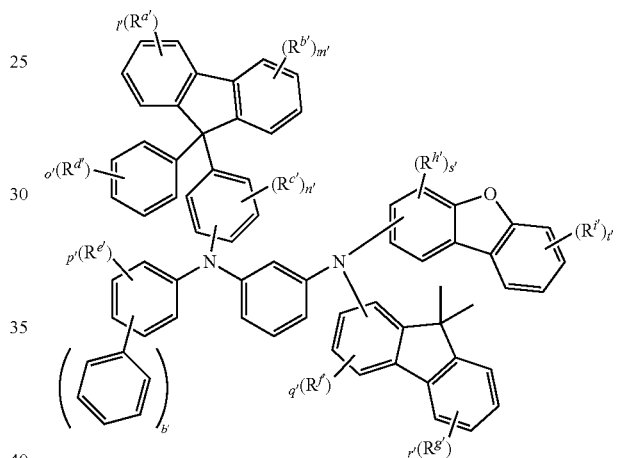

<Formula O> wherein, $R^{a'}$, $R^{b'}$, $R^{c'}$, l', m', n', $Ar_{3'}$ and $Ar_{4'}$ are the same as defined in claim 21, $R^{e'}$, $R^{f'}$, $R^{g'}$, $R^{h'}$ and $R^{i'}$ are each independently selected from the group consisting of hydrogen, deuterium, halogen, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom selected from the group consisting of O, N, S, Si, and P, $C_3$-$C_{20}$ cycloalkyl group, and a fused ring group formed by a $C_3$-$C_{60}$ aliphatic ring with a $C_6$-$C_{60}$ aromatic ring, and adjacent groups may be optionally linked to each other to form a ring, p', r' and t' are each independently an integer of 0 to 3, q' and s' are each independently an integer of 0 to 4, where each of these is an integer of 2 or more, each of $R^{e'}$s, each of $R^{f'}$s, each of $R^{g'}$s, each of $R^{h'}$s, and each of $R^{i'}$s is each the same or different from each other, b' is an integer of 0 to 3, $R^{e'}$, $R^{f'}$, $R^{g'}$, $R^{h'}$ and $R^{i'}$ may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, a $C_8$-$C_{20}$ arylalkenyl group and a combination thereof.

26. The compound of claim 21, wherein the compound represented by Formula A is one of the following compounds:

G-1
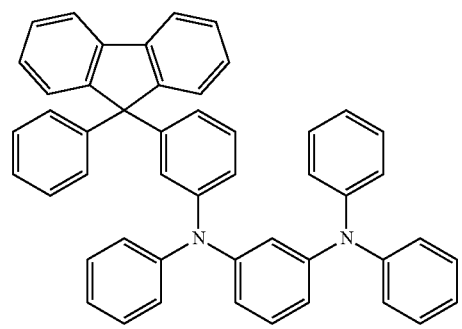

G-2
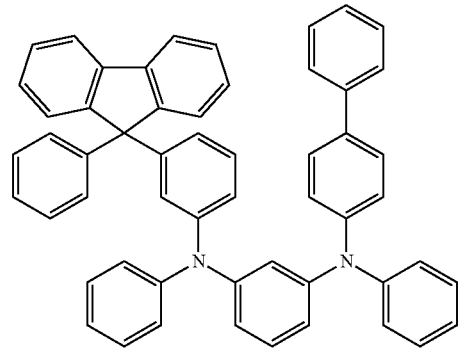

G-3
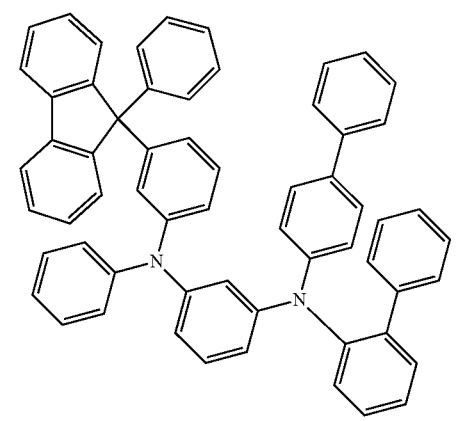

G-4
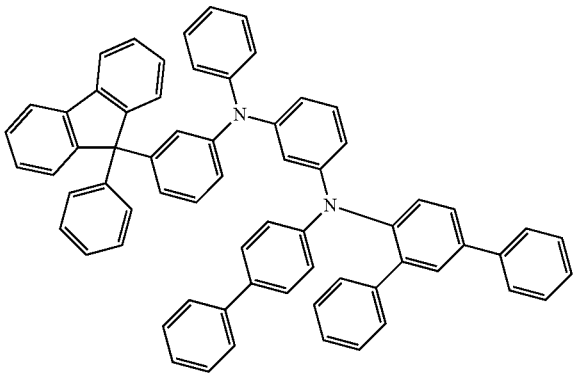

-continued

G-5
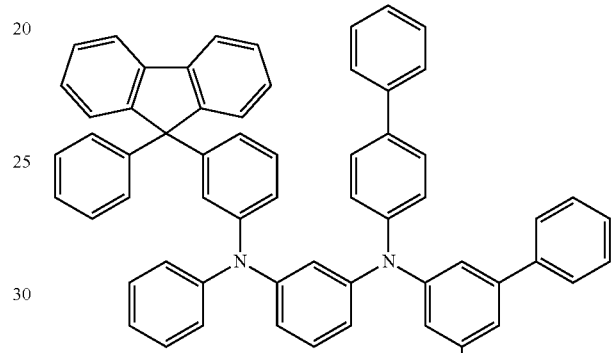

G-6
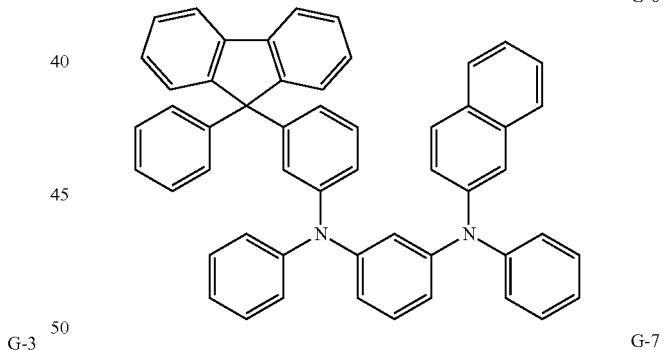

G-7
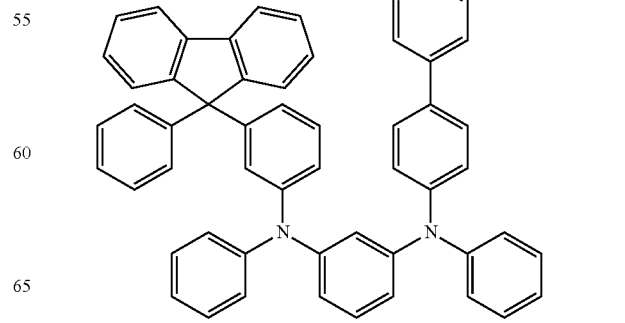

G-8
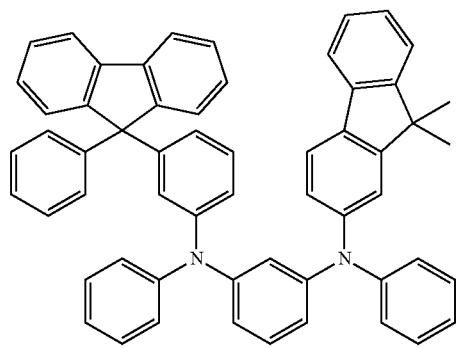
G-9
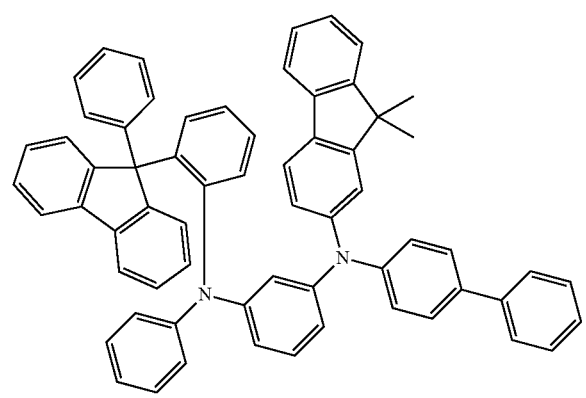
G-10
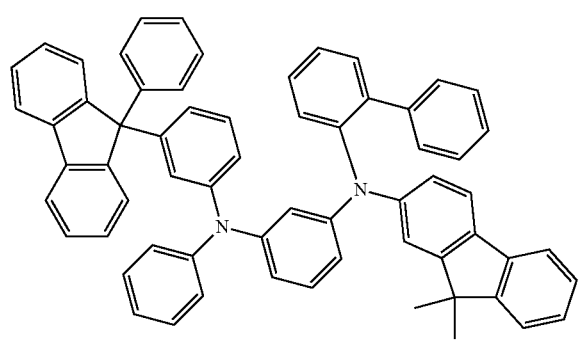
G-11
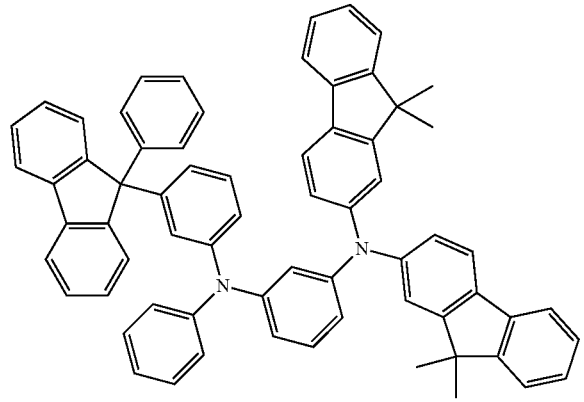
G-12
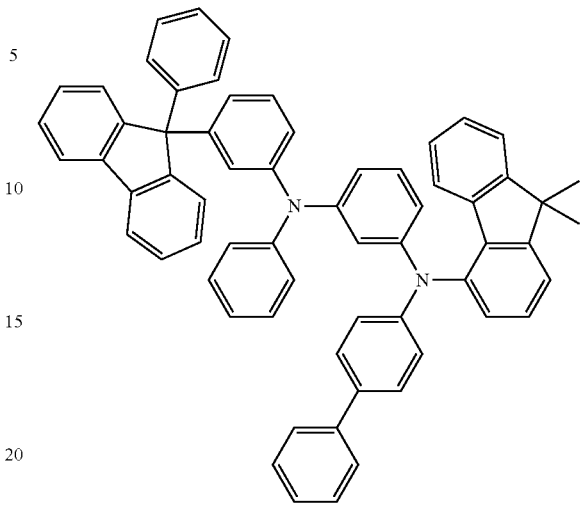
G-13
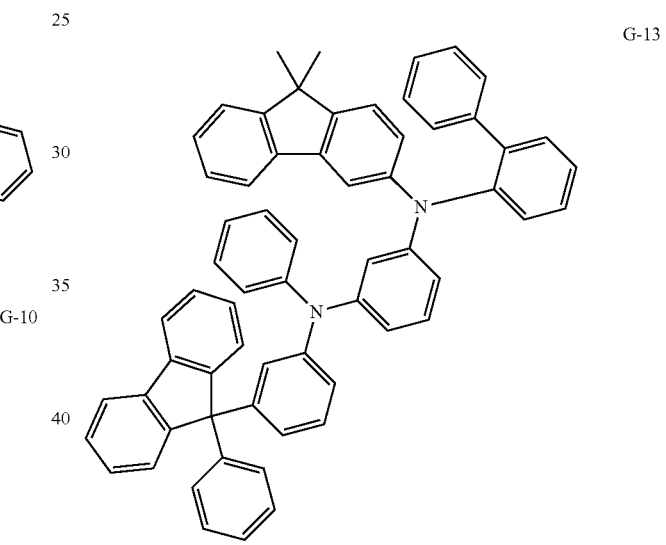
G-14
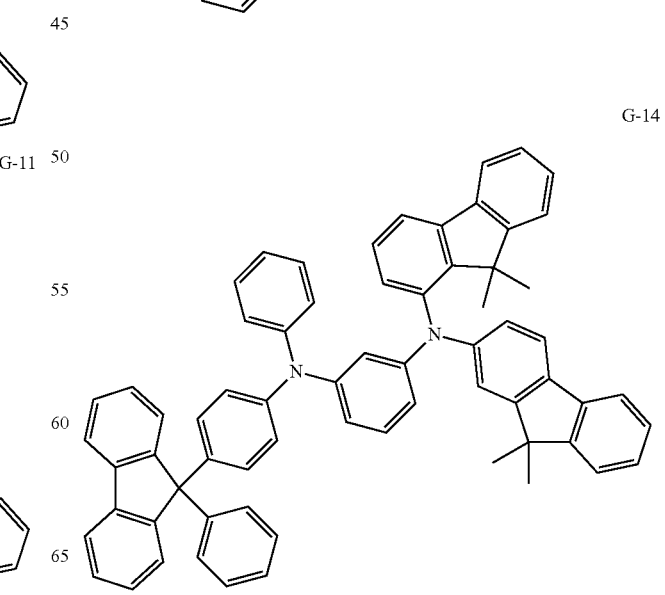

G-15
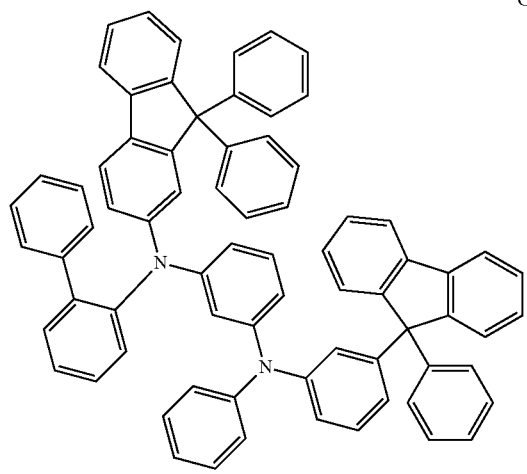
G-18
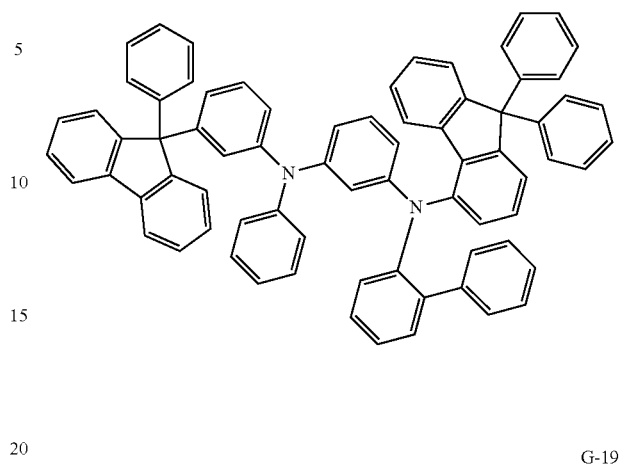
G-16
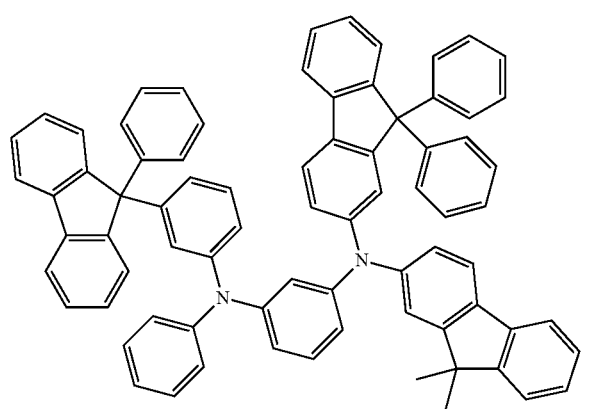
G-19
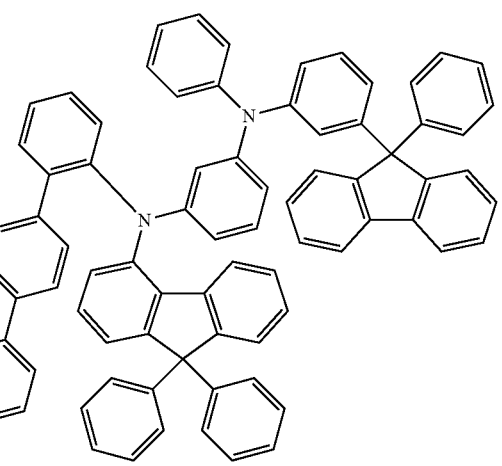
G-17
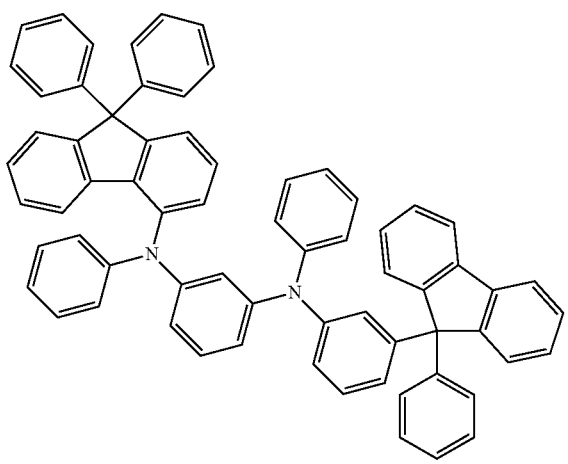
G-20
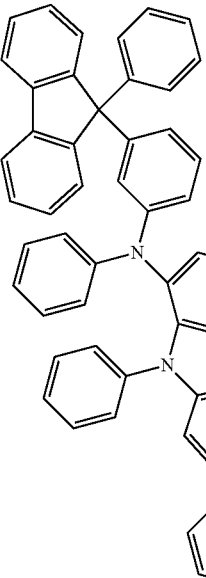

G-21
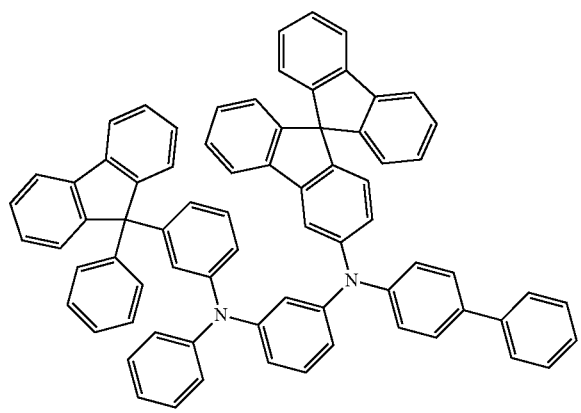
G-24
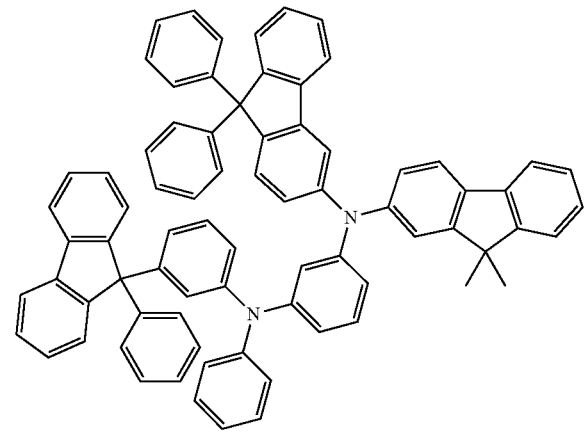
G-22
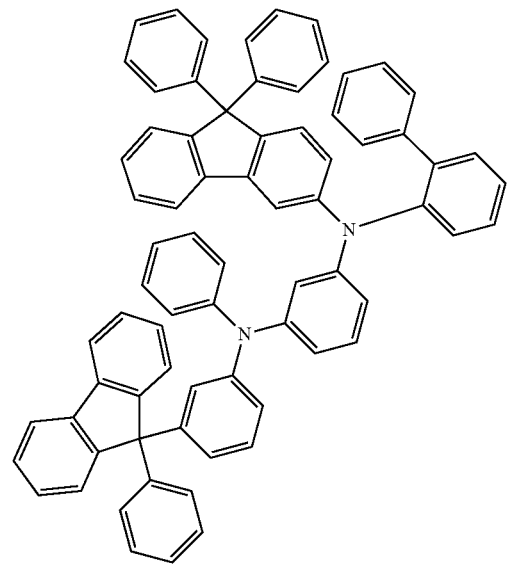
G-25
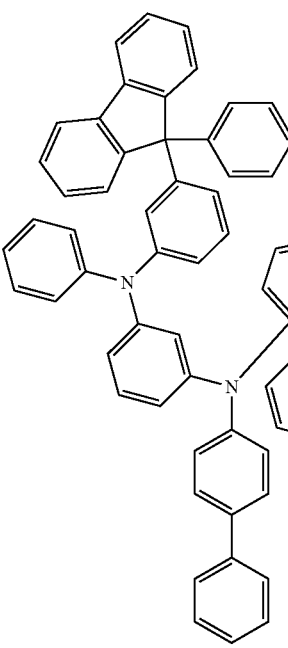
G-23
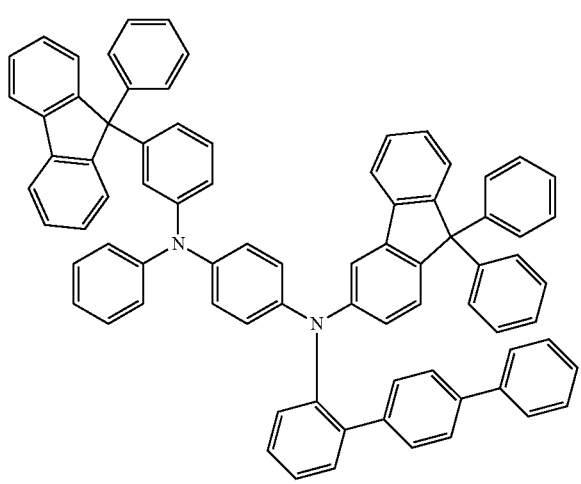
G-26
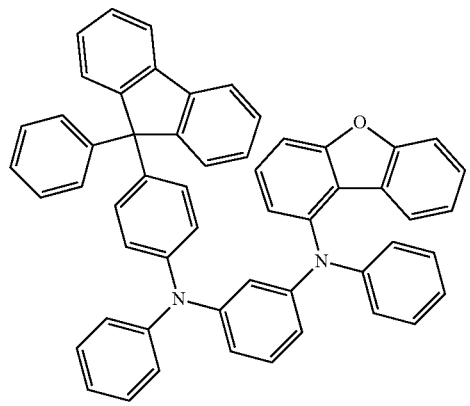

G-27
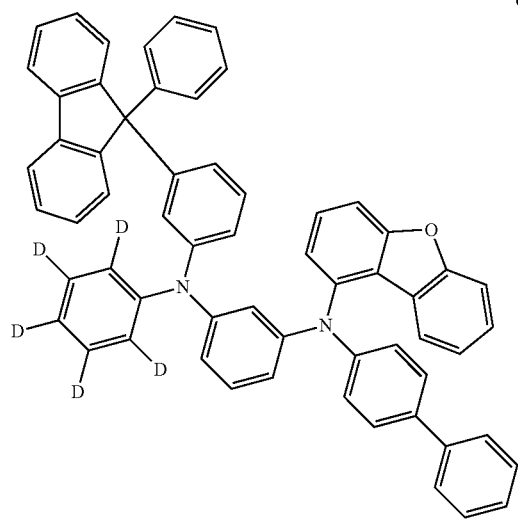
G-28
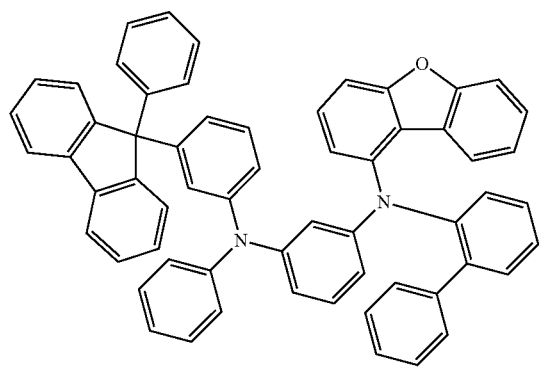
G-29
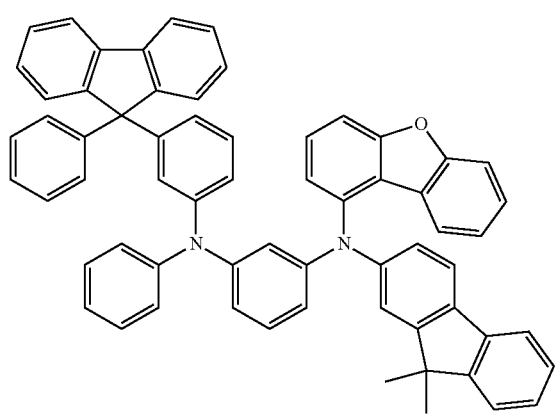
G-30
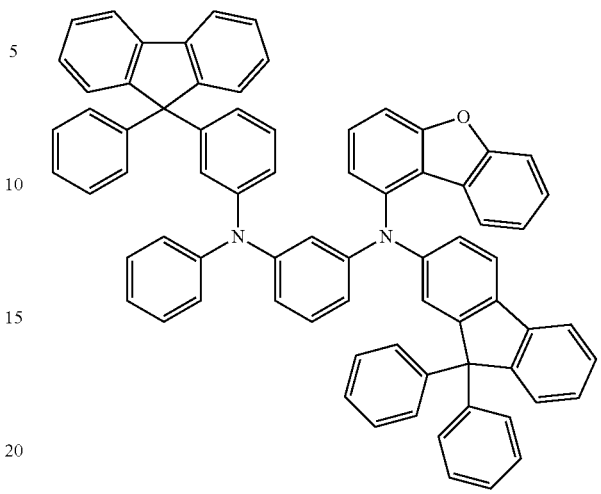
G-31
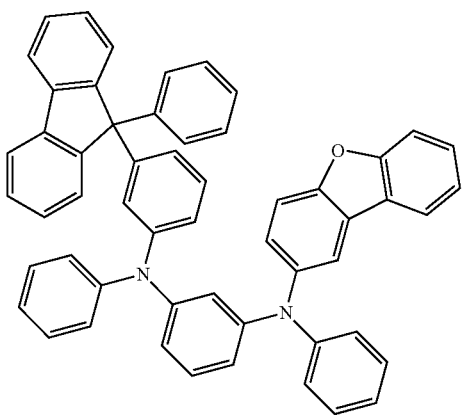
G-32
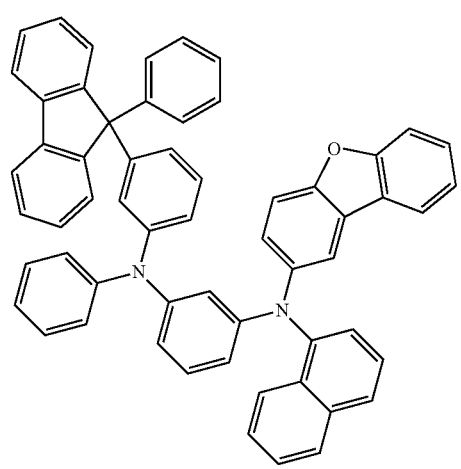

G-33
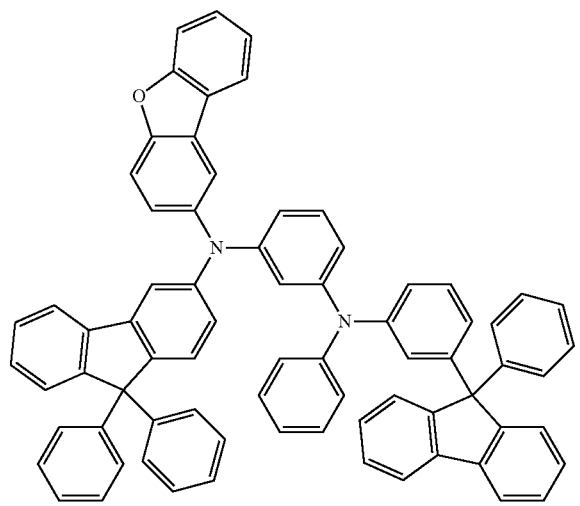
G-36
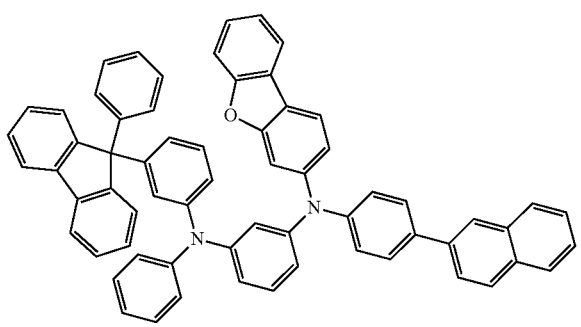
G-34
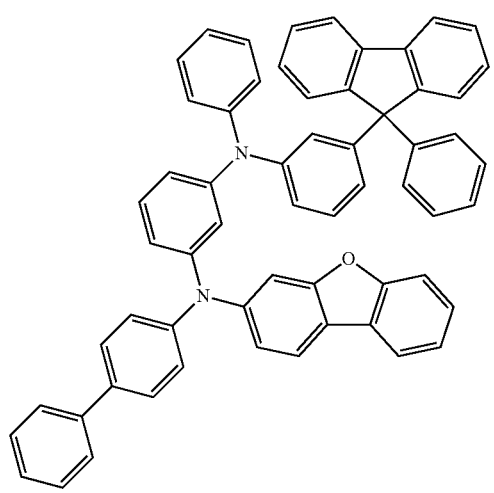
G-37
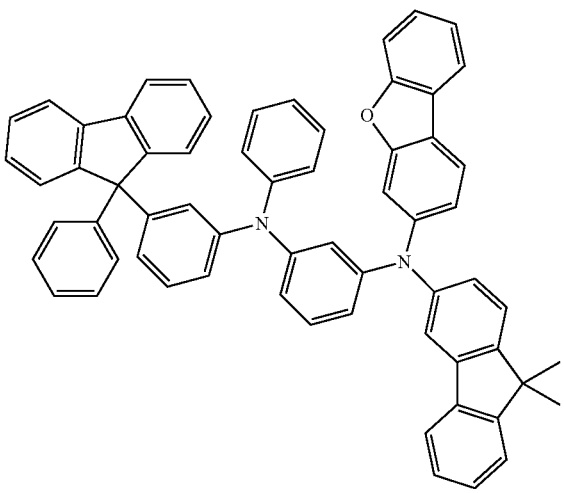
G-35
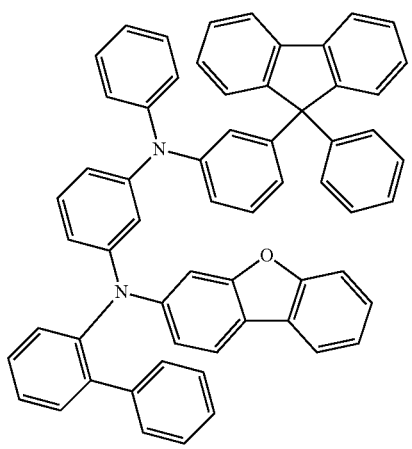
G-38
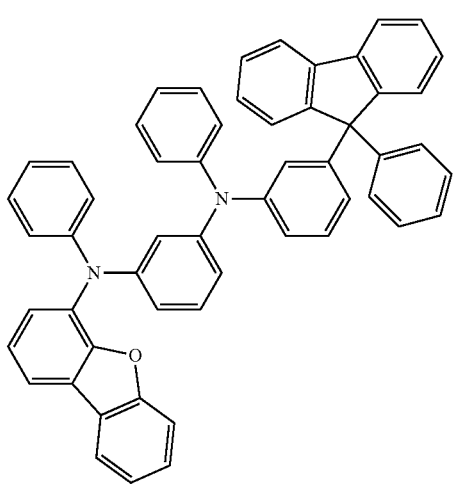

-continued

G-39

G-40

G-41

G-42

-continued

G-43

G-44

G-45

G-46
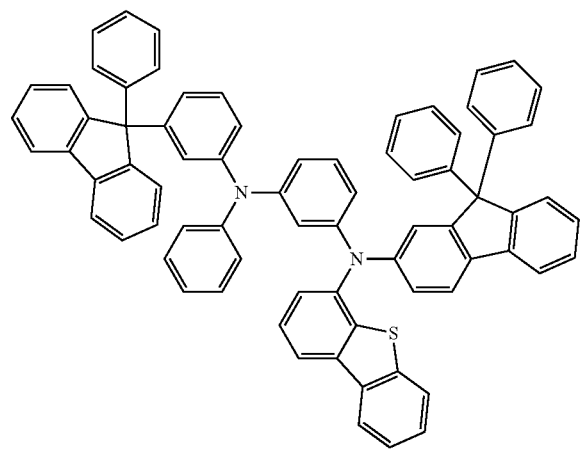
G-49
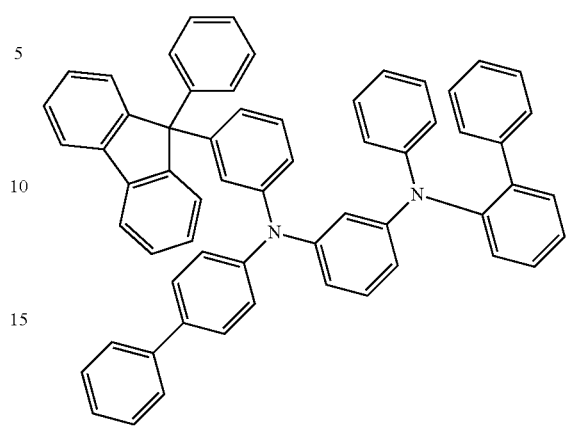
G-47
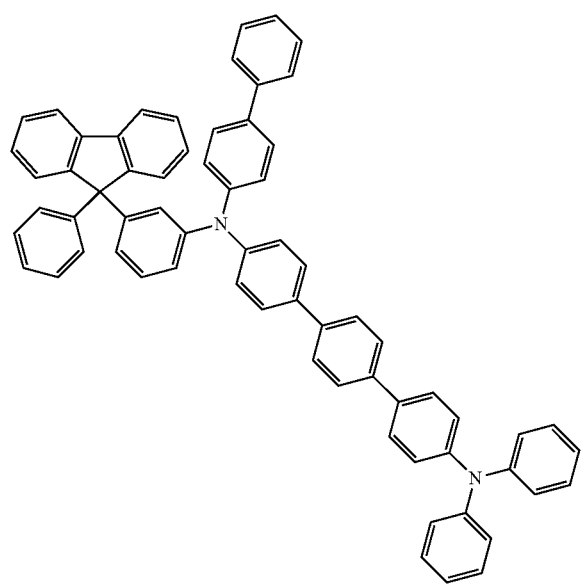
G-50
G-48
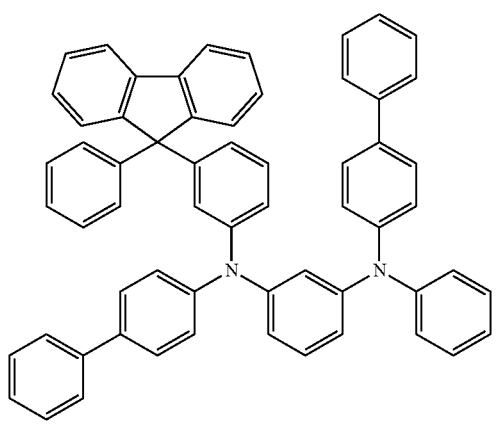
G-51
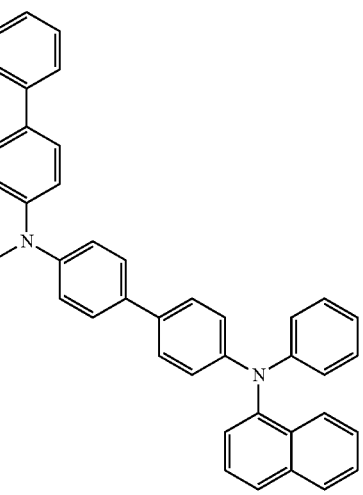

G-52
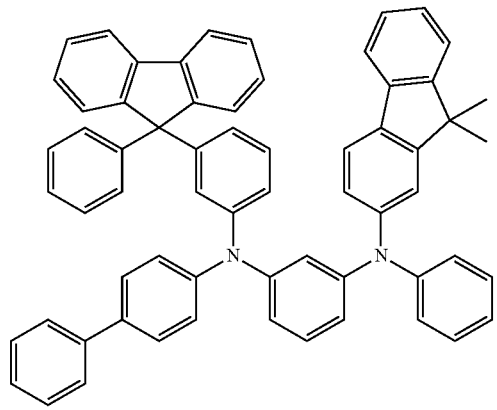
G-53
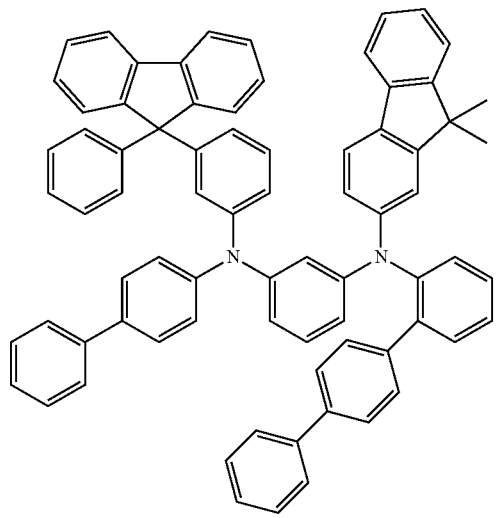
G-54
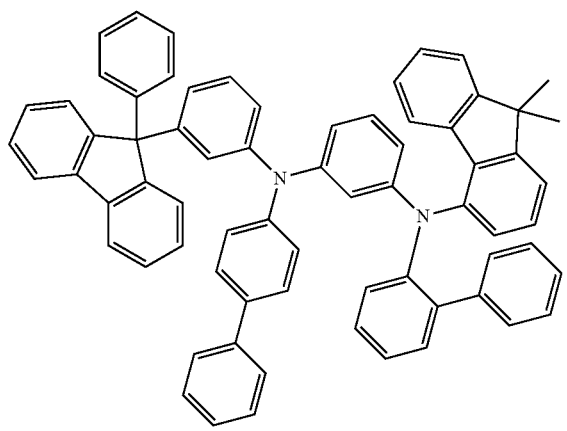
G-55
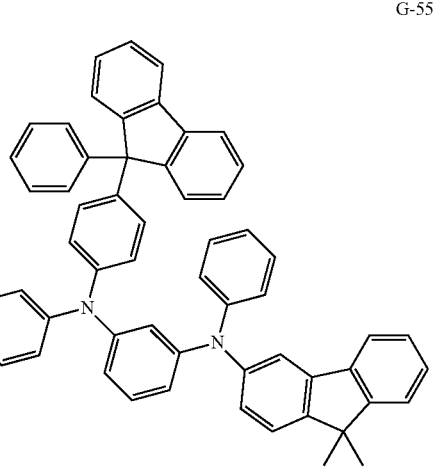
G-56
G-57

G-58
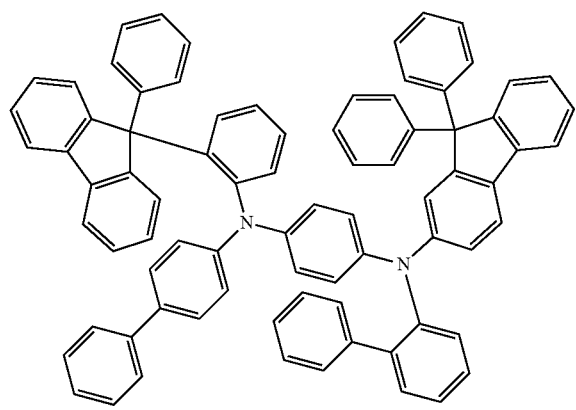
G-59
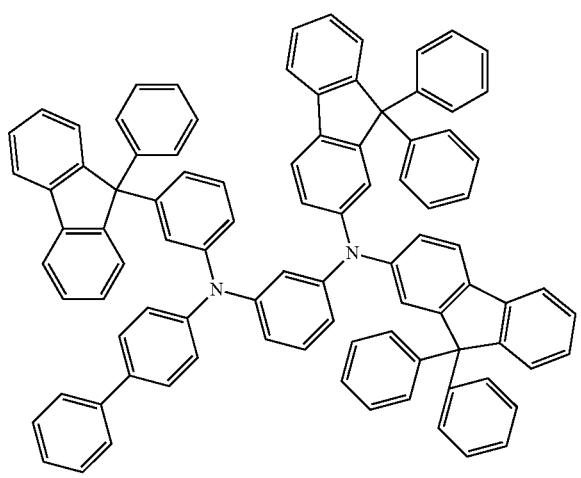
G-60
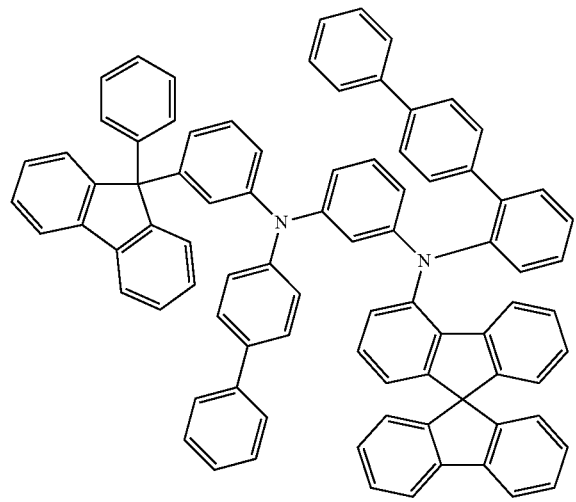
G-61
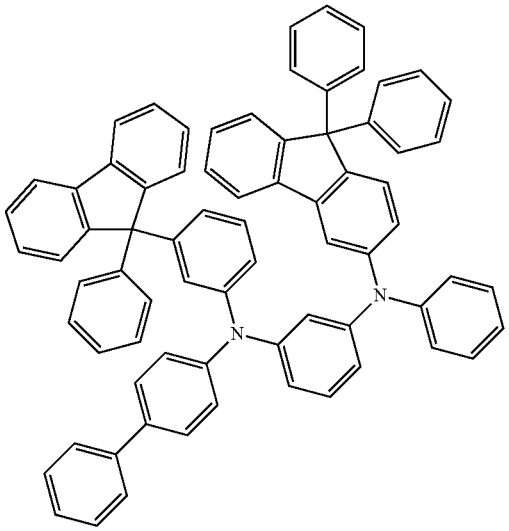
G-62
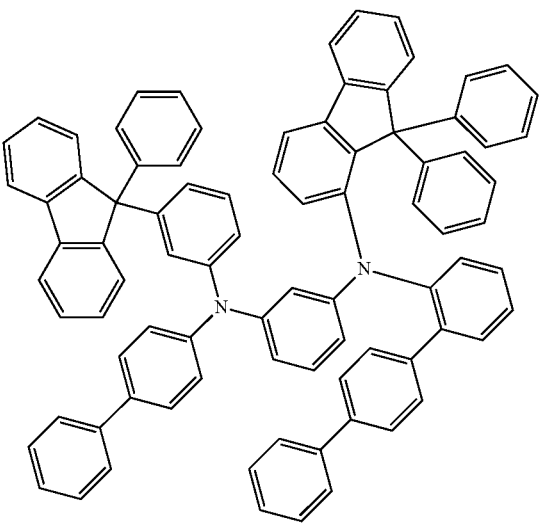
G-63
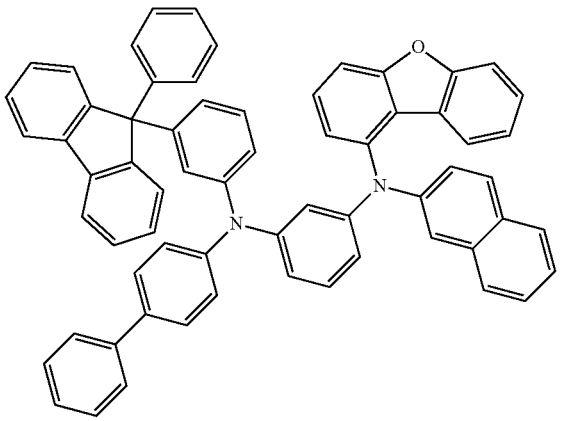

-continued
G-64
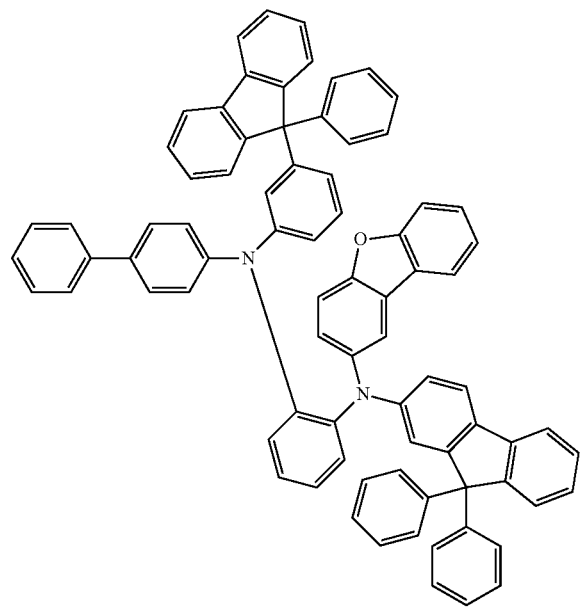
G-65
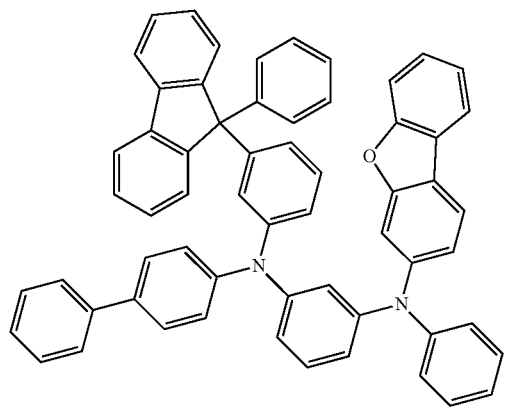
G-66
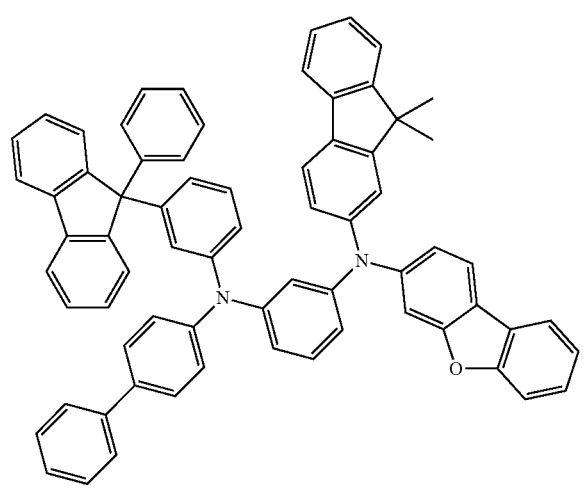
-continued
G-67
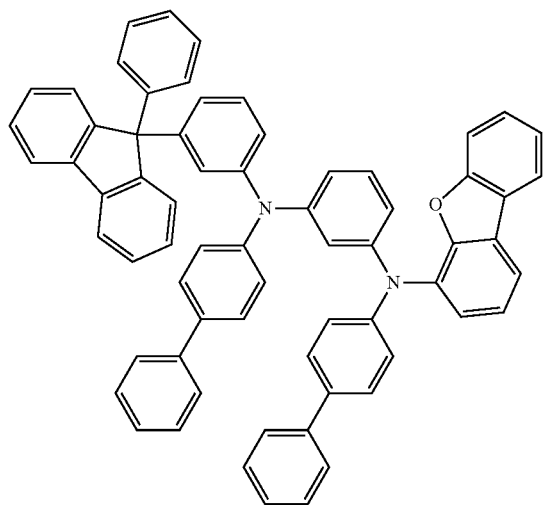
G-68
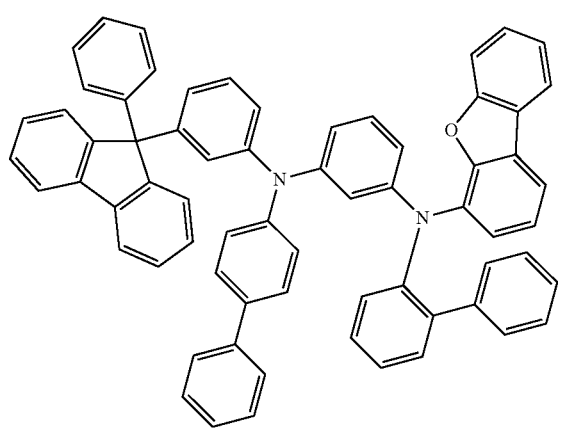
G-69
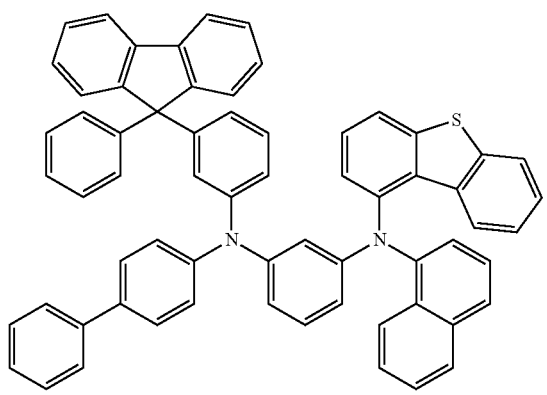

G-70
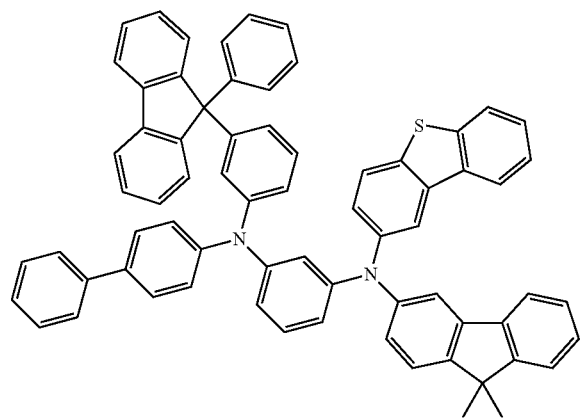
G-73
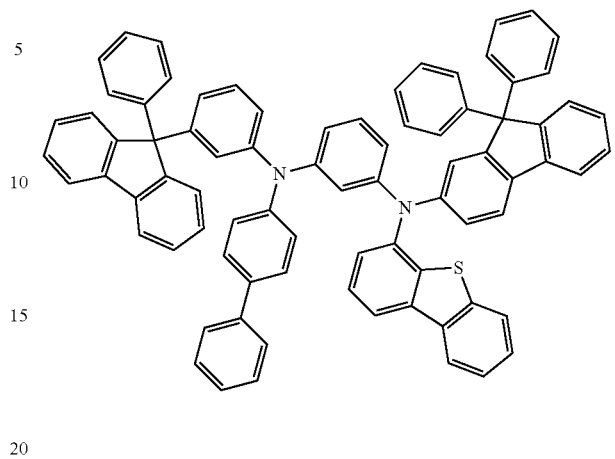
G-71
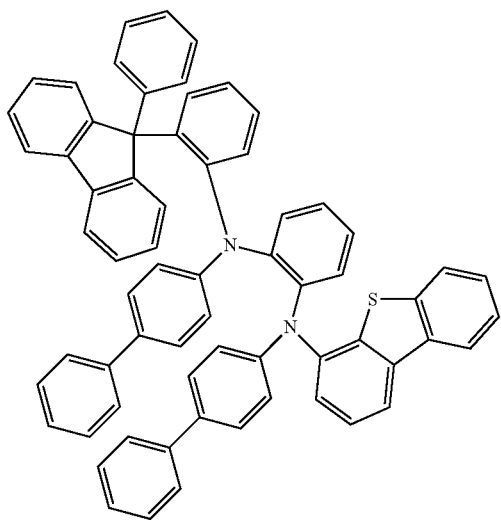
G-74
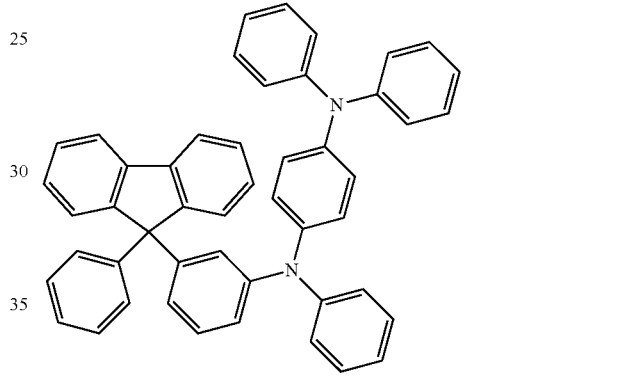
G-72
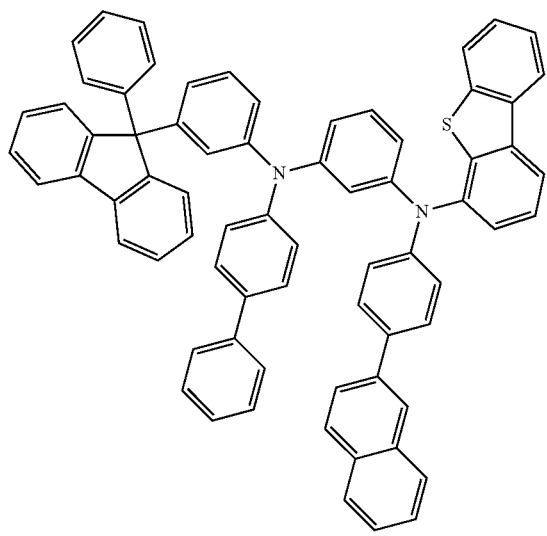
G-75
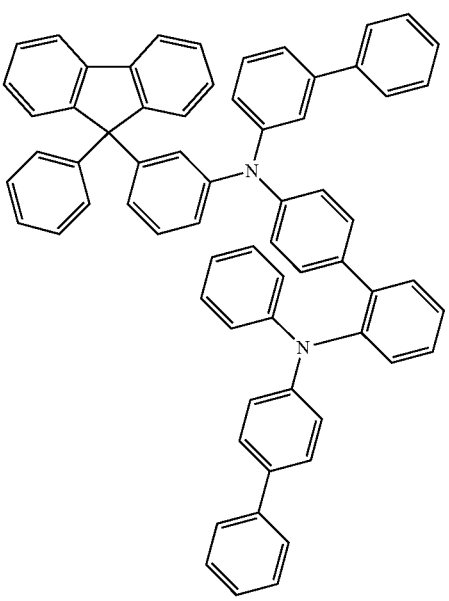

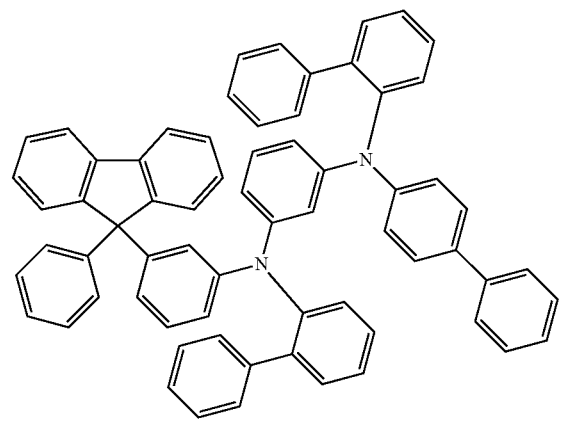
G-76
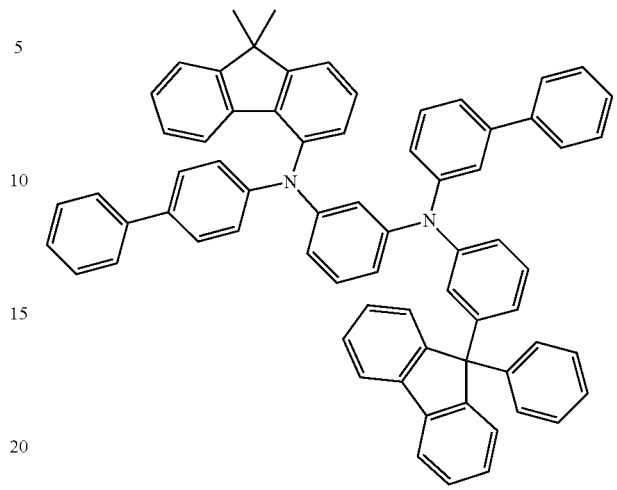
G-79
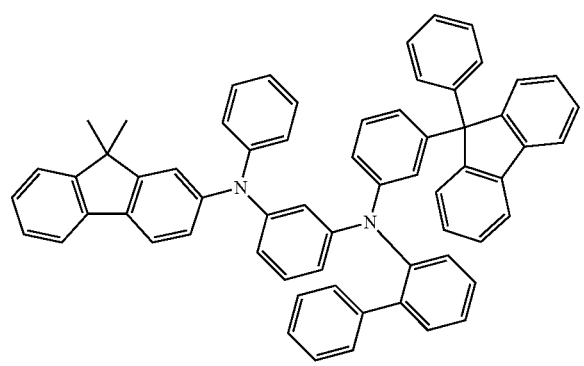
G-77
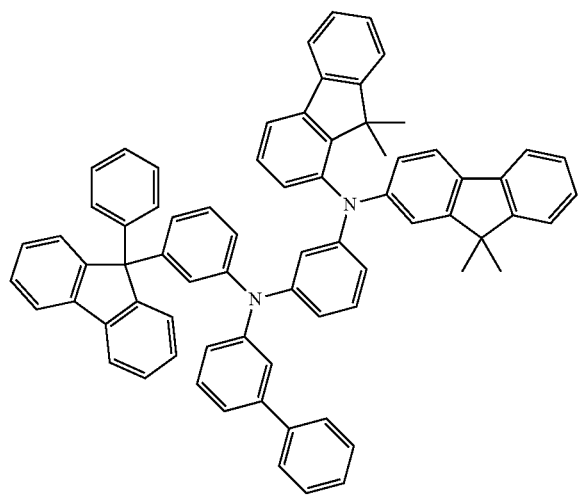
G-80
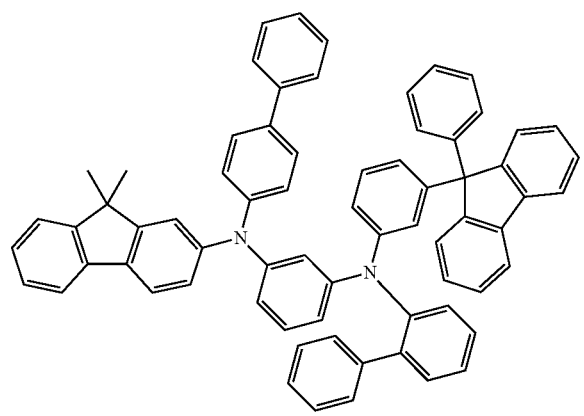
G-78
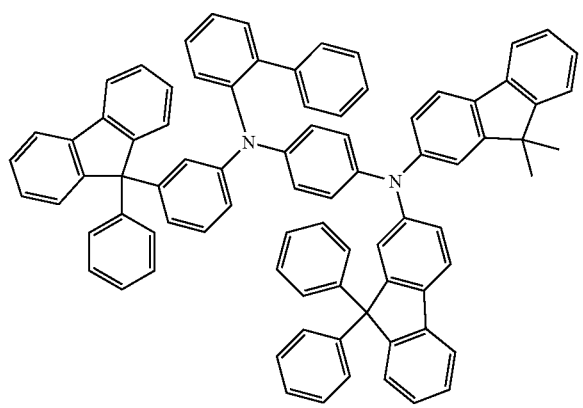
G-81

G-82
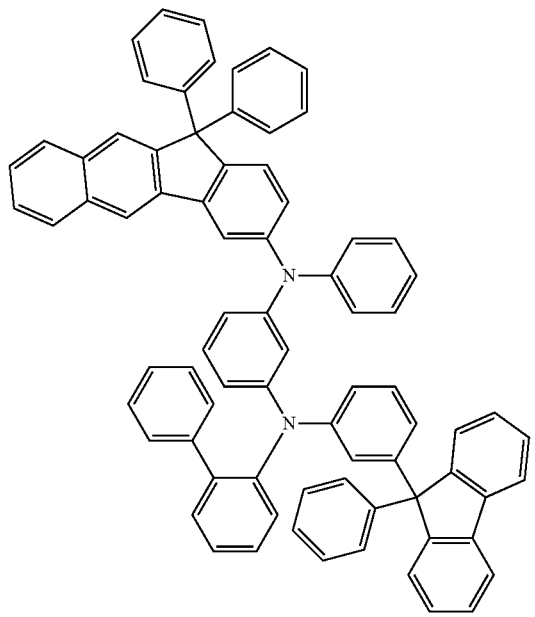
G-84
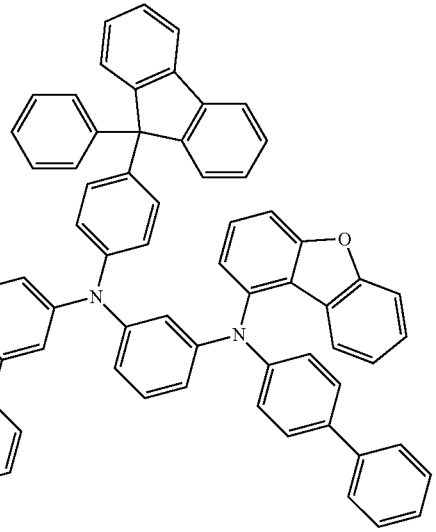
G-85
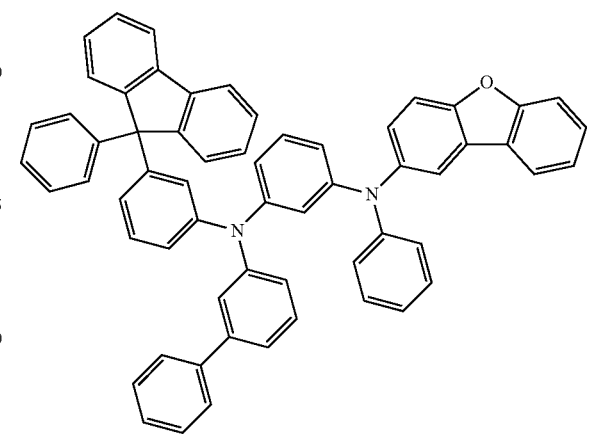
G-83
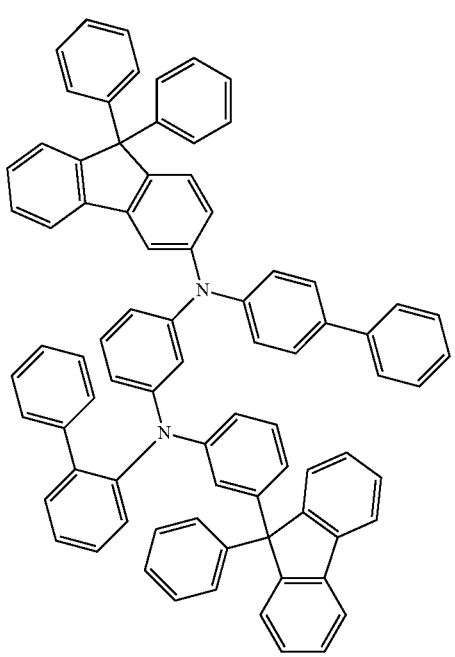
G-86
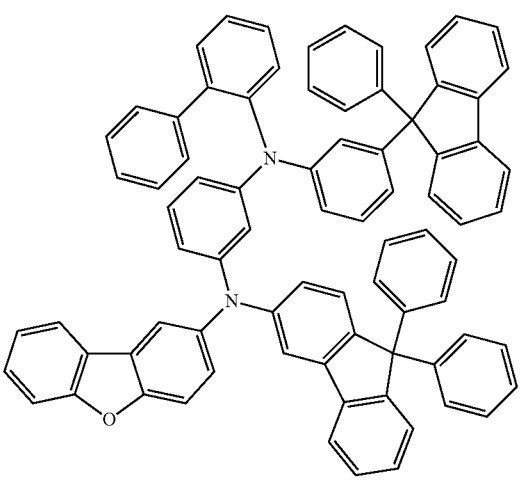

G-87
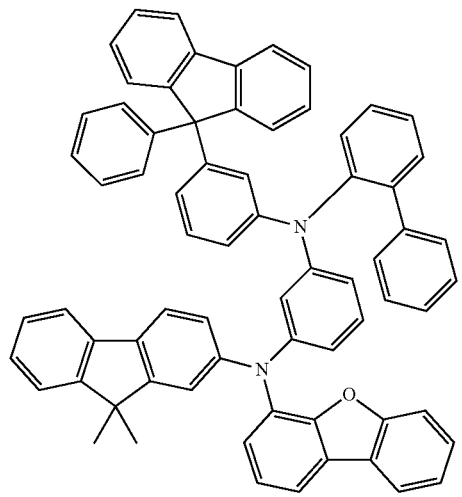
G-90
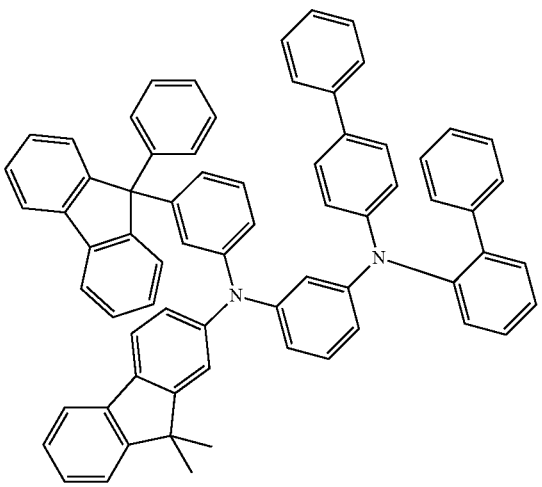
G-88
G-91
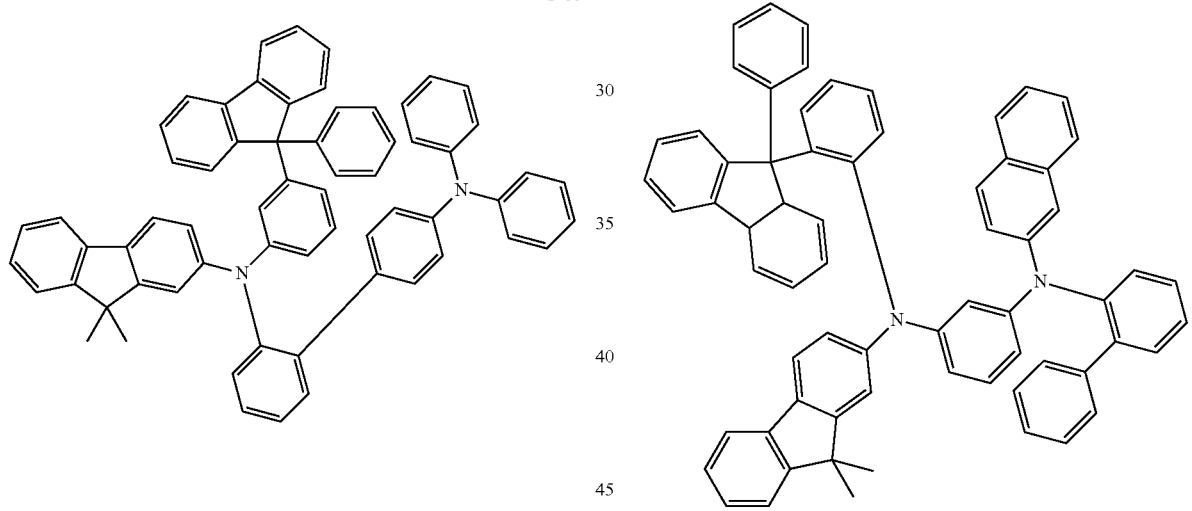
G-89
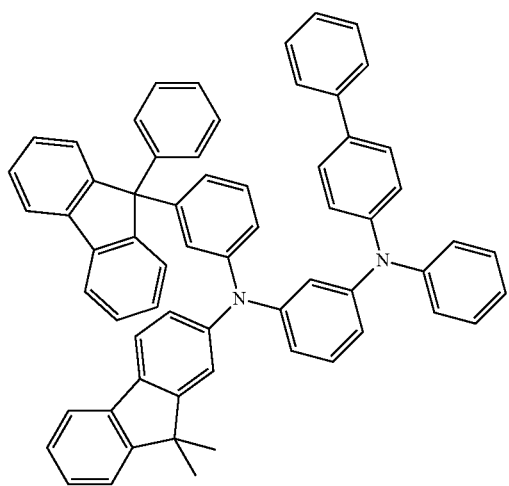
G-92
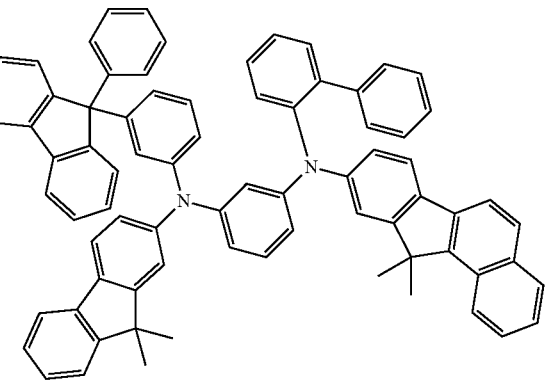

G-93
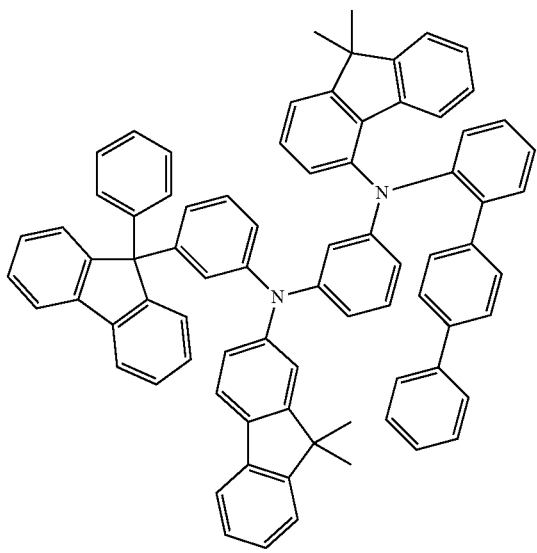
G-94
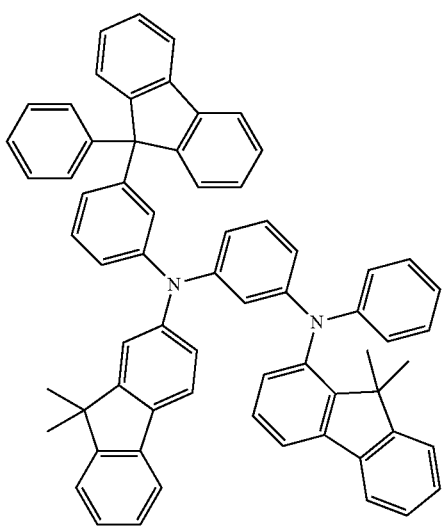
G-95
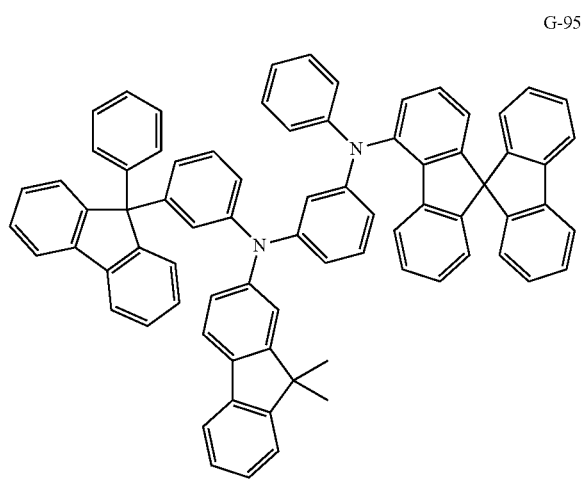
G-96
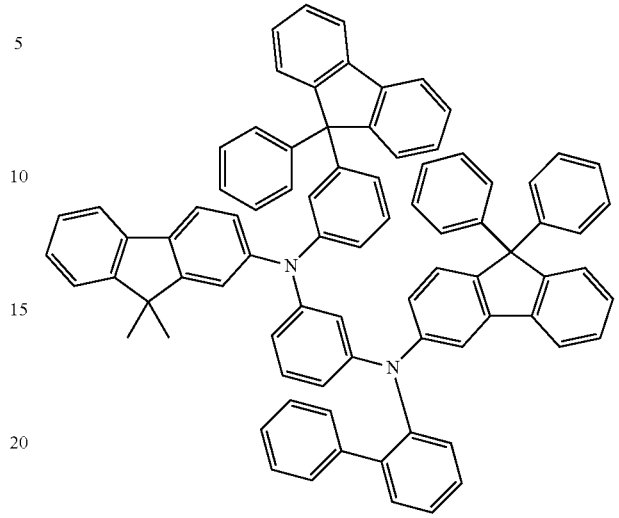
G-97
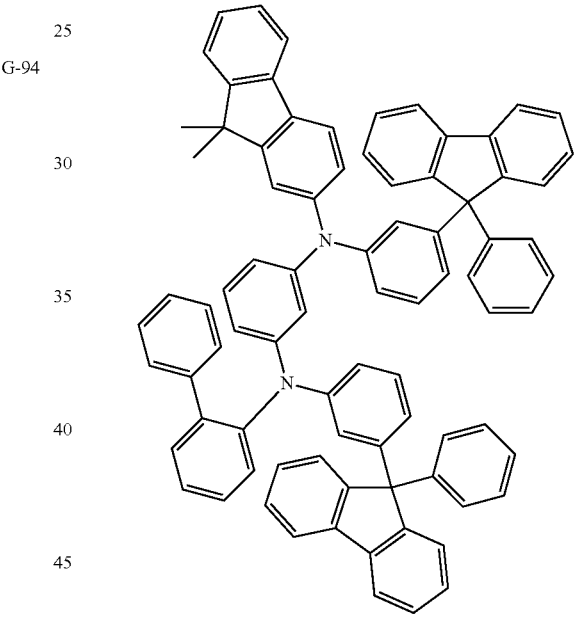
G-98
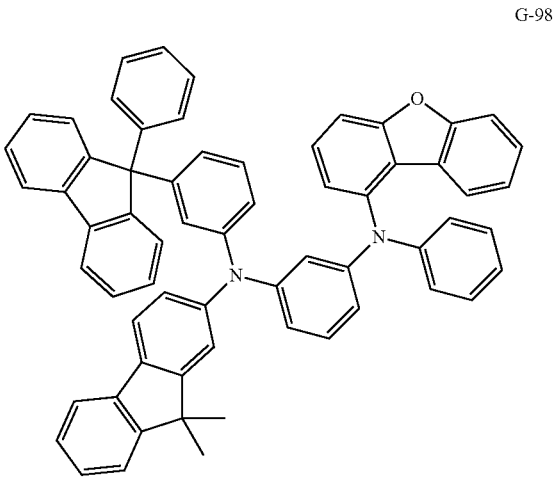

G-99
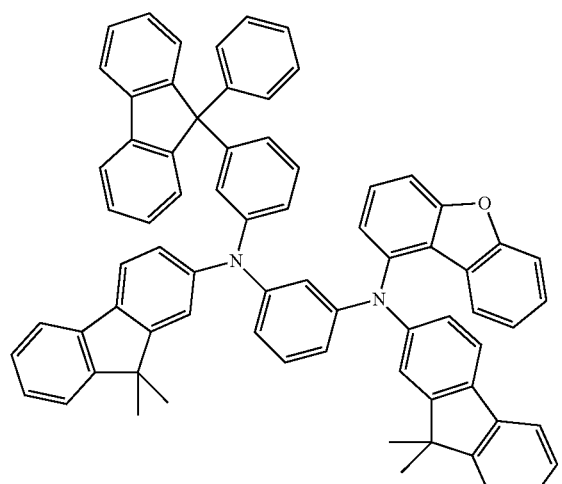
G-100
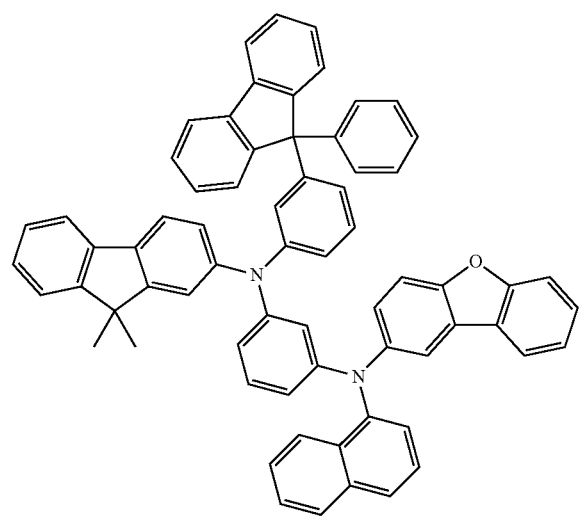
G-101
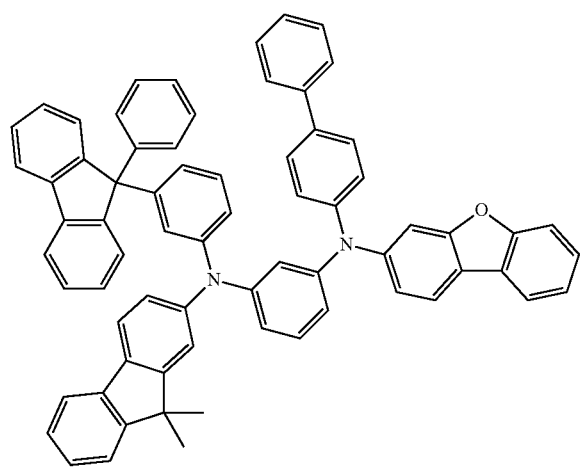
G-102
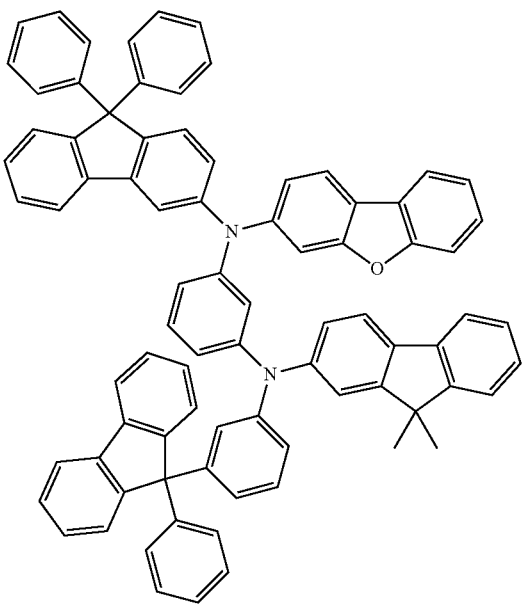
G-103
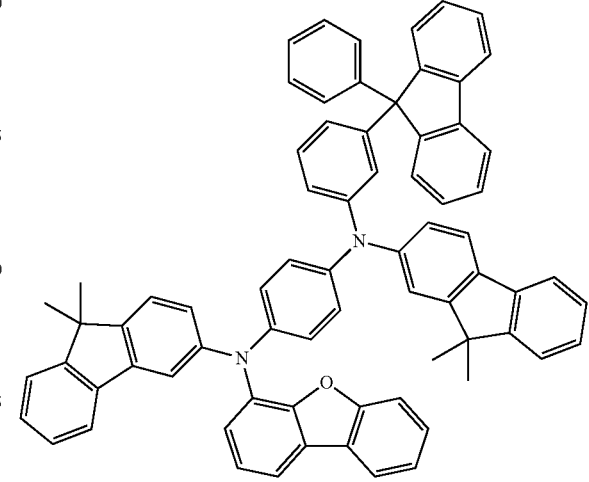
G-104
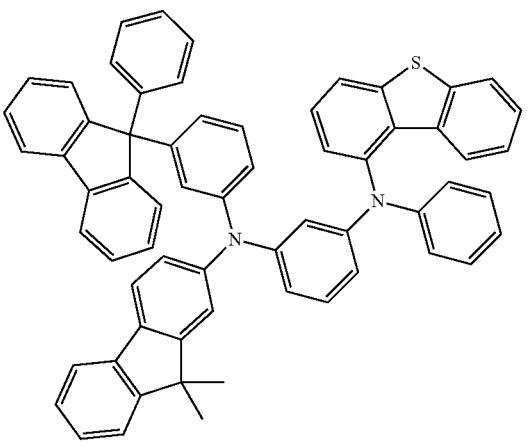

G-105
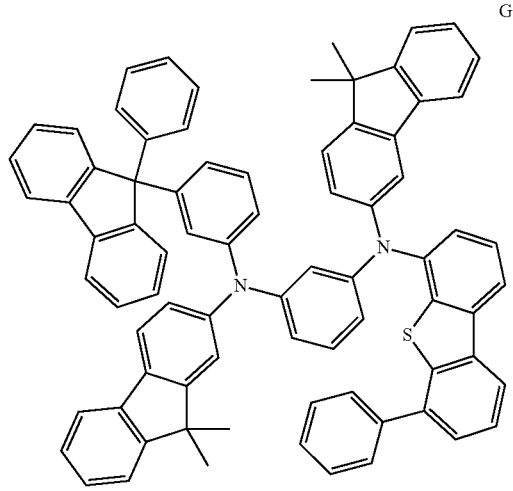
G-108
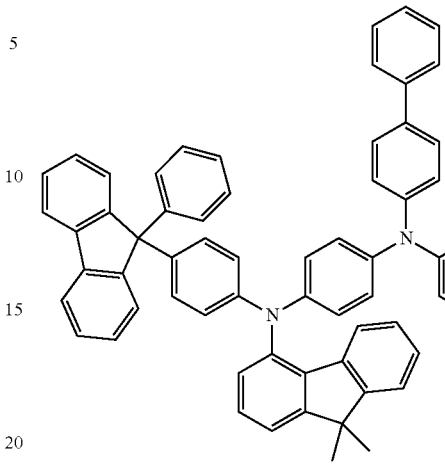
G-106
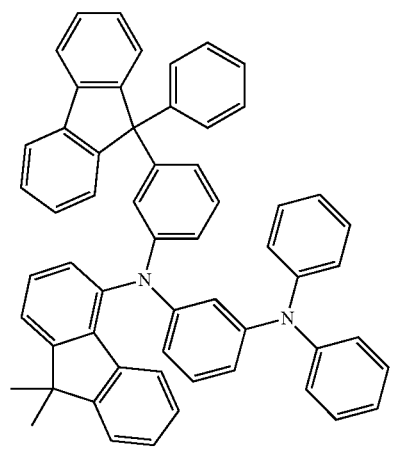
G-109
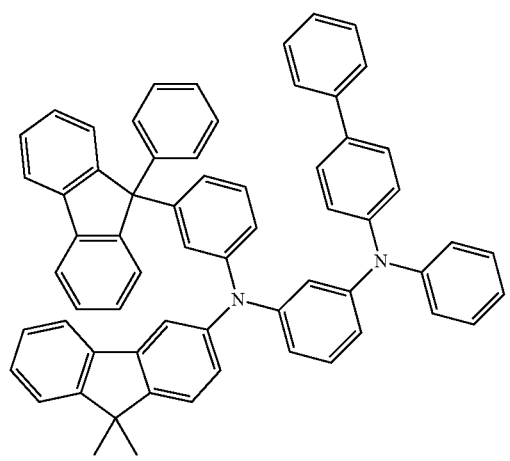
G-107
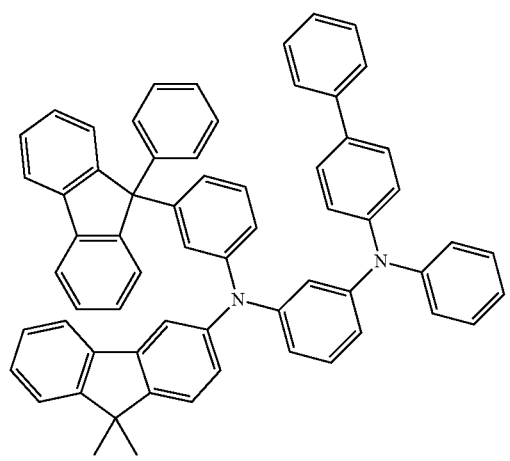
G-110
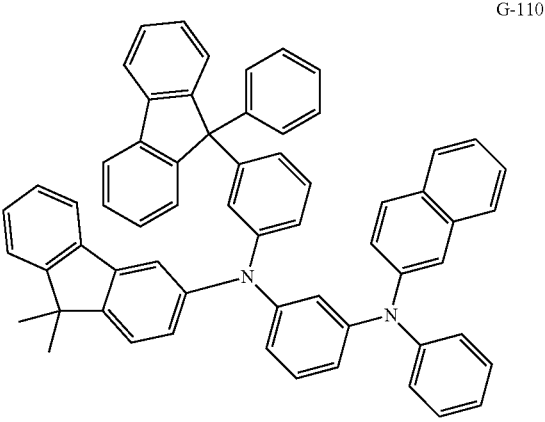

G-111
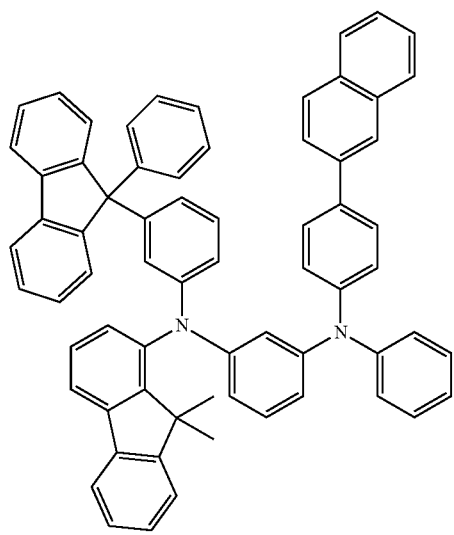
G-114
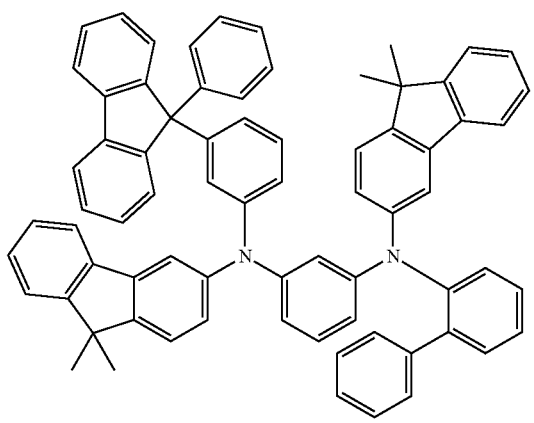
G-112
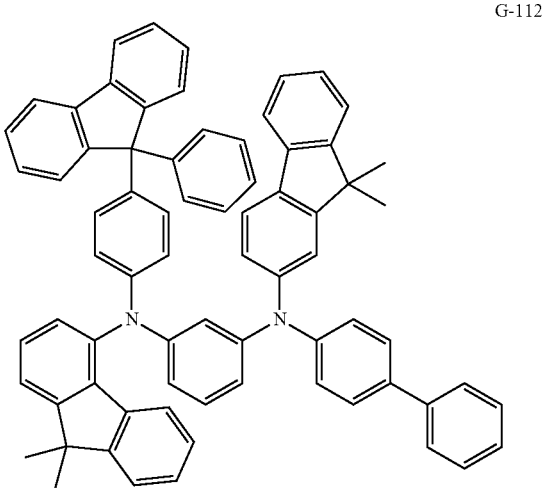
G-115
G-113
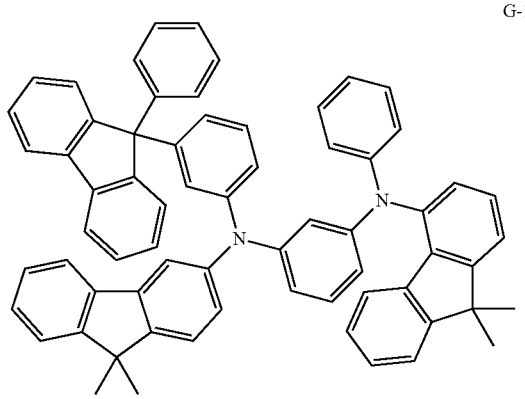
G-116
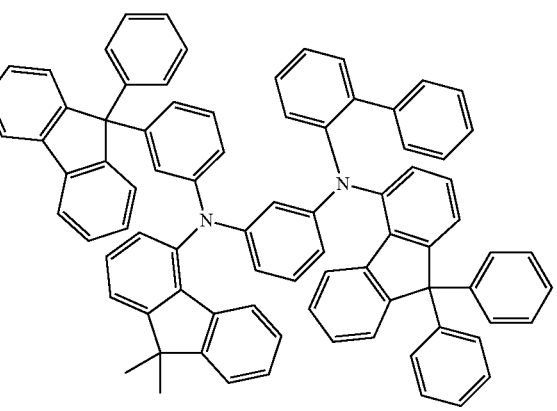

G-117
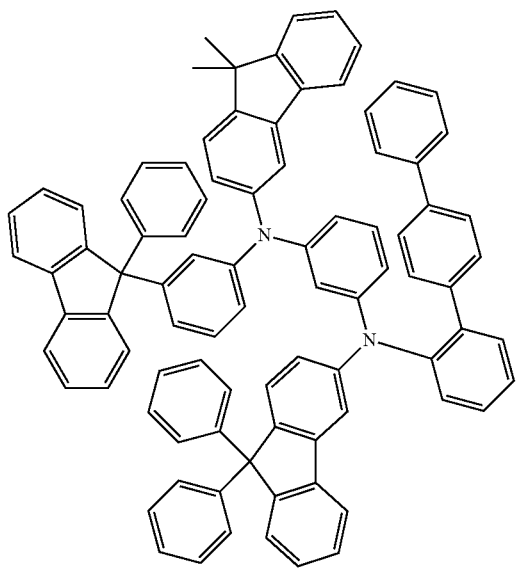
G-120
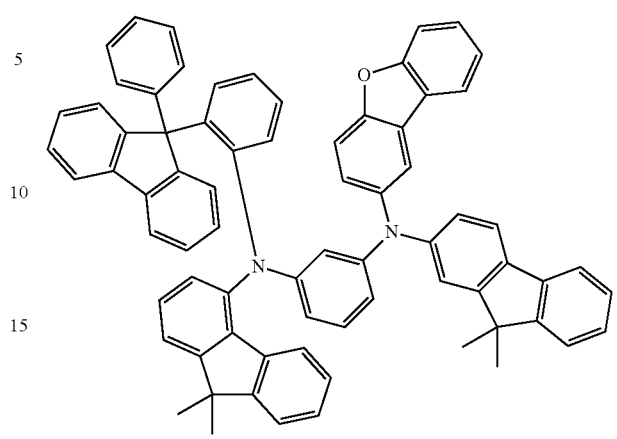
G-118
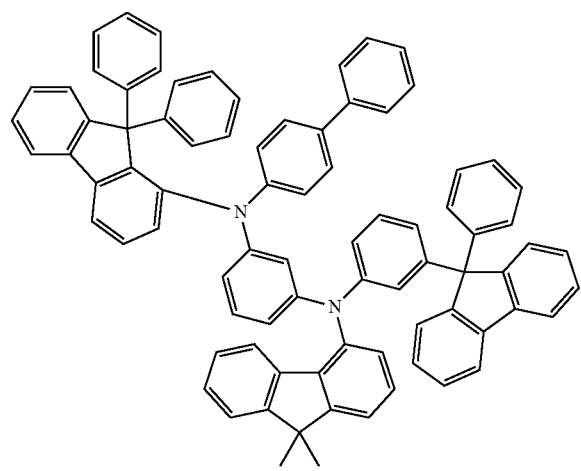
G-121
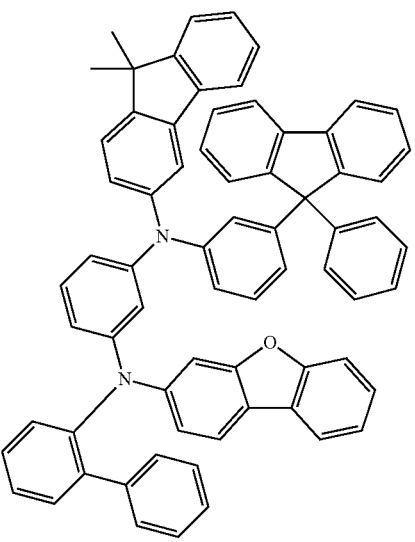
G-119
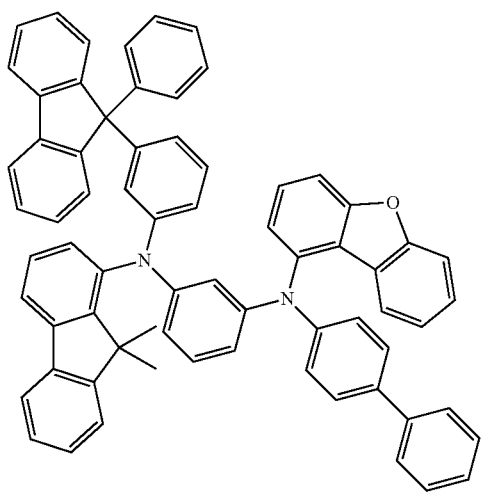
G-122
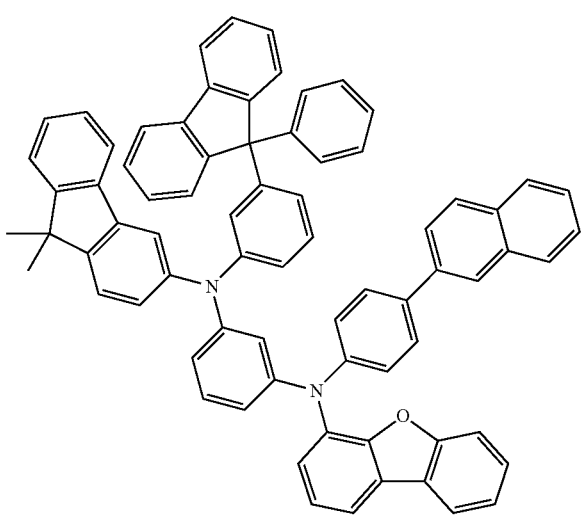

G-123
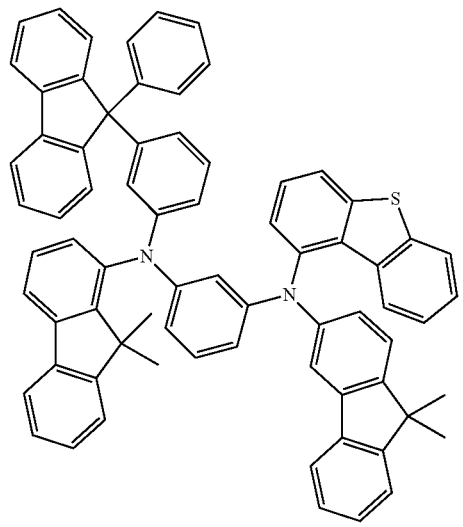
G-124
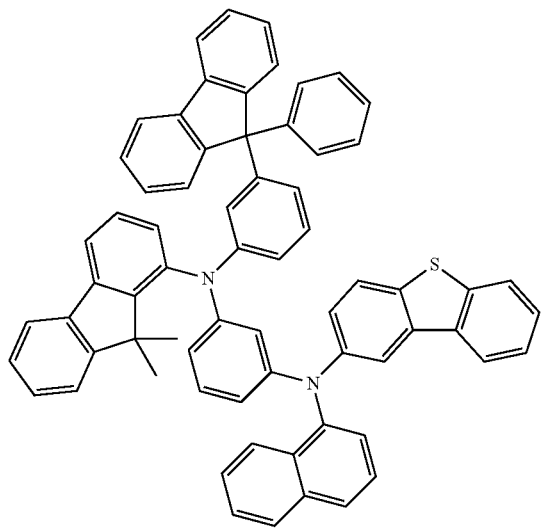
G-125
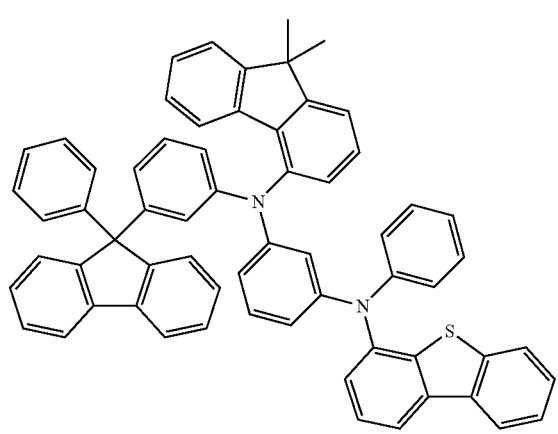
G-126
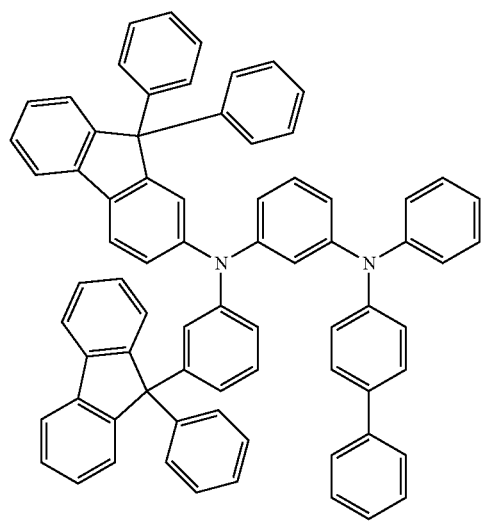
G-127
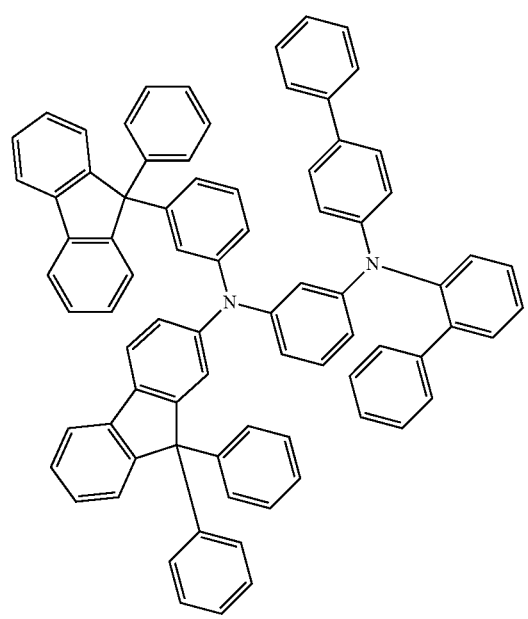
G-128
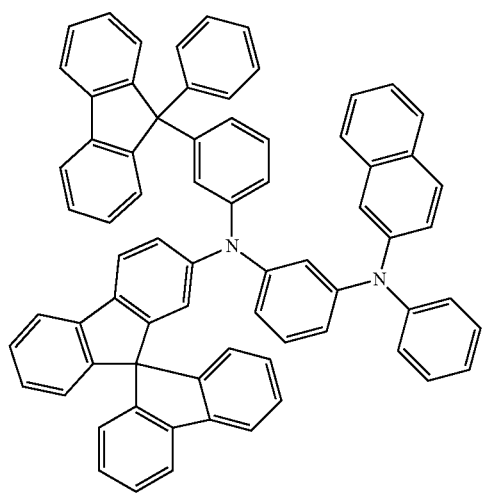

-continued
G-129
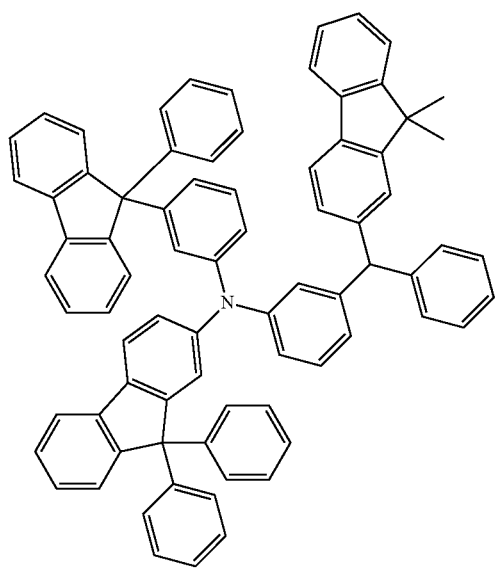
G-130
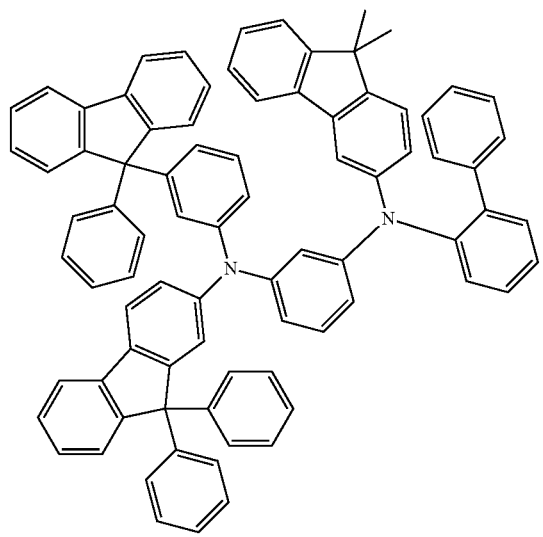
G-131
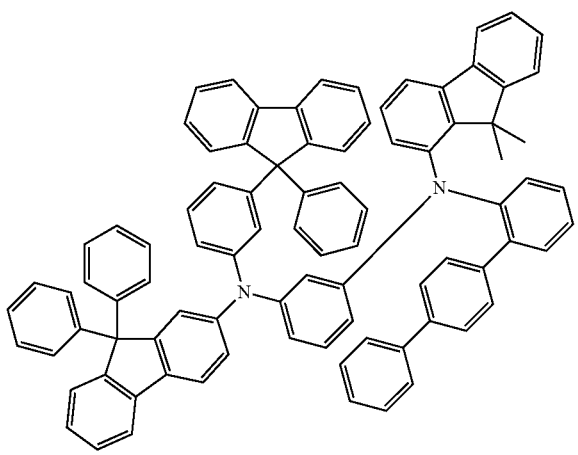
-continued
G-132
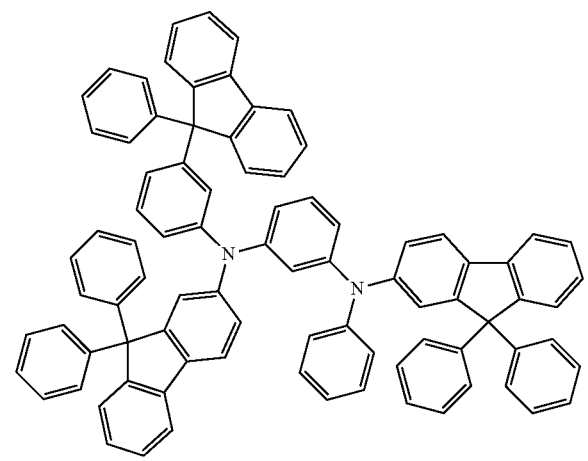
G-133
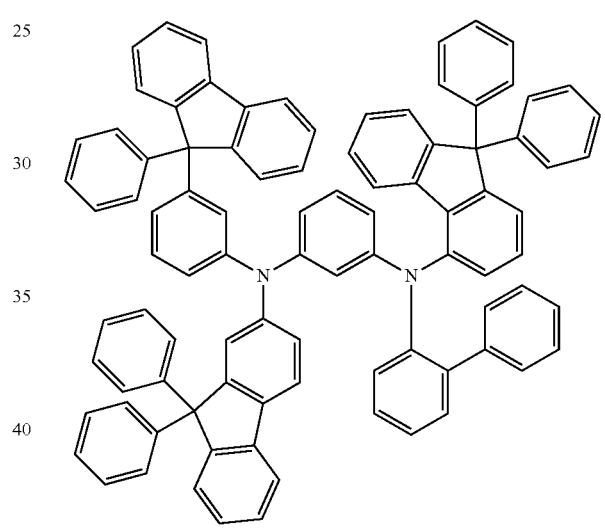
G-134
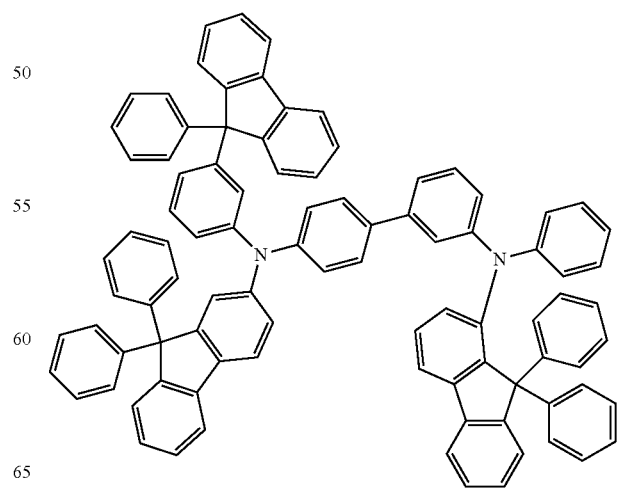

G-135
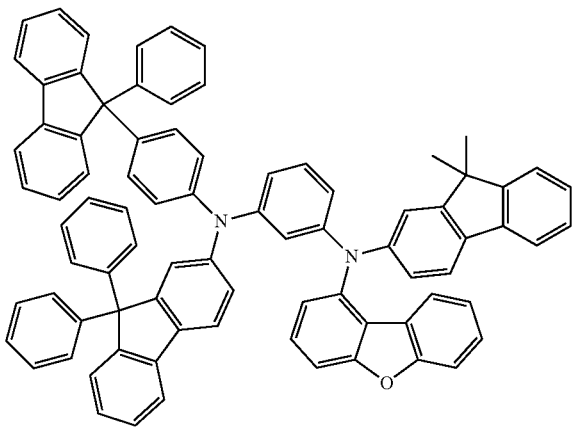
G-136
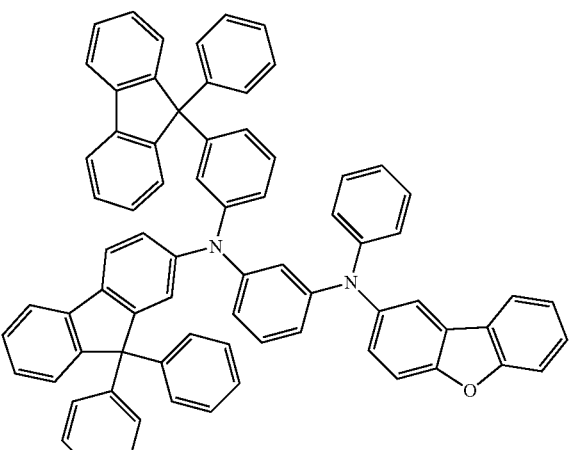
G-137
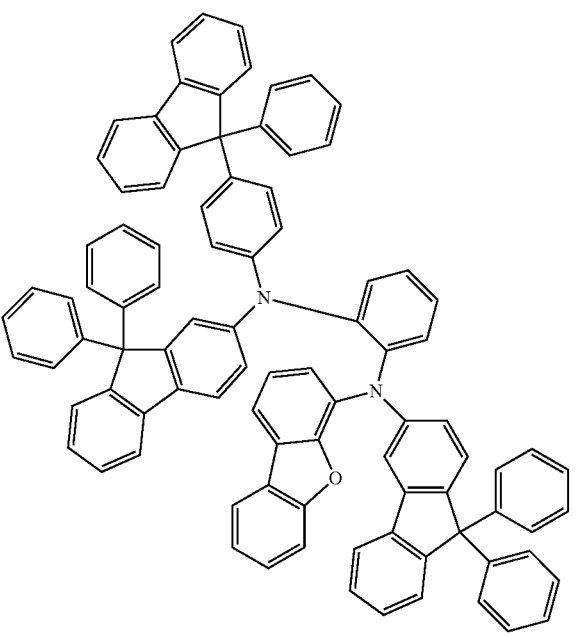
G-138
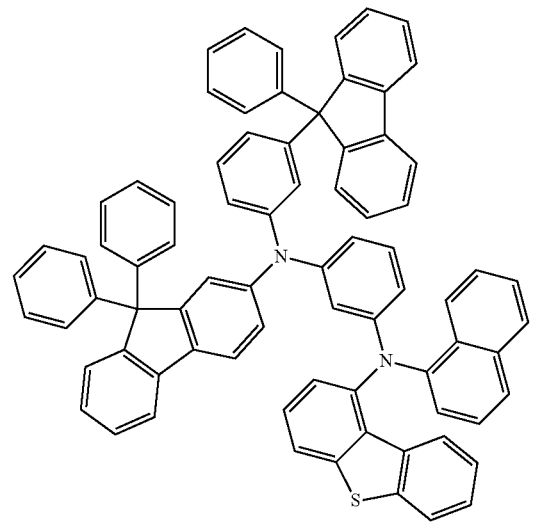
G-139
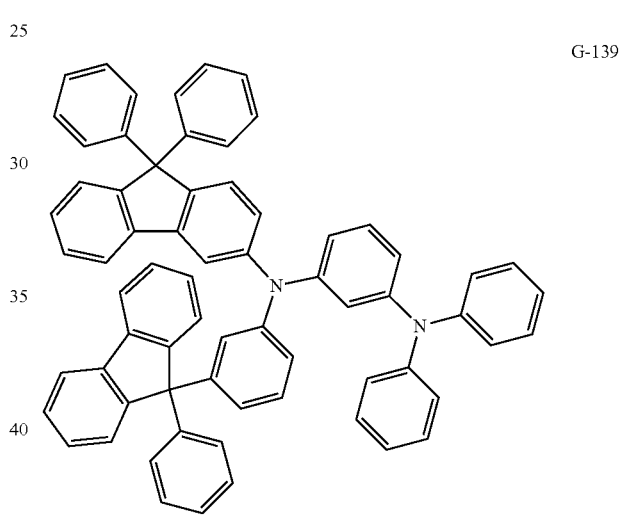
G-140
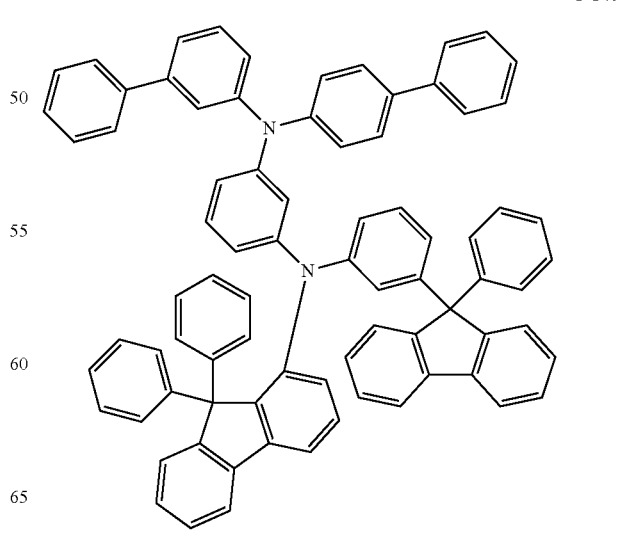

G-141
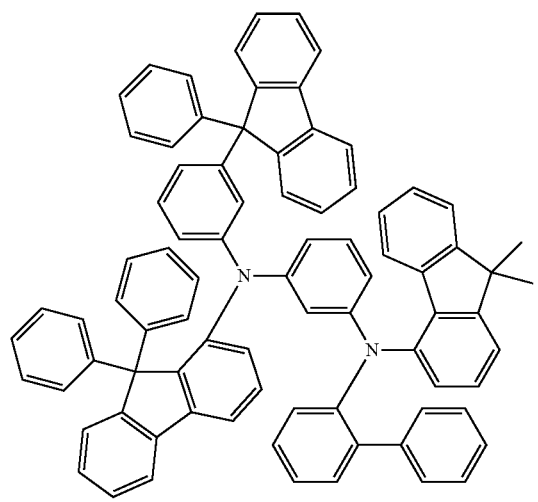
G-143
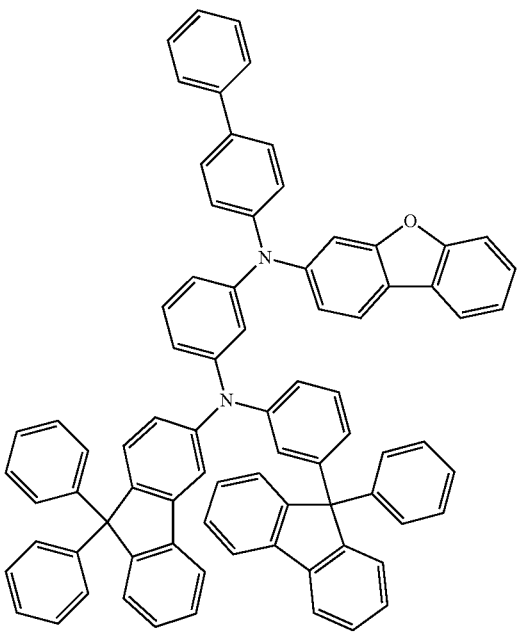
G-142
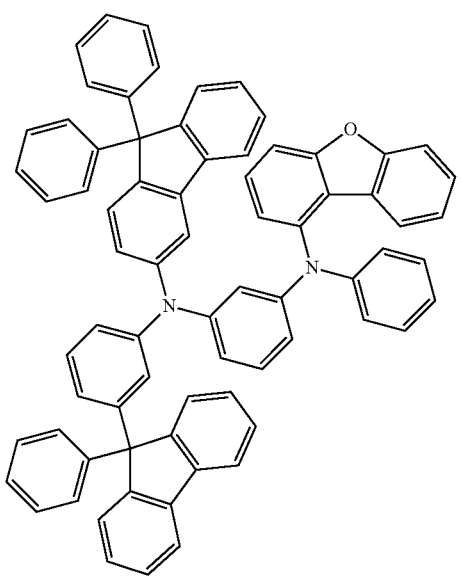
G-144
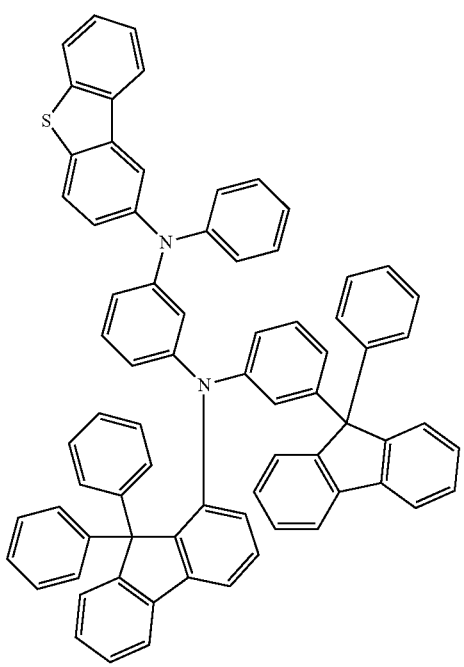

G-145
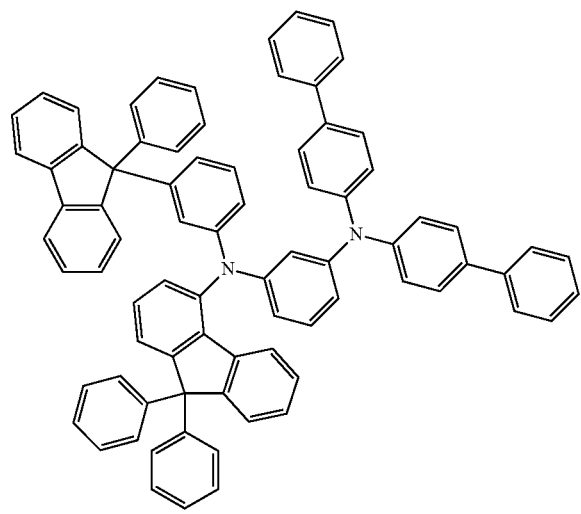
G-148
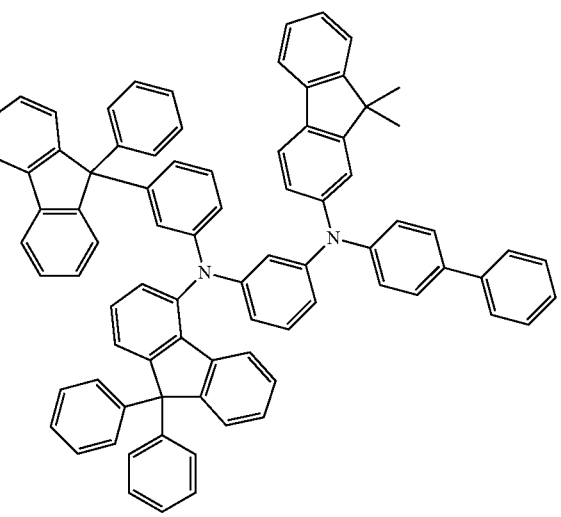
G-146
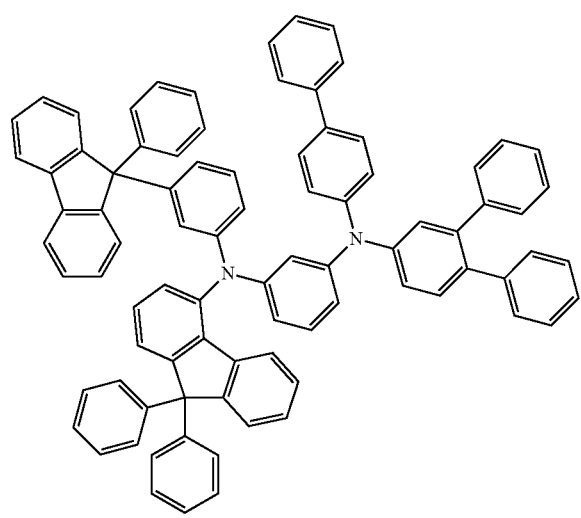
G-149
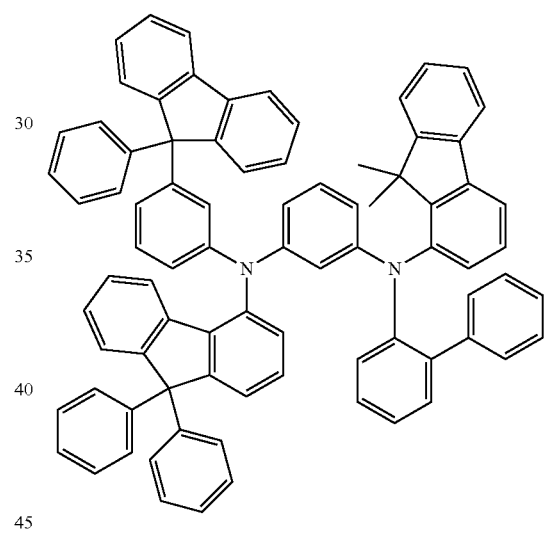
G-147
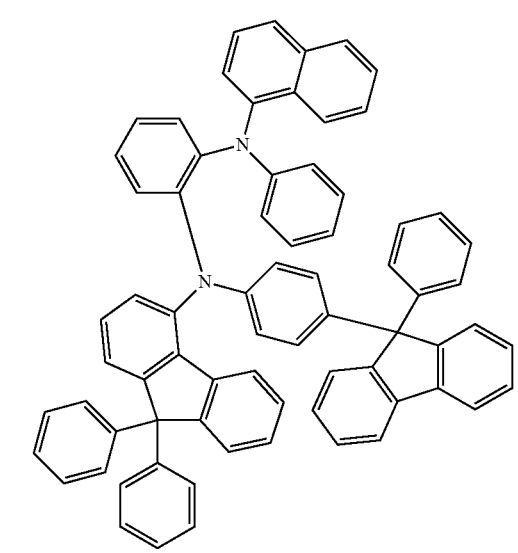
G-150
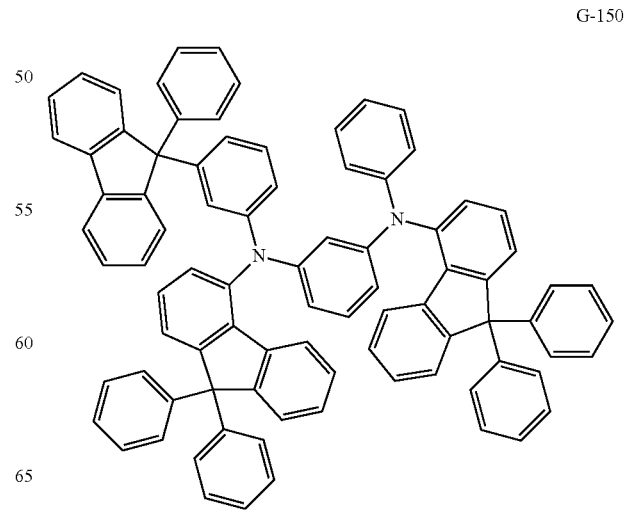

-continued
G-151
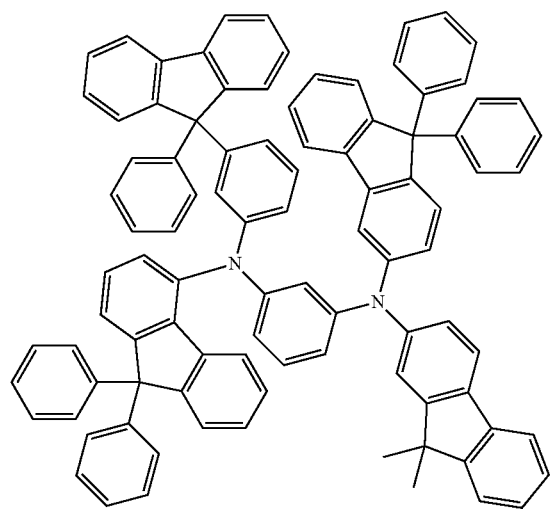
G-154
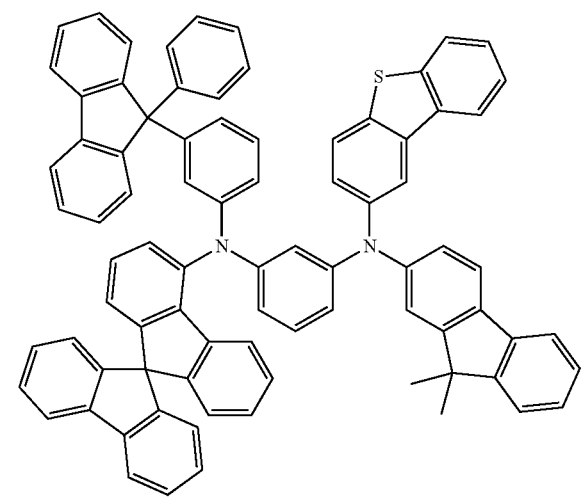
G-152
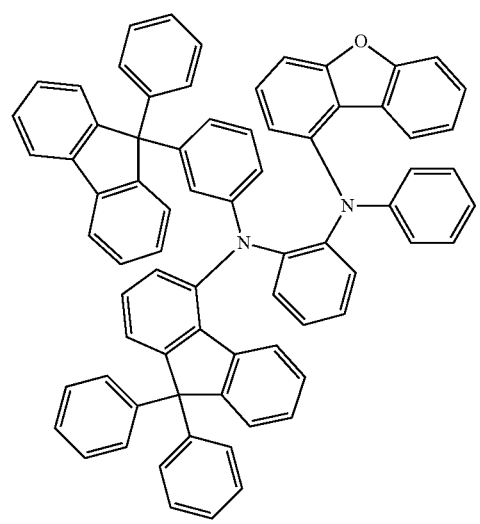
G-155
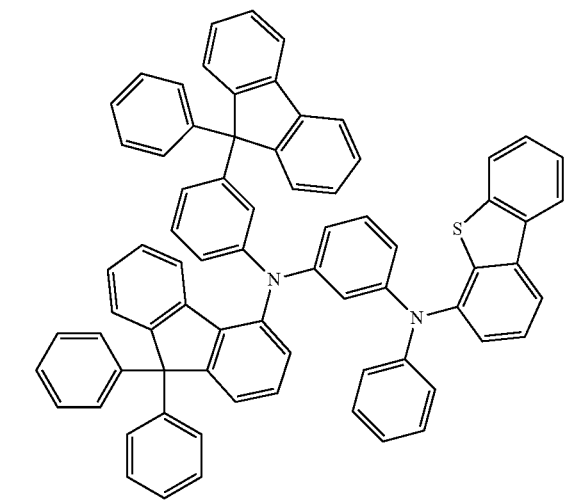
G-153
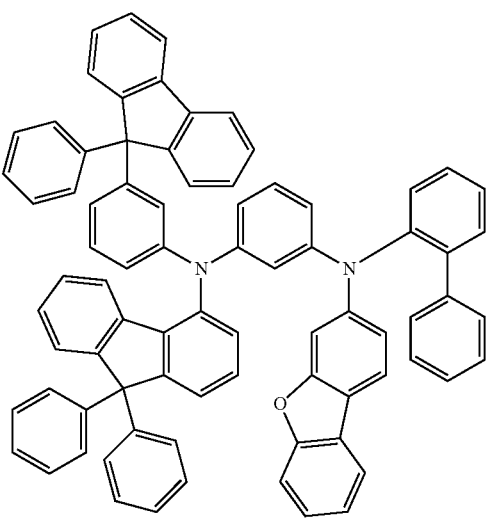
G-156
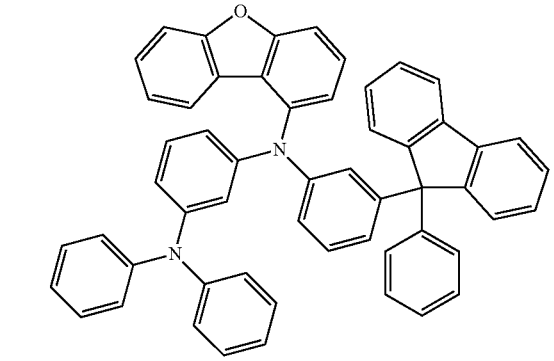

G-157
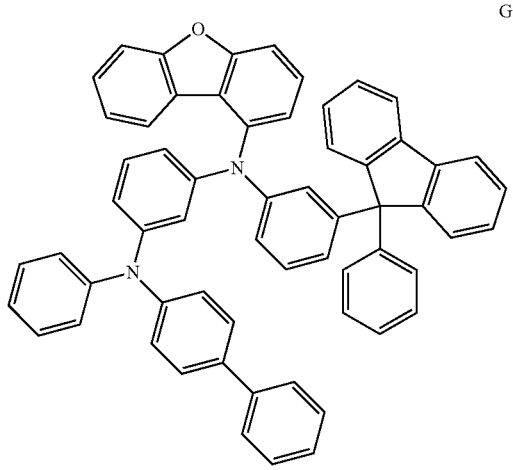
G-160
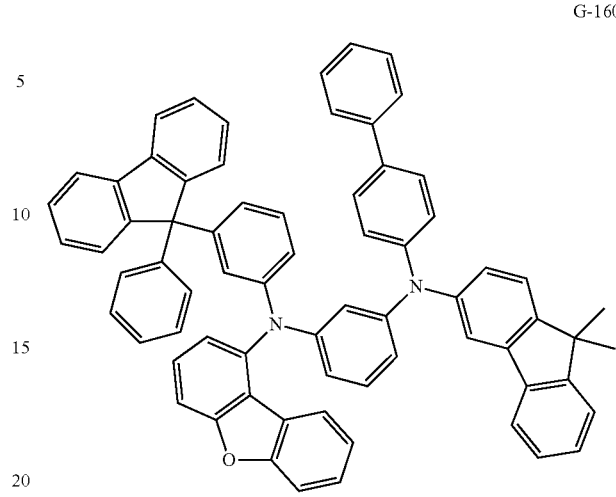
G-158
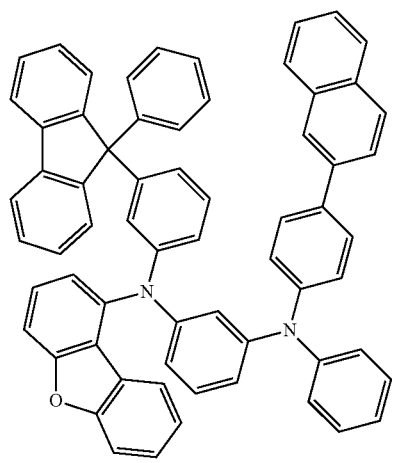
G-161
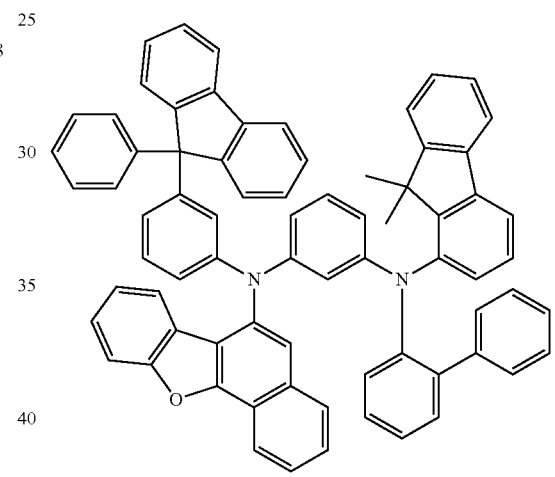
G-159
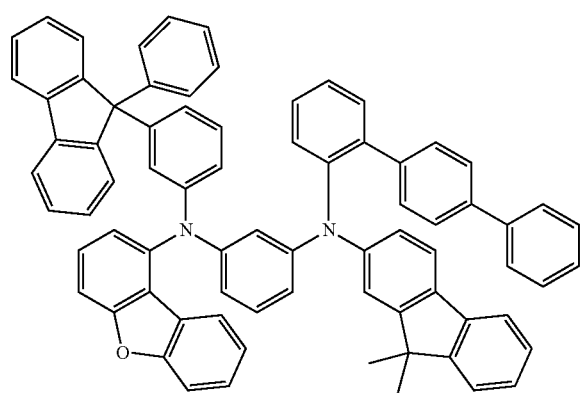
G-162
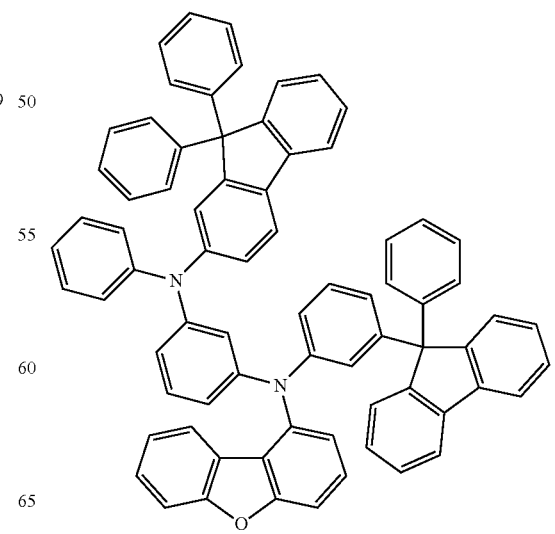

G-163
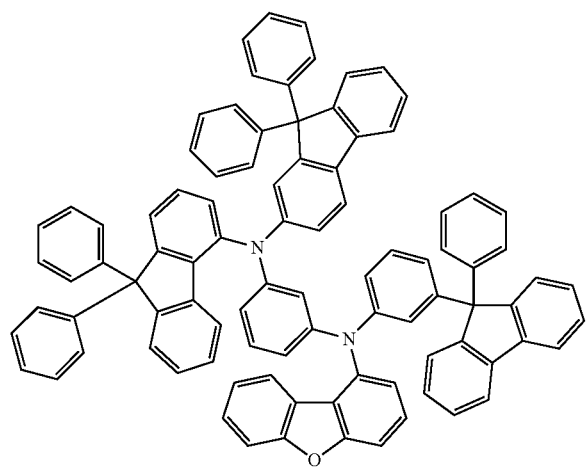
G-166
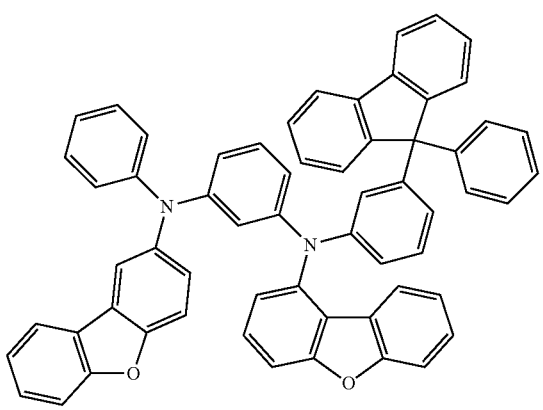
G-164
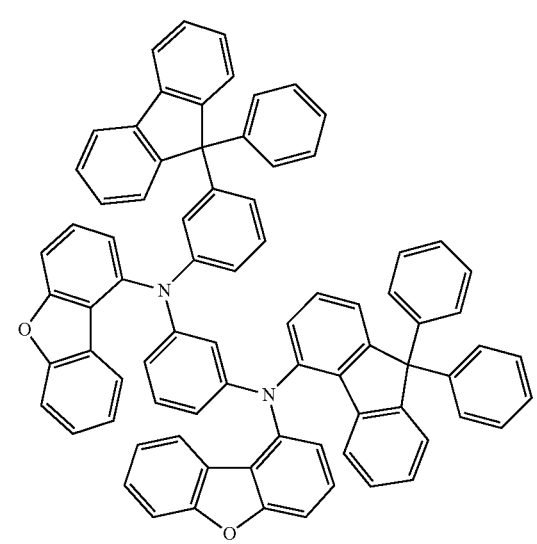
G-167
G-165
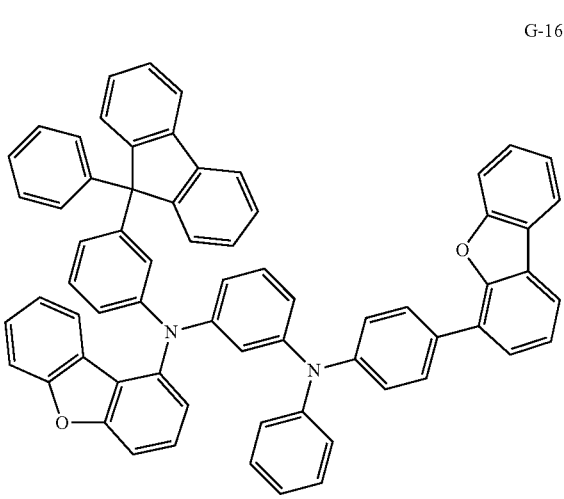
G-168

G-169
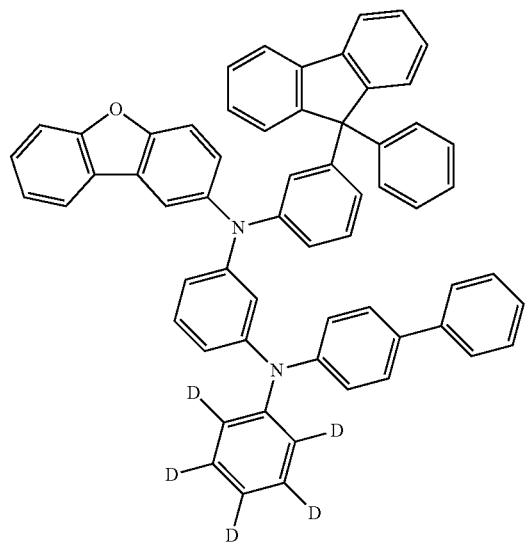
G-170
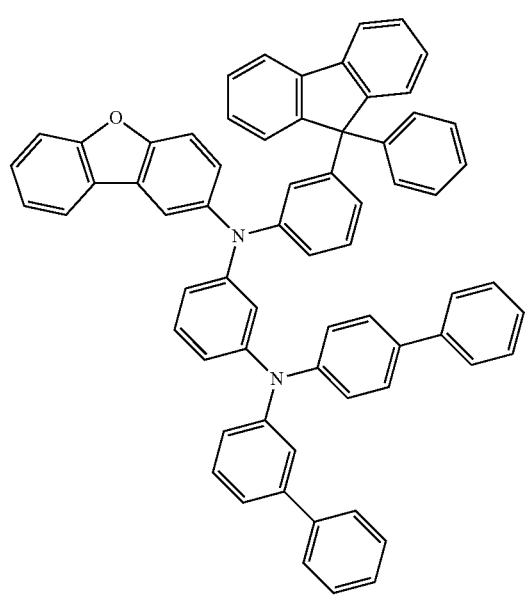
G-171
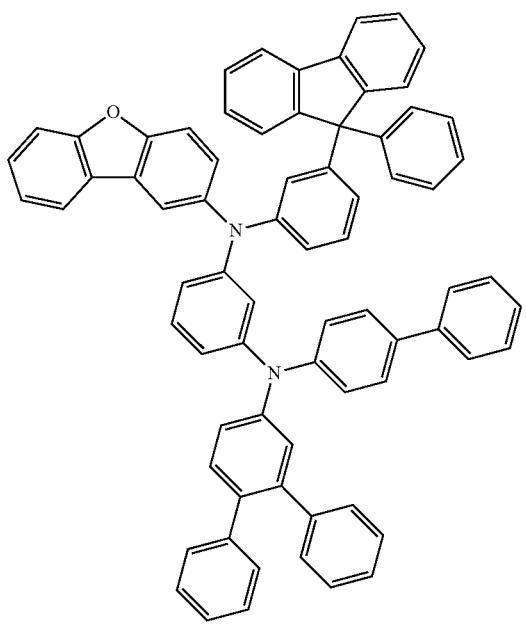
G-172
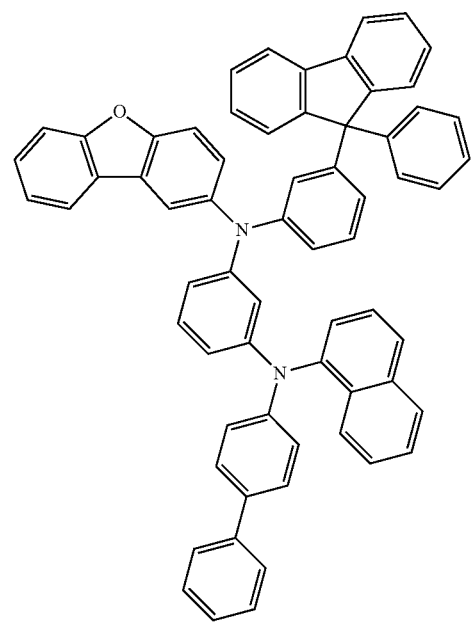

G-173
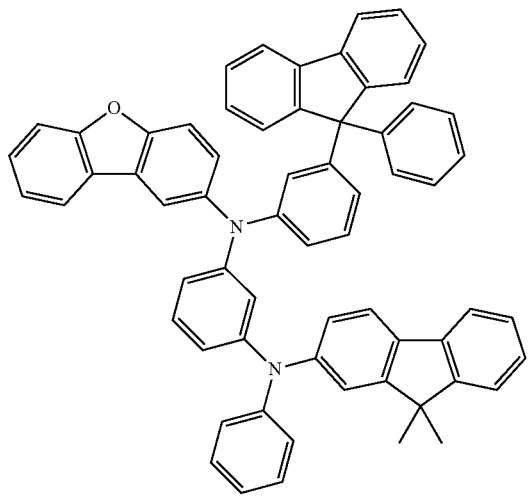
G-174
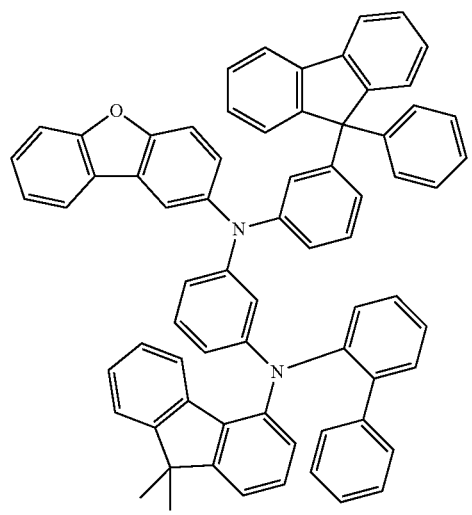
G-175
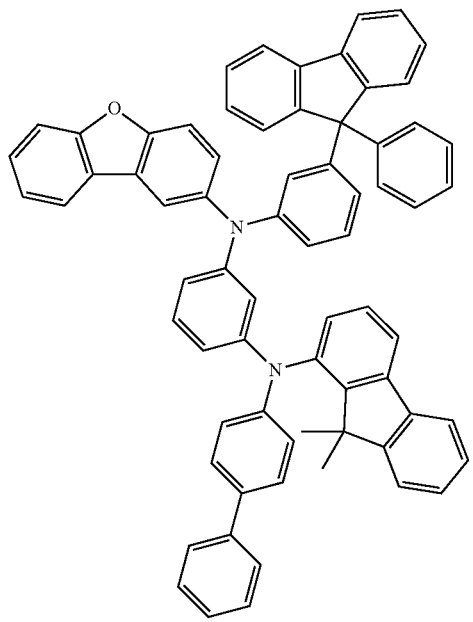
G-176
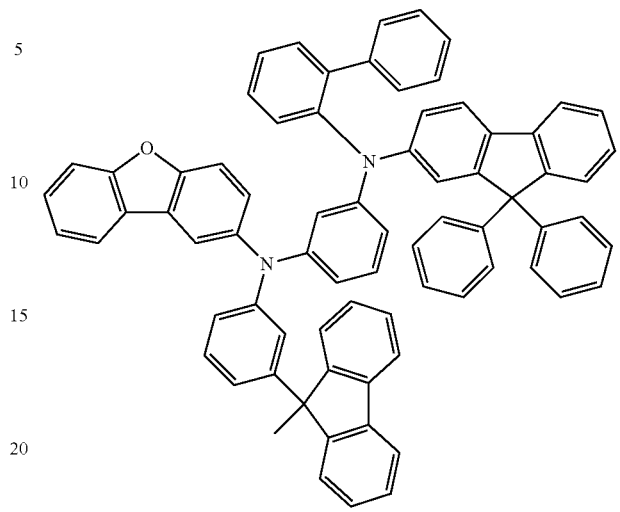
G-177
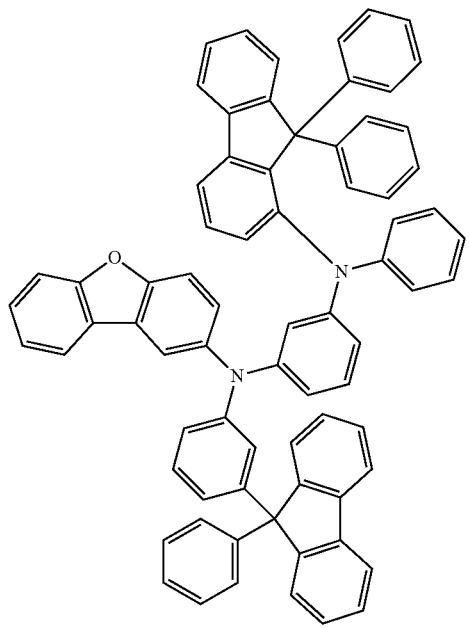
G-178
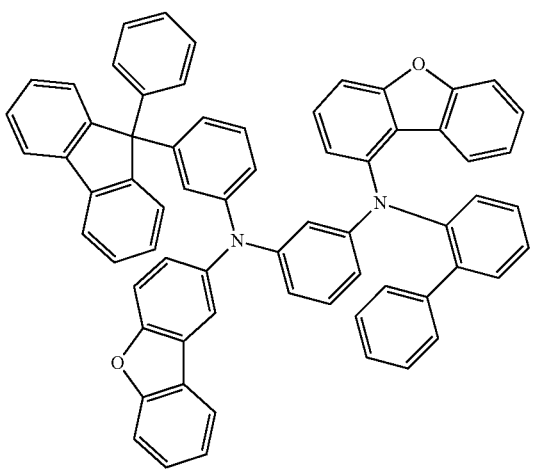

G-179
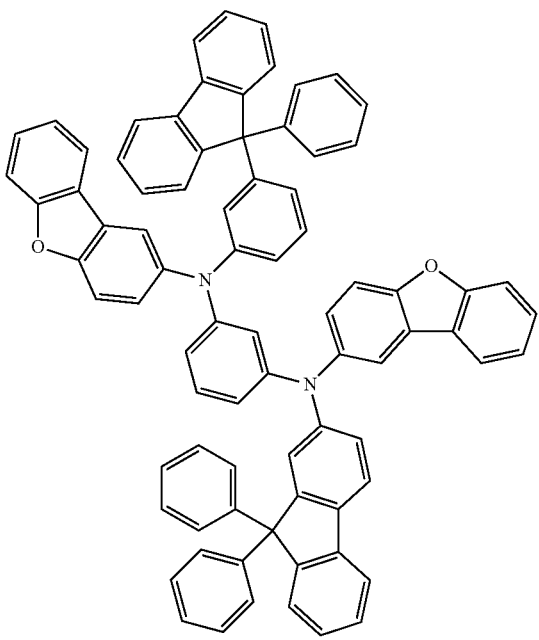
G-180
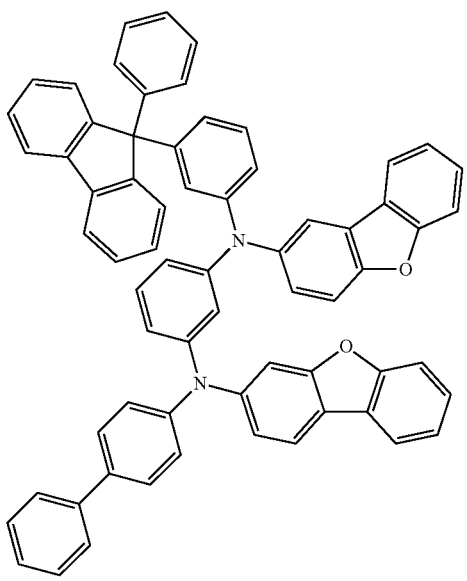
G-181, G-182, G-183
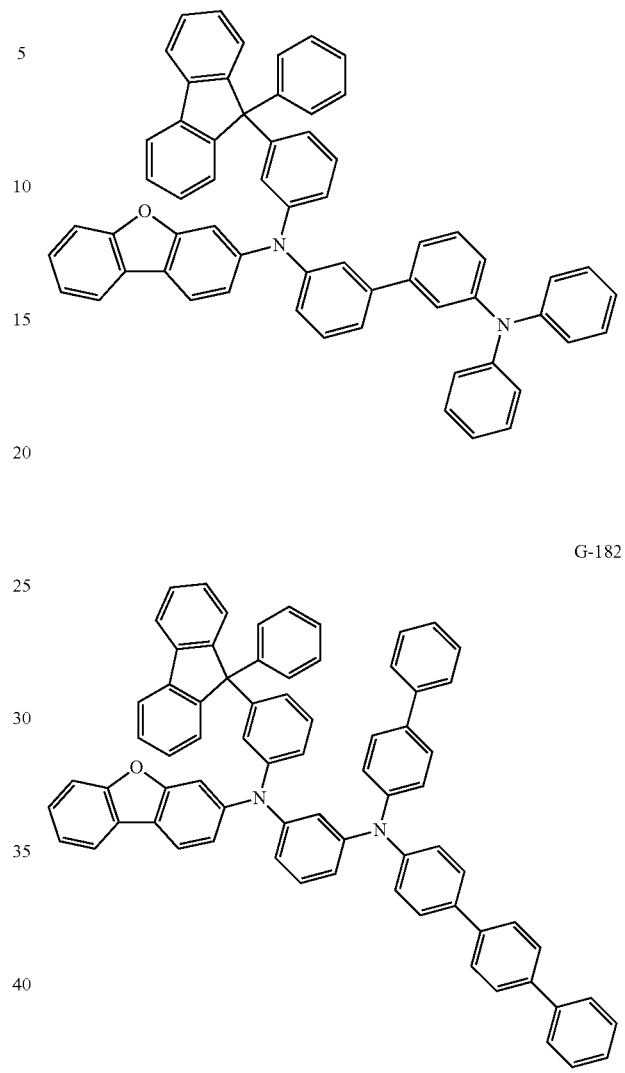

-continued
G-184
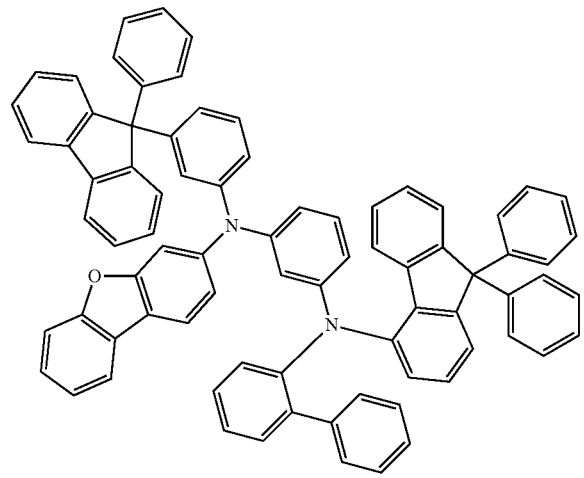
G-185
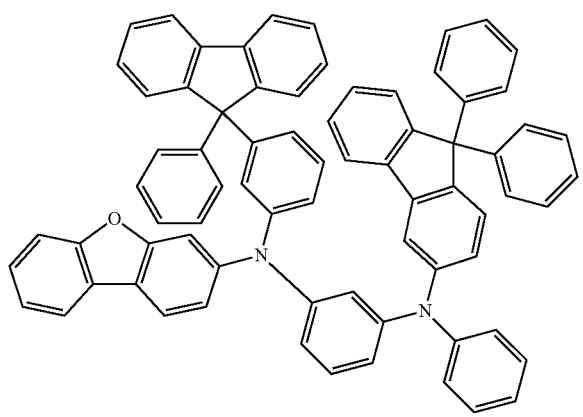
G-186
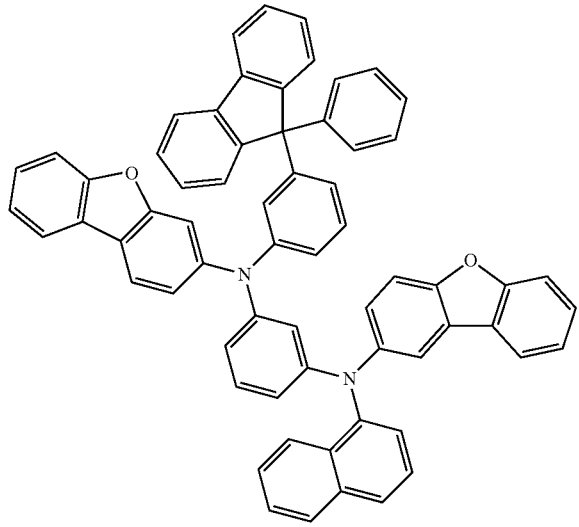
-continued
G-187
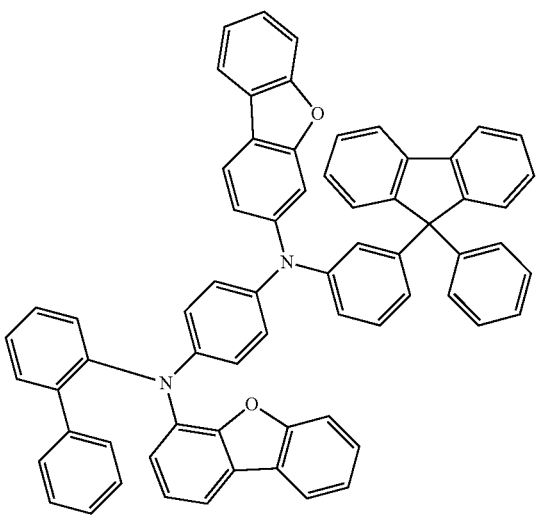
G-188
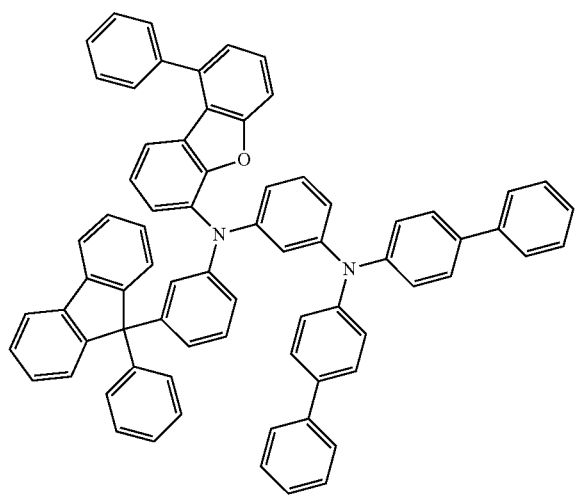
G-189
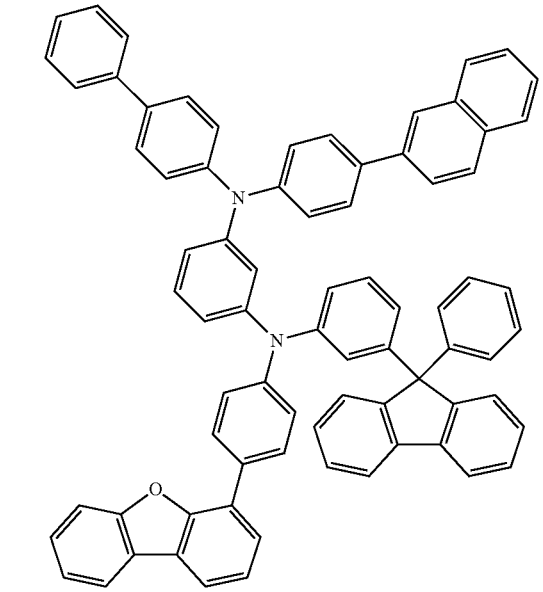

G-190
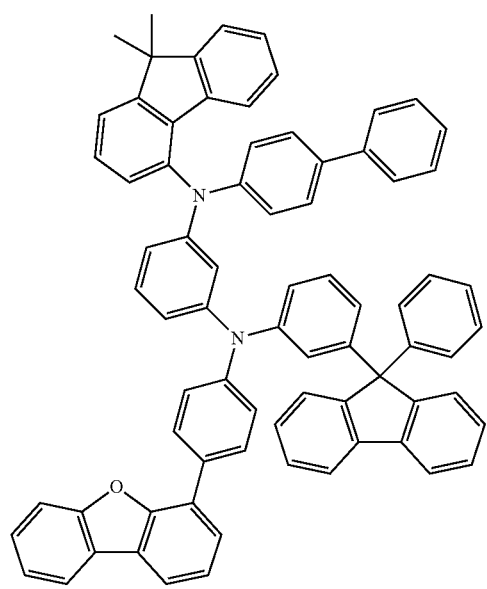
G-191
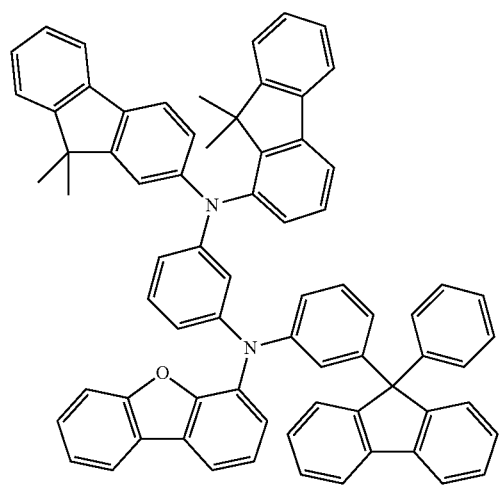
G-192
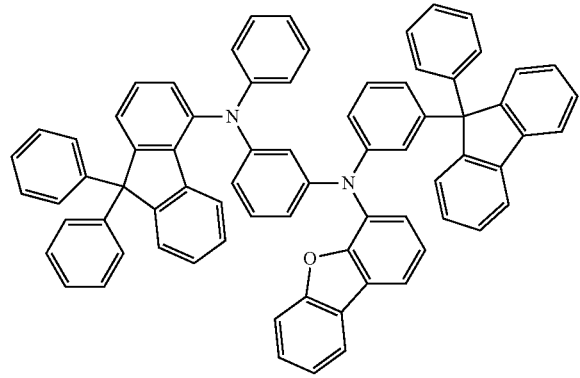
G-193
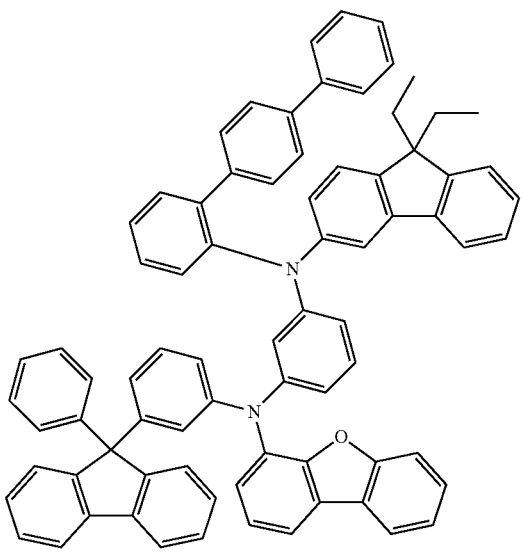
G-194
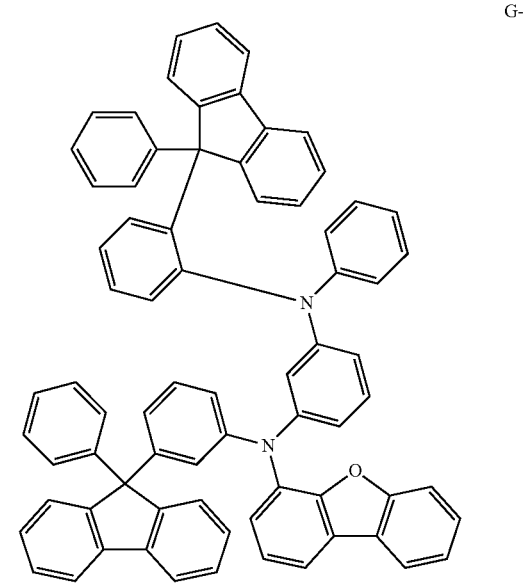
G-195
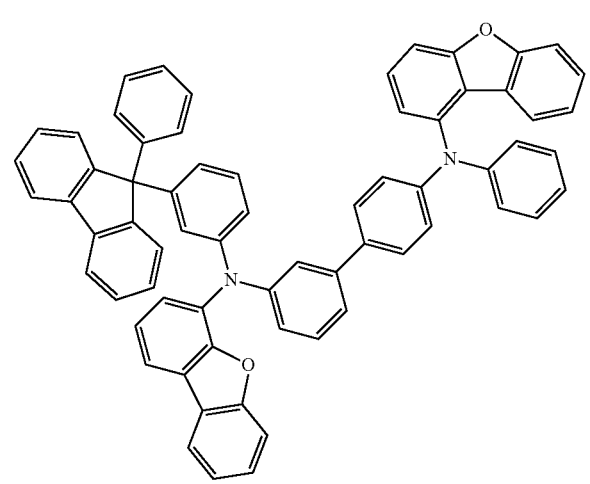

-continued
G-196
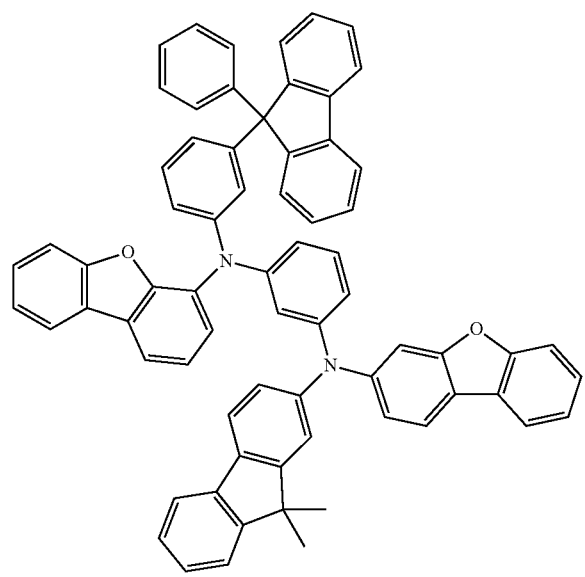
G-197
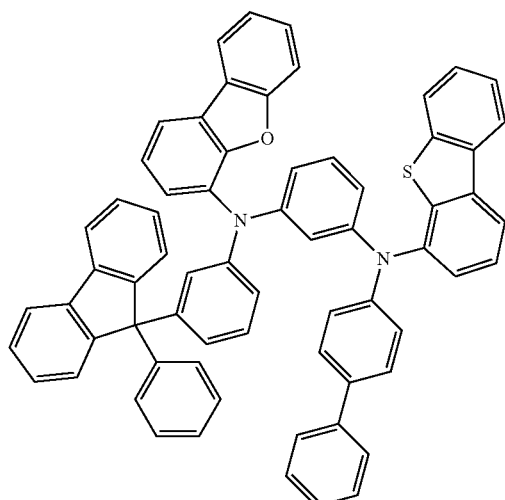
G-198
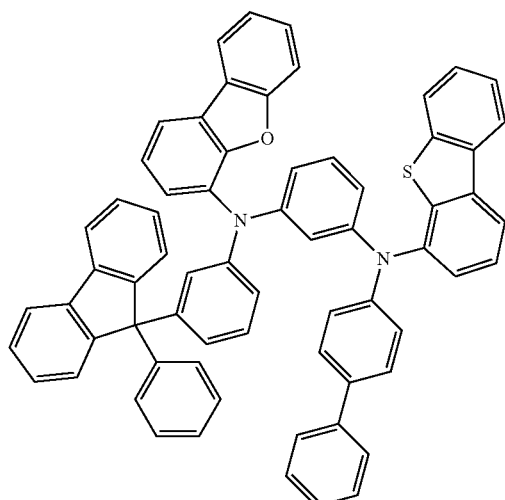
G-199
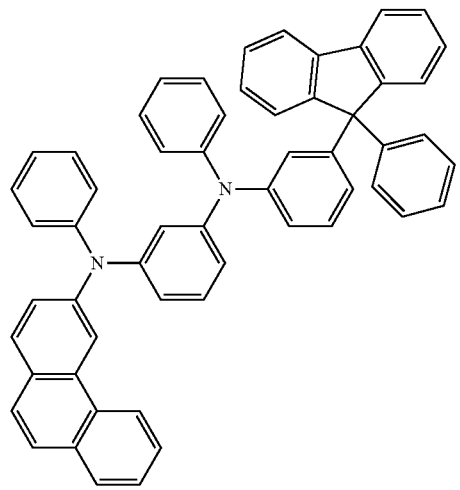
G-200
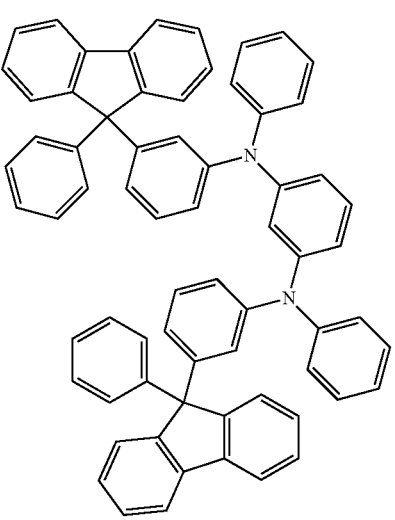
G-201
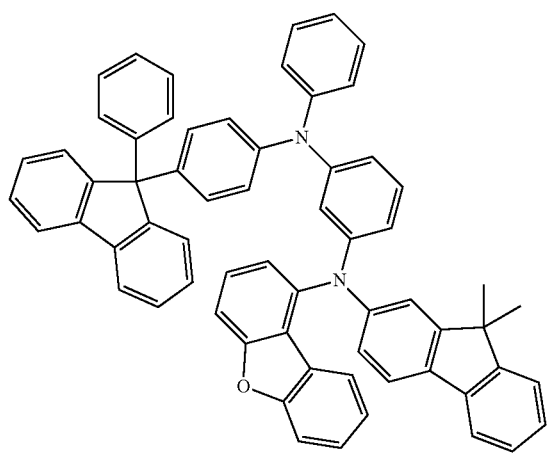

-continued

G-202
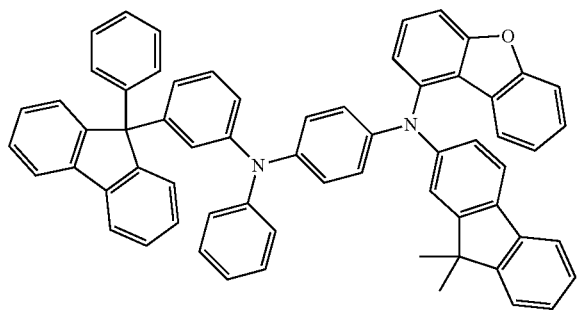

-continued

G-204
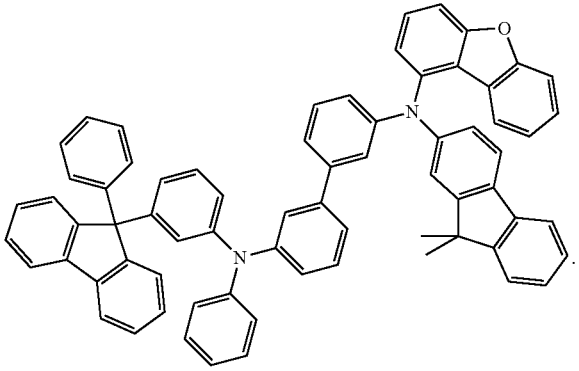

G-203
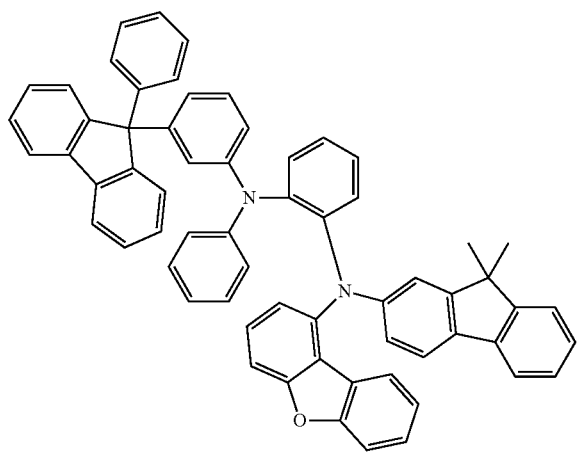

27. An organic electric element comprising a first electrode, a second electrode, and an organic material layer formed between the first electrode and the second electrode, wherein the organic material layer comprises at least one layer of a hole injection layer, a hole transport layer, an emission-auxiliary layer, a light emitting layer, an electron transport auxiliary layer, an electron transport layer and an electron injection layer, and the organic material layer comprises a single compound or two or more compounds represented by the Formula A of claim 21.

28. The organic electric element of claim 27, wherein the compound is comprised in the emission-auxiliary layer.

29. The organic electric element of claim 28, wherein the compound is comprised in a green emission-auxiliary layer of the emission-auxiliary layer.

30. An electronic device comprising a display device and a control unit for driving the display device, wherein the display device comprises the organic electric element of claim 7.

* * * * *